US012447153B2

(12) United States Patent
Ellis et al.

(10) Patent No.: US 12,447,153 B2
(45) Date of Patent: Oct. 21, 2025

(54) HER2 MUTATION INHIBITORS

(71) Applicant: Array BioPharma Inc., Boulder, CO (US)

(72) Inventors: Bryan Daniel Ellis, Denver, CO (US); Erik James Hicken, Longmont, CO (US); Ellen Ruth Laird, Longmont, CO (US); Nicholas Charles Lazzara, Denver, CO (US); Bradley Jon Newhouse, Broomfield, CO (US); Spencer Phillip Pajk, Boulder, CO (US); Rachel Zoe Rosen, Broomfield, CO (US); Russell Andrew Shelp, Boulder, CO (US)

(73) Assignee: Pfizer Inc., New York, NY (US)

( * ) Notice: Subject to any disclaimer, the term of this patent is extended or adjusted under 35 U.S.C. 154(b) by 482 days.

(21) Appl. No.: 17/849,621

(22) Filed: Jun. 25, 2022

(65) Prior Publication Data

US 2023/0041385 A1 Feb. 9, 2023

Related U.S. Application Data

(60) Provisional application No. 63/350,495, filed on Jun. 9, 2022, provisional application No. 63/294,590, filed on Dec. 29, 2021, provisional application No. 63/215,435, filed on Jun. 26, 2021.

(51) Int. Cl.

| | |
|---|---|
| ***A61K 31/519*** | (2006.01) |
| ***A61K 31/337*** | (2006.01) |
| ***A61K 31/44*** | (2006.01) |
| ***A61K 31/502*** | (2006.01) |
| ***A61K 31/506*** | (2006.01) |
| ***A61K 31/5386*** | (2006.01) |
| ***A61K 31/55*** | (2006.01) |
| ***A61K 31/551*** | (2006.01) |
| ***A61K 31/573*** | (2006.01) |
| ***A61K 31/655*** | (2006.01) |
| ***A61K 31/704*** | (2006.01) |
| ***A61K 31/7048*** | (2006.01) |
| ***A61K 38/14*** | (2006.01) |
| ***A61K 39/395*** | (2006.01) |
| ***C07D 471/04*** | (2006.01) |
| ***C07D 519/00*** | (2006.01) |

(52) U.S. Cl.

CPC .......... *A61K 31/519* (2013.01); *A61K 31/337* (2013.01); *A61K 31/44* (2013.01); *A61K 31/502* (2013.01); *A61K 31/506* (2013.01); *A61K 31/5386* (2013.01); *A61K 31/55* (2013.01); *A61K 31/551* (2013.01); *A61K 31/573* (2013.01); *A61K 31/655* (2013.01); *A61K 31/704* (2013.01); *A61K 31/7048* (2013.01); *A61K 38/14* (2013.01); *A61K 39/3955* (2013.01); *C07D 471/04* (2013.01); *C07D 519/00* (2013.01)

(58) Field of Classification Search

CPC .... A61K 31/519; A61K 31/337; A61K 31/44; A61K 31/502; A61K 31/506; A61K 31/5386; A61K 31/55; A61K 31/551; A61K 31/573; A61K 31/655; A61K 31/704; A61K 31/7048; A61K 38/14; A61K 39/3955; C07D 471/04; C07D 519/00

See application file for complete search history.

(56) References Cited

FOREIGN PATENT DOCUMENTS

| | | |
|---|---|---|
| EP | 3677583 | 7/2020 |
| WO | 2005/016346 | 2/2005 |
| WO | 2007/059257 | 5/2007 |
| WO | 2021/127397 | 6/2021 |
| WO | 2021/156178 | 8/2021 |
| WO | 2021/156180 | 8/2021 |
| WO | 2021/213800 | 10/2021 |
| WO | 2022/003575 | 1/2022 |
| WO | 2022/006386 | 1/2022 |
| WO | 2022/221227 | 10/2022 |
| WO | WO-2022266458 A1 * | 12/2022 |

* cited by examiner

*Primary Examiner* — James H Alstrum-Acevedo

*Assistant Examiner* — Justin Christopher Sanchez

(74) *Attorney, Agent, or Firm* — Corey M. Williams

(57) ABSTRACT

This invention relates to compounds of Formula (I):

(I)

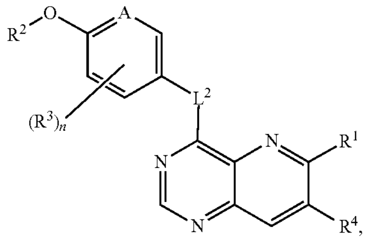

and enantiomers thereof, and to pharmaceutically acceptable salts of Formula (I) and said enantiomers, wherein A, $L^2$, $R^1$, $R^2$, $R^3$, $R^4$, and n are as defined herein. The invention further relates to pharmaceutical compositions comprising such compounds and salts, and to methods and uses of such compounds, salts, and compositions for the treatment of abnormal cell growth, including cancer, in a subject in need thereof.

18 Claims, No Drawings

Specification includes a Sequence Listing.

HER2 MUTATION INHIBITORS

BACKGROUND OF THE INVENTION

Reference to Sequence Listing

This application was filed electronically via EFS-Web and includes an electronically submitted sequence listing in .txt format. The .txt file contains a sequence listing entitled "PC072760A_SEQ_LISTING_ST25.txt" created on Jun. 13, 2022 and having a size of 6 KB. The sequence listing contained in this .txt file is part of the specification and is herein incorporated by reference in its entirety.

Field of the Invention

The invention relates to pyrido[3,2-d]pyrimidine compounds that act as covalent HER2 inhibitors. The invention relates to compounds of Formula (I) and pharmaceutically acceptable salts thereof, to pharmaceutical compositions comprising such compounds and salts, and to the uses thereof. The invention also relates to the preparation of the compounds of the invention and intermediates in their preparation, compositions containing the compounds of the invention, and uses of compounds of the invention including treatment of abnormal cell growth, such as cancer, in a subject.

Description of the State of the Art

Human epidermal growth factor receptor 2 (ErbB2, also known as HER2) is a receptor tyrosine kinase that belongs to a family of four kinases (EGFR, ErbB2, ErbB3 and ErbB4). The role of HER2 amplification in oncology is well known, particularly breast, gastric, lung and colon cancers. HER2 amplified breast and lung cancers are also known to metastasize and develop brain metastases. HER2 inhibitors are known, such as tucatinib, lapatinib, neratinib, sapitinib, poziotinib, canertinib, TAK-285 and varlitinib, but not all those HER2 inhibitors are selective. Additionally, there are monoclonal antibodies used for HER2 positive cancers, such as trastuzumab and pertuzumab.

Activating mutations in the HER2 gene are becoming increasingly reported. One common type of HER2 mutation is an insertion mutation. A frequently occurring insertion mutation is the HER2 YVMA mutation in exon 20. HER2 mutation cancers are also known to metastasize and develop brain metastases. See Subramanian, Janakiraman, et al. "Emergence of ErbB2 Mutation as a Biomarker and an Actionable Target in Solid Cancers." *The Oncologist.* 24(12) (2019): pp. e1303-e1314; and Offin, Michael, et al. "Frequency and outcomes of Brain Metastases in Patients with HER2-Mutant Lung Cancers." *Cancer.* 125(24) (2019): pp. 4380-4387.

There remains a need to discover HER2 mutation inhibitors having novel activity profiles, such as selective HER2 mutation inhibitors, which may be useful for the treatment of HER2 mutation cancers or other proliferative diseases or conditions. Furthermore, brain penetrant HER2 mutation inhibitors may be useful in treating brain metastases from HER2 amplified or HER2 positive cancers, including brain metastases from HER2 mutation amplified or HER2 mutation positive cancers.

BRIEF SUMMARY OF THE INVENTION

The present invention provides, in part, compounds of Formula (I) and pharmaceutically acceptable salts thereof. Such compounds can covalently inhibit the activity of HER2, including HER2 mutations, thereby effecting biological functions. In some embodiments, the invention provides compounds that are selective for HER2 mutations. In some embodiments, the invention provides compound with an affinity for inhibiting HER2 and HER2 mutations greater than their affinity for inhibiting EGFR. In some embodiments, the invention provides compounds that can inhibit the activity of brain metasteses from HER2 positive or HER2 amplified cancers. In a further embodiment, the invention provides compounds that can inhibit the activity of brain metasteses from HER2 mutation positive or HER2 mutation amplified cancers. Also provided are pharmaceutical compositions and medicaments, comprising the compounds or salts of the invention, alone or in combination with additional anti-cancer therapeutic agents.

The present invention also provides, in part, methods for preparing the compounds, pharmaceutically acceptable salts and compositions of the invention, and methods of using the foregoing.

In one aspect, the invention provides a compound of Formula (I):

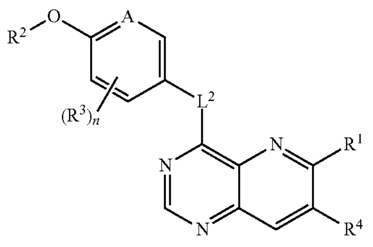

(I)

or a pharmaceutically acceptable salt thereof, wherein A, $L_1$, $L_2$, $R^1$, $R^2$, $R^3$, $R^4$ and n are as defined herein.

In another aspect, the invention provides a pharmaceutical composition comprising a compound of Formula (I), or a pharmaceutically acceptable salt thereof. In a further aspect, the invention provides a pharmaceutical composition comprising a compound of Formula (I), or a pharmaceutically acceptable salt thereof, and a pharmaceutically acceptable excipient. In a still further aspect, the pharmaceutical composition comprises two or more pharmaceutically acceptable excipients.

In another aspect, the invention provides a pharmaceutical composition for the treatment of a disease or condition for which an inhibitor of HER2 mutations is indicated, comprising a compound of Formula (I), or a pharmaceutically acceptable salt thereof.

In another aspect, the invention provides a pharmaceutical composition for the treatment of a disease or condition for which a brain penetrant inhibitor of HER2 is indicated, comprising a compound of Formula (I), or a pharmaceutically acceptable salt thereof. In a further aspect, the invention provides a pharmaceutical composition for the treatment of a disease or condition for which a brain penetrant inhibitor of HER2 mutations is indicated, comprising a compound of Formula (I), or a pharmaceutically acceptable salt thereof.

The invention also provides therapeutic methods and uses comprising administering a compound of Formula (I), or a pharmaceutically acceptable salt thereof, to a subject.

In another aspect, the invention provides a compound of Formula (I), or a pharmaceutically acceptable salt thereof, for use in the treatment of a subject in need of such treatment. In some embodiments, the invention provides a compound of Formula (I), or a pharmaceutically acceptable salt thereof, for use in the treatment of abnormal cell growth, in particular cancer, in a subject.

In another aspect, the invention provides a compound of Formula (I), or a pharmaceutically acceptable salt thereof, for use as a medicament, in particular a medicament for the treatment of abnormal cell growth, such as cancer.

In yet another aspect, the invention provides the use of a compound of Formula (I), or a pharmaceutically acceptable salt thereof, as defined in any of the embodiments described herein, for the manufacture of a medicament for treating a disease or condition for which an inhibitor of HER2 mutations is indicated.

In yet another aspect, the invention provides the use of a compound of Formula (I), or a pharmaceutically acceptable salt thereof, as defined in any of the embodiments described herein, for the manufacture of a medicament for treating a disease or condition for which a brain penetrant inhibitor of HER2 is indicated. In a further aspect, the invention provides the use of a compound of Formula (I), or a pharmaceutically acceptable salt thereof, as defined in any of the embodiments described herein, for the manufacture of a medicament for treating a disease or condition for which a brain penetrant inhibitor of HER2 mutations is indicated.

In yet another aspect, the invention provides a compound of Formula (I), or a pharmaceutically acceptable salt thereof, as defined in any of the embodiments described herein, for use in the treatment of a disease or condition for which an inhibitor of HER2 mutations is indicated.

In yet another aspect, the invention provides a compound of Formula (I), or a pharmaceutically acceptable salt thereof, as defined in any of the embodiments described herein, for use in the treatment of a disease or condition for which a brain penetrant inhibitor of HER2 is indicated. In a further aspect, the invention provides a compound of Formula (I), or a pharmaceutically acceptable salt thereof, as defined in any of the embodiments described herein, for use in the treatment of a disease or condition for which a brain penetrant inhibitor of HER2 mutations is indicated.

In another aspect, the invention provides a compound of Formula (I), or a pharmaceutically acceptable salt thereof, as defined in any of the embodiments herein, for use in the treatment of cancer.

In another aspect, the invention provides a compound of Formula (I), or a pharmaceutically acceptable salt thereof, as defined in any of the embodiments herein, for use as a medicament.

In another aspect, the invention provides a compound of Formula (I), or a pharmaceutically acceptable salt thereof, as defined in any of the embodiments herein, for use in therapy.

In yet another aspect, the invention provides a compound of Formula (I), or a pharmaceutically acceptable salt thereof, as defined in any of the embodiments herein, for use in the treatment of a disease or condition for which a brain penetrant inhibitor of HER2 is indicated.

In a further aspect, the invention provides a compound of Formula (I), or a pharmaceutically acceptable salt thereof, as defined in any of the embodiments herein, for use in the treatment of a disease or condition for which a brain penetrant inhibitor of HER2 mutations is indicated.

In one aspect, the invention provides a method for treating abnormal cell growth, in particular cancer, in a subject in need thereof, comprising administering to the subject a therapeutically effective amount of a compound of Formula (I), or a pharmaceutically acceptable salt thereof. Compounds of Formula (I) may be administered as single agents or may be administered in combination with other anti-cancer therapeutic agents, in particular with standard of care agents appropriate for the particular cancer.

In another aspect, the invention provides a method for treating abnormal cell growth, in particular cancer, comprising administering a therapeutically effective amount of a compound of Formula (I), or a pharmaceutically acceptable salt thereof.

In another aspect, the invention provides a method for treating or ameliorating abnormal cell growth, in particular cancer, in a patient in need thereof comprising administering to the patient a compound of Formula (I), or a pharmaceutically acceptable salt thereof.

In another aspect, the invention provides a method for treating a disorder mediated by HER2 mutations in a subject, comprising administering to the subject a compound of Formula (I), or a pharmaceutically acceptable salt thereof, in an amount that is effective for treating said disorder, in particular cancer.

In another aspect, the invention provides a method for treating a disorder mediated by brain metasteses from HER2 amplified or HER2 positive cancer in a subject, comprising administering to the subject a compound of Formula (I), or a pharmaceutically acceptable salt thereof, in an amount that is effective for treating said disorder.

In another aspect, the invention provides a method for treating or preventing a disease or disorder modulated by HER2 mutations, comprising administering to a mammal in need of such treatment an effective amount of a compound of Formula (I), or a pharmaceutically acceptable salt thereof.

In another aspect, the invention provides a method for treating or preventing a disease or disorder modulated by brain metasteses from HER2 amplified or HER2 positive cancer, comprising administering to a mammal in need of such treatment an effective amount of a compound of Formula (I), or a pharmaceutically acceptable salt thereof.

In a further aspect, the invention provides a method for treating abnormal cell growth, in particular cancer, in a subject in need thereof, comprising administering to the subject an amount of a compound of Formula (I), or a pharmaceutically acceptable salt thereof, in combination with an amount of an additional anti-cancer therapeutic agent, which amounts are together effective in treating said abnormal cell growth.

In another aspect, the invention provides a method of inhibiting HER2 mutation activity in a patient in need thereof comprising administering to the patient a compound of Formula (I), or a pharmaceutically acceptable salt thereof.

In another aspect, the invention provides a method of inhibiting brain metastasis activity from HER2 amplified or HER2 positive cancer in a patient in need thereof comprising administering to the patient a compound of Formula (I), or a pharmaceutically acceptable salt thereof.

Each of the embodiments of the compounds of the present invention described below can be combined with one or more other embodiments of the compounds of the present invention described herein not inconsistent with the embodiment(s) with which it is combined.

In addition, each of the embodiments below describing the invention envisions within its scope the pharmaceutically acceptable salts of the compounds of the invention. Accordingly, the phrase "or a pharmaceutically acceptable salt thereof" is implicit in the description of all compounds described herein unless explicitly indicated to the contrary.

Besides being useful for human treatment, compounds of Formula (I) are also useful for veterinary treatment of companion animals, exotic animals and farm animals.

DETAILED DESCRIPTION OF THE INVENTION

The present invention may be understood more readily by reference to the following detailed description of the preferred embodiments of the invention and the Examples included herein. It is to be understood that the terminology used herein is for the purpose of describing specific embodiments only and is not intended to be limiting. It is further to be understood that unless specifically defined herein, the terminology used herein is to be given its traditional meaning as known in the relevant art. In the event that one or more of the incorporated literature and similar materials differs from or contradicts this application, including but not limited to defined terms, term usage, described techniques, or the like, this application controls.

Definitions

As used herein, the singular form "a", "an", and "the" include plural references unless indicated otherwise. For example, "a" substituent includes one or more substituents.

The invention described herein may be practiced in the absence of any element(s) not specifically disclosed herein. Thus, for example, in each instance herein any of the terms "comprising", "consisting essentially of", and "consisting of" may be replaced with either of the other two terms.

Compounds of the invention means the compounds of Formula (I), Formula (Ia), Formula (II) or Formula (III), as well as all of the Examples.

"Alkyl", as used herein, means a saturated, monovalent aliphatic hydrocarbon radical including straight chain and branched chain groups having the specified number of carbon atoms.

Some alkyl moieties have been abbreviated, for example, methyl ("Me"), ethyl ("Et"), propyl ("Pr") and butyl ("Bu"), and further abbreviations are used to designate specific isomers of compounds, for example, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), 1,1-dimethylethyl or t-butyl ("t-Bu") and the like. The abbreviations are sometimes used in conjunction with elemental abbreviations and chemical structures, for example, methanol ("MeOH") or ethanol ("EtOH").

When a substituent is defined as a combination of two groups (e.g., alkoxyalkyl) the moiety concerned is always attached through the second of the two groups named (in this case alkyl). Thus, for example, ethoxymethyl corresponds to $CH_2CH_3—O—CH_2—$.

"Heterocycle" or "heterocyclic" or "heterocyclyl", as used herein, may be used interchangeably to mean a non-aromatic, saturated ring system containing the specified number of ring atoms, containing at least one heteroatom selected from N, O and S as a ring member, where ring S atoms are optionally substituted by one or two oxo groups (i.e., $S(O)_q$, where q is 0, 1 or 2) and where the heterocyclic ring is connected to the base molecule via a ring atom, which may be C or N. Heterocyclic rings include rings that are spirocyclic, bridged, or fused to one or more other heterocyclic or carbocyclic rings, provided the point of attachment to the base molecule is an atom of the heterocyclic portion of the ring system. Preferably, heterocyclic rings contain 1 to 4 heteroatoms selected from N, O, and $S(O)_q$ as ring members, and more preferably 1 to 2 ring heteroatoms, provided that such heterocyclic rings do not contain two contiguous oxygen atoms.

Heterocycles typically include 3-10 membered heterocyclyl groups, and more preferably 4-10 or 4-7 membered heterocyclyl groups, in accordance with the definition herein.

Examples of saturated heterocycles include, but are not limited to, oxirane (oxiranyl), thiirane (thiaranyl), aziridine (aziridinyl), oxetane (oxetanyl), thietane (thietanyl), azetidine (azetidinyl), tetrahydrofuran (tetrahydrofuranyl), tetrahydrothiophene (tetrahydrothiophenyl), pyrrolidine (pyrrolidinyl), tetrahydropyran (tetrahydropyranyl), tetrahydrothiopyran (tetrahydrothiopyranyl), piperidine (piperidinyl), 1,4-dioxane (1,4-dioxanyl), 1,4-oxathiarane (1,4-oxathiaranyl), morpholine (morpholinyl), 1,4-dithiane (1,4-dithianyl), piperazine (piperazinyl), thiomorpholine (thiomorpholinyl), oxepane (oxepanyl), thiepane (thiepanyl), azepane (azepanyl), 1,4-dioxepane (1,4-dioxepanyl), 1,4-oxathiepane (1,4-oxathiepanyl), 1,4-oxaazepane (1,4-oxaazepanyl), 1,4-thieazepane (1,4-thieazapanyl), 1,4-diazepane (1,4-diazepanyl), and 1,4-dithiepane (1,4-dithiepanyl).

It is understood that no more than two N, O or S atoms are ordinarily connected sequentially, except where an oxo group is attached to S to form a sulfonyl group, or in the case of certain heteroaryl rings, such as triazole, tetrazole, oxadiazole, thiadiazole, triazine and the like.

"Aryl", as used herein, means an optionally substituted monocyclic or fused bicyclic or polycyclic ring system having the well-known characteristics of aromaticity, wherein at least one ring contains a completely conjugated pi-electron system.

"Heteroaryl", as used herein, means a monocyclic or fused bicyclic or polycyclic ring systems having the well-known characteristics of aromaticity that contain the specified number of ring atoms as defined above under "aryl" which include at least one heteroatom selected from N, O and S as a ring member in an aromatic ring. The inclusion of a heteroatom permits aromaticity in 5-membered rings as well as 6-membered rings. Typically, heteroaryl groups contain 5 to 12 ring atoms ("5-12 membered heteroaryl"), and more preferably 5 to 10 ring atoms ("5-10 membered heteroaryl"). In a preferred embodiment, the heteroaryl group contains 9 to 10 members ("9-10 membered heteroaryl"). Heteroaryl rings are attached to the base molecule via a ring atom of the heteroaromatic ring, such that aromaticity is maintained. Thus, 6-membered heteroaryl rings may be attached to the base molecule via a ring C atom, while 5-membered heteroaryl rings may be attached to the base molecule via a ring C or N atom. Heteroaryl groups may also be fused to another aryl or heteroaryl ring or fused to a saturated or partially unsaturated carbocyclic or heterocyclic ring. Examples of unsubstituted heteroaryl groups include, but are not limited to, monocyclic heteroaryl groups such as pyrrole (pyrrolyl), furan (furanyl), thiophene (thiophenyl), pyrazole (pyrazolyl), imidazole (imidazolyl), isoxazole (isoxazolyl), oxazole (oxazolyl), isothiazole (isothiazolyl), thiazole (thiazolyl), 1,2,3-triazole (1,2,3-triazolyl), 1,3,4-triazole (1,3,4-triazolyl), 1-oxa-2,3-diazole (1-oxa-2,3-diazolyl), 1-oxa-2,4-diazole (1-oxa-2,4-diazolyl), 1-oxa-2,5-diazole (1-oxa-2,5-diazolyl), 1-oxa-3,4-diazole (1-oxa-3,4-diazolyl), 1-thia-2,3-diazole (1-thia-2,3-diazolyl), 1-thia-2,4-diazole (1-thia-2,4-diazolyl), 1-thia-2,5-diazole (1-thia-2,5-diazolyl), 1-thia-3,4-diazole (1-thia-3,4-diazolyl), tetrazole (tetrazolyl), pyridine (pyridinyl), pyridazine (pyridazinyl), pyrimidine (pyrimidinyl) and pyrazine (pyrazinyl), and fused heteroaryl groups such as benzofuran (benzofuranyl), benzothiophene (benzothiophenyl), indole (indolyl), benzimidazole (benzimidazolyl), indazole (indazolyl), benzotriazole (benzotriazolyl), pyrrolo[2,3-b]pyridine (pyrrolo[2,3-b]pyridinyl), pyrrolo[2,3-c]pyridine (pyrrolo[2,3-c]pyridinyl), pyrrolo[3,2-c]pyridine (pyrrolo[3,2-c]pyridinyl), pyrrolo[3,2-b]pyridine (pyrrolo[3,2-b]pyridinyl), imidazo[4,5-b]pyridine (imidazo[4,5-b]pyridinyl), imidazo[4,5-c]pyridine (imidazo[4,5-c]pyridinyl), pyrazolo[4,3-d]pyridine (pyrazolo[4,3-d]pyridinyl), pyrazolo[4,3-c]pyridine (pyrazolo[4,3-c]pyridinyl), pyrazolo[3,4-c]pyridine (pyrazolo[3,4-c]pyridinyl), pyrazolo[3,4-b]pyridine (pyrazolo[3,4-b]pyridinyl), isoindole (isoindolyl), indazole (indazolyl), purine (purinyl), indolizine (indolizinyl), imidazo[1,2-a]pyridine (imidazo[1,2-a]pyridinyl, imidazo[1,5-a]pyridine (imidazo[1,5-a]pyridinyl, pyrazolo[1,5-a]pyridine (pyrazolo[1,5-a]pyridinyl), pyrrolo[1,2-b]pyridazine (pyrrolo[1,2-b]pyridazinyl), imidazo[1,2-c]pyrimidine (imidazo[1,2-b]pyridazinyl), quinoline (quinolinyl), isoquinoline (isoquinolinyl), cinnoline (cinnolinyl), quinazoline (quinazolinyl), quinoxaline (quinoxalinyl), phthalazine (phthalazinyl), 1,5-naphthyridine (1,5-napthyridinyl), 1,6-naphthyridine (1,6-napthyridinyl), 1,7-naphthyridine (1,7-napthyridinyl), 1,8-naphthyridine (1,8-napthyridinyl), 2,6-naphthyridine (2,6-napthyridinyl), 2,7-naphthyridine (2,7-napthyridinyl), pyrido[3,2-d]pyrimidine (pyrido[3,2-d]pyrimidinyl), pyrido[4,3-d]pyrimidine (pyrido[4,3-d]pyrimidinyl), pyrido[3,4-d]pyrimidine (pyrido[3,4-d]pyrimidinyl), pyrido[2,3-d]pyrimidine (pyrido[2,3-d]pyrimidinyl), pyrido[2,3-b]pyrazine (pyrido[2,3-b]pyrazinyl), pyrido[3,4-b]pyrazine (pyrido[3,4-b]pyrazinyl), pyrimido[5,4-d]pyrimidine (pyrimido[5,4-d]pyrimindinyl), pyrazino[2,3-b]pyrazine (pyrazino[2,3-b]pyrazinyl), and pyrimido[4,5-d]pyrimidine (pyrimido[4,5-d]pyrimidinyl). The heteroaryl group is unsubstituted or substituted as further described herein.

"Acrylamide", as used herein, means a $CH_2{=}CHC({=}O)NH_2$ group, where the group may be attached via the nitrogen, $CH_2{=}CHC({=}O)NH{-}$, or via the carbon $-CHCHC({=}O)NH_2$. The acrylamide group may be substituted, such as N-methyl-3-acrylamide $-CH{=}CHC({=}O)NHCH_3$.

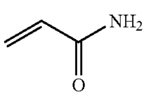
acrylamide

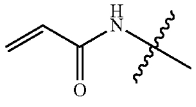
attached via N

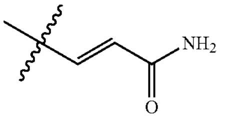
attached via C

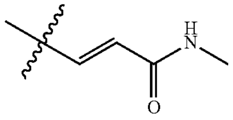
N-methyl-3-acrylamide

"Halogen" or "halo", as used herein, means fluoro, chloro, bromo and iodo (F, Cl, Br, I). Preferably, halo refers to fluoro or chloro (F or Cl).

"Oxo", as used herein, refers to a double bonded oxygen (=O).

"Vinylsulfonyl" as used herein, means a $-S({=}O)_2CH{=}CH_2$ group.

"Optional" or "optionally" means that the subsequently described event or circumstance may but need not occur, and the description includes instances where the event or circumstance occurs and instances in which it does not.

The terms "optionally substituted" and "substituted or unsubstituted" are used interchangeably to indicate that the particular group being described may have no non-hydrogen substituents (i.e., unsubstituted), or the group may have one or more non-hydrogen substituents (i.e., substituted). If not otherwise specified, the total number of substituents that may be present is equal to the number of H atoms present on the unsubstituted form of the group being described. Where an optional substituent is attached via a double bond, such as an oxo (=O) substituent, the group occupies two available valences, so the total number of other substituents that are included is reduced by two. In the case where optional substituents are selected independently from a list of alternatives, the selected groups are the same or different. Throughout the disclosure, it will be understood that the number and nature of optional substituent groups will be limited to the extent that such substitutions make chemical sense.

Frequently, a group described herein as optionally substituted by "one or more" substituent groups is optionally substituted by 1 to 4, preferably optionally substituted by 1 to 3, and more preferably optionally substituted by 1 to 2 such substituents. The recitation herein that a group is "optionally substituted by one or more" of a list of optional substituents may be replaced by "optionally substituted by 1 to 4", "optionally substituted by 1 to 3", "optionally substituted by 1 to 2", "optionally substituted by one, two, three or four", "optionally substituted by one, two or three" or "optionally substituted by one or two" of such optional substituent groups.

If substituents are described as being "independently selected" from a group, each substituent is selected independent of the other. Each substituent therefore may be identical to or different from the other substituent(s).

"Pharmaceutically acceptable", as used herein, means that the substance or composition is compatible chemically and/or toxicologically, with the other ingredients comprising a formulation, and/or the mammal being treated therewith.

"HER2 mutations", as used herein, means one or more mutations in the HER2 receptor tyrosine-protein kinase. In certain embodiments, the HER2 mutation is the YVMA (SEQ ID NO: 2) insertion at exon 20 of HER2 ("HER2-YVMA"). A HER2 mutation may mean one or more mutations in the HER2 receptor tyrosine-protein kinase.

"Selective", as used herein to describe a functionally defined receptor ligand or enzyme inhibitor, means selective for the defined receptor or enzyme subtype as compared with other receptor or enzyme subtypes in the same family. For instance, a selective HER2 mutation inhibitor is a compound that inhibits the HER2-YVMA (SEQ ID NO: 2) insert enzyme subtype more potently than EGFR enzyme subtype. Such selectivity is, in one embodiment, at least 2-fold (as measured using conventional binding assays), or, in another embodiment, at least 10-fold, or, in a further embodiment, at least 100-fold.

Additional abbreviations used throughout the application include: approximately ("~"), acetyl ("Ac"), acetonitrile ("ACN"), acetoxy ("AcO" or "OAc"), aqueous ("aq"), benzyl ("Bn"), methylene chloride/dichloromethane/$CH_2Cl_2$ ("DCM"), diethylamine ("DEA"), diisopropylethyl amine ("DIPEA"), N,N-dimethylacetamide ("DMA"), 4-dimethylaminopyridine ("DMAP"), N,N-dimethyl formamide ("DMF"), dimethylsulfoxide ("DMSO"), ethyl acetate ("EtOAc"), hours ("h"), 1-[bis(dimethylamino)methylene]-1H-1,2,3-triazolo[4,5-b]pyridinium 3-oxid hexafluorophosphate ("HATU"), acetic acid ("HOAc" or "AcOH"), isopropyl alcohol ("IPA"), minutes ("min"), mass spectrometry ("MS"), methyl tert-butyl ether ("MTBE"), phenyl ("Ph"), retention fraction ("Rf"), retention time ("rt"), saturated ("sat."), supercritical fluid chromatography ("SFC"), propylphosphonic anhydride ("T3P"), trifluoroacetic acid ("TFA"), tetrahydrofuran ("THF"), thin layer chromatography ("TLC").

A bond drawn into a ring system (as opposed to connected at a distinct vertex) indicates that the bond may be attached to any of the suitable ring atoms. A wavy line (  )

across a bond indicates the point of attachment.

HER2 Mutation Inhibitor Compounds

In one aspect, the invention provides a compound of Formula (I):

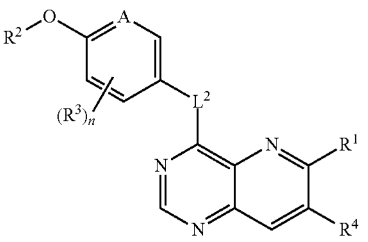 (I)

or a pharmaceutically acceptable salt thereof, wherein:

A is selected from carbon and nitrogen, wherein $R^3$ may be bound to A when it is carbon;

$R^1$ is selected from the group consisting of $-L^1-R^5$, $—NR^6R^7$, N-methyl-3-acrylamide, and prop-1-en-2-yl;

$R^2$ is a 9-10 membered bicyclic heteroaryl containing one, two, or three heteroatoms selected from N, O and S, wherein the bicyclic heteroaryl may be optionally substituted with one or two groups selected from halogen and $C_1$-$C_3$ alkyl;

each $R^3$ is independently selected from halogen, methyl, difluoromethyl, and trifluoromethyl;

$R^4$ is hydrogen, chloro, or methoxy;

$L^1$ is selected from the group consisting of a bond, $CHR^8$, O, $NR^8$ and S;

$L^2$ is selected from NH and O;

$R^5$ is a 4 to 10 membered heterocycle containing 1 to 3 heteroatoms selected from the group consisting of N, O and S, wherein the heterocycle is substituted by one $R^6$, and is additionally optionally substituted with 1 or 2 groups independently selected from methyl, ethyl, isopropyl, tert-butyl, difluoromethyl, trifluoromethyl, methoxymethyl, ethynyl, cyclopropyl, and cyclobutyl;

$R^6$ is selected from the group consisting of cyano, 1-prop-2-en-1-one, 1-(2-fluoroprop-2-en-1-one), 1-(2-methylprop-2-en-1-one), N—(N-methylacrylamide), 1-but-2-yn-1-one, vinylsulfonyl, and (bicyclo[1.1.0]butan-1-yl) methanone;

$R^7$ and $R^8$ are independently hydrogen or methyl; and n is 0, 1 or 2.

In a preferred embodiment of Formula (I), A is carbon wherein $R^3$ may be bound to A.

In a preferred embodiment of Formula (I), $L^2$ is NH.

In one embodiment of Formula (I), $R^1$ is selected from the group consisting of $-L^1-R^5$, $—NR^6R^7$, N-methyl-3-acrylamide, and prop-1-en-2-yl. In one embodiment of Formula (I), $R^1$ is selected from the group consisting of 1-acryloylpiperidin-4-olate, 6-acryloyl-3,6-diazabicyclo[3.1.1]heptan-3-yl, 1-acryloylhexahydropyrrolo[3,4-b]pyrrol-5(1)-yl, 1-(bicyclo[1.1.0]butane-1-carbonyl)hexahydropyrrolo[3,4-b] pyrrol-5(1)-yl, (1-acryloylpiperidin-4-yl)thio, 2-acryloyl-2,6-diazabicyclo[3.2.1]octan-6-yl, 4-acryloylpiperazin-1-yl, 4-acryloyl-3,3-dimethylpiperazin-1-yl, (1-acryloylpiperidin-4-yl)(methyl)amino, 1-acryloylpiperidin-3-yl, 1-acryloyl-6,6-dimethylpiperidin-3-yl, 1-acryloyloctahydrocyclopenta[b]pyrrol-5-yl, 1-acryloylpiperidin-4-yl, 3-acryloyl-3,6-diazabicyclo[3.1.1]heptan-6-yl, (1-acryloylazetidin-3-yl) thio, 4-acryloyl-5,5-dimethyl-1,4-diazepan-1-yl, 4-acryloyl-3,3-dimethyl-1,4-diazepan-1-yl, 5-acryloyl-2,5-diazabicyclo[2.2.1]heptan-2-yl, 4-acryloyl-3-(trifluoromethyl)piperazin-1-yl, 4-acryloyl-3-methylpiperazin-1-yl, 4-acryloyl-1,4-diazepan-1-yl, 6-acryloyl-2,6-diazaspiro[3.3]heptan-2-yl, 6-acryloyl-3,6-diazabicyclo[3.2.1]octan-3-yl, 4-acryloyl-3,5-dimethylpiperazin-1-yl, 6-acryloyl-3,6-diazabicyclo[3.2.0]heptan-3-yl, 1-acryloylpyrrolidin-3-yl, 1-acryloylazepan-4-yl, 1-acryloyl-2-methylpiperidin-4-yl, 1-acryloyl-5-methylpyrrolidin-3-yl, 1-acryloyl-3-methylpiperidin-4-yl, 1-acryloylazepan-3-yl, 1-acryloyl-2,2-dimethylpiperidin-4-yl, 4-acryloyl-4-azaspiro[2.5]octan-7-yl, 8-acryloyl-8-azabicyclo[3.2.1] octan-3-yl, 1-acryloyloctahydrocyclopenta[b]pyrrol-4-yl, 2-acryloyloctahydrocyclopenta[c]pyrrol-5-yl, 1-acryloyl-6,6-dimethylazepan-4-yl, N-acrylamide, N-but-2-ynamide, N-ethenesulfonamide, N-methyl-N-ethenesulfonamide, N-methyl-3-acrylamide, N-methyl-N-acrylamide, prop-2-en-1-one, 9-acryloyl-3-oxa-9-azabicyclo[3.3.1]nonan-7-yl, 4-acryloyl-3-cyclopropylpiperazin-1-yl, 4-acryloyl-3-ethylpiperazin-1-yl, 1-acryloyl-2,6-dimethylpiperidin-4-yl, 4-(but-2-ynoyl)-3-(difluoromethyl)piperazin-1-yl, 1-acryloyl-6-methylpiperidin-3-yl, 5-acryloyl-2,5-diazabicyclo [2.2.2]octan-2-yl, 2-(but-2-ynoyl)-2,6-diazabicyclo[3.2.1] octan-6-yl, 4-(but-2-ynoyl)-3-methylpiperazin-1-yl, 4-(but-2-ynoyl)-3,3-dimethylpiperazin-1-yl, 4-(but-2-ynoyl)-3-(methoxymethyl)piperazin-1-yl, 4-(but-2-ynoyl)-4,7-diazaspiro[2.5]octan-7-yl, 4-(but-2-ynoyl)-3-(trifluoromethyl)piperazin-1-yl, 4-(2-fluoroacryloyl) piperazin-1-yl, 4-(bicyclo[1.1.0]butane-1-carbonyl)-3,3-dimethylpiperazin-1-yl, 4-(2-fluoroacryloyl)-3,3-dimethylpiperazin-1-yl, 1-(but-2-ynoyl)-1,6-diazaspiro[3.3] heptan-6-yl, 4-acryloyl-4-azaspiro[2.5]octan-6-yl, 2-acryloyl-2-azabicyclo[2.2.1]heptan-5-yl, 2-acryloyl-2-azabicyclo[2.2.1]heptan-6-yl, 8-(2-fluoroacryloyl)-8-azabicyclo[3.2.1]octan-3-yl, 8-(but-2-ynoyl)-8-azabicyclo[3.2.1] octan-3-yl, 1-(but-2-ynoyl)azepan-4-yl, 7-acryloyl-7-azabicyclo[2.2.1]heptan-2-yl, 2-acryloyl-2-azabicyclo [2.2.2]octan-5-yl, 3-acryloyl-3-azabicyclo[3.2.1]octan-8-yl, 8-acryloyl-3,8-diazabicyclo[3.2.1]octan-3-yl, 8-(but-2-ynoyl)-3,8-diazabicyclo[3.2.1]octan-3-yl, 3-acryloyl-3,8-diazabicyclo[3.2.1]octan-8-yl, 4-cyano-3,3-dimethylpiperazin-1-yl, 3-(but-2-ynoyl)-3,8-diazabicyclo[3.2.1]octan-8-yl, 4-acryloyl-3-isopropylpiperazin-1-yl, 1-acryloyl-1,6-diazaspiro[3.3]heptan-6-yl, 1-acryloylazetidin-3-yl, 4-acryloyl-4,7-diazaspiro[2.5]octan-7-yl, 6-acryloyl-1,6-diazaspiro[3.3]heptan-1-yl, 4-acryloyl-3-(tert-butyl)piperazin-1-yl, 1-acryloyl-5,5-dimethylpyrrolidin-3-yl, 4-acryloyl-3-(difluoromethyl)piperazin-1-yl, (1-acryloylazetidin-3-yl)methyl, 1-(1-acryloylazetidin-3-yl)ethyl, 1-acryloyl-5-cyclopropylpyrrolidin-3-yl, 4-acryloyl-3-cyclobutylpiperazin-1-yl, 1-acryloyl-5-(methoxymethyl) pyrrolidin-3-yl, 2-acryloyl-2,6-diazaspiro[3.4]octan-6-yl, 5-acryloyl-5,8-diazaspiro[3.5]nonan-8-yl, 5-(but-2-ynoyl)-2,5-diazabicyclo[2.2.1]heptan-2-yl, 4-acryloyl-3-ethynylpiperazin-1-yl, 6-acryloyl-3,6-diazabicyclo[3.2.2]nonan- 3-yl, 4-methacryloyl-3,3-dimethylpiperazin-1-yl, 4-acryloyl-3-(methoxymethyl)piperazin-1-yl, N-(1-pyrrolidin-3-yl)-N-methylacrylamide, 4-methacryloylpiperazin-1-yl, 6-acryloyl-6-azabicyclo[3.2.1]octan-2-yl, 6-acryloyl-6-azabicyclo[3.2.1]octan-3-yl, 2-acryloyl-2-azabicyclo[2.2.2]octan-6-yl, 2-acryloyloctahydrocyclopenta[c]pyrrol-4-yl, 8-acryloyl-8-azabicyclo[3.2.1]octan-6-yl, and 8-acryloyl-8-azabicyclo[3.2.1]octan-2-yl.

In one embodiment of Formula (I), $R^1$ is selected from the group consisting of -$L^1$-$R^5$, —$NR^6R^7$, N-methyl-3-acrylamide, and prop-1-en-2-yl. In one embodiment of Formula (I), $R^1$ is selected from the group consisting of 1-acryloylpiperidin-4-olate, 6-acryloyl-3,6-diazabicyclo[3.1.1]heptan-3-yl, 1-acryloylhexahydropyrrolo[3,4-b]pyrrol-5(1)-yl, 1-(bicyclo[1.1.0]butane-1-carbonyl)hexahydropyrrolo[3,4-b]pyrrol-5(1)-yl, (1-acryloylpiperidin-4-yl)thio, 2-acryloyl-2,6-diazabicyclo[3.2.1]octan-6-yl, 4-acryloylpiperazin-1-yl, 4-acryloyl-3,3-dimethylpiperazin-1-yl, (1-acryloylpiperidin-4-yl)(methyl)amino, 1-acryloylpiperidin-3-yl, 1-acryloyl-6,6-dimethylpiperidin-3-yl, 1-acryloyloctahydrocyclopenta[b]pyrrol-5-yl, 1-acryloylpiperidin-4-yl, 3-acryloyl-3,6-diazabicyclo[3.1.1]heptan-6-yl, (1-acryloylazetidin-3-yl)thio, 4-acryloyl-5,5-dimethyl-1,4-diazepan-1-yl, 4-acryloyl-3,3-dimethyl-1,4-diazepan-1-yl, 5-acryloyl-2,5-diazabicyclo[2.2.1]heptan-2-yl, 4-acryloyl-3-(trifluoromethyl)piperazin-1-yl, 4-acryloyl-3-methylpiperazin-1-yl, 4-acryloyl-1,4-diazepan-1-yl, 6-acryloyl-2,6-diazaspiro[3.3]heptan-2-yl, 6-acryloyl-3,6-diazabicyclo[3.2.1]octan-3-yl, 4-acryloyl-3,5-dimethylpiperazin-1-yl, 6-acryloyl-3,6-diazabicyclo[3.2.0]heptan-3-yl, 1-acryloylpyrrolidin-3-yl, 1-acryloylazepan-4-yl, 1-acryloyl-2-methylpiperidin-4-yl, 1-acryloyl-5-methylpyrrolidin-3-yl, 1-acryloyl-3-methylpiperidin-4-yl, 1-acryloylazepan-3-yl, 1-acryloyl-2,2-dimethylpiperidin-4-yl, 4-acryloyl-4-azaspiro[2.5]octan-7-yl, 8-acryloyl-8-azabicyclo[3.2.1]octan-3-yl, 1-acryloyloctahydrocyclopenta[b]pyrrol-4-yl, 2-acryloyloctahydrocyclopenta[c]pyrrol-5-yl, 1-acryloyl-6,6-dimethylazepan-4-yl, N-acrylamide, N-but-2-ynamide, N-ethenesulfonamide, N-methyl-N-ethenesulfonamide, N-methyl-3-acrylamide, N-methyl-N-acrylamide, and prop-2-en-1-one.

In a preferred embodiment of Formula (I), $R^1$ is selected from the group consisting of -$L^1$-$R^5$ and —$NR^6R^7$. In one embodiment of Formula (I), $R^1$ is selected from the group consisting of 1-acryloylpiperidin-4-olate, 6-acryloyl-3,6-diazabicyclo[3.1.1]heptan-3-yl, 1-acryloylhexahydropyrrolo[3,4-b]pyrrol-5(1H)-yl, 1-(bicyclo[1.1.0]butane-1-carbonyl)hexahydropyrrolo[3,4-b]pyrrol-5(1H)-yl, (1-acryloylpiperidin-4-yl)thio, 2-acryloyl-2,6-diazabicyclo[3.2.1]octan-6-yl, 4-acryloylpiperazin-1-yl, 4-acryloyl-3,3-dimethylpiperazin-1-yl, (1-acryloylpiperidin-4-yl)(methyl)amino, 1-acryloylpiperidin-3-yl, 1-acryloyl-6,6-dimethylpiperidin-3-yl, 1-acryloyloctahydrocyclopenta[b]pyrrol-5-yl, 1-acryloylpiperidin-4-yl, 3-acryloyl-3,6-diazabicyclo[3.1.1]heptan-6-yl, (1-acryloylazetidin-3-yl)thio, 4-acryloyl-5,5-dimethyl-1,4-diazepan-1-yl, 4-acryloyl-3,3-dimethyl-1,4-diazepan-1-yl, 5-acryloyl-2,5-diazabicyclo[2.2.1]heptan-2-yl, 4-acryloyl-3-(trifluoromethyl)piperazin-1-yl, 4-acryloyl-3-methylpiperazin-1-yl, 4-acryloyl-1,4-diazepan-1-yl, 6-acryloyl-2,6-diazaspiro[3.3]heptan-2-yl, 6-acryloyl-3,6-diazabicyclo[3.2.1]octan-3-yl, 4-acryloyl-3,5-dimethylpiperazin-1-yl, 6-acryloyl-3,6-diazabicyclo[3.2.0]heptan-3-yl, 1-acryloylpyrrolidin-3-yl, 1-acryloylazepan-4-yl, 1-acryloyl-2-methylpiperidin-4-yl, 1-acryloyl-5-methylpyrrolidin-3-yl, 1-acryloyl-3-methylpiperidin-4-yl, 1-acryloylazepan-3-yl, 1-acryloyl-2,2-dimethylpiperidin-4-yl, 4-acryloyl-4-azaspiro[2.5]octan-7-yl, 8-acryloyl-8-azabicyclo[3.2.1]octan-3-yl, 1-acryloyloctahydrocyclopenta[b]pyrrol-4-yl, 2-acryloyloctahydrocyclopenta[c]pyrrol-5-yl, 1-acryloyl-6,6-dimethylazepan-4-yl, N-acrylamide, N-but-2-ynamide, N-ethenesulfonamide, N-methyl-N-ethenesulfonamide, N-methyl-N-acrylamide, 9-acryloyl-3-oxa-9-azabicyclo[3.3.1]nonan-7-yl, 4-acryloyl-3-cyclopropylpiperazin-1-yl, 4-acryloyl-3-ethylpiperazin-1-yl, 1-acryloyl-2,6-dimethylpiperidin-4-yl, 4-(but-2-ynoyl)-3-(difluoromethyl)piperazin-1-yl, 1-acryloyl-6-methylpiperidin-3-yl, 5-acryloyl-2,5-diazabicyclo[2.2.2]octan-2-yl, 2-(but-2-ynoyl)-2,6-diazabicyclo[3.2.1]octan-6-yl, 4-(but-2-ynoyl)-3-methylpiperazin-1-yl, 4-(but-2-ynoyl)-3,3-dimethylpiperazin-1-yl, 4-(but-2-ynoyl)-3-(methoxymethyl)piperazin-1-yl, 4-(but-2-ynoyl)-4,7-diazaspiro[2.5]octan-7-yl, 4-(but-2-ynoyl)-3-(trifluoromethyl)piperazin-1-yl, 4-(2-fluoroacryloyl)piperazin-1-yl, 4-(bicyclo[1.1.0]butane-1-carbonyl)-3,3-dimethylpiperazin-1-yl, 4-(2-fluoroacryloyl)-3,3-dimethylpiperazin-1-yl, 1-(but-2-ynoyl)-1,6-diazaspiro[3.3]heptan-6-yl, 4-acryloyl-4-azaspiro[2.5]octan-6-yl, 2-acryloyl-2-azabicyclo[2.2.1]heptan-5-yl, 2-acryloyl-2-azabicyclo[2.2.1]heptan-6-yl, 8-(2-fluoroacryloyl)-8-azabicyclo[3.2.1]octan-3-yl, 8-(but-2-ynoyl)-8-azabicyclo[3.2.1]octan-3-yl, 1-(but-2-ynoyl)azepan-4-yl, 7-acryloyl-7-azabicyclo[2.2.1]heptan-2-yl, 2-acryloyl-2-azabicyclo[2.2.2]octan-5-yl, 3-acryloyl-3-azabicyclo[3.2.1]octan-8-yl, 8-acryloyl-3,8-diazabicyclo[3.2.1]octan-3-yl, 8-(but-2-ynoyl)-3,8-diazabicyclo[3.2.1]octan-3-yl, 3-acryloyl-3,8-diazabicyclo[3.2.1]octan-8-yl, 4-cyano-3,3-dimethylpiperazin-1-yl, 3-(but-2-ynoyl)-3,8-diazabicyclo[3.2.1]octan-8-yl, 4-acryloyl-3-isopropylpiperazin-1-yl, 1-acryloyl-1,6-diazaspiro[3.3]heptan-6-yl, 1-acryloylazetidin-3-yl, 4-acryloyl-4,7-diazaspiro[2.5]octan-7-yl, 6-acryloyl-1,6-diazaspiro[3.3]heptan-1-yl, 4-acryloyl-3-(tert-butyl)piperazin-1-yl, 1-acryloyl-5,5-dimethylpyrrolidin-3-yl, 4-acryloyl-3-(difluoromethyl)piperazin-1-yl, (1-acryloylazetidin-3-yl)methyl, 1-(1-acryloylazetidin-3-yl)ethyl, 1-acryloyl-5-cyclopropylpyrrolidin-3-yl, 4-acryloyl-3-cyclobutylpiperazin-1-yl, 1-acryloyl-5-(methoxymethyl)pyrrolidin-3-yl, 2-acryloyl-2,6-diazaspiro[3.4]octan-6-yl, 5-acryloyl-5,8-diazaspiro[3.5]nonan-8-yl, 5-(but-2-ynoyl)-2,5-diazabicyclo[2.2.1]heptan-2-yl, 4-acryloyl-3-ethynylpiperazin-1-yl, 6-acryloyl-3,6-diazabicyclo[3.2.2]nonan-3-yl, 4-methacryloyl-3,3-dimethylpiperazin-1-yl, 4-acryloyl-3-(methoxymethyl)piperazin-1-yl, N-(1-pyrrolidin-3-yl)-N-methylacrylamide, 4-methacryloylpiperazin-1-yl, 6-acryloyl-6-azabicyclo[3.2.1]octan-2-yl, 6-acryloyl-6-azabicyclo[3.2.1]octan-3-yl, 2-acryloyl-2-azabicyclo[2.2.2]octan-6-yl, 2-acryloyloctahydrocyclopenta[c]pyrrol-4-yl, 8-acryloyl-8-azabicyclo[3.2.1]octan-6-yl, and 8-acryloyl-8-azabicyclo[3.2.1]octan-2-yl.

In a preferred embodiment of Formula (I), $R^1$ is selected from the group consisting of -$L^1$-$R^5$ and —$NR^6R^7$. In one embodiment of Formula (I), $R^1$ is selected from the group consisting of 1-acryloylpiperidin-4-olate, 6-acryloyl-3,6-diazabicyclo[3.1.1]heptan-3-yl, 1-acryloylhexahydropyrrolo[3,4-b]pyrrol-5(1H)-yl, 1-(bicyclo[1.1.0]butane-1-carbonyl)hexahydropyrrolo[3,4-b]pyrrol-5(1H)-yl, (1-acryloylpiperidin-4-yl)thio, 2-acryloyl-2,6-diazabicyclo[3.2.1]octan-6-yl, 4-acryloylpiperazin-1-yl, 4-acryloyl-3,3-dimethylpiperazin-1-yl, (1-acryloylpiperidin-4-yl)(methyl)amino, 1-acryloylpiperidin-3-yl, 1-acryloyl-6,6-dimethylpiperidin-3-yl, 1-acryloyloctahydrocyclopenta[b]pyrrol-5-yl, 1-acryloylpiperidin-4-yl, 3-acryloyl-3,6-diazabicyclo[3.1.1]heptan-6-yl, (1-acryloylazetidin-3-yl)thio, 4-acryloyl-5,5-dimethyl-1,4-diazepan-1-yl, 4-acryloyl-3,3-dimethyl-1,4-diazepan-1-yl, 5-acryloyl-2,5-diazabicyclo[2.2.1]heptan-2-yl, 4-acryloyl-3-(trifluoromethyl)piperazin-1-yl, 4-acryloyl-3-methylpiperazin-1-yl, 4-acryloyl-1,4-diazepan-1-yl, 6-acryloyl-2,6-diazaspiro[3.3]heptan-2-yl, 6-acryloyl-3,6-diazabicyclo[3.2.1]octan-3-yl, 4-acryloyl-3,5-dimethylpiperazin-1-yl, 6-acryloyl-3,6-diazabicyclo[3.2.0]heptan-3-yl, 1-acryloylpyrrolidin-3-yl, 1-acryloylazepan-4-yl, 1-acryloyl-2-methylpiperidin-4-yl, 1-acryloyl-5-methylpyrrolidin-3-yl, 1-acryloyl-3-methylpiperidin-4-yl, 1-acryloylazepan-3-yl, 1-acryloyl-2,2-dimethylpiperidin-4-yl, 4-acryloyl-4-azaspiro[2.5]octan-7-yl, 8-acryloyl-8-azabicyclo[3.2.1]octan-3-yl, 1-acryloyloctahydrocyclopenta[b]pyrrol-4-yl, 2-acryloyloctahydrocyclopenta[c]pyrrol-5-yl, 1-acryloyl-6,6-dimethylazepan-4-yl, N-acrylamide, N-but-2-ynamide, N-ethenesulfonamide, N-methyl-N-ethenesulfonamide, and N-methyl-N-acrylamide.

In a further preferred embodiment of Formula (I), $R^1$ is $-L^1-R^5$. In one embodiment of Formula (I), $R^1$ is selected from the group consisting of 1-acryloylpiperidin-4-olate, 6-acryloyl-3,6-diazabicyclo[3.1.1]heptan-3-yl, 1-acryloylhexahydropyrrolo[3,4-b]pyrrol-5(1)-yl, 1-(bicyclo[1.1.0]butane-1-carbonyl)hexahydropyrrolo[3,4-b]pyrrol-5(1)-yl, (1-acryloylpiperidin-4-yl)thio, 2-acryloyl-2,6-diazabicyclo[3.2.1]octan-6-yl, 4-acryloylpiperazin-1-yl, 4-acryloyl-3,3-dimethylpiperazin-1-yl, (1-acryloylpiperidin-4-yl)(methyl)amino, 1-acryloylpiperidin-3-yl, 1-acryloyl-6,6-dimethylpiperidin-3-yl, 1-acryloyloctahydrocyclopenta[b]pyrrol-5-yl, 1-acryloylpiperidin-4-yl, 3-acryloyl-3,6-diazabicyclo[3.1.1]heptan-6-yl, (1-acryloylazetidin-3-yl)thio, 4-acryloyl-5,5-dimethyl-1,4-diazepan-1-yl, 4-acryloyl-3,3-dimethyl-1,4-diazepan-1-yl, 5-acryloyl-2,5-diazabicyclo[2.2.1]heptan-2-yl, 4-acryloyl-3-(trifluoromethyl)piperazin-1-yl, 4-acryloyl-3-methylpiperazin-1-yl, 4-acryloyl-1,4-diazepan-1-yl, 6-acryloyl-2,6-diazaspiro[3.3]heptan-2-yl, 6-acryloyl-3,6-diazabicyclo[3.2.1]octan-3-yl, 4-acryloyl-3,5-dimethylpiperazin-1-yl, 6-acryloyl-3,6-diazabicyclo[3.2.0]heptan-3-yl, 1-acryloylpyrrolidin-3-yl, 1-acryloylazepan-4-yl, 1-acryloyl-2-methylpiperidin-4-yl, 1-acryloyl-5-methylpyrrolidin-3-yl, 1-acryloyl-3-methylpiperidin-4-yl, 1-acryloylazepan-3-yl, 1-acryloyl-2,2-dimethylpiperidin-4-yl, 4-acryloyl-4-azaspiro[2.5]octan-7-yl, 8-acryloyl-8-azabicyclo[3.2.1]octan-3-yl, 1-acryloyloctahydrocyclopenta[b]pyrrol-4-yl, 2-acryloyloctahydrocyclopenta[c]pyrrol-5-yl, 1-acryloyl-6,6-dimethylazepan-4-yl, 9-acryloyl-3-oxa-9-azabicyclo[3.3.1]nonan-7-yl, 4-acryloyl-3-cyclopropylpiperazin-1-yl, 4-acryloyl-3-ethylpiperazin-1-yl, 1-acryloyl-2,6-dimethylpiperidin-4-yl, 4-(but-2-ynoyl)-3-(difluoromethyl)piperazin-1-yl, 1-acryloyl-6-methylpiperidin-3-yl, 5-acryloyl-2,5-diazabicyclo[2.2.2]octan-2-yl, 2-(but-2-ynoyl)-2,6-diazabicyclo[3.2.1]octan-6-yl, 4-(but-2-ynoyl)-3-methylpiperazin-1-yl, 4-(but-2-ynoyl)-3,3-dimethylpiperazin-1-yl, 4-(but-2-ynoyl)-3-(methoxymethyl)piperazin-1-yl, 4-(but-2-ynoyl)-4,7-diazaspiro[2.5]octan-7-yl, 4-(but-2-ynoyl)-3-(trifluoromethyl)piperazin-1-yl, 4-(2-fluoroacryloyl)piperazin-1-yl, 4-(bicyclo[1.1.0]butane-1-carbonyl)-3,3-dimethylpiperazin-1-yl, 4-(2-fluoroacryloyl)-3,3-dimethylpiperazin-1-yl, 1-(but-2-ynoyl)-1,6-diazaspiro[3.3]heptan-6-yl, 4-acryloyl-4-azaspiro[2.5]octan-6-yl, 2-acryloyl-2-azabicyclo[2.2.1]heptan-5-yl, 2-acryloyl-2-azabicyclo[2.2.1]heptan-6-yl, 8-(2-fluoroacryloyl)-8-azabicyclo[3.2.1]octan-3-yl, 8-(but-2-ynoyl)-8-azabicyclo[3.2.1]octan-3-yl, 1-(but-2-ynoyl)azepan-4-yl, 7-acryloyl-7-azabicyclo[2.2.1]heptan-2-yl, 2-acryloyl-2-azabicyclo[2.2.2]octan-5-yl, 3-acryloyl-3-azabicyclo[3.2.1]octan-8-yl, 8-acryloyl-3,8-diazabicyclo[3.2.1]octan-3-yl, 8-(but-2-ynoyl)-3,8-diazabicyclo[3.2.1]octan-3-yl, 3-acryloyl-3,8-diazabicyclo[3.2.1]octan-8-yl, 4-cyano-3,3-dimethylpiperazin-1-yl, 3-(but-2-ynoyl)-3,8-diazabicyclo[3.2.1]octan-8-yl, 4-acryloyl-3-isopropylpiperazin-1-yl, 1-acryloyl-1,6-diazaspiro[3.3]heptan-6-yl, 1-acryloylazetidin-3-yl, 4-acryloyl-4,7-diazaspiro[2.5]octan-7-yl, 6-acryloyl-1,6-diazaspiro[3.3]heptan-1-yl, 4-acryloyl-3-(tert-butyl)piperazin-1-yl, 1-acryloyl-5,5-dimethylpyrrolidin-3-yl, 4-acryloyl-3-(difluoromethyl)piperazin-1-yl, (1-acryloylazetidin-3-yl)methyl, 1-(1-acryloylazetidin-3-yl)ethyl, 1-acryloyl-5-cyclopropylpyrrolidin-3-yl, 4-acryloyl-3-cyclobutylpiperazin-1-yl, 1-acryloyl-5-(methoxymethyl)pyrrolidin-3-yl, 2-acryloyl-2,6-diazaspiro[3.4]octan-6-yl, 5-acryloyl-5,8-diazaspiro[3.5]nonan-8-yl, 5-(but-2-ynoyl)-2,5-diazabicyclo[2.2.1]heptan-2-yl, 4-acryloyl-3-ethynylpiperazin-1-yl, 6-acryloyl-3,6-diazabicyclo[3.2.2]nonan-3-yl, 4-methacryloyl-3,3-dimethylpiperazin-1-yl, 4-acryloyl-3-(methoxymethyl)piperazin-1-yl, N-(1-pyrrolidin-3-yl)-N-methylacrylamide, 4-methacryloylpiperazin-1-yl, 6-acryloyl-6-azabicyclo[3.2.1]octan-2-yl, 6-acryloyl-6-azabicyclo[3.2.1]octan-3-yl, 2-acryloyl-2-azabicyclo[2.2.2]octan-6-yl, 2-acryloyloctahydrocyclopenta[c]pyrrol-4-yl, 8-acryloyl-8-azabicyclo[3.2.1]octan-6-yl, and 8-acryloyl-8-azabicyclo[3.2.1]octan-2-yl. In a further preferred embodiment of Formula (I), $R^1$ is $-L^1-R^5$. In one embodiment of Formula (I), $R^1$ is selected from the group consisting of 1-acryloylpiperidin-4-olate, 6-acryloyl-3,6-diazabicyclo[3.1.1]heptan-3-yl, 1-acryloylhexahydropyrrolo[3,4-b]pyrrol-5(1H)-yl, 1-(bicyclo[1.1.0]butane-1-carbonyl)hexahydropyrrolo[3,4-b]pyrrol-5(1H)-yl, (1-acryloylpiperidin-4-yl)thio, 2-acryloyl-2,6-diazabicyclo[3.2.1]octan-6-yl, 4-acryloylpiperazin-1-yl, 4-acryloyl-3,3-dimethylpiperazin-1-yl, (1-acryloylpiperidin-4-yl)(methyl)amino, 1-acryloylpiperidin-3-yl, 1-acryloyl-6,6-dimethylpiperidin-3-yl, 1-acryloyloctahydrocyclopenta[b]pyrrol-5-yl, 1-acryloylpiperidin-4-yl, 3-acryloyl-3,6-diazabicyclo[3.1.1]heptan-6-yl, (1-acryloylazetidin-3-yl)thio, 4-acryloyl-5,5-dimethyl-1,4-diazepan-1-yl, 4-acryloyl-3,3-dimethyl-1,4-diazepan-1-yl, 5-acryloyl-2,5-diazabicyclo[2.2.1]heptan-2-yl, 4-acryloyl-3-(trifluoromethyl)piperazin-1-yl, 4-acryloyl-3-methylpiperazin-1-yl, 4-acryloyl-1,4-diazepan-1-yl, 6-acryloyl-2,6-diazaspiro[3.3]heptan-2-yl, 6-acryloyl-3,6-diazabicyclo[3.2.1]octan-3-yl, 4-acryloyl-3,5-dimethylpiperazin-1-yl, 6-acryloyl-3,6-diazabicyclo[3.2.0]heptan-3-yl, 1-acryloylpyrrolidin-3-yl, 1-acryloylazepan-4-yl, 1-acryloyl-2-methylpiperidin-4-yl, 1-acryloyl-5-methylpyrrolidin-3-yl, 1-acryloyl-3-methylpiperidin-4-yl, 1-acryloylazepan-3-yl, 1-acryloyl-2,2-dimethylpiperidin-4-yl, 4-acryloyl-4-azaspiro[2.5]octan-7-yl, 8-acryloyl-8-azabicyclo[3.2.1]octan-3-yl, 1-acryloyloctahydrocyclopenta[b]pyrrol-4-yl, 2-acryloyloctahydrocyclopenta[c]pyrrol-5-yl, and 1-acryloyl-6,6-dimethylazepan-4-yl.

In one embodiment of Formula (I), $R^1$ is selected from the group consisting of $-L^1-R^5$, $—NR^6R^7$, N-methyl-3-acrylamide, and prop-1-en-2-yl, wherein $R^1$ is not 1-acryloylpiperidin-4-olate.

In one embodiment of Formula (I), $R^1$ is selected from the group consisting of 6-acryloyl-3,6-diazabicyclo[3.1.1]heptan-3-yl, 1-acryloylhexahydropyrrolo[3,4-b]pyrrol-5(1)-yl, 1-(bicyclo[1.1.0]butane-1-carbonyl)hexahydropyrrolo[3,4-b]pyrrol-5(1H)-yl, (1-acryloylpiperidin-4-yl)thio, 2-acryloyl-2,6-diazabicyclo[3.2.1]octan-6-yl, 4-acryloylpiperazin-1-yl, 4-acryloyl-3,3-dimethylpiperazin-1-yl, (1-acryloylpiperidin-4-yl)(methyl)amino, 1-acryloylpiperidin-3-yl, 1-acryloyl-6,6-dimethylpiperidin-3-yl, 1-acryloyloctahydrocyclopenta[b]pyrrol-5-yl, 1-acryloylpiperidin-4-yl, 3-acryloyl-3,6-diazabicyclo[3.1.1]heptan-6-yl, (1-acryloylazetidin-3-yl)thio, 4-acryloyl-5,5-dimethyl-1,4-diazepan-1-yl, 4-acryloyl-3,3-dimethyl-1,4-diazepan-1-yl, 5-acryloyl-2,5-diazabicyclo[2.2.1]heptan-2-yl, 4-acryloyl-3-(trifluoromethyl)piperazin-1-yl, 4-acryloyl-3-methylpiperazin-1-yl, 4-acryloyl-1,4-diazepan-1-yl, 6-acryloyl-2,6-diazaspiro[3.3]heptan-2-yl, 6-acryloyl-3,6-diazabicyclo[3.2.1]octan-3-yl, 4-acryloyl-3,5-dimethylpiperazin-1-yl, 6-acryloyl-3,6-diazabicyclo[3.2.0]heptan-3-yl, 1-acryloylpyrrolidin-3-yl, 1-acryloylazepan-4-yl, 1-acryloyl-2-methylpiperidin-4-yl, 1-acryloyl-5-methylpyrrolidin-3-yl, 1-acryloyl-3-methylpiperidin-4-yl, 1-acryloylazepan-3-yl, 1-acryloyl-2,2-dimethylpiperidin-4-yl, 4-acryloyl-4-azaspiro[2.5]octan-7-yl, 8-acryloyl-8-azabicyclo[3.2.1]octan-3-yl, 1-acryloyloctahydrocyclopenta[b]pyrrol-4-yl, 2-acryloyloctahydrocyclopenta[c]pyrrol-5-yl, 1-acryloyl-6,6-dimethylazepan-4-yl, N-acrylamide, N-but-2-ynamide, N-ethenesulfonamide, N-methyl-N-ethenesulfonamide, N-methyl-3-acrylamide, N-methyl-N-acrylamide, prop-2-en-1-one, 9-acryloyl-3-oxa-9-azabicyclo[3.3.1]nonan-7-yl, 4-acryloyl-3-cyclopropylpiperazin-1-yl, 4-acryloyl-3-ethylpiperazin-1-yl, 1-acryloyl-2,6-dimethylpiperidin-4-yl, 4-(but-2-ynoyl)-3-(difluoromethyl)piperazin-1-yl, 1-acryloyl-6-methylpiperidin-3-yl, 5-acryloyl-2,5-diazabicyclo[2.2.2]octan-2-yl, 2-(but-2-ynoyl)-2,6-diazabicyclo[3.2.1]octan-6-yl, 4-(but-2-ynoyl)-3-methylpiperazin-1-yl, 4-(but-2-ynoyl)-3,3-dimethylpiperazin-1-yl, 4-(but-2-ynoyl)-3-(methoxymethyl)piperazin-1-yl, 4-(but-2-ynoyl)-4,7-diazaspiro[2.5]octan-7-yl, 4-(but-2-ynoyl)-3-(trifluoromethyl)piperazin-1-yl, 4-(2-fluoroacryloyl)piperazin-1-yl, 4-(bicyclo[1.1.0]butane-1-carbonyl)-3,3-dimethylpiperazin-1-yl, 4-(2-fluoroacryloyl)-3,3-dimethylpiperazin-1-yl, 1-(but-2-ynoyl)-1,6-diazaspiro[3.3]heptan-6-yl, 4-acryloyl-4-azaspiro[2.5]octan-6-yl, 2-acryloyl-2-azabicyclo[2.2.1]heptan-5-yl, 2-acryloyl-2-azabicyclo[2.2.1]heptan-6-yl, 8-(2-fluoroacryloyl)-8-azabicyclo[3.2.1]octan-3-yl, 8-(but-2-ynoyl)-8-azabicyclo[3.2.1]octan-3-yl, 1-(but-2-ynoyl)azepan-4-yl, 7-acryloyl-7-azabicyclo[2.2.1]heptan-2-yl, 2-acryloyl-2-azabicyclo[2.2.2]octan-5-yl, 3-acryloyl-3-azabicyclo[3.2.1]octan-8-yl, 8-acryloyl-3,8-diazabicyclo[3.2.1]octan-3-yl, 8-(but-2-ynoyl)-3,8-diazabicyclo[3.2.1]octan-3-yl, 3-acryloyl-3,8-diazabicyclo[3.2.1]octan-8-yl, 4-cyano-3,3-dimethylpiperazin-1-yl, 3-(but-2-ynoyl)-3,8-diazabicyclo[3.2.1]octan-8-yl, 4-acryloyl-3-isopropylpiperazin-1-yl, 1-acryloyl-1,6-diazaspiro[3.3]heptan-6-yl, 1-acryloylazetidin-3-yl, 4-acryloyl-4,7-diazaspiro[2.5]octan-7-yl, 6-acryloyl-1,6-diazaspiro[3.3]heptan-1-yl, 4-acryloyl-3-(tert-butyl)piperazin-1-yl, 1-acryloyl-5,5-dimethylpyrrolidin-3-yl, 4-acryloyl-3-(difluoromethyl)piperazin-1-yl, (1-acryloylazetidin-3-yl)methyl, 1-(1-acryloylazetidin-3-yl)ethyl, 1-acryloyl-5-cyclopropylpyrrolidin-3-yl, 4-acryloyl-3-cyclobutylpiperazin-1-yl, 1-acryloyl-5-(methoxymethyl)pyrrolidin-3-yl, 2-acryloyl-2,6-diazaspiro[3.4]octan-6-yl, 5-acryloyl-5,8-diazaspiro[3.5]nonan-8-yl, 5-(but-2-ynoyl)-2,5-diazabicyclo[2.2.1]heptan-2-yl, 4-acryloyl-3-ethynylpiperazin-1-yl, 6-acryloyl-3,6-diazabicyclo[3.2.2]nonan-3-yl, 4-methacryloyl-3,3-dimethylpiperazin-1-yl, 4-acryloyl-3-(methoxymethyl)piperazin-1-yl, N-(1-pyrrolidin-3-yl)-N-methylacrylamide, 4-methacryloylpiperazin-1-yl, 6-acryloyl-6-azabicyclo[3.2.1]octan-2-yl, 6-acryloyl-6-azabicyclo[3.2.1]octan-3-yl, 2-acryloyl-2-azabicyclo[2.2.2]octan-6-yl, 2-acryloyloctahydrocyclopenta[c]pyrrol-4-yl, 8-acryloyl-8-azabicyclo[3.2.1]octan-6-yl, and 8-acryloyl-8-azabicyclo[3.2.1]octan-2-yl.

In one embodiment of Formula (I), $R^1$ is selected from the group consisting of $-L^1-R^5$, $—NR^6R^7$, N-methyl-3-acrylamide, and prop-1-en-2-yl, wherein $R^1$ is not 1-acryloylpiperidin-4-olate. In one embodiment of Formula (I), $R^1$ is selected from the group consisting of 6-acryloyl-3,6-diazabicyclo[3.1.1]heptan-3-yl, 1-acryloylhexahydropyrrolo[3,4-b]pyrrol-5(1)-yl, 1-(bicyclo[1.1.0]butane-1-carbonyl)hexahydropyrrolo[3,4-b]pyrrol-5(1)-yl, (1-acryloylpiperidin-4-yl)thio, 2-acryloyl-2,6-diazabicyclo[3.2.1]octan-6-yl, 4-acryloylpiperazin-1-yl, 4-acryloyl-3,3-dimethylpiperazin-1-yl, (1-acryloylpiperidin-4-yl)(methyl)amino, 1-acryloylpiperidin-3-yl, 1-acryloyl-6,6-dimethylpiperidin-3-yl, 1-acryloyloctahydrocyclopenta[b]pyrrol-5-yl, 1-acryloylpiperidin-4-yl, 3-acryloyl-3,6-diazabicyclo[3.1.1]heptan-6-yl, (1-acryloylazetidin-3-yl)thio, 4-acryloyl-5,5-dimethyl-1,4-diazepan-1-yl, 4-acryloyl-3,3-dimethyl-1,4-diazepan-1-yl, 5-acryloyl-2,5-diazabicyclo[2.2.1]heptan-2-yl, 4-acryloyl-3-(trifluoromethyl)piperazin-1-yl, 4-acryloyl-3-methylpiperazin-1-yl, 4-acryloyl-1,4-diazepan-1-yl, 6-acryloyl-2,6-diazaspiro[3.3]heptan-2-yl, 6-acryloyl-3,6-diazabicyclo[3.2.1]octan-3-yl, 4-acryloyl-3,5-dimethylpiperazin-1-yl, 6-acryloyl-3,6-diazabicyclo[3.2.0]heptan-3-yl, 1-acryloylpyrrolidin-3-yl, 1-acryloylazepan-4-yl, 1-acryloyl-2-methylpiperidin-4-yl, 1-acryloyl-5-methylpyrrolidin-3-yl, 1-acryloyl-3-methylpiperidin-4-yl, 1-acryloylazepan-3-yl, 1-acryloyl-2,2-dimethylpiperidin-4-yl, 4-acryloyl-4-azaspiro[2.5]octan-7-yl, 8-acryloyl-8-azabicyclo[3.2.1]octan-3-yl, 1-acryloyloctahydrocyclopenta[b]pyrrol-4-yl, 2-acryloyloctahydrocyclopenta[c]pyrrol-5-yl, 1-acryloyl-6,6-dimethylazepan-4-yl, N-acrylamide, N-but-2-ynamide, N-ethenesulfonamide, N-methyl-N-ethenesulfonamide, N-methyl-3-acrylamide, N-methyl-N-acrylamide, and prop-2-en-1-one.

In one embodiment of Formula (I), $R^1$ is selected from the group consisting of $-L^1-R^5$, $—NR^6R^7$, N-methyl-3-acrylamide, and prop-1-en-2-yl, wherein $R^1$ is not 4-acryloylpiperazin-1-yl. In one embodiment of Formula (I), $R^1$ is selected from the group consisting of 1-acryloylpiperidin-4-olate, 6-acryloyl-3,6-diazabicyclo[3.1.1]heptan-3-yl, 1-acryloylhexahydropyrrolo[3,4-b]pyrrol-5(1H)-yl, 1-(bicyclo[1.1.0]butane-1-carbonyl)hexahydropyrrolo[3,4-b]pyrrol-5(1H)-yl, (1-acryloylpiperidin-4-yl)thio, 2-acryloyl-2,6-diazabicyclo[3.2.1]octan-6-yl, 4-acryloyl-3,3-dimethylpiperazin-1-yl, (1-acryloylpiperidin-4-yl)(methyl)amino, 1-acryloylpiperidin-3-yl, 1-acryloyl-6,6-dimethylpiperidin-3-yl, 1-acryloyloctahydrocyclopenta[b]pyrrol-5-yl, 1-acryloylpiperidin-4-yl, 3-acryloyl-3,6-diazabicyclo[3.1.1]heptan-6-yl, (1-acryloylazetidin-3-yl)thio, 4-acryloyl-5,5-dimethyl-1,4-diazepan-1-yl, 4-acryloyl-3,3-dimethyl-1,4-diazepan-1-yl, 5-acryloyl-2,5-diazabicyclo[2.2.1]heptan-2-yl, 4-acryloyl-3-(trifluoromethyl)piperazin-1-yl, 4-acryloyl-3-methylpiperazin-1-yl, 4-acryloyl-1,4-diazepan-1-yl, 6-acryloyl-2,6-diazaspiro[3.3]heptan-2-yl, 6-acryloyl-3,6-diazabicyclo[3.2.1]octan-3-yl, 4-acryloyl-3,5-dimethylpiperazin-1-yl, 6-acryloyl-3,6-diazabicyclo[3.2.0]heptan-3-yl, 1-acryloylpyrrolidin-3-yl, 1-acryloylazepan-4-yl, 1-acryloyl-2-methylpiperidin-4-yl, 1-acryloyl-5-methylpyrrolidin-3-yl, 1-acryloyl-3-methylpiperidin-4-yl, 1-acryloylazepan-3-yl, 1-acryloyl-2,2-dimethylpiperidin-4-yl, 4-acryloyl-4-azaspiro[2.5]octan-7-yl, 8-acryloyl-8-azabicyclo[3.2.1]octan-3-yl, 1-acryloyloctahydrocyclopenta[b]pyrrol-4-yl, 2-acryloyloctahydrocyclopenta[c]pyrrol-5-yl, 1-acryloyl-6,6-dimethylazepan-4-yl, N-acrylamide, N-but-2-ynamide, N-ethenesulfonamide, N-methyl-N-ethenesulfonamide, N-methyl-3-acrylamide, N-methyl-N-acrylamide, prop-2-en-1-one, 9-acryloyl-3-oxa-9-azabicyclo[3.3.1]nonan-7-yl, 4-acryloyl-3-cyclopropylpiperazin-1-yl, 4-acryloyl-3-ethylpiperazin-1-yl, 1-acryloyl-2,6-dimethylpiperidin-4-yl, 4-(but-2-ynoyl)-3-(difluoromethyl)piperazin-1-yl, 1-acryloyl-6-methylpiperidin-3-yl, 5-acryloyl-2,5-diazabicyclo[2.2.2]octan-2-yl, 2-(but-2-ynoyl)-2,6-diazabicyclo[3.2.1]octan-6-yl, 4-(but-2-ynoyl)-3-methylpiperazin-1-yl, 4-(but-2-ynoyl)-3,3-dimethylpiperazin-1-yl, 4-(but-2-ynoyl)-3-(methoxymethyl)piperazin-1-yl, 4-(but-2-ynoyl)-4,7-diazaspiro[2.5]octan-7-yl, 4-(but-2-ynoyl)-3-(trifluoromethyl)piperazin-1-yl, 4-(2-fluoroacryloyl)piperazin-1-yl, 4-(bicyclo[1.1.0]butane-1-carbonyl)-3,3-dimethylpiperazin-1-yl, 4-(2-fluoroacryloyl)-3,3-dimethylpiperazin-1-yl, 1-(but-2-ynoyl)-1,6-diazaspiro[3.3]heptan-6-yl, 4-acryloyl-4-azaspiro[2.5]octan-6-yl, 2-acryloyl-2-azabicyclo[2.2.1]heptan-5-yl, 2-acryloyl-2-azabicyclo[2.2.1]heptan-6-yl, 8-(2-fluoroacryloyl)-8-azabicyclo[3.2.1]octan-3-yl, 8-(but-2-ynoyl)-8-azabicyclo[3.2.1]octan-3-yl, 1-(but-2-ynoyl)azepan-4-yl, 7-acryloyl-7-azabicyclo[2.2.1]heptan-2-yl, 2-acryloyl-2-azabicyclo[2.2.2]octan-5-yl, 3-acryloyl-3-azabicyclo[3.2.1]octan-8-yl, 8-acryloyl-3,8-diazabicyclo[3.2.1]octan-3-yl, 8-(but-2-ynoyl)-3,8-diazabicyclo[3.2.1]octan-3-yl, 3-acryloyl-3,8-diazabicyclo[3.2.1]octan-8-yl, 4-cyano-3,3-dimethylpiperazin-1-yl, 3-(but-2-ynoyl)-3,8-diazabicyclo[3.2.1]octan-8-yl, 4-acryloyl-3-isopropylpiperazin-1-yl, 1-acryloyl-1,6-diazaspiro[3.3]heptan-6-yl, 1-acryloylazetidin-3-yl, 4-acryloyl-4,7-diazaspiro[2.5]octan-7-yl, 6-acryloyl-1,6-diazaspiro[3.3]heptan-1-yl, 4-acryloyl-3-(tert-butyl)piperazin-1-yl, 1-acryloyl-5,5-dimethylpyrrolidin-3-yl, 4-acryloyl-3-(difluoromethyl)piperazin-1-yl, (1-acryloylazetidin-3-yl)methyl, 1-(1-acryloylazetidin-3-yl)ethyl, 1-acryloyl-5-cyclopropylpyrrolidin-3-yl, 4-acryloyl-3-cyclobutylpiperazin-1-yl, 1-acryloyl-5-(methoxymethyl)pyrrolidin-3-yl, 2-acryloyl-2,6-diazaspiro[3.4]octan-6-yl, 5-acryloyl-5,8-diazaspiro[3.5]nonan-8-yl, 5-(but-2-ynoyl)-2,5-diazabicyclo[2.2.1]heptan-2-yl, 4-acryloyl-3-ethynylpiperazin-1-yl, 6-acryloyl-3,6-diazabicyclo[3.2.2]nonan-3-yl, 4-methacryloyl-3,3-dimethylpiperazin-1-yl, 4-acryloyl-3-(methoxymethyl)piperazin-1-yl, N-(1-pyrrolidin-3-yl)-N-methylacrylamide, 4-methacryloylpiperazin-1-yl, 6-acryloyl-6-azabicyclo[3.2.1]octan-2-yl, 6-acryloyl-6-azabicyclo[3.2.1]octan-3-yl, 2-acryloyl-2-azabicyclo[2.2.2]octan-6-yl, 2-acryloyloctahydrocyclopenta[c]pyrrol-4-yl, 8-acryloyl-8-azabicyclo[3.2.1]octan-6-yl, and 8-acryloyl-8-azabicyclo[3.2.1]octan-2-yl.

In one embodiment of Formula (I), $R^1$ is selected from the group consisting of -$L^1$-$R^5$, —$NR^6R^7$, N-methyl-3-acrylamide, and prop-1-en-2-yl, wherein $R^1$ is not 4-acryloylpiperazin-1-yl. In one embodiment of Formula (I), $R^1$ is selected from the group consisting of 1-acryloylpiperidin-4-olate, 6-acryloyl-3,6-diazabicyclo[3.1.1]heptan-3-yl, 1-acryloylhexahydropyrrolo[3,4-b]pyrrol-5(1H)-yl, 1-(bicyclo[1.1.0]butane-1-carbonyl)hexahydropyrrolo[3,4-b]pyrrol-5(1H)-yl, (1-acryloylpiperidin-4-yl)thio, 2-acryloyl-2,6-diazabicyclo[3.2.1]octan-6-yl, 4-acryloyl-3,3-dimethylpiperazin-1-yl, (1-acryloylpiperidin-4-yl)(methyl)amino, 1-acryloylpiperidin-3-yl, 1-acryloyl-6,6-dimethylpiperidin-3-yl, 1-acryloyloctahydrocyclopenta[b]pyrrol-5-yl, 1-acryloylpiperidin-4-yl, 3-acryloyl-3,6-diazabicyclo[3.1.1]heptan-6-yl, (1-acryloylazetidin-3-yl)thio, 4-acryloyl-5,5-dimethyl-1,4-diazepan-1-yl, 4-acryloyl-3,3-dimethyl-1,4-diazepan-1-yl, 5-acryloyl-2,5-diazabicyclo[2.2.1]heptan-2-yl, 4-acryloyl-3-(trifluoromethyl)piperazin-1-yl, 4-acryloyl-3-methylpiperazin-1-yl, 4-acryloyl-1,4-diazepan-1-yl, 6-acryloyl-2,6-diazaspiro[3.3]heptan-2-yl, 6-acryloyl-3,6-diazabicyclo[3.2.1]octan-3-yl, 4-acryloyl-3,5-dimethylpiperazin-1-yl, 6-acryloyl-3,6-diazabicyclo[3.2.0]heptan-3-yl, 1-acryloylpyrrolidin-3-yl, 1-acryloylazepan-4-yl, 1-acryloyl-2-methylpiperidin-4-yl, 1-acryloyl-5-methylpyrrolidin-3-yl, 1-acryloyl-3-methylpiperidin-4-yl, 1-acryloylazepan-3-yl, 1-acryloyl-2,2-dimethylpiperidin-4-yl, 4-acryloyl-4-azaspiro[2.5]octan-7-yl, 8-acryloyl-8-azabicyclo[3.2.1]octan-3-yl, 1-acryloyloctahydrocyclopenta[b]pyrrol-4-yl, 2-acryloyloctahydrocyclopenta[c]pyrrol-5-yl, 1-acryloyl-6,6-dimethylazepan-4-yl, N-acrylamide, N-but-2-ynamide, N-ethenesulfonamide, N-methyl-N-ethenesulfonamide, N-methyl-3-acrylamide, N-methyl-N-acrylamide, and prop-2-en-1-one.

In one embodiment of Formula (I), $R^1$ is selected from the group consisting of -$L^1$-$R^5$, —$NR^6R^7$, N-methyl-3-acrylamide, and prop-1-en-2-yl, wherein $R^1$ is not 1-acryloylpiperidin-4-olate or 4-acryloylpiperazin-1-yl. In one embodiment of Formula (I), $R^1$ is selected from the group consisting of 6-acryloyl-3,6-diazabicyclo[3.1.1]heptan-3-yl, 1-acryloylhexahydropyrrolo[3,4-b]pyrrol-5(1H)-yl, 1-(bicyclo[1.1.0]butane-1-carbonyl)hexahydropyrrolo[3,4-b]pyrrol-5(1)-yl, (1-acryloylpiperidin-4-yl)thio, 2-acryloyl-2,6-diazabicyclo[3.2.1]octan-6-yl, 4-acryloyl-3,3-dimethylpiperazin-1-yl, (1-acryloylpiperidin-4-yl)(methyl)amino, 1-acryloylpiperidin-3-yl, 1-acryloyl-6,6-dimethylpiperidin-3-yl, 1-acryloyloctahydrocyclopenta[b]pyrrol-5-yl, 1-acryloylpiperidin-4-yl, 3-acryloyl-3,6-diazabicyclo[3.1.1]heptan-6-yl, (1-acryloylazetidin-3-yl)thio, 4-acryloyl-5,5-dimethyl-1,4-diazepan-1-yl, 4-acryloyl-3,3-dimethyl-1,4-diazepan-1-yl, 5-acryloyl-2,5-diazabicyclo[2.2.1]heptan-2-yl, 4-acryloyl-3-(trifluoromethyl)piperazin-1-yl, 4-acryloyl-3-methylpiperazin-1-yl, 4-acryloyl-1,4-diazepan-1-yl, 6-acryloyl-2,6-diazaspiro[3.3]heptan-2-yl, 6-acryloyl-3,6-diazabicyclo[3.2.1]octan-3-yl, 4-acryloyl-3,5-dimethylpiperazin-1-yl, 6-acryloyl-3,6-diazabicyclo[3.2.0]heptan-3-yl, 1-acryloylpyrrolidin-3-yl, 1-acryloylazepan-4-yl, 1-acryloyl-2-methylpiperidin-4-yl, 1-acryloyl-5-methylpyrrolidin-3-yl, 1-acryloyl-3-methylpiperidin-4-yl, 1-acryloylazepan-3-yl, 1-acryloyl-2,2-dimethylpiperidin-4-yl, 4-acryloyl-4-azaspiro[2.5]octan-7-yl, 8-acryloyl-8-azabicyclo[3.2.1]octan-3-yl, 1-acryloyloctahydrocyclopenta[b]pyrrol-4-yl, 2-acryloyloctahydrocyclopenta[c]pyrrol-5-yl, 1-acryloyl-6,6-dimethylazepan-4-yl, N-acrylamide, N-but-2-ynamide, N-ethenesulfonamide, N-methyl-N-ethenesulfonamide, N-methyl-3-acrylamide, N-methyl-N-acrylamide, prop-2-en-1-one, 9-acryloyl-3-oxa-9-azabicyclo[3.3.1]nonan-7-yl, 4-acryloyl-3-cyclopropylpiperazin-1-yl, 4-acryloyl-3-ethylpiperazin-1-yl, 1-acryloyl-2,6-dimethylpiperidin-4-yl, 4-(but-2-ynoyl)-3-(difluoromethyl)piperazin-1-yl, 1-acryloyl-6-methylpiperidin-3-yl, 5-acryloyl-2,5-diazabicyclo[2.2.2]octan-2-yl, 2-(but-2-ynoyl)-2,6-diazabicyclo[3.2.1]octan-6-yl, 4-(but-2-ynoyl)-3-methylpiperazin-1-yl, 4-(but-2-ynoyl)-3,3-dimethylpiperazin-1-yl, 4-(but-2-ynoyl)-3-(methoxymethyl)piperazin-1-yl, 4-(but-2-ynoyl)-4,7-diazaspiro[2.5]octan-7-yl, 4-(but-2-ynoyl)-3-(trifluoromethyl)piperazin-1-yl, 4-(2-fluoroacryloyl)piperazin-1-yl, 4-(bicyclo[1.1.0]butane-1-carbonyl)-3,3-dimethylpiperazin-1-yl, 4-(2-fluoroacryloyl)-3,3-dimethylpiperazin-1-yl, 1-(but-2-ynoyl)-1,6-diazaspiro[3.3]heptan-6-yl, 4-acryloyl-4-azaspiro[2.5]octan-6-yl, 2-acryloyl-2-azabicyclo[2.2.1]heptan-5-yl, 2-acryloyl-2-azabicyclo[2.2.1]heptan-6-yl, 8-(2-fluoroacryloyl)-8-azabicyclo[3.2.1]octan-3-yl, 8-(but-2-ynoyl)-8-azabicyclo[3.2.1]octan-3-yl, 1-(but-2-ynoyl)azepan-4-yl, 7-acryloyl-7-azabicyclo[2.2.1]heptan-2-yl, 2-acryloyl-2-azabicyclo[2.2.2]octan-5-yl, 3-acryloyl-3-azabicyclo[3.2.1]octan-8-yl, 8-acryloyl-3,8-diazabicyclo[3.2.1]octan-3-yl, 8-(but-2-ynoyl)-3,8-diazabicyclo[3.2.1]octan-3-yl, 3-acryloyl-3,8-diazabicyclo[3.2.1]octan-8-yl, 4-cyano-3,3-dimethylpiperazin-1-yl, 3-(but-2-ynoyl)-3,8-diazabicyclo[3.2.1]octan-8-yl, 4-acryloyl-3-isopropylpiperazin-1-yl, 1-acryloyl-1,6-diazaspiro[3.3]heptan-6-yl, 1-acryloylazetidin-3-yl, 4-acryloyl-4,7-diazaspiro[2.5]octan-7-yl, 6-acryloyl-1,6-diazaspiro[3.3]heptan-1-yl, 4-acryloyl-3-(tert-butyl)piperazin-1-yl, 1-acryloyl-5,5-dimethylpyrrolidin-3-yl, 4-acryloyl-3-(difluoromethyl)piperazin-1-yl, (1-acryloylazetidin-3-yl)methyl, 1-(1-acryloylazetidin-3-yl)ethyl, 1-acryloyl-5-cyclopropylpyrrolidin-3-yl, 4-acryloyl-3-cyclobutylpiperazin-1-yl, 1-acryloyl-5-(methoxymethyl)pyrrolidin-3-yl, 2-acryloyl-2,6-diazaspiro[3.4]octan-6-yl, 5-acryloyl-5,8-diazaspiro[3.5]nonan-8-yl, 5-(but-2-ynoyl)-2,5-diazabicyclo[2.2.1]heptan-2-yl, 4-acryloyl-3-ethynylpiperazin-1-yl, 6-acryloyl-3,6-diazabicyclo[3.2.2]nonan-3-yl, 4-methacryloyl-3,3-dimethylpiperazin-1-yl, 4-acryloyl-3-(methoxymethyl)piperazin-1-yl, N-(1-pyrrolidin-3-yl)-N-methylacrylamide, 4-methacryloylpiperazin-1-yl, 6-acryloyl-6-azabicyclo[3.2.1]octan-2-yl, 6-acryloyl-6-azabicyclo[3.2.1]octan-3-yl, 2-acryloyl-2-azabicyclo[2.2.2]octan-6-yl, 2-acryloyloctahydrocyclopenta[c]pyrrol-4-yl, 8-acryloyl-8-azabicyclo[3.2.1]octan-6-yl, and 8-acryloyl-8-azabicyclo[3.2.1]octan-2-yl.

In one embodiment of Formula (I), $R^1$ is selected from the group consisting of $-L^1-R^5$, $—NR^6R^7$, N-methyl-3-acrylamide, and prop-1-en-2-yl, wherein $R^1$ is not 1-acryloylpiperidin-4-olate or 4-acryloylpiperazin-1-yl. In one embodiment of Formula (I), $R^1$ is selected from the group consisting of 6-acryloyl-3,6-diazabicyclo[3.1.1]heptan-3-yl, 1-acryloylhexahydropyrrolo[3,4-b]pyrrol-5(1H)-yl, 1-(bicyclo[1.1.0]butane-1-carbonyl)hexahydropyrrolo[3,4-b]pyrrol-5(1)-yl, (1-acryloylpiperidin-4-yl)thio, 2-acryloyl-2,6-diazabicyclo[3.2.1]octan-6-yl, 4-acryloyl-3,3-dimethylpiperazin-1-yl, (1-acryloylpiperidin-4-yl)(methyl)amino, 1-acryloylpiperidin-3-yl, 1-acryloyl-6,6-dimethylpiperidin-3-yl, 1-acryloyloctahydrocyclopenta[b]pyrrol-5-yl, 1-acryloylpiperidin-4-yl, 3-acryloyl-3,6-diazabicyclo[3.1.1]heptan-6-yl, (1-acryloylazetidin-3-yl)thio, 4-acryloyl-5,5-dimethyl-1,4-diazepan-1-yl, 4-acryloyl-3,3-dimethyl-1,4-diazepan-1-yl, 5-acryloyl-2,5-diazabicyclo[2.2.1]heptan-2-yl, 4-acryloyl-3-(trifluoromethyl)piperazin-1-yl, 4-acryloyl-3-methylpiperazin-1-yl, 4-acryloyl-1,4-diazepan-1-yl, 6-acryloyl-2,6-diazaspiro[3.3]heptan-2-yl, 6-acryloyl-3,6-diazabicyclo[3.2.1]octan-3-yl, 4-acryloyl-3,5-dimethylpiperazin-1-yl, 6-acryloyl-3,6-diazabicyclo[3.2.0]heptan-3-yl, 1-acryloylpyrrolidin-3-yl, 1-acryloylazepan-4-yl, 1-acryloyl-2-methylpiperidin-4-yl, 1-acryloyl-5-methylpyrrolidin-3-yl, 1-acryloyl-3-methylpiperidin-4-yl, 1-acryloylazepan-3-yl, 1-acryloyl-2,2-dimethylpiperidin-4-yl, 4-acryloyl-4-azaspiro[2.5]octan-7-yl, 8-acryloyl-8-azabicyclo[3.2.1]octan-3-yl, 1-acryloyloctahydrocyclopenta[b]pyrrol-4-yl, 2-acryloyloctahydrocyclopenta[c]pyrrol-5-yl, 1-acryloyl-6,6-dimethylazepan-4-yl, N-acrylamide, N-but-2-ynamide, N-ethenesulfonamide, N-methyl-N-ethenesulfonamide, N-methyl-3-acrylamide, N-methyl-N-acrylamide, and prop-2-en-1-one.

In one embodiment of Formula (I), $R^1$ is selected from the group consisting of $-L^1-R^5$, $—NR^6R^7$, N-methyl-3-acrylamide, and prop-1-en-2-yl, wherein $R^1$ is not 1-acryloylpiperidin-4-olate, 4-acryloylpiperazin-1-yl, or 1-acryloylpiperidin-4-yl. In one embodiment of Formula (I), $R^1$ is selected from the group consisting of 6-acryloyl-3,6-diazabicyclo[3.1.1]heptan-3-yl, 1-acryloylhexahydropyrrolo[3,4-b]pyrrol-5(1H)-yl, 1-(bicyclo[1.1.0]butane-1-carbonyl)hexahydropyrrolo[3,4-b]pyrrol-5(1H)-yl, (1-acryloylpiperidin-4-yl)thio, 2-acryloyl-2,6-diazabicyclo[3.2.1]octan-6-yl, 4-acryloyl-3,3-dimethylpiperazin-1-yl, (1-acryloylpiperidin-4-yl)(methyl)amino, 1-acryloylpiperidin-3-yl, 1-acryloyl-6,6-dimethylpiperidin-3-yl, 1-acryloyloctahydrocyclopenta[b]pyrrol-5-yl, 3-acryloyl-3,6-diazabicyclo[3.1.1]heptan-6-yl, (1-acryloylazetidin-3-yl)thio, 4-acryloyl-5,5-dimethyl-1,4-diazepan-1-yl, 4-acryloyl-3,3-dimethyl-1,4-diazepan-1-yl, 5-acryloyl-2,5-diazabicyclo[2.2.1]heptan-2-yl, 4-acryloyl-3-(trifluoromethyl)piperazin-1-yl, 4-acryloyl-3-methylpiperazin-1-yl, 4-acryloyl-1,4-diazepan-1-yl, 6-acryloyl-2,6-diazaspiro[3.3]heptan-2-yl, 6-acryloyl-3,6-diazabicyclo[3.2.1]octan-3-yl, 4-acryloyl-3,5-dimethylpiperazin-1-yl, 6-acryloyl-3,6-diazabicyclo[3.2.0]heptan-3-yl, 1-acryloylpyrrolidin-3-yl, 1-acryloylazepan-4-yl, 1-acryloyl-2-methylpiperidin-4-yl, 1-acryloyl-5-methylpyrrolidin-3-yl, 1-acryloyl-3-methylpiperidin-4-yl, 1-acryloylazepan-3-yl, 1-acryloyl-2,2-dimethylpiperidin-4-yl, 4-acryloyl-4-azaspiro[2.5]octan-7-yl, 8-acryloyl-8-azabicyclo[3.2.1]octan-3-yl, 1-acryloyloctahydrocyclopenta[b]pyrrol-4-yl, 2-acryloyloctahydrocyclopenta[c]pyrrol-5-yl, 1-acryloyl-6,6-dimethylazepan-4-yl, N-acrylamide, N-but-2-ynamide, N-ethenesulfonamide, N-methyl-N-ethenesulfonamide, N-methyl-3-acrylamide, N-methyl-N-acrylamide, prop-2-en-1-one, 9-acryloyl-3-oxa-9-azabicyclo[3.3.1]nonan-7-yl, 4-acryloyl-3-cyclopropylpiperazin-1-yl, 4-acryloyl-3-ethylpiperazin-1-yl, 1-acryloyl-2,6-dimethylpiperidin-4-yl, 4-(but-2-ynoyl)-3-(difluoromethyl)piperazin-1-yl, 1-acryloyl-6-methylpiperidin-3-yl, 5-acryloyl-2,5-diazabicyclo[2.2.2]octan-2-yl, 2-(but-2-ynoyl)-2,6-diazabicyclo[3.2.1]octan-6-yl, 4-(but-2-ynoyl)-3-methylpiperazin-1-yl, 4-(but-2-ynoyl)-3,3-dimethylpiperazin-1-yl, 4-(but-2-ynoyl)-3-(methoxymethyl)piperazin-1-yl, 4-(but-2-ynoyl)-4,7-diazaspiro[2.5]octan-7-yl, 4-(but-2-ynoyl)-3-(trifluoromethyl)piperazin-1-yl, 4-(2-fluoroacryloyl)piperazin-1-yl, 4-(bicyclo[1.1.0]butane-1-carbonyl)-3,3-dimethylpiperazin-1-yl, 4-(2-fluoroacryloyl)-3,3-dimethylpiperazin-1-yl, 1-(but-2-ynoyl)-1,6-diazaspiro[3.3]heptan-6-yl, 4-acryloyl-4-azaspiro[2.5]octan-6-yl, 2-acryloyl-2-azabicyclo[2.2.1]heptan-5-yl, 2-acryloyl-2-azabicyclo[2.2.1]heptan-6-yl, 8-(2-fluoroacryloyl)-8-azabicyclo[3.2.1]octan-3-yl, 8-(but-2-ynoyl)-8-azabicyclo[3.2.1]octan-3-yl, 1-(but-2-ynoyl)azepan-4-yl, 7-acryloyl-7-azabicyclo[2.2.1]heptan-2-yl, 2-acryloyl-2-azabicyclo[2.2.2]octan-5-yl, 3-acryloyl-3-azabicyclo[3.2.1]octan-8-yl, 8-acryloyl-3,8-diazabicyclo[3.2.1]octan-3-yl, 8-(but-2-ynoyl)-3,8-diazabicyclo[3.2.1]octan-3-yl, 3-acryloyl-3,8-diazabicyclo[3.2.1]octan-8-yl, 4-cyano-3,3-dimethylpiperazin-1-yl, 3-(but-2-ynoyl)-3,8-diazabicyclo[3.2.1]octan-8-yl, 4-acryloyl-3-isopropylpiperazin-1-yl, 1-acryloyl-1,6-diazaspiro[3.3]heptan-6-yl, 1-acryloylazetidin-3-yl, 4-acryloyl-4,7-diazaspiro[2.5]octan-7-yl, 6-acryloyl-1,6-diazaspiro[3.3]heptan-1-yl, 4-acryloyl-3-(tert-butyl)piperazin-1-yl, 1-acryloyl-5,5-dimethylpyrrolidin-3-yl, 4-acryloyl-3-(difluoromethyl)piperazin-1-yl, (1-acryloylazetidin-3-yl)methyl, 1-(1-acryloylazetidin-3-yl)ethyl, 1-acryloyl-5-cyclopropylpyrrolidin-3-yl, 4-acryloyl-3-cyclobutylpiperazin-1-yl, 1-acryloyl-5-(methoxymethyl)pyrrolidin-3-yl, 2-acryloyl-2,6-diazaspiro[3.4]octan-6-yl, 5-acryloyl-5,8-diazaspiro[3.5]nonan-8-yl, 5-(but-2-ynoyl)-2,5-diazabicyclo[2.2.1]heptan-2-yl, 4-acryloyl-3-ethynylpiperazin-1-yl, 6-acryloyl-3,6-diazabicyclo[3.2.2]nonan-3-yl, 4-methacryloyl-3,3-dimethylpiperazin-1-yl, 4-acryloyl-3-(methoxymethyl)piperazin-1-yl, N-(1-pyrrolidin-3-yl)-N-methylacrylamide, 4-methacryloylpiperazin-1-yl, 6-acryloyl-6-azabicyclo[3.2.1]octan-2-yl, 6-acryloyl-6-azabicyclo[3.2.1]octan-3-yl, 2-acryloyl-2-azabicyclo[2.2.2]octan-6-yl, 2-acryloyloctahydrocyclopenta[c]pyrrol-4-yl, 8-acryloyl-8-azabicyclo[3.2.1]octan-6-yl, and 8-acryloyl-8-azabicyclo[3.2.1]octan-2-yl.

In one embodiment of Formula (I), $R^1$ is selected from the group consisting of $-L^1-R^5$, $—NR^6R^7$, N-methyl-3-acrylamide, and prop-1-en-2-yl, wherein $R^1$ is not 1-acryloylpiperidin-4-olate, 4-acryloylpiperazin-1-yl, or 1-acryloylpiperidin-4-yl. In one embodiment of Formula (I), $R^1$ is selected from the group consisting of 6-acryloyl-3,6-diazabicyclo[3.1.1]heptan-3-yl, 1-acryloylhexahydropyrrolo[3,4-b]pyrrol-5(1H)-yl, 1-(bicyclo[1.1.0]butane-1-carbonyl)hexahydropyrrolo[3,4-b]pyrrol-5(1H)-yl, (1-acryloylpiperidin-4-yl)thio, 2-acryloyl-2,6-diazabicyclo[3.2.1]octan-6-yl, 4-acryloyl-3,3-dimethylpiperazin-1-yl, (1-acryloylpiperidin-4-yl)(methyl)amino, 1-acryloylpiperidin-3-yl, 1-acryloyl-6,6-dimethylpiperidin-3-yl, 1-acryloyloctahydrocyclopenta[b]pyrrol-5-yl, 3-acryloyl-3,6-diazabicyclo[3.1.1]heptan-6-yl, (1-acryloylazetidin-3-yl)thio, 4-acryloyl-5,5-dimethyl-1,4-diazepan-1-yl, 4-acryloyl-3,3-dimethyl-1,4-diazepan-1-yl, 5-acryloyl-2,5-diazabicyclo[2.2.1]heptan-2-yl, 4-acryloyl-3-(trifluoromethyl)piperazin-1-yl, 4-acryloyl-3-methylpiperazin-1-yl, 4-acryloyl-1,4-diazepan-1-yl, 6-acryloyl-2,6-diazaspiro[3.3]heptan-2-yl, 6-acryloyl-3,6-diazabicyclo[3.2.1]octan-3-yl, 4-acryloyl-3,5-dimethylpiperazin-1-yl, 6-acryloyl-3,6-diazabicyclo[3.2.0]heptan-3-yl, 1-acryloylpyrrolidin-3-yl, 1-acryloylazepan-4-yl, 1-acryloyl-2-methylpiperidin-4-yl, 1-acryloyl-5-methylpyrrolidin-3-yl, 1-acryloyl-3-methylpiperidin-4-yl, 1-acryloylazepan-3-yl, 1-acryloyl-2,2-dimethylpiperidin-4-yl, 4-acryloyl-4-azaspiro[2.5]octan-7-yl, 8-acryloyl-8-azabicyclo[3.2.1]octan-3-yl, 1-acryloyloctahydrocyclopenta[b]pyrrol-4-yl, 2-acryloyloctahydrocyclopenta[c]pyrrol-5-yl, 1-acryloyl-6,6-dimethylazepan-4-yl, N-acrylamide, N-but-2-ynamide, N-ethenesulfonamide, N-methyl-N-ethenesulfonamide, N-methyl-3-acrylamide, N-methyl-N-acrylamide, and prop-2-en-1-one.

In a preferred embodiment of Formula (I), $R^1$ is selected from the group consisting of 4-acryloyl-3,3-dimethylpiperazin-1-yl, 6-acryloyl-3,6-diazabicyclo[3.2.1]octan-3-yl, and 8-acryloyl-8-azabicyclo[3.2.1]octan-3-yl.

In one embodiment of Formula (I), $L^1$ is selected from the group consisting of a bond, O, $NR^8$ and S. In a preferred embodiment of Formula (I), $L^1$ is selected from the group consisting of a bond or O. In a further preferred embodiment, $L^1$ is a bond (i.e., $R^1$ is $R^5$).

In one embodiment of Formula (I), $R^5$ is a 4 to 9 membered heterocycle containing 1 or 2 heteroatoms selected from nitrogen and oxygen, wherein the heterocycle is substituted by one $R^6$, and is additionally optionally substituted with 1 or 2 groups independently selected from methyl, ethyl, isopropyl, tert-butyl, difluoromethyl, trifluoromethyl, methoxymethyl, ethynyl, cyclopropyl, and cyclobutyl. In some embodiments of Formula (I), $R^5$ is connected to $L^1$ via a nitrogen heteroatom in the heterocycle. In some embodiments of Formula (I), $R^5$ is connected to $L^1$ via a carbon atom in the heterocycle. In one embodiment of Formula (I), $R^6$ is a substitution on a ring nitrogen atom of $R^5$.

In one embodiment of Formula (I), $R^5$ is a 4 to 8 membered heterocycle containing 1 or 2 nitrogen heteroatoms, wherein the heterocycle is substituted by one $R^6$, and is additionally optionally substituted with 1 or 2 groups independently selected from methyl and trifluoromethyl. In some embodiments of Formula (I), $R^5$ is connected to $L^1$ via a nitrogen heteroatom in the heterocycle. In some embodiments of Formula (I), $R^5$ is connected to $L^1$ via a carbon atom in the heterocycle. In one embodiment of Formula (I), $R^6$ is a substituted on a ring nitrogen atom of $R^5$.

In a preferred embodiment of Formula (I), $R^5$ is a 4 to 8 membered heterocycle containing 1 or 2 nitrogen heteroatoms, wherein the heterocycle is substituted by one $R^6$, and is also substituted with 1 or 2 groups methyl groups. In a further preferred embodiment of Formula (I), $R^5$ is a 4 to 8 membered heterocycle containing 1 or 2 nitrogen heteroatoms, wherein the heterocycle is substituted by one $R^6$, and is also substituted with 2 groups methyl groups. In a still further preferred embodiment of Formula (I), $R^5$ is a 6 membered heterocycle containing 1 or 2 nitrogen heteroatoms, wherein the heterocycle is substituted by one $R^6$, and is also substituted with 2 groups methyl groups. In certain embodiments of Formula (I), $R^5$ is selected from the group consisting of 4-acryloyl-3,3-dimethylpiperazin-1-yl, 1-acryloyl-6,6-dimethylpiperidin-3-yl, 4-acryloyl-5,5-dimethyl-1,4-diazepan-1-yl, 4-acryloyl-3,3-dimethyl-1,4-diazepan-1-yl, 4-acryloyl-3,5-dimethylpiperazin-1-yl, 1-acryloyl-2,2-dimethylpiperidin-4-yl, and 1-acryloyl-6,6-dimethylazepan-4-yl.

In a preferred embodiment of Formula (I), $L^1$ is a bond, and $R^5$ is a 4 to 7 membered monocyclic heterocycle containing 1 or 2 heteroatoms selected from the group consisting of N and O, wherein the heterocycle is attached via a ring nitrogen atom, wherein the heterocycle is substituted by one $R^6$, and is additionally optionally substituted with 1 or 2 groups independently selected from methyl, ethyl, isopropyl, tert-butyl, difluoromethyl, trifluoromethyl, methoxymethyl, ethynyl, cyclopropyl, and cyclobutyl. In a further preferred embodiment of Formula (I), $R^6$ is selected from 1-prop-2-en-1-one and 1-but-2-yn-1-one. In a preferred embodiment of Formula (I), $R^6$ is 1-prop-2-en-1-one. In a further embodiment of Formula (I), $R^5$ is a 6 membered monocyclic heterocycle containing 1 or 2 nitrogen heteroatoms, wherein the heterocycle is attached via a ring nitrogen atom, wherein the heterocycle is substituted by one $R^6$, and is additionally optionally substituted with 1 or 2 methyl groups. In a preferred embodiment of Formula (I), $R^5$ is a 6 membered monocyclic heterocycle containing 2 nitrogen heteroatoms, wherein the heterocycle is attached via a ring nitrogen atom, wherein the heterocycle is substituted by one $R^6$, and is substituted with 1 or 2 methyl groups.

In one embodiment of Formula (I), $R^6$ is selected from the group consisting of cyano, 1-prop-2-en-1-one ($-C(=O)C(H)=CH_2$), 1-(2-fluoroprop-2-en-1-one) ($-C(=O)C(F)=CH_2$), 1-(2-methylprop-2-en-1-one) ($-C(=O)C(CH_3)=CH_2$), N—(N-methylacrylamide) ($-N(CH_3)C(=O)C(H)=CH_2$), 1-but-2-yn-1-one ($-C(=O)C\equiv CCH_3$), vinylsulfonyl, and (bicyclo[1.1.0]butan-1-yl)methanone. In another embodiment of Formula (I), $R^6$ is selected from the group consisting of 1-prop-2-en-1-one, 1-but-2-yn-1-one, vinylsulfonyl, and (bicyclo[1.1.0]butan-1-yl)methanone. In a preferred embodiment of Formula (I), $R^6$ is 1-prop-2-en-1-one.

In another embodiment, the invention provides a compound of Formula (I), wherein $R^2$ is a 9 membered bicyclic heteroaryl containing two to three heteroatoms selected from N and S, wherein the bicyclic heteroaryl may be optionally substituted with one methyl group.

In one embodiment of Formula (I), the invention provides a compound of Formula (I), wherein $R^2$ is selected from the group consisting of triazolopyridine, indazole, benzothiazole, imidazopyridine, pyrazolopyridine, benzoimidazole, and imidazopyridazine, wherein each may be optionally substituted with one or two groups selected from halogen and $C_1$-$C_3$ alkyl. In a further embodiment of Formula (I), $R^2$ is selected from the group consisting of triazolopyridine, indazole, benzothiazole, imidazopyridine, pyrazolopyridine, benzoimidazole, and imidazopyridazine, wherein each may be optionally substituted with one group selected from halogen and $C_1$-$C_3$ alkyl. In another further embodiment of Formula (I), $R^2$ is selected from the group consisting of triazolopyridine, indazole, benzothiazole, imidazopyridine, pyrazolopyridine, and benzoimidazole, wherein each may be optionally substituted with one or two groups selected from methyl and fluorine. In another further embodiment of Formula (I), $R^2$ is selected from the group consisting of triazolopyridine, indazole, benzothiazole, imidazopyridine, pyrazolopyridine, and benzoimidazole, wherein each may be optionally substituted with one methyl group.

In another embodiment, the invention provides a compound of Formula (I), wherein $R^2$ is selected from the group consisting of [1,2,4]triazolo[1,5-a]pyridine-7-yl, 2H-indazol-6-yl, benzo[d]thiazol-5-yl, imidazo[1,2-b]pyridazin-7-yl, 2H-pyrazolo[4,3-b]pyridine-6-yl, imidazo[1,2-a]pyridine-7-yl, 1H-benzo[d]imidazol-5-yl, 2H-pyrazolo[4,3-c]pyridine-6-yl, and 3H-imidazo[4,5-b]pyridin-6-yl, wherein each may be optionally substituted with one or two groups selected from halogen and $C_1$-$C_3$ alkyl. In a further embodiment of Formula (I), $R^2$ is selected from the group consisting of [1,2,4]triazolo[1,5-a]pyridine-7-yl, 2H-indazol-6-yl, benzo[d]thiazol-5-yl, imidazo[1,2-b]pyridazin-7-yl, 2H-pyrazolo[4,3-b]pyridine-6-yl, and imidazo[1,2-a]pyridine-7-yl, 1H-benzo[d]imidazol-5-yl, 2H-pyrazolo[4,3-c]pyridine-6-yl, and 3H-imidazo[4,5-b]pyridin-6-yl wherein each may be optionally substituted with one or two groups selected from methyl and fluoro. In a further embodiment of Formula (I), $R^2$ is selected from the group consisting of [1,2,4]triazolo[1,5-a]pyridine-7-yl, 2H-indazol-6-yl, benzo[d]thiazol-5-yl, imidazo[1,2-b]pyridazin-7-yl, 2H-pyrazolo[4,3-b]pyridine-6-yl, and imidazo[1,2-a]pyridine-7-yl, 1H-benzo[d]imidazol-5-yl, 2H-pyrazolo[4,3-c]pyridine-6-yl, and 3H-imidazo[4,5-b]pyridin-6-yl wherein each may be optionally substituted with one methyl group.

In a preferred embodiment, the invention provides a compound of Formula (I), wherein $R^2$ is selected from the group consisting of:

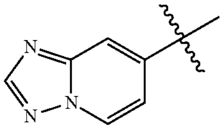 , 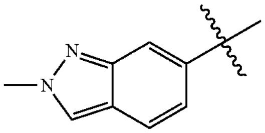 ,

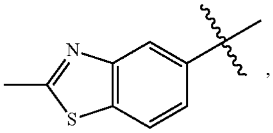 , 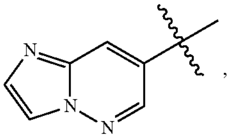 ,

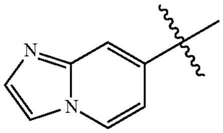 , 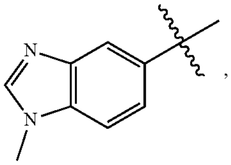 ,

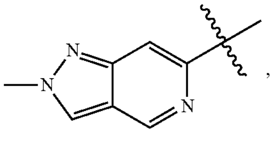 , 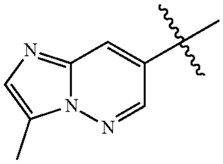 ,

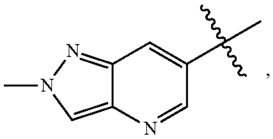 , 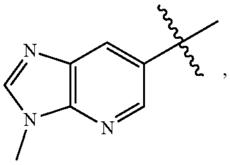 ,

-continued

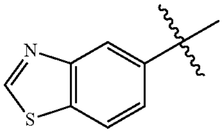 , and 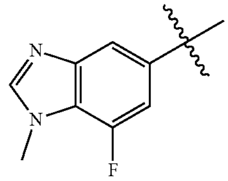 .

In another embodiment, the invention provides a compound of Formula (I), wherein $R^2$ is selected from the group consisting of:

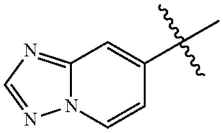 , 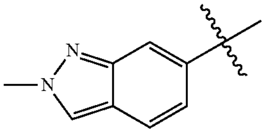 ,

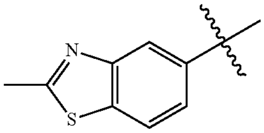 , 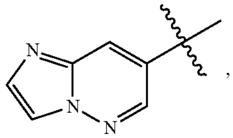 ,

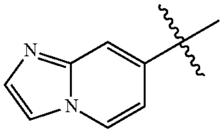 , 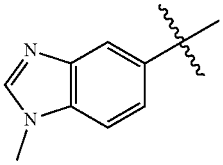 ,

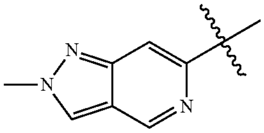 , 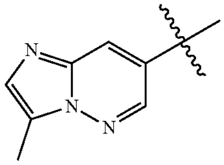 ,

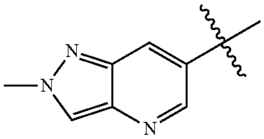 , and

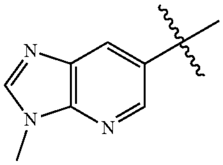 .

In an even more preferred embodiment of Formula (I), $R^2$ is selected from the group consisting of:

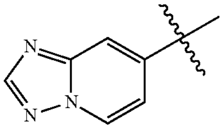 , 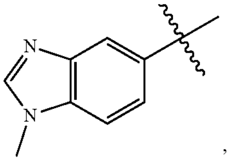 , and

-continued

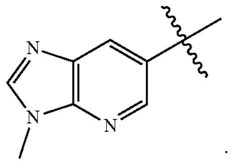

.

In a further preferred embodiment, the invention provides a compound of Formula (I), wherein $R^2$ is selected from the group consisting of:

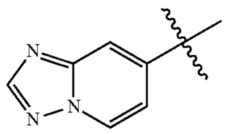

and

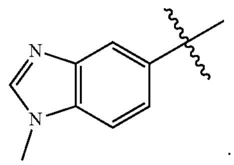

.

In a further preferred embodiment, the invention provides a compound of Formula (I), wherein $R^2$ is:

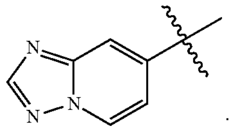 [SMILES: *c1ccn2ncnc2c1]

.

In another further preferred embodiment, the invention provides a compound of Formula (I), wherein $R^2$ is:

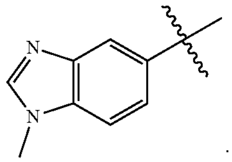

.

In another embodiment, the invention provides a compound of Formula (I), wherein each $R^3$ is independently selected from the group consisting of fluoro, chloro, and methyl.

In another embodiment, the invention provides a compound of Formula (I), wherein n is 1 or 2.

In another embodiment of Formula (I), each $R^3$ is independently selected from the group consisting of fluoro, chloro, difluoromethyl, trifluoromethyl and methyl, and n is 1 or 2. In a further embodiment, each $R^3$ is independently selected from halogen and methyl. In a preferred embodiment of Formula (I), each $R^3$ is independently selected from the group consisting of fluoro, chloro, and methyl, and n is 1 or 2.

In one embodiment of Formula (I), $R^4$ is hydrogen, chloro, or methoxy. In a preferred embodiment of Formula (I), $R^4$ is hydrogen.

In one embodiment of Formula I, a compound of Example 1 to 456 is provided. In one embodiment of Formula I, a compound of Example 1 to 160 is provided.

In another aspect, the invention provides a compound of Formula (Ia):

(Ia)

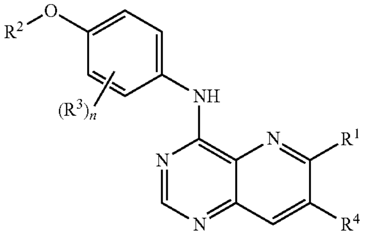

or a pharmaceutically acceptable salt thereof. The above embodiments for Formula (I) also apply to Formula (Ia), where appropriate (i.e., not embodiments relating to $L^2$, etc.). In one embodiment of Formula (Ia):

$R^1$ is selected from the group consisting of -$L^1$-$R^5$, —$NR^6R^7$, N-methyl-3-acrylamide, and prop-1-en-2-yl;

$R^2$ is a 9-10 membered bicyclic heteroaryl containing one, two, or three heteroatoms selected from N, O and S, wherein the bicyclic heteroaryl may be optionally substituted with one or two groups selected from halogen and $C_1$-$C_3$ alkyl;

each $R^3$ is independently selected from halogen and methyl;

$R^4$ is hydrogen, chloro, or methoxy;

$L^1$ is selected from the group consisting of a bond, O, $NR^a$ and S;

$R^5$ is a 4 to 8 membered heterocycle containing 1 to 3 heteroatoms selected from the group consisting of N, O and S, wherein the heterocycle is substituted by one $R^6$, and is additionally optionally substituted with 1 or 2 groups independently selected from methyl and trifluoromethyl;

$R^6$ is selected from the group consisting of 1-prop-2-en-1-one, 1-but-2-yn-1-one, vinylsulfonyl, and (bicyclo[1.1.0]butan-1-yl)methanone;

$R^7$ and $R^8$ are independently hydrogen or methyl; and n is 0, 1 or 2.

In another aspect, the invention provides a compound of Formula (II):

(II)

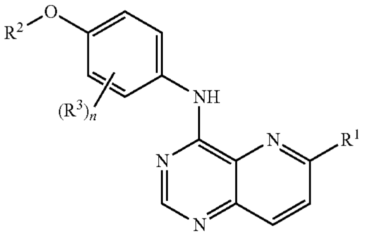

or a pharmaceutically acceptable salt thereof, wherein:

$R^1$ is 1-acryloylpiperidin-4-olate;

$R^2$ is a 9-10 membered bicyclic heteroaryl containing one, two, or three heteroatoms selected from N, O and S, wherein the bicyclic heteroaryl may be optionally substituted with one or two groups selected from halogen and $C_1$-$C_3$ alkyl;

each $R^3$ is independently selected from halogen and methyl; and n is 0, 1 or 2.

In another embodiments, the invention provides compounds of Formula (II), or pharmaceutically acceptable salts thereof, wherein:

$R^1$ is 1-acryloylpiperidin-4-olate;

$R^2$ is selected from the group consisting of [1,2,4]triazolo[1,5-a]pyridine-7-yl, 2H-indazol-6-yl, benzo[d]thiazol-5-yl, imidazo[1,2-b]pyridazin-7-yl, 2H-pyrazolo[4,3-b]pyridine-6-yl, imidazo[1,2-a]pyridine-7-yl, wherein each may be optionally substituted with one methyl group;

each $R^3$ is independently selected from the group consisting of fluoro, chloro, and methyl; and n is 1 or 2.

In another embodiment, the invention provides a compound of Formula (II), wherein $R^2$ is a 9 membered bicyclic heteroaryl containing two to three heteroatoms selected from N and S, wherein the bicyclic heteroaryl may be optionally substituted with one methyl group.

In another embodiment, the invention provides a compound of Formula (II), wherein $R^2$ is selected from the group consisting of triazolopyridine, indazole, benzothiazole, imidazopyridine, and pyrazolopyridine, wherein each may be optionally substituted with one or two groups selected from halogen and $C_1$-$C_3$ alkyl. In a further embodiment, $R^2$ is selected from the group consisting of triazolopyridine, indazole, benzothiazole, imidazopyridine, and pyrazolopyridine, wherein each may be optionally substituted with one group selected from halogen and $C_1$-$C_3$ alkyl. In another further embodiment, $R^2$ is selected from the group consisting of triazolopyridine, indazole, benzothiazole, imidazopyridine, and pyrazolopyridine, wherein each may be optionally substituted with one methyl group.

In another embodiment, the invention provides a compound of Formula (II), wherein $R^2$ is selected from the group consisting of [1,2,4]triazolo[1,5-a]pyridine-7-yl, 2H-indazol-6-yl, benzo[d]thiazol-5-yl, imidazo[1,2-b]pyridazin-7-yl, 2H-pyrazolo[4,3-b]pyridine-6-yl, imidazo[1,2-a]pyridine-7-yl, 1H-benzo[d]imidazol-5-yl, 2H-pyrazolo[4,3-c]pyridine-6-yl, and 3H-imidazo[4,5-b]pyridin-6-yl, wherein each may be optionally substituted with one or two groups selected from halogen and $C_1$-$C_3$ alkyl. In a further embodiment of Formula (II), $R^2$ is selected from the group consisting of [1,2,4]triazolo[1,5-a]pyridine-7-yl, 2H-indazol-6-yl, benzo[d]thiazol-5-yl, imidazo[1,2-b]pyridazin-7-yl, 2H-pyrazolo[4,3-b]pyridine-6-yl, and imidazo[1,2-a]pyridine-7-yl, 1H-benzo[d]imidazol-5-yl, 2H-pyrazolo[4,3-c]pyridine-6-yl, and 3H-imidazo[4,5-b]pyridin-6-yl wherein each may be optionally substituted with one methyl group.

In another embodiment, the invention provides a compound of Formula (II), wherein $R^2$ is selected from the group consisting of [1,2,4]triazolo[1,5-a]pyridine-7-yl, 2H-indazol-6-yl, benzo[d]thiazol-5-yl, imidazo[1,2-b]pyridazin-7-yl, 2H-pyrazolo[4,3-b]pyridine-6-yl, and imidazo[1,2-a]pyridine-7-yl, wherein each may be optionally substituted with one or two groups selected from halogen and $C_1$-$C_3$ alkyl. In a further embodiment, $R^2$ is selected from the group consisting of [1,2,4]triazolo[1,5-a]pyridine-7-yl, 2H-indazol-6-yl, benzo[d]thiazol-5-yl, imidazo[1,2-b]pyridazin-7-yl, 2H-pyrazolo[4,3-b]pyridine-6-yl, and imidazo[1,2-a]pyridine-7-yl, wherein each may be optionally substituted with one methyl group.

In one embodiment, the invention provides a compound of Formula (II), wherein $R^2$ is selected from the group consisting of:

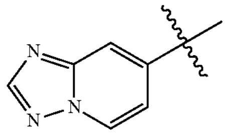 , 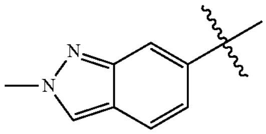 ,

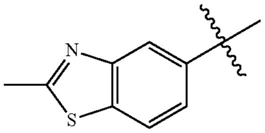 , 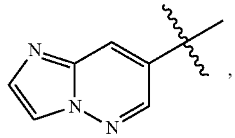 ,

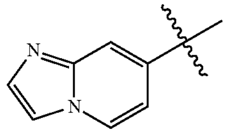 , 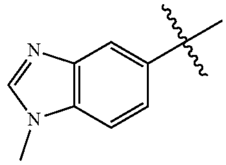 ,

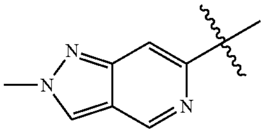 , 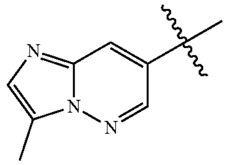 ,

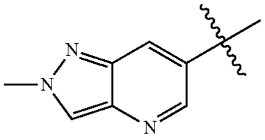 , and

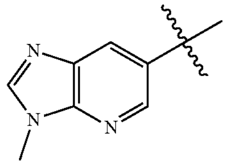 .

In another embodiments, the invention provides a compound of Formula (II), wherein $R^2$ is selected from the group consisting of:

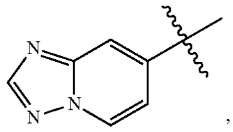 , 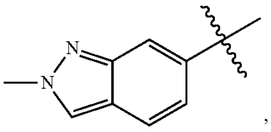 ,

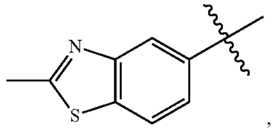 , 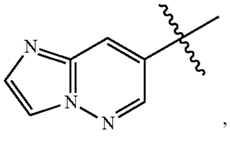 , and

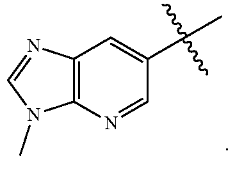 .

In a preferred embodiment, the invention provides a compound of Formula (II), wherein $R^2$ is selected from the group consisting of:

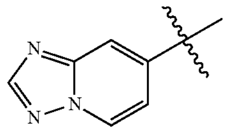

and

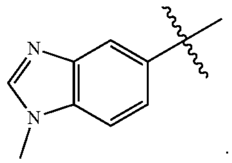 [SMILES: *c1ccc2c(c1)ncn2C]

.

In another embodiment, the invention provides a compound of Formula (II), wherein each $R^3$ is independently selected from the group consisting of fluoro, chloro, and methyl.

In another embodiment, the invention provides a compound of Formula (II), wherein n is 1 or 2.

In a preferred embodiment of Formula (II), each $R^3$ is independently selected from the group consisting of fluoro, chloro, and methyl, and n is 1 or 2.

In another embodiments, a compound of Examples 1 to 17 is provided.

In another aspect, the invention provides a compound of Formula (III):

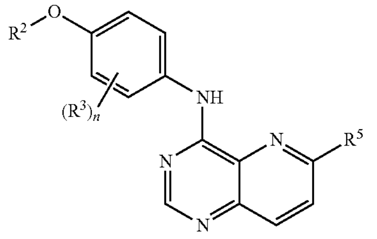

(III)

or a pharmaceutically acceptable salt thereof, wherein:

$R^2$ is a 9-10 membered bicyclic heteroaryl containing one, two, or three heteroatoms selected from N, O and S, wherein the bicyclic heteroaryl may be optionally substituted with one or two groups selected from halogen and $C_1$-$C_3$ alkyl;

each $R^3$ is independently selected from halogen and methyl;

$R^5$ is a 4 to 9 membered heterocycle containing 1 to 3 heteroatoms selected from the group consisting of N, O and S, wherein the heterocycle is substituted by one $R^6$, and is additionally optionally substituted with 1 or 2 groups independently selected from methyl, ethyl, isopropyl, tert-butyl, difluoromethyl, trifluoromethyl, methoxymethyl, ethynyl, cyclopropyl, and cyclobutyl;

$R^6$ is selected from the group consisting of 1-prop-2-en-1-one, 1-(2-fluoroprop-2-en-1-one), 1-(2-methylprop-2-en-1-one), and 1-but-2-yn-1-one;

n is 1 or 2.

In one embodiment, the invention provides a compound of Formula (III), wherein $R^2$ is selected from the group consisting of:

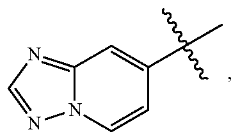

,

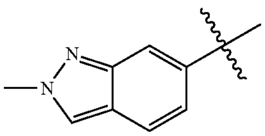

,

-continued

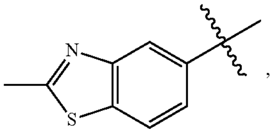

,

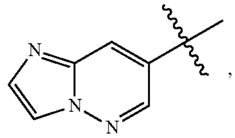

,

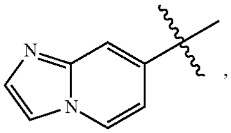

,

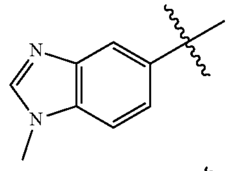

,

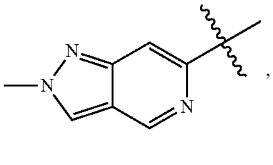

,

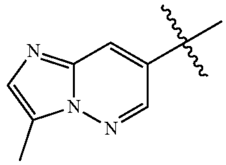

,

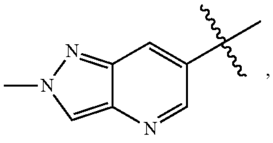

,

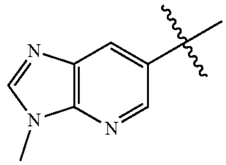

,

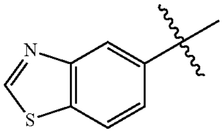

, and

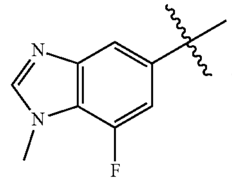

.

In another embodiment, the invention provides a compound of Formula (III), wherein $R^5$ is a 4 to 7 membered monocyclic heterocycle containing 1 or 2 heteroatoms selected from the group consisting of N and O, wherein the heterocycle is attached via a ring nitrogen atom, wherein the heterocycle is substituted by one $R^6$, and is additionally optionally substituted with 1 or 2 groups independently selected from methyl, ethyl, isopropyl, tert-butyl, difluoromethyl, trifluoromethyl, methoxymethyl, ethynyl, cyclopropyl, and cyclobutyl. In a further embodiment of Formula (III), $R^6$ is selected from 1-prop-2-en-1-one and 1-but-2-yn-1-one. In a preferred embodiment of Formula (III), $R^6$ is 1-prop-2-en-1-one. In a further embodiment of Formula (III), $R^5$ is a 6 membered monocyclic heterocycle containing 1 or 2 nitrogen heteroatoms, wherein the heterocycle is attached via a ring nitrogen atom, wherein the heterocycle is substituted by one $R^6$, and is additionally optionally substituted with 1 or 2 methyl groups. In a preferred embodiment of Formula (III), $R^5$ is a 6 membered monocyclic heterocycle containing 2 nitrogen heteroatoms, wherein the heterocycle is attached via a ring nitrogen atom, wherein the heterocycle is substituted by one $R^6$, and is substituted with 1 or 2 methyl groups.

Unless indicated otherwise, all references herein to the inventive compounds include references to salts, solvates, hydrates and complexes thereof, and to solvates, hydrates and complexes of salts thereof, including polymorphs, stereoisomers, and isotopically labelled versions thereof.

Compounds of the invention may exist in the form of pharmaceutically acceptable salts such as, acid addition salts and base addition salts of the compounds of one of the formulae provided herein.

"Pharmaceutically acceptable salt", as used herein, means those salts which retain the biological effectiveness and properties of the parent compound. The phrase "pharmaceutically acceptable salt(s)", as used herein, unless otherwise indicated, includes salts of acidic or basic groups which may be present in the compounds of the formulae disclosed herein.

The compounds described herein also include other salts of such compounds that are not necessarily pharmaceutically acceptable salts, and which may be useful as intermediates for preparing and/or purifying compounds described herein and/or for separating enantiomers of compounds described herein. For example, the compounds of the invention that are basic in nature are capable of forming a wide variety of salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention can be prepared by treating the base compound with a substantially equivalent amount of the selected mineral or organic acid in an aqueous solvent medium or in a suitable organic solvent, such as methanol or ethanol. Upon evaporation of the solvent, the desired solid salt is obtained. The desired acid salt can also be precipitated from a solution of the free base in an organic solvent by adding an appropriate mineral or organic acid to the solution.

The acids that may be used to prepare pharmaceutically acceptable acid addition salts of such basic compounds of those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and 1,1'-methylene-bis-(2-hydroxy-3-naphthoate) (i.e., pamoate) salts.

Examples of salts include, but are not limited to, acetate, acrylate, adipate, aspartate, benzenesulfonate, benzoate (such as chlorobenzoate, methylbenzoate, dinitrobenzoate, hydroxybenzoate, and methoxybenzoate), besylate, bicarbonate, bisulfate, bisulfite, bitartrate, borate, bromide, butyne-1,4-dioate, calcium edetate, camsylate, carbonate, chloride, caproate, caprylate, clavulanate, citrate, decanoate, dihydrochloride, dihydrogenphosphate, edetate, edislyate, estolate, esylate, ethylsuccinate, formate, fumarate, gluceptate, gluconate, glucoronate, glutamate, glycollate, glycollylarsanilate, heptanoate, hexafluorophosphate, hexyne-1,6-dioate, hexylresorcinate, hibenzate, hydrabamine, hydrobromide, hydrochloride, hydroiodide, γ-hydroxybutyrate, iodide, isobutyrate, isethionate, lactate, lactobionate, laurate, malate, maleate, malonate, mandelate, mesylate, metaphosphate, methane-sulfonate, methylsulfate, monohydrogenphosphate, mucate, napsylate, naphthalene-1-sulfonate, naphthalene-1,5-disulfonic acid, naphthalene-2-sulfonate, naphthylate, 2-napsylate, nicotinate, nitrate, oleate, orotate, oxalate, pamoate (embonate), palmitate, pamoate, pantothenate, phenylacetates, phenylbutyrate, phenylpropionate, phthalate, phospate/diphosphate, polygalacturonate, propanesulfonate, propionate, propiolate, pyroglutamate, pyrophosphate, pyrosulfate, saccharate, salicylate, stearate, subacetate, suberate, succinate, sulfate, sulfonate, sulfite, tannate, tartrate, teoclate, tosylate, triethiodode, trifluoroacetate, valerate and xinofoate salts.

Illustrative examples of suitable salts include organic salts derived from amino acids, such as glycine and arginine, ammonia, primary, secondary, and tertiary amines and cyclic amines, such as piperidine, morpholine and piperazine, and inorganic salts derived from sodium, calcium, potassium, magnesium, manganese, iron, copper, zinc, aluminum and lithium.

The compounds of the invention that include a basic moiety, such as an amino group, may form pharmaceutically acceptable salts with various amino acids, in addition to the acids mentioned above.

Alternatively, the compounds that are acidic in nature may be capable of forming base salts with various pharmacologically acceptable cations. Examples of such salts include the alkali metal or alkaline-earth metal salts, and particularly, the sodium and potassium salts. These salts are all prepared by conventional techniques. The chemical bases that are used as reagents to prepare the pharmaceutically acceptable base salts of this invention are those which form non-toxic base salts with the acidic compounds herein. These salts may be prepared by any suitable method, for example, treatment of the free acid with an inorganic or organic base, such as an amine (primary, secondary or tertiary), an alkali metal hydroxide or alkaline earth metal hydroxide, or the like. These salts can also be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The chemical bases that may be used as reagents to prepare pharmaceutically acceptable base salts of the compounds of the invention that are acidic in nature are those that form non-toxic base salts with such compounds. Such non-toxic base salts include, but are not limited to, those derived from such pharmacologically acceptable cations such as alkali metal cations (e.g., potassium and sodium) and alkaline earth metal cations (e.g., calcium and magnesium), ammonium or water-soluble amine addition salts, such as N-methylglucamine-(meglumine), and the lower alkanolammonium and other base salts of pharmaceutically acceptable organic amines.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

For a review on suitable salts, see Stahl, P. Heinrich and Camilli G. Wermuth, Eds. *Handbook of Pharmaceutical Salts: Properties, Selection, and Use*. New York: Wiley-VCH, 2011. Methods for making pharmaceutically acceptable salts of compounds of the invention, and of interconverting salt and free base forms, are known to one of skill in the art.

Salts of the present invention can be prepared according to methods known to those of skill in the art. A pharmaceutically acceptable salt of the inventive compounds can be readily prepared by mixing together solutions of the compound and the desired acid or base, as appropriate. The salt may precipitate from solution and be collected by filtration or may be recovered by evaporation of the solvent. The degree of ionization in the salt may vary from completely ionized to almost non-ionized.

It will be understood by those of skill in the art that the compounds of Formula (I) or (II) in free base form having a basic functionality may be converted to the acid addition salts by treating with a stoichiometric excess of the appropriate acid. The acid addition salts of the compounds of the invention may be reconverted to the corresponding free base by treating with a stoichiometric excess of a suitable base, such as potassium carbonate or sodium hydroxide, typically in the presence of aqueous solvent, and at a temperature of between about 0° C. and 100° C. The free base form may be isolated by conventional means, such as extraction with an organic solvent. In addition, acid addition salts of the compounds of the invention may be interchanged by taking advantage of differential solubilities of the salts, volatilities or acidities of the acids, or by treating with the appropriately loaded ion exchange resin. For example, the interchange may be affected by the reaction of a salt of the compounds of the invention with a slight stoichiometric excess of an acid of a lower pK than the acid component of the starting salt. This conversion is typically carried out at a temperature between about 0° C. and the boiling point of the solvent being used as the medium for the procedure. Similar exchanges are possible with base addition salts, typically via the intermediacy of the free base form.

It will also be understood by those of skill in the art that some of the embodiments include compounds that may exist in various salt forms or free base form, while other compounds may not form salts. For instance, lapatinib may exist in its free base form, as lapatinib ditosylate or as another salt. For convenience, certain embodiments of the present invention list compounds by their name (e.g., compounds of Formula (I) or (II) or lapatinib) with the nomenclatures "or salts thereof" or "or pharmaceutically acceptable salts thereof." In such instances, those of skill in the art will recognize that some of those compounds within the list may exist in various salt forms or as a free base (e.g., compounds of Formula (I) or (II) or lapatinib), while other compounds may not exist in salt forms (e.g., trastuzumab), even though the language appears to apply to all the compounds within the list.

The compounds of the invention may exist in both unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm. "Solvate", as used herein, means a molecular complex comprising the compound of Formula (I) or (II) and one or more pharmaceutically acceptable solvent molecules, for example, ethanol. "Hydrate", as used herein, means a solvate where the solvent is water. Pharmaceutically acceptable solvates in accordance with the invention include hydrates and solvates wherein the solvent of crystallization may be isotopically substituted, e.g., $D_2O$, $d_6$-acetone ($(CD_3)_2CO$), $d_6$-DMSO ($(CD_3)_2SO$).

A currently accepted classification system for organic hydrates is one that defines isolated site, channel, or metal-ion coordinated hydrates, see Brittain, Harry G., Ed. *Polymorphism in Pharmaceutical Solids*. New York: Informa Healthcare USA, Inc., 2016. Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex may have a well-defined stoichiometry independent of humidity. When, however, the solvent or water is weakly bound, as in channel solvates and hygroscopic compounds, the water/solvent content may be dependent on humidity and drying conditions. In such cases, non-stoichiometry will be the norm.

Also included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components, which may be in stoichiometric or non-stoichiometric amounts. The resulting complexes may be ionized, partially ionized, or non-ionized. For a review of such complexes, see Haleblian, J K. "Characterization of habits and crystalline modification of solids and their pharmaceutical applications." *J Pharm Sci.* 64(8) (1975): pp. 1269-1288, the disclosure of which is incorporated herein by reference in its entirety.

The invention also relates to prodrugs of the compounds of the formulae provided herein. Thus, certain derivatives of compounds of Formula (I) or (II) that may have little or no pharmacological activity themselves can, when administered to a patient, be converted into the compounds of the invention having the desired activity, for example, by hydrolytic cleavage. Such derivatives are referred to as "prodrugs." Further information on the use of prodrugs may be found in Higuchi, T., and V. Stella, Eds. *Pro-drugs as Novel Delivery Systems*. ACS Symposium Series Vol. 14, Washington DC: American Chemical Society, 1975 and Roche, Edward P. *Bioreversible Carriers in Drug Design: Theory and Application*. New York: Pergamon Press, 1987, the disclosures of which are incorporated herein by reference in their entireties.

Prodrugs in accordance with the invention can, for example, be produced by replacing appropriate functionalities present in the inventive compounds with certain moieties known to those skilled in the art as 'pro-moieties' as described, for example, in Bundgaard, Hans, ed. *Design of Prodrugs*. New York: Elsevier, 1985, the disclosure of which is incorporated herein by reference in its entirety.

Thus, a prodrug in accordance with the invention is (a) an ester or amide derivative of a carboxylic acid in a compound of Formula (I) or (II); (b) an ester, carbonate, carbamate, phosphate or ether derivative of a hydroxyl group in a compound of Formula (I) or (II); (c) an amide, imine, carbamate or amine derivative of an amino group in a compound form Formula (I) or (II); (d) a thioester, thiocarbonate, thiocarbamate or sulfide derivatives of a thiol group in a compound of Formula (I) or (II); or (e) an oxime or imine derivative of a carbonyl group in a compound of Formula (I) or (II).

Some non-limiting examples of prodrugs in accordance with the invention include:

(i) where the compound of the invention contains a carboxylic acid functionality (—COOH), an ester thereof, for example, replacement of the hydrogen with $C_1$-$C_8$ alkyl;

(ii) where the compound contains an alcohol functionality (—OH), an ether thereof, for example, replacement of the hydrogen with $C_1$-$C_6$ alkanoyloxymethyl, or with a phosphate ether group; and (iii) where the compound contains a primary or secondary amino functionality (—$NH_2$ or —NHR where R≠H), an amide thereof, for example, replacement of one or both hydrogens with a suitably metabolically labile group, such as an amide, carbamate, urea, phosphonate, sulfonate, etc.

Further examples of replacement groups in accordance with the foregoing examples and examples of other prodrug types may be found in the aforementioned references. Finally, certain inventive compounds may themselves act as prodrugs of other of the inventive compounds.

Also included within the scope of the invention are metabolites of compounds of the formulae described herein, i.e., compounds formed in vivo upon administration of the drug.

The compounds of the formulae provided herein may have asymmetric carbon atoms as part of substituent groups or optional substituents attached to these groups. At such asymmetric centers, a solid line is used to indicate that all possible stereoisomers at that carbon atom are included, while a solid or dotted wedge indicates that only the isomer shown is meant to be included at such stereocenter, unless otherwise indicated. Compounds of the formulae herein can include substituent groups containing cis and trans geometric isomers, rotational isomers, atropisomers, conformational isomers, and tautomers, including compounds exhibiting more than one type of isomerism.

Also included are acid addition salts or base addition salts, wherein the counterion is optically active, for example, d-lactate or l-lysine, or racemic, for example, dl-tartrate or dl-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The compounds of the invention may exhibit the phenomena of tautomerism and structural isomerism. For example, the compounds may exist in several tautomeric forms, including the enol and imine form, and the keto and enamine form and geometric isomers and mixtures thereof. All such tautomeric forms are included within the scope of compounds of the invention. Tautomers exist as mixtures of a tautomeric set in solution. In solid form, usually one tautomer predominates. Even though one tautomer may be described, the present invention includes all tautomers of the compounds of the formulae provided. It must be emphasised that while, for conciseness, the compounds of Formula (I) or (II) have been drawn herein in a single tautomeric form, all possible tautomeric forms are included within the scope of the invention.

In addition, some of the compounds of the invention may form atropisomers (e.g., substituted biaryls). Atropisomers are conformational stereoisomers which occur when rotation about a single bond in the molecule is prevented, or greatly slowed, as a result of steric interactions with other parts of the molecule and the substituents at both ends of the single bond are unsymmetrical. The interconversion of atropisomers is slow enough to allow separation and isolation under predetermined conditions. The energy barrier to thermal racemization may be determined by the steric hindrance to free rotation of one or more bonds forming a chiral axis.

Compounds of Formula (I) or (II) containing one or more asymmetric carbon atoms can exist as two or more stereoisomers. Where a compound of the invention contains an alkenyl group, geometric cis/trans (or Z/E) isomers are possible. Cis/trans isomers may be separated by conventional techniques well known to those skilled in the art, for example, chromatography and fractional crystallization. It follows that a single compound may exhibit more than one type of isomerism.

Conventional techniques for the preparation/isolation of individual enantiomers include chiral synthesis from a suitable optically pure precursor or resolution of the racemate (or the racemate of a salt or derivative) using, for example, chiral high-pressure liquid chromatography ("HPLC") or superfluid critical chromatography ("SFC").

Alternatively, the racemate (or a racemic precursor) may be reacted with a suitable optically active compound, for example, an alcohol, or, in the case where the compound contains an acidic or basic moiety, an acid or base, such as tartaric acid or 1-phenylethylamine. The resulting diastereomeric mixture may be separated by chromatography and/or fractional crystallization and one or both diastereoisomers converted to the corresponding pure enantiomer(s) by means well known to one skilled in the art.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Stereoisomeric conglomerates may be separated by conventional techniques known to those skilled in the art; see, for example, Eliel, E. and Wilen, S. *Stereochemistry of Organic Compounds*. New York: John Wiley & Sons, Inc., 1994, and Lochmuller, C. H., et al. "Chromatographic resolution of enantiomers: Selective review." *J. Chromatogr.* 113(3) (1975): pp. 283-302, the disclosures of which are incorporated herein by reference in its entirety.

The enantiomeric purity of compounds described herein may be described in terms of enantiomeric excess ("ee"), which indicates the degree to which a sample contains one enantiomer in greater amounts than the other. A racemic mixture has an ee of 0%, while a single completely pure enantiomer has an ee of 100%. Similarly, diastereomeric purity may be described in terms of diasteriomeric excess ("de"). "Enantiomerically pure" or "substantially enantiomerically pure", as used herein, means a compound that comprises one enantiomer of the compound and is substantially free of the opposite enantiomer of the compound. A typical enantiomerically pure compound comprises greater than about 95% by weight of one enantiomer of the compound and less than about 5% by weight of the opposite enantiomer of the compound, preferably greater than about 97% by weight of one enantiomer of the compound and less than about 3% by weight of the opposite enantiomer of the compound, more preferably greater than about 98% by weight of one enantiomer of the compound and less than about 2% by weight of the opposite enantiomer of the compound, and even more preferably greater than about 99% by weight of one enantiomer of the compound and less than about 1% by weight of the opposite enantiomer of the compound.

The present invention also includes isotopically-labeled compounds, which are identical to those recited in one of the formulae provided, but for the fact that one or more atoms are replaced by an atom having an atomic mass or mass number different from the atomic mass or mass number usually found in nature. Isotopically-labeled compounds can generally be prepared by conventional techniques known to those skilled in the art or by processes analogous to those described herein, using an appropriate isotopically-labeled reagent in place of the non-labeled reagent otherwise employed. Examples of isotopes that may be incorporated into compounds of the invention include isotopes of hydrogen, carbon, nitrogen, oxygen, phosphorus, fluorine and chlorine, such as, but not limited to, $^{2}H$, $^{3}H$, $^{13}C$, $^{14}C$ $^{15}N$, $^{18}O$, $^{17}O$, $^{31}P$, $^{32}P$, $^{35}S$, $^{18}F$, and $^{36}Cl$. Certain isotopically-labeled compounds of the invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically-labeled compounds may generally be prepared by carrying out the procedures disclosed in the Schemes and/or in the Examples below, by substituting an isotopically-labeled reagent for a non-isotopically-labeled reagent.

Compounds of the invention intended for pharmaceutical use may be administered as crystalline or amorphous products, or mixtures thereof. They may be obtained, for example, as solid plugs, powders, or films by methods such as precipitation, crystallization, freeze drying, spray drying, or evaporative drying. Microwave or radio frequency drying may be used for this purpose.

The compounds of the invention may exist in a continuum of solid states ranging from fully amorphous to fully crystalline. "Amorphous", as used herein, means a state in which the material lacks long range order at the molecular level and, depending upon temperature, may exhibit the physical properties of a solid or a liquid. Typically, such materials do not give distinctive X-ray diffraction patterns and, while exhibiting the properties of a solid, are more formally described as a liquid. Upon heating, a change from solid to liquid properties occurs, which is characterised by a change of state, typically second order (glass transition). "Crystalline", as used herein, means a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order (melting point).

The compounds of Formula (I) or (II) may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as thermotropic, and that resulting from the addition of a second component, such as water or another solvent, is described as lyotropic. Compounds that have the potential to form lyotropic mesophases are described as amphiphilic and consist of molecules that possess an ionic (such as $—COO^{-}Na^{+}$, $—COO^{-}K^{+}$, or $—SO_3^{-}Na^{+}$) or non-ionic (such as $—N—N^{+}(CH_3)_3$) polar head group, see Hartshorne, N. H. and A. Stuart. *Crystals and the Polarizing Microscope*. London: Edward Arnold Publishers Ltd., 1970.

The compounds of Formula (I) or (II) may exhibit polymorphism and/or one or more kinds of isomerism (e.g., optical, geometric, or tautomeric isomerism). The compounds of Formula (I) or (II) may also be isotopically labelled. Such variation is implicit to the compounds of Formula (I) or (II) defined as they are by reference to their structural features and therefore within the scope of the invention.

Synthesis of Compounds

Compounds described herein may be synthesized by synthetic routes that include processes analogous to those well-known in the chemical arts, particularly in light of the description contained herein. The starting materials are generally available from commercial sources, such as MilliporeSigma (St. Louis, MO), Alfa Aesar (Ward Hill, MA), TCI (Portland, OR) or the like, or are readily prepared using methods well known to those skilled in the art (e.g., prepared by methods generally described in Louis F. Fieser and Mary Fieser, *Reagents for Organic Synthesis*. v. 1-23, New York: Wiley 1967-2006 ed. (also available via the Wiley InterScience® website), or *Beilsteins Handbuch der organischen Chemie,* 4, Aufl. ed. Springer-Verlag, Berlin, including supplements (also available via the Beilstein online database)).

In preparing compounds of Formula (I) or (II), protection of remote functionalities (e.g., primary, or secondary amines, etc.) of intermediates may be necessary. The need for such protection will vary depending on the nature of the remote functionality and the conditions of the preparation methods. Suitable amino-protecting groups (NH-Pg) include acetyl, trifluoroacetyl, t-butyloxycarbonyl ("Boc"), benzyloxycarbonyl ("CBz") and 9-fluorenylmethyleneoxycarbonyl ("Fmoc"). The need for such protection is readily determined by one skilled in the art. For a general description of protecting groups and their use, see T. W. Greene, et al. *Greene's Protective Groups in Organic Synthesis*. New York: Wiley Interscience, 2006.

Formulations and Administration

A typical formulation or composition is prepared by mixing a compound described herein and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients. Chicago, Pharmaceutical Press,* 2005, the disclosures of which are herein incorporated by reference.

"Pharmaceutical composition", as used herein, means a mixture of one or more of the compounds of Formula (I) or (II), or a pharmaceutically acceptable salt, solvate, hydrate or prodrug thereof as an active ingredient, and at least one pharmaceutically acceptable excipient. In another embodiment, the pharmaceutical composition comprises two or more pharmaceutically acceptable carriers and/or excipients. In another embodiment, the pharmaceutical composition further comprises at least one additional anti-cancer therapeutic agent, whether as a fixed dose combination or a separate composition. In another embodiment, the combination provides an additive, greater than additive, or synergistic anti-cancer effect.

In one aspect, the invention provides a pharmaceutical composition comprising a compound of Formula (I) or (II), or a pharmaceutically acceptable salt thereof. In a further aspect, the invention provides a pharmaceutical composition comprising a compound of Formula (I) or (II), or a pharmaceutically acceptable salt thereof, and a pharmaceutically acceptable carrier or excipient. In another embodiment, the pharmaceutical composition comprises two or more pharmaceutically acceptable carriers and/or excipients.

In another aspect, the invention provides a pharmaceutical composition for the treatment of a disease or condition for which an inhibitor of HER2 mutations is indicated, comprising a compound of Formula (I) or (II), or a pharmaceutically acceptable salt thereof.

In another aspect, the invention provides a pharmaceutical composition for the treatment of a disease or condition for which a brain penetrant inhibitor of HER2 is indicated, comprising a compound of Formula (I) or (II), or a pharmaceutically acceptable salt thereof. In a further aspect, the invention provides a pharmaceutical composition for the treatment of a disease or condition for which a brain penetrant inhibitor of HER2 mutations is indicated, comprising a compound of Formula (I) or (II), or a pharmaceutically acceptable salt thereof.

In another aspect, the invention provides a pharmaceutical composition comprising a compound of Formula (I) or (II), or a pharmaceutically acceptable salt thereof, for use in the treatment of abnormal cell growth.

In yet another aspect, the invention provides a pharmaceutical composition for use in the treatment of abnormal cell growth in a subject in need thereof, which pharmaceutical composition comprises a compound of Formula (I) or (II), or a pharmaceutically acceptable salt thereof. In a further aspect, the invention provides a pharmaceutical composition for use in the treatment of abnormal cell growth in a subject in need thereof, which pharmaceutical composition comprises a compound of Formula (I) or (II), or a pharmaceutically acceptable salt thereof, and a pharmaceutically acceptable excipient.

"Additive", as used herein, means that the result of the combination of two compounds, components or targeted agents is no greater than the sum of each compound, component, or targeted agent individually.

"Synergy" or "synergistic", as used herein, mean that the result of the combination of two compounds, components or targeted agents is greater than the sum of each compound, component, or targeted agent individually. This improvement in the disease, condition or disorder being treated is a "synergistic" effect. A "synergistic amount" is an amount of the combination of the two compounds, components or targeted agents that results in a synergistic effect.

Determining a synergistic interaction between one or two components, the optimum range for the effect and absolute dose ranges of each component for the effect may be definitively measured by administration of the components over different dose ranges, and/or dose ratios to patients in need of treatment. However, the observation of synergy in in vitro models or in vivo models can be predictive of the effect in humans and other species and in vitro models or in vivo models exist, as described herein, to measure a synergistic effect. The results of such studies can also be used to predict effective dose and plasma concentration ratio ranges and the absolute doses and plasma concentrations required in humans and other species such as by the application of pharmacokinetic and/or pharmacodynamics methods.

"Pharmaceutically acceptable carrier", as used herein, means a carrier or diluent that does not cause significant irritation to an organism and does not abrogate the biological activity and properties of the administered compound.

The pharmaceutical acceptable carrier may comprise any conventional pharmaceutical carrier or excipient. The choice of carrier and/or excipient will to a large extent depend on factors, such as the particular mode of administration, the effect of the carrier or excipient on solubility and stability, and the nature of the dosage form.

Suitable pharmaceutical carriers include inert diluents or fillers, water, and various organic solvents (such as hydrates and solvates). The pharmaceutical compositions may, if desired, contain additional ingredients, such as flavorings, binders, excipients, and the like. Thus, for oral administration, tablets containing various excipients, such as citric acid, may be employed together with various disintegrants, such as starch, alginic acid and certain complex silicates, and with binding agents, such as sucrose, gelatin and acacia. Examples, without limitation, of excipients include calcium carbonate, calcium phosphate, various sugars and types of starch, cellulose derivatives, gelatin, vegetable oils and polyethylene glycols. Additionally, lubricating agents such as magnesium stearate, sodium lauryl sulfate and talc are often useful for tableting purposes. Solid compositions of a similar type may also be employed in soft and hard filled gelatin capsules. Non-limiting examples of materials, therefore, include lactose or milk sugar and high molecular weight polyethylene glycols. When aqueous suspensions or elixirs are desired for oral administration, the active compound therein may be combined with various sweetening or flavoring agents, coloring matters or dyes and, if desired, emulsifying agents or suspending agents, together with diluents, such as water, ethanol, propylene glycol, glycerin, or combinations thereof.

Administration of the compounds of Formula (I) or (II) may be affected by any method that enables delivery of the compounds to the site of action. These methods include oral routes, intraduodenal routes, parenteral injection (including intravenous, subcutaneous, intramuscular, intravascular or infusion), topical, and rectal administration.

The pharmaceutical composition may, for example, be in a form suitable for oral administration as a tablet, capsule, pill, powder, sustained release formulations, solution suspension, for parenteral injection as a sterile solution, suspension or emulsion, for topical administration as an ointment or cream or for rectal administration as a suppository.

Exemplary parenteral administration forms include solutions or suspensions of active compounds in sterile aqueous solutions, for example, aqueous propylene glycol or dextrose solutions. Such dosage forms may be suitably buffered, if desired.

The pharmaceutical composition may be in unit dosage forms suitable for single administration of precise dosages.

Pharmaceutical compositions suitable for the delivery of compounds of Formula (I) or (II) and methods for their preparation will be readily apparent to those skilled in the art. Such compositions and methods for their preparation can be found, for example, in Gennaro, supra.

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations, such as tablets, capsules containing particulates, liquids, powders, lozenges (including liquid-filled), chews, multi- and nano-particulates, gels, solid solution, liposome, films (including muco-adhesive), ovules, sprays, and liquid formulations.

Liquid formulations include suspensions, solutions, syrups, and elixirs. Such formulations may be used as fillers in soft or hard capsules and typically include a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms, such as those described in Liang, Alfred C. and Li-Ian H. Chen. "Fast-dissolving intraoral drug delivery systems." *Expert Opinion in Therapeutic Patents*. Vol. 11, No. 6 (2001): pp. 981-986, the disclosure of which is incorporated herein by reference in its entirety.

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch, and dibasic calcium phosphate dihydrate.

Tablets may also optionally include surface active agents, such as sodium lauryl sulfate and polysorbate 80, and glidants, such as silicon dioxide and talc. When present, surface active agents are typically in amounts of from 0.2 wt % to 5 wt % of the tablet, and glidants typically from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally are present in amounts from 0.25 wt % to 10 wt %, preferably from 0.5 wt % to 3 wt % of the tablet.

Other conventional ingredients include anti-oxidants, colorants, flavoring agents, preservatives, and taste-masking agents.

Exemplary tablets contain up to about 80 wt % drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tableting. The final formulation may include one or more layers and may be coated, uncoated, or encapsulated. The formulation of tablets is discussed in detail in Ansel, supra.

Solid formulations for oral administration may be formulated to be immediate and/or modified release. Modified release formulations include delayed, sustained, pulsed, controlled, targeted, and programmed release.

Suitable modified release formulations are described in U.S. Pat. No. 6,106,864. Details of other suitable release technologies, such as high energy dispersions and osmotic and coated particles can be found in Verma, Rajan K., and Sanjay Garg. "Current Status of Drug Delivery Technologies and Future Directions." *Pharmaceutical Technology On-Line*. 25(2) (2001): pp. 1-14. The use of chewing gum to achieve controlled release is described in WO 00/35298. The disclosures of these references are incorporated herein by reference in their entireties.

The compounds of Formula (I) or (II) may also be administered directly into the blood stream, into muscle, or into an internal organ. Suitable means for parenteral administration includes intravenous, intraarterial, intraperitoneal, intrathecal, intraventricular, intraurethral, intrasternal, intracranial, intramuscular, and subcutaneous. Suitable devices for parenteral administration include needle (including micro needle) injectors, needle-free injectors and infusion techniques.

Parenteral formulations are typically aqueous solutions, which may contain excipients such as salts, carbohydrates and buffering agents (preferably a pH of 3 to 9), but, for some applications, they may be more suitably formulated as a sterile, non-aqueous solution or as a dried form to be used in conjunction with a suitable vehicle, such as sterile, pyrogen-free water.

The preparation of parenteral formulations under sterile conditions, for example, by lyophilization, may readily be accomplished using standard pharmaceutical techniques well known to those skilled in the art.

The solubility of compounds of Formula (I) or (II) used in the preparation of parenteral solutions may be increased using appropriate formulation techniques, such as the incorporation of solubility-enhancing agents.

Formulations for parenteral administration may be formulated to be immediate and/or modified release. Modified release formulations include delayed, sustained, pulsed, controlled, targeted, and programmed release. Thus, compounds of the invention may be formulated as a solid, semi-solid, or thixotropic liquid for administration as an implanted depot providing modified release of the active compound. Examples of such formulations include drug-coated stents and PGLA microspheres.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used.

Typical carriers include alcohol, water, mineral oil, liquid petrolatum, white petrolatum, glycerin, polyethylene glycol and propylene glycol. Penetration enhancers may be incorporated; see, for example, Finnin, Barrie C. and Timothy M. Morgan. "Transdermal penetration enhancers: Applications, limitations, and potential." *J Pharm Sci.* 88(10) (1999): pp. 955-958, the disclosure of which is herein incorporated by reference in its entirety. Other means of topical administration include delivery by electroporation, iontophoresis, phonophoresis, sonophoresis and micro needle or needle-free (e.g., Powderject™, Bioject™, etc.) injection.

Formulations for topical administration may be formulated to be immediate and/or modified release. Modified release formulations include delayed, sustained, pulsed, controlled, targeted and programmed release.

The compounds of Formula (I) or (II) can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may include a bioadhesive agent, for example, chitosan or cyclodextrin.

The pressurized container, pump, spray, atomizer, or nebulizer contains a solution or suspension of a compound of Formula (I) or (II), comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules (made, for example, from gelatin or HPMC), blisters and cartridges for use in an inhaler or insufflator may be formulated to contain a powder mix of the compound of Formula (I) or (II), a suitable powder base, such as lactose or starch, and a performance modifier, such as l-leucine, mannitol, or magnesium stearate. The lactose may be anhydrous or in the form of lactose monohydrate, preferably the latter. Other suitable excipients include dextran, glucose, maltose, sorbitol, xylitol, fructose, sucrose, and trehalose.

A suitable solution formulation for use in an atomizer using electrohydrodynamics to produce a fine mist may contain from 1 μg to 20 mg of the compound of Formula (I) or (II) per actuation, and the actuation volume may vary from 1 μL to 100 μL. A typical formulation includes a compound of Formula (I) or (II), propylene glycol, sterile water, ethanol, and sodium chloride. Alternative solvents that may be used instead of propylene glycol include glycerol and polyethylene glycol.

Suitable flavors, such as menthol and levomenthol, or sweeteners, such as saccharin or saccharin sodium, may be added to those formulations intended for inhaled/intranasal administration.

Formulations for inhaled/intranasal administration may be formulated to be immediate and/or modified release using, for example, poly(D,L-lactic-coglycolic acid) (PLGA). Modified release formulations include delayed, sustained, pulsed, controlled, targeted, and programmed release.

In the case of dry powder inhalers and aerosols, the dosage unit is determined by means of a valve, which delivers a metered amount. Units in accordance with the invention are typically arranged to administer a metered dose or "puff" containing a desired mount of the compound of Formula (I) or (II). The overall daily dose may be administered in a single dose or, more usually, as divided doses throughout the day.

Compounds of Formula (I) or (II) may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed, sustained, pulsed, controlled, targeted, and programmed release.

Compounds of Formula (I) or (II) may also be administered directly to the eye or ear, typically in the form of drops of a micronized suspension or solution in isotonic, pH-adjusted, sterile saline. Other formulations suitable for ocular and aural administration include ointments, biodegradable (e.g., absorbable gel sponges, collagen) and non-biodegradable (e.g., silicone) implants, wafers, lenses and particulate or vesicular systems, such as niosomes or liposomes. A polymer, such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed, sustained, pulsed, controlled, targeted, or programmed release.

Compounds of Formula (I) or (II) may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e., as a carrier, diluent, or solubilizer. Most commonly used for these purposes are alpha-, beta- and gamma-cyclodextrins, examples of which may be found in PCT Publication Nos. WO 91/11172, WO 94/02518 and WO 98/55148, the disclosures of which are incorporated herein by reference in their entireties.

Dosage regimens may be adjusted to provide the optimum desired response. For example, a single bolus may be administered, several divided doses may be administered over time, or the dose may be proportionally reduced or increased as indicated by the exigencies of the therapeutic situation. It is especially advantageous to formulate parenteral compositions in dosage unit form for ease of administration and uniformity of dosage. "Dosage unit form", as used herein, means physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention is dictated by and directly dependent on (a) the unique characteristics of the therapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens for administration of the chemotherapeutic agent are well-known in the relevant art and would be understood to be encompassed by the skilled artisan once provided the teachings disclosed herein.

The amount of the compound of Formula (I) or (II) administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.1 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

Therapeutic Methods and Uses

The invention further provides therapeutic methods and uses comprising administering the compounds of Formula (I) or (II), or pharmaceutically acceptable salts thereof, alone or in combination with other therapeutic agents or palliative agents.

In one aspect, the invention provides a method for treating abnormal cell growth in a subject in need thereof, comprising administering to the subject a therapeutically effective amount of a compound of Formula (I) or (II), or a pharmaceutically acceptable salt thereof.

In another aspect, the invention provides a method for treating abnormal cell growth comprising administering a therapeutically effective amount of a compound of Formula (I) or (II), or a pharmaceutically acceptable salt thereof, to a patient in need thereof.

In another aspect, the invention provides a method for treating or ameliorating the severity of abnormal cell growth in a patient in need thereof comprising administering to the patient a compound of Formula (I) or (II), or a pharmaceutically acceptable salt thereof. In a further embodiment, the invention provides a method for treating the severity of abnormal cell growth in a patient in need thereof comprising administering to the patient a compound of Formula (I) or (II), or a pharmaceutically acceptable salt thereof. In another further embodiment, the invention provides a method for ameliorating the severity of abnormal cell growth in a patient in need thereof comprising administering to the patient a compound of Formula (I) or (II), or a pharmaceutically acceptable salt thereof.

In a preferred aspect, the invention provides a method for treating a disorder mediated by HER2 mutations in a subject, comprising administering to the subject a compound of Formula (I) or (II), or a pharmaceutically acceptable salt thereof, in an amount that is effective for treating said disorder, in particular cancer.

In a preferred aspect, the invention provides a method for treating a disorder mediated by brain metasteses from HER2 amplified or HER2 positive cancer in a subject, comprising administering to the subject a compound of Formula (I) or (II), or a pharmaceutically acceptable salt thereof, in an amount that is effective for treating said disorder, in particular cancer. In a further preferred aspect, the invention provides a method for treating a disorder mediated by brain metasteses from HER2 mutation amplified or HER2 mutation positive cancer in a subject, comprising administering to the subject a compound of Formula (I) or (II), or a pharmaceutically acceptable salt thereof, in an amount that is effective for treating said disorder, in particular cancer. In a preferred embodiment, the method for treating is of a disorder mediated by brain metasteses from HER2 amplified cancer. In a preferred embodiment, the method for treating is of a disorder mediated by brain metasteses from HER2 positive cancer. In a preferred embodiment, the method for treating is of a disorder mediated by brain metasteses from HER2 mutation amplified cancer. In a preferred embodiment, the method for treating is of a disorder mediated by brain metasteses from HER2 mutation positive cancer.

In some methods of the present invention, the methods are for treating brain metasteses. These brain metasteses occur when cancer cells spread from their original site to the brain. In a preferred embodiment of the present invention, the brain metasteses come from HER2 positive or HER2 amplified cancer. In another preferred embodiment of the present invention, the brain metasteses come from HER2 mutations positive or HER2 mutations amplified cancer.

In another preferred aspect, the invention provides a method for treating a disease or disorder modulated by HER2 mutations, comprising administering to a mammal in need of such treatment an amount of a compound of Formula (I) or (II), or a pharmaceutically acceptable salt thereof. In another preferred aspect, the invention provides a method for treating or preventing a disease or disorder modulated by HER2 mutations, comprising administering to a mammal in need of such treatment an effective amount of a compound of Formula (I) or (II), or a pharmaceutically acceptable salt thereof.

In another preferred aspect, the invention provides a method for treating or preventing a disease or disorder modulated by brain metasteses from HER2 amplified or HER2 positive cancer, comprising administering to a mammal in need of such treatment an amount of a compound of Formula (I) or (II), or a pharmaceutically acceptable salt thereof. In a further preferred aspect, the invention provides a method for treating or preventing a disease or disorder modulated by brain metasteses from HER2 mutation amplified or HER2 mutation positive cancer, comprising administering to a mammal in need of such treatment an amount of a compound of Formula (I) or (II), or a pharmaceutically acceptable salt thereof. In another preferred aspect, the invention provides a method for treating or preventing a disease or disorder modulated by brain metasteses from HER2 amplified or HER2 positive cancer, comprising administering to a mammal in need of such treatment an effective amount of a compound of Formula (I) or (II), or a pharmaceutically acceptable salt thereof. In a further preferred aspect, the invention provides a method for treating or preventing a disease or disorder modulated by brain metastases from HER2 mutation amplified or HER2 mutation positive cancer, comprising administering to a mammal in need of such treatment an effective amount of a compound of Formula (I) or (II), or a pharmaceutically acceptable salt thereof. In certain embodiments, the method for treating or preventing is a disease or disorder modulated by HER2 amplified cancer. In a preferred embodiment, the method for treating or preventing is a disease or disorder modulated by HER2 positive cancer. In another preferred embodiment, the method for treating or preventing is a disease or disorder modulated by HER2 mutation amplified cancer. In another preferred embodiment, the method for treating or preventing is a disease or disorder modulated by HER2 mutation positive cancer.

In another aspect, the invention provides a method of inhibiting cancer cell proliferation in a subject, comprising administering to the subject a compound of Formula (I) or (II), or a pharmaceutically acceptable salt thereof, in an amount effective to inhibit cell proliferation.

In another aspect, the invention provides a method of inhibiting cancer cell invasiveness in a subject, comprising administering to the subject a compound of Formula (I) or (II), or a pharmaceutically acceptable salt thereof, in an amount effective to inhibit cell invasiveness.

In another aspect, the invention provides a method of inducing apoptosis in cancer cells in a subject, comprising administering to the subject a compound of Formula (I) or (II), or a pharmaceutically acceptable salt thereof, in an amount effective to induce apoptosis.

In another aspect, the invention provides a method of inhibiting cancer cell metastasis in a subject, comprising administering to the subject a compound of Formula (I) or (II), or a pharmaceutically acceptable salt thereof, in an amount effective to inhibit cell metastasis.

In another aspect, the invention provides a method of inhibiting angiogenesis in a subject, comprising administering to the subject a compound of Formula (I) or (II), or a pharmaceutically acceptable salt thereof, in an amount effective to inhibit angiogenesis.

In one aspect, the invention provides a compound of Formula (I) or (II), or a pharmaceutically acceptable salt thereof, for use in treatment. In a further aspect, the invention provides a compound of Formula (I) or (II), or a pharmaceutically acceptable salt thereof, for use in the treatment of abnormal cell growth. In another aspect, the invention provides a compound of Formula (I) or (II), or a pharmaceutically acceptable salt thereof, for use in the treatment of abnormal cell growth in a subject.

In another aspect, the invention provides a compound of Formula (I) or (II), or a pharmaceutically acceptable salt thereof, for use in the treatment of a subject in need of such treatment. In another embodiment, the treatment is for abnormal cell growth.

In another aspect, the invention provides a compound of Formula (I) or (II), or a pharmaceutically acceptable salt thereof, for use as a medicament. In a further aspect, the invention provides a compound of Formula (I) or (II), or a pharmaceutically acceptable salt thereof, for use as a medicament for the treatment of abnormal cell growth in a subject.

In another aspect, the invention provides a compound of Formula (I) or (II), or a pharmaceutically acceptable salt thereof, for use in therapy. In a further aspect, the invention provides a compound of Formula (I) or (II), or a pharmaceutically acceptable salt thereof, for use in therapy for the treatment of abnormal cell growth. In another aspect, the invention provides a compound of Formula (I) or (II), or a pharmaceutically acceptable salt thereof, for use in therapy for the treatment of abnormal cell growth in a subject.

In one aspect, the invention provides a compound of Formula (I) or (II), or a pharmaceutically acceptable salt thereof, for use in the treatment of a disease or condition for which an inhibitor of HER2 mutations is indicated. In another aspect, the invention provides a compound of Formula (I) or (II), or a pharmaceutically acceptable salt thereof, for use in the treatment of a subject with a disease or condition for which an inhibitor of HER2 mutations is indicated.

In one preferred aspect, the invention provides a compound of Formula (I) or (II), or a pharmaceutically acceptable salt thereof, for use in the treatment of a disease or condition for which a brain penetrant inhibitor of HER2 is indicated. In a further preferred aspect, the invention provides a compound of Formula (I) or (II), or a pharmaceutically acceptable salt thereof, for use in the treatment of a disease or condition for which a brain penetrant inhibitor of HER2 mutations is indicated. In another preferred aspect, the invention provides a compound of Formula (I) or (II), or a pharmaceutically acceptable salt thereof, for use in the treatment of a subject with a disease or condition for which a brain penetrant inhibitor of HER2 is indicated. In a further preferred aspect, the invention provides a compound of Formula (I) or (II), or a pharmaceutically acceptable salt thereof, for use in the treatment of a subject with a disease or condition for which a brain penetrant inhibitor of HER2 mutations is indicated.

In another aspect, the invention provides the use of a compound of Formula (I) or (II), or a pharmaceutically acceptable salt thereof, for the treatment of a subject in need of such treatment. In a further aspect, the invention provides the use of a compound of Formula (I) or (II), or a pharmaceutically acceptable salt thereof, for the treatment of a subject with abnormal cell growth.

In yet another aspect, the invention provides the use of a compound of Formula (I) or (II), or a pharmaceutically acceptable salt thereof, in the manufacture of a medicament for treatment. In a further aspect, the invention provides the use of a compound of Formula (I) or (II), or a pharmaceutically acceptable salt thereof, in the manufacture of a medicament for treatment of a subject. In another aspect, the invention provides the use of a compound of Formula (I) or (II), or a pharmaceutically acceptable salt thereof, in the manufacture of a medicament for the treatment of abnormal cell growth in a subject.

In another preferred aspect, the invention provides the use of a compound of Formula (I) or (II), or a pharmaceutically acceptable salt thereof, in the manufacture of a medicament for treating a disease or condition for which an inhibitor of HER2 mutations is indicated. In another preferred aspect, the invention provides the use of a compound of Formula (I) or (II), or a pharmaceutically acceptable salt thereof, in the manufacture of a medicament for treating a disease or condition in a subject for which an inhibitor of HER2 mutations is indicated.

In another preferred aspect, the invention provides the use of a compound of Formula (I) or (II), or a pharmaceutically acceptable salt thereof, in the manufacture of a medicament for treating a disease or condition for which a brain penetrant inhibitor of HER2 is indicated. In a further preferred aspect, the invention provides the use of a compound of Formula (I) or (II), or a pharmaceutically acceptable salt thereof, in the manufacture of a medicament for treating a disease or condition for which a brain penetrant inhibitor of HER2 mutations is indicated. In another preferred aspect, the invention provides the use of a compound of Formula (I) or (II), or a pharmaceutically acceptable salt thereof, in the manufacture of a medicament for treating a disease or condition in a subject for which a brain penetrant inhibitor of HER2 is indicated. In a further preferred aspect, the invention provides the use of a compound of Formula (I) or (II), or a pharmaceutically acceptable salt thereof, in the manufacture of a medicament for treating a disease or condition in a subject for which a brain penetrant inhibitor of HER2 mutations is indicated.

"Abnormal cell growth", as used herein, unless otherwise indicated, means cell growth that is independent of normal regulatory mechanisms (e.g., loss of contact inhibition). Abnormal cell growth may be benign (not cancerous) or malignant (cancerous).

Abnormal cell growth includes the abnormal growth of: (1) tumor cells (tumors) that show increased expression of HER2 mutation; (2) tumors that proliferate by aberrant HER2 mutation activation; (3) tumors characterized by amplification or overexpression of HER2 mutation; and (4) tumors that are resistant to HER2 therapy or HER2 inhibition.

In frequent preferred embodiments of the methods provided herein, the abnormal cell growth is cancer. "Cancer", as used herein, means the physiological condition in mammals that is typically characterized by abnormal or unregulated cell growth. Cancer includes solid tumors named for the type of cells that form them, cancer of blood, bone marrow, or the lymphatic system. Examples of solid tumors include sarcomas and carcinomas. Cancers of the blood include, but are not limited to, leukemia, lymphoma and myeloma. Cancer also includes primary cancer that originates at a specific site in the body, a metastatic cancer that has spread from the place in which it started to other parts of the body, a recurrence from the original primary cancer after remission, and a second primary cancer that is a new primary cancer in a person with a history of previous cancer of a different type from the latter one.

In another embodiment, the methods provided result in one or more of the following effects: (1) inhibiting cancer cell proliferation; (2) inhibiting cancer cell invasiveness; (3) inducing apoptosis of cancer cells; (4) inhibiting cancer cell metastasis; or (5) inhibiting angiogenesis.

"Ameliorating", as used herein, means a lessening or improvement of one or more symptoms upon treatment with a compound described herein, as compared to not administering the compound. Ameliorating also includes shortening or reduction in duration of a symptom.

As used herein, an "effective dosage" or "effective amount" of drug, compound or pharmaceutical composition is an amount sufficient to affect any one or more beneficial or desired, including biochemical, histological and/or behavioral symptoms, of the disease, its complications and intermediate pathological phenotypes presenting during development of the disease. For therapeutic use, a "therapeutically effective amount" refers to that amount of a compound being administered that will relieve to some extent one or more of the symptoms of the disorder being treated. In reference to the treatment of cancer, a therapeutically effective amount refers to that amount which has the effect of (1) reducing the size of the tumor, (2) inhibiting (that is, slowing to some extent, preferably stopping) tumor metastasis, (3) inhibiting to some extent (that is, slowing to some extent, preferably stopping) tumor growth or tumor invasiveness, (4) relieving to some extent (or, preferably, eliminating) one or more signs or symptoms associated with the cancer, (5) decreasing the dose of other medications required to treat the disease, and/or (6) enhancing the effect of another medication, and/or (7) delaying the progression of the disease in a patient.

An effective dosage can be administered in one or more administrations. For the purposes of this invention, an effective dosage of drug, compound, or pharmaceutical composition is an amount sufficient to accomplish prophylactic or therapeutic treatment either directly or indirectly. As is understood in the clinical context, an effective dosage of drug, compound or pharmaceutical composition may or may not be achieved in conjunction with another drug, compound, or pharmaceutical composition.

"Tumor" as it applies to a subject diagnosed with, or suspected of having, a cancer refers to a malignant or potentially malignant neoplasm or tissue mass of any size and includes primary tumors and secondary neoplasms. A solid tumor is an abnormal growth or mass of tissue that usually does not contain cysts or liquid areas. Examples of solid tumors are sarcomas, carcinomas, and lymphomas. Leukemias (cancers of the blood) generally do not form solid tumors.

"Tumor burden" or "tumor load", as used herein, means the total amount of tumorous material distributed throughout the body. Tumor burden refers to the total number of cancer cells or the total size of tumor(s), throughout the body, including lymph nodes and bone marrow. Tumor burden can be determined by a variety of methods known in the art, such as, e.g., using calipers, or while in the body using imaging techniques, e.g., ultrasound, bone scan, computed tomography (CT), or magnetic resonance imaging (MRI) scans.

"Tumor size", as used herein, means the total size of the tumor which can be measured as the length and width of a tumor. Tumor size may be determined by a variety of methods known in the art, such as, e.g., by measuring the dimensions of tumor(s) upon removal from the subject, e.g., using calipers, or while in the body using imaging techniques, e.g., bone scan, ultrasound, CR or MRI scans.

"Mammal", as used herein, means a warm-blooded animal that has or is at risk of developing a disease described herein and includes, but is not limited to, guinea pigs, dogs, cats, rats, mice, hamsters, and primates, including humans.

"Subject", as used herein, means a human or animal subject. In another embodiment, the subject is a mammal. In a preferred embodiment, the subject is a human.

"Treat" or "treating", as used herein, means to administer a compound of Formula (I) or (II) to a subject having the condition to be treated to achieve at least one positive therapeutic effect. For example, treating cancer means to administer a compound of Formula (I) or (II) to a subject having cancer, or diagnosed with cancer, to achieve at least one positive therapeutic effect, such as, for example, reduced number of cancer cells, reduced tumor size, reduced rate of cancer cell infiltration into peripheral organs, or reduced rate of tumor metastases or tumor growth, reversing, alleviating, or inhibiting the progress of, the disorder or condition to which such term applies, or one or more symptoms of such disorder or condition. The term "treatment", as used herein, unless otherwise indicated, means the act of treating as "treating" is defined immediately above. The term "treating" also includes adjuvant and neo-adjuvant treatment of a subject.

For the purposes of this invention, beneficial or desired clinical results include, but are not limited to, one or more of the following: reducing the proliferation of (or destroying) neoplastic or cancerous cell; inhibiting metastasis or neoplastic cells; shrinking or decreasing the size of a tumor; remission of the cancer; decreasing symptoms resulting from the cancer; increasing the quality of life of those suffering from the cancer; decreasing the dose of other medications required to treat the cancer; delaying the progression of the cancer; curing the cancer; overcoming one or more resistance mechanisms of the cancer; and/or prolonging survival of patients the cancer. Positive therapeutic effects in cancer can be measured in a number of ways (see, for example, Weber, Wolfgang A. "Assessing Tumor Response to Therapy." *J. Nucl. Med.* 50 Suppl. 1 (2009): 1S-10S).

In another embodiment, the treatment achieved by a compound of Formula (I) or (II) is defined by reference to any of the following: partial response (PR), complete response (CR), overall response (OR), progression free survival (PFS), disease free survival (DFS) and overall survival (OS). PFS, also referred to as "Time to Tumor Progression" indicates the length of time during and after treatment that the cancer does not grow and includes the amount of time patients have experienced a CR or PR, as well as the amount of time patients have experienced stable disease (SD). DFS refers to the length of time during and after treatment that the patient remains free of disease. OS refers to a prolongation in life expectancy as compared to naïve or untreated subjects or patients. In another embodiment, response to a combination of the invention is any of PR, CR, PFS, DFS, OR or OS that is assessed using Response Evaluation Criteria in Solid Tumors (RECIST) 1.1 response criteria.

The treatment regimen for a compound of Formula (I) or (II) that is effective to treat a cancer patient may vary according to factors such as the disease state, age, and weight of the patient, and the ability of the therapy to elicit an anti-cancer response in the subject. While an embodiment of any of the aspects of the invention may not be effective in achieving a positive therapeutic effect in every subject, it should do so in a statistically significant number of subjects as determined by any statistical test known in the art such as the Student's t-test, the chi2-test the U-test according to Mann and Whitney, the Kruskal-Wallis test (H-test), Jonckheere-Terpstrat-testy and the Wilcon on-test.

The terms "treatment regimen", "dosing protocol" and "dosing regimen" are used interchangeably to refer to the dose and timing of administration of each compound of Formula (I) or (II), alone or in combination with another therapeutic agent.

In a preferred embodiment of the compounds, compositions, methods and uses described herein, the compounds of Formula (I) or (II) are selective for inhibiting HER2 mutations over EGFR inhibition. In a preferred embodiment, the compounds of the invention are selective for HER2-YVMA (SEQ ID NO: 2) over EGFR.

In frequent embodiments of the methods provided herein, the abnormal cell growth is cancer. In another embodiment, the cancer is selected from breast cancer, ovarian cancer, bladder cancer, uterine cancer, prostate cancer, lung cancer (including NSCLC, SCLC, squamous cell carcinoma or adenocarcinoma), esophageal cancer, head and neck cancer, colorectal cancer, kidney cancer (including RCC), liver cancer (including HCC), pancreatic cancer, stomach (i.e., gastric) cancer or thyroid cancer. In further embodiments of the methods provided herein, the cancer is breast cancer, ovarian cancer, bladder cancer, uterine cancer, prostate cancer, lung cancer, esophageal cancer, liver cancer, pancreatic cancer, or stomach cancer.

In a preferred embodiment, the cancer is selected from breast cancer, lung cancer, colon cancer, ovarian cancer, and gastric cancer. In a preferred embodiment, the cancer is selected from breast cancer, lung cancer, and colon cancer. In a preferred embodiment, the cancer is breast cancer. In a preferred embodiment, the cancer is lung cancer. In a preferred embodiment, the cancer is colon cancer. In a preferred embodiment, the cancer is ovarian cancer. In a preferred embodiment, the cancer is gastric cancer.

In another embodiment, the cancer is breast cancer, including, e.g., ER-positive/HR-positive, HER2-negative breast cancer; ER-positive/HR-positive, HER2-positive breast cancer; triple negative breast cancer (TNBC); or inflammatory breast cancer. In a preferred embodiment, the breast cancer is endocrine resistant breast cancer, trastuzumab resistant breast cancer, or breast cancer demonstrating primary or acquired resistance to HER2 inhibition. In another embodiment, the breast cancer is advanced or metastatic breast cancer. In a preferred embodiment of each of the foregoing, the breast cancer is characterized by amplification or overexpression of HER2 mutations or HER2-YVMA (SEQ ID NO: 2).

In another embodiment of the methods provided herein, the cancer is breast cancer, ovarian cancer, bladder cancer, uterine cancer, prostate cancer, lung cancer (including SCLC or NSCLC), esophageal cancer, liver cancer, pancreatic cancer, or stomach cancer.

In a preferred embodiment, the cancer is HER2 positive. In another preferred embodiment, the cancer is HER2 mutations positive.

In a preferred embodiment, the cancer is HER2 amplified. In another preferred embodiment, the cancer is HER2 mutations amplified.

In a preferred embodiment of the methods provided herein, the abnormal cell growth is cancer characterized by amplification or overexpression of HER2 mutations. In another preferred embodiment of the methods provided herein, the subject is identified as having a cancer characterized by amplification or overexpression of HER2 mutations.

In a preferred embodiment of the methods provided herein, the abnormal cell growth is cancer characterized by metastasis in the brain. In another preferred embodiment of the methods provided herein, the subject is identified as having a cancer characterized by metastasis in the brain.

In a preferred embodiment of the methods provided herein, the abnormal cell growth is cancer characterized by metastasis in the brain having amplification or overexpression of HER2 mutations. In another preferred embodiment of the methods provided herein, the subject is identified as having a cancer characterized by metastasis in the brain having amplification or overexpression of HER2 mutations.

In another embodiment, the cancer is selected from the group consisting of breast cancer, lung cancer, colon cancer, ovarian cancer, and gastric cancer. In a preferred such embodiment, the cancer is breast cancer, lung cancer, colon cancer, ovarian cancer or gastric cancer characterized by amplification or overexpression of HER2 mutations. In another preferred embodiment, the cancer is (a) breast cancer or ovarian cancer; (b) characterized by amplification or overexpression of HER2 mutations; or (c) both (a) and (b).

In a preferred embodiment, the cancer is metastasis in the brain caused by other cancers characterized by amplification or overexpression of HER2. In a further preferred embodiment, the cancer is metastasis in the brain caused by other cancers characterized by amplification or overexpression of HER2 mutations.

In a preferred embodiment, the cancer is metastasis in the brain characterized by amplification or overexpression of HER2 caused by other cancers characterized by amplification or overexpression of HER2. In a further preferred embodiment, the cancer is metastasis in the brain characterized by amplification or overexpression of HER2 mutations caused by other cancers characterized by amplification or overexpression of HER2 mutations.

In another embodiment, the compound of Formula (I) or (II), or a pharmaceutically acceptable salt thereof, is administered as first line therapy. In another embodiment, the compound of Formula (I) or (II) is administered as second (or later) line therapy. In another embodiment, the compound of Formula (I) or (II), or a pharmaceutically acceptable salt thereof, is administered as second (or later) line therapy following treatment with trastuzumab. In another embodiment, the compound of Formula (I) or (II), or a pharmaceutically acceptable salt thereof, is administered as second (or later) line therapy following treatment with trastuzumab, pertuzumab and either paclitaxel or docetaxel. In another embodiment, the compound of Formula (I) or (II), or a pharmaceutically acceptable salt thereof, is administered as second (or later) line therapy following treatment with monoclonal antibodies (such as trastuzumab, pertuzumab or margetuximab), antibody-drug conjugates (such as ado-trastuzumab emtansine ("t-dm1"), sacituzumab or govitecan-hziy), HER2 inhibitors (such as neratinib, lapatinib or tucatinib), CDK 4/6 inhibitors (such as palbociclib, ribociclib or abemaciclib), mTOR inhibitors (such as everolimus), PI3K inhibitors (such as alpelisib) or PARP inhibitors (such as olaparib or talazoparib). In another embodiment, the compound of Formula (I) or (II), or a pharmaceutically acceptable salt thereof, is administered as second (or later) line therapy following treatment with monoclonal antibodies, such as trastuzumab, pertuzumab or margetuximab. In another embodiment, the compound of Formula (I) or (II), or a pharmaceutically acceptable salt thereof, is administered as second (or later) line therapy following treatment with antibody-drug conjugates, such as t-dm1, sacituzumab or govitecan-hziy. In another embodiment, the compound of Formula (I) or (II), or a pharmaceutically acceptable salt thereof, is administered as second (or later) line therapy following treatment with HER2 inhibitors, such as neratinib, lapatinib or tucatinib. In another embodiment, the compound of Formula (I) or (II), or a pharmaceutically acceptable salt thereof, is administered as second (or later) line therapy following treatment with CDK 4/6 inhibitors, such as palbociclib, ribociclib or abemaciclib. In another embodiment, the compound of Formula (I) or (II), or a pharmaceutically acceptable salt thereof, is administered as second (or later) line therapy following treatment with mTOR inhibitors, such as everolimus. In another embodiment, the compound of Formula (I) or (II), or a pharmaceutically acceptable salt thereof, is administered as second (or later) line therapy following treatment with PI3K inhibitors, such as alpelisib. In another embodiment, the compound of Formula (I) or (II), or a pharmaceutically acceptable salt thereof, is administered as second (or later) line therapy following treatment with PARP inhibitors, such as olaparib or talazoparib.

Combination Therapy

Compounds of Formula (I) or (II), or a pharmaceutically acceptable salt thereof, may be administered as single agents or may be administered in combination with other anti-cancer therapeutic agents, in particular standard of care agents appropriate for the particular cancer. In another embodiment, the methods and uses comprise a compound of Formula (I) or (II), or a pharmaceutically acceptable salt thereof, co-administered with at least one other anti-cancer therapeutic agent. In a further embodiment, the methods and uses comprise a compound of Formula (I) or (II), or a pharmaceutically acceptable salt thereof, co-administered with at least one other anti-cancer therapeutic agent to treat or ameliorate abnormal cell growth. In another further embodiment, the methods and uses comprise a compound of Formula (I) or (II), or a pharmaceutically acceptable salt thereof, co-administered with at least one other anti-cancer therapeutic agent to treat abnormal cell growth.

"Combination therapy" or "co-administration", as used herein, means the administration of a compound of Formula (I) or (II), or a pharmaceutically acceptable salt thereof, together with at least one additional pharmaceutical or therapeutic agent (e.g., an anti-cancer agent), wherein said compound of Formula (I) or (II) and said additional pharmaceutical or therapeutic agent are part of the same or separate dosage forms and are administered via the same or different routes of administration and on the same or different schedules.

As noted above, the compounds of the invention may be used in combination with one or more additional anti-cancer agents. The efficacy of the compounds of Formula (I) or (II), or a pharmaceutically acceptable salt thereof, in certain tumors may be enhanced by combination with other approved or experimental cancer therapies, e.g., radiation, surgery, chemotherapeutic agents, targeted therapies, agents that inhibit other signaling pathways that are dysregulated in tumors, and other immune enhancing agents, such as PD-1 antagonists and the like.

In one aspect, the invention provides a method for the treatment of abnormal cell growth in a subject in need thereof, comprising administering to the subject an amount of a compound of Formula (I) or (II), or a pharmaceutically acceptable salt thereof, in combination with an amount of an additional therapeutic agent (e.g., an anti-cancer therapeutic agent), which amounts are together effective in treating said abnormal cell growth.

When a combination therapy is used, the one or more additional anti-cancer agents may be administered sequentially or simultaneously with the compound of Formula (I) or (II), or a pharmaceutically acceptable salt thereof. In one embodiment, the additional anti-cancer agent is administered to a mammal (e.g., a human) prior to administration of the compound of Formula (I) or (II), or a pharmaceutically acceptable salt thereof. In another embodiment, the additional anti-cancer agent is administered to the mammal after administration of the compound of Formula (I) or (II), or a pharmaceutically acceptable salt thereof. In another embodiment, the additional anti-cancer agent is administered to the mammal (e.g., a human) simultaneously with the administration of the compound of Formula (I) or (II), or a pharmaceutically acceptable salt thereof.

The invention also relates to a pharmaceutical composition for the treatment of abnormal cell growth in a mammal, including a human, which comprises an amount of a compound of Formula (I) or (II), including hydrates, solvates and polymorphs or pharmaceutically acceptable salts thereof, in combination with one or more (preferably one, two, or three) additional anti-cancer therapeutic agents.

"Additional anti-cancer therapeutic agent", as used herein, means any one or more therapeutic agent, other than a compound of Formula (I) or (II), or a pharmaceutically acceptable salt thereof, that is or can be used in the treatment of cancer. In another embodiment, such additional anti-cancer therapeutic agents include compounds derived from the following classes: mitotic inhibitors, alkylating agents, antimetabolites, antitumor antibiotics, anti-angiogenesis agents, topoisomerase I and II inhibitors, plant alkaloids, hormonal agents and antagonists, growth factor inhibitors, radiation, signal transduction inhibitors, such as inhibitors of protein tyrosine kinases and/or serine/threonine kinases, cell cycle inhibitors, biological response modifiers, enzyme inhibitors, antisense oligonucleotides or oligonucleotide derivatives, cytotoxics, immuno-oncology agents, and the like. In another embodiment, the additional anti-cancer therapeutic agent is a standard of care agent. In another embodiment, the additional anti-cancer therapeutic agent is discussed below in this Combination Therapy section, such as monoclonal antibodies, antibody-drug conjugates, HER2 inhibitors, CDK 4/6 inhibitors, mTOR inhibitors, PI3K inhibitors, PARP inhibitors, chemotherapy, anti-PD-1 monoclonal antibody, aromatase inhibitors, endocrine therapy, chemotherapeutic agents, and anti-HER2 agents.

In another embodiment, a compound of Formula (I) or (II), or a pharmaceutically acceptable salt thereof, may be administered with monoclonal antibodies (such as trastuzumab, pertuzumab or margetuximab), antibody-drug conjugates (such as t-dm1, sacituzumab or govitecan-hziy), HER2 inhibitors (such as neratinib, lapatinib or tucatinib), CDK 4/6 inhibitors (such as palbociclib, ribociclib or abemaciclib), mTOR inhibitors (such as everolimus), PI3K inhibitors (such as alpelisib), PARP inhibitors (such as olaparib or talazoparib), and pharmaceutically acceptable salts thereof, or combinations thereof. In another embodiment, a compound of Formula (I) or (II), or a pharmaceutically acceptable salt thereof, may be administered with monoclonal antibodies (such as trastuzumab, pertuzumab or margetuximab), antibody-drug conjugates (such as t-dm1, sacituzumab or govitecan-hziy), HER2 inhibitors (such as neratinib, lapatinib ortucatinib), CDK 4/6 inhibitors (such as palbociclib, ribociclib or abemaciclib), mTOR inhibitors (such as everolimus), PI3K inhibitors (such as alpelisib) or PARP inhibitors (such as olaparib ortalazoparib), and pharmaceutically acceptable salts thereof. In another embodiment, a compound of Formula (I) or (II), or a pharmaceutically acceptable salt thereof, may be administered with monoclonal antibodies (such as trastuzumab, pertuzumab or margetuximab), antibody-drug conjugates (such as t-dm1, sacituzumab or govitecan-hziy), HER2 inhibitors (such as neratinib, lapatinib ortucatinib), CDK 4/6 inhibitors (such as palbociclib, ribociclib or abemaciclib), mTOR inhibitors (such as everolimus), PI3K inhibitors (such as alpelisib), PARP inhibitors (such as olaparib or talazoparib), and pharmaceutically acceptable salts thereof, or combinations thereof.

In another embodiment, a compound of Formula (I) or (II), or a pharmaceutically acceptable salt thereof, may be administered in combination with a standard of care agent.

In another embodiment, a compound of Formula (I) or (II), or a pharmaceutically acceptable salt thereof, may be administered with trastuzumab. In another embodiment, a compound of Formula (I) or (II) may be administered with trastuzumab, doxorubicin, cyclophosphamide and either paclitaxel or docetaxel. In another embodiment, a compound of Formula (I) or (II), or a pharmaceutically acceptable salt thereof, may be administered with trastuzumab, docetaxel and carboplatin. In another embodiment, a compound of Formula (I) or (II), or a pharmaceutically acceptable salt thereof, may be administered with trastuzumab and paclitaxel. In another embodiment, a compound of Formula (I) or (II), or a pharmaceutically acceptable salt thereof, may be administered with trastuzumab, cisplatin and either capecitabine or 5-fluorouracil.

In another embodiment, a compound of Formula (I) or (II), or a pharmaceutically acceptable salt thereof, may be administered with pertuzumab. In another embodiment, a compound of Formula (I) or (II), or a pharmaceutically acceptable salt thereof, may be administered with pertuzumab and trastuzumab. In another embodiment, a compound of Formula (I) or (II), or a pharmaceutically acceptable salt thereof, may be administered with pertuzumab, trastuzumab and docetaxel. In another embodiment, a compound of Formula (I) or (II), or a pharmaceutically acceptable salt thereof, may be administered with pertuzumab, trastuzumab and chemotherapy.

In another embodiment, a compound of Formula (I) or (II), or a pharmaceutically acceptable salt thereof, may be administered with margetuximab. In another embodiment, a compound of Formula (I) or (II), or a pharmaceutically acceptable salt thereof, may be administered with margetuximab and chemotherapy. In another embodiment, a compound of Formula (I) or (II), or a pharmaceutically acceptable salt thereof, may be administered with margetuximab and an anti-PD-1 monoclonal antibody. In another embodiment, a compound of Formula (I) or (II), or a pharmaceutically acceptable salt thereof, may be administered with margetuximab and an anti-PD-1 monoclonal antibody selected from the group consisting of cemiplimab, nivolumab, pembrolizumab, avelumab, durvalumab and atezolizumab.

In another embodiment, a compound of Formula (I) or (II), or a pharmaceutically acceptable salt thereof, may be administered with t-dm1.

In another embodiment, a compound of Formula (I) or (II), or a pharmaceutically acceptable salt thereof, may be administered with sacituzumab govitecan-hziy.

In another embodiment, a compound of Formula (I) or (II), or a pharmaceutically acceptable salt thereof, may be administered with neratinib, or a pharmaceutically acceptable salt thereof. In another embodiment, a compound of Formula (I) or (II), or a pharmaceutically acceptable salt thereof, may be administered with neratinib and capecitabine, or a pharmaceutically acceptable salt thereof.

In another embodiment, a compound of Formula (I) or (II), or a pharmaceutically acceptable salt thereof, may be administered with lapatinib, or a pharmaceutically acceptable salt thereof. In another embodiment, a compound of Formula (I) or (II), or a pharmaceutically acceptable salt thereof, may be administered with lapatinib and capecitabine, or a pharmaceutically acceptable salt thereof. In another embodiment, a compound of Formula (I) or (II), or a pharmaceutically acceptable salt thereof, may be administered with lapatinib and letrozole, or a pharmaceutically acceptable salt thereof.

In another embodiment, a compound of Formula (I) or (II), or a pharmaceutically acceptable salt thereof, may be administered with tucatinib, or a pharmaceutically acceptable salt thereof. In another embodiment, a compound of Formula (I) or (II), or a pharmaceutically acceptable salt thereof, may be administered with tucatinib, trastuzumab and capecitabine, or a pharmaceutically acceptable salt thereof.

In another embodiment, a compound of Formula (I) or (II), or a pharmaceutically acceptable salt thereof, may be administered with palbociclib, or a pharmaceutically acceptable salt thereof. In another embodiment, a compound of Formula (I) or (II), or a pharmaceutically acceptable salt thereof, may be administered with palbociclib and fulvestrant, or a pharmaceutically acceptable salt thereof. In another embodiment, a compound of Formula (I) or (II), or a pharmaceutically acceptable salt thereof, may be administered with palbociclib and an aromatase inhibitor, or a pharmaceutically acceptable salt thereof. In a further embodiment, a compound of Formula (I) or (II), or a pharmaceutically acceptable salt thereof, may be administered with palbociclib and an aromatase inhibitor selected from the group consisting of aminoglutethimide, testolactone, anastrozole, letrozole, exemestane, vorozole, formetsane, fadrozole, 1,4,6-androstatrien-3,17-dione ("ATD") and 4-androstene-3,6,17-trione ("6-OXO"), or a pharmaceutically acceptable salt thereof.

In another embodiment, a compound of Formula (I) or (II), or a pharmaceutically acceptable salt thereof, may be administered with ribociclib, or a pharmaceutically acceptable salt thereof. In another embodiment, a compound of Formula (I) or (II), or a pharmaceutically acceptable salt thereof, may be administered with ribociclib and fulvestrant, or a pharmaceutically acceptable salt thereof. In another embodiment, a compound of Formula (I) or (II), or a pharmaceutically acceptable salt thereof, may be administered with ribociclib and an aromatase inhibitor, or a pharmaceutically acceptable salt thereof. In a further embodiment, a compound of Formula (I) or (II), or a pharmaceutically acceptable salt thereof, may be administered with ribociclib and an aromatase inhibitor selected from the group consisting of aminoglutethimide, testolactone, anastrozole, letrozole, exemestane, vorozole, formetsane, fadrozole, ATD and 6-OXO, or a pharmaceutically acceptable salt thereof.

In another embodiment, a compound of Formula (I) or (II), or a pharmaceutically acceptable salt thereof, may be administered with abemaciclib, or a pharmaceutically acceptable salt thereof. In another embodiment, a compound of Formula (I) or (II), or a pharmaceutically acceptable salt thereof, may be administered with abemaciclib and fulvestrant, or a pharmaceutically acceptable salt thereof. In another embodiment, a compound of Formula (I) or (II), or a pharmaceutically acceptable salt thereof, may be administered with abemaciclib and an aromatase inhibitor, or a pharmaceutically acceptable salt thereof. In a further embodiment, a compound of Formula (I) or (II), or a pharmaceutically acceptable salt thereof, may be administered with abemaciclib and an aromatase inhibitor selected from the group consisting of aminoglutethimide, testolactone, anastrozole, letrozole, exemestane, vorozole, formetsane, fadrozole, ATD and 6-OXO, or a pharmaceutically acceptable salt thereof.

In another embodiment, a compound of Formula (I) or (II), or a pharmaceutically acceptable salt thereof, may be administered with everolimus. In another embodiment, a compound of Formula (I) or (II), or a pharmaceutically acceptable salt thereof, may be administered with everolimus and exemestane. In another embodiment, a compound of Formula (I) or (II), or a pharmaceutically acceptable salt thereof, may be administered with everolimus and sunitinib or sorafenib, or a pharmaceutically acceptable salt thereof. In a further embodiment, a compound of Formula (I) or (II), or a pharmaceutically acceptable salt thereof, may be administered with everolimus and sunitinib, or a pharmaceutically acceptable salt thereof. In a further embodiment, a compound of Formula (I) or (II), or a pharmaceutically acceptable salt thereof, may be administered with everolimus and sorafenib, or a pharmaceutically acceptable salt thereof.

In another embodiment, a compound of Formula (I) or (II), or a pharmaceutically acceptable salt thereof, may be administered with alpelisib, or a pharmaceutically acceptable salt thereof. In another embodiment, a compound of Formula (I) or (II), or a pharmaceutically acceptable salt thereof, may be administered with alpelisib and fulvestrant, or a pharmaceutically acceptable salt thereof.

In another embodiment, a compound of Formula (I) or (II), or a pharmaceutically acceptable salt thereof, may be administered with olaparib. In another embodiment, a compound of Formula (I) or (II), or a pharmaceutically acceptable salt thereof, may be administered with olaparib and bevacizumab.

In another embodiment, a compound of Formula (I) or (II), or a pharmaceutically acceptable salt thereof, may be administered with talazoparib, or a pharmaceutically acceptable salt thereof.

In another embodiment, a compound of Formula (I) or (II), or a pharmaceutically acceptable salt thereof, may be administered with rucaparib, or a pharmaceutically acceptable salt thereof.

In another embodiment, a compound of Formula (I) or (II), or a pharmaceutically acceptable salt thereof, may be administered with paclitaxel or docetaxel. In a further embodiment, a compound of Formula (I) or (II), or a pharmaceutically acceptable salt thereof, may be administered with paclitaxel. In a further embodiment, a compound of Formula (I) or (II), or a pharmaceutically acceptable salt thereof, may be administered with docetaxel.

In another embodiment, a compound of Formula (I) or (II), or a pharmaceutically acceptable salt thereof, may be administered with docetaxel and carboplatin.

In another embodiment, a compound of Formula (I) or (II), or a pharmaceutically acceptable salt thereof, may be administered with carboplatin.

In another embodiment, a compound of Formula (I) or (II), or a pharmaceutically acceptable salt thereof, may be administered with cisplatin and either capecitabine or 5-fluorouracil. In a further embodiment, a compound of Formula (I) or (II), or a pharmaceutically acceptable salt thereof, may be administered with cisplatin and capecitabine. In a further embodiment, a compound of Formula (I) or (II), or a pharmaceutically acceptable salt thereof, may be administered with cisplatin and 5-fluorouracil.

In another embodiment, a compound of Formula (I) or (II), or a pharmaceutically acceptable salt thereof, may be administered with cisplatin.

In another embodiment, a compound of Formula (I) or (II), or a pharmaceutically acceptable salt thereof, may be administered with 5-fluorouracil.

In another embodiment, a compound of Formula (I) or (II), or a pharmaceutically acceptable salt thereof, may be administered with capecitabine.

In another embodiment, a compound of Formula (I) or (II), or a pharmaceutically acceptable salt thereof, may be administered with letrozole.

In another embodiment, a compound of Formula (I) or (II), or a pharmaceutically acceptable salt thereof, may be administered with trastuzumab and capecitabine.

In another embodiment, a compound of Formula (I) or (II), or a pharmaceutically acceptable salt thereof, may be administered with chemotherapy. In another embodiment, chemotherapy is selected from the group consisting of cyclophosphamide, methotrexate, 5-fluorouracil, vinorelbine, doxorubicin, paclitaxel, docetaxel, bleomycin, vinblastine, dacarbazine, mustine, vincristine, procarbazine, prednisolone, etoposide, cisplatin, carboplatin, epirubicin, capecitabine, folinic acid and oxaliplatin. In another embodiment, chemotherapy is selected from the group consisting of cyclophosphamide, methotrexate, 5-fluorouracil, vinorelbine, and doxorubicin.

In another embodiment, a compound of Formula (I) or (II), or a pharmaceutically acceptable salt thereof, may be administered with trastuzumab, pertuzumab, margetuximab, t-dm1, sacituzumab govitecan-hziy, neratinib, lapatinib, tucatinib, palbociclib, ribociclib, abemaciclib, everolimus, alpelisib, olaparib, talazoparib, chemotherapy (such as cyclophosphamide, methotrexate, 5-fluorouracil, vinorelbine, doxorubicin, paclitaxel, docetaxel, bleomycin, vinblastine, dacarbazine, mustine, vincristine, procarbazine, prednisolone, etoposide, cisplatin, carboplatin, epirubicin, capecitabine, folinic acid and oxaliplatin), anti-PD-1 monoclonal antibody (such as cemiplimab, nivolumab, pembrolizumab, avelumab, durvalumab and atezolizumab), aromatase inhibitor (such as aminoglutethimide, testolactone, anastrozole, letrozole, exemestane, vorozole, formetsane, fadrozole, ATD and 6-OXO), fulvestrant, sunitinib, sorafenib, bevacizumab, and pharmaceutically acceptable salts thereof, or combinations thereof. In a further embodiment, a compound of Formula (I) or (II), or a pharmaceutically acceptable salt thereof, may be administered with trastuzumab, pertuzumab, margetuximab, t-dm1, sacituzumab govitecan-hziy, neratinib, lapatinib, tucatinib, palbociclib, ribociclib, abemaciclib, everolimus, alpelisib, olaparib, talazoparib, cyclophosphamide, methotrexate, 5-fluorouracil, vinorelbine, doxorubicin, paclitaxel, docetaxel, bleomycin, vinblastine, dacarbazine, mustine, vincristine, procarbazine, prednisolone, etoposide, cisplatin, carboplatin, epirubicin, capecitabine, folinic acid, oxaliplatin, cemiplimab, nivolumab, pembrolizumab, avelumab, durvalumab, atezolizumab, aminoglutethimide, testolactone, anastrozole, letrozole, exemestane, vorozole, formetsane, fadrozole, ATD, 6-OXO, fulvestrant, sunitinib, sorafenib, bevacizumab, and pharmaceutically acceptable salts thereof, or combinations thereof. In another embodiment, a compound of Formula (I) or (II), or a pharmaceutically acceptable salt thereof, may be administered with trastuzumab, pertuzumab, margetuximab, t-dm1, sacituzumab govitecan-hziy, neratinib, lapatinib, tucatinib, palbociclib, ribociclib, abemaciclib, everolimus, alpelisib, olaparib, talazoparib, cyclophosphamide, methotrexate, 5-fluorouracil, vinorelbine, doxorubicin, paclitaxel, docetaxel, bleomycin, vinblastine, dacarbazine, mustine, vincristine, procarbazine, prednisolone, etoposide, cisplatin, carboplatin, epirubicin, capecitabine, folinic acid, oxaliplatin, cemiplimab, nivolumab, pembrolizumab, avelumab, durvalumab, atezolizumab, aminoglutethimide, testolactone, anastrozole, letrozole, exemestane, vorozole, formetsane, fadrozole, ATD, 6-OXO, fulvestrant, sunitinib, sorafenib and bevacizumab, and pharmaceutically acceptable salts thereof.

In another embodiment, a compound of Formula (I) or (II), or a pharmaceutically acceptable salt thereof, may be administered with chemotherapy (such as cyclophosphamide, methotrexate, 5-fluorouracil, vinorelbine, doxorubicin, paclitaxel, docetaxel, bleomycin, vinblastine, dacarbazine, mustine, vincristine, procarbazine, prednisolone, etoposide, cisplatin, carboplatin, epirubicin, capecitabine, folinic acid and oxaliplatin), anti-PD-1 monoclonal antibody (such as cemiplimab, nivolumab, pembrolizumab, avelumab, durvalumab and atezolizumab), aromatase inhibitor (such as aminoglutethimide, testolactone, anastrozole, letrozole, exemestane, vorozole, formetsane, fadrozole, ATD and 6-OXO), fulvestrant, sunitinib, sorafenib, bevacizumab, and pharmaceutically acceptable salts thereof, or combinations thereof. In a further embodiment, a compound of Formula (I) or (II), or a pharmaceutically acceptable salt thereof, may be administered with cyclophosphamide, methotrexate, 5-fluorouracil, vinorelbine, doxorubicin, paclitaxel, docetaxel, bleomycin, vinblastine, dacarbazine, mustine, vincristine, procarbazine, prednisolone, etoposide, cisplatin, carboplatin, epirubicin, capecitabine, folinic acid, oxaliplatin, cemiplimab, nivolumab, pembrolizumab, avelumab, durvalumab, atezolizumab, aminoglutethimide, testolactone, anastrozole, letrozole, exemestane, vorozole, formetsane, fadrozole, ATD, 6-OXO, fulvestrant, sunitinib, sorafenib, bevacizumab, and pharmaceutically acceptable salts thereof, or combinations thereof. In another embodiment, a compound of Formula (I) or (II), or a pharmaceutically acceptable salt thereof, may be administered with cyclophosphamide, methotrexate, 5-fluorouracil, vinorelbine, doxorubicin, paclitaxel, docetaxel, bleomycin, vinblastine, dacarbazine, mustine, vincristine, procarbazine, prednisolone, etoposide, cisplatin, carboplatin, epirubicin, capecitabine, folinic acid, oxaliplatin, cemiplimab, nivolumab, pembrolizumab, avelumab, durvalumab, atezolizumab, aminoglutethimide, testolactone, anastrozole, letrozole, exemestane, vorozole, formetsane, fadrozole, ATD, 6-OXO, fulvestrant, sunitinib, sorafenib and bevacizumab, and pharmaceutically acceptable salts thereof.

In another embodiment, a compound of Formula (I) or (II), or a pharmaceutically acceptable salt thereof, may be administered in combination with endocrine therapy, e.g., agents such as letrozole, fulvestrant, tamoxifen, exemestane, or anastrozole. In another embodiment, a compound of Formula (I) or (II), or a pharmaceutically acceptable salt thereof, may be administered in combination with a chemotherapeutic agent, e.g., docetaxel, paclitaxel, cisplatin, carboplatin, capecitabine, gemcitabine or vinorelbine. In another embodiment, a compound of Formula (I) or (II), or a pharmaceutically acceptable salt thereof, may be administered in combination with an anti-HER2 agent, e.g., trastuzumab and/or pertuzumab.

In another embodiment, the additional anti-cancer therapeutic agent is an anti-angiogenesis agent, including for example VEGF inhibitors, VEGFR inhibitors, TIE-2 inhibitors, PDGFR inhibitors, angiopoietin inhibitors, PKCβ inhibitors, COX-2 (cyclooxygenase II) inhibitors, integrins (alpha-v/beta-3), MMP-2 (matrix-metalloproteinase 2) inhibitors, and MMP-9 (matrix-metalloproteinase 9) inhibitors. Preferred anti-angiogenesis agents include sunitinib (Sutent™) bevacizumab (Avastin™), axitinib (AG 13736), SU 14813 (Pfizer), and AG 13958 (Pfizer). Additional anti-angiogenesis agents include vatalanib (CGP 79787), sorafenib (Nexavar™) pegaptanib octasodium (Macugen™), vandetanib (Zactima™), PF-0337210 (Pfizer), SU 14843 (Pfizer), AZD 2171 (AstraZeneca), ranibizumab (Lucentis™), Neovastat™ (AE 941), tetrathiomolybdata (Coprexa™), AMG 706 (Amgen), VEGF Trap (AVE 0005), CEP 7055 (Sanofi-Aventis), XL 880 (Exelixis), telatinib (BAY 57-9352), and CP-868,596 (Pfizer). Other anti-angiogenesis agents include enzastaurin (LY 317615), midostaurin (CGP 41251), perifosine (KRX 0401), teprenone (Selbex™) and UCN 01 (Kyowa Hakko). Other examples of anti-angiogenesis agents include celecoxib (Celebrex™), parecoxib (Dynastat™), deracoxib (SC 59046), lumiracoxib (Preige™), valdecoxib (Bextra™), rofecoxib (Vioxx™), iguratimod (Careram™), IP 751 (Invedus), SC-58125 (Pharmacia) and etoricoxib (Arcoxia™). Yet further anti-angiogenesis agents include exisulind (Aptosyn™), salsalate (Amigesic™), diflunisal (Dolobid™), ibuprofen (Motrin™), ketoprofen (Orudis™), nabumetone (Relafen™), piroxicam (Feldene™), naproxen (Aleve™, Naprosyn™), diclofenac (Voltaren™), indomethacin (Indocin™), sulindac (Clinoril™), tolmetin (Tolectin™), etodolac (Lodine™), ketorolac (Toradol™), and oxaprozin (Daypro™). Yet further anti-angiogenesis agents include ABT 510 (Abbott), apratastat (TMI 005), AZD 8955 (AstraZeneca), incyclinide (Metastat™), and PCK 3145 (Procyon). Yet further anti-angiogenesis agents include acitretin (Neotigason™), plitidepsin (Aplidine™), cilengtide (EMD 121974), combretastatin A4 (CA4P), fenretinide (4 HPR), halofuginone (Tempostatin™), Panzem™ (2-methoxyestradiol), PF-03446962 (Pfizer), rebimastat (BMS 275291), catumaxomab (Removab™), lenalidomide (Revlimid™), squalamine (EVIZON™), thalidomide (Thalomid™), Ukrain™ (NSC 631570), Vitaxin™ (MEDI 522), and zoledronic acid (Zometa™).

In another embodiment, the additional anti-cancer therapeutic agent is a signal transduction inhibitor (e.g., inhibiting the means by which regulatory molecules that govern the fundamental processes of cell growth, differentiation, and survival communicated within the cell). Signal transduction inhibitors include small molecules, antibodies, and antisense molecules. Signal transduction inhibitors include for example kinase inhibitors (e.g., tyrosine kinase inhibitors or serine/threonine kinase inhibitors) and cell cycle inhibitors. More specifically signal transduction inhibitors include, for example, farnesyl protein transferase inhibitors, EGF inhibitor, ErbB-1 (EGFR) inhibitors, ErbB2 inhibitors, pan-ErbB inhibitors, IGF1R inhibitors, MEK inhibitors, c-Kit inhibitors, FLT-3 inhibitors, K-Ras inhibitors, PI3 kinase inhibitors, JAK inhibitors, STAT inhibitors, Raf kinase inhibitors, Akt inhibitors, mTOR inhibitor, P70S6 kinase inhibitors, inhibitors of the WNT pathway, and multi-targeted kinase inhibitors. Additional examples of signal transduction inhibitors that may be used in conjunction with a compound of Formula (I) or (II) and pharmaceutical compositions described herein include BMS 214662 (Bristol-Myers Squibb), lonafarnib (Sarasar™), pelitrexol (AG 2037), matuzumab (EMD 7200), nimotuzumab (TheraCIM h-R3™), panitumumab (Vectibix™), Vandetanib (Zactima™), pazopanib (SB 786034), ALT 110 (Alteris Therapeutics), BIBW 2992 (Boehringer Ingelheim), and Cervene™ (TP 38). Other examples of signal transduction inhibitors include gefitinib (Iressa™), cetuximab (Erbitux™) erlotinib (Tarceva™), trastuzumab (Herceptin™), sunitinib (Sutent™), imatinib (Gleevec™) tucatinib (Tukysa™), crizotinib (Pfizer), lorlatinib (Pfizer), dacomitinib (Pfizer), bosutinib (Pfizer), gedatolisib (Pfizer), canertinib (CI 1033), pertuzumab (Omnitarg™), lapatinib (Tykerb™), pelitinib (EKB 569), miltefosine (Miltefosin™), BMS 599626 (Bristol-Myers Squibb), Lapuleucel-T (Neuvenge™), NeuVax™ (E75 cancer vaccine), Osidem™ (IDM 1), mubritinib (TAK-165), CP-724,714 (Pfizer), panitumumab (Vectibix™), selumetinib (AstraZeneca), everolimus (Certican™) zotarolimus (Endeavor™), temsirolimus (Torisel™), AP 23573 (ARIAD), VX 680 (Vertex), XL 647 (Exelixis), sorafenib (Nexavar™), LE-AON (Georgetown University), GI-4000 (GlobeImmune), binimetinib, and encorafenib. Other signal transduction inhibitors include ABT 751 (Abbott), alvocidib (flavopiridol), BMS 387032 (Bristol Myers), EM 1421 (Erimos), indisulam (E 7070), seliciclib (CYC 200), BIO 112 (Onc Bio), BMS 387032 (Bristol-Myers Squibb), palbociclib (Pfizer), and AG 024322 (Pfizer).

In another embodiment, the additional anti-cancer therapeutic agent is a classical antineoplastic agent. Classical antineoplastic agents include, but are not limited to, hormonal modulators, such as hormonal, anti-hormonal, androgen agonist, androgen antagonist and anti-estrogen therapeutic agents, histone deacetylase (HDAC) inhibitors, DNA methyltransferase inhibitors, silencing agents or gene activating agents, ribonucleases, proteomics, Topoisomerase I inhibitors, Camptothecin derivatives, Topoisomerase II inhibitors, alkylating agents, antimetabolites, poly(ADP-ribose) polymerase-1 (PARP-1) inhibitor (such as, e.g., talazoparib, olaparib, rucaparib, niraparib, iniparib, veliparib), microtubulin inhibitors, antibiotics, plant derived spindle inhibitors, platinum-coordinated compounds, gene therapeutic agents, antisense oligonucleotides, vascular targeting agents (VTAs), and statins. Examples of classical antineoplastic agents used in combination therapy with a compound of Formula (I) or (II), or a pharmaceutically acceptable salt thereof, optionally with one or more other agents include, but are not limited to, glucocorticoids, such as dexamethasone, prednisone, prednisolone, methylprednisolone, hydrocortisone, and progestins, such as medroxyprogesterone, megestrol acetate (Megace), mifepristone (RU-486), Selective Estrogen Receptor Modulators (SERMs; such as tamoxifen, raloxifene, lasofoxifene, afimoxifene, arzoxifene, bazedoxifene, fispemifene, ormeloxifene, ospemifene, tesmilifene, toremifene, and CHF 4227 (Chiesi)), trilostane, Selective Estrogen-Receptor Downregulators (SERD's; such as fulvestrant), exemestane (Aromasin), anastrozole (Arimidex), atamestane, fadrozole, letrozole (Femara), formestane, gonadotropin-releasing hormone (GnRH; also commonly referred to as luteinizing hormone-releasing hormone [LHRH]) agonists, such as buserelin (Suprefact), goserelin (Zoladex), leuprorelin (Lupron), and triptorelin (Trelstar), abarelix (Plenaxis), cyproterone, flutamide (Eulexin), megestrol, nilutamide (Nilandron), and osaterone, dutasteride, epristeride, finasteride, Serenoa repens, PHL 00801, abarelix, goserelin, leuprorelin, triptorelin, bicalutamide, antiandrogen agents, such as enzalutamide, abiraterone acetate, bicalutamide (Casodex), and combinations thereof. Other examples of classical antineoplastic agents used in combination with a compound of Formula (I) or (II), or a pharmaceutically acceptable salt thereof, include, but are not limited to, suberolanilide hydroxamic acid (SAHA, Merck Inc./Aton Pharmaceuticals), depsipeptide (FR901228 or FK228), G2M-777, MS-275, pivaloyloxymethyl butyrate and PXD-101, Onconase (ranpirnase), PS-341 (MLN-341), Velcade (bortezomib), 9-aminocamptothecin, belotecan, BN-80915 (Roche), camptothecin, diflomotecan, edotecarin, exatecan (Daiichi), gimatecan, 10-hydroxycamptothecin, irinotecan HCl (Camptosar), lurtotecan, Orathecin (rubitecan, Supergen), SN-38, topotecan, camptothecin, 10-hydroxycamptothecin, 9-aminocamptothecin, irinotecan, edotecarin, topotecan, aclarubicin, adriamycin, amonafide, amrubicin, annamycin, daunorubicin, doxorubicin, elsamitrucin, epirubicin, etoposide, idarubicin, galarubicin, hydroxycarbamide, nemorubicin, novantrone (mitoxantrone), pirarubicin, pixantrone, procarbazine, rebeccamycin, sobuzoxane, tafluposide, valrubicin, Zinecard (dexrazoxane), nitrogen mustard N-oxide, cyclophosphamide, AMD-473, altretamine, AP-5280, apaziquone, brostallicin, bendamustine, busulfan, carboquone, carmustine, chlorambucil, dacarbazine, estramustine, fotemustine, glufosfamide, ifosfamide, KW-2170, lomustine, mafosfamide, mechlorethamine, melphalan, mitobronitol, mitolactol, mitomycin C, mitoxatrone, nimustine, ranimustine, temozolomide, thiotepa, and platinum-coordinated alkylating compounds, such as cisplatin, Paraplatin (carboplatin), eptaplatin, lobaplatin, nedaplatin, Eloxatin (oxaliplatin, Sanofi), satraplatin, streptozocin, and combinations thereof.

In still another embodiment, the additional anti-cancer therapeutic agent is a dihydrofolate reductase inhibitors, such as methotrexate and NeuTrexin (trimetresate glucuronate), purine antagonists, such as 6-mercaptopurine riboside, mercaptopurine, 6-thioguanine, cladribine, clofarabine (Clolar), fludarabine, nelarabine, and raltitrexed, pyrimidine antagonists, such as 5-fluorouracil (5-FU), Alimta (premetrexed disodium, LY231514, MTA), capecitabine (Xeloda™) cytosine arabinoside, Gemzar™ (gemcitabine), Tegafur (UFT Orzel or Uforal and including TS-1 combination of tegafur, gimestat and otostat), doxifluridine, carmofur, cytarabine (including ocfosfate, phosphate stearate, sustained release and liposomal forms), enocitabine, 5-azacitidine (Vidaza), decitabine, and ethynylcytidine, and other antimetabolites, such as eflornithine, hydroxyurea, leucovorin, nolatrexed (Thymitaq), triapine, trimetrexate, raltitrexed, AG-014699 (Pfizer Inc.), ABT-472 (Abbott Laboratories), INO-1001 (Inotek Pharmaceuticals), KU-0687 (KuDOS Pharmaceuticals) and GPI 18180 (Guilford Pharm Inc) and combinations thereof.

Other examples of classical antineoplastic cytotoxic agents include, but are not limited to, Abraxane (Abraxis BioScience, Inc.), Batabulin (Amgen), EPO 906 (Novartis), Vinflunine (Bristol-Myers Squibb Company), actinomycin D, bleomycin, mitomycin C, neocarzinostatin (Zinostatin), vinblastine, vincristine, vindesine, vinorelbine (Navelbine), docetaxel (Taxotere™), Ortataxel, paclitaxel (including Taxoprexin a DHA/paclitaxel conjugate), cisplatin, carboplatin, nedaplatin, oxaliplatin (Eloxatin), Satraplatin, Camptosar, capecitabine (Xeloda), oxaliplatin (Eloxatin), Taxotere alitretinoin, Canfosfamide (Telcyta™), DMXAA (Antisoma), ibandronic acid, L-asparaginase, pegaspargase (Oncaspar™), Efaproxiral (Efaproxyn™), bexarotene (Targretin™) tesmilifene, Theratope™ (Biomira), Tretinoin (Vesanoid™), tirapazamine (Trizaone™), motexafin gadolinium (Xcytrin™), Cotara™ (mAb), NBI-3001 (Protox Therapeutics), polyglutamate-paclitaxel (Xyotax™) and combinations thereof. Further examples of classical antineoplastic agents include, but are not limited to, Advexin (ING 201), TNFerade (GeneVec), RB94 (Baylor College of Medicine), Genasense (Oblimersen, Genta), Combretastatin A4P (CA4P), Oxi-4503, AVE-8062, ZD-6126, TZT-1027, atorvastatin, pravastatin, lovastatin, simvastatin, fluvastatin, cerivastatin, rosuvastatin, niacin, amlodipine besylate and atorvastatin calcium, torcetrapib, and combinations thereof.

In another embodiment, the additional anti-cancer therapeutic agent is an epigenetic modulator, for example an inhibitor or EZH2, SMARCA4, PBRM1, ARID1A, ARID2, ARID1B, DNMT3A, TET2, MLL1/2/3, NSD1/2, SETD2, BRD4, DOT1L, HKMTsanti, PRMT1-9, LSD1, UTX, IDH1/2 or BCL6.

In further embodiments, the additional anti-cancer therapeutic agent is an immunomodulatory agent, such as an inhibitor of CTLA-4, PD-1 or PD-L1 (e.g., pembrolizumab, nivolumab or avelumab), LAG-3, TIM-3, TIGIT, 4-1BB, OX40, GITR, CD40, or a CAR-T-cell therapy.

Kit-of-Parts

Inasmuch as it may be desirable to administer a combination of active compounds, for example, for the purpose of treating a particular disease or condition, it is within the scope of the present invention that two or more pharmaceutical compositions, at least one of which contains a compound of Formula (I) or (II), or a pharmaceutically acceptable salt thereof, may conveniently be combined in the form of a kit suitable for coadministration of the compositions. Thus, the kit of the invention includes two or more separate pharmaceutical compositions, at least one of which contains a compound of Formula (I) or (II), or a pharmaceutically acceptable salt thereof, and means for separately retaining said compositions, such as a container, divided bottle, or divided foil packet. An example of such a kit is the familiar blister pack used for the packaging of tablets, capsules, and the like.

The kit of the invention is particularly suitable for administering different dosage forms, for example, oral and parenteral, for administering the separate compositions at different dosage intervals, or for titrating the separate compositions against one another. To assist compliance, the kit typically includes directions for administration and may be provided with a memory aid.

EXAMPLES

In order that this invention may be better understood, the following examples are set forth. These examples are for purposes of illustration only and are not to be construed as limiting the scope of the invention in any manner. Persons skilled in the art will recognize that the chemical reactions described may be readily adapted to prepare a number of other compounds described herein, and alternative methods for preparing the compounds are deemed to be within the scope of this invention. For example, the synthesis of non-exemplified compounds may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds described herein.

In the Examples described below, unless otherwise indicated all temperatures are set forth in degrees Celsius. Reagents were purchased from commercial suppliers such as MilliporeSigma, Alfa Aesar, TCI, etc., and were used without further purification unless otherwise indicated.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was done on a Biotage system (Manufacturer: Dyax Corporation) having a silica gel column or on a silica SepPak cartridge (Waters) (unless otherwise stated). $^1$H NMR spectra were recorded on a Varian instrument operating at 400 MHz. $^1$H-NMR spectra were obtained as $CDCl_3$, $CD_3OD$, $D_2O$, $(CD_3)_2SO$, $(CD_3)_2CO$, $C_6D_6$, $CD_3CN$ solutions (reported in ppm), using tetramethylsilane (0.00 ppm) or residual solvent ($CDCl_3$: 7.26 ppm; $CD_3OD$: 3.31 ppm; $D_2O$: 4.79 ppm; $(CD_3)_2SO$: 2.50 ppm; $(CD_3)_2CO$: 2.05 ppm; $C_6D_6$: 7.16 ppm; $CD_3CN$: 1.94 ppm) as the reference standard. When peak multiplicities are reported, the following abbreviations are used: s (singlet), d (doublet), t (triplet), q (quartet), m (multiplet), br (broadened), dd (doublet of doublets), dt (doublet of triplets). Coupling constants, when given, are reported in Hertz (Hz).

The compounds and intermediates described herein were named using the naming convention provided with ChemDraw Professional, Version 19.0.0.22 (Perkin Elmer Informatics, Inc., Waltham, Mass.).

Every Example or pharmaceutically acceptable salt thereof may be claimed individually or grouped together in any combination with any number of each and every embodiment described herein.

Intermediate Example A

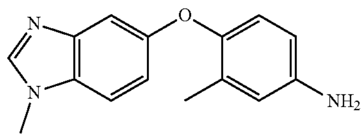 [SMILES: Cc1cc(N)ccc1Oc1ccc2c(c1)ncn2C]

3-methyl-4-((1-methyl-1H-benzo[d]imidazol-5-yl)oxy)aniline

Step A: A solution of 1-fluoro-2-methyl-4-nitrobenzene (1.05 g, 6.75 mmol) and 1-methyl-1H-benzo[d]imidazol-5-ol (1.0 g, 6.75 mmol) in DMF (22 mL) was treated with $Cs_2CO_3$ (4.40 g, 13.5 mmol). The mixture was warmed to 50° C. and stirred for 2 hours. The mixture was cooled to ambient temperature and then diluted with EtOAc. The mixture was then washed with brine (2×), dried over $Na_2SO_4$, filtered and concentrated, to provide 1-methyl-5-(2-methyl-4-nitrophenoxy)-1H-benzo[d]imidazole (1.9 g, quant.). m/z (APCI-pos) $M^+1$=284.1.

Step B: A solution of 1-methyl-5-(2-methyl-4-nitrophenoxy)-1H-benzo[d]imidazole (2.2 g, 7.8 mmol) in MeOH (78 mL) was treated with Palladium hydroxide on carbon (2.0 g, 10 wt %). The mixture was then put through a vacuum/purge cycle three times with hydrogen gas. The mixture was then held under balloon pressure stirring for 5.5 hours. The reaction mixture was purged with Argon and filtered, and the filter cake was washed with MeOH. The filtrate was then concentrated to give 3-methyl-4-((1-methyl-1H-benzo[d]imidazol-5-yl)oxy)aniline (1.5 g, 76%) as a solid that was used directly in the subsequent step. m/z (APCI-pos) $M^+1$=254.1.

Intermediate Example B

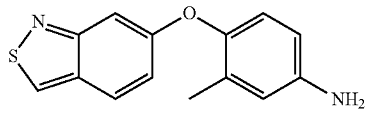

4-(benzo[c]isothiazol-6-yloxy)-3-methylaniline

Step A: Thionyl chloride (28.6 mL, 394.3 mmol) was added to a solution of methanesulfonamide (25 g, 263 mmol) in benzene (45.0 mL), and the mixture was refluxed at 90° C. for 16 hours. Benzene was then removed under reduced pressure. The residue was distilled at 99-100° C. at 0.3 mm Hg pressure to afford N-(oxo-$\lambda^4$-sulfanylidene) methanesulfonamide (28 g, 75% yield) as a liquid. m/z ($M^+$)=141.0 (GC-MS).

Step B: N-(Oxo-$\lambda^4$-sulfanylidene)methanesulfonamide (20.6 g, 146 mmol, in 20 mL of benzene) to a solution of 5-methoxy-2-methylaniline (5 g, 36.4 mmol) in benzene (20 mL), which was followed by the addition of pyridine (5.9 mL, 72.9 mmol, in 10 mL benzene). The mixture was refluxed at 90° C. for 48 hours. Benzene was then removed by evaporation under reduced pressure, and the residue was diluted with ice water and DCM. The organic layer was separated, washed with brine, dried over anhydrous $Na_2SO_4$, filtered, and concentrated under reduced pressure to provide the crude material, which was purified by silica gel column chromatography (10-12% EtOAc/hexane) to afford 6-methoxybenzo[c]isothiazole (1.2 gm, 20% yield) as an oil. $^1H$ NMR (400 MHz, $(CD_3)_2SO$) δ9.05 (s, 1H), 7.60 (d, J=9.2 Hz, 1H), 7.07 (s, 1H), 6.94 (dd, J=9.2, 1.2 Hz, 2H); m/z ($M^+$)=165.1.

Step C: $BBr_3$ (2.85 mL, 30.12 mmol) was added to a stirred solution of 6-methoxybenzo[c]isothiazole (1 g, 6.02 mmol) in DCM (8 mL) at 0° C., and the mixture was stirred at 0° C. for 2 hours. The volatilities were evaporated under reduced pressure, and the reaction mixture was diluted with ice water and DCM. The organic layer was separated, washed with saturated $NaHCO_3$ solution, dried over anhydrous $Na_2SO_4$, filtered, and concentrated under reduced pressure to provide the crude product. The crude product was mixed with another batch (batch size 200 mg), and the combined material was purified by silica gel column chromatography (40-45% EtOAc/hexane) to afford benzo[c]isothiazol-6-ol (850 mg, 78% yield) as a solid. $^1H$ NMR (400 MHz, $(CD_3)_2SO$) δ 10.37 (s, 1H), 9.56 (s, 1H), 7.72 (d, J=9.2 Hz, 1H), 6.92-6.91 (m, 2H); m/z ($M^+$)=151.0.

Step D: A solution of benzo[c]isothiazol-6-ol (0.05 g, 0.33 mmol) and 1-fluoro-2-methyl-4-nitrobenzene (0.062 g, 0.4 mmol) in DMF (3.3 mL) was treated with $Cs_2CO_3$ (0.22 g, 0.66 mmol). The mixture was warmed to 100° C. and stirred for 17 hours. The mixture was cooled to ambient temperature and diluted with EtOAc and $H_2O$. The aqueous layer was extracted with EtOAc (2×). The organics were washed with brine (3×), dried over $Na_2SO_4$, and concentrated to give 6-(2-methyl-4-nitrophenoxy)benzo[c]isothiazole (0.095, quant.). m/z (APCI-pos) $M^+1$=287.

Step E: A solution of 6-(2-methyl-4-nitrophenoxy)benzo[c]isothiazole (0.33 g, 5.1 mmol) in THF (5.1 mL) was treated with aqueous ammonium chloride (5.1 mL) and cooled to 0° C. Zinc dust (0.22 g, 3.3 mmol) was added to the mixture. The mixture was warmed to ambient temperature. After 48 hours, the mixture was diluted with $H_2O$ and EtOAc, and filtered. The filter cake was washed with EtOAc. The aqueous layer was extracted with EtOAc (3×), the organics were washed with brine, dried over $Na_2SO_4$, and concentrated. The product was purified via normal phase chromatography (0 to 40% EtOAc/hexanes). Fractions containing the desired product were pooled and concentrated to provide 4-(benzo[c]isothiazol-6-yloxy)-3-methylaniline (0.053 g, 20%). m/z (APCI-pos) $M^+1$=257.1.

Intermediate Example C

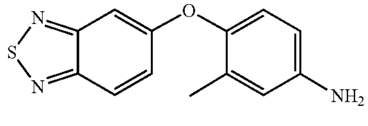 [SMILES: Cc1cc(N)ccc1Oc1ccc2csnc2c1]

4-(benzo[c][1,2,5]thiadiazol-5-yloxy)-3-methylaniline

Step A: A solution of benzo[c][1,2,5]thiadiazol-5-ol (0.25 g, 1.64 mmol) and 1-fluoro-2-methyl-4-nitrobenzene (0.305 g, 1.97 mmol) in DMA (8.2 mL) was treated with $Cs_2CO_3$ (1.07 g, 3.29 mmol). The mixture was heated to 50° C. and stirred for 6 hours. The mixture was diluted with brine, extracted with EtOAc (2×), dried over $Na_2SO_4$ and concentrated. The product was purified via normal phase chromatography (5 to 75% EtOAc/hexanes). Fractions containing the desired product were pooled and concentrated to provide 5-(2-methyl-4-nitrophenoxy)benzo[c][1,2,5]thiadiazole (0.326 g, 69.1%) as a solid.

Step B: A solution of 5-(2-methyl-4-nitrophenoxy)benzo[c][1,2,5]thiadiazole (0.326 g, 1.13 mmol) in THF (10 mL) and aqueous saturated ammonium chloride (10 mL) was treated with zinc dust (0.742 g, 11.3 mmol). The mixture stirred at ambient temperature for 1.5 hours. The mixture was diluted with $H_2O$ and EtOAc and filtered. The filtrated was extracted with EtOAc (2×), combined organics were dried over $Na_2SO_4$ and concentrated to give 4-(benzo[c][1,2,5]thiadiazol-5-yloxy)-3-methylaniline (0.291 g, 99.7%) as a solid. m/z (APCI-pos) $M^{+}1$=257.1.

Intermediate Example D

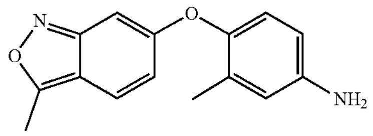 [SMILES: Cc1cc(N)ccc1Oc1ccc2c(C)onc2c1]

3-methyl-4-((3-methylbenzo[c]isoxazol-6-yl)oxy)aniline

Step A: A solution of tert-butyl (4-hydroxy-3-methylphenyl)carbamate (0.175 g, 0.784 g) and 1-(4-fluoro-2-nitrophenyl)ethan-1-one (0.144 g, 0.784 mmol) in DMF (7.8 mL was treated with $Cs_2CO_3$ (0.511 g, 1.57 mmol). The mixture was heated to 50° C. and stirred for 17 hours. The mixture was diluted with $H_2O$ and DCM. The aqueous layer was extracted with DCM (3×), the combined organics were washed with brine, dried over $Na_2SO_4$, and concentrated to give tert-butyl (4-(4-acetyl-3-nitrophenoxy)-3-methylphenyl)carbamate (0.300 g, 99.1%) as a solid that was used in subsequent step without purification. m/z (APCI-pos) $M^{-}$Boc=287.1.

Step B: A solution of tert-butyl (4-(4-acetyl-3-nitrophenoxy)-3-methylphenyl)carbamate (0.0814 g, 0.211 mmol) in 1:1 EtOAc/MeOH (2 mL) was treated with dichloro-12-stannane dihydrate (0.143 g, 0.632 mmol). The mixture was stirred at ambient temperature for 19 hours. The mixture was diluted with aqueous saturated $NaHCO_3$. The aqueous layer was extracted with EtOAc (3×). The combined organics were washed with brine, dried over $Na_2SO_4$, and concentrated to give tert-butyl (3-methyl-4-((3-methylbenzo[c]isoxazole-6-yl)oxy)phenyl)carbamate (0.0792 g, quant.) as a solid. m/z (APCI-pos) M+1=355.2.

Step C: Trifluoroacetic acid (1.19 mL, 15.5 mmol) was added to a solution of tert-butyl (3-methyl-4-((3-methylbenzo[c]isoxazol-6-yl)oxy)phenyl)carbamate (0.11 g, 0.31 mmol) in DCM (3.1 mL). The reaction mixture was stirred at ambient temperature for 90 minutes. The reaction mixture was diluted with aqueous 10% potassium carbonate and stirred for 10 minutes. The aqueous layer was extracted with DCM (3×). The combined organics were washed with brine, dried over $Na_2SO_4$, and concentrated to give 3-methyl-4-((3-methylbenzo[c]isoxazol-6-yl)oxy)aniline (0.020, 25.3%). m/z (APCI-pos) $M^{+}1$=255.1.

Intermediate Example E

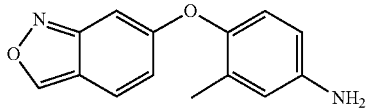 [SMILES: Cc1cc(N)ccc1Oc1ccc2conc2c1]

4-(benzo[c]isoxazol-6-yloxy)-3-methylaniline

Step A: A mixture of tert-butyl (4-hydroxy-3-methylphenyl)carbamate (0.51 g, 2.3 mmol), 4-fluoro-2-nitrobenzaldehyde (0.39 g, 2.3 mmol), DMF (23 mL) and cesium carbonate (1.5 g, 4.6 mmol) was heated to 60° C. for 2 hours and allowed to cool to ambient temperature. The mixture was diluted with water/brine and extracted with EtOAc. The organics were washed with brine, dried over sodium sulfate, and concentrated under reduced pressure. Flash chromatography (hexane:EtOAc, 5-15%) afforded tert-butyl (4-(4-formyl-3-nitrophenoxy)-3-methylphenyl)carbamate (0.31 g, 36%). m/z (APCI-pos) $M^{-}$Boc=273.1.

Step B: A mixture of tert-butyl (4-(4-formyl-3-nitrophenoxy)-3-methylphenyl)carbamate (0.31 g, 0.82 mmol), $SnCl_2 \cdot 2\ H_2O$ (0.55 g, 2.5 mmol), and methanol/EtOAc 1:1 (8 mL) was stirred at room temperature for 20 hours. The mixture was diluted with 10% aqueous potassium carbonate and extracted with EtOAc. The organics were dried over sodium sulfate and concentrated under reduced pressure. Flash chromatography (5% EtOAc/Hexanes to 50% EtOAc/hexanes) afforded tert-butyl (4-(benzo[c]isoxazol-6-yloxy)-3-methylphenyl)carbamate (0.19 g, 67%). m/z (APCI-pos) M+1=341.1.

Step C: A mixture of tert-butyl (4-(benzo[c]isoxazol-6-yloxy)-3-methylphenyl)carbamate (0.19 g, 0.55 mmol), DCM (5 mL) and TFA (20 eq.) was stirred at room temperature for 30 minutes. The mixture was then diluted with EtOAc and washed with 10% aqueous potassium carbonate. The organics were dried over sodium sulfate and concentrated under reduced pressure to give 4-(benzo[c]isoxazol-6-yloxy)-3-methylaniline (0.12 g, 94%). m/z (APCI-pos) $M^{+}1$=241.1.

Intermediate Example F

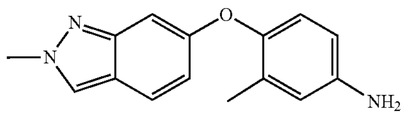 [SMILES: Cc1cc(N)ccc1Oc1ccc2cn(C)nc2c1]

3-methyl-4-((2-methyl-2H-indazol-6-yl)oxy)aniline

Step A: Trimethylorthoformate (20.4 mL, 186.6 mmol) and $H_2SO_4$ (1 mL) were added to a stirred solution of 1H-indazol-6-ol (5 g, 37.3 mmol) in toluene (150 mL). The reaction mixture was refluxed for 16 hours. The reaction mixture was cooled down to ambient temperature and poured into water, and the mixture was extracted with EtOAc. The combined organic layers were dried over anhydrous $Na_2SO_4$, filtered, and concentrated under reduced pressure. The crude product was purified by silica gel column chromatography (50% EtOAc/Hexane) to afford 2-methyl-2H-indazol-6-ol (1.2 g, 22% yield) as a solid. m/z (esi) $M^+1$=148.8.

Step B: 1-Fluoro-2-methyl-4-nitrobenzene (523 mg, 3.37 mmol) and $K_2CO_3$ (933 mg, 6.74 mmol) were added to a stirred solution of 2-methyl-2H-indazol-6-ol (500 mg, 3.37 mmol) in DMSO (15 mL). The reaction mixture was heated at 80° C. for 6 hours. The reaction was quenched with water and extracted with EtOAc. The combined organic layers were dried over anhydrous $Na_2SO_4$, filtered, and concentrated under reduced pressure. The crude product was purified by silica gel column chromatography (50% EtOAc/Hexane) to afford 2-methyl-6-(2-methyl-4-nitrophenoxy)-2H-indazole (800 mg, 84% yield) as a solid. m/z (esi) $M^+1$=284.

Step C: Pd/C (50 mg, 10% wet) was added to a stirred solution of 2-methyl-6-(2-methyl-4-nitrophenoxy)-2H-indazole (500 mg, 1.76 mmol) in THF (10 mL) and purged with $N_2$ for 10 minutes. The reaction mixture was stirred under $H_2$ balloon atmosphere at room temperature for 16 hours. After completion of the reaction, the reaction mixture was filtered through a Celite® bed, washed with DCM, and the filtrate was concentrated under reduced pressure to afford 3-methyl-4-((2-methyl-2H-indazol-6-yl)oxy)aniline (crude) as a solid, which was used directly without further purification. m/z (esi) $M^+1$=253.9.

Intermediate Example G

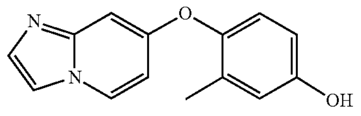 [SMILES: Cc1cc(O)ccc1Oc1ccn2ccnc2c1]

4-(imidazo[1,2-a]pyridin-7-yloxy)-3-methylphenol

Step A: Tribasic potassium phosphate (2.15 g, 10.2 mmol), copper(I) iodide (0.193 g, 1.02 mmol), 4-(benzyloxy)-2-methylphenol (2.17 g, 10.2 mmol), 7-bromoimidazo[1,2-a]pyridine (1.0 g, 5.08 mmol), dimethylglycine (0.314 g, 3.05 mmol), and DMSO (10.2 mL) were charged to a 20 mL glass microwave vessel equipped with a stir bar. The mixture was stirred at 90° C. overnight. The mixture was cooled to room temperature and then diluted with $H_2O$ and $NH_4Cl$. The aqueous layer was extracted with $CHCl_3$ (3×). The combined organic extracts were washed with brine (5×), dried over $Na_2SO_4$, and concentrated in vacuo to yield an oil. Purification by column chromatography (Redisep 40 g, 50-100% ethyl acetate/hexanes) delivered 7-(4-(benzyloxy)-2-methylphenoxy)imidazo[1,2-a]pyridine (1.09 g, 65%). m/z (APCI-pos) $M^+1$=331.1.

Step B: 7-(4-(Benzyloxy)-2-methylphenoxy)imidazo[1,2-a]pyridine (1.09 g, 3.45 mmol), dihydroxypalladium (0.8 g, 1.14 mmol), and MeOH (34.5 mL, 3.45 mmol) were charged to a 100 mL round bottom flask equipped with a stir bar. The mixture was placed under an $N_2$ atmosphere and stirred at room temperature. The mixture was purged with $H_2$ via a double-walled balloon and subline for 2 minutes. The nitrogen inlet was removed, and the mixture was stirred at room temperature for 2 hours. The mixture was sparged with nitrogen, diluted with MeOH, and filtered. Organics were concentrated in vacuo and purified by column chromatography (Redisep 40 g, 0-20% MeOH/DCM) to furnish 4-(imidazo[1,2-a]pyridin-7-yloxy)-3-methylphenol (0.284 g, 34%). m/z (APCI-pos) $M^+1$=241.1.

Intermediate Example H

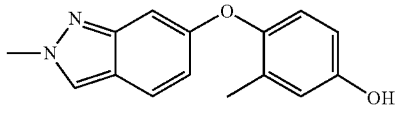 [SMILES: Cc1cc(O)ccc1Oc1ccc2cn(C)nc2c1]

3-methyl-4-((2-methyl-2H-indazol-6-yl)oxy)phenol

3-Methyl-4-((2-methyl-2H-indazol-6-yl)oxy)phenol was prepared according to Example 23, Steps A and B, substituting 6-bromo-2-methyl-2H-indazole for 5-bromo-1-methyl-1H-benzo[d]imidazole in Step A. m/z (APCI-pos) M+1=255.1.

Intermediate Example I

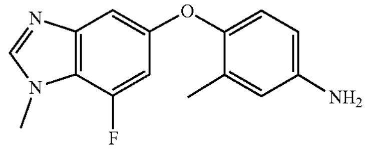 [SMILES: Cc1cc(N)ccc1Oc1cc(F)c2c(c1)ncn2C]

4-((7-fluoro-1-methyl-1H-benzo[d]imidazol-5-yl)oxy)-3-methylaniline

Step A: Powdered potassium carbonate (0.96 g, 1.5 mmol) was added to a mixture of 5-bromo-7-fluoro-1H-benzo[d]imidazole (1.0 g, 4.7 mmol) in DMA (23 mL), followed by MeI (0.86 g, 1.3 mmol). This mixture was stirred at room temperature for 48 hours. The mixture was diluted with water/bine and extracted with EtOAc. The organics were washed with brine, dried over sodium sulfate, and concentrated under reduced pressure. The product was purified via reverse phase column chromatography (5 to 85% ACN/$H_2O$ with 1% TFA buffer). Fractions containing the regioisomers were pooled separately, then treated with 10% aqueous $K_2CO_3$. The mixtures were then extracted with 20% IPA/$CH_2Cl_2$, the extracts were combined, dried over $Na_2SO_4$, filtered, and concentrated to afford two regioisomers, with the desired 5-bromo-7-fluoro-1-methyl-1H-benzo[d]imidazole eluting first (0.19 g, 17%). m/z (APCI-pos) $M^+1$=255.1. The undesired regioisomer was isolated in 23% yield (0.25 g).

Step B: 4-((7-Fluoro-1-methyl-1H-benzo[d]imidazol-5-yl)oxy)-3-methylaniline was isolated by following the procedure according to Example 24, Step A, substituting tert-butyl (4-hydroxy-3-methylphenyl)carbamate for 4-(benzyloxy)-2-methylphenol and 5-bromo-7-fluoro-1-methyl-1H-benzo[d]imidazole for 5-bromo-1-methyl-1H-benzo[d]imidazole. m/z (APCI-pos) $M^+1$=272.1.

Intermediate Example J

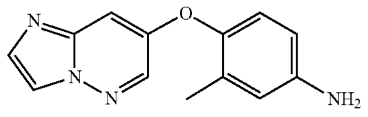 [SMILES: Cc1cc(N)ccc1Oc1cnn2ccnc2c1]

4-(imidazo[1,2-b]pyridazin-7-yloxy)-3-methylaniline

A solution of 7-chloroimidazo[1,2-b]pyridazine (0.36 g, 2.35 mmol), tert-butyl (4-hydroxy-3-methylphenyl)carbamate (0.58 g, 2.61 mmol), and cesium carbonate (2.55 g, 7.83 mmol) in DMF (5.22 mL) was heated to 100° C. for 18 hours. Upon cooling to ambient temperature, the mixture was partitioned between EtOAc and $NH_4Cl$ (saturated, aqueous). The phases were separated, and the aqueous phase was further extracted with EtOAc (2×). The combined organic extracts were washed with brine, dried over anhydrous sodium sulfate, filtered, and concentrated in vacuo. Purification by C18 reverse phase HPLC (10-95% water/MeCN with 0.1% TFA buffer) provided 4-(imidazo[1,2-b]pyridazin-7-yloxy)-3-methylaniline (0.99 g, 11% yield). m/z (APCI-pos) $M^{+}1$=241.1.

Intermediate Example K

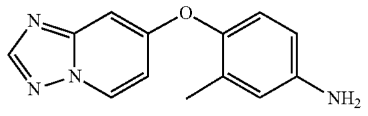 [SMILES: Cc1cc(N)ccc1Oc1ccn2ncnc2c1]

4-([1,2,4]triazolo[1,5-a]pyridin-7-yloxy)-3-methylaniline

Step A: TEA (0.25 mL, 1.65 mmol) was added to a stirred solution of 6-chloropyrido[3,2-d]pyrimidin-4-ol (150 mg, 0.83 mmol) in toluene (3.0 mL), followed by the addition of phosphoryl chloride (0.39 mL, 4.13 mmol). The mixture was stirred at 120° C. for 2 hours. After the completion of the reaction, the reaction mixture was evaporated to dryness. The crude product was neutralized with a saturated aqueous $NaHCO_3$ solution at 0° C. The reaction mixture was extracted with EtOAc, and the combined organic layers were washed with brine. The combined organic layers were dried over anhydrous $Na_2SO_4$, filtered, and concentrated under reduced pressure to afford 4,6-dichloropyrido[3,2-d]pyrimidine (122 mg, crude), which was used in the subsequent reaction without further purification. m/z (esi) $M^{+}1$=199.0.

Step B: $K_2CO_3$ (484.7 mg, 3.51 mmol) was added to a stirred solution of [1,2,4]triazolo[1,5-a]pyridin-7-ol hydrochloride (200 mg, 1.17 mmol) in DMSO:THF (1:2) solution (4.5 mL), and the mixture was stirred at room temperature for 5 minutes. 1-Fluoro-2-methyl-4-nitrobenzene (181.3 mg, 1.17 mmol) was added to the mixture, and the mixture was stirred at 80° C. for 4 hours. After completion of the reaction, the reaction mixture was extracted with EtOAc, and the combined organic layers were washed with cold water followed by brine. The combined organic layers were dried over anhydrous $Na_2SO_4$, filtered, and concentrated under reduced pressure. The crude product was purified by silica gel column chromatography (35% EtOAc/hexane) to afford 7-(2-methyl-4-nitrophenoxy)-[1,2,4]triazolo[1,5-a]pyridine (220 mg, 70% yield) as a solid. m/z (esi) $M^{+}1$=271.2.

Step C: Zn powder (675.5 mg, 10.3 mmol) was added to the stirred solution of 7-(2-methyl-4-nitrophenoxy)-[1,2,4]triazolo[1,5-a]pyridine (280 mg, 1.03 mmol) in THF (5.0 mL) at 0° C. $NH_4Cl$ (552.7 mg, 10.3 mmol) in water (1.0 mL) was added to the solution at 0° C., and the reaction mixture was stirred at room temperature for 30 minutes. After completion of the reaction, the reaction mixture was filtered through a sintered funnel, and filtrate was concentrated under reduced pressure to provide the crude product. The crude product was dissolved in EtOAc and washed with water and then brine. The combined organic layers were dried over anhydrous $Na_2SO_4$, filtered, and concentrated under reduced pressure to afford 4-([1,2,4]triazolo[1,5-a]pyridin-7-yloxy)-3-methylaniline, which was used in the next step without further purification. m/z (esi) $M^{+}1$=241.2.

Intermediate Example L

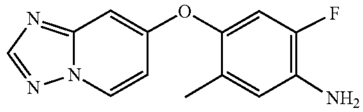 [SMILES: Cc1cc(N)c(F)cc1Oc1ccn2ncnc2c1]

4-([1,2,4]triazolo[1,5-a]pyridin-7-yloxy)-2-fluoro-5-methylaniline

Step A: To a stirred solution of 7-chloro-[1,2,4]triazolo[1,5-a]pyridine (300 mg, 1.95 mmol) and 4-bromo-5-fluoro-2-methylphenol (600.79 mg, 2.93 mmol) in DMA (6 mL) was added $Cs_2CO_3$ (1.27 g, 3.90 mmol) and CsF (593.0 mg, 3.90 mmol). The vessel was sealed, and the reaction mixture heated at 150° C. for 3 hours. The reaction mixture was then diluted with water and the mixture was extracted with EtOAc. The combined organic layers were dried over $Na_2SO_4$ filtered and concentrated to get the crude product which was purified by column chromatography (15% EtOAc-Hexane) to afford 7-(4-bromo-5-fluoro-2-methylphenoxy)-[1,2,4]triazolo[1,5-a]pyridine (350 mg, 56% yield) as a solid. m/z (esi) M+1=321.9.

Step B: To a stirred solution of 7-(4-bromo-5-fluoro-2-methylphenoxy)-[1,2,4]triazolo[1,5-a]pyridine (350 mg, 1.09 mmol) in dioxane (3 mL) was added Boc-$NH_2$ (191 mg, 1.63 mmol) and $Cs_2CO_3$ (708 mg, 2.17 mmol) and the mixture was degassed for 5 minutes under argon atmosphere. Finally, $Pd_2dba_3$ (199 mg, 0.21 mmol) and X-Phos (103.6 mg, 0.21 mmol) were added; the mixture was degassed for another 5 minutes and then heated at 100° C. for 16 hours. The reaction mixture was then diluted with EtOAc, and the mixture filtered through a Celite® pad. The organic filtrate was washed with brine, dried over $Na_2SO_4$, filtered, and concentrated to get the crude product which was purified by silica gel column chromatography (3% EtOAc/Hex) to afford tert-butyl (4-([1,2,4]triazolo[1,5-a]pyridin-7-yloxy)-2-fluoro-5-methylphenyl)carbamate (210 mg, 54% yield) as a solid. m/z (esi) M+1=359.0.

Step C: To a stirred solution of tert-butyl (4-([1,2,4]triazolo[1,5-a]pyridin-7-yloxy)-2-fluoro-5-methylphenyl)carbamate (210 mg, 0.58 mmol) in DCM (2 mL) was added TFA (0.6 mL) under an argon atmosphere. The reaction mixture was stirred at 0° C. for 2 hours. The reaction mixture was then concentrated, the residue was then diluted with 5% MeOH-DCM and washed with $H_2O$ followed by a saturated $NaHCO_3$ solution. The organic layer was dried over $Na_2SO_4$, filtered, and concentrated to get 4-([1,2,4]triazolo[1,5-a]pyridin-7-yloxy)-2-fluoro-5-methylaniline (150 mg crude), which was used for next step without further purification. m/z (esi) M+1=258.8.

Intermediate Example M

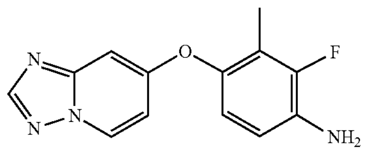 [SMILES: Cc1c(Oc2ccn3ncnc3c2)ccc(N)c1F]

4-([1,2,4]triazolo[1,5-a]pyridin-7-yloxy)-2-fluoro-3-methylaniline

Step A: To a stirred solution of 7-chloro-[1,2,4]triazolo[1,5-a]pyridine (400 mg, 2.61 mmol) and 4-bromo-3-fluoro-2-methylphenol (504 mg, 2.48 mmol) in DMA (4 mL) was added $Cs_2CO_3$ (1.7 g, 5.22 mmol) and CsF (790 mg, 5.22 mmol) and the mixture was stirred at 150° C. for 4 hours. The reaction mixture was diluted with water and extracted with EtOAc. The combined organic layers were washed with water, followed by brine, then dried and concentrated. The crude product was purified by silica gel column chromatography (15-20% EtOAC-Hexane) to afford 7-(4-bromo-3-fluoro-2-methylphenoxy)-[1,2,4]triazolo[1,5-a]pyridine (350 mg, 42% yield) as a solid. m/z (esi) M+1=321.7.

Step B: To a stirred solution 7-(4-bromo-3-fluoro-2-methylphenoxy)-[1,2,4]triazolo[1,5-a]pyridine (500 mg, 1.55 mol) and tert-butyl carbamate (547 mg, 4.67 mmol) in dioxane (5 mL) was added $Cs_2CO_3$ (1.51 g, 4.67 mmol) and then degassed with argon for 5 min. Xphos (148 mg, 0.31 mmol) and $Pd_2(dba)_3$ (285 mg, 0.31 mmol) were added and the mixture was degassed for another 5 minutes. The reaction mixture was stirred at 100° C. for 16 hours in a sealed tube. The reaction mixture was filtered through a Celite® pad and washed with DCM. The filtrate was concentrated, and the crude residue was purified by silica column chromatography (20-30% EtOAC-Hexane) to afford tert-butyl (4-([1,2,4]triazolo[1,5-a]pyridin-7-yloxy)-2-fluoro-3-methylphenyl)carbamate (400 mg, 71% yield) as a gummy liquid. m/z (esi) M+1=358.6.

Step C: To a stirred solution of tert-butyl (4-([1,2,4]triazolo[1,5-a]pyridin-7-yloxy)-2-fluoro-3-methylphenyl)carbamate (400 mg, 1.11 mmol) in DCM (5 mL) was added TFA (3 mL) at 0° C. and stirred for 1 hour. The reaction mixture was then concentrated, and the crude residue was diluted with saturated $NaHCO_3$ solution and extracted with 10% MeOH-DCM twice. The combined organic layers were dried and concentrated to afford 4-([1,2,4]triazolo[1,5-a]pyridin-7-yloxy)-2-fluoro-3-methylaniline (260 mg, 90% yield) as a solid. m/z (esi) M+1=259.0.

Intermediate Example N

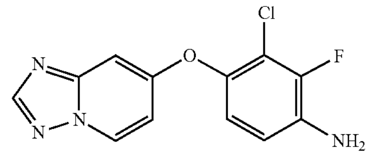 [SMILES: Nc1ccc(Oc2ccn3ncnc3c2)c(Cl)c1F]

4-([1,2,4]triazolo[1,5-a]pyridin-7-yloxy)-3-chloro-2-fluoroaniline

Step A: To a stirred solution of [1,2,4]triazolo[1,5-a]pyridin-7-ol (50 mg, 0.37 mmol) and 2-chloro-1,3-difluoro-4-nitrobenzene (71.7 mg, 0.37 mmol) in DMSO (1 mL) was added $K_2CO_3$ (102.2 mg, 0.74 mmol) and the mixture was stirred at 100° C. for 4 hours. The reaction mixture was then diluted with water and extracted with EtOAc. The combined organic layers were washed with water, followed by brine, dried, filtered, and concentrated. The crude product was purified by silica gel column chromatography to afford mixture of isomers of 7-(2-chloro-3-fluoro-4-nitrophenoxy)-[1,2,4]triazolo[1,5-a]pyridine (50 mg, mixture of isomers) as a solid. m/z (esi) M+1=309.0 & 309.2.

Step B: To a stirred solution of a mixture of isomers of 7-(2-chloro-3-fluoro-4-nitrophenoxy)-[1,2,4]triazolo[1,5-a]pyridine (150 mg, 0.49 mmol) in THF:$H_2O$ (5:1) (6 mL) at 0° C. was added Zn (331.2 mg, 4.87 mmol) and $NH_4Cl$ (263 mg, 4.87 mmol). The mixture was stirred at room temperature for 2 hours. The mixture was filtered through a sintered funnel, and the solid was washed with EtOAc. The filtrate was washed with water, dried, filtered and concentrated to get the crude product which was purified by silica gel column chromatography (0-2% MeOH/DCM) to get 4-([1,2,4]triazolo[1,5-a]pyridin-7-yloxy)-3-chloro-2-fluoroaniline (120 mg, 88% yield) as a solid. m/z (esi) M+1=278.9.

Intermediate Example O

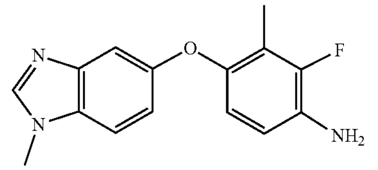 [SMILES: Cc1c(Oc2ccc3c(c2)ncn3C)ccc(N)c1F]

2-fluoro-3-methyl-4-((1-methyl-1H-benzo[d]imidazol-5-yl)oxy)aniline

Step A: To a stirred solution of 2-chloro-4-fluoro-3-methyl-1-nitrobenzene (10.0 g, 52.7 mmol) and 1-methyl-1H-benzo[d]imidazol-5-ol (7.8 g, 52 mmol) in DMA (45 ml) was added $Cs_2CO_3$ (42.8 g, 131.9 mmol) and the mixture was stirred at 80° C. for 2 hours. The reaction mixture was diluted with EtOAc, washed with water, followed by brine. The organic layer was dried over anhydrous $Na_2SO_4$, filtered, and concentrated to afford the crude material which was purified by silica gel column chromatography (0-2% MeOH-DCM) to afford 5-(3-chloro-2-methyl-4-nitrophenoxy)-1-methyl-1H-benzo[d]imidazole (14.5 g, 85% yield) as a solid. m/z (Esi) M+1=317.4.

Step B: To a stirred solution of 5-(3-chloro-2-methyl-4-nitrophenoxy)-1-methyl-1H-benzo[d]imidazole (2.0 g, 6.3 mmol) in DMSO (25.2 mL) was added CsF (9.5 g, 63.1 mmol) and stirred for 16 hours at 110° C. The reaction mixture was diluted with EtOAc, washed with water, followed by brine. The organic layer was dried over $Na_2SO_4$, filtered and concentrated. The crude product was purified by silica gel column chromatography (0-1% MeOH-DCM) to afford 5-(3-fluoro-2-methyl-4-nitrophenoxy)-1-methyl-1H-benzo[d]imidazole (1.4 g, impure) as a solid. m/z (esi) M+1=301.6.

Step C: To a stirred solution of 5-(3-fluoro-2-methyl-4-nitrophenoxy)-1-methyl-1H-benzo[d]imidazole (1.4 g, 4.65 mmol) in MeOH (10.0 mL) was added Pd/C (900 mg). The reaction mixture was purged with $H_2$ and then stirred for 3 hours under a Hydrogen atmosphere. The reaction mixture was filtered through Celite®. The filtrate was concentrated, and the crude product was purified by column chromatography (0-1% MeOH-DCM) then triturated with diethyl ether to afford 2-fluoro-3-methyl-4-((1-methyl-1H-benzo[d]imidazol-5-yl)oxy)aniline (800 mg, 47% in 2 steps yield). $^1$H NMR (400 MHz, DMSO-$d_6$) δ 8.12 (s, 1H), 7.49 (d, J=8.6 Hz, 1H), 6.96-6.86 (m, 2H), 6.62 (t, J=9.3 Hz, 1H), 6.55 (d, J=8.8 Hz, 1H), 4.92 (s, 2H), 3.81 (s, 3H), 2.02 (s, 3H). m/z (esi) M+1=272.09.

Intermediate Example P

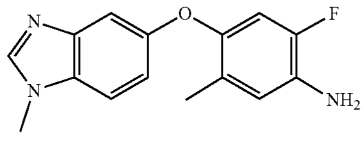 [SMILES: Cc1cc(N)c(F)cc1Oc1ccc2c(c1)ncn2C]

2-fluoro-5-methyl-4-((1-methyl-1H-benzo[d]imidazol-5-yl)oxy)aniline

Step A: To a stirred solution of 1-chloro-5-fluoro-4-methyl-2-nitrobenzene (10 g, 52.743 mmol) and 1-methyl-1H-benzo[d]imidazol-5-ol (7.8 g, 52.7 mmol) in DMA (500 ml) was added $Cs_2CO_3$ (34.4 g, 105.485 mmol) and the mixture was heated to 80° C. for 2 hours. The mixture was cooled to RT and diluted with EtOAc. The mixture was washed with water, followed by brine, then dried over $Na_2SO_4$, filtered and concentrated. The crude product was triturated with 10% EtOAc/Hexanes and the solid was dried under reduced pressure to get 5-(5-chloro-2-methyl-4-nitrophenoxy)-1-methyl-1H-benzo[d]imidazole (14 g, 84% yield) as a solid. m/z (esi) M+1=317.4.

Step B: To a stirred solution of 5-(5-chloro-2-methyl-4-nitrophenoxy)-1-methyl-1H-benzo[d]imidazole (5.0 g, 15.8 mmol) in DMSO (64 mL) was added CsF (23.9 g, 157.7 mmol) and stirred at 110° C. for 16 hours. The reaction mixture was then cooled to room temperature and diluted with EtOAc. The mixture was then washed with water, followed by brine, then dried over $Na_2SO_4$, filtered and concentrated. The crude product was purified with silica gel column chromatography (1-2% MeOH/DCM) to get 5-(5-fluoro-2-methyl-4-nitrophenoxy)-1-methyl-1H-benzo[d] imidazole (3.2 g, 67% yield) as a solid. m/z (esi) M+1=302.0.

Step C: To a stirred solution of 5-(5-fluoro-2-methyl-4-nitrophenoxy)-1-methyl-1H-benzo[d]imidazole (2.0 g, 6.645 mmol) in MeOH (20 mL) and THF (2 mL) was added Pd/C (1.0 g). The mixture was then stirred at room temperature under hydrogen atmosphere for 4 hours. The reaction mixture was then filtered through a celite bed and washed with MeOH. The filtrate was concentrated under reduced pressure and the crude material was purified by silica gel column chromatography (2-3% MeOH/DCM) to get 2-fluoro-5-methyl-4-((1-methyl-1H-benzo[d]imidazol-5-yl)oxy)aniline (1.2 g, 67% yield) as a solid. $^1$H NMR (400 MHz, DMSO-$d_6$) b 8.13 (s, 1H), 7.50 (d, J=8.6 Hz, 1H), 6.96-6.86 (m, 2H), 6.67 (dd, J=11.0, 15.2 Hz, 2H), 4.92 (s, 2H), 3.81 (s, 3H), 2.00 (s, 3H). m/z (esi) M+1=272.20.

Intermediate Example Q

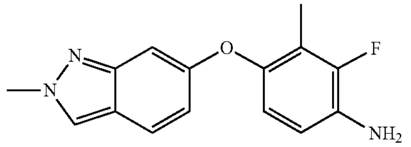 [SMILES: Cc1c(Oc2ccc3cn(C)nc3c2)ccc(N)c1F]

2-fluoro-3-methyl-4-((2-methyl-2H-indazol-6-yl)oxy)aniline

Step A: To a stirred solution of 6-methoxy-1H-indazole (1.0 g, 6.75 mmol) in DMF (7.0 mL) was added $K_2CO_3$ (1.8 g, 13.5 mmol) and MeI (0.9 mL, 13.5 mmol) at 0° C., and the mixture was stirred for 1 hour at 50° C. The cooled reaction mixture was diluted with EtOAc, washed with water, followed by brine. The organic layer was dried over anhydrous $Na_2SO_4$, filtered, and concentrated under reduced pressure to afford the crude product which was purified by silica gel silica gel column chromatography (10-25% EtOAc-Hexane) to afford 6-methoxy-2-methyl-2H-indazole (350 mg, 32% yield) as a liquid. m/z (esi) M+1=162.9.

Step B: To a solution of 6-methoxy-2-methyl-2H-indazole (1.4 g, 8.6 mmol) in DCM (8 mL) at 0° C. was added $BBr_3$ in DCM (17.0 mL, 17.2 mmol) under an Argon atmosphere and the reaction mixture was stirred for 3 hours at room temperature. The reaction mixture was then concentrated, and the reaction quenched by the addition of a saturated $NaHCO_3$ solution. The mixture was then extracted with EtOAc, and the combined organic layers were dried over anhydrous $Na_2SO_4$, filtered, and concentrated to afford the crude product which was purified by column chromatography (10-50% EtOAc/Hexane) to afford 2-methyl-2H-indazol-6-ol (1.0 g, 78% yield) as a solid. m/z (esi) M+1=148.8.

Step C: To a stirred solution of 2-methyl-2H-indazol-6-ol (2.7 g, 18.24 mmol) in DMSO (16 mL) were added $K_2CO_3$ (7.5 g, 54.73 mmol) and 1,3-difluoro-2-methyl-4-nitrobenzene (3.47 g, 20.07 mmol). The reaction mixture was stirred for 2 hours at 80° C. The reaction mixture was concentrated under reduced pressure and the crude reaction mixture was then extracted with EtOAc. The combined organic phases were washed with water and brine, dried over anhydrous $Na_2SO_4$, filtered, and concentrated under reduced pressure. The crude product was purified by silica gel column chromatography (20-50% EtOAc/Hexane) to afford 6-(3-fluoro-2-methyl-4-nitrophenoxy)-2-methyl-2H-indazole (4.0 g, mixture of two positional isomers), as a solid. m/z (esi) M+1=302.2.

Step D: To a stirred solution of 6-(3-fluoro-2-methyl-4-nitrophenoxy)-2-methyl-2H-indazole (4.0 g, 13.3 mmol) in THF (40.0 mL) was added Zn powder (8.7 g, 132.9 mmol) at 0° C., followed by addition of $NH_4Cl$ (7.1 g, 132.9 mmol) in water (10 mL). The reaction mixture was stirred at room temperature for 2 hours. The reaction mixture was filtered, and the filtrate concentrated under reduced pressure to get the crude mixture, which was extracted with EtOAc, washed with water and brine. The combined organic layers were dried over anhydrous $Na_2SO_4$, filtered, and concentrated under reduced pressure. The crude product was purified by prep-SFC (45-55% $C_{02}$: (0.3% Isopropylamine in MeOH), 25 g/min) to afford the desired isomer of 2-fluoro-3-methyl-4-((2-methyl-2H-indazol-6-yl)oxy)aniline (900 mg, 18% yield in 2 steps), as a solid. m/z (esi) M+1=272.0.

Intermediate Example R

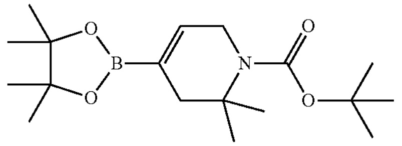 [SMILES: CC(C)(C)OC(=O)N1CC=C(B2OC(C)(C)C(C)(C)O2)CC1(C)C]

tert-butyl 2,2-dimethyl-4-(4,4,5,5-tetramethyl-1,3,2-dioxaborolan-2-yl)-3,6-dihydropyridine-1(2H)-carboxylate Step A: A round bottom flask equipped with a stir bar was charged with tert-butyl 2,2-dimethyl-4-oxopiperidine-1-carboxylate (500 mg, 2.20 mmol) and 22 mL of dry THF under a nitrogen atmosphere. This mixture was chilled to −78° C. and LiHMDS (2.86 mL, 1M in THF) was added by syringe, and the mixture was stirred at −78° C. for 1 hour. At this point, a THF solution of phenyl triflamide (1.02 g, 2.86 mmol, in 10 mL of THF) was added by syringe. Once the addition was complete, the mixture was stirred at −78° C. for 15 minutes, then allowed to warm to room temperature. After two hours at room temperature, the mixture was quenched with saturated ammonium chloride solution, diluted with water, extracted with EtOAc, extracts dried over sodium sulfate and concentrated under reduced pressure. Flash chromatography purification afforded tert-butyl 2,2-dimethyl-4-(((trifluoromethyl)sulfonyl)oxy)-3,6-dihydropyridine-1(2H)-carboxylate (477 mg, 60%). $^1$H NMR (400 MHz, CDCl3) δ 5.77 (ddd, J=3.7, 2.6, 1.1 Hz, 1H), 4.07 (dt, J=3.7, 2.6 Hz, 2H), 2.39 (td, J=2.5, 1.1 Hz, 2H), 1.49 (s, 6H), 1.46 (s, 9H).

Step B: A pressure tube containing tert-butyl 2,2-dimethyl-4-(((trifluoromethyl)sulfonyl)oxy)-3,6-dihydropyridine-1(2H)-carboxylate (475 mgs, 1.32 mmol) was charged with 4,4,4',4',5,5,5',5'-octamethyl-2,2'-bi(1,3,2-dioxaborolane) (839 mgs, 3.30 mmol), dioxane (13 mL), KOAc (389 mgs, 3.97 mmol) and $PdCl_2(dppf)\text{-}CH_2Cl_2$ adduct (108 mg, 0.132 mmol). The mixture was purged with argon for a few minutes, tube sealed, and the mixture warmed to 100° C. for 16 hours, then allowed to cool to room temperature. The mixture was diluted with EtOAc/water and filtered through GF/F filter paper. The filtrate was extracted with EtOAc, extracts dried over sodium sulfate and concentrated under reduced pressure. Flash chromatography purification afforded tert-butyl 2,2-dimethyl-4-(4,4,5,5-tetramethyl-1,3,2-dioxaborolan-2-yl)-3,6-dihydropyridine-1(2H)-carboxylate (187 mg, 42%). $^1$H NMR (400 MHz, CDCl3) δ 6.68-6.61 (m, 1H), 3.93 (dt, J=3.8, 1.8 Hz, 2H), 2.21 (d, J=1.6 Hz, 2H), 1.46 (s, 9H), 1.38 (s, 6H), 1.27 (s, 12H).

Intermediate Example S

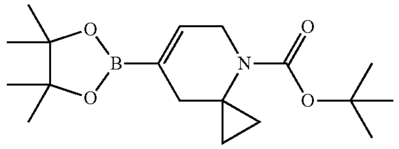 [SMILES: CC(C)(C)OC(=O)N1CC=C(B2OC(C)(C)C(C)(C)O2)CC12CC2]

tert-butyl 7-(4,4,5,5-tetramethyl-1,3,2-dioxaborolan-2-yl)-4-azaspiro[2.5]oct-6-ene-4-carboxylate Step A: A round bottom flask equipped with a stir bar and nitrogen inlet was charged with tert-butyl 7-oxo-4-azaspiro[2.5]octane-4-carboxylate (576 mgs, 2.56 mmol) and 25 mL of dry THF. This mixture was chilled to −78° C. and LiHMDS (3.32 mL, 3.32 mmol, 1M THF solution) was then added by syringe. Once the addition was complete the mixture was stirred at −78° C. for 45 minutes. At this point a THF solution of 1,1,1-trifluoro-N-phenyl-N-((trifluoromethyl)sulfonyl)methanesulfonamide (1.19 g, 3.32 mmol, in 10 mL of THF) was added, mixture stirred at −78° C. for 10 minutes, then allowed to warm to room temperature. The mixture was then quenched with saturated ammonium chloride solution, diluted with water, extracted with EtOAc, extracts dried over sodium sulfate and concentrated under reduced pressure. The resulting crude was purified by flash chromatography to give tert-butyl 7-(((trifluoromethyl)sulfonyl)oxy)-4-azaspiro[2.5]oct-6-ene-4-carboxylate (746 mg, 82%). $^1$H NMR (400 MHz, CDCl3) δ 5.87 (tt, J=3.2, 1.4 Hz, 1H), 4.07 (s, 2H), 2.35 (s, 2H), 1.01-0.93 (m, 2H), 0.76 (s, 2H).

Step B: A pressure tube containing tert-butyl 7-(((trifluoromethyl)sulfonyl)oxy)-4-azaspiro[2.5]oct-6-ene-4-carboxylate (745 mg, 2.08 mmol) was charged with dioxane (21 mL), 4,4,4',4',5,5,5',5'-octamethyl-2,2'-bi(1,3,2-dioxaborolane) (1.06 g, 4.17 mmol), KOAc (614 mgs, 6.25 mmol) and $PdCl_2(dppf)\text{-}CH_2Cl_2$ adduct (170 mg, 4.17 mmol). This mixture was purged with argon for a few minutes, tube sealed, and the mixture warmed to 100° C. for 16 hours, then allowed to cool to room temperature. The mixture was diluted with EtOAc/water and filtered through GF/F filter paper. The filtrate was extracted with EtOAc, extracts dried over sodium sulfate and concentrated under reduced pressure. Flash chromatography purification afforded tert-butyl 7-(4,4,5,5-tetramethyl-1,3,2-dioxaborolan-2-yl)-4-azaspiro[2.5]oct-6-ene-4-carboxylate (557 mg, 80%). 1H NMR (400 MHz, CDCl3) δ 6.54 (s, 1H), 4.07-4.00 (m, 2H), 2.14 (s, 2H), 1.44 (s, 9H), 1.26 (d, J=1.5 Hz, 12H), 0.90-0.82 (m, 2H), 0.66-0.58 (m, 2H).

Intermediate Example T

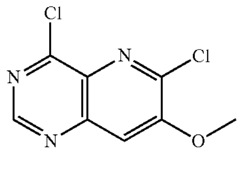

4,6-dichloro-7-methoxypyrido[3,2-d]-pyrimidine

Step A: 3-Amino-6-chloro-5-methoxypicolinic acid (4.9 g, 24 mmol) and formamide (31 mL) were charged to a 125 mL round bottom flask equipped with a stir bar. The mixture was heated to 150° C. for 30 hours. The reaction was diluted with water and solids were collected via vacuum filtration. The solid was washed with water, ethyl acetate, and dried overnight on high vacuum at 100° C. to furnish 6-chloro-7-methoxypyrido[3,2-d]pyrimidin-4-ol (3.6 g, 70%), carried on crude. m/z (APCI-pos) $M^{+}1=212.1$.

Step B: 6-Chloro-7-methoxypyrido[3,2-d]pyrimidin-4-ol (0.28 g, 1.3 mmol) and Hunig's base (0.34 g, 2.7 mmol) were added to $POCl_3$ (6.6 mL, 1.32 mmol) in a 25 mL round bottom flask equipped with a stir bar. The mixture was heated to 110° C. for 2.5 hours and then concentrated in vacuo and diluted with EtOAc. Organics were washed twice with saturated aqueous sodium bicarbonate, dried over $Na_2SO_4$, filtered, and concentrated in vacuo. The material was purified by column chromatography (0 to 40% EtOAc in heptane) to furnish 4,6-dichloro-7-methoxypyrido[3,2-d]pyrimidine (0.16 g, 53%). m/z (APCI-pos) $M^{+}1=230.1$.

Intermediate Example U

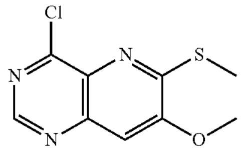

4-chloro-7-methoxy-6-(methylthio)pyrido[3,2-d]pyrimidine

In a 50 mL recovery flask equipped with a stir bar was charged Hunig's base (0.78 mL, 4.5 mmol), 7-methoxy-6-(methylthio)pyrido[3,2-d]pyrimidin-4-ol (0.50 g, 2.2 mmol), and $POCl_3$ (11 mL, 2.2 mmol). The mixture was equipped with a cold water condenser and heated to 110° C. for 1.5 hours. Volatiles were removed in vacuo and the mixture was constituted in ethyl acetate. Organics were washed ×3 with saturated aqueous sodium bicarbonate, dried over sodium sulfate, and concentrated in vacuo. The crude residue was purified over 24 g silica cartridge, eluting with a gradient of 0% to 20% EtOAc in heptane to afford 4-chloro-7-methoxy-6-(methylthio)pyrido[3,2-d]pyrimidine (0.30 g, 56%). m/z (APCI-pos) $M^{+}1=242.1$.

Intermediate Example V

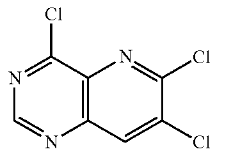 [SMILES: Clc1cc2ncnc(Cl)c2nc1Cl]

4,6,7-trichloropyrido[3,2-d]pyrimidine

Synthesized in the manner of Intermediate Example T, substituting 3-amino-5,6-dichloropicolinic acid in place of 3-amino-6-chloro-5-methoxypicolinic acid in Step A to furnish 4,6,7-trichloropyrido[3,2-d]pyrimidine (50 mg, 13%). $^{1}H$ NMR (400 MHz, CDCl3) δ 9.12 (s, 1H), 8.48 (s, 1H).

Intermediate Example W

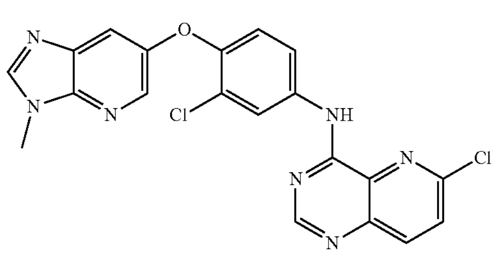 [SMILES: Cn1cnc2cc(Oc3ccc(Nc4ncnc5ccc(Cl)nc45)cc3Cl)cnc21]

6-chloro-N-(3-chloro-4-((3-methyl-3H-imidazo[4,5-b]pyridin-6-yl)oxy)phenyl)pyrido[3,2-d]pyrimidin-4-amine Step A: 3-Methyl-3H-imidazo[4,5-b]pyridin-6-ol (431 mg, 1 Eq, 2.89 mmol) was added to a stirred solution of 2-chloro-1-fluoro-4-nitrobenzene (507 mg, 1 Eq, 2.89 mmol) and $Cs_2CO_3$ (1.88 g, 2 Eq, 5.78 mmol) in DMSO (29 mL) at 65° C. for 16 hours, then allowed to cool to room temperature. The reaction was partitioned between Water and EtOAc. The organic layer was washed with water/brine, dried over sodium sulfate, filtered, and concentrated in vacuo to give 6-(2-chloro-4-nitrophenoxy)-3-methyl-3H-imidazo[4,5-b]pyridine (756 mg, 86%). m/z (APCI-pos) M+1=305.20.

Step B: Zinc (1.62 g, 10 Eq, 24.8 mmol) was added to a stirred solution of 6-(2-chloro-4-nitrophenoxy)-3-methyl-3H-imidazo[4,5-b]pyridine (756 mg, 1 Eq, 2.48 mmol) and saturated ammonium chloride (12 mL) solution in THF (12 mL). This mixture was stirred at room temperature for 16 hours. The reaction was partitioned between water and EtOAc, and filtered through GF/F filter paper. The filtrate was extracted with EtOAc, dried over sodium sulfate, filtered, and concentrated in vacuo to give 3-chloro-4-((3-methyl-3H-imidazo[4,5-b]pyridin-6-yl)oxy)aniline (127 mg, 19%). m/z (APCI-pos) M+1=275.20.

Step C: 3-Chloro-4-((3-methyl-3H-imidazo[4,5-b]pyridin-6-yl)oxy)aniline (55 mg, 1 Eq, 0.20 mmol) was added to a stirred solution of 4,6-dichloropyrido[3,2-d]pyrimidine (40 mg, 1 Eq, 0.20 mmol) in 2-propanol (2 mL). This mixture was warmed to 65° C. for 3 hours, then allowed to cool to room temperature. The mixture was diluted with DCM, washed with 10% aqueous k-carb, dried over sodium sulfate, and concentrated under reduced pressure to give 6-chloro-N-(3-chloro-4-((3-methyl-3H-imidazo[4,5-b]pyridin-6-yl)oxy)phenyl)pyrido[3,2-d]pyrimidin-4-amine (77.5 mg, 88%). m/z (APCI-pos) M+1=438.1.

Intermediate Example X

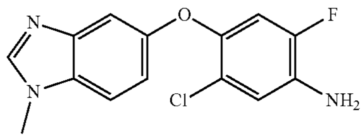 [SMILES: Cn1cnc2cc(Oc3cc(F)c(N)cc3Cl)ccc21]

5-chloro-2-fluoro-4-((1-methyl-1H-benzo[d]imidazol-5-yl)oxy)aniline

Step A: To a stirred solution of 1-methyl-1H-benzo[d]imidazol-5-ol (5.00 g, 33.8 mmol) and 1-chloro-2,4-difluoro-5-nitrobenzene (7.82 g, 40.5 mmol) in ACN (50 mL), was added DIPEA (17.62 mL, 101.4 mmol) and stirred at room temperature for 48 hours. The reaction mixture was filtered, and the residue was washed with diethyl ether then extracted with EtOAc. The organic phase was washed with brine, dried over $Na_2SO_4$, filtered, and concentrated under reduced pressure to get pure 5-(2-chloro-5-fluoro-4-nitrophenoxy)-1-methyl-1H-benzo[d]imidazole (2.90 gm, 27% yield) as a solid. m/z (esi) M+1=322.02.

Step B: To a mixture of 5-(2-chloro-5-fluoro-4-nitrophenoxy)-1-methyl-1H-benzo[d]imidazole (3.5 g, 10.90 mmol) in THF:$H_2O$ (4:1; 35 mL) was added Zn (6.11 g, 109 mmol) and $NH_4Cl$ (5.83 g, 109 mmol) at 0° C. The mixture was stirred the mixture at room temperature for 2 hours. The reaction mixture was diluted by EtOAc, filtered through pad of Celite®, filtrate was washed with brine, dried over $Na_2SO_4$, concentrated under reduced pressure to get 5-chloro-2-fluoro-4-((1-methyl-1H-benzo[d]imidazol-5-yl)oxy)aniline (1.8 g, 57% yield) as a solid. The structure of the compound was confirmed by HMBC. $^1H$ NMR (400 MHz, DMSO-d6) δ 8.16 (s, 1H), 7.52 (d, J=8.7 Hz, 1H), 7.00 (d, J=2.0 Hz, 1H), 6.98-6.88 (m, 3H), 5.29 (d, J=7.1 Hz, 2H), 3.82 (s, 3H). m/z (esi) M+1=292.18.

Intermediate Example Y

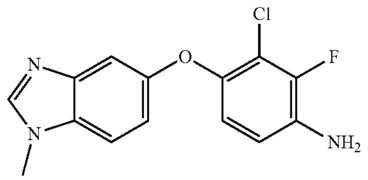 [SMILES: Cn1cnc2cc(Oc3ccc(N)c(F)c3Cl)ccc21]

3-chloro-2-fluoro-4-((1-methyl-1H-benzo[d]imidazol-5-yl)oxy)aniline

Step A: Cesium carbonate (776 mg, 2.38 mmol) was added to a stirred solution of 2,3-dichloro-1-fluoro-4-nitrobenzene (250 mg, 1.19 mmol) and 1-methyl-1H-benzo[d]imidazol-5-ol (176 mg, 1.19 mmol) in DMA (11.9 mL). The mixture was warmed to 80° C. and stirred for 2 hours before cooling to room temperature. The reaction was partitioned between $H_2O$ and EtOAc. The organic layer was washed with $H_2O$ and brine (2×), dried over sodium sulfate, filtered, and concentrated. The crude residue was purified via column chromatography, eluting with 10% MeOH in $CH_2Cl_2$ to afford 5-(2,3-dichloro-4-nitrophenoxy)-1-methyl-1H-benzo[d]imidazole (299 mg). m/z (APCI-pos) M+1=338.00.

Step B: In an oven-dried vial, 5-(2,3-dichloro-4-nitrophenoxy)-1-methyl-1H-benzo[d]imidazole (200 mg, 591 μmol) and cesium fluoride (359 mg, 2.37 mmol) were suspended in dry DMF under nitrogen. The reaction mixture was stirred at 100° C. for 4 hours before cooling to room temperature. The reaction was diluted with chloroform, and the solids filtered off. The filtrate was washed with $NaHCO_3$ and $H_2O$, dried over sodium sulfate, filtered, and concentrated. The crude residue was purified via column chromatography, eluting with a gradient of 1 to 8% (MeOH/$CH_2Cl_2$) to afford 5-(2-chloro-3-fluoro-4-nitrophenoxy)-1-methyl-1H-benzo[d]imidazole (95.8 mg). m/z (esi) M+1=322.0.

Step C: Pearlman's catalyst (13 mg) was added to a stirred solution of 5-(2-chloro-3-fluoro-4-nitrophenoxy)-1-methyl-1H-benzo[d]imidazole (30 mg, 93 μmol) in methanol (0.93 mL). The reaction mixture was subjected to a balloon of hydrogen for 1 hour at 45° C. The mixture was purged with nitrogen, diluted with methanol, and filtered through Celite® to give 3-chloro-2-fluoro-4-((1-methyl-1H-benzo[d]imidazol-5-yl)oxy)aniline (27 mg). m/z (APCI-pos) M+1=292.05.

Intermediate Example Z

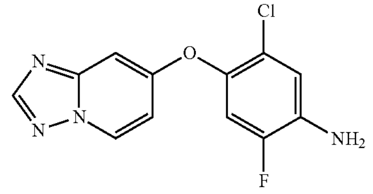 [SMILES: Nc1cc(Cl)c(Oc2ccn3ncnc3c2)cc1F]

4-([1,2,4]triazolo[1,5-a]pyridin-7-yloxy)-5-chloro-2-fluoroaniline

Step A: To a stirred solution of [1,2,4]triazolo[1,5-a]pyridin-7-ol (10 g, 51.82 mmol) and 1-chloro-2,4-difluoro-5-nitrobenzene (7 gm, 51.82 mmol) in DMF (50 mL) was added DIPEA (27 mL, 155.46 mmol) and stirred at 25° C. for 7 hours. After completion of reaction, it was diluted with EtOAc and was washed with water, brine, dried over $Na_2SO_4$, filtered, and concentrated under reduced pressure. The crude product was purified with silica gel column chromatography (0-20% EtOAc/Hexane) to get a mixture of 7-(2-chloro-5-fluoro-4-nitrophenoxy)-[1,2,4]triazolo[1,5-a]pyridine compound and 7-(4-chloro-5-fluoro-2-nitrophenoxy)-[1,2,4]triazolo[1,5-a]pyridine (11.0 gm, 69% yield) as a solid. m/z (esi) M+1=309.0.

Step B: To a stirred solution of 7-(2-chloro-5-fluoro-4-nitrophenoxy)-[1,2,4]triazolo[1,5-a]pyridine and 7-(4-chloro-5-fluoro-2-nitrophenoxy)-[1,2,4]triazolo[1,5-a]pyridine (11 g, 35.71 mmol) in THF:$H_2O$ (120 mL) was added Zn (23.21 g, 357.13 mmol) dust and $NH_4Cl$ (19.10 g, 357.13 mmol) and the reaction was allowed to stir at room temperature for 2 hours. After completion of the reaction, it was filtered through a bed of Celite®, and the filtrate was washed with water and extracted using EtOAc. The organic layer was washed with brine, dried over $Na_2SO_4$ filtered and concentrated. The crude product was purified by silica gel column chromatography (20-65% EtOAc/Hexane) followed by silica gel column chromatography (0-1.5 MeOH/DCM) to get 4-([1,2,4]triazolo[1,5-a]pyridin-7-yloxy)-5-chloro-2-fluoroaniline (4.60 g, 63% yield) as a solid. $^1H$ NMR (400 MHz, DMSO-d6) δ 8.90 (d, J=7.2 Hz, 1H), 8.39 (s, 1H), 7.27 (d, J=11.4 Hz, 1H), 7.03-6.94 (m, 2H), 6.82 (d, J=2.4 Hz, 1H), 5.52 (d, J=6.2 Hz, 2H). m/z (esi) M+1=279.15.

Intermediate Example AB

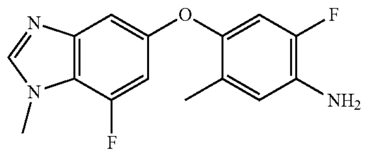 [SMILES: Cc1cc(N)c(F)cc1Oc1cc(F)c2c(c1)ncn2C]

2-fluoro-4-((7-fluoro-1-methyl-1H-benzo[d]imidazol-5-yl)oxy)-5-methylaniline

Step A: To a stirred solution of 5-bromo-1,2-difluoro-3-nitrobenzene (8 g, 33.61 mmol) and methyl amine (84.04 mL, 168.07 mmol) in THF (15 mL) in a sealed round bottom flask was added DIPEA (11.71 mL, 67.23 mmol), and the mixture was stirred at 60° C. for 16 hours. After completion, the reaction mixture was concentrated to afford 4-bromo-2-fluoro-N-methyl-6-nitroaniline (7.1 g, 85% yield) as a solid.

Step B: To a stirred solution of 4-bromo-2-fluoro-N-methyl-6-nitroaniline (5.1 g, 20.47 mmol) in THF (42 mL) and $H_2O$ (8 mL) was added Zn powder (13.38 g, 204.78 mmol) and $NH_4Cl$ (10.95 g, 204.78 mmol). The reaction mixture was stirred at room temperature for 2 hours. After completion, the reaction mixture was filtered through a pad of Celite® and washed with EtOAc. The organic layer of the filtrate was separated and dried over anhydrous $Na_2SO_4$, filtered and concentrated. The crude product was purified by silica gel column chromatography (1% MeOH/DCM) to afford 4-bromo-6-fluoro-N1-methylbenzene-1,2-diamine (3.8 g, 85% yield) as a solid. m/z (esi) M+1=219.1.

Step C: Ethyl orthoformate (6.83 mL, 41.08 mmol) and PTSA (35 mg, 0.20 mmol) were added to a mixture of 4-bromo-6-fluoro-N1-methylbenzene-1,2-diamine (4.5 g, 20.54 mmol) in toluene (50 mL) under argon, and the resulting solution was heated at reflux for 2 hours. The cooled reaction mixture was concentrated, and the residue was purified by silica gel column chromatography (1% MeOH-DCM) to afford 5-bromo-7-fluoro-1-methyl-1H-benzo[d]imidazole (3.8 g, 82% yield) as a solid. m/z (esi) M+1=229.2.

Step D: To a stirred solution of 5-bromo-7-fluoro-1-methyl-1H-benzo[d]imidazole (6.5 g, 28.37 mmol) and 4,4,4',4',5,5,5',5'-octamethyl-2,2'-bi(1,3,2-dioxaborolane) (14.41 g, 56.75 mmol) in dioxane (80 mL) were added KOAc (5.57 g, 56.75 mmol) and degassed for 5 minutes under argon atmosphere. Finally, $Pd(dppf)Cl_2 \cdot DCM$ (3.47 g, 4.25 mmol) was added, degassed for another 5 minutes, and heated at 90° C. for 5 hours. After completion, the reaction mixture was filtered through a pad of Celite®, and the filtrate was concentrated. The crude material was diluted with EtOAc and washed with water, followed by brine, dried over $Na_2SO_4$, filtered, and concentrated under reduced pressure. The crude material was purified by silica gel column chromatography (1% MeOH-DCM) to afford 7-fluoro-1-methyl-5-(4,4,5,5-tetramethyl-1,3,2-dioxaborolan-2-yl)-1H-benzo[d]imidazole (5.9 g, 75% yield) as a solid. m/z (esi) M+1=276.9.

Step E: To a stirred solution of 7-fluoro-1-methyl-5-(4,4,5,5-tetramethyl-1,3,2-dioxaborolan-2-yl)-1H-benzo[d]imidazole (5.5 g, 19.91 mmol) in THF/$H_2O$ (1:1) (100 mL) was added sodium perborate tetrahydrate (15.32 g, 99.59 mmol), and the reaction mixture was stirred at room temperature for 4 hours. After completion, reaction mixture was concentrated. The crude material was dissolved in ethyl acetate and washed with water, followed by saturated aqueous sodium chloride. The organic layer was dried over sodium sulfate, filtered, and concentrated to afford 7-fluoro-1-methyl-1H-benzo[d]imidazol-5-ol (3.0 g crude), which was used in the next step without further purification.

Step F: To a stirred solution of 7-fluoro-1-methyl-1H-benzo[d]imidazol-5-ol (4.5 g, 27.08 mmol) and 1,5-difluoro-2-methyl-4-nitrobenzene (4.65 g, 29.79 mmol) in DMSO (50 mL) was added $K_2CO_3$ (11.21 g, 81.24 mmol) and stirred at room temperature for 4 hours. After completion of the reaction, it was diluted with EtOAc, washed with water, followed by brine, dried over $Na_2SO_4$, filtered, and concentrated under reduced pressure. The crude material was purified by silica gel column chromatography (1% MeOH-DCM) to afford mixture of 7-fluoro-5-(5-fluoro-2-methyl-4-nitrophenoxy)-1-methyl-1H-benzo[d]imidazole and other regio-isomer (7.2 g, mixture of isomers) as a solid. m/z (esi) M+1=319.8.

Step G: To a stirred solution of 7-fluoro-5-(5-fluoro-2-methyl-4-nitrophenoxy)-1-methyl-1H-benzo[d]imidazole and other regio-isomer (mixture of isomer) (250 mg, 0.78 mmol) in THF (4 mL) and $H_2O$ (1 mL) were added Zn powder (510.33 mg, 7.80 mmol), $NH_4Cl$ (417.52 mg, 7.80 mmol). The reaction mixture was stirred at room temperature for 2 hours. After completion, the reaction mixture filtered through a pad of Celite® and washed with EtOAc. The organic layer was separated, dried over with anhydrous $Na_2SO_4$, filtered and concentrated. The crude material was purified by reverse phase with Prep-HPLC (30-95% ACN: water (20 mM ammonium bicarbonate)) to afford 2-fluoro-4-((7-fluoro-1-methyl-1H-benzo[d]imidazol-5-yl)oxy)-5-methylaniline (50 mg, 22% yield in 2 steps) as a solid. $^1H$ NMR (400 MHz, MeOD) δ 8.18 (s, 1H), 6.79 (dd, J1=1.84 Hz, J2=12.36 Hz, 1H), 6.69 (d, J=9.8 Hz, 1H), 6.53-6.49 (m, 2H), 4.05 (s, 3H), 1.91 (s, 3H). m/z (esi) M+1=289.8.

Intermediate Example AC

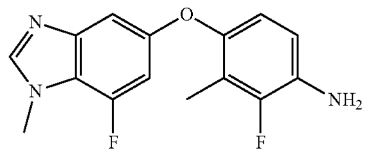 [SMILES: Cc1c(Oc2cc(F)c3c(c2)ncn3C)ccc(N)c1F]

2-fluoro-4-((7-fluoro-1-methyl-1H-benzo[d]imidazol-5-yl)oxy)-3-methylaniline

Step A: To a stirred solution of 7-fluoro-1-methyl-1H-benzo[d]imidazol-5-ol (200 mg, 1.35 mmol) and 1,3-difluoro-2-methyl-4-nitrobenzene (261 mg, 1.35 mmol) in DMSO (10 mL) was added $K_2CO_3$ (373 mg, 2.70 mmol) in a sealed tube and stirred at room temperature for 2 hours. After completion of the reaction, it was diluted with EtOAc and was washed with water, followed by brine, dried over $Na_2SO_4$, filtered and concentrated. The crude product was purified with silica gel column chromatography (0-22% EtOAc/Hexane) to get 7-fluoro-5-(3-fluoro-2-methyl-4-nitrophenoxy)-1-methyl-1H-benzo[d]imidazole along with the other regio-isomer. $^1H$ NMR and LC/MS showed the material was a mixture of both the regio-isomers. Proceeded to next step without further purification (300 mg, mixture of isomers) as a solid. m/z (esi) M+1=319.9.

Step B: To a stirred solution of 7-fluoro-5-(3-fluoro-2-methyl-4-nitrophenoxy)-1-methyl-1H-benzo[d]imidazole along with other regio-isomer (300 mg, 0.94 mmol) in THF:$H_2O$ (4:1) (5 mL) was added Zn dust (611.15 mg, 9.40 mmol) and $NH_4Cl$ (502.93 mg, 9.40 mmol), and the reaction was allowed to stir at 25° C. for 2 hours. After completion of the reaction, it was filtered through a bed of Celite®, and the filtrate was washed with EtOAc. The organic layer of the filtrate was washed with brine, dried over $Na_2SO_4$, filtered and concentrated. The crude product was purified by reverse phase chromatography with Prep-HPLC (Xterra C18 (250×19 mm, 10p), 30-95% ACN:water (20 mM Ammonium Bicarbonate), 16 mL/min) to get 2-fluoro-4-((7-fluoro-1-methyl-1H-benzo[d]imidazol-5-yl)oxy)-3-methylaniline (70 mg, 26% yield 2 steps) as a solid. The structure of desired isomer was confirmed by HMBC. $^1H$ NMR (400 MHz, DMSO-d6) δ 8.13 (s, 1H), 6.80-6.57 (m, 4H), 4.97 (d, J=8.6 Hz, 2H), 3.93 (s, 3H), 2.00 (s, 3H). m/z (esi) M+1=290.1.

Intermediate Example AD

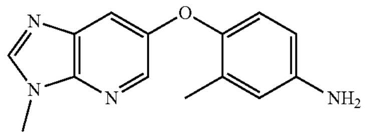 [SMILES: Cc1cc(N)ccc1Oc1cnc2c(c1)ncn2C]

3-methyl-4-((3-methyl-3H-imidazo[4,5-b]pyridin-6-yl)oxy)aniline

Step A: In a sealed tube was combined 3-methyl-6-(4,4,5,5-tetramethyl-1,3,2-dioxaborolan-2-yl)-3H-imidazo[4,5-b]pyridine (2.5 g, 9.65 mmol), sodium perborate tetrahydrate (7.42 g, 48.24 mmol), THF (36 mL) and water (36 mL) to give a solution. The reaction was stirred at 25° C. for 4 hours and then concentrated. The resulting crude material was dissolved in ethyl acetate and washed with water, followed by saturated aqueous sodium chloride. The organic layer was dried over sodium sulfate, filtered, and concentrated to afford 3-methyl-3H-imidazo[4,5-b]pyridin-6-ol (300 mg). The aqueous layers were then concentrated to dryness, and the resulting solids were treated with tetrahydrofuran and vigorous stirring for 3 hours. The mixture was then filtered to afford an additional 3-methyl-3H-imidazo[4,5-b]pyridin-6-ol (1 g). This material was used in the next step without further purification. (1.3 g, crude) as solid. m/z (esi) M+1=150.0.

Step B: To a stirred solution of 1-fluoro-2-methyl-4-nitrobenzene (1.5 g, 9.68 mmol) and 3-methyl-3H-imidazo[4,5-b]pyridin-6-ol (1.44 g, 9.68 mmol) in DMSO (10 mL) was added $K_2CO_3$ (4.01 g, 29.03 mmol) and stirred at 80° C. for 4 hours. After completion of the reaction, it was diluted with EtOAc and was washed with water, followed by brine, then dried over $Na_2SO_4$, filtered, and concentrated under reduced pressure. The crude was purified with silica gel column chromatography (0-20% EtOAc/Hexane) to get 3-methyl-6-(2-methyl-4-nitrophenoxy)-3H-imidazo[4,5-b]pyridine (1.8 g, 65% yield, 2 steps) as a solid. m/z (esi) M+1=285.0.

Step C: To a stirred solution of 3-methyl-6-(2-methyl-4-nitrophenoxy)-3H-imidazo[4,5-b]pyridine (2 g, 7.04 mmol) in THF:$H_2O$ (4:1) (30 mL) was added Zn dust (4.58 g, 70.42 mmol) and $NH_4Cl$ (3.77 mg, 70.42 mmol), and the reaction was allowed to stir at room temperature for 2 hours. After completion of the reaction, it was filtered through a bed of Celite®, and the Celite® was washed with EtOAc and water. The organic layer of the filtrate was washed with brine, dried over $Na_2SO_4$, filtered and concentrated. The crude was purified by silica gel column chromatography (1-2% MeOH/DCM) to get 3-methyl-4-((3-methyl-3H-imidazo[4,5-b]pyridin-6-yl)oxy)aniline (1.6 g, 89% yield) as a solid. $^1H$ NMR (400 MHz, DMSO-d6) δ 8.36 (s, 1H), 8.12 (d, J=2.1 Hz, 1H), 7.30 (d, J=2.2 Hz, 1H), 6.68 (d, J=8.4 Hz, 1H), 6.50 (d, J=1.6 Hz, 1H), 6.42 (dd, J=2.6, 8.5 Hz, 1H), 4.93 (s, 2H), 3.81 (s, 3H), 2.02 (s, 3H). m/z (esi) M+1=255.

Intermediate Example AE

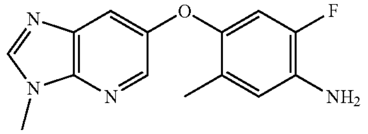 [SMILES: Cc1cc(N)c(F)cc1Oc1cnc2c(c1)ncn2C]

2-fluoro-5-methyl-4-((3-methyl-3H-imidazo[4,5-b]pyridin-6-yl)oxy)aniline

Step A: To a stirred solution of 3-methyl-3H-imidazo[4,5-b]pyridin-6-ol (2 g, 13.42 mmol) and 1,5-difluoro-2-methyl-4-nitrobenzene (2.32 g, 13.42 mmol) in DMSO (20 mL) was added $K_2CO_3$ (5.55 g) and stirred at room temperature for 4 hours. After completion of reaction, it was diluted with EtOAc and was washed with water, followed by brine, dried over $Na_2SO_4$, filtered, and concentrated under reduced pressure. The crude product was purified with silica gel column chromatography (1-2% MeOH/DCM) to get 6-(5-fluoro-2-methyl-4-nitrophenoxy)-3-methyl-3H-imidazo[4,5-b]pyridine along with the other regio-isomer. $^1H$ NMR and LCMS showed the material was a mixture of both the regio-isomers. Proceeded to next step without further purification. (3 g, mixture of isomers) as a gum. m/z (esi) M+1=303.0.

Step B: To a stirred solution of 6-(5-fluoro-2-methyl-4-nitrophenoxy)-3-methyl-3H-imidazo[4,5-b]pyridine along with other regio-isomer (6 g, 19.86 mmol) in THF:$H_2O$ (4:1) (80 mL) was added Zn dust (12.9 g, 198.67 mmol) and $NH_4Cl$ (10.62 g, 198.67 mmol), and the reaction was allowed to stir at 25° C. for 2 hours. After completion of the reaction, it was filtered through a bed of Celite®, and the Celite® was washed with EtOAc. The organic layer of the filtrate was washed with brine, dried over $Na_2SO_4$, filtered and concentrated. The crude product was purified with silica gel combiflash (0.5-1% MeOH/DCM) to get 2-fluoro-5-methyl-4-((3-methyl-3H-imidazo[4,5-b]pyridin-6-yl)oxy)aniline (3.9 g, 72% yield 2 steps) as a solid. The structure of desired isomer was confirmed by HMBC. $^1H$ NMR (400 MHz, DMSO-d6) δ 8.39 (s, 1H), 8.14 (d, J=1.9 Hz, 1H), 7.40 (d, J=1.9 Hz, 1H), 6.71 (dd, J=6.7, 11.0 Hz, 2H), 4.97 (s, 2H), 3.82 (s, 3H), 2.03 (s, 3H). m/z (esi) M+1=273.2.

Intermediate Example AF

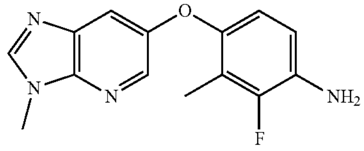 [SMILES: Cc1c(Oc2cnc3c(c2)ncn3C)ccc(N)c1F]

2-fluoro-3-methyl-4-((3-methyl-3H-imidazo[4,5-b]pyridin-6-yl)oxy)aniline

Step A: To a stirred solution of 3-methyl-3H-imidazo[4,5-b]pyridin-6-ol (7.7 g, 51.68 mmol) and 1,3-difluoro-2-methyl-4-nitrobenzene (9.77 g, 51.68 mmol) in DMSO (60 mL) was added $K_2CO_3$ (14.26 g, 103.35 mmol) and stirred for 16 hours at room temperature. After completion, the reaction mixture was diluted with EtOAc, washed with cold water, followed by brine. The organic part was dried over $Na_2SO_4$, filtered, and concentrated to afford the crude material which was purified by silica gel column chromatography (0-1% MeOH-DCM) to afford 6-(3-fluoro-2-methyl-4-nitrophenoxy)-3-methyl-3H-imidazo[4,5-b]pyridine (10 g, mixture of two regioisomers) as a solid. m/z (esi) M+1=302.8.

Step B: To a stirred solution of 6-(3-fluoro-2-methyl-4-nitrophenoxy)-3-methyl-3H-imidazo[4,5-b]pyridine (mixture of two regioisomers) (9.5 g, 31.46 mmol) in THF:$H_2O$ (5:1) (120 mL) was added Zn (21.4 g, 314.5 mmol) and $NH_4Cl$ (16.98 g, 314.5 mmol) at 0° C. and stirred for 2 hours at room temperature. After completion, the reaction mixture was filtered through sintered funnel and washed with EtOAc. The filtrate was washed with water, and the organic layer was separated and dried over $Na_2SO_4$, filtered and concentrated. The crude material was purified by Prep-SFC (50% $CO_2$+50% (MEOH), 60 g/min) to afford 2-fluoro-3-methyl-4-((3-methyl-3H-imidazo[4,5-b]pyridin-6-yl)oxy)aniline (1.5 g, 11% in 2 steps) as a solid. m/z (esi) M+1=273.1. (Note: Structure was confirmed by HMBC)

Intermediate Example AG

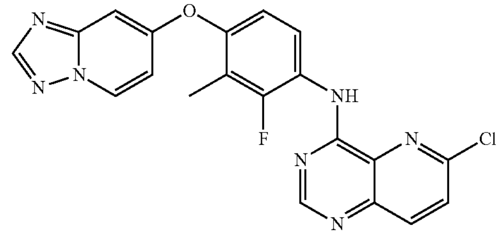 [SMILES: Cc1c(Oc2ccn3ncnc3c2)ccc(Nc2ncnc3ccc(Cl)nc23)c1F]

N-(4-([1,2,4]triazolo[1,5-a]pyridin-7-yloxy)-2-fluoro-3-methylphenyl)-6-chloropyrido[3,2-d]pyrimidin-4-amine A mixture of 4-([1,2,4]triazolo[1,5-a]pyridin-7-yloxy)-2-fluoro-3-methylaniline (0.302 g, 1.17 mmol) and 4,6-dichloropyrido[3,2-d]pyrimidine (257 mg, 1.29 mmol) in IPA (11.7 mL) was heated to 70° C. where it stirred for 4 hours. The mixture was then cooled to ambient temperature and diluted with water and saturated aqueous $NaHCO_3$. The resulting solid was isolated by vacuum filtration. The solid was then dissolved in $CH_2Cl_2$ and dried over $Na_2SO_4$, filtered and concentrated. The crude product was then purified via column chromatography (1-5% MeOH/CHCl3) to afford the desired product (466 mg, 94%) as a solid. m/z (APCI-pos) M+1=422.1.

The compounds in Table 1 were prepared using an analogous method to that employed for Intermediate Example AG using the appropriate intermediates.

TABLE 1

| Example No. | Structure | Name | LCMS $M^{+}1$ |
|---|---|---|---|
| AH | 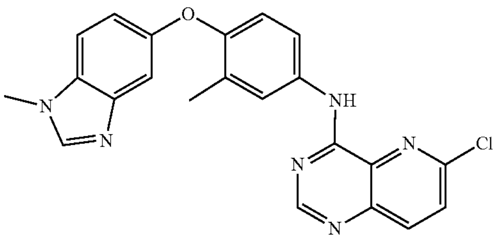 [SMILES: Cc1cc(Nc2ncnc3ccc(Cl)nc23)ccc1Oc1ccc2c(c1)ncn2C] | 6-chloro-N-(3-methyl-4-((1-methyl-1H-benzo[d]imidazol-5-yl)oxy)phenyl)pyrido[3,2-d]pyrimidin-4-amine | 416.8 |
| AI | 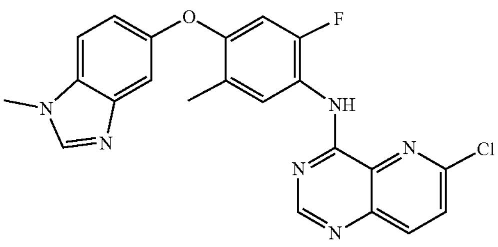 [SMILES: Cc1cc(Nc2ncnc3ccc(Cl)nc23)c(F)cc1Oc1ccc2c(c1)ncn2C] | 6-chloro-N-(2-fluoro-5-methyl-4-((1-methyl-1H-benzo[d]imidazol-5-yl)oxy)phenyl)pyrido[3,2-d]pyrimidin-4-amine | 435.2 |

TABLE 1-continued

| Example No. | Structure | Name | LCMS M+1 |
|---|---|---|---|
| AJ | 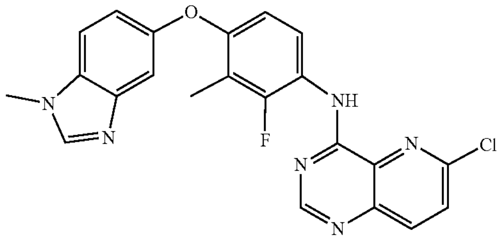 [SMILES: Cc1c(Oc2ccc3c(c2)ncn3C)ccc(Nc2ncnc3ccc(Cl)nc23)c1F] | 6-chloro-N-(2-fluoro-3-methyl-4-((1-methyl-1H-benzo[d]imidazole-5-yl)oxy)phenyl)pyrido[3,2-d]pyrimidin-4-amine | 434.7 |
| AK | 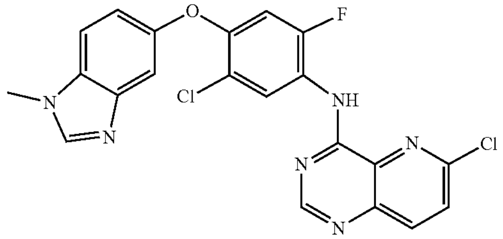 [SMILES: Cn1cnc2cc(Oc3cc(F)c(Nc4ncnc5ccc(Cl)nc45)cc3Cl)ccc21] | 6-chloro-N-(5-chloro-2-fluoro-4-((1-methyl-1H-benzo[d]imidazol-5-yl)oxy)phenyl)pyrido[3,2-d]pyrimidin-4-amine | 455.1 |
| AL | 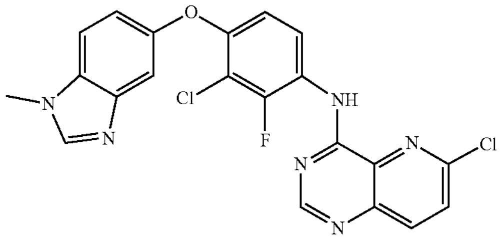 [SMILES: Cn1cnc2cc(Oc3ccc(Nc4ncnc5ccc(Cl)nc45)c(F)c3Cl)ccc21] | 6-chloro-N-(3-chloro-2-fluoro-4-((1-methyl-1H-benzo[d]imidazol-5-yl)oxy)phenyl)pyrido[3,2-d]pyrimidin-4-amine | 455.1 |
| AM | 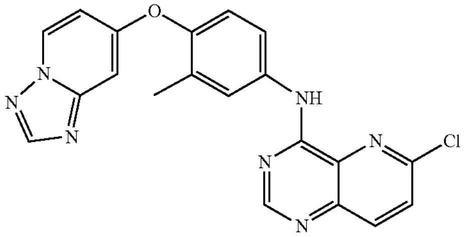 [SMILES: Cc1cc(Nc2ncnc3ccc(Cl)nc23)ccc1Oc1ccn2ncnc2c1] | N-(4-([1,2,4]triazolo[1,5-a]pyridin-7-yloxy)-3-methylphenyl)-6-chloropyrido[3,2-d]pyrimidin-4-amine | 404.0 |
| AN | 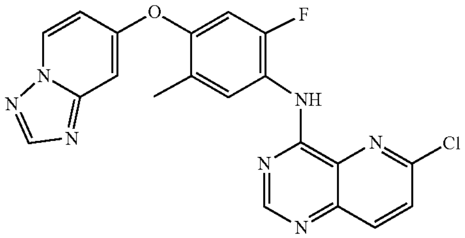 [SMILES: Cc1cc(Nc2ncnc3ccc(Cl)nc23)c(F)cc1Oc1ccn2ncnc2c1] | N-(4-([1,2,4]triazolo[1,5-a]pyridin-7-yloxy)-2-fluoro-5-methylphenyl)-6-chloropyrido[3,2-d]pyrimidin-4-amine | 422.0 |
| AO | 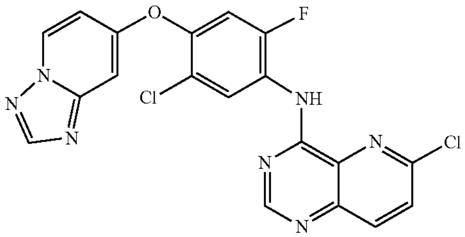 [SMILES: Fc1cc(Oc2ccn3ncnc3c2)c(Cl)cc1Nc1ncnc2ccc(Cl)nc12] | N-(4-([1,2,4]triazolo[1,5-a]pyridin-7-yloxy)-5-chloro-2-fluorophenyl)-6-chloropyrido[3,2-d]pyrimidin-4-amine | 442.0 |

TABLE 1-continued

| Example No. | Structure | Name | LCMS M+1 |
|---|---|---|---|
| AP | 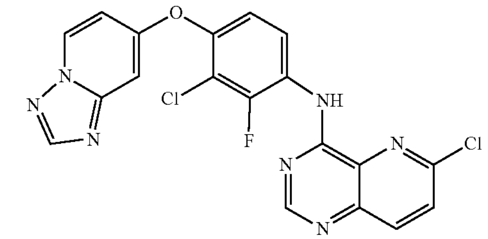 [SMILES: Fc1c(Nc2ncnc3ccc(Cl)nc23)ccc(Oc2ccn3ncnc3c2)c1Cl] | N-(4-([1,2,4]triazolo[1,5-a]pyridin-7-yloxy)-3-chloro-2-fluorophenyl)-6-chloropyrido[3,2-d]pyrimidin-4-amine | 442.1 |
| AQ | 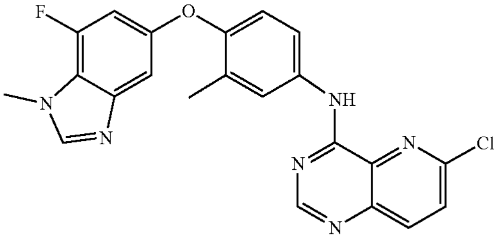 [SMILES: Cc1cc(Nc2ncnc3ccc(Cl)nc23)ccc1Oc1cc(F)c2c(c1)ncn2C] | 6-chloro-N-(4-((7-fluoro-1-methyl-1H-benzo[d]imidazol-5-yl)oxy)-3-methylphenyl)pyrido[3,2-d]pyrimidin-4-amine | 435.1 |
| AR | 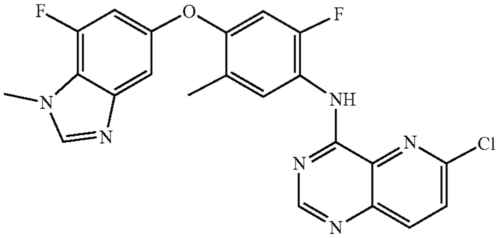 [SMILES: Cc1cc(Nc2ncnc3ccc(Cl)nc23)c(F)cc1Oc1cc(F)c2c(c1)ncn2C] | 6-chloro-N-(2-fluoro-4-((7-fluoro-1-methyl-1H-benzo[d]imidazol-5-yl)oxy)-5-methylphenyl)pyrido[3,2-d]pyrimidin-4-amine | 453.1 |
| AS | 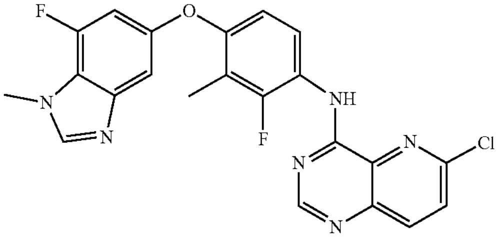 [SMILES: Cc1c(Oc2cc(F)c3c(c2)ncn3C)ccc(Nc2ncnc3ccc(Cl)nc23)c1F] | 6-chloro-N-(2-fluoro-4-((7-fluoro-1-methyl-1H-benzo[d]imidazol-5-yl)oxy)-3-methylphenyl)pyrido[3,2-d]pyrimidin-4-amine | 453.1 |
| AT | 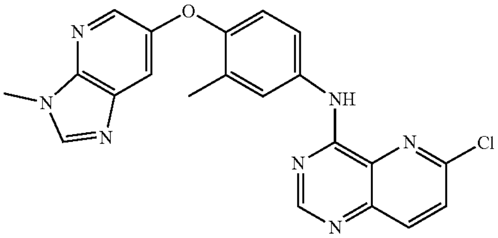 [SMILES: Cc1cc(Nc2ncnc3ccc(Cl)nc23)ccc1Oc1cnc2c(c1)ncn2C] | 6-chloro-N-(3-methyl-4-((3-methyl-3H-imidazo[4,5-b]pyridin-6-yl)oxy)phenyl)pyrido[3,2-d]pyrimidin-4-amine | 418.1 |
| AU | 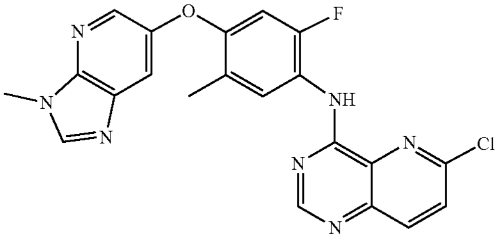 [SMILES: Cc1cc(Nc2ncnc3ccc(Cl)nc23)c(F)cc1Oc1cnc2c(c1)ncn2C] | 6-chloro-N-(2-fluoro-5-methyl-4-((3-methyl-3H-imidazo[4,5-b]pyridin-6-yl)oxy)phenyl)pyrido[3,2-d]pyrimidin-4-amine | 436.1 |

TABLE 1-continued

| Example No. | Structure | Name | LCMS $M^+1$ |
|---|---|---|---|
| AV | 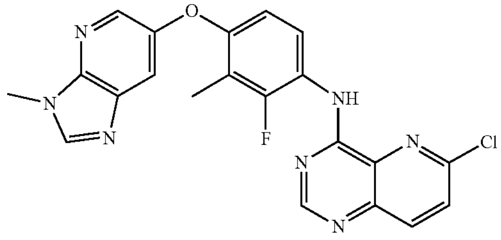 [SMILES: Cc1c(Oc2cnc3c(c2)ncn3C)ccc(Nc2ncnc3ccc(Cl)nc23)c1F] | 6-chloro-N-(2-fluoro-3-methyl-4-((3-methyl-3H-imidazo[4,5-b]pyridin-6-yl)oxy)phenyl)pyrido[3,2-d]pyrimidin-4-amine | 436.0 |
| AW | 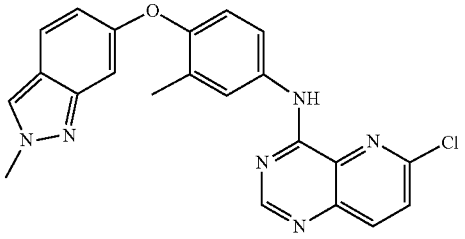 [SMILES: Cc1cc(Nc2ncnc3ccc(Cl)nc23)ccc1Oc1ccc2cn(C)nc2c1] | 6-chloro-N-(3-methyl-4-((2-methyl-2H-indazol-6-yl)oxy)phenyl)pyrido[3,2-d]pyrimidin-4-amine | 417.0 |
| AX | 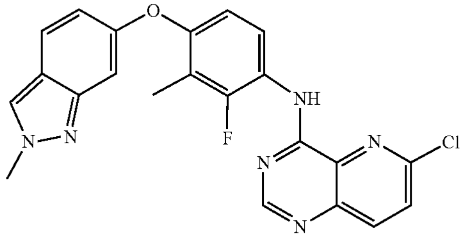 [SMILES: Cc1c(Oc2ccc3cn(C)nc3c2)ccc(Nc2ncnc3ccc(Cl)nc23)c1F] | 6-chloro-N-(2-fluoro-3-methyl-4-((2-methyl-2H-indazol-6-yl)oxy)phenyl)pyrido[3,2-d]pyrimidin-4-amine | 435.2 |

Intermediate Example AY

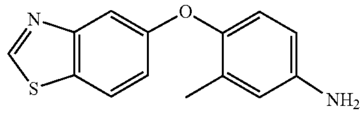 [SMILES: Cc1cc(N)ccc1Oc1ccc2scnc2c1]

4-(benzo[d]thiazol-5-yloxy)-3-methylaniline

Step A: 1-Fluoro-2-methyl-4-nitrobenzene (1.710 g, 11 mmol), benzo[d]thiazol-5-ol (2.000 g, 13.23 mmol), potassium carbonate (3.047 g, 22 mmol), and DMSO (26 mL) were charged to a 250 mL round bottom flask equipped with a stir bar. After 2 hours stirring at ambient temperature, the reaction was quenched with water. The reaction mixture was extracted twice with EtOAc. The combined organic layers were washed with brine, dried over $MgSO_4$, filtered, and concentrated to a solid. The crude material was purified by silica gel chromatography (0 to 8% MeOH in DCM) to yield the product as a solid, 5-(2-methyl-4-nitrophenoxy)benzo[d]thiazole (2.7522 g, 87%). m/z (esi) M+1=287.1.

Step B: A 500 mL round bottom flask was charged with 5-(2-methyl-4-nitrophenoxy)enzo[d]thiazole (2.7522 g, 9.6 mmol), saturated ammonium chloride aqueous solution (2.7 mL), and THF (48 mL). The reaction mixture was cooled to 0° C. and zinc (6.285 g, 96.1 mmol) was added as a single portion. After 5 minutes, the flask was removed from the ice bath and stirred at ambient temperature for 24 hours. The reaction mixture was filtered over GF/F paper. The filter pad was washed several times with EtOAc. The combined organic layers were collected and washed with water and brine. The organic layers were dried over $MgSO_4$, filtered, and concentrated to a thick oil. The crude material was purified by silica gel chromatography (10 to 60% EtOAc in n-heptane) to obtain 4-(benzo[d]thiazol-5-yloxy)-3-methylaniline (1.7099 g, 69%). m/z (esi) M+1=257.1.

Intermediate Example AZ

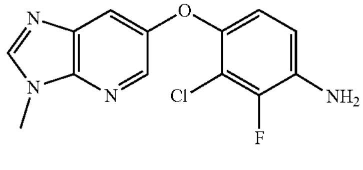 [SMILES: Cn1cnc2cc(Oc3ccc(N)c(F)c3Cl)cnc21]

3-chloro-2-fluoro-4-((3-methyl-3H-imidazo[4,5-b]pyridin-6-yl)oxy)aniline

Step A: A 250 mL round bottom flask was charged with 2-chloro-1,3-difluoro-4-nitrobenzene (882 mg, 4.56 mmol), cesium carbonate (2.97 g, 9.12 mmol), and DMSO (23 mL). 3-Methyl-3H-imidazo[4,5-b]pyridin-6-ol (0.680 g, 4.56 mmol) was added as a single portion. The reaction mixture was stirred for 17 hours at ambient temperature. The mixture was quenched by addition of water (150 mL). The mixture was extracted three times with EtOAc (50 mL). The combined organic layers were washed with brine (50 mL), dried over $MgSO_4$, filtered, and concentrated to a thick oil. The crude material was purified by silica gel column chromatography (0 to 8% MeOH in DCM) deliver a mixture of regioisomers, 6-(2-chloro-3-fluoro-4-nitrophenoxy)-3-methyl-3H-imidazo[4,5-b]pyridine and 6-(2-chloro-3-fluoro-6-nitrophenoxy)-3-methyl-3H-imidazo[4,5-b]pyridine (1.059 g, 72%). m/z (esi) M+1=323.1.

Step B: The mixture from Step A (1.059 g) was charged to a 250 mL flask. THF (16 mL) and saturated ammonium chloride aqueous solution (1 mL) were added. Zinc (2.146 g, 33 mmol) was added as a single portion at ambient temperature. After 17 hours stirring, the reaction mixture was filtered through GF/F paper. The filter pad was washed several times with EtOAc. The organic layers were collected and washed with brine (25 mL), dried over $MgSO_4$, and concentrated. The crude material was subjected to silica gel chromatography (0 to 5% MeOH in EtOAc). Mixed fractions were further purified by a second round of silica gel chromatography (0 to 15% MeOH in EtOAc) to yield the product, 3-chloro-2-fluoro-4-((3-methyl-3H-imidazo[4,5-b]pyridin-6-yl)oxy)aniline (32.6 mg, 3%). m/z (esi) M+1=293.1. $^1H$ NMR (400 MHz, $CDCl_3$) δ 8.31 (d, J=2.5 Hz, 1H), 8.13 (s, 1H), 7.52 (d, J=2.6 Hz, 1H), 6.76-6.61 (m, 2H), 4.39 (br s, 2H), 3.93 (s, 3H).

Intermediate Example BA

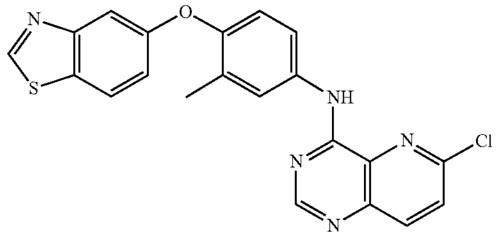 [SMILES: Cc1cc(Nc2ncnc3ccc(Cl)nc23)ccc1Oc1ccc2scnc2c1]

N-(4-(benzo[d]thiazol-5-yloxy)-3-methylphenyl)-6-chloropyrido[3,2-d]pyrimidin-4-amine A mixture of 4-(benzo[d]thiazol-5-yloxy)-3-methylaniline (449 mg, 1.75 mmol) and 4,6-dichloropyrido[3,2-d]pyrimidine (350 mg, 1.75 mmol) in IPA (8.75 mL) was heated to 70° C. where it stirred for 75 minutes. The mixture was then cooled to ambient temperature and volatiles were removed under reduced pressure. The resulting solid was purified by silica gel chromatography (0 to 16% MeOH in DCM) to yield solid N-(4-(benzo[d]thiazol-5-yloxy)-3-methylphenyl)-6-chloropyrido[3,2-d]pyrimidin-4-amine (547 mg, 74%). m/z (APCI-pos) M+1=420.1.

Example 1

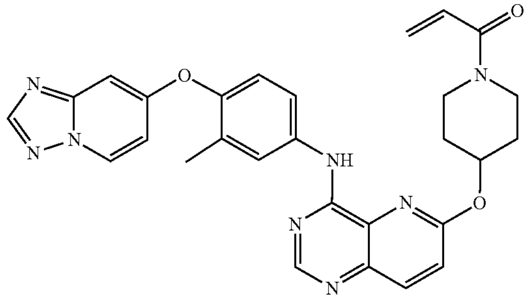 [SMILES: C=CC(=O)N1CCC(Oc2ccc3ncnc(Nc4ccc(Oc5ccn6ncnc6c5)c(C)c4)c3n2)CC1]

1-(4-((4-((4-([1,2,4]triazolo[1,5-a]pyridin-7-yloxy)-3-methylphenyl)amino)pyrido[3,2-d]pyrimidin-6-yl)oxy)piperidin-1-yl)prop-2-en-1-one Step A: to a stirred solution of 4-([1,2,4]triazolo[1,5-a]pyridin-7-yloxy)-3-methylaniline (80 mg, 0.33 mmol) in isopropyl alcohol (3.0 mL) was added 4,6-dichloropyrido[3,2-d]pyrimidine (93.45 mg, 0.47 mmol), and the reaction mixture was refluxed at 85° C. for 1 hour. After completion, the reaction mixture was evaporated to dryness to provide the crude product. The crude product was washed with n-pentane to afford N-(4-([1,2,4]triazolo[1,5-a]pyridin-7-yloxy)-3-methylphenyl)-6-chloropyrido[3,2-d]pyrimidin-4-amine as a solid, which was used for the next step without further purification. m/z (esi) $M^+1$=404.0.

Step B: Sodium hydride (60% dispersion in mineral oil) (57 mg, 1.42 mmol) was added to a stirred solution of tert-butyl 4-hydroxypiperidine-1-carboxylate (286.58 mg, 1.42 mmol) in DMA (0.5 mL), and the reaction mixture was stirred at room temperature under $N_2$ atmosphere for 15 minutes. N-(4-([1,2,4]Triazolo[1,5-a]pyridin-7-yloxy)-3-methylphenyl)-6-chloropyrido[3,2-d]pyrimidin-4-amine (230 mg, 0.57 mmol) was added to the reaction mixture, and the reaction mixture was stirred at 120° C. for 3 hours. After completion of the reaction, the reaction mixture was taken up in EtOAc and washed with cold water, followed by brine. The organic layer was dried over anhydrous $Na_2SO_4$, filtered, and concentrated under reduced pressure and the crude product was purified by silica gel column chromatography (0-1% MeOH/DCM) to afford tert-butyl 4-((4-((4-([1,2,4]triazolo[1,5-a]pyridin-7-yloxy)-3-methylphenyl)amino)pyrido[3,2-d]pyrimidin-6-yl)oxy)piperidine-1-carboxylate (250 mg, 57% yield in three steps) as a solid. m/z (esi) $M^+1$=569.4.

Step C: HCl (4M) in 1,4-dioxane (2.5 mL) was added to a stirred solution of tert-butyl 4-((4-((4-([1,2,4]triazolo[1,5-a]pyridin-7-yloxy)-3-methylphenyl)amino)pyrido[3,2-d]pyrimidin-6-yl)oxy)piperidine-1-carboxylate (200 mg, 0.35 mmol) in DCM (2.5 mL) at 0° C. The reaction mixture was then warmed to ambient temperature and stirred for 1 hour. The reaction mixture was evaporated under reduced pressure to dryness and washed with n-pentane to afford N-(4-([1,2,4]triazolo[1,5-a]pyridin-7-yloxy)-3-methylphenyl)-6-(piperidin-4-yloxy)pyrido[3,2-d]pyrimidin-4-amine hydrochloride as a solid, which was used in the next step without further purification. m/z (esi) $M^+1$-HCl=469.4.

Step D: DIPEA (0.13 mL, 0.45 mmol) was added to the stirred solution of N-(4-([1,2,4]triazolo[1,5-a]pyridin-7-yloxy)-3-methylphenyl)-6-(piperidin-4-yloxy)pyrido[3,2-d]

pyrimidin-4-amine hydrochloride (190 mg, 0.38 mmol) in DMF (1 mL) at 0° C., and the reaction mixture was stirred for 2 minutes. Then acrylic acid (0.03 mL, 0.42 mmol) and $T_3P$ (50% in EtOAc) (0.3 mL, 0.45 mmol) were added to the reaction mixture at 0° C., and the mixture was stirred at 0° C. for 1 hour. The reaction mixture was then quenched with water. It was then evaporated under reduced pressure, and the crude product was purified by reverse-phase Prep HPLC (20-95% ACN:$H_2O$ (20 mM Ammonium Bicarbonate)) to afford 1-(4-((4-((4-([1,2,4]triazolo[1,5-a]pyridin-7-yloxy)-3-methylphenyl)amino)pyrido[3,2-d]pyrimidin-6-yl)oxy) piperidin-1-yl)prop-2-en-1-one (19.95 mg, 11% yield in 2 steps) as a sticky solid. $^1H$ NMR (400 MHz, $(CD_3)_2SO$) δ 9.51 (s, 1H), 8.95 (d, J=7.5 Hz, 1H), 8.59 (s, 1H), 8.38 (s, 1H), 8.13 (d, J=9.0 Hz, 1H), 7.99-7.88 (m, 2H), 7.38 (d, J=9.0 Hz, 1H), 7.26 (d, J=8.6 Hz, 1H), 7.04 (dd, J=2.6, 7.5 Hz, 1H), 6.87 (dd, J=10.5, 16.7 Hz, 1H), 6.79 (d, J=2.6 Hz, 1H), 6.13 (dd, J=2.5, 16.7 Hz, 1H), 5.94-5.83 (m, 1H), 5.69 (dd, J=2.5, 10.4 Hz, 1H), 4.10-3.78 (m, 2H), 3.70-3.43 (m, 2H), 2.21 (s, 3H), 2.17-2.02 (m, 2H), 1.81-1.62 (m, 2H); m/z (esi) $M^+1$=523.2.

Example 2

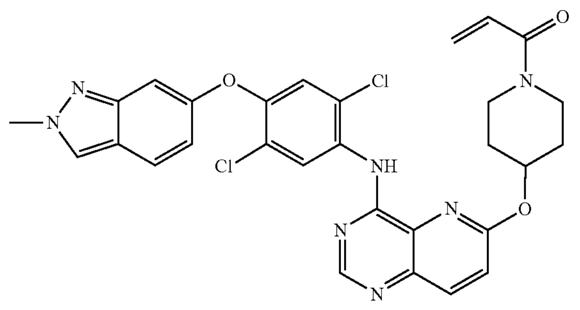 [SMILES: C=CC(=O)N1CCC(Oc2ccc3ncnc(Nc4cc(Cl)c(Oc5ccc6cn(C)nc6c5)cc4Cl)c3n2)CC1]

1-(4-((4-((2,5-dichloro-4-((2-methyl-2H-indazol-6-yl)oxy)phenyl)amino)pyrido[3,2-d]pyrimidin-6-yl) oxy)piperidin-1-yl)prop-2-en-1-one Step A: 1,4-Dichloro-2-fluoro-5-nitrobenzene (282.4 mg, 1.35 mmol) and $K_2CO_3$ (559.5 mg, 4.05 mmol) were added to a stirred solution of 2-methyl-2H-indazol-6-ol (200 mg, 1.35 mmol) in THF (3 mL) and DMSO (1.5 mL) at room temperature and then warmed to 80° C. where it stirred for 16 hours. The reaction mixture was diluted with EtOAc and washed with water. The organic layer was dried over anhydrous $Na_2SO_4$, filtered, and concentrated under reduced pressure. The crude product was purified by silica gel column chromatography (50% EtOAc/hexane) to afford 6-(2,5-dichloro-4-nitrophenoxy)-2-methyl-2H-indazole (410 mg, 90% yield) as a solid. m/z (esi) $M^+1$=337.8.

Step B: $NH_4Cl$ (666.8 mg, 12.46 mmol) was added to a stirred solution of 6-(2,5-dichloro-4-nitrophenoxy)-2-methyl-2H-indazole (420 mg, 1.25 mmol) in THF:$H_2O$ (5:1) (10 mL) at room temperature. Zn dust (815.1 mg, 12.46 mmol) was added, and the mixture was stirred for 15 minutes at the same temperature. After completion, the reaction mixture was filtered through a bed of Celite®, and the filtrate was concentrated under reduced pressure. The crude residue was taken up in water and $CH_2Cl_2$ and the mixture was extracted with $CH_2Cl_2$. The combined organic layers were dried over anhydrous $Na_2SO_4$, filtered, and concentrated under reduced pressure to provide crude 2,5-dichloro-4-((2-methyl-2H-indazol-6-yl)oxy)aniline (335 mg, crude) as a solid, which was used in the next step without further purification. m/z (esi) M+1=308.0.

Step C: A stirred solution of 2,5-dichloro-4-((2-methyl-2H-indazol-6-yl)oxy)aniline (45 mg, 0.15 mmol) and 4,6-dichloropyrido[3,2-d]pyrimidine (40.84 mg, 0.21 mmol) in isopropyl alcohol (1 mL) was heated to 80° C. and stirred for 1 hour. Solvent was evaporated under reduced pressure, and crude product was purified by silica gel column chromatography (2% MeOH/DCM) to afford 6-chloro-N-(2,5-dichloro-4-((2-methyl-2H-indazol-6-yl)oxy)phenyl)pyrido[3,2-d]pyrimidin-4-amine (60 mg, 87% yield) as a solid. m/z (esi) $M^+1$=292.0.

Step D: NaH (60% dispersion in mineral oil) (20.39 mg, 0.53 mmol) was added to a stirred solution of 6-chloro-N-(2,5-dichloro-4-((2-methyl-2H-indazol-6-yl)oxy)phenyl) pyrido[3,2-d]pyrimidin-4-amine (100 mg, 0.21 mmol) and tert-butyl 4-hydroxypiperidine-1-carboxylate (85.53 mg, 0.43 mmol) in DMA (2 mL) at 0° C. The mixture was stirred for 10 minutes at 0° C. and then stirred at 130° C. for 16 hours. The mixture was cooled to ambient temperature, diluted with EtOAc, and washed with water. The organic part was dried over anhydrous $Na_2SO_4$, filtered, and concentrated under reduced pressure to provide the crude product, which was purified by silica gel column chromatography (0-5% MeOH/DCM) to afford tert-butyl 4-((4-((2,5-dichloro-4-((2-methyl-2H-indazol-6-yl)oxy)phenyl)amino) pyrido[3,2-d]pyrimidin-6-yl)oxy)piperidine-1-carboxylate (90 mg, 66% yield) as a sticky mass. m/z (esi) $M^+1$=649.4.

Step E: HCl (4N) in 1,4-dioxane (2 mL) was added to a stirred solution of tert-butyl 4-((4-((2,5-dichloro-4-((2-methyl-2H-indazol-6-yl)oxy)phenyl)amino)pyrido[3,2-d] pyrimidin-6-yl)oxy)piperidine-1-carboxylate (90 mg, 0.14 mmol) in DCM (2 mL) at 0° C. and stirred for 2 hours. The solvent was evaporated under reduced pressure to provide crude N-(2,5-dichloro-4-((2-methyl-2H-indazol-6-yl)oxy) phenyl)-6-(piperidin-4-yloxy)pyrido[3,2-d]pyrimidin-4-amine hydrochloride, which was used in the next step without further purification. m/z (esi) $M^+1$-HCl=549.0.

Step F: DIPEA (0.05 mL, 0.28 mmol) was added to a stirred solution of N-(2,5-dichloro-4-((2-methyl-2H-indazol-6-yl)oxy)phenyl)-6-(piperidin-4-yloxy)pyrido[3,2-d]pyrimidin-4-amine hydrochloride (81 mg, 0.14 mmol) in DMF (1 mL), followed by acrylic acid (0.011 mL, 0.16 mmol) and $T_3P$ (50% in EtOAc) (0.1 mL, 0.17 mmol) at 0° C. The mixture was stirred for 1 hour at the same temperature. Then it was diluted with EtOAc and washed with water. The organic layer was dried over anhydrous $Na_2SO_4$, filtered, and concentrated under reduced pressure to provide the crude product, which was purified by reverse prep-HPLC (40-95% ACN:water (20 mM Ammonium Bicarbonate)) to get 1-(4-((4-((2,5-dichloro-4-((2-methyl-2H-indazol-6-yl) oxy)phenyl)amino)pyrido[3,2-d]pyrimidin-6-yl)oxy)piperidin-1-yl)prop-2-en-1-one as a solid (8 mg, 10% in 2 steps). $^1H$ NMR (400 MHz, $(CD_3)_2SO$) δ 9.51 (s, 1H), 8.88 (s, 1H), 8.70 (s, 1H), 8.36 (s, 1H), 8.20 (d, J=9.2 Hz, 1H), 7.78 (d, J=8.9 Hz, 1H), 7.44 (d, J=8.0 Hz, 2H), 6.97 (s, 1H), 6.92-6.80 (m, 2H), 6.11 (dd, J=2.5, 16.7 Hz, 1H), 5.68 (dd, J=2.5, 10.5 Hz, 1H), 5.56-5.47 (m, 1H), 4.13 (s, 3H), 4.08-3.99 (m, 1H), 3.99-3.89 (m, 1H), 3.55-3.44 (m, 1H), 3.41-3.35 (m, 1H), 2.25-2.10 (m, 2H), 1.83-1.63 (m, 2H); m/z (esi) $M^+1$=590.1.

Example 3

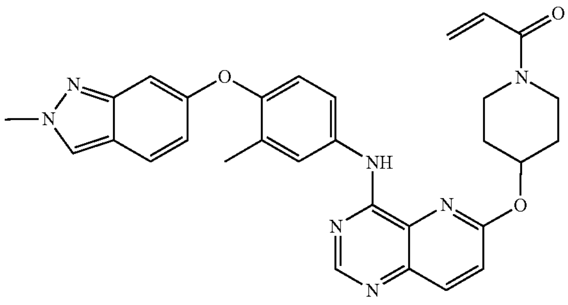 [SMILES: C=CC(=O)N1CCC(Oc2ccc3ncnc(Nc4ccc(Oc5ccc6cn(C)nc6c5)c(C)c4)c3n2)CC1]

1-(4-((4-((3-methyl-4-((2-methyl-2H-indazol-6-yl)oxy)phenyl)amino)pyrido[3,2-d]pyrimidin-6-yl)oxy)piperidin-1-yl)prop-2-en-1-one Step A: 4,6-Dichloropyrido[3,2-d]pyrimidine (154 mg, 0.77 mmol) was added to a stirred solution of 3-methyl-4-((2-methyl-2H-indazol-6-yl)oxy)aniline (150 mg, 0.59 mmol) in isopropyl alcohol (5 mL), and the mixture was stirred at 80° C. for 1 hour. The reaction mixture was concentrated under reduced pressure, and the crude product was purified by silica gel column chromatography (2% MeOH/DCM) to afford 6-chloro-N-(3-methyl-4-((2-methyl-2H-indazol-6-yl)oxy)phenyl)pyrido[3,2-d]pyrimidin-4-amine (230 mg, 92% yield) as a solid. m/z (esi) $M^{+}1$=417.0.

Step B: NaH (60 wt % in paraffin) (40 mg, 0.96 mmol) was added to a stirred solution of tert-butyl 4-hydroxypiperidine-1-carboxylate (193 mg, 0.96 mmol) in DMA (5 mL), and the mixture was stirred for 10 minutes at room temperature. 6-Chloro-N-(3-methyl-4-((2-methyl-2H-indazol-6-yl)oxy)phenyl)pyrido[3,2-d]pyrimidin-4-amine (200 mg, 0.48 mmol) was added, and the mixture was stirred at 130° C. for 16 hours. The reaction mixture was diluted with water and extracted with EtOAc. The combined organic layers were dried over anhydrous $Na_2SO_4$, filtered, and concentrated under reduced pressure. The crude product was purified by silica gel column chromatography (2% MeOH-DCM) to afford tert-butyl 4-((4-((3-methyl-4-((2-methyl-2H-indazol-6-yl)oxy)phenyl)amino)pyrido[3,2-d]pyrimidin-6-yl)oxy)piperidine-1-carboxylate (130 mg, 46% yield) as a solid. m/z (esi) $M^{+}1$=582.0.

Step C: HCl (4M) in 1,4-dioxane (3 mL) was added to a stirred solution of tert-butyl 4-((4-((3-methyl-4-((2-methyl-2H-indazol-6-yl)oxy)phenyl)amino)pyrido[3,2-d]pyrimidin-6-yl)oxy)piperidine-1-carboxylate (120 mg, 0.20 mmol) in DCM (1 mL) at 0° C., and the mixture was stirred at room temperature for 1 hour. The reaction mixture was then concentrated to dryness, and the crude product was triturated with $Et_2O$ to afford N-(3-methyl-4-((2-methyl-2H-indazol-6-yl)oxy)phenyl)-6-(piperidin-4-yloxy)pyrido[3,2-d]pyrimidin-4-amine hydrochloride (105 mg, crude) as a solid. m/z (esi) $M^{+}1$-HCl=482.0.

Step D: DIPEA (0.33 mL, 1.80 mmol) was added to a stirred solution of N-(3-methyl-4-((2-methyl-2H-indazol-6-yl)oxy)phenyl)-6-(piperidin-4-yloxy)pyrido[3,2-d]pyrimidin-4-amine hydrochloride (100 mg, 0.18 mmol) in DCM (2 mL), followed by acryloyl chloride (16 mg, 0.18 mmol) in DCM (0.2 mL) at 0° C., and the mixture was stirred for 1 hour at 0° C. The reaction mixture was quenched with ice and concentrated under reduced pressure. The crude product was purified by reverse phase Prep-HPLC (30-75% ACN: water (20 mM Ammonium Bicarbonate), 16 mL/min) to afford 1-(4-((4-((3-methyl-4-((2-methyl-2H-indazol-6-yl)oxy)phenyl)amino)pyrido[3,2-d]pyrimidin-6-yl)oxy)piperidin-1-yl)prop-2-en-1-one (30 mg, 31% yield in 2 steps) as a solid. $^{1}$H NMR (400 MHz, $(CD_3)_2SO$) δ 9.45 (s, 1H), 8.55 (s, 1H), 8.29 (s, 1H), 8.11 (d, J=9.0 Hz, 1H), 7.83 (s, 1H), 7.79 (dd, J=2.6, 8.6 Hz, 1H), 7.71 (d, J=9.0 Hz, 1H), 7.36 (d, J=9.0 Hz, 1H), 7.05 (d, J=8.6 Hz, 1H), 6.92-6.80 (m, 2H), 6.71 (d, J=2.0 Hz, 1H), 6.12 (dd, J=2.5, 16.7 Hz, 1H), 5.91-5.82 (m, 1H), 5.69 (dd, J=2.5, 10.5 Hz, 1H), 4.09 (s, 3H), 4.03-3.79 (m, 2H), 3.68-3.41 (m, 2H), 2.23 (s, 3H), 2.17-2.01 (m, 2H), 1.80-1.60 (m, 2H); m/z (esi) $M^{+}1$=536.3.

Example 4

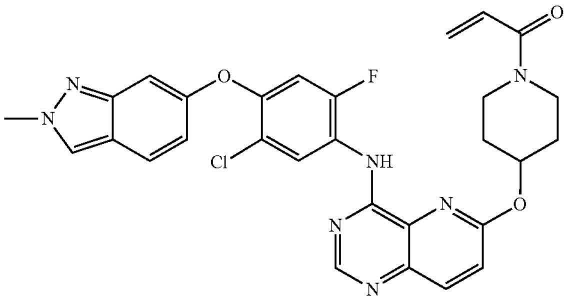 [SMILES: C=CC(=O)N1CCC(Oc2ccc3ncnc(Nc4cc(Cl)c(Oc5ccc6cn(C)nc6c5)cc4F)c3n2)CC1]

1-(4-((4-((5-chloro-2-fluoro-4-((2-methyl-2H-indazol-6-yl)oxy)phenyl)amino)pyrido[3,2-d]pyrimidin-6-yl)oxy)piperidin-1-yl)prop-2-en-1-one Step A: 1-Chloro-2,4-difluoro-5-nitrobenzene (652 mg, 3.37 mmol) and $K_2CO_3$ (933 mg, 6.74 mmol) were added to a stirred solution of 2-methyl-2H-indazol-6-ol (500 mg, 3.37 mmol) in DMSO (15 mL), and the mixture was heated to 80° C. and stirred for 1 hour. Water was added, and the mixture was extracted with ethyl acetate. The combined organic layers were dried over anhydrous $Na_2SO_4$, filtered, and concentrated under reduced pressure. The crude product was purified by silica gel column chromatography (50% EtOAc/hexane) to afford a mixture of two isomers 6-(2-chloro-5-fluoro-4-nitrophenoxy)-2-methyl-2H-indazole and 6-(4-chloro-5-fluoro-2-nitrophenoxy)-2-methyl-2H-indazole (600 mg) as a solid, which were used directly in the next step. m/z (esi) $M^{+}1$=322.

Step B: Ammonium chloride (711 mg, 11 mmol) and Zn powder (608 mg, 11 mmol) were added to a mixture of 6-(2-chloro-5-fluoro-4-nitrophenoxy)-2-methyl-2H-indazole and 6-(4-chloro-5-fluoro-2-nitrophenoxy)-2-methyl-2H-indazole (350 mg, 1.08 mmol) in a biphasic solvent THF/water (3:1) at 0° C. The reaction mixture was then stirred at room temperature for 1 hour. The mixture was filtered through the Celite® and washed with DCM, and the filtrate was concentrated under reduced pressure to obtain the crude residue. The residue was taken up in DCM and washed with water. The organic layer was washed with brine, dried over anhydrous $Na_2SO_4$, and filtered. The solvent was evaporated under reduced pressure. The crude product was purified by prep HPLC (SFC) (NP) to afford the desired compound 5-chloro-2-fluoro-4-((2-methyl-2H-indazol-6-yl)oxy)aniline (120 mg, 38%) as a solid. m/z (esi) $M^{+}1$=291.8.

Step C: 4,6-Dichloropyrido[3,2-d]pyrimidine (75 mg, 0.4 mmol) was added to a stirred solution of 5-chloro-2-fluoro-4-((2-methyl-2H-indazol-6-yl)oxy)aniline (100 mg, 0.34 mmol) in IPA (4 mL), and the reaction mixture was heated at 80° C. for 1 hour. The solvent was then evaporated, and the crude mixture was purified on silica gel column chromatography (1% MeOH/DCM) to afford 6-chloro-N-(5-chloro-2-fluoro-4-((2-methyl-2H-indazol-6-yl)oxy)phenyl) pyrido[3,2-d]pyrimidin-4-amine (130 mg, 83% yield) as a solid. m/z (esi) $M^{+}1$=455.1.

Step D: t-BuOK (220 mg, 1.97 mmol) was added to a solution of tert-butyl 4-hydroxypiperidine-1-carboxylate (442 mg, 2.2 mmol) in DMSO (2 mL) and was stirred for 30 minutes. 6-Chloro-N-(5-chloro-2-fluoro-4-((2-methyl-2H-indazol-6-yl)oxy)phenyl)pyrido[3,2-d]pyrimidin-4-amine (100 mg, 0.22 mmol) was added, and the mixture was heated to 100° C. and stirred for 1.5 hours. The mixture was diluted with water and extracted with ethyl acetate (3×30 mL). The organic layer was washed with brine, dried over anhydrous sodium sulphate, and filtered, and the solvent was evaporated under reduced pressure. The crude product was purified by silica gel column chromatography (90% EtOAc/hexane) to afford tert-butyl 4-((4-((5-chloro-2-fluoro-4-((2-methyl-2H-indazol-6-yl)oxy)phenyl)amino)pyrido[3,2-d] pyrimidin-6-yl)oxy)piperidine-1-carboxylate (85 mg, 62% yield) as a solid. m/z (esi) $M^{+}1$=620.3.

Step E: HCl (4M) in 1,4-dioxane (3 mL) was added to a stirred solution of tert-butyl 4-((4-((5-chloro-2-fluoro-4-((2-methyl-2H-indazol-6-yl)oxy)phenyl)amino)pyrido[3,2-d] pyrimidin-6-yl)oxy)piperidine-1-carboxylate (60.0 mg, 0.09 mmol) in DCM (2 mL) at 0° C., and the mixture was then warmed to room temperature and stirred for 1 hour. The reaction mixture was concentrated, and the crude solid triturated with $Et_2O$ to afford N-(5-chloro-2-fluoro-4-((2-methyl-2H-indazol-6-yl)oxy)phenyl)-6-(piperidin-4-yloxy) pyrido[3,2-d] pyrimidin-4-amine hydrochloride (70 mg, crude) as a solid. m/z (esi) $M^{+}1$-HCl=520.4.

Step F: DIPEA (0.2 mL, 1.44 mmol) was added to a stirred solution of N-(5-chloro-2-fluoro-4-((2-methyl-2H-indazol-6-yl)oxy)phenyl)-6-(piperidin-4-yloxy)pyrido[3,2-d]pyrimidin-4-amine hydrochloride (80 mg, 0.144 mmol) in DCM (2 mL), followed by acryloyl chloride (13 mg, 0.144 mmol) at 0° C., and the mixture was stirred at 0° C. for 3 hours. The reaction mixture was concentrated, and the crude product purified by reverse phase Prep-HPLC (30-95% ACN:water (20 mM Ammonium Bicarbonate), 16 mL/min) to afford 1-(4-((4-((5-chloro-2-fluoro-4-((2-methyl-2H-indazol-6-yl)oxy)phenyl)amino)pyrido[3,2-d]pyrimidin-6-yl) oxy)piperidin-1-yl)prop-2-en-1-one (20 mg, 20%) as a solid. $^{1}$H NMR (400 MHz, $(CD_3)_2SO$) δ 9.44 (s, 1H), 8.58 (s, 1H), 8.36 (s, 1H), 8.30 (d, J=8.0 Hz, 1H), 8.15 (d, J=9.0 Hz, 1H), 7.79 (d, J=9.0 Hz, 1H), 7.40 (d, J=9.0 Hz, 1H), 7.25 (d, J=11.0 Hz, 1H), 6.98 (d, J=2.1 Hz, 1H), 6.92-6.80 (m, 2H), 6.12 (dd, J=2.5, 16.7 Hz, 1H), 5.74-5.60 (m, 2H), 4.13 (s, 3H), 4.08-3.87 (m, 2H), 3.60-3.45 (m, 1H), 3.45-3.34 (m, 1H), 2.22-2.01 (m, 2H), 1.80-1.62 (m, 2H); m/z (esi) $M^{+}1$=574.1.

Example 5

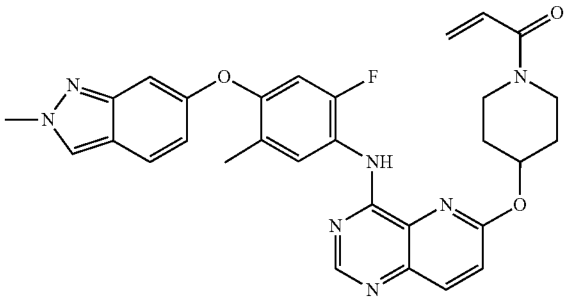 [SMILES: C=CC(=O)N1CCC(Oc2ccc3ncnc(Nc4cc(C)c(Oc5ccc6cn(C)nc6c5)cc4F)c3n2)CC1]

1-(4-((4-((2-fluoro-5-methyl-4-((2-methyl-2H-indazol-6-yl)oxy)phenyl)amino)pyrido[3,2-d]pyrimidin-6-yl)oxy)piperidin-1-yl)prop-2-en-1-one Step A: $K_2CO_3$ (431 mg, 3.12 mmol) was added to a stirred solution of 1,5-difluoro-2-methyl-4-nitrobenzene (180.0 mg, 1.04 mmol), 2-methyl-2H-indazol-6-ol (154.03 mg, 1.04 mmol) in DMSO (2 mL). The reaction mixture was stirred at room temperature for 16 hours. The mixture was diluted with EtOAc, washed with water, followed by brine, and then concentrated. The crude product was mixed with another batch of crude product obtained by the same process (60 mg of compound 1,5-difluoro-2-methyl-4-nitrobenzene) and was purified by silica gel column chromatography (50-55% EtOAc/hexane) to afford 6-(5-fluoro-2-methyl-4-nitrophenoxy)-2-methyl-2H-indazole (347 mg, 83% yield) as a solid. The isolated compound contained two possible isomers. m/z (esi) $M^{+}1$=302.2.

Step B: Zn dust (577.44 mg, 8.83 mmol) was added to a stirred solution of 6-(5-fluoro-2-methyl-4-nitrophenoxy)-2-methyl-2H-indazole (along with the other isomer) (266.0 mg, 0.883 mmol) in THF (3 mL) and water (0.6 mL), followed by $NH_4Cl$ (472.37 mg, 8.829 mmol) at 0° C. The mixture was then stirred at room temperature for 1 hour. The reaction mixture was filtered through a pad of Celite®, and the filtrate was concentrated under reduced pressure to provide the crude product, which was mixed with another batch (50 mg of compound 6-(5-fluoro-2-methyl-4-nitrophenoxy)-2-methyl-2H-indazole). The combined material was purified by prep HPLC SFC (Chiralpak IG (250×21 mm) 5p 55% $CO_2$+45% (0.3% isopropylamine in methanol), 25 g/min), ABPR: 110 bar, temperature: 35° C.) to afford 2-fluoro-5-methyl-4-((2-methyl-2H-indazol-6-yl)oxy)aniline, the desired isomer (210 mg, 69% yield) as a semisolid. The structure of the compound was confirmed by HMBC. m/z (esi) $M^{+}1$=272.4.

Step C: 4,6-Dichloropyrido[3,2-d]pyrimidine (119.44 mg, 0.597 mmol) was added to a stirred solution of 2-fluoro-5-methyl-4-((2-methyl-2H-indazol-6-yl)oxy)aniline (162 mg, 0.597 mmol) in IPA (3 mL), and the mixture was then stirred at 90° C. for 1 hour. The reaction mixture was concentrated, and the crude product was purified by silica gel column chromatography (0-10% MeOH/DCM) to afford 6-chloro-N-(2-fluoro-5-methyl-4-((2-methyl-2H-indazol-6-yl)oxy)phenyl)pyrido[3,2-d]pyrimidin-4-amine (258 mg, 99% yield) as a semi solid. m/z (esi) $M^+1$=435.2.

Step D: NaH (60% in mineral oil, 24 mg, 0.575 mmol) was added to a stirred solution of tert-butyl 4-hydroxypiperidine-1-carboxylate (115.71 mg, 0.575 mmol) in DMA (1 mL) at 0° C. under inert atmosphere. The mixture was warmed to ambient temperature and stirred for 15 minutes. 6-Chloro-N-(2-fluoro-5-methyl-4-((2-methyl-2H-indazol-6-yl)oxy)phenyl)pyrido[3,2-d]pyrimidin-4-amine (100.0 mg, 0.23 mmol) was added to the solution, and the reaction mixture was stirred at 140° C. for 5 hours. The reaction mixture was cooled to room temperature and diluted with EtOAc. The mixture was washed with water, followed by brine, dried over anhydrous $Na_2SO_4$, and concentrated under reduced pressure to provide the crude product. The crude material was purified by silica gel column chromatography (2-3% MeOH/DCM) to get tert-butyl 4-((4-((2-fluoro-5-methyl-4-((2-methyl-2H-indazol-6-yl)oxy)phenyl)amino)pyrido[3,2-d]pyrimidin-6-yl)oxy)piperidine-1-carboxylate (110 mg, 80% yield) as a solid. m/z (esi) $M^+1$=600.2.

Step E: HCl (4M) in 1,4-dioxane (3 mL) was added to a stirred solution of tert-butyl 4-((4-((2-fluoro-5-methyl-4-((2-methyl-2H-indazol-6-yl)oxy)phenyl)amino)pyrido[3,2-d]pyrimidin-6-yl)oxy)piperidine-1-carboxylate (110.0 mg, 0.184 mmol) in DCM (3 mL) at 0° C., and the mixture was stirred at 0° C. for 1 hour. The mixture was concentrated under reduced pressure to afford N-(2-fluoro-5-methyl-4-((2-methyl-2H-indazol-6-yl)oxy)phenyl)-6-(piperidin-4-yloxy)pyrido[3,2-d]pyrimidin-4-amine hydrochloride (91 mg, crude) as a solid that was used in the next step without further purification. m/z (esi) $M^+1$=500.4.

Step F: DIPEA (0.08 mL, 0.48 mmol) was added to a stirred solution of N-(2-fluoro-5-methyl-4-((2-methyl-2H-indazol-6-yl)oxy)phenyl)-6-(piperidin-4-yloxy)pyrido[3,2-d]pyrimidin-4-amine hydrochloride (80.0 mg, 0.16 mmol) and acrylic acid (12.69 mg, 0.176 mmol) in DMF (1 mL), followed by $T_3P$ (50% in EtOAc) (0.06 mL, 0.192 mmol) at 0° C., and the mixture was stirred for 1 hour. The mixture was then diluted with EtOAc and was washed with water followed by brine. The mixture was dried over anhydrous $Na_2SO_4$, filtered, and concentrated under reduced pressure to afford the crude product, which was mixed with another batch (90 mg of compound N-(2-fluoro-5-methyl-4-((2-methyl-2H-indazol-6-yl)oxy)phenyl)-6-(piperidin-4-yloxy)pyrido[3,2-d]pyrimidin-4-amine hydrochloride, and the combined material was purified by reverse phase Prep-HPLC (20-95% ACN:water (20 mM ammonium bicarbonate), 16 mL/min) to afford 1-(4-((4-((2-fluoro-5-methyl-4-((2-methyl-2H-indazol-6-yl)oxy)phenyl)amino)pyrido[3,2-d]pyrimidin-6-yl)oxy)piperidin-1-yl)prop-2-en-1-one (25 mg, 11% yield in 2 steps) as a solid. $^1H$ NMR (400 MHz, $(CD_3)_2SO$) δ 9.42 (s, 1H), 8.50 (s, 1H), 8.34 (s, 1H), 8.12 (d, J=9.0 Hz, 1H), 7.84 (d, J=8.7 Hz, 1H), 7.76 (d, J=9.6 Hz, 1H), 7.37 (d, J=9.0 Hz, 1H), 6.97 (d, J=11.0 Hz, 1H), 6.92-6.80 (m, 3H), 6.12 (dd, J=2.5, 16.6 Hz, 1H), 5.69 (dd, J=2.8, 10.7 Hz, 2H), 4.12 (s, 3H), 4.09-3.87 (m, 2H), 3.59-3.45 (m, 1H), 3.46-3.34 (m, 1H), 2.23 (s, 3H), 2.20-2.02 (m, 2H), 1.78-1.57 (m, 2H); m/z (esi) $M^+1$=554.2.

Example 6

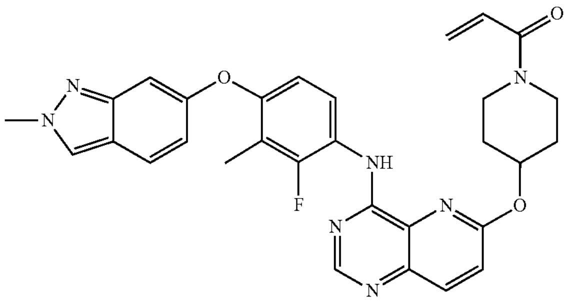 [SMILES: C=CC(=O)N1CCC(Oc2ccc3ncnc(Nc4ccc(Oc5ccc6cn(C)nc6c5)c(C)c4F)c3n2)CC1]

1-(4-((4-((2-fluoro-3-methyl-4-((2-methyl-2H-indazol-6-yl)oxy)phenyl)amino)pyrido[3,2-d]pyrimidin-6-yl)oxy)piperidin-1-yl)prop-2-en-1-one Step A: $K_2CO_3$ (839.2 mg, 6.08 mmol) was added to a stirred solution of 2-methyl-2H-indazol-6-ol (300 mg, 2.03 mmol) in DMSO (4 mL), followed by 1,3-difluoro-2-methyl-4-nitrobenzene (346.62 mg, 2.03 mmol). The reaction mixture was stirred at room temperature for 16 hours. The mixture was then concentrated under reduced pressure, and the crude reaction mixture was diluted with EtOAc. The organic phase was washed with water and brine, dried over anhydrous $Na_2SO_4$, filtered, and concentrated under reduced pressure. The crude product was purified by silica gel column chromatography (40-55% EtOAc/hexane) to afford 6-(3-fluoro-2-methyl-4-nitrophenoxy)-2-methyl-2H-indazole (520 mg, a mixture of two isomeric compounds), as a solid. m/z (esi) $M^+1$=302.2.

Step B: Zn powder (1130 mg, 17.28 mmol) was added to a stirred solution of 6-(3-fluoro-2-methyl-4-nitrophenoxy)-2-methyl-2H-indazole (520 mg, 1.73 mmol) in THF (7.5 mL) at 0° C., followed by $NH_4Cl$ (924 mg, 17.3 mmol) in water (1.5 mL). The reaction mixture was stirred at room temperature for 30 minutes. The reaction mixture was filtered and concentrated under reduced pressure to provide the crude product. The crude product was diluted with EtOAc and washed with water and brine. The organic layer was then dried over anhydrous $Na_2SO_4$, filtered, and concentrated under reduced pressure to provide the crude product, which was mixed with another batch (batch size of 310 mg of 6-(3-fluoro-2-methyl-4-nitrophenoxy)-2-methyl-2H-indazole). The combined material was purified by prep HPLC (SFC) (0.3% isopropylamine in MeOH) to afford the desired isomer of 2-fluoro-3-methyl-4-((2-methyl-2H-indazol-6-yl)oxy)aniline (180 mg, 27%, over two steps) as a solid, along with the other undesired isomer (520 mg). m/z (esi) $M^+1$=272.0. Structure of desired compound was confirmed by HMBC NMR.

Step C: 4,6-Dichloropyrido[3,2-d]pyrimidine (97 mg, 0.48 mmol) was added to a stirred solution of 2-fluoro-3-methyl-4-((2-methyl-2H-indazol-6-yl)oxy)aniline (110 mg, 0.405 mmol) in IPA (2 mL), and the reaction mixture was refluxed at 80° C. for 1 hour. The reaction mixture was evaporated to dryness to provide the crude product, which was washed with pentane to afford 6-chloro-N-(2-fluoro-3-methyl-4-((2-methyl-2H-indazol-6-yl)oxy)phenyl)pyrido[3,2-d]pyrimidin-4-amine as a solid (210 mg, crude), which was used in the next step without further purification. m/z (esi) $M^+1$=435.2.

Step D: NaH (60% dispersion in mineral oil) (24 mg, 0.58 mmol) was added to a stirred solution of tert-butyl 4-hydroxypiperidine-1-carboxylate (100 mg, 0.23 mmol) in DMA (1.5 mL) at room temperature under an Ar atmosphere. The reaction mixture was stirred at room temperature for 15 minutes. 6-Chloro-N-(2-fluoro-3-methyl-4-((2-methyl-2H-indazol-6-yl)oxy)phenyl)pyrido[3,2-d]pyrimidin-4-amine was added to the solution, and the mixture was stirred at 140° C. for 5 hours. The reaction mixture was diluted with EtOAc and washed with water and brine. The organic layer was dried over anhydrous $Na_2SO_4$, filtered, and concentrated under reduced pressure to provide the crude product, which was purified by silica gel column chromatography (1% MeOH/DCM) to afford tert-butyl 4-((4-((2-fluoro-3-methyl-4-((2-methyl-2H-indazol-6-yl)oxy)phenyl)amino)pyrido[3,2-d]pyrimidin-6-yl)oxy)piperidine-1-carboxylate (135 mg, 83% two steps) as a sticky solid. m/z (esi) $M^{+}1$=600.4.

Step E: HCl (4M) in 1,4-dioxane (3.0 mL) was added to a stirred solution of tert-butyl 4-((4-((2-fluoro-3-methyl-4-((2-methyl-2H-indazol-6-yl)oxy)phenyl)amino)pyrido[3,2-d]pyrimidin-6-yl)oxy)piperidine-1-carboxylate (270 mg, 0.45 mmol) in DCM (3.0 mL) at 0° C. The reaction mixture was then stirred at room temperature for 1 hour. The reaction mixture was concentrated to dryness, and the solid washed with pentane to afford N-(2-fluoro-3-methyl-4-((2-methyl-2H-indazol-6-yl)oxy)phenyl)-6-(piperidin-4-yloxy)pyrido[3,2-d]pyrimidin-4-amine hydrochloride (230 mg, crude) as a solid, which was used in the next step without further purification. m/z (esi) $M^{+}1$-HCl=500.2.

Step F: DIPEA (0.1 mL, 0.6 mmol) was added to a stirred solution of N-(2-fluoro-3-methyl-4-((2-methyl-2H-indazol-6-yl)oxy)phenyl)-6-(piperidin-4-yloxy)pyrido[3,2-d]pyrimidin-4-amine hydrochloride (160 mg, 0.3 mmol) in DMF (1.4 mL) at 0° C., and the reaction mixture was stirred for 2 minutes. Then acrylic acid (0.02 mL, 0.33 mmol) and $T_3P$ (50% in EtOAc) (0.2 mL, 0.36 mmol) were added to the reaction mixture at 0° C. and stirred at 0° C. for 2 hours. The reaction was quenched with one drop of water, and the reaction mixture was evaporated to dryness to provide the crude product, which was mixed with another batch (batch size 50.0 mg of N-(2-fluoro-3-methyl-4-((2-methyl-2H-indazol-6-yl)oxy)phenyl)-6-(piperidin-4-yloxy)pyrido[3,2-d]pyrimidin-4-amine hydrochloride). The combined material was purified by reverse phase Prep-HPLC (10-90% ACN: water (50 µL TFA)) to afford 1-(4-((4-((2-fluoro-3-methyl-4-((2-methyl-2H-indazol-6-yl)oxy)phenyl)amino)pyrido[3,2-d]pyrimidin-6-yl)oxy)piperidin-1-yl)prop-2-en-1-one (15 mg, 10% yield in 2 steps) as a solid. $^{1}$H NMR (400 MHz, $CD_3OD$) δ 8.51 (s, 1H), 8.22-8.11 (m, 2H), 8.07 (d, J=9.0 Hz, 1H), 7.71 (d, J=9.0 Hz, 1H), 7.35 (d, J=9.1 Hz, 1H), 6.96-6.77 (m, 5H), 6.22 (dd, J=2.0, 16.8 Hz, 1H), 5.76 (dd, J=2.0, 10.6 Hz, 1H), 5.67 (dt, J=4.0, 7.7 Hz, 1H), 4.15 (s, 3H), 4.11-3.93 (m, 2H), 3.66 (d, J=12.2 Hz, 2H), 2.28-2.11 (m, 4H), 2.00-1.81 (m, 2H); m/z (esi) $M^{+}1$=554.2.

Example 7

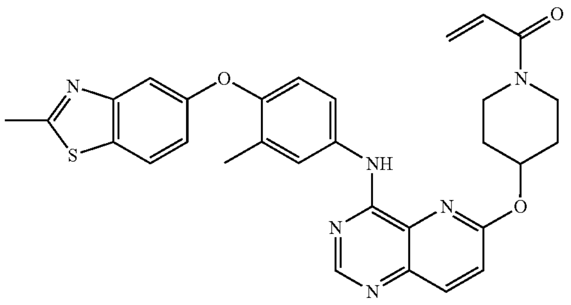 [SMILES: C=CC(=O)N1CCC(Oc2ccc3ncnc(Nc4ccc(Oc5ccc6sc(C)nc6c5)c(C)c4)c3n2)CC1]

1-(4-((4-((3-methyl-4-((2-methylbenzo[d]thiazol-5-yl)oxy)phenyl)amino)pyrido[3,2-d]pyrimidin-6-yl)oxy)piperidin-1-yl)prop-2-en-1-one Step A: 1-Fluoro-2-methyl-4-nitrobenzene (282 mg, 1.82 mmol) and $K_2CO_3$ (502.4 mg, 3.67 mmol) were added to a solution of 2-methylbenzo[d]thiazol-5-ol (300 mg, 1.82 mmol) in DMSO (10 mL). The mixture was heated at 40° C. for 3 hours. After completion, water was added, and the mixture was extracted with EtOAc. The organic phase was dried over anhydrous sodium sulfate, filtered, and concentrated under reduced pressure. The crude product was purified by silica gel column chromatography (30-40% EtOAc/hexane) to afford 2-methyl-5-(2-methyl-4-nitrophenoxy)benzo[d]thiazole (500 mg, 90% yield) as a solid. m/z (esi) $M^{+}1$=300.9.

Step B: Ammonium chloride (446 mg, 8.33 mmol) and Fe-powder (930.6 mg, 1.7 mmol) were added to a stirred solution of 2-methyl-5-(2-methyl-4-nitrophenoxy)benzo[d]thiazole (500 mg, 1.7 mmol), in a mixture of methanol/water (1:1; 6 mL) at room temperature. The reaction mixture was refluxed for 2 hours at 80° C. After completion, the reaction mixture was filtered through a Celite® pad, washed with DCM and concentrated under reduced pressure to obtain the crude residue, which was diluted with water and extracted with DCM. The organic phase was washed with brine, dried over anhydrous $Na_2SO_4$, and filtered. The solvent was evaporated under reduced pressure to afford 3-methyl-4-((2-methylbenzo[d]thiazol-5-yl)oxy)aniline (410 mg, 90% yield) as a solid. m/z (esi) $M^{+}1$=271.3.

Step C: 4,6-Dichloropyrido[3,2-d]pyrimidine (97.25 mg, 0.48 mmol) was added to a stirred solution of 3-methyl-4-((2-methylbenzo[d]thiazol-5-yl)oxy)aniline (120 mg, 0.444 mmol) in IPA (4 mL), and the reaction mixture was heated at 80° C. for 2 hours. The reaction solvent was evaporated under reduced pressure, and the crude material was purified by silica gel column chromatography (0-1% MeOH/DCM) to afford 6-chloro-N-(3-methyl-4-((2-methylbenzo[d]thiazol-5-yl)oxy)phenyl)pyrido[3,2-d]pyrimidin-4-amine (84 mg, 43% yield) as a solid. m/z (esi) $M^{+}1$=433.7.

Step D: NaH (37 mg, 0.92 mmol) was added to a solution of tert-butyl 4-hydroxypiperidine-1-carboxylate (747.28 mg, 3.69 mmol) in DMA (5 mL), and the mixture was stirred for 30 minutes. 6-Chloro-N-(3-methyl-4-((2-methylbenzo[d]thiazol-5-yl)oxy)phenyl)pyrido[3,2-d]pyrimidin-4-amine (200 mg, 0.462 mmol) was added and heated at 120° C. for 16 hours. After completion of the reaction, water was added. The mixture was extracted with EtOAc. The organic phase was dried over anhydrous sodium sulphate, filtered, and evaporated under reduced pressure. The crude product was purified by chromatography on silica gel column chromatography (0-10% MeOH/DCM) to afford tert-butyl 4-((4-((3-methyl-4-((2-methylbenzo[d]thiazol-5-yl)oxy)phenyl) amino)pyrido[3,2-d]pyrimidin-6-yl)oxy)piperidine-1-carboxylate (150 mg, 54%) as a solid. m/z (esi) $M^{+}1$=598.9.

Step E: 4M HCl in dioxane (5 mL) was added to a stirred solution of tert-butyl 4-((4-((3-methyl-4-((2-methylbenzo[d] thiazol-5-yl)oxy)phenyl)amino)pyrido[3,2-d]pyrimidin-6-yl)oxy)piperidine-1-carboxylate (150.0 mg, 0.24 mmol) in DCM (3 mL) at 0° C. and allowed to stir for 1 hour. The reaction mixture was concentrated and triturated with ether to afford crude N-(3-methyl-4-((2-methylbenzo[d]thiazol-5-yl)oxy)phenyl)-6-(piperidin-4-yloxy)pyrido[3,2-d]pyrimidin-4-amine hydrochloride (140 mg, crude) as a solid. m/z (esi) $M^{+}1$-HCl=498.9.

Step F: Acryloyl chloride (20.33 mg, 0.225 mmol) was added to a stirred solution of N-(3-methyl-4-((2-methylbenzo[d]thiazol-5-yl)oxy)phenyl)-6-(piperidin-4-yloxy) pyrido[3,2-d]pyrimidin-4-amine hydrochloride (120 mg, 0.24 mmol) in DCM (2 mL) and DIPEA (0.41 mL, 2.24 mmol) at 0° C. and stirred for 3 hours. The reaction mixture was concentrated, and the crude material was purified by prep HPLC (20-80% ACN:$H_2O$ (20 mM ammonium bicarbonate)) to afford 1-(4-((4-((3-methyl-4-((2-methylbenzo[d] thiazol-5-yl)oxy)phenyl)amino)pyrido[3,2-d]pyrimidin-6-yl)oxy)piperidin-1-yl)prop-2-en-1-one (15.17 mg, 12% over 2 steps) as a solid. $^{1}H$ NMR (400 MHz, $(CD_3)_2SO$) δ 9.46 (s, 1H), 8.55 (s, 1H), 8.11 (d, J=9.0 Hz, 1H), 8.00 (d, J=8.8 Hz, 1H), 7.85 (d, J=2.6 Hz, 1H), 7.80 (dd, J=2.7, 8.6 Hz, 1H), 7.37 (d, J=9.0 Hz, 1H), 7.29 (d, J=2.4 Hz, 1H), 7.12-7.03 (m, 2H), 6.86 (dd, J=10.4, 16.7 Hz, 1H), 6.12 (dd, J=2.5, 16.7 Hz, 1H), 5.86 (d, J=5.3 Hz, 1H), 5.69 (dd, J=2.5, 10.4 Hz, 1H), 4.04-3.81 (m, 2H), 3.70-3.40 (m, 2H), 2.77 (s, 3H), 2.23 (s, 3H), 2.17-2.00 (m, 2H), 1.81-1.61 (m, 2H); m/z (esi) $M^{+}1$=553.20.

Example 8

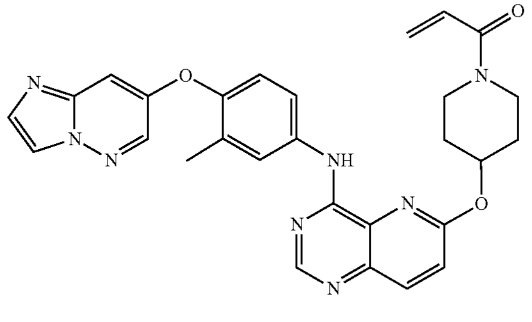 [SMILES: C=CC(=O)N1CCC(Oc2ccc3ncnc(Nc4ccc(Oc5cnn6ccnc6c5)c(C)c4)c3n2)CC1]

1-(4-((4-((4-(imidazo[1,2-b]pyridazin-7-yloxy)-3-methylphenyl)amino)pyrido[3,2-d]pyrimidin-6-yl) oxy)piperidin-1-yl)prop-2-en-1-one Step A: $K_2CO_3$ (612.74 mg, 4.44 mmol) was added to a stirred solution of imidazo[1,2-b]pyridazin-7-ol (400 mg, 2.96 mmol) and 1-fluoro-2-methyl-4-nitrobenzene (505.12 mg, 3.25 mmol) in DMSO (4 mL), and the mixture was stirred for 4 hours at 80° C. The reaction mixture was quenched with water and extracted with EtOAc. The combined organic layers were dried, filtered, and concentrated. The crude product was purified by silica gel column chromatography with (0-5% MeOH/DCM) to afford 7-(2-methyl-4-nitrophenoxy)imidazo[1,2-b]pyridazine (500 mg, 62%) as a solid. m/z (esi) $M^{+}1$=270.6.

Step B: to a stirred solution of 7-(2-methyl-4-nitrophenoxy)imidazo[1,2-b]pyridazine (500 mg, 1.85 mmol) in MeOH (10 mL) was added 10% Pd/C (50% moist; 250 mg) and stirred for 2 hours under $H_2$ atmosphere. The reaction mixture was filtered through a Celite® pad and washed with 10% MeOH-DCM. The filtrate was concentrated to afford 4-(imidazo[1,2-b]pyridazin-7-yloxy)-3-methylaniline (400 mg, 90% yield) as a solid. m/z (esi) $M^{+}1$=241.2.

Step C: 4,6-Dichloropyrido[3,2-d]pyrimidine (182 mg, 0.91 mmol) was added to a stirred solution of 4-(imidazo [1,2-b]pyridazin-7-yloxy)-3-methylaniline (200 mg, 0.83 mmol) in IPA (4 mL) and stirred at 80° C. for 1 hour. The reaction mixture was concentrated under reduced pressure and triturated with pentane and ether to afford 6-chloro-N-(4-(imidazo[1,2-b]pyridazin-7-yloxy)-3-methylphenyl) pyrido[3,2-d]pyrimidin-4-amine (320 mg, 95% yield) as a solid. m/z (esi) $M^{+}1$=404.0.

Step D: NaH (60% weight in paraffin; 60 mg, 1.55 mol) was added to a stirred solution of tert-butyl 4-hydroxypiperidine-1-carboxylate (311 mg, 1.55 mmol) in DMA (3 mL), and the mixture was stirred for 10 minutes at room temperature. 6-Chloro-N-(4-(imidazo[1,2-b]pyridazin-7-yloxy)-3-methylphenyl)pyrido[3,2-d]pyrimidin-4-amine (250 mg, 0.62 mol) was added, and the mixture was heated to 130° C. for 1 hour in a microwave. The reaction mixture was cooled to ambient temperature and diluted with water. The mixture was extracted with EtOAc, and the combined organic layers were dried over $Na_2SO_4$, filtered and concentrated. The crude product was purified by silica gel column chromatography (0-1% MeOH-DCM) to afford tert-butyl 4-((4-((4-(imidazo[1,2-b]pyridazin-7-yloxy)-3-methylphenyl)amino)pyrido[3,2-d]pyrimidin-6-yl)oxy) piperidine-1-carboxylate (90 mg, 21%) as a gummy solid. m/z (esi) $M^{+}1$=569.2.

Step E: Dioxane-HCl (4M; 1 mL) was added to a stirred solution of tert-butyl 4-((4-((4-(imidazo[1,2-b]pyridazin-7-yloxy)-3-methylphenyl)amino)pyrido[3,2-d]pyrimidin-6-yl)oxy)piperidine-1-carboxylate (90 mg, 1.58 mmol) in DCM (1 mL) at 0° C., and the mixture was stirred for 1 hour. After completion, the reaction mixture was concentrated. The crude material was basified with saturated aqueous $NaHCO_3$ solution and extracted with 10% MeOH-DCM. The combined organic layers were dried, filtered, concentrated, and then purified by amine silica gel column chromatography (0-5% MeOH/DCM) to afford N-(4-(imidazo [1,2-b]pyridazin-7-yloxy)-3-methylphenyl)-6-(piperidin-4-yloxy)pyrido[3,2-d]pyrimidin-4-amine (50 mg, 67%) as a solid. m/z (esi) $M^{+}1$=469.1.

Step F: Acryloyl chloride (10 mg, 0.11 mmol) in DCM (1 mL) was added to a stirred solution of N-(4-(imidazo[1,2-b]pyridazin-7-yloxy)-3-methylphenyl)-6-(piperidin-4-yloxy)pyrido[3,2-d]pyrimidin-4-amine (50 mg, 0.09 mmol) in DCM (2 mL) and DIPEA (0.04 mL, 0.24 mmol) in 0° C. and stirred for 1 hour. The reaction mixture was quenched with ice and concentrated. The crude product was purified by reverse phase Prep HPLC (5-95% ACN:$H_2O$ (0.1% $NH_4HCO_3$)) to afford 1-(4-((4-((4-(imidazo[1,2-b] pyridazin-7-yloxy)-3-methylphenyl)amino)pyrido[3,2-d] pyrimidin-6-yl)oxy)piperidin-1-yl)prop-2-en-1-one (7 mg, 13%) as a solid. $^{1}H$ NMR (400 MHz, $(CD_3)_2SO$) δ 9.49 (s, 1H), 8.63 (d, J=2.8 Hz, 1H), 8.58 (s, 1H), 8.21 (s, 1H), 8.12 (d, J=9.0 Hz, 1H), 7.97-7.86 (m, 2H), 7.65 (s, 1H), 7.38 (d, J=9.0 Hz, 1H), 7.25 (d, J=8.7 Hz, 1H), 7.06 (d, J=2.8 Hz, 1H), 6.86 (dd, J=10.4, 16.7 Hz, 1H), 6.12 (dd, J=2.4, 16.7

Hz, 1H), 5.96-5.82 (m, 1H), 5.69 (dd, J=2.5, 10.5 Hz, 1H), 4.05-3.78 (m, 2H), 3.64-3.45 (m, 2H), 2.26 (s, 3H), 2.14-2.04 (m, 2H), 1.79-1.62 (m, 2H); m/z (esi) $M^{+}1$=523.1.

Example 9

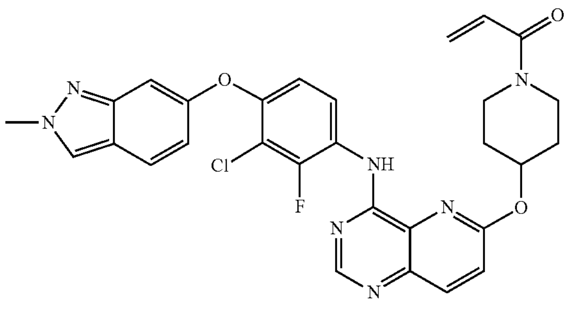 [SMILES: C=CC(=O)N1CCC(Oc2ccc3ncnc(Nc4ccc(Oc5ccc6cn(C)nc6c5)c(Cl)c4F)c3n2)CC1]

1-(4-((4-((3-chloro-2-fluoro-4-((2-methyl-2H-indazol-6-yl)oxy)phenyl)amino)pyrido[3,2-d]pyrimidin-6-yl)oxy)piperidin-1-yl)prop-2-en-1-one Step A: 2-Chloro-1,3-difluoro-4-nitrobenzene (652.03 mg, 3.38 mmol) and $K_2CO_3$ (699.32 mg, 5.07 mmol) was added to a stirred solution of 2-methyl-2H-indazol-6-ol (500 mg, 3.38 mmol) in DMSO (4.0 mL), and the mixture was stirred at 80° C. for 4 hours. The reaction mixture was then diluted with water and extracted with EtOAc. The combined organic layers were dried over $Na_2SO_4$, filtered and concentrated. The crude product was purified by silica gel column chromatography (0-1% MeOH/DCM) to afford 6-(2-chloro-3-fluoro-4-nitrophenoxy)-2-methyl-2H-indazole (750 mg, mixture of two isomers) as a solid. m/z (esi) M+1=322.2.

Step B: Zn powder (3.26 g, 49.84 mmol) and $NH_4Cl$ (2.67 g, 49.84 mmol) were added to a solution of 6-(2-chloro-3-fluoro-4-nitrophenoxy)-2-methyl-2H-indazole (along with other isomer; 1.6 g, 5.0 mmol) in THF (15 mL) and $H_2O$ (3 mL). The reaction was stirred at room temperature for 2 hours. The reaction mixture was filtered through sintered funnel and washed with EtOAc. The filtrate layers were separated, and the organic phase was dried over anhydrous $Na_2SO_4$, filtered, and concentrated under reduced pressure. The crude product was purified by SFC (C Amylose A (250×30 mm) 5p, 120 bar, 35° C., 50% $CO_2$+50% (0.3% isopropylamine in MeOH), to afford 3-chloro-2-fluoro-4-((2-methyl-2H-indazol-6-yl)oxy)aniline (350 mg, 24% yield) as a solid. m/z (esi) $M^{+}1$=292.1. Structure of desired isomer was confirmed by HMBC.

Step C: Potassium tert-butoxide (153 mg, 1.3 mmol) was added to a stirred solution of 3-chloro-2-fluoro-4-((2-methyl-2H-indazol-6-yl)oxy)aniline (200 mg, 0.68 mmol) and 4,6-dichloropyrido[3,2-d]pyrimidine (150 mg, 0.75 mmol) in DMSO (3 mL) and stirred at 80° C. for 2 hours. The reaction mixture was quenched with water and extracted with EtOAc. The organic layer was dried over sodium sulphate and concentrated. The crude product was purified by silica gel column chromatography using (0-2% MeOH-DCM) to afford 6-chloro-N-(3-chloro-2-fluoro-4-((2-methyl-2H-indazol-6-yl)oxy)phenyl)pyrido[3,2-d]pyrimidin-4-amine (280 mg, 45% yield) as a semi solid. m/z (esi) $M^{+}1$=455.0.

Step D: NaH (60 weight % in paraffin; 22 mg, 0.54 mmol) was added to a stirred solution of tert-butyl 4-hydroxypiperidine-1-carboxylate (100 mg, 0.22 mmol) in DMA (1.5 mL) was added at 0° C., and the mixture was stirred for 30 minutes. Then 6-chloro-N-(3-chloro-2-fluoro-4-((2-methyl-2H-indazol-6-yl)oxy)phenyl)pyrido[3,2-d]pyrimidin-4-amine (132 mg, 0.65 mmol) was added to the reaction mixture, which was stirred at 60° C. for 16 hours. The reaction mixture was quenched with water and extracted with EtOAc. The combined organic layers were washed with ice cold water and dried over $Na_2SO_4$, filtered and concentrated. The crude product was purified by silica gel column chromatography (0-1% MeOH-DCM) to afford tert-butyl 4-((4-((3-chloro-2-fluoro-4-((2-methyl-2H-indazol-6-yl)oxy)phenyl)amino)pyrido[3,2-d]pyrimidin-6-yl)oxy)piperidine-1-carboxylate (130 mg, 80% yield) as a semi solid. m/z (esi) M+1=620.2.

Step E: 4N HCl in 1,4-dioxane (1.5 mL) was added to a stirred solution of tert-butyl 4-((4-((3-chloro-2-fluoro-4-((2-methyl-2H-indazol-6-yl)oxy)phenyl)amino)pyrido[3,2-d]pyrimidin-6-yl)oxy)piperidine-1-carboxylate (45 mg, 0.07 mmol) in DCM (1 mL) and stirred at room temperature for 1 hour. The reaction mixture was concentrated. The crude material was triturated with diethyl ether to obtain a solid compound that was isolated by vacuum filtration and then dried in vacuo to afford N-(3-chloro-2-fluoro-4-((2-methyl-2H-indazol-6-yl)oxy)phenyl)-6-(piperidin-4-yloxy)pyrido[3,2-d]pyrimidin-4-amine hydrochloride salt (45 mg, crude) as a solid. m/z (esi) $M^{+}1$=520.0.

Step F: Acryloyl chloride (11 mg, 0.12 mmol) in DCM (1 mL) was added to a stirred solution at 0° C. of N-(3-chloro-2-fluoro-4-((2-methyl-2H-indazol-6-yl)oxy)phenyl)-6-(piperidin-4-yloxy)pyrido[3,2-d]pyrimidin-4-amine hydrochloride (70 mg, 0.12 mmol) in DCM (1 mL) and DIPEA (0.3 mL, 1.3 mmol) and stirred for 30 minutes. The reaction mixture was quenched with water and extracted with 10% MeOH-DCM. The combined organic layers were dried over $Na_2SO_4$, filtered and concentrated. The crude product was purified by reverse phase prep HPLC (20-95% ACN:$H_2O$ (20 mM Ammonium Bicarbonate)) to afford 1-(4-((4-((3-chloro-2-fluoro-4-((2-methyl-2H-indazol-6-yl)oxy)phenyl)amino)pyrido[3,2-d]pyrimidin-6-yl)oxy)piperidin-1-yl)prop-2-en-1-one (12 mg, 15% 2 step yield) as a white solid. $^{1}H$ NMR (400 MHz, $(CD_3)_2SO$) δ 9.54 (s, 1H), 8.52 (d, J=2.3 Hz, 1H), 8.37 (s, 1H), 8.13 (d, J=9.0 Hz, 1H), 7.82 (dd, J=9.1, 21.6 Hz, 2H), 7.39 (d, J=9.0 Hz, 1H), 7.04 (d, J=6.9 Hz, 2H), 6.93-6.81 (m, 2H), 6.12 (dd, J=2.6, 16.7 Hz, 1H), 5.69 (dd, J=2.7, 10.8 Hz, 2H), 4.14 (s, 3H), 4.07-3.86 (m, 2H), 3.60-3.35 (m, 2H), 2.19-2.01 (m, 2H), 1.81-1.60 (m, 2H); m/z (esi) M+1=574.2.

Example 10

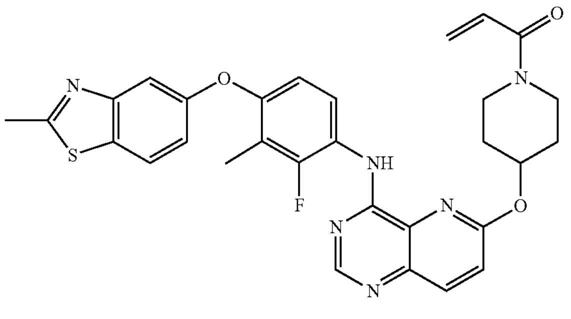 [SMILES: C=CC(=O)N1CCC(Oc2ccc3ncnc(Nc4ccc(Oc5ccc6sc(C)nc6c5)c(C)c4F)c3n2)CC1]

1-(4-((4-((2-fluoro-3-methyl-4-((2-methylbenzo[d]thiazol-5-yl)oxy)phenyl)amino)pyrido[3,2-d]pyrimidin-6-yl)oxy)piperidin-1-yl)prop-2-en-1-one Step A: $K_2CO_3$ (5 g, 36.36 mmol) and 1,3-difluoro-2-methyl-4-nitrobenzene (2.3 g, 13.33 mmol) was added to a stirred solution of 2-methylbenzo[d]thiazol-5-ol (2.0 g, 12.21 mmol) in DMSO (10 mL). The mixture was stirred at ambient temperature for 16 hours. The reaction mixture was diluted with EtOAc, then washed with cold water followed by a cold brine solution. The organic phase was dried over $Na_2SO_4$, filtered and concentrated. The crude product was purified by silica gel column chromatography (10-20% EtOAc-Hexane) to afford a mixture of two isomers, which included 5-(3-fluoro-2-methyl-4-nitrophenoxy)-2-methylbenzo[d]thiazole (3.3 g, mixture of two isomer) as a solid. m/z (esi) $M^{+}1=319$.

Step B: $NH_4Cl$ (5.89 g, 110.06 mmol) and Zn dust (7.2 g, 110.06 mmol) was added to a stirred solution of the two isomers of 5-(3-fluoro-2-methyl-4-nitrophenoxy)-2-methylbenzo[d]thiazole (3.5 g, 11.01 mmol) in THF:$H_2O$ (5:1, 36 mL). The reaction was stirred for 1 hour at 0° C. The reaction was then filtered through a Celite® bed and washed with EtOAc. The filtrate was concentrated, then diluted with water and extracted with EtOAc. The combined organic phase was concentrated to provide the mixture of isomers (3 g) as a solid. The two isomers were separated by prep-SFC (50% $CO_2$+50% MeOH, 25 g/min) to afford the desired product, 2-fluoro-3-methyl-4-((2-methylbenzo[d]thiazol-5-yl)oxy)aniline (520 mg, yield 15%, 2 steps) as a solid. m/z (esi) $M^{+}1=289.0$. The structure of desired isomer was confirmed by HMBC.

Step C: 4,6-Dichloropyrido[3,2-d]pyrimidine (114 mg, 0.6 mmol) was added to a solution of 2-fluoro-3-methyl-4-((2-methylbenzo[d]thiazol-5-yl)oxy)aniline (150 mg, 0.52 mmol) in IPA (3.0 mL). The mixture was heated to 90° C., where it stirred for 1 hour. The reaction mixture was then evaporated to dryness to afford the crude product, which was purified by silica gel column chromatography (30-50% EtOAc/Hexane) to afford 6-chloro-N-(2-fluoro-3-methyl-4-((2-methylbenzo[d]thiazol-5-yl)oxy)phenyl)pyrido[3,2-d]pyrimidin-4-amine (190 mg, 82%) as a solid. m/z (esi) $M^{+}1=452.0$.

Step D: t-BuOK (75 mg, 0.67 mmol) was added to a stirred solution of tert-butyl 4-hydroxypiperidine-1-carboxylate (155 mg, 0.78 mmol) in THF (2 mL) and stirred for 30 minutes at room temperature. 6-Chloro-N-(2-fluoro-3-methyl-4-((2-methylbenzo[d]thiazol-5-yl)oxy)phenyl)pyrido[3,2-d]pyrimidin-4-amine (50 mg, 0.11 mmol) was added, and the mixture was heated to 100° C. where it stirred for 16 hours. The reaction was cooled to ambient temperature and diluted with water. The reaction was extracted with 5% MeOH-DCM, and the combined extracts were washed with brine. The organic phase was dried over $Na_2SO_4$, filtered, and concentrated to afford tert-butyl 4-((4-((2-fluoro-3-methyl-4-((2-methylbenzo[d]thiazol-5-yl)oxy)phenyl)amino)pyrido[3,2-d]pyrimidin-6-yl)oxy)piperidine-1-carboxylate (200 mg, crude) as a solid. m/z (esi) $M^{+}1=617.2$.

Step-E: HCl (4M) in 1,4-dioxane (3.0 mL) was added to a stirred solution at 0° C. of tert-butyl 4-((4-((2-fluoro-3-methyl-4-((2-methylbenzo[d]thiazol-5-yl)oxy)phenyl)amino)pyrido[3,2-d]pyrimidin-6-yl)oxy)piperidine-1-carboxylate (200 mg, 0.33 mmol) in DCM (3.0 mL) and stirred for 1 hour. The reaction mixture was then concentrated. The residue was taken up in 5% MeOH-DCM and washed with a saturated aqueous $NaHCO_3$ solution. The organic phase was dried over $Na_2SO_4$, filtered and concentrated to afford the crude product, which was purified by silica gel column chromatography (10-15% MeOH-DCM) to afford N-(2-fluoro-3-methyl-4-((2-methylbenzo[d]thiazol-5-yl)oxy)phenyl)-6-(piperidin-4-yloxy)pyrido[3,2-d]pyrimidin-4-amine (60 mg, 40% yield in 2 steps) as a solid. m/z (esi) $M^{+}1=517.0$.

Step F: Acryloyl chloride (18 mg, 0.20 mmol) was added to a stirred solution of N-(2-fluoro-3-methyl-4-((2-methylbenzo[d]thiazol-5-yl)oxy)phenyl)-6-(piperidin-4-yloxy)pyrido[3,2-d]pyrimidin-4-amine (105 mg, 0.20 mmol) in DCM (2 mL) and DIPEA (0.1 mL, 0.4 mmol), and the mixture was stirred for 1 hour at 0° C. The reaction was then quenched with ice, and the mixture was concentrated to dryness. The crude product was purified by Prep-HPLC (20-95% ACN:$H_2O$ (20 mM ammonium bicarbonate)) to afford 1-(4-((4-((2-fluoro-3-methyl-4-((2-methylbenzo[d]thiazol-5-yl)oxy)phenyl)amino)pyrido[3,2-d]pyrimidin-6-yl)oxy)piperidin-1-yl)prop-2-en-1-one (37 mg, 32% yield) as a solid. $^{1}H$ NMR (400 MHz, $(CD_3)_2SO$) δ 9.39 (s, 1H), 8.51 (s, 1H), 8.13 (d, J=9.0 Hz, 1H), 8.05 (d, J=8.7 Hz, 1H), 7.92-7.80 (m, 1H), 7.44-7.34 (m, 2H), 7.14 (dd, J=2.4, 8.7 Hz, 1H), 6.95-6.81 (m, 2H), 6.12 (dd, J=2.4, 16.7 Hz, 1H), 5.69 (dd, J=2.3, 10.6 Hz, 2H), 4.09-3.86 (m, 2H), 3.60-3.48 (m, 1H), 3.47-3.36 (m, 1H), 2.79 (s, 3H), 2.21 (s, 3H), 2.17-2.06 (m, 2H), 1.80-1.61 (m, 2H); m/z (esi) $M^{+}1=571.5$.

Example 11

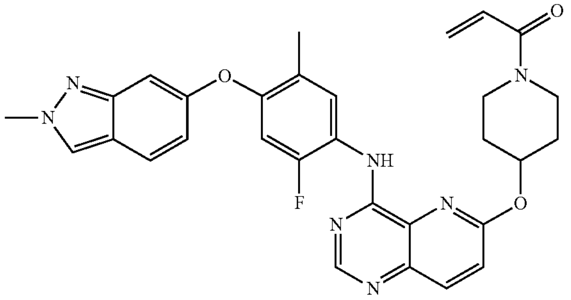 [SMILES: C=CC(=O)N1CCC(Oc2ccc3ncnc(Nc4cc(C)c(Oc5ccc6cn(C)nc6c5)cc4F)c3n2)CC1]

1-(4-((4-((2-fluoro-5-methyl-4-((2-methyl-2H-indazol-6-yl)oxy)phenyl)amino)pyrido[3,2-d]pyrimidin-6-yl)oxy)piperidin-1-yl)prop-2-en-1-one Step A: $K_2CO_3$ (431 mg, 3.12 mmol) was added to a stirred solution of 1,5-difluoro-2-methyl-4-nitrobenzene (180.0 mg, 1.04 mmol) and 2-methyl-2H-indazol-6-ol (154.03 mg, 1.04 mmol) in DMSO (2 mL). The reaction mixture was stirred at room temperature for 16 hours. The mixture was then diluted with EtOAc and was washed with water followed by brine. The organic phase was then concentrated to provide the crude product which was combined with another batch of crude material (450 mg of combined crude material). The crude product was purified by silica gel column chromatography (50-55% EtOAc/Hexane) to afford 6-(5-fluoro-2-methyl-4-nitrophenoxy)-2-methyl-2H-indazole (347 mg) as a solid. The isolated compound contained two possible isomers. m/z (esi) $M^{+}1=302.2$.

Step B: Zn dust (577.44 mg, 8.83 mmol) was added to a stirred solution of 6-(5-fluoro-2-methyl-4-nitrophenoxy)-2-methyl-2H-indazole (along with the other isomer; 266.0 mg, 0.883 mmol) in THF (3 mL) and water (0.6 mL), followed by $NH_4Cl$ (472.37 mg, 8.829 mmol) at 0° C. and stirred for 1 hour. The reaction mixture was filtered through a pad of Celite®, and the filtrate was concentrated under reduced pressure. The crude product was mixed with another batch of crude material (additional 50 mg of crude material), and the combined lot was purified by prep HPLC SFC (Chiralpak IG (250×21 mm) 5p 55% $CO_2$+45% (0.3% isopropylamine in methanol), 25 g/min), ABPR: 110 bar, temperature: 35° C.) to afford 2-fluoro-5-methyl-4-((2-methyl-2H-indazol-6-yl)oxy)aniline, the desired isomer (210 mg, 69% yield) as a semisolid. The structure of the compound was confirmed by HMBC. m/z (esi) $M^+1$=272.4.

Step C: 4,6-Dichloropyrido[3,2-d]pyrimidine (119.44 mg, 0.597 mmol) was added to a stirred solution of 2-fluoro-5-methyl-4-((2-methyl-2H-indazol-6-yl)oxy)aniline (162 mg, 0.597 mmol) in IPA (3 mL), and the mixture was stirred at 90° C. for 1 hour. The reaction mixture was then concentrated, and the crude material was purified by silica gel column chromatography (0-10% MeOH/DCM) to afford 6-chloro-N-(2-fluoro-5-methyl-4-((2-methyl-2H-indazol-6-yl)oxy)phenyl)pyrido[3,2-d]pyrimidin-4-amine (258 mg, 99% yield) as a semi solid. m/z (esi) $M^+1$=435.2.

Step D: NaH (60% in mineral oil, 24 mg, 0.575 mmol) was added to a stirred solution of tert-butyl 4-hydroxypiperidine-1-carboxylate (115.71 mg, 0.575 mmol) in DMA (1 mL) at 0° C. under inert atmosphere and then stirred for 15 minutes at room temperature. 6-Chloro-N-(2-fluoro-5-methyl-4-((2-methyl-2H-indazol-6-yl)oxy)phenyl)pyrido[3,2-d]pyrimidin-4-amine (100 mg, 0.23 mmol) was added to the solution, and the mixture was warmed to 140° C. where it stirred for 5 hours. The mixture was cooled to room temperature and diluted with EtOAc. The mixture was washed with water, followed by brine, and then dried over anhydrous $Na_2SO_4$, filtered, and concentrated under reduced pressure. The crude product was purified by silica gel column chromatography (2-3% MeOH/DCM) to get tert-butyl 4-{[4-({2-fluoro-5-methyl-4-[(2-methyl-2H-indazol-6-yl)oxy]phenyl}amino)pyrido[3,2-d]pyrimidin-6-yl]oxy}piperidine-1-carboxylate (110 mg, 80% yield) as a solid. m/z (esi) $M^+1$=600.2.

Step E: HCl (4M) in 1,4-dioxane (3 mL) was added to a stirred solution at 0° C. of tert-butyl 4-((4-((2-fluoro-5-methyl-4-((2-methyl-2H-indazol-6-yl)oxy)phenyl)amino)pyrido[3,2-d]pyrimidin-6-yl)oxy)piperidine-1-carboxylate (110.0 mg, 0.184 mmol) in DCM (3 mL) and was stirred at 0° C. for 1 hour. The mixture was concentrated under reduced pressure and was used in the next step without further purification to afford N-(2-fluoro-5-methyl-4-((2-methyl-2H-indazol-6-yl)oxy)phenyl)-6-(piperidin-4-yloxy)pyrido[3,2-d]pyrimidin-4-amine hydrochloride (91 mg, crude) as a solid. m/z (esi) $M^+1$=500.4.

Step F: DIPEA (0.08 mL, 0.48 mmol) was added to a stirred solution of N-(2-fluoro-5-methyl-4-((2-methyl-2H-indazol-6-yl)oxy)phenyl)-6-(piperidin-4-yloxy)pyrido[3,2-d]pyrimidin-4-amine hydrochloride (80.0 mg, 0.16 mmol) and acrylic acid (12.69 mg, 0.176 mmol) in DMF (1 mL), followed by T3P (50% in EtOAc; 0.06 mL, 0.192 mmol) at 0° C. and was stirred at 0° C. for 1 hour. The mixture was taken up in EtOAc and was washed with water followed by brine and dried over anhydrous $Na_2SO_4$, filtered, and concentrated under reduced pressure. The crude product was mixed with another batch of material (an additional 90 mg was added), and the combined material was purified by reverse phase Prep-HPLC (20-95% ACN:water (20 mM Ammonium bicarbonate), 16 mL/min) to afford 1-(4-((4-((2-fluoro-5-methyl-4-((2-methyl-2H-indazol-6-yl)oxy)phenyl)amino)pyrido[3,2-d]pyrimidin-6-yl)oxy)piperidin-1-yl)prop-2-en-1-one (25 mg, 11% yield in 2 steps) as a solid. $^1H$ NMR (400 MHz, $(CD_3)_2SO$) δ 9.42 (s, 1H), 8.50 (s, 1H), 8.34 (s, 1H), 8.12 (d, J=9.0 Hz, 1H), 7.84 (d, J=8.7 Hz, 1H), 7.76 (d, J=9.6 Hz, 1H), 7.37 (d, J=9.0 Hz, 1H), 6.97 (d, J=11.0 Hz, 1H), 6.92-6.80 (m, 3H), 6.12 (dd, J=2.5, 16.6 Hz, 1H), 5.69 (dd, J=2.8, 10.7 Hz, 2H), 4.12 (s, 3H), 4.09-3.87 (m, 2H), 3.59-3.45 (m, 1H), 3.46-3.34 (m, 1H), 2.23 (s, 3H), 2.20-2.02 (m, 2H), 1.78-1.57 (m, 2H); m/z (esi) $M^+1$=554.2.

Example 12

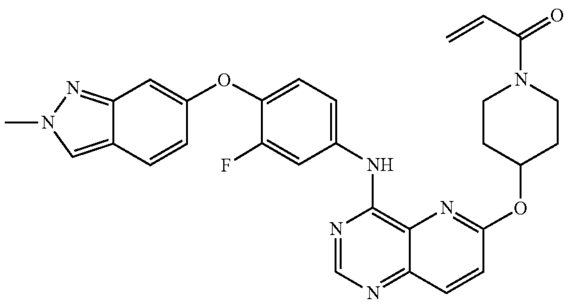 [SMILES: C=CC(=O)N1CCC(Oc2ccc3ncnc(Nc4ccc(Oc5ccc6cn(C)nc6c5)c(F)c4)c3n2)CC1]

1-(4-((4-((3-fluoro-4-((2-methyl-2H-indazol-6-yl)oxy)phenyl)amino)pyrido[3,2-d]pyrimidin-6-yl)oxy)piperidin-1-yl)prop-2-en-1-one Step A: 1,2-Difluoro-4-nitrobenzene (430 mg, 2.7 mmol) and $K_2CO_3$ (746 mg, 5.4 mmol), was added to a stirred solution of 2-methyl-2H-indazol-6-ol (400 mg, 2.7 mmol) in DMSO (15 mL), and the reaction mixture was warmed to 40° C. where it stirred for 1 hour. After cooling to ambient temperature, water was added, and the mixture extracted with ethyl acetate (3×). The combined organic layers were dried over anhydrous $Na_2SO_4$, filtered, and concentrated under reduced pressure. The crude product was purified by silica gel flash column chromatography (eluent: 50% EtOAc-hexane) to afford 6-(2-fluoro-4-nitrophenoxy)-2-methyl-2H-indazole (550 mg, 70%) as a solid. m/z (esi) $M^+1$=288.0.

Step B: Ammonium chloride (205 mg, 3.82 mmol) and Fe-powder (1.07 g, 0.35 mmol) was added to a solution of 6-(2-fluoro-4-nitrophenoxy)-2-methyl-2H-indazole (550 mg, 1.9 mmol) in a mixture of methanol/water (1:1) at room temperature, and the reaction mixture was refluxed for 2 hours at 80° C. The reaction mixture was then cooled to ambient temperature, filtered through the Celite®, and washed with dichloromethane. The filtrate was concentrated under reduced pressure to obtain a crude residue, which was diluted with water and extracted with dichloromethane (3×30 mL). The organic layer was washed with brine, dried over anhydrous $Na_2SO_4$, filtered, and concentrated under reduced pressure to obtain 3-fluoro-4-((2-methyl-2H-indazol-6-yl)oxy)aniline (450 mg, 90%) as a solid. m/z (esi) $M^+1$=258.1.

Step C: 4,6-Dichloropyrido[3,2-d]pyrimidine (103 mg, 0.5 mmol) was added to a stirred solution of 3-fluoro-4-((2-methyl-2H-indazol-6-yl)oxy)aniline (120 mg, 0.46 mmol) in IPA (4 mL), and the reaction mixture was heated to 80° C. where it stirred for 1 hour. The mixture was cooled to ambient temperature. The solvent was evaporated, and the crude was purified by silica gel (100-200) flash column chromatography (eluent: 1% MeOH-dichloromethane) to afford 6-chloro-N-(3-fluoro-4-((2-methyl-2H-indazol-6-yl)oxy)phenyl)pyrido[3,2-d]pyrimidin-4-amine (180 mg, 90%) as a solid. m/z (esi) $M^{+}1$=421.0.

Step D: t-BuOK (240 mg, 2.14 mmol) to a solution of tert-butyl 4-hydroxypiperidine-1-carboxylate (478 mg, 2.37 mmol) in DMSO (2 mL) and stirred for 30 minutes at room temperature. 6-Chloro-N-(3-fluoro-4-((2-methyl-2H-indazol-6-yl)oxy)phenyl)pyrido[3,2-d]pyrimidin-4-amine (100 mg, 0.23 mmol) was added, and the reaction was heated at 100° C. for 1 hour. After cooling to ambient temperature, the reaction mixture was diluted with water and extracted with ethyl acetate (3×). The combined organic layers were washed with brine, dried over anhydrous $Na_2SO_4$, filtered, and evaporated under reduced pressure. The crude product was purified by silica gel flash column chromatography (eluent: 70% EtOAc-hexane) to afford tert-butyl 4-((4-((3-fluoro-4-((2-methyl-2H-indazol-6-yl)oxy)phenyl)amino)pyrido[3,2-d]pyrimidin-6-yl)oxy)piperidine-1-carboxylate (70 mg, 50%) as a solid. m/z (esi) $M^{+}1$=586.1.

Step E: (4M) HCl in dioxane (4 mL) was added to a stirred solution of tert-butyl 4-((4-((3-fluoro-4-((2-methyl-2H-indazol-6-yl)oxy)phenyl)amino)pyrido[3,2-d]pyrimidin-6-yl)oxy)piperidine-1-carboxylate (70.0 mg, 0.12 mmol) in dichloromethane (2 mL) at 0° C. and stirred for 1 hour. The reaction mixture was concentrated, and the crude residue triturated with diethyl ether to afford N-(3-fluoro-4-((2-methyl-2H-indazol-6-yl)oxy)phenyl)-6-(piperidin-4-yloxy)pyrido[3,2-d]pyrimidin-4-amine HCl salt (72 mg) as a crude solid. m/z (esi) $M^{+}1$-HCl=485.9.

Step F: Acryloyl chloride (12.5 mg, 0.13 mmol) was added to a stirred solution of N-(3-fluoro-4-((2-methyl-2H-indazol-6-yl)oxy)phenyl)-6-(piperidin-4-yloxy)pyrido[3,2-d]pyrimidin-4-amine HCl salt (72.0 mg, 0.138 mmol) in dichloromethane (2 mL) and DIPEA (0.25 mL, 1.38 mmol) at 0° C. where it stirred for 3 hours. The reaction mixture was concentrated, and the crude product was purified by reverse phase Prep-HPLC (30-95% ACN:water (20 mM ammonium bicarbonate with a flow rate of 16 mL/min) to afford 1-(4-((4-((3-fluoro-4-((2-methyl-2H-indazol-6-yl)oxy)phenyl)amino)pyrido[3,2-d]pyrimidin-6-yl)oxy)piperidin-1-yl)prop-2-en-1-one (18 mg, 24%, 2 steps) as a solid. $^{1}$H NMR (400 MHz, $(CD_3)_2SO$) δ 9.59 (s, 1H), 8.62 (s, 1H), 8.32 (s, 1H), 8.24-8.11 (m, 2H), 7.76 (dd, J=8.7, 22.6 Hz, 2H), 7.39 (d, J=9.1 Hz, 1H), 7.32 (t, J=9.1 Hz, 1H), 6.93-6.80 (m, 3H), 6.12 (d, J=14.7 Hz, 1H), 5.95-5.82 (m, 1H), 5.69 (d, J=9.6 Hz, 1H), 4.11 (s, 3H), 4.04-3.79 (m, 2H), 3.66-3.40 (m, 2H), 2.21-1.98 (m, 2H), 1.79-1.61 (m, 2H); m/z (esi) $M^{+}1$=540.12.

Example 13

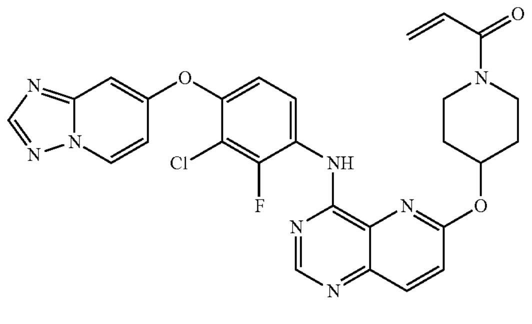

1-(4-((4-((4-([1,2,4]triazolo[1,5-a]pyridin-7-yloxy)-3-chloro-2-fluorophenyl)amino)pyrido[3,2-d]pyrimidin-6-yl)oxy)piperidin-1-yl)prop-2-en-1-one Step A: 2-Chloro-1,3-difluoro-4-nitrobenzene (112 mg, 0.58 mmol) and $K_2CO_3$ (241 mg, 1.75 mmol) were added to a stirred solution of [1,2,4]triazolo[1,5-a]pyridin-7-ol hydrochloride (100 mg, 0.58 mmol) in THF (1.4 mL) and DMSO (0.7 mL) at room temperature and stirred for 1 hour at 80° C. The reaction was cooled to ambient temperature and diluted with water. The reaction mixture was extracted with EtOAc. The combined layers were dried over $Na_2SO_4$, filtered, and concentrated under reduced pressure. The crude mixture of isomers was purified with silica gel column chromatography (20-60% EtOAc/Hexane), and two isomers of 7-(2-chloro-3-fluoro-4-nitrophenoxy)-[1,2,4]triazolo[1,5-a]pyridine were separated (45 mg and 35 mg respectively) as a solid. m/z (esi) $M^{+}1$=309; m/z (esi) $M^{+}1$=308.8.

Step B: $NH_4Cl$ (347.4 mg, 6.49 mmol) was added to a stirred solution of 7-(2-chloro-3-fluoro-4-nitrophenoxy)-[1,2,4]triazolo[1,5-a]pyridine (200 mg, 0.65 mmol) in THF:$H_2O$ (5:1; 3.6 mL) at room temperature, and the reaction mixture was cooled to 0° C. Then Zn dust (424.68 mg, 6.49 mmol) was added, and the mixture was stirred for 1 hour at the same temperature. After completion, the mixture was filtered through a Celite® bed and washed with EtOAc. The filtrate was concentrated, and the residue was treated with water and extracted with EtOAc. The combined organic layers were dried over $Na_2SO_4$, filtered, and concentrated under reduced pressure, and then triturated with diethyl ether to get 4-([1,2,4]triazolo[1,5-a]pyridin-7-yloxy)-3-chloro-2-fluoroaniline (154 mg, 85% yield) as a solid. Structure was confirmed by HMBC. m/z (esi) $M^{+}1$=279.1.

Step C: A stirred solution of 4-([1,2,4]triazolo[1,5-a]pyridin-7-yloxy)-3-chloro-2-fluoroaniline (150 mg, 0.54 mmol) and 4,6-dichloropyrido[3,2-d]pyrimidine (161.06 mg, 0.81 mmol) in IPA (5 mL) was heated at 80° C. for 1 hour. The reaction mixture was then concentrated, and the crude product was purified by silica gel column chromatography (5-10% MeOH/DCM) to get N-(4-([1,2,4]triazolo[1,5-a]pyridin-7-yloxy)-3-chloro-2-fluorophenyl)-6-chloropyrido[3,2-d]pyrimidin-4-amine (200 mg, 83% yield) as a solid. m/z (esi) $M^{+}1$=442.0.

Step D: NaH (60% in mineral oil; 30 mg, 0.79 mmol) was added to a stirred solution at 0° C. of tert-butyl 4-hydroxypiperidine-1-carboxylate (319.05 mg, 1.58 mmol) in DMA (1 mL) and stirred for 30 minutes. Then N-(4-([1,2,4]triazolo[1,5-a]pyridin-7-yloxy)-3-chloro-2-fluorophenyl)-6-chloropyrido[3,2-d]pyrimidin-4-amine (70 mg, 0.16 mmol) was added, and the mixture was heated to 60° C. where it stirred for 16 hours. The mixture was cooled to ambient temperature, and then saturated aqueous $NH_4Cl$ solution was added. The mixture was extracted with EtOAc. The combined organic layers were dried over $Na_2SO_4$, filtered, and concentrated. The crude product was purified with silica gel column chromatography (0-2% MeOH/DCM) to get tert-butyl 4-((4-((4-([1,2,4]triazolo[1,5-a]pyridin-7-yloxy)-3-chloro-2-fluorophenyl)amino)pyrido[3,2-d]pyrimidin-6-yl)oxy)piperidine-1-carboxylate (50 mg, 52% yield) as a sticky mass. m/z (esi) $M^{+}1$=607.4.

Step E: 4N HCl in dioxane (0.5 mL) was added to a stirred solution at 0° C. of tert-butyl 4-((4-((4-([1,2,4]triazolo[1,5-a]pyridin-7-yloxy)-3-chloro-2-fluorophenyl)amino)pyrido[3,2-d]pyrimidin-6-yl)oxy)piperidine-1-carboxylate (50 mg, 0.08 mmol) in DCM (0.5 mL) and stirred for 1 hour. The mixture was then concentrated and triturated with diethyl ether to get N-(4-([1,2,4]triazolo[1,5-a]pyridin-7-yloxy)-3-chloro-2-fluorophenyl)-6-(piperidin-4-yloxy)pyrido[3,2-d]pyrimidin-4-amine hydrochloride (40 mg, crude) as a solid, which was used for next step. m/z (esi) $M^{+}1$=507.0.

Step F: Acryloyl chloride (6.63 mg, 0.07 mmol) in DCM (0.2 mL) was added to a stirred solution at 0° C. of N-(4-([1,2,4]triazolo[1,5-a]pyridin-7-yloxy)-3-chloro-2-fluorophenyl)-6-(piperidin-4-yloxy)pyrido[3,2-d]pyrimidin-4-amine hydrochloride (40 mg, 0.07 mmol) in DCM (0.8 mL) and DIPEA (0.05 mL, 0.3 mmol), and the mixture was stirred for 1 hour at 0° C. Then the mixture was diluted with DCM and washed with water. The organic layer was dried over $Na_2SO_4$, filtered, and concentrated under reduced pressure. The crude product was purified by reverse phase prep-HPLC chromatography (20-80% ACN:water (20 mM ammonium bicarbonate)) to get 1-(4-((4-((4-([1,2,4]triazolo[1,5-a]pyridin-7-yloxy)-3-chloro-2-fluorophenyl)amino)pyrido[3,2-d]pyrimidin-6-yl)oxy)piperidin-1-yl)prop-2-en-1-one (7 mg, 15% yield in 2 steps) as a solid. $^1$H NMR (400 MHz, $(CD_3)_2SO$) δ 9.55 (s, 1H), 9.01 (d, J=7.9 Hz, 1H), 8.57 (s, 1H), 8.45 (s, 1H), 8.16 (d, J=9.1 Hz, 1H), 8.09 (t, J=8.6 Hz, 1H), 7.45-7.36 (m, 2H), 7.12 (d, J=6.4 Hz, 2H), 6.87 (dd, J=10.5, 16.7 Hz, 1H), 6.12 (dd, J=2.4, 16.6 Hz, 1H), 5.69 (dd, J=2.4, 10.3 Hz, 2H), 4.10-3.81 (m, 2H), 3.65-3.36 (m, 2H), 2.25-2.03 (m, 2H), 1.82-1.62 (m, 2H); m/z (esi) $M^{+}1$=561.08.

Example 14

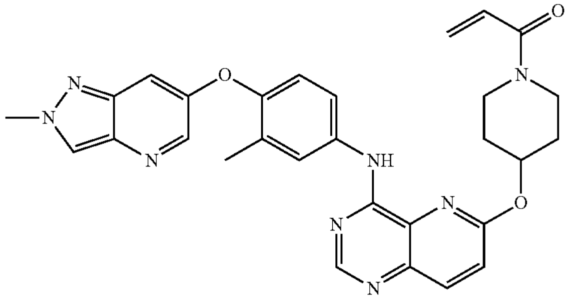 [SMILES: C=CC(=O)N1CCC(Oc2ccc3ncnc(Nc4ccc(Oc5cnc6cn(C)nc6c5)c(C)c4)c3n2)CC1]

1-(4-((4-((3-methyl-4-((2-methyl-2H-pyrazolo[4,3-b]pyridin-6-yl)oxy)phenyl)amino)pyrido[3,2-d]pyrimidin-6-yl)oxy)piperidin-1-yl)prop-2-en-1-one Step A: Trimethyloxonium tetrafluoroborate (1.45 g, 9.84 mmol) was added to a stirred solution of 6-bromo-2H-pyrazolo[4,3-b]pyridine (1.5 g, 7.57 mmol) in EtOAc (30 mL). The mixture was stirred at room temperature for 5 hours under N atmosphere. The reaction mixture was diluted with EtOAc and washed with saturated aqueous $NaHCO_3$ solution. The organic layer was separated, and the aqueous layer was extracted with EtOAc. The combined organic layers were dried over anhydrous $Na_2SO_4$, filtered, and concentrated. The crude product was purified by silica gel column chromatography (10-50% EtOAc/hexane) to afford 6-bromo-2-methyl-2H-pyrazolo[4,3-b] pyridine (600 mg, 37% yield) as a solid. m/z (esi) $M^{+}1$=212.2.

Step B: Potassium hydroxide to a stirred solution of 6-bromo-2-methyl-2H-pyrazolo[4,3-b]pyridine (450 mg, 2.12 mmol) in 1,4-dioxane:water (2:1; 9 mL), and the reaction mixture was degassed for 15 minutes with bubbling argon. t-BuXPhos and $Pd_2(dba)_3$ were then added to the reaction mixture, and Ar purging was continued for another 10 minutes. The reaction mixture was heated at 100° C. for 4 hours. The reaction mixture was concentrated, and the residue was triturated with n-pentane and diethyl ether to remove a coloured impurity and a non-polar spot to obtain crude 2-methyl-2H-pyrazolo[4,3-b]pyridin-6-ol (350 mg, 71% yield) as a solid, which was used directly in the next step. m/z (esi) $M^{+}1$=150.0.

Step C: 1-Fluoro-2-methyl-4-nitrobenzene (312 mg, 2.01 mmol) and $K_2CO_3$ (556 mg, 4.02 mmol) was added to a stirred solution of 2-methyl-2H-pyrazolo[4,3-b]pyridin-6-ol (300 mg, 2.01 mmol) in DMSO (5 mL), and the mixture was stirred at 80° C. for 4 hours. After cooling to ambient temperature, water was added, and the mixture was extracted with EtOAc. The combined organic layers were dried over $Na_2SO_4$, filtered, and concentrated. The crude product was purified by silica gel column chromatography (20-50% EtOAc-hexane) to afford 2-methyl-6-(2-methyl-4-nitrophenoxy)-2H-pyrazolo[4,3-b]pyridine (370 mg, 65% yield) as a solid. m/z (esi) $M^{+}1$=285.2.

Step D: Zn dust (644 mg, 9.85 mmol) and $NH_4Cl$ (527 mg, 9.85 mmol) were added to a solution at 0° C. of 2-methyl-6-(2-methyl-4-nitrophenoxy)-2H-pyrazolo[4,3-b]pyridine (280 mg, 0.98 mmol) in THF-$H_2O$ (5:1; 12 mL). The reaction was stirred at 0° C. for 1 hour. The reaction mixture was filtered through a bed of Celite®, and the filtrate was concentrated under reduced pressure. Water was added to the residue, and the mixture was extracted with DCM. The combined organic layers were dried over anhydrous $Na_2SO_4$, filtered, and concentrated under reduced pressure. The crude product was purified by silica gel column chromatography (0-2% MeOH/DCM) to afford 3-methyl-4-((2-methyl-2H-pyrazolo[4,3-b] pyridin-6-yl)oxy)aniline (240 mg, 95% yield) as a solid. m/z (esi) $M^{+}1$=254.6.

Step E: 4,6-Dichloropyrido[3,2-d]pyrimidine (77 mg, 0.386 mmol) was added to a stirred solution of 3-methyl-4-((2-methyl-2H-pyrazolo[4,3-b]pyridin-6-yl)oxy)aniline (90 mg, 0.354 mmol) in IPA (5 mL), and the mixture was stirred at 80° C. for 2 hours. The reaction mixture was concentrated under reduced pressure. The crude product was triturated with n-pentane and diethyl ether to get the desired compound 6-chloro-N-(3-methyl-4-((2-methyl-2H-pyrazolo[4,3-b]pyridin-6-yl)oxy)phenyl)pyrido[3,2-d]pyrimidin-4-amine (90 mg, 60% yield) as a solid. m/z (esi) $M^{+}1$=418.12.

Step F: t-BuOK (1.135 g, 10.12 mmol) was added to a solution of tert-butyl 4-hydroxypiperidine-1-carboxylate (2.263 g, 11.24 mmol) in DMSO (10 mL), and the mixture was stirred for 30 minutes. 6-Chloro-N-(3-methyl-4-((2-methyl-2H-pyrazolo[4,3-b]pyridin-6-yl)oxy)phenyl)pyrido[3,2-d]pyrimidin-4-amine (470 mg, 1.12 mmol) was added, and the reaction was stirred at 100° C. for 1 hour. The reaction mixture was cooled to ambient temperature then diluted with water and extracted with EtOAc. The combined organic layers were dried over anhydrous sodium sulphate, filtered, and concentrated. The crude product was purified by silica gel column chromatography (0-5% MeOH-DCM) to afford tert-butyl 4-((4-((3-methyl-4-((2-methyl-2H-pyrazolo[4,3-b]pyridin-6-yl)oxy)phenyl)amino)pyrido[3,2-d]pyrimidin-6-yl)oxy)piperidine-1-carboxylate (350 mg, yield 53%) as a solid. m/z (esi) $M^{+}1$=583.1.

Step G: (4M) HCl in dioxane (5 mL) to a stirred solution at 0° C. of tert-butyl 4-((4-((3-methyl-4-((2-methyl-2H-pyrazolo[4,3-b]pyridin-6-yl)oxy)phenyl)amino)pyrido[3,2-d]pyrimidin-6-yl)oxy)piperidine-1-carboxylate (350 mg, 0.60 mmol) in DCM (5 mL) and stirred for 2 hours. The reaction mixture was concentrated, and the residue triturated with diethyl ether to afford N-(3-methyl-4-((2-methyl-2H-pyrazolo[4,3-b]pyridin-6-yl)oxy)phenyl)-6-(piperidin-4-yloxy)pyrido[3,2-d]pyrimidin-4-amine hydrochloride (350 mg, crude) as a solid. m/z (esi) $M^+$1-HCl=482.9.

Step H: Acryloyl chloride (34.87 mg, 0.385 mmol) to a stirred solution at 0° C. of N-(3-methyl-4-((2-methyl-2H-pyrazolo[4,3-b]pyridin-6-yl)oxy)phenyl)-6-(piperidin-4-yloxy)pyrido[3,2-d]pyrimidin-4-amine hydrochloride (200 mg, 0.385 mmol) in DCM (3 mL) and DIPEA (0.71 mL, 3.85 mmol) and stirred for 1 hour at 0° C. After completion, the reaction mixture was quenched with ice and then concentrated. The crude product was purified by reverse phase prep HPLC (20-95% ACN:water (20 mM ammonium bicarbonate)) to afford 1-(4-((4-((3-methyl-4-((2-methyl-2H-pyrazolo[4,3-b]pyridin-6-yl)oxy)phenyl)amino)pyrido[3,2-d]pyrimidin-6-yl)oxy)piperidin-1-yl)prop-2-en-1-one (28 mg, 14% yield in 2 steps) as a sticky solid. $^1$H NMR (400 MHz, $(CD_3)_2SO$) δ 9.47 (s, 1H), 8.63 (s, 1H), 8.56 (s, 1H), 8.44 (d, J=2.6 Hz, 1H), 8.11 (d, J=9.0 Hz, 1H), 7.89 (s, 1H), 7.83 (d, J=8.4 Hz, 1H), 7.37 (d, J=9.0 Hz, 1H), 7.11 (d, J=8.8 Hz, 2H), 6.86 (dd, J=10.4, 16.6 Hz, 1H), 6.12 (dd, J=2.5, 16.6 Hz, 1H), 5.87 (s, 1H), 5.69 (dd, J=2.5, 10.5 Hz, 1H), 4.15 (s, 3H), 4.05-3.82 (m, 2H), 3.66-3.42 (m, 2H), 2.25 (s, 3H), 2.17-1.99 (m, 2H), 1.81-1.57 (m, 2H); m/z (esi) $M^+$1=537.2.

Example 15

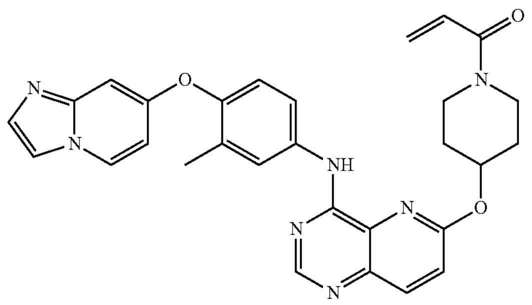 [SMILES: C=CC(=O)N1CCC(Oc2ccc3ncnc(Nc4ccc(Oc5ccn6ccnc6c5)c(C)c4)c3n2)CC1]

1-(4-((4-((4-(imidazo[1,2-a]pyridin-7-yloxy)-3-methylphenyl)amino)pyrido[3,2-d]pyrimidin-6-yl)oxy)piperidin-1-yl)prop-2-en-1-one Step A: 1-Fluoro-2-methyl-4-nitrobenzene (347 mg, 2.23 mmol) and $K_2CO_3$ (618 mg, 4.47 mmol) were added to a stirred solution of imidazo[1,2-a]pyridin-7-ol (300 mg, 2.23 mmol) in DMSO (10 mL), and the reaction mixture was heated at 40° C. for 1 hour. After cooling to ambient temperature, water was added, and the mixture was extracted with ethyl acetate (3×). The combined organic layers were dried over anhydrous $Na_2SO_4$, filtered, and concentrated under reduced pressure. The crude product was purified by silica gel (100-200) flash column chromatography (eluent: 50% EtOAc-hexane) to afford 7-(2-methyl-4-nitrophenoxy)imidazo[1,2-a]pyridine (400 mg, 66%) as a solid. m/z (esi) $M^+$1=269.7

Step B: Ammonium chloride (378 mg, 7.06 mmol) and Fe-powder (789 mg, 14.12 mmol) were added to a solution of 7-(2-methyl-4-nitrophenoxy)imidazo[1,2-a]pyridine (380 mg, 1.4 mmol) in a mixture of methanol/water (1:1) at room temperature, and the reaction mixture was refluxed at 80° C. for 2 hours. After cooling to ambient temperature, the reaction mixture was filtered through the Celite® and washed with dichloromethane, and the filtrate was concentrated under reduced pressure. The crude residue was treated with water, and the mixture extracted with dichloromethane (3×). The combined organic layers were washed with brine, dried over anhydrous $Na_2SO_4$, filtered, and the solvent was evaporated under reduced pressure to obtain 4-(imidazo[1,2-a]pyridin-7-yloxy)-3-methylaniline (300 mg, 88%) as a solid. m/z (esi) $M^+$1=239.8

Step C: 4,6-Dichloropyrido[3,2-d]pyrimidine (110 mg, 0.55 mmol) was added to a stirred solution of 4-(imidazo[1,2-a]pyridin-7-yloxy)-3-methylaniline (120 mg, 0.50 mmol) in IPA (4 mL), and the reaction mixture was heated at 80° C. for 1 hour. The mixture was then concentrated, and the crude material was purified by silica gel (100-200) flash column chromatography (eluent: 1% MeOH-dichloromethane) to afford 6-chloro-N-(4-(imidazo[1,2-a]pyridin-7-yloxy)-3-methylphenyl)pyrido[3,2-d]pyrimidin-4-amine (130 mg, 64%) as a solid. m/z (esi) $M^+$1=403.

Step D: t-BuOK (201 mg, 1.79 mmol) was added to a solution of tert-butyl 4-hydroxypiperidine-1-carboxylate (402 mg, 1.99 mmol) in DMSO (3 mL) and stirred for 30 minutes. 6-Chloro-N-(4-(imidazo[1,2-a]pyridin-7-yloxy)-3-methylphenyl)pyrido[3,2-d]pyrimidin-4-amine (80 mg, 0.2 mmol) was added, and the reaction was heated at 100° C. where it stirred for 1.5 hour. After cooling to ambient temperature, the reaction mixture was diluted with water and extracted with ethyl acetate (3×). The combined organic layers were washed with brine, dried over anhydrous $Na_2SO_4$, filtered, and the solvent was evaporated under reduced pressure. The crude product was purified by silica gel (100-200) flash column chromatography (eluent: 70% EtOAc-hexane) to afford tert-butyl 4-((4-((4-(imidazo[1,2-a]pyridin-7-yloxy)-3-methylphenyl)amino)pyrido [3,2-d] pyrimidin-6-yl)oxy)piperidine-1-carboxylate (70 mg, 50%) as a solid. m/z (esi) $M^+$1=568.6.

Step E: (4M) HCl in dioxane (4 mL) to a stirred solution at 0° C. of tert-butyl 4-((4-((4-(imidazo[1,2-a]pyridin-7-yloxy)-3-methylphenyl)amino)pyrido[3,2-d]pyrimidin-6-yl)oxy)piperidine-1-carboxylate (70.0 mg, 0.12 mmol) in dichloromethane (2 mL) and stirred for 1 hour. The reaction mixture was then concentrated and triturated with diethyl ether to afford N-(4-(imidazo[1,2-a]pyridin-7-yloxy)-3-methylphenyl)-6-(piperidin-4-yloxy)pyrido[3,2-d]pyrimidin-4-amine HCl salt (55 mg) as a crude solid. m/z (esi) $M^+$1-HCl=468.4.

Step F: Acryloyl chloride (11 mg, 0.12 mmol) was added to a stirred solution at 0° C. of N-(4-(imidazo[1,2-a]pyridin-7-yloxy)-3-methylphenyl)-6-(piperidin-4-yloxy)pyrido[3,2-d]pyrimidin-4-amine HCl salt (60 mg, 0.12 mmol) in dichloromethane (2 mL) and DIPEA (0.22 mL, 1.2 mmol) where it stirred for 3 hours. The reaction mixture was concentrated, and the crude product was purified by reverse phase prep-HPLC (30-100% ACN:water (20 mM ammonium bicarbonate with a flow rate of 16 mL/min) to afford 1-(4-((4-((4-(imidazo[1,2-a]pyridin-7-yloxy)-3-methylphenyl)amino) pyrido[3,2-d]pyrimidin-6-yl)oxy)piperidin-1-yl)prop-2-en-1-one (10.27 mg, 16%) as a solid. $^1$H NMR (400 MHz, $(CD_3)_2SO$) δ 9.48 (s, 1H), 8.60-8.52 (m, 2H), 8.12 (d, J=9.0 Hz, 1H), 7.92-7.81 (m, 3H), 7.43 (s, 1H), 7.37 (d, J=9.0 Hz, 1H), 7.19 (d, J=8.6 Hz, 1H), 6.92-6.77 (m, 2H), 6.53 (d, J=2.5 Hz, 1H), 6.12 (dd, J=2.6, 16.8 Hz, 1H), 5.94-5.80 (m, 1H), 5.69 (dd, J=2.6, 10.4 Hz, 1H), 4.07-3.81 (m, 2H), 3.68-3.41 (m, 2H), 2.22 (s, 3H), 2.17-2.02 (m, 2H), 1.80-1.60 (m, 2H). m/z (esi) $M^+$1=522.38.

Example 16

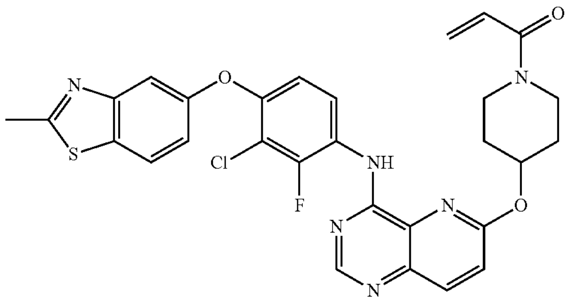 [SMILES: C=CC(=O)N1CCC(Oc2ccc3ncnc(Nc4ccc(Oc5ccc6sc(C)nc6c5)c(Cl)c4F)c3n2)CC1]

1-(4-((4-((3-chloro-2-fluoro-4-((2-methylbenzo[d]thiazol-5-yl)oxy)phenyl)amino)pyrido[3,2-d]pyrimidin-6-yl)oxy)piperidin-1-yl)prop-2-en-1-one Step A: $K_2CO_3$ (2.50 g, 18.2 mmol) was added to a stirred solution of 2-methylbenzo[d]thiazol-5-ol (1.0 g, 6.06 mmol) in DMSO (5.0 mL) and stirred for 5 minutes. 2-Chloro-1,3-difluoro-4-nitrobenzene (1.28 g, 6.7 mmol) was added to the solution and stirred at room temperature for 16 hours. The reaction mixture was then diluted with water and extracted with EtOAc. The combined organic layers were washed with cold water, followed by brine solution, then dried over $Na_2SO_4$, filtered, and concentrated. The crude product was purified by silica gel column chromatography (10-20% EtOAc-Hexane) to afford 5-(2-chloro-3-fluoro-4-nitrophenoxy)-2-methylbenzo[d]thiazole (1.6 g, mixture of isomers) as a solid. m/z (esi) $M^{+}1$=338.6.

Step B: Zn powder (3.3 g, 50.2 mmol) was added to a stirred solution at 0° C. of 5-(2-chloro-3-fluoro-4-nitrophenoxy)-2-methylbenzo[d]thiazole (1.7 g, 5.02 mmol) in THF (16 mL). $NH_4Cl$ (2.7 g, 50.2 mmol) in water (4 mL) was added to the solution at 0° C. and was stirred for 1 hour. The reaction mixture was then filtered through a Celite® bed and washed with EtOAc. The filtrate was diluted with water and extracted with EtOAc. The combined organic layers were washed with water and brine, then dried over $Na_2SO_4$, filtered, and concentrated to afford crude product (1.5 g). The crude mixture of two isomers was separated by Prep SFC (70% $CO_2$+30% (0.5% isopropylamine in EtOH), 25 g/min) to afford 3-chloro-2-fluoro-4-((2-methyl benzo[d]thiazol-5-yl)oxy)aniline (250 mg, 14% yield. 2 steps) as a solid. m/z (esi) $M^{+}1$=308.9.

Step C: 4,6-Dichloropyrido[3,2-d]pyrimidine (116 mg, 0.6 mmol) was added to a stirred solution of 3-chloro-2-fluoro-4-((2-methylbenzo[d]thiazol-5-yl)oxy)aniline (150 mg, 0.58 mmol) in IPA (3 mL) was stirred at 90° C. for 1 hour. The reaction mixture was concentrated to dryness to afford crude product, which was purified by silica gel column chromatography (1-5% MeOH/DCM) to afford 6-chloro-N-(3-chloro-2-fluoro-4-((2-methylbenzo[d]thiazol-5-yl)oxy)phenyl)pyrido[3,2-d]pyrimidin-4-amine (205 mg, 87% yield) as a solid. m/z (esi) $M^{+}1$=472.0.

Step D: t-BuOK (53 mg, 0.49 mmol) was added to a stirred solution of tert-butyl 4-hydroxypiperidine-1-carboxylate (107 mg, 0.53 mmol) in THF (2.0 mL) and stirred for 30 minutes at room temperature. 6-Chloro-N-(3-chloro-2-fluoro-4-((2-methylbenzo[d]thiazol-5-yl)oxy)phenyl)pyrido[3,2-d]pyrimidin-4-amine (50 mg, 0.11 mmol) was added to the solution and heated at 100° C. for 16. After cooling to ambient temperature, the reaction mixture was diluted with water and extracted with EtOAc. The combined organic layers were washed with brine, dried and concentrated. The crude product was purified by silica gel column chromatography using amine silica gel, (0-15% DCM-Hexane) to afford tert-butyl 4-((4-((3-chloro-2-fluoro-4-((2-methylbenzo[d]thiazol-5-yl)oxy)phenyl)amino)pyrido[3,2-d]pyrimidin-6-yl)oxy)piperidine-1-carboxylate (25 mg, 35% yield) as a sticky solid. m/z (esi) $M^{+}1$=637.2.

Step E: HCl (4M) in dioxane (1.0 mL) was added to a stirred solution at 0° C. of tert-butyl 4-((4-((3-chloro-2-fluoro-4-((2-methylbenzo[d]thiazol-5-yl)oxy)phenyl)amino)pyrido[3,2-d]pyrimidin-6-yl)oxy)piperidine-1-carboxylate (60 mg, 0.1 mmol) in DCM (1.0 mL) and stirred for 1 hour. The reaction mixture was concentrated to dryness, then washed with pentane to afford N-(3-chloro-4-((3-(2,4-dimethylthiazol-5-yl)allyl)oxy)-2-fluorophenyl)-6-(piperidin-4-yloxy)pyrido[3,2-d]pyrimidin-4-amine hydrochloride (60 mg, crude) as a sticky solid. m/z (esi) $M^{+}1$=537.2.

Step F: Acryloyl chloride (14 mg, 0.15 mmol) was added to a stirred solution at 0° C. of N-(3-chloro-4-((3-(2,4-dimethylthiazol-5-yl)allyl)oxy)-2-fluorophenyl)-6-(piperidin-4-yloxy)pyrido[3,2-d]pyrimidin-4-amine hydrochloride (85 mg, 0.15 mmol) in DCM (2.0 mL) and DIPEA (0.05 mL, 0.3 mmol), and the reaction stirred for 1 hour at 0° C. The reaction was quenched with ice and concentrated to dryness to afford crude product, which was purified by reverse phase Prep-HPLC ((30%-95% ACN:Water), 20 Mm $NH_4HCO_3$) to afford 1-(4-((4-((3-chloro-2-fluoro-4-((2-methylbenzo[d]thiazol-5-yl)oxy)phenyl)amino)pyrido[3,2-d]pyrimidin-6-yl)oxy)piperidin-1-yl)prop-2-en-1-one (19 mg, 21% yield, in 2 steps) as a solid. $^{1}H$ NMR (400 MHz, $(CD_3)_2SO$) δ 9.55 (s, 1H), 8.52 (d, J=2.4 Hz, 1H), 8.12 (dd, J=8.9, 17.2 Hz, 2H), 7.87 (q, J=9.2 Hz, 1H), 7.53 (d, J=2.5 Hz, 1H), 7.39 (d, J=9.0 Hz, 1H), 7.20 (dd, J=2.6, 8.7 Hz, 1H), 7.07 (d, J=9.2 Hz, 1H), 6.87 (dd, J=10.5, 16.7 Hz, 1H), 6.12 (dd, J=2.5, 16.7 Hz, 1H), 5.79-5.63 (m, 2H), 4.06-3.83 (m, 2H), 3.60-3.50 (m, 1H), 3.48-3.36 (m, 1H), 2.80 (s, 3H), 2.11 (s, 2H), 1.70 (s, 2H); m/z (esi) $M^{+}1$=591.04.

Example 17

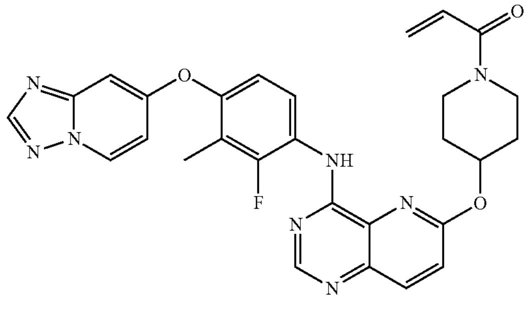 [SMILES: C=CC(=O)N1CCC(Oc2ccc3ncnc(Nc4ccc(Oc5ccn6ncnc6c5)c(C)c4F)c3n2)CC1]

1-(4-((4-((4-([1,2,4]triazolo[1,5-a]pyridin-7-yloxy)-2-fluoro-3-methylphenyl)amino)pyrido[3,2-d]pyrimidin-6-yl)oxy)piperidin-1-yl)prop-2-en-1-one Step A: To a stirred solution of [1,2,4]triazolo[1,5-a]pyridin-7-ol (1.0 g, 7.4 mmol) in DMSO (8 mL) were added $K_2CO_3$ (3.0 g, 2.22 mmol) and 1,3-difluoro-2-methyl-4-nitrobenzene (1.4 g, 8.15 mmol). The reaction mixture was stirred for 2 hours at 90° C. After completion, the reaction mixture was diluted with EtOAc, washed with cold water, brine. The organic part was dried over $Na_2SO_4$ and concentrated to crude which was purified by column chromatography (0-30% EtOAc-Hexane) to afford 7-(3-fluoro-2-methyl-6-nitrophenoxy)-[1,2,4]triazolo[1,5-a]pyridine (900 mg, 44% yield) and 7-(3-fluoro-2-methyl-4-nitrophenoxy)-[1,2,4]triazolo[1,5-a]pyridine (220 mg, 10% yield) as a solid. m/Z (Esi) $M^+1$=289.3.

Step B: To a stirred solution of 7-(3-fluoro-2-methyl-4-nitrophenoxy)-[1,2,4]triazolo[1,5-a]pyridine (200 mg, 0.69 mmol) in THF:$H_2O$ (5.0 mL) were added Zn (456 mg, 6.9 mmol), $NH_4Cl$ (371 mg, 6.94 mmol) at ice cold condition and stirred for 1 hour at room temperature. After completion, the reaction mixture was filtered through Celite® with EtOAc, the filtrate part was washed with brine. The organic part was dried over $Na_2SO_4$ and evaporated to dryness to afford of 4-([1,2,4]triazolo[1,5-a]pyridin-7-yloxy)-2-fluoro-3-methylaniline (170 mg, crude) as a sticky solid. m/z (esi) $M^+1$=259.3. Note: Structure was confirmed by HMBC.

Step C: To a stirred solution of 4-([1,2,4]triazolo[1,5-a]pyridin-7-yloxy)-2-fluoro-3-methylaniline (200 mg, 0.77 mmol) in IPA (3 mL) was added 4,6-dichloropyrido[3,2-d]pyrimidine (154 mg, 0.775 mmol) and stirred for 1 hour at 80° C. After completion, the reaction mixture was evaporated to dryness and diluted with 5% MeOH-DCM, washed with water and brine. The organic part was dried over $Na_2SO_4$, concentrated to afford crude which was purified by silica gel column chromatography (0-2% MeOH-DCM) to afford N-(4-([1,2,4]triazolo[1,5-a]pyridin-7-yloxy)-2-fluoro-3-methylphenyl)-6-chloropyrido[3,2-d]pyrimidin-4-amine (230 mg, 66% yield in 2 steps) as a solid. m/z (esi) M+1=421.4.

Step D: To a stirred solution of tert-butyl 4-hydroxypiperidine-1-carboxylate (716 mg, 3.56 mmol) in THF (6 mL) was added Kt-BuO (360 mg, 3.20 mmol) and stirred for 30 minutes. After that N-(4-([1,2,4]triazolo[1,5-a]pyridin-7-yloxy)-2-fluoro-3-methylphenyl)-6-chloropyrido[3,2-d]pyrimidin-4-amine (150 mg, 0.36 mmol) was added and stirred for 16 hours at 80° C. After completion, the reaction mixture was diluted with 5% MeOH-DCM, washed with water, brine. The organic part was dried over $Na_2SO_4$, concentrated to afford tert-butyl 4-((4-((4-([1,2,4]triazolo[1,5-a]pyridin-7-yloxy)-2-fluoro-3-methylphenyl)amino)pyrido[3,2-d]pyrimidin-6-yl)oxy)piperidine-1-carboxylate (150 mg, crude) as a solid. m/z (esi) M+1=587.2.

Step E: To a stirred solution of tert-butyl 4-((4-((4-([1,2,4]triazolo[1,5-a]pyridin-7-yloxy)-2-fluoro-3-methylphenyl)amino)pyrido[3,2-d]pyrimidin-6-yl)oxy)piperidine-1-carboxylate (150 mg, 0.26 mmol) in DCM (3 mL) was added 4M HCl in dioxane (2.0 mL) at ice cold condition and stirred the reaction mixture for 1 hour. After completion, the reaction mixture concentrated and was diluted with 5% MeOH-DCM washed with $NaHCO_3$ solution. The organic part was dried over $Na_2SO_4$, concentrated to afford crude, which was purified by amine bound silica gel column chromatography (0-5% MeOH-DCM) to afford N-(4-([1,2,4]triazolo[1,5-a]pyridin-7-yloxy)-2-fluoro-3-methylphenyl)-6-(piperidin-4-yloxy)pyrido[3,2-d]pyrimidin-4-amine (68 mg, 39% yield in 2 steps) as a solid. m/z (esi) M+1=486.8.

Step F: To a stirred solution of N-(4-([1,2,4]triazolo[1,5-a]pyridin-7-yloxy)-2-fluoro-3-methylphenyl)-6-(piperidin-4-yloxy)pyrido[3,2-d]pyrimidin-4-amine (60 mg, 0.12 mmol) in DCM (1.5 mL) was added DIPEA (0.04 mL, 0.24 mmol) at 0° C. and stirred the reaction mixture for 5 minutes. Acrolyl chloride (11 mg, 0.12 mmol) in DCM (0.5 mL) was added to the solution and stirred for 1 hour at 0° C. After completion, the reaction was quenched with pinch of ice and evaporated to dryness afford to crude which was purified by Prep-HPLC (30-70% ACN:$H_2O$ (20 mM Ammonium Bicarbonate)) to afford 1-(4-((4-((4-([1,2,4]triazolo[1,5-a]pyridin-7-yloxy)-2-fluoro-3-methylphenyl)amino)pyrido[3,2-d]pyrimidin-6-yl)oxy)piperidin-1-yl)prop-2-en-1-one (30 mg, 44%) as a sticky solid. $^1H$ NMR (400 MHz, DMSO-$d_6$) δ 9.41 (s, 1H), 8.98 (d, J=7.5 Hz, 1H), 8.56 (s, 1H), 8.41 (s, 1H), 8.15 (d, J=9.0 Hz, 1H), 8.04 (t, J=8.8 Hz, 1H), 7.40 (d, J=9.1 Hz, 1H), 7.17 (d, J=8.9 Hz, 1H), 7.07 (dd, J=2.7, 7.5 Hz, 1H), 6.96-6.81 (m, 2H), 6.13 (dd, J=2.5, 16.7 Hz, 1H), 5.73-5.64 (m, 2H), 4.10-3.85 (m, 2H), 3.63-3.33 (m, 2H), 2.21-2.11 (m, 5H), 1.72 (s, 2H). m/z (esi) M+1=541.3.

Example 18

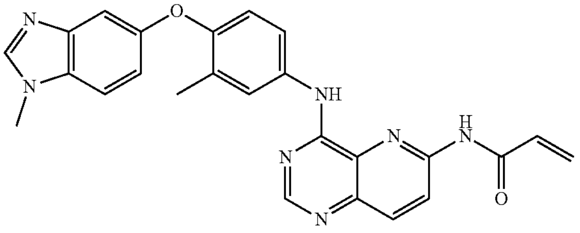

N-(4-((3-methyl-4-((1-methyl-1H-benzo[d]imidazol-5-yl)oxy)phenyl)amino)pyrido[3,2-d]pyrimidin-6-yl)acrylamide Step A: $K_2CO_3$ (1957 mg, 14 mmol) was added to a stirred solution of 1-fluoro-2-methyl-4-nitrobenzene (700 mg, 4.73 mmol), 1-methyl-1H-benzo[d]imidazol-5-ol (733 mg, 4.73 mmol) in THF:DMSO (2:1, 9 mL). The reaction mixture was stirred at 80° C. for 16 hours. After cooling to ambient temperature, the reaction mixture was diluted with EtOAc and washed with water, followed by brine, and then concentrated. The crude product obtained was purified by silica gel column chromatography (30-55 EtOAc/Hexane) to get 1-methyl-5-(2-methyl-4-nitrophenoxy)-1H-benzo[d]imidazole (1.24 g, 93% yield) as a solid. m/z (esi) $M^+1$=283.8.

Step B: 10% Pd/C (300 mg) was added to a solution of 1-methyl-5-(2-methyl-4-nitrophenoxy)-1H-benzo[d]imidazole (600 mg, 2.12 mmol) in MeOH (12 mL). The reaction was stirred at room temperature for 2 hours under hydrogen atmosphere. The reaction mixture was then filtered through sintered funnel and washed with 10% MeOH-DCM. The filtrate was concentrated to afford 3-methyl-4-((1-methyl-1H-benzo[d]imidazol-5-yl)oxy)aniline (500 mg, 93% yield) as a solid. m/z (esi) $M^+1$=254.1.

Step C: 4,6-Dichloropyrido[3,2-d]pyrimidine (432 mg, 2.17 mmol) was added to a stirred solution of 3-methyl-4-((1-methyl-1H-benzo[d]imidazol-5-yl)oxy)aniline (500 mg, 1.98 mmol) in IPA (3 mL) and was stirred at 80° C. for 1 hour. The reaction mixture was then concentrated in vacuo, and the residue was taken up in EtOAc and washed with water followed by saturated aqueous $NaHCO_3$. The organic layer was dried over $Na_2SO_4$, filtered and concentrated. The crude product was purified by silica gel column chromatography (0-4% MeOH/DCM) to get 6-chloro-N-(3-methyl-4-

((1-methyl-1H-benzo[d]imidazol-5-yl)oxy)phenyl)pyrido[3,2-d]pyrimidin-4-amine (750 mg, 91% yield) as a solid. m/z (esi) $M^{+}1$=416.8.

Step D: KOtBu (80.92 mg, 0.72 mmol) was added to a stirred solution of 6-chloro-N-(3-methyl-4-((1-methyl-1H-benzo[d]imidazol-5-yl)oxy)phenyl)pyrido[3,2-d]pyrimidin-4-amine (150 mg, 0.361 mmol) and acrylamide (61.29 mg, 0.721 mmol) in 1,4-dioxane. The mixture was degassed with bubbling argon for 5 minutes. Xantphos (42 mg, 0.072 mmol) and $Pd_2(dba)_3$ (33 mg, 0.036 mmol) were added, and the mixture was degassed with argon for another 5 minutes. The reaction mixture was stirred at 100° C. for 8 hours. The reaction mixture was filtered through a Celite® pad and washed with DCM. The filtrate was evaporated, and the crude material was purified by silica gel column chromatography (2-5% MeOH/DCM) followed by reverse phase prep HPLC (20-95% ACN:water (20 mM Ammonium bicarbonate)) to afford N-(4-((3-methyl-4-((1-methyl-1H-benzo[d]imidazol-5-yl)oxy)phenyl)amino)pyrido[3,2-d]pyrimidin-6-yl)acrylamide (14 mg, 9% yield) as a solid. $^1$H NMR (400 MHz, $(CD_3)_2SO$) δ 11.15 (s, 1H), 9.27 (s, 1H), 8.68 (d, J=9.2 Hz, 1H), 8.63 (s, 1H), 8.26 (d, J=9.2 Hz, 1H), 8.17 (s, 1H), 7.92 (s, 1H), 7.74 (d, J=8.8 Hz, 1H), 7.57 (d, J=8.7 Hz, 1H), 7.11 (s, 1H), 7.01 (d, J=8.8 Hz, 1H), 6.89 (d, J=8.8 Hz, 1H), 6.67 (dd, J=10.2, 17.0 Hz, 1H), 6.41 (d, J=16.9 Hz, 1H), 5.90 (d, J=11.1 Hz, 1H), 3.84 (s, 3H), 2.27 (s, 3H). m/z (esi) $M^{+}1$=452.0.

Example 19

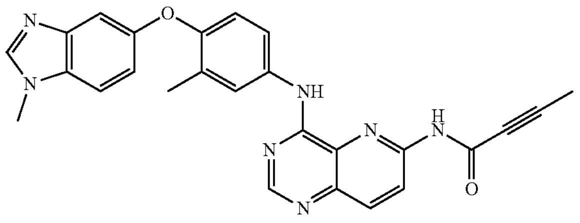 [SMILES: CC#CC(=O)Nc1ccc2ncnc(Nc3ccc(Oc4ccc5c(c4)ncn5C)c(C)c3)c2n1]

N-(4-((3-methyl-4-((1-methyl-1H-benzo[d]imidazol-5-yl)oxy)phenyl)amino)pyrido[3,2-d]pyrimidin-6-yl)but-2-ynamide Step A: To ethyl but-2-ynoate (5 g, 44.64 mmol) was added $NH_4OH$ (17 mL) at 0° C. and the mixture was stirred for 6 hours as it gradually warmed to ambient temperature. The resulting white solid was collected by vacuum filtration and purified by silica gel column chromatography (3-5% MeOH-DCM) to afford but-2-ynamide (1.6 g, 43% yield) as a solid.

Step B: To a stirred solution of 6-chloro-N-(3-methyl-4-((1-methyl-1H-benzo[d]imidazol-5-yl)oxy)phenyl)pyrido[3,2-d]pyrimidin-4-amine (200 mg, 0.48 mmol) and but-2-ynamide (200 mg, 2.40 mmol) in dioxane (6 mL) was added $KO^tBu$ (108 mg, 0.96 mmol) and the mixture was degassed with bubbling argon for 5 minutes. t-BuBrettphos palladacycle Gen-3 (131 mg, 0.14 mmol) was added and the mixture was degassed with argon for another 5 minutes. The reaction mixture was warmed to 100° C. where it stirred for 8 hours. After cooling to ambient temperature, the mixture was filtered through a pad of celite and washed with DCM. The filtrate was evaporated and the crude material was purified by silica gel column chromatography (1-2% MeOH-DCM) to isolate the product (~50 mg) which was further purified by Prep HPLC (20-90% ACN:$H_2O$ (0.1% $NH_4HCO_3$) to afford N-(4-((3-methyl-4-((1-methyl-1H-benzo [d]imidazol-5-yl)oxy) phenyl) amino) pyrido[3,2-d] pyrimidin-6-yl)but-2-ynamide (11 mg, 5% yield) as a solid. $^1$H NMR (400 MHz, DMSO-$d_6$) δ 11.37 (s, 1H), 9.27 (s, 1H), 8.63 (s, 1H), 8.40 (d, J=9.0 Hz, 1H), 8.24 (d, J=9.2 Hz, 1H), 8.17 (s, 1H), 7.89 (s, 1H), 7.75 (d, J=8.8 Hz, 1H), 7.57 (d, J=8.7 Hz, 1H), 7.11 (d, J=2.3 Hz, 1H), 7.00 (dd, J=2.3, 8.8 Hz, 1H), 6.91 (d, J=8.8 Hz, 1H), 3.84 (s, 3H), 2.28 (s, 3H), 2.10 (s, 3H). m/z (esi) M+1=464.3.

Example 20

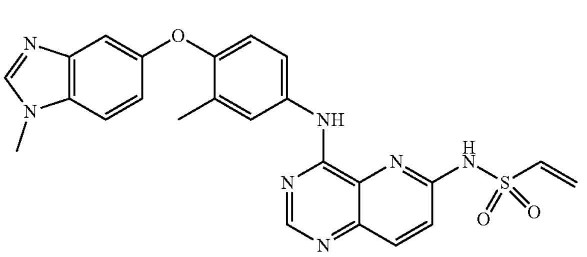 [SMILES: C=CS(=O)(=O)Nc1ccc2ncnc(Nc3ccc(Oc4ccc5c(c4)ncn5C)c(C)c3)c2n1]

N-(4-((3-methyl-4-((1-methyl-1H-benzo[d]imidazol-5-yl)oxy)phenyl)amino)pyrido[3,2-d]pyrimidin-6-yl)ethenesulfonamide To a stirred solution of 6-chloro-N-(3-methyl-4-((1-methyl-1H-benzo[d]imidazol-5-yl)oxy)phenyl)pyrido[3,2-d]pyrimidin-4-amine (200 mg, 0.481 mmol) and ethenesulfonamide (103 mg, 0.962 mmol) in 1,4 dioxane was added KOtBu (107.89 mg, 0.962 mmol) and the mixture was degassed with bubbling argon for 5 min. Xantphos (55.57 mg, 0.096 mmol) and $Pd_2(dba)_3$ (43.99 mg, 0.048 mmol) were added and the mixture was degassed with argon for another 5 min. The reaction mixture was stirred at 100° C. for 8 h. After cooling to ambient temperature, the reaction mixture was filtered through a celite pad and washed with DCM. The filtrate was concentrated and the crude product was purified by silica gel column chromatography (2-5% MeOH/DCM) followed by reverse phase prep HPLC (20-95% ACN:water (20 mM Ammonium bicarbonate)) followed by lyophilization to afford N-(4-((3-methyl-4-((1-methyl-1H-benzo[d]imidazol-5-yl)oxy) phenyl)amino) pyrido[3,2-d]pyrimidin-6-yl)ethenesulfonamide (26 mg, 11% yield) as light-yellow solid. $^1$H NMR (400 MHz, DMSO-$d_6$) δ 11.70-11.37 (m, 1H), 8.86 (s, 1H), 8.58 (s, 1H), 8.19-8.10 (m, 2H), 7.81 (s, 1H), 7.68 (d, J=8.9 Hz, 1H), 7.56 (d, J=8.7 Hz, 1H), 7.43 (d, J=8.9 Hz, 1H), 7.29 (dd, J=9.9, 16.3 Hz, 1H), 7.10 (d, J=2.3 Hz, 1H), 7.00 (dd, J=2.4, 8.7 Hz, 1H), 6.92 (d, J=8.7 Hz, 1H), 6.45 (d, J=16.5 Hz, 1H), 6.23 (d, J=9.9 Hz, 1H), 3.84 (s, 3H), 2.27 (s, 3H). m/z (esi) M+1=488.3.

Example 21

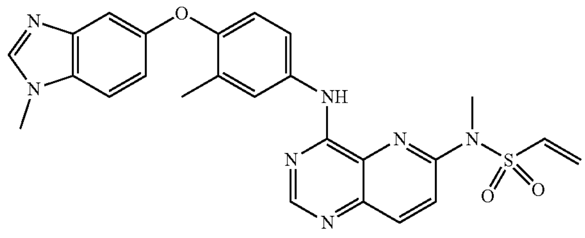 [SMILES: C=CS(=O)(=O)N(C)c1ccc2ncnc(Nc3ccc(Oc4ccc5c(c4)ncn5C)c(C)c3)c2n1]

N-methyl-N-(4-((3-methyl-4-((1-methyl-1H-benzo[d]imidazol-5-yl)oxy)phenyl)amino)pyrido[3,2-d]pyrimidin-6-yl)ethenesulfonamide Step A: To a stirred solution of 3-methyl-4-((1-methyl-1H-benzo[d]imidazol-5-yl)oxy)aniline (500 mg, 1.98 mmol) in IPA (3 mL) was added 4,6-dichloropyrido[3,2-d]pyrimidine (432.6 mg, 2.17 mmol) and the mixture was stirred at 80° C. for 1 h. The reaction mixture was concentrated, and the residue was taken up in EtOAc and washed with water followed by saturated aqueous $NaHCO_3$. The organic layer was dried over $Na_2SO_4$, filtered, and concentrated and the crude material was purified by silica gel column chromatography (0-4% MeOH/DCM) to get 6-chloro-N-(3-methyl-4-((1-methyl-1H-benzo[d]imidazol-5-yl)oxy)phenyl)pyrido[3,2-d]pyrimidin-4-amine (750 mg 91% yield) as a solid. m/z (esi) M+1=416.8.

Step B: To a stirred solution of 6-chloro-N-(3-methyl-4-((1-methyl-1H-benzo[d]imidazol-5-yl)oxy)phenyl)pyrido[3,2-d]pyrimidin-4-amine (100 mg, 0.24 mmol) and N-methylethenesulfonamide (58.18 mg, 0.481 mmol) in dioxane was added KOt-Bu (54 mg, 0.48 mmol) and the mixture was degassed with bubbling argon for 5 min. Xantphos (27.78 mg, 0.048 mmol) and $Pd_2dba_3$ (21.99 mg, 0.024 mmol) were added and the mixture was degassed with argon for another 5 min. The reaction mixture was stirred at 100° C. for 10 h. The mixture was then concentrated, and the residue was dissolved in 5% MeOH/DCM and washed with water followed by brine then dried over $Na_2SO_4$, filtered, and concentrated under reduced pressure. The crude product was purified by silica gel column chromatography (2-4% MeOH/DCM) followed by reverse phase prep HPLC (LYMC Triart C18 (250×4.6 mm, 5μ)) 20-95% ACN:water (20 mM Ammonium bicarbonate), 16 mL/min) to get N-methyl-N-(4-((3-methyl-4-((1-methyl-1H-benzo[d]imidazol-5-yl)oxy)phenyl)amino)pyrido[3,2-d]pyrimidin-6-yl)ethenesulfonamide (4 mg, 3% yield) as a solid. $^1H$ NMR (400 MHz, DMSO-$d_6$) δ 9.56 (s, 1H), 8.60 (s, 1H), 8.26-8.09 (m, 2H), 8.01 (d, J=9.1 Hz, 1H), 7.80 (s, 1H), 7.72 (d, J=8.5 Hz, 1H), 7.57 (d, J=8.6 Hz, 1H), 7.15-7.05 (m, 2H), 7.00 (d, J=8.8 Hz, 1H), 6.90 (d, J=8.8 Hz, 1H), 6.37-6.23 (m, 2H), 3.84 (s, 3H), 3.55 (s, 3H), 2.26 (s, 3H). m/z (esi) M+1=502.39.

Example 22

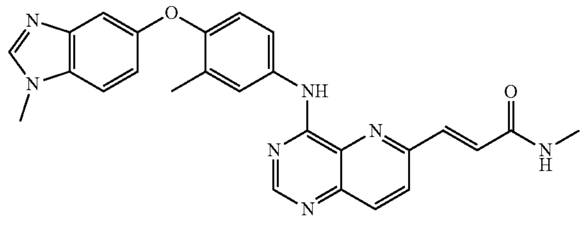 [SMILES: CNC(=O)/C=C/c1ccc2ncnc(Nc3ccc(Oc4ccc5c(c4)ncn5C)c(C)c3)c2n1]

(E)-N-methyl-3-(4-((3-methyl-4-((1-methyl-1H-benzo[d]imidazol-5-yl)oxy)phenyl)amino)pyrido[3,2-d]pyrimidin-6-yl)acrylamide To a stirred solution of 6-chloro-N-(3-methyl-4-((1-methyl-1H-benzo[d]imidazol-5-yl)oxy)phenyl)pyrido[3,2-d]pyrimidin-4-amine (150 mg, 0.36 mmol) and N-methylacrylamide (61 mg, 0.48 mmol) in dioxane (5 mL) was added KOt-Bu (81 mg, 0.72 mmol) and the reaction mixture was degassed with bubbling argon for 5 minutes. Xantphos (42 mg, 0.07 mmol) and Pd2(dba3) (33 mg, 0.04 mmol) were added, and the mixture was degassed with argon for another 5 minutes. The reaction mixture was stirred at 100° C. for 8 hours in sealed tube. After completion, the reaction mixture was filtered through a Celite® pad and washed with DCM. The filtrate was concentrated, and the crude product was purified by silica gel column chromatography (2-3% MeOH-DCM) to obtain product which is further purified by Prep HPLC (12-90% ACN:$H_2O$ (0.1% $NH_4HCO_3$) to afford (E)-N-methyl-3-(4-((3-methyl-4-((1-methyl-1H-benzo[d]imidazol-5-yl)oxy) phenyl)amino)pyrido[3,2-d]pyrimidin-6-yl)acrylamide (15 mg, 19% yield) as a solid. $^1H$ NMR (400 MHz, DMSO-$d_6$) δ 9.98 (s, 1H), 8.64 (s, 1H), 8.22 (d, J=9.0 Hz, 2H), 8.17 (s, 1H), 8.12 (d, J=8.7 Hz, 1H), 7.94 (s, 1H), 7.85 (d, J=11.1 Hz, 1H), 7.68 (d, J=15.7 Hz, 1H), 7.57 (d, J=8.8 Hz, 1H), 7.30 (d, J=15.7 Hz, 1H), 7.11 (d, J=2.4 Hz, 1H), 7.00 (dd, J=2.3, 8.8 Hz, 1H), 6.90 (d, J=8.8 Hz, 1H), 3.84 (s, 3H), 2.76 (d, J=4.6 Hz, 3H), 2.27 (s, 3H). m/z (esi) M+1=466.43.

Example 23

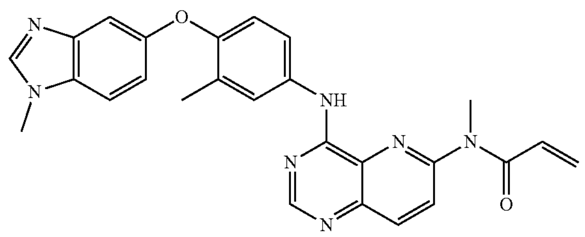 [SMILES: C=CC(=O)N(C)c1ccc2ncnc(Nc3ccc(Oc4ccc5c(c4)ncn5C)c(C)c3)c2n1]

N-methyl-N-(4-((3-methyl-4-((1-methyl-1H-benzo[d]imidazol-5-yl)oxy)phenyl)amino)pyrido[3,2-d]pyrimidin-6-yl)acrylamide To a stirred solution of 6-chloro-N-(3-methyl-4-((1-methyl-1H-benzo[d]imidazol-5-yl)oxy)phenyl)pyrido[3,2-d]pyrimidin-4-amine (400 mg, 0.96 mmol) and N-methyl-acrylamide (163 mg, 1.92 mmol) in dioxane (5 mL) was added KOtBu (215 mg, 1.92 mmol), and the mixture was degassed with bubbling argon for 5 minutes. Xantphos (111 mg, 0.19 mmol) and $Pd_2(dba_3)$ (88 mg, 0.09 mmol) were added, and the mixture was degassed with argon for another 5 minutes. The reaction mixture was stirred at 100° C. for 8 hours. The reaction mixture was filtered through a Celite® pad and washed with DCM. The filtrate was concentrated, and the crude product was purified by silica gel column chromatography (2-3% MeOH-DCM) to obtain the product which was further purified by Prep HPLC (7-65% ACN: H2O (0.1% $NH_4HCO_3$) to afford N-methyl-N-(4-((3-methyl-4-((1-methyl-1H-benzo[d]imidazol-5-yl)oxy)phenyl)amino)pyrido[3,2-d]pyrimidin-6-yl)acrylamide (22 mg, 5% yield) as a solid. $^1$H NMR (400 MHz, DMSO-d6) δ 9.72 (s, 1H), 8.63 (s, 1H), 8.22 (d, J=8.9 Hz, 1H), 8.17 (s, 1H), 7.93 (d, J=8.9 Hz, 1H), 7.86 (s, 1H), 7.76 (d, J=11.6 Hz, 1H), 7.56 (d, J=8.7 Hz, 1H), 7.10 (d, J=2.4 Hz, 1H), 6.99 (dd, J=2.4, 8.6 Hz, 1H), 6.88 (d, J=8.8 Hz, 1H), 6.60 (dd, J=10.4, 16.7 Hz, 1H), 6.28 (dd, J=2.2, 16.7 Hz, 1H), 5.76 (dd, J=2.3, 10.3 Hz, 1H), 3.84 (s, 3H), 3.59 (s, 3H), 2.25 (s, 3H). m/z (esi) $M^+1$=466.2.

Example 24

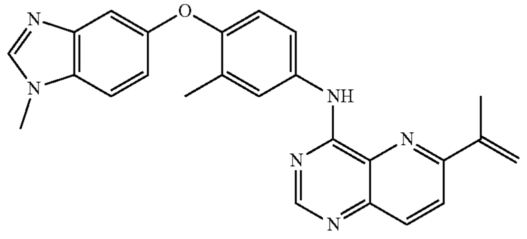 [SMILES: C=C(C)c1ccc2ncnc(Nc3ccc(Oc4ccc5c(c4)ncn5C)c(C)c3)c2n1]

N-(3-methyl-4-((1-methyl-1H-benzo[d]imidazol-5-yl)oxy)phenyl)-6-(prop-1-en-2-yl)pyrido[3,2-d]pyrimidin-4-amine 6-Chloro-N-(3-methyl-4-((1-methyl-1H-benzo[d]imidazol-5-yl)oxy)phenyl)pyrido[3,2-d]pyrimidin-4-amine (0.060 g, 0.14 mmol), potassium trifluoro(prop-1-en-2-yl) borate (0.021 g, 0.14 mmol), potassium carbonate (2M aqueous) (0.22 ml, 0.43 mmol), palladium tetrakis (0.017 g, 0.014 mmol), and dioxane (1.4 mL, 0.14 mmol) were charged to a 10 mL glass microwave vessel equipped with a stir bar. The mixture was sparged with argon, sealed, and heated to 100° C. overnight. The mixture was diluted with water and ethyl acetate. The organic layer was extracted ×3 with ethyl acetate and organics were combined, dried over $Na_2SO_4$, and concentrated in vacuo. The crude material was purified by column chromatography (Redisep 12 g, 0 to 10% MeOH/DCM with 2% $NH_4OH$) to furnish N-(3-methyl-4-((1-methyl-1H-benzo[d]imidazol-5-yl)oxy)phenyl)-6-(prop-1-en-2-yl)pyrido[3,2-d]pyrimidin-4-amine (45.0 mg, 74% yield). $^1$H NMR (400 MHz, $CDCl_3$) δ 9.07 (s, 1H), 8.73 (s, 1H), 8.10 (d, J=8.8 Hz, 1H), 8.02 (d, J=8.9 Hz, 1H), 7.85 (s, 1H), 7.77 (d, J=2.7 Hz, 1H), 7.68 (dd, J=8.7, 2.7 Hz, 1H), 7.36-7.30 (m, 2H), 7.06 (dd, J=8.8, 2.2 Hz, 1H), 6.95 (d, J=8.7 Hz, 1H), 5.97 (t, J=1.0 Hz, 1H), 5.56 (s, 1H), 3.85 (s, 3H), 2.37 (dd, J=1.5, 0.8 Hz, 3H), 2.36 (s, 3H); m/z (APCI-pos) M+1=423.2.

Example 25

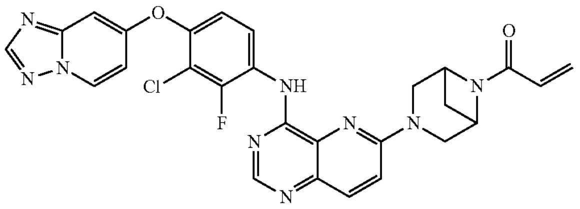 [SMILES: C=CC(=O)N1C2CC1CN(c1ccc3ncnc(Nc4ccc(Oc5ccn6ncnc6c5)c(Cl)c4F)c3n1)C2]

1-(3-(4-((4-([1,2,4]triazolo[1,5-a]pyridin-7-yloxy)-3-chloro-2-fluorophenyl)amino)pyrido[3,2-d]pyrimidin-6-yl)-3,6-diazabicyclo[3.1.1]heptan-6-yl)prop-2-en-1-one Step A: A 1-dram vial was charged with tert-butyl 3,6-diazabicyclo[3.1.1]heptane-6-carboxylate (67 mg, 0.34 mmol), N-(4-([1,2,4]triazolo[1,5-a]pyridin-7-yloxy)-3-chloro-2-fluorophenyl)-6-chloropyrido[3,2-d]pyrimidin-4-amine (0.050 g, 0.11 mmol), and DMSO (1.1 mL). The vial was capped and heated to 100° C. for 2 hours, upon which the mixture was partitioned between EtOAc and $K_2CO_3$ (sat., aq.). The phases were separated, and the organic extract was washed with brine, dried over anhydrous sodium sulfate, filtered, and concentrated in vacuo. Purification by column chromatography (silica, 12 g, 0-6% MeOH/DCM) provided tert-butyl 3-(4-((4-([1,2,4]triazolo[1,5-a]pyridin-7-yloxy)-3-chloro-2-fluorophenyl)amino)pyrido[3,2-d]pyrimidin-6-yl)-3,6-diazabicyclo[3.1.1]heptane-6-carboxylate (46 mg, 67%). m/z (APCI-pos) M+1=604.2.

Step B: A 1-dram vial was charged with tert-butyl 3-(4-((4-([1,2,4]triazolo[1,5-a]pyridin-7-yloxy)-3-chloro-2-fluorophenyl)amino)pyrido[3,2-d]pyrimidin-6-yl)-3,6-diazabicyclo[3.1.1]heptane-6-carboxylate (46 mg, 76 μmol) and DCM (0.50 mL). The mixture was cooled to 0° C. and 2,2,2-trifluoroacetic acid (0.17 mL, 2.3 mmol) was added. After stirring for 30 minutes, the reaction mixture was diluted with DCM and washed with $K_2CO_3$ (sat., aq., 2×) and brine. The organic extract was dried over anhydrous sodium sulfate, filtered, and concentrated in vacuo, providing N-(4-([1,2,4]triazolo[1,5-a]pyridin-7-yloxy)-3-chloro-2-fluorophenyl)-6-(3,6-diazabicyclo[3.1.1]heptan-3-yl)pyrido[3,2-d]pyrimidin-4-amine (40 mg, quant.). No further purification was performed. m/z (APCI-pos) M+1=504.2.

Step C: A 1-dram vial was charged with N-(4-([1,2,4]triazolo[1,5-a]pyridin-7-yloxy)-3-chloro-2-fluorophenyl)-6-(3,6-diazabicyclo[3.1.1]heptan-3-yl)pyrido[3,2-d]pyrimidin-4-amine (40 mg, 79 μmol), N-ethyl-N-isopropylpropan-2-amine (34 μL, 200 μmol), and DCM (0.80 mL). The contents of the flask were cooled to 0° C. with an ice/water bath and acryloyl chloride (5.2 μL, 34 μmol) was added in one aliquot. The vial was capped and stirred for 2 hours, upon which the mixture was partitioned between DCM and $K_2CO_3$ (sat., aq.). The phases were separated, and the organic extract was dried over anhydrous sodium sulfate, filtered, and concentrated in vacuo.

Purification by column chromatography (silica, 12 g, 0-8% MeOH/DCM) provided 1-(3-(4-((4-([1,2,4]triazolo[1,5-a]pyridin-7-yloxy)-3-chloro-2-fluorophenyl)amino)pyrido[3,2-d]pyrimidin-6-yl)-3,6-diazabicyclo[3.1.1]heptan-6-yl)prop-2-en-1-one (29 mg, 65% yield). $^1$H NMR (400 MHz, $CDCl_3$) δ 9.16 (d, J=3.4 Hz, 1H), 9.02 (t, J=8.9 Hz, 1H), 8.66 (s, 1H), 8.57-8.50 (m, 1H), 8.25 (s, 1H), 8.04 (d, J=9.3 Hz, 1H), 7.22-7.12 (m, 2H), 6.96-6.89 (m, 2H), 6.37 (dd, J=17.0, 2.1 Hz, 1H), 6.29 (dd, J=16.9, 9.9 Hz, 1H), 5.73 (dd, J=9.9, 2.1 Hz, 1H), 4.76 (dd, J=11.8, 6.1 Hz, 2H), 4.37 (d, J=11.1 Hz, 1H), 4.00 (s, 2H), 3.79 (t, J=11.6 Hz, 1H), 2.92 (dt, J=8.7, 6.4 Hz, 1H), 1.77 (d, J=8.8 Hz, 1H); m/z (APCI-pos) M+1=558.2.

Example 26

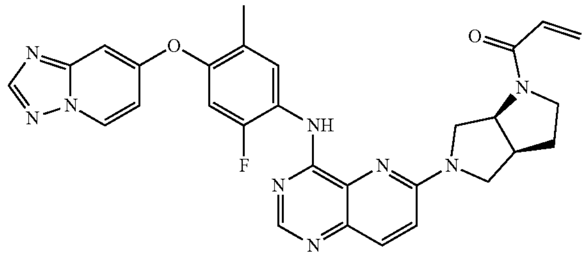 [SMILES: C=CC(=O)N1CC[C@H]2CN(c3ccc4ncnc(Nc5cc(C)c(Oc6ccn7ncnc7c6)cc5F)c4n3)C[C@H]21]

1-((3aS,6aS)-5-(4-((4-([1,2,4]triazolo[1,5-a]pyridin-7-yloxy)-2-fluoro-5-methylphenyl)amino)pyrido[3,2-d]pyrimidin-6-yl)hexahydropyrrolo[3,4-b]pyrrol-1(2H)-yl)prop-2-en-1-one Step A: 4-([1,2,4]Triazolo[1,5-a]pyridin-7-yloxy)-2-fluoro-5-methylaniline (120 mg, 0.46 mmol) and 4,6-dichloropyrido[3,2-d]pyrimidine (139.4 mg, 0.69 mmol) were suspended in IPA (3 mL). The reaction mixture stirred at 80° C. for 2 hours. The reaction mixture was then concentrated to dryness and the crude product was purified by silica gel column chromatography (75% EtOAc-Hex) to afford N-(4-([1,2,4]triazolo[1,5-a]pyridin-7-yloxy)-2-fluoro-5-methylphenyl)-6-chloropyrido[3,2-d]pyrimidin-4-amine (150 mg, 61% yield in two step) as a solid. m/z (esi) M+1=421.8.

Step B: To a stirred solution of N-(4-([1,2,4]triazolo[1,5-a]pyridin-7-yloxy)-2-fluoro-5-methylphenyl)-6-chloropyrido[3,2-d]pyrimidin-4-amine (50 mg, 0.11 mmol) and tert-butyl (3aS,6aS)-hexahydropyrrolo[3,4-b]pyrrole-1(2H)-carboxylate (37.7 mg, 0.17 mmol) in DMSO (1 mL) was added DIPEA (0.04 mg, 0.23 mmol). The reaction mixture stirred at 100° C. for 2 hours. The reaction mixture was diluted with $H_2O$ and extracted with EtOAc. The combined organic layers were dried over $Na_2SO_4$, filtered and concentrated. The crude product was purified by silica gel column chromatography (0.5% MeOH-DCM) to afford tert-butyl (3aS,6aS)-5-(4-((4-([1,2,4]triazolo[1,5-a]pyridin-7-yloxy)-2-fluoro-5-methylphenyl)amino)pyrido[3,2-d]pyrimidin-6-yl)hexahydropyrrolo[3,4-b]pyrrole-1(2H)-carboxylate (55 mg, 78% yield) as a solid. m/z (esi) M+1=598.4.

Step C: To a stirred solution of tert-butyl (3aS,6aS)-5-(4-((4-([1,2,4]triazolo[1,5-a]pyridin-7-yloxy)-2-fluoro-5-methylphenyl)amino)pyrido[3,2-d]pyrimidin-6-yl)hexahydropyrrolo[3,4-b]pyrrole-1(2H)-carboxylate (50 mg, 0.08 mmol) in DCM (2 mL) was added TFA (0.3 mL) under argon atmosphere. The reaction mixture was stirred at 0° C. for 2 hours. The reaction mixture was then concentrated in a rotary evaporator and the residue diluted with 5% MeOH-DCM and washed with $H_2O$ followed by a saturated $NaHCO_3$ solution. The organic layer was dried over $Na_2SO_4$, filtered and concentrated to get N-(4-([1,2,4]triazolo[1,5-a]pyridin-7-yloxy)-2-fluoro-5-methylphenyl)-6-((3aS,6aS)-hexahydropyrrolo[3,4-b]pyrrol-5(1H)-yl)pyrido[3,2-d]pyrimidin-4-amine (40 mg crude) which was used in the next step without further purification. m/z (esi) M+1=498.2.

Step D: To a stirred solution of N-(4-([1,2,4]triazolo[1,5-a]pyridin-7-yloxy)-2-fluoro-5-methylphenyl)-6-((3aS,6aS)-hexahydropyrrolo[3,4-b]pyrrol-5(1H)-yl)pyrido[3,2-d]pyrimidin-4-amine (40 mg, 0.07 mmol) in DCM (1 mL) was added DIPEA (0.13 mL, 0.79 mmol) followed by the addition of acryloyl chloride (7.1 mg, 0.07 mmol) in DCM (1 mL) at 0° C., and stirred at 0° C. for 1 hour. The reaction mixture was quenched with ice and concentrated under reduced pressure. The crude product was purified by reverse phase prep HPLC purification (30-55% ACN:water (20 mM Ammonium Bicarbonate)) to get 1-((3aS,6aS)-5-(4-((4-([1,2,4]triazolo[1,5-a]pyridin-7-yloxy)-2-fluoro-5-methylphenyl)amino)pyrido[3,2-d]pyrimidin-6-yl)hexahydropyrrolo[3,4-b]pyrrol-1(2H)-yl)prop-2-en-1-one (25.1 mg, 55% yield) as a solid. $^1H$ NMR (400 MHz, DMSO-$d_6$) δ 9.06 (s, 1H), 8.86 (d, J=6.8 Hz, 1H), 8.45 (d, J=10.4 Hz, 2H), 8.32 (s, 1H), 7.93 (d, J=9.2 Hz, 1H), 7.24 (t, J=11.2 Hz, 2H), 7.03-6.94 (m, 2H), 6.60 (d, J=12.4 Hz, 1H), 6.18 (d, J=16.8 Hz, 1H), 5.68 (d, J=10.4 Hz, 1H), 4.69 (s, 1H), 4.01 (s, 1H), 3.87 (t, J=10.4, 10.8 Hz, 1H), 3.78-3.56 (m, 4H), 3.21 (d, J=6.6 Hz, 1H), 2.23 (s, 3H), 2.22-2.09 (m, 1H), 2.00-1.84 (m, 1H). m/z (esi) M+1=552.2.

Example 27

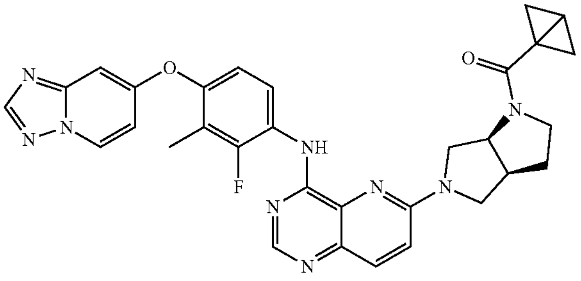 [SMILES: Cc1c(Oc2ccn3ncnc3c2)ccc(Nc2ncnc3ccc(N4C[C@@H]5CCN(C(=O)C67CC6C7)[C@@H]5C4)nc23)c1F]

((3aS,6aS)-5-(4-((4-([1,2,4]triazolo[1,5-a]pyridin-7-yloxy)-2-fluoro-3-methylphenyl)amino)pyrido[3,2-d]pyrimidin-6-yl)hexahydropyrrolo[3,4-b]pyrrol-1(2H)-yl)(bicyclo[1.1.0]butan-1-yl)methanone To a stirred solution of N-(4-([1,2,4]triazolo[1,5-a]pyridin-7-yloxy)-2-fluoro-3-methylphenyl)-6-((3aS,6aS)-hexahydropyrrolo[3,4-b]pyrrol-5(1H)-yl)pyrido[3,2-d]pyrimidin-4-amine (50 mg, 0.10 mmol) and potassium bicyclo[1.1.0]butane-1-carboxylate (23 mg, 0.20 mmol) in DMF (1 mL) were added DIPEA (0.10 mL, 0.50 mmol) followed by $T_3P$ (50% sol in EtOAc, 127 mg, 0.20 mmol) and stirred at room temperature for 16 hours. The reaction mixture was diluted with water and extracted with EtOAc. The combined organic layers were dried, filtered, and concentrated. The crude product was purified by reverse phase prep HPLC purification (20-95% ACN:water (20 mM Ammonium bicarbonate)) to afford ((3aS,6aS)-5-(4-((4-([1,2,4]triazolo[1,5-a]pyridin-7-yloxy)-2-fluoro-3-methylphenyl)amino)pyrido[3,2-d]pyrimidin-6-yl)hexahydropyrrolo[3,4-b]pyrrol-1(2H)-yl)(bicyclo[1.1.0]butan-1-yl)methanone (15 mg, 26% yield) as a solid. $^1H$ NMR (400 MHz, DMSO-$d_6$) δ 9.10 (s, 1H), 8.85 (d, J=7.4 Hz, 1H), 8.53-8.43 (m, 2H), 8.32 (s, 1H), 7.94 (d, J=9.2 Hz, 1H), 7.26 (d, J=9.3 Hz, 1H), 7.11 (dd, J=1.7, 8.9 Hz, 1H), 7.00 (dd, J=2.6, 7.4 Hz, 1H), 6.96 (d, J=2.6 Hz, 1H), 4.73 (s, 1H), 4.01-3.81 (m, 3H), 3.80-3.66 (m, 2H), 3.59 (dd, J=5.2, 11.4 Hz, 1H), 3.24-3.11 (m, 1H), 2.31-2.06 (m, 7H), 1.98-1.85 (m, 1H), 1.08 (dd, J=2.3, 14.6 Hz, 2H). m/z (esi) M+1=578.4.

Example 28

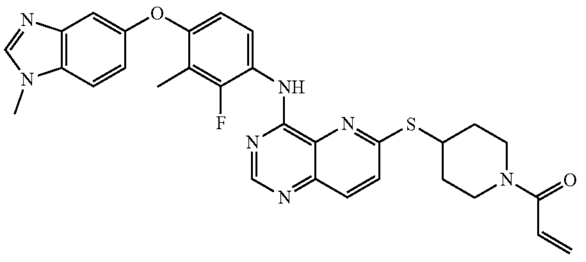 [SMILES: C=CC(=O)N1CCC(Sc2ccc3ncnc(Nc4ccc(Oc5ccc6c(c5)ncn6C)c(C)c4F)c3n2)CC1]

1-(4-((4-((2-fluoro-3-methyl-4-((1-methyl-1H-benzo[d]imidazol-5-yl)oxy)phenyl)amino)pyrido[3,2-d]pyrimidin-6-yl)thio)piperidin-1-yl)prop-2-en-1-one Step A: To a solution of 6-chloro-N-(2-fluoro-3-methyl-4-((1-methyl-1H-benzo[d]imidazol-5-yl)oxy)phenyl)pyrido[3,2-d]pyrimidin-4-amine (40 mg, 92 μmol) and tert-butyl 4-mercaptopiperidine-1-carboxylate (30 mg, 0.14 mmol) in dry DMF (0.46 mL) was added $Cs_2CO_3$ (60 mg, 0.18 mmol). The mixture was then warmed to 80° C. where it stirred for 1.5 hours. The reaction was then cooled to ambient temperature and quenched with the addition of water (5 mL) and saturated aqueous $NH_4Cl$ (5 mL). The mixture was stirred for 5 minutes and the solid was isolated by vacuum filtration. The solid was then dissolved in EtOAc, dried over anhydrous sodium sulfate, filtered and concentrated. The crude product was taken on as is to the next step. m/z (APCI-pos) M+1=616.2.

Step B: To a vial containing tert-butyl 4-((4-((2-fluoro-3-methyl-4-((1-methyl-1H-benzo[d]imidazol-5-yl)oxy)phenyl)amino)pyrido[3,2-d]pyrimidin-6-yl)thio)piperidine-1-carboxylate (57 mg, 93 μmol) was added $CH_2Cl_2$ (0.62 mL) and the solution was treated with trifluoroacetic acid (0.14 mL, 1.9 mmol). The mixture was then stirred at ambient temperature for 1.5 hours. The mixture was neutralized with saturated aqueous $NaHCO_3$, and the resulting mixture was extracted with $CHCl_3$ (3×). The combined extracts were then dried over $Na_2SO_4$, filtered and concentrated. The crude product was used directly in the subsequent step. m/z (APCI-pos) M+1=516.2.

Step C: To a vial was added N-(2-fluoro-3-methyl-4-((1-methyl-1H-benzo[d]imidazol-5-yl)oxy)phenyl)-6-(piperidin-4-ylthio)pyrido[3,2-d]pyrimidin-4-amine (47 mg, 91 μmol), $CH_2Cl_2$ (0.91 mL) and Hunig's base (32 μL, 0.18 mmol). The mixture was cooled to 0° C. in an ice/water bath and then acryloyl chloride (7.4 μL, 91 μmol) was added. The mixture was stirred at 0° C. for 1 hour, then treated with saturated aqueous $NaHCO_3$. The mixture was extracted with $CHCl_3$ (3×), and the combined organic extracts were dried over $Na_2SO_4$, filtered and concentrated. The crude product was then purified via column chromatography (2 to 5% MeOH/$CH_2Cl_2$) to afford 1-(4-((4-((2-fluoro-3-methyl-4-((1-methyl-1H-benzo[d]imidazol-5-yl)oxy)phenyl)amino)pyrido[3,2-d]pyrimidin-6-yl)thio)piperidin-1-yl)prop-2-en-1-one (37 mg, 68%) as a solid. $^1$H NMR (400 MHz, $CDCl_3$) δ 9.17 (d, J=3.6 Hz, 1H), 8.72 (s, 1H), 8.65 (t, J=9.2 Hz, 1H), 7.95 (d, J=8.8 Hz, 1H), 7.86 (s, 1H), 7.50 (d, J=8.8 Hz, 1H), 7.35 (dd, J=8.7, 0.6 Hz, 1H), 7.32 (dd, J=2.3, 0.6 Hz, 1H), 7.07 (dd, J=8.7, 2.3 Hz, 1H), 6.79 (dd, J=9.1, 1.7 Hz, 1H), 6.64 (dd, J=16.8, 10.6 Hz, 1H), 6.32 (dd, J=16.8, 1.9 Hz, 1H), 5.72 (dd, J=10.6, 1.9 Hz, 1H), 4.47 (d, J=13.5 Hz, 1H), 4.29 (tt, J=10.0, 4.0 Hz, 1H), 4.08-3.98 (m, 1H), 3.86 (s, 3H), 3.50 (t, J=12.0 Hz, 1H), 3.32 (t, J=11.8 Hz, 1H), 2.40-2.31 (m, 2H), 2.30 (d, J=2.1 Hz, 3H), 1.85 (q, J=10.0 Hz, 2H). m/z (APCI-pos) M+1=570.1.

Example 29

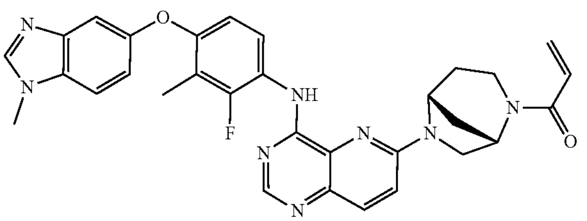 [SMILES: C=CC(=O)N1CC[C@@H]2C[C@H]1CN2c1ccc2ncnc(Nc3ccc(Oc4ccc5c(c4)ncn5C)c(C)c3F)c2n1]

1-((1 S,5R)-6-(4-((2-fluoro-3-methyl-4-((1-methyl-1H-benzo[d]imidazol-5-yl)oxy)phenyl)amino)pyrido[3,2-d]pyrimidin-6-yl)-2,6-diazabicyclo[3.2.1]octan-2-yl)prop-2-en-1-one Step A: To a vial was added 6-chloro-N-(2-fluoro-3-methyl-4-((1-methyl-1H-benzo[d]imidazol-5-yl)oxy)phenyl)pyrido[3,2-d]pyrimidin-4-amine (28 mg, 64 μmol) and tert-butyl (1S,5R)-2,6-diazabicyclo[3.2.1]octane-2-carboxylate (27 mg, 0.13 mmol) followed by DMSO (0.43 mL). The mixture was then warmed to 100° C. where it stirred for 3 hours. The mixture was then cooled to ambient temperature and diluted with water. The solid was isolated by vacuum filtration. The solid was then dissolved in $CH_2Cl_2$ and the filtrate was dried over $Na_2SO_4$, filtered and concentrated. The crude product was then purified via column chromatography (1-8% MeOH/$CHCl_3$) to afford tert-butyl (1S,5R)-6-(4-((2-fluoro-3-methyl-4-((1-methyl-1H-benzo[d]imidazol-5-yl)oxy)phenyl)amino)pyrido[3,2-d]pyrimidin-6-yl)-2,6-diazabicyclo[3.2.1]octane-2-carboxylate (34 mg, 86%) as a solid. m/z (APCI-pos) $M^+1$=611.2.

Step B: To a vial containing tert-butyl (1S,5R)-6-(4-((2-fluoro-3-methyl-4-((1-methyl-1H-benzo[d]imidazol-5-yl)oxy)phenyl)amino)pyrido[3,2-d]pyrimidin-6-yl)-2,6-diazabicyclo[3.2.1]octane-2-carboxylate (34 mg, 56 μmol) was added $CH_2Cl_2$ (0.56 mL) and the solution was treated with TFA (86 μL, 1.1 mmol). The mixture was then stirred at ambient temperature for 1.5 hours. The mixture was neutralized with saturated aqueous $NaHCO_3$, and the resulting mixture was extracted with $CHCl_3$ (3×). The combined extracts were then dried over $Na_2SO_4$, filtered and concentrated. The crude product (27 mg, 95%) was used directly in the subsequent step. m/z (APCI-pos) $M^+1$=511.2.

Step C: To a vial was added 6-((1S,5R)-2,6-diazabicyclo[3.2.1]octan-6-yl)-N-(2-fluoro-3-methyl-4-((1-methyl-1H-benzo[d]imidazol-5-yl)oxy)phenyl)pyrido[3,2-d]pyrimidin-4-amine (27 mg, 53 μmol), $CH_2Cl_2$ (1.1 mL) and i-$Pr_2EtN$ (18 μL, 0.11 mmol). The mixture was cooled to 0° C. in an ice/water bath and then acryloyl chloride (4.8 mg, 53 μmol) was added. The mixture was then stirred at 0° C. for 1 hour.

The mixture was then treated with saturated aqueous $NaHCO_3$, and the mixture was extracted with $CHCl_3$ (3×). The combined organic extracts were dried over $Na_2SO_4$, filtered and concentrated. The crude product was then purified via column chromatography (2 to 5% $MeOH/CH_2Cl_2$) to afford 1-((1 S,5R)-6-(4-((2-fluoro-3-methyl-4-((1-methyl-1H-benzo[d]imidazol-5-yl)oxy)phenyl)amino)pyrido[3,2-d]pyrimidin-6-yl)-2,6-diazabicyclo[3.2.1]octan-2-yl)prop-2-en-1-one (19 mg, 64%) as a solid. $^1H$ NMR (400 MHz, CDC13) δ 9.04 (s, 1H), 8.61-8.51 (m, 2H), 7.95 (d, J=9.1 Hz, 1H), 7.85 (s, 1H), 7.37-7.30 (m, 2H), 7.06 (dd, J=8.8, 2.3 Hz, 1H), 7.01 (d, J=9.4 Hz, 1H), 6.77 (dd, J=9.1, 1.7 Hz, 1H), 6.71-6.49 (m, 1H), 6.38-6.27 (m, 1H), 5.75 (dd, J=17.5, 10.6 Hz, 1H), 4.95-4.41 (m, 2H), 3.96-3.86 (m, 2H), 3.85 (s, 3H), 3.81-3.51 (m, 1H), 3.37-2.80 (m, 2H), 2.32-2.19 (m, 1H), 2.28 (d, J=2.1 Hz, 3H), 2.20-2.10 (m, 1H), 2.02-1.80 (m, 2H). m/z (APCI-pos) $M^+1$=565.2.

Example 30

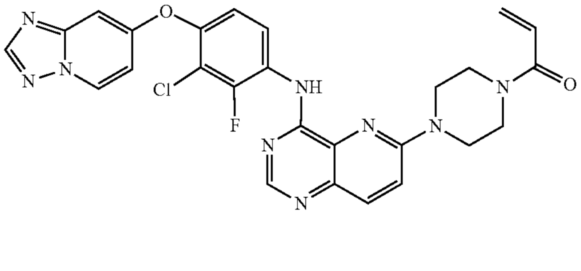 [SMILES: C=CC(=O)N1CCN(c2ccc3ncnc(Nc4ccc(Oc5ccn6ncnc6c5)c(Cl)c4F)c3n2)CC1]

1-(4-(4-((4-([1,2,4]triazolo[1,5-a]pyridin-7-yloxy)-3-chloro-2-fluorophenyl)amino)pyrido[3,2-d]pyrimidin-6-yl)piperazin-1-yl)prop-2-en-1-one Step A: 4,6-Dichloropyrido[3,2-d]pyrimidine (72.5 mg, 362 μmol) was added to a stirred solution of 4-([1,2,4]triazolo[1,5-a]pyridin-7-yloxy)-3-chloro-2-fluoroaniline (0.101 g, 362 μmol) in 2-propanol (4 mL) at 80° C. under sealed tube. After 1 hour, the reaction mixture was concentrated to afford N-(4-([1,2,4]triazolo[1,5-a]pyridin-6-yloxy)-3-chloro-2-fluorophenyl)-6-chloropyrido[3,2-d]pyrimidin-4-amine (160 mg, 99.8%). m/z (APCI-pos) M+1=442.0.

Step B: Hunig's base (0.07 g, 0.6 mmol) was added to a stirred solution of tert-butyl piperazine-1-carboxylate (0.06 g, 0.3 mmol) and N-(4-([1,2,4]triazolo[1,5-a]pyridin-6-yloxy)-3-chloro-2-fluorophenyl)-6-chloropyrido[3,2-d]pyrimidin-4-amine (0.05 g, 0.1 mmol) in DMSO (1 mL) at 100° C. under sealed tube. After 4 hours 30 minutes, the reaction mixture was cooled to ambient temperature, and the reaction mixture was concentrated. This crude material was purified via normal phase chromatography using a gradient of 0 to 30% 20% MeOH in $CH_2Cl_2$ in $CH_2Cl_2$ to afford tert-butyl 4-(4-((4-([1,2,4]triazolo[1,5-a]pyridin-6-yloxy)-3-chloro-2-fluorophenyl)amino)pyrido[3,2-d]pyrimidin-6-yl)piperazine-1-carboxylate (0.046 g, 70%). m/z (APCI-pos) M+1=592.1.

Step C: 2,2,2-Trifluoroacetic acid (0.18 g, 1.6 mmol) was added to a stirred solution of tert-butyl 4-(4-((4-([1,2,4]triazolo[1,5-a]pyridin-6-yloxy)-3-chloro-2-fluorophenyl)amino)pyrido[3,2-d]pyrimidin-6-yl)piperazine-1-carboxylate (0.046 g, 78 μmol) in DCM (2 mL) at ambient temperature. After 2 hours, the reaction mixture was concentrated to afford N-(4-([1,2,4]triazolo[1,5-a]pyridin-6-yloxy)-3-chloro-2-fluorophenyl)-6-(piperazin-1-yl)pyrido[3,2-d]pyrimidin-4-amine (0.038 g, 99%). m/z (APCI-pos) M+1=492.1.

Step D: Acryloyl chloride (4.6 μL, 57 μmol) was added to a stirred solution of Hunig's base (0.18 g, 1.4 mmol) and N-(4-([1,2,4]triazolo[1,5-a]pyridin-7-yloxy)-3-chloro-2-fluorophenyl)-6-(piperazin-1-yl)pyrido[3,2-d]pyrimidin-4-amine (0.035 g, 71 μmol) in $CH_2Cl_2$ (1 mL) at 0° C. After 15 minutes, the reaction mixture was concentrated and purified via normal phase chromatography (40 g, $SiO_2$) using a gradient of 0 to 50% 20% MeOH in DCM in DCM. Product containing fractions were combined and concentrated to afford 1-(4-(4-((4-([1,2,4]triazolo[1,5-a]pyridin-7-yloxy)-3-chloro-2-fluorophenyl)amino)pyrido[3,2-d]pyrimidin-6-yl)piperazin-1-yl)prop-2-en-1-one (0.011 g, 28% yield). $^1H$ NMR (400 MHz, $CDCl_3$) δ 9.10 (m, 1H), 9.00 (t, J=8.9 Hz, 1H), 8.68 (s, 1H), 8.54 (dd, J=7.1, 1.1 Hz, 1H), 8.25 (s, 1H), 8.04 (d, J=9.3 Hz, 1H), 7.33 (d, J=9.4 Hz, 2H), 7.16 (dd, J=9.2, 2.1 Hz, 1H), 6.92 (m, 1H), 6.65 (m, 1H), 6.39 (m, 1H), 5.80 (m, 1H), 3.86 (m, 8H); m/z (APCI-pos) M+1=546.1.

Example 31

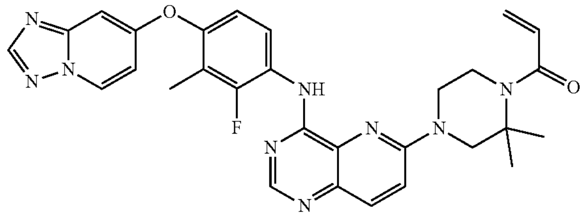 [SMILES: C=CC(=O)N1CCN(c2ccc3ncnc(Nc4ccc(Oc5ccn6ncnc6c5)c(C)c4F)c3n2)CC1(C)C]

1-(4-(4-((4-([1,2,4]triazolo[1,5-a]pyridin-7-yloxy)-2-fluoro-3-methylphenyl)amino)pyrido[3,2-d]pyrimidin-6-yl)-2,2-dimethylpiperazin-1-yl)prop-2-en-1-one Step A: tert-Butyl 2,2-dimethylpiperazine-1-carboxylate (73 mg, 0.34 mmol) was added to a stirred solution of N-(4-([1,2,4]triazolo[1,5-a]pyridin-7-yloxy)-3-chloro-2-fluorophenyl)-6-chloropyrido[3,2-d]pyrimidin-4-amine (0.050 g, 0.11 mmol) in DMSO at 100° C. in a sealed tube. After 48 hours, the reaction mixture was heated to 120° C. After 72 hours, the material was diluted with water and DCM, and the aqueous and organic phases were separated. The aqueous phase was extracted with DCM (2×), the combined organic phases were washed with brine (3×), dried over $Na_2SO_4$, and concentrated to afford N-(4-([1,2,4]triazolo[1,5-a]pyridin-7-yloxy)-3-chloro-2-fluorophenyl)-6-(3,3-dimethylpiperazin-1-yl)pyrido[3,2-d]pyrimidin-4-amine (40.6 mg, 69%). m/z (APCI-pos) M+1=520.2.

Step B: Acryloyl chloride (8.1 μL, 100 μmol) was added to a stirred solution of N-ethyl-N-isopropylpropan-2-amine (80.9 mg, 626 μmol) and N-(4-([1,2,4]triazolo[1,5-a]pyridin-7-yloxy)-2-fluoro-3-methylphenyl)-6-(3,3-dimethylpiperazin-1-yl)pyrido[3,2-d]pyrimidin-4-amine (0.0625 g, 125 μmol) in DCM (1 mL) at 0° C. After 15 minutes, the reaction mixture was concentrated. The resulting crude oil was purified via normal phase chromatography (24 g, $SiO_2$) using a gradient of 0 to 50% 20% MeOH in $CH_2Cl_2$ in $CH_2Cl_2$ to afford 1-(4-(4-((4-([1,2,4]triazolo[1,5-a]pyridin-7-yloxy)-2-fluoro-3-methylphenyl)amino)pyrido[3,2-d]pyrimidin-6-yl)-2,2-dimethylpiperazin-1-yl)prop-2-en-1-one (0.007 g, 10% yield). $^{1}$H NMR (400 MHz, $CDCl_3$) δ 9.12 (d, J=3.6 Hz, 1H), 8.84 (t, J=9.1 Hz, 1H), 8.64 (s, 1H), 8.51 (dd, J=7.2, 0.9 Hz, 1H), 8.23 (s, 1H), 8.01 (d, J=9.3 Hz, 1H), 7.16 (d, J=9.4 Hz, 1H), 7.01 (m, 1H), 6.88 (m, 1H), 6.58 (dd, J=16.8, 10.6 Hz, 1H), 6.26 (dd, J=16.8, 1.8 Hz, 1H), 5.69 (dd, 10.6, 1.8 Hz, 1H), 4.01 (t, J=5.7 Hz, 2H), 3.93 (s, 3H), 3.85 (t, J=5.7 Hz, 2H), 2.21 (d, J=2.2 Hz, 3H), 1.63 (s, 6H); m/z (APCI-pos); M+1=554.3.

Example 32

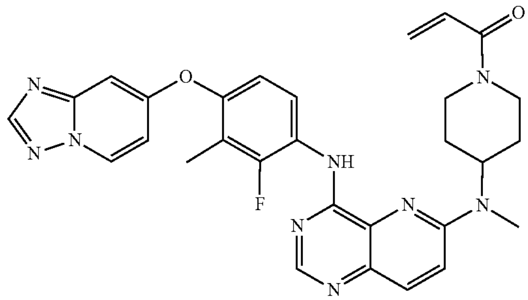 [SMILES: C=CC(=O)N1CCC(N(C)c2ccc3ncnc(Nc4ccc(Oc5ccn6ncnc6c5)c(C)c4F)c3n2)CC1]

1-(4-((4-((4-([1,2,4]triazolo[1,5-a]pyridin-7-yloxy)-2-fluoro-3-methylphenyl)amino)pyrido[3,2-d]pyrimidin-6-yl)(methyl)amino)piperidin-1-yl)prop-2-en-1-one Step A: N-Ethyl-N-isopropylpropan-2-amine (1.55 mL, 8.91 mmol) was added to a stirred solution of N-(4-([1,2,4]triazolo[1,5-a]pyridin-7-yloxy)-2-fluoro-3-methylphenyl)-6-chloropyrido[3,2-d]pyrimidin-4-amine (0.376 g, 8.91 μmol) and tert-butyl 4-(methylamino)piperidine-1-carboxylate (1.91 g, 8.91 mmol) in DMSO (1 mL) at 100° C. under sealed tube. The reaction was partitioned between water and $CHCl_3$. The combined organic layers were washed with brine (5×), dried over sodium sulfate, and concentrated in vacuo to afford tert-butyl 4-((4-((4-([1,2,4]triazolo[1,5-a]pyridin-7-yloxy)-2-fluoro-3-methylphenyl)amino)pyrido[3,2-d]pyrimidin-6-yl)(methyl)amino)piperidine-1-carboxylate (0.53 g, 99%). m/z (APCI-pos) M+1=600.3.

Step B: 2,2,2-Trifluoroacetic acid (1.37 mL, 17.8 mmol) was added to a stirred solution of tert-butyl 4-((4-((4-([1,2,4]triazolo[1,5-a]pyridin-7-yloxy)-2-fluoro-3-methylphenyl)amino)pyrido[3,2-d]pyrimidin-6-yl)(methyl)amino)piperidine-1-carboxylate (0.535 g, 892 μmol) in DCM (10 mL) at ambient temperature. After 1 hour, an additional 20 equivalents of TFA were added (40 equivalents total). After 21 hour, an additional 40 equivalents of TFA were added (80 equivalents). After another 23 hours, the reaction mixture was diluted with DCM and quenched via the addition of 10% $K_2CO_3$ (aq). After 10 minutes, the aqueous solution was extracted with $CHCl_3$ (3×), dried over $Na_2SO_4$, and concentrated. The resulting crude solid was purified via reverse phase chromatography using a gradient of 10 to 50% ACN (0.1% TFA)/water (0.1% TFA) over 65 minutes. Product containing fractions were combined and treated with 10% $K_2CO_3$ (aq). After 10 minutes, the aqueous solution was extracted with $CHCl_3$ (3×), dried over $Na_2SO_4$, and concentrated to afford N4-(4-([1,2,4]triazolo[1,5-a]pyridin-7-yloxy)-2-fluoro-3-methylphenyl)-N6-methyl-N6-(piperidin-4-yl)pyrido[3,2-d]pyrimidine-4,6-diamine (0.225 g, 50.5%). m/z (APCI-pos) M+1=500.3.

Step C: Acryloyl chloride (37.1 μL, 456 μmol) was added to a stirred solution of N4-(4-([1,2,4]triazolo[1,5-a]pyridin-7-yloxy)-2-fluoro-3-methylphenyl)-N6-methyl-N6-(piperidin-4-yl)pyrido[3,2-d]pyrimidine-4,6-diamine (0.228 g, 456 μmol) and acryloyl chloride (37.1 μL, 456 μmol) in DCM (5 mL) at 0° C. After 10 minutes, the reaction mixture was diluted with DCM, washed with 10% $K_2CO_3$ (aq) (2×), followed by brine, dried over $Na_2SO_4$, and concentrated. The crude residue was purified via reverse phase chromatography using a gradient of 5 to 50% ACN (0.1% TFA)/water (0.1% TFA) over 65 minutes. Product containing fractions were combined and treated with 10% saturated $K_2CO_3$ (aq). After 10 minutes, the aqueous solution was extracted with $CHCl_3$ (5×), dried over $Na_2SO_4$, and concentrated to afford 1-(4-((4-((4-([1,2,4]triazolo[1,5-a]pyridin-7-yloxy)-2-fluoro-3-methylphenyl)amino)pyrido[3,2-d]pyrimidin-6-yl)(methyl)amino)piperidin-1-yl)prop-2-en-1-one (0.114 g, 45% yield). $^{1}$H NMR (400 MHz, $CDCl_3$) δ 9.19 (d, J=3.7 Hz, 1H), 8.92 (t, J=9.1 Hz, 1H), 8.63 (s, 1H), 8.51 (dd, J=7.4, 0.8 Hz, 1H), 8.23 (s, 1H), 7.98 (d, J=9.4 Hz, 1H), 7.20 (d, J=9.3 Hz, 1H), 7.01 (dd, J=9.0, 1.8 Hz, 1H), 6.88 (m, 2H), 6.67 (dd, J=16.8, 10.5 Hz, 1H), 6.35 (dd, J=16.8, 2.0 Hz, 1H), 5.74 (dd, J=10.6, 2.0 Hz, 1H), 4.95 (m, 2H), 4.24 (m, 1H), 3.32 (m, 1H), 3.06 (s, 3H), 2.84 (m, 1H), 2.21 (d, J=2.1 Hz, 3H), 1.97 (m, 2H), 1.80 (m, 2H); m/z (APCI-pos) M+1=554.3.

Example 33

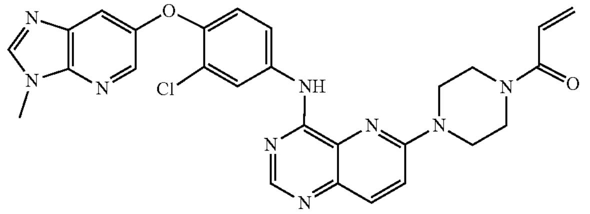 [SMILES: C=CC(=O)N1CCN(c2ccc3ncnc(Nc4ccc(Oc5cnc6c(c5)ncn6C)c(Cl)c4)c3n2)CC1]

1-(4-(4-((3-chloro-4-((3-methyl-3H-imidazo[4,5-b]pyridin-6-yl)oxy)phenyl)amino)pyrido[3,2-d]pyrimidin-6-yl)piperazin-1-yl)prop-2-en-1-one Step A: 3-Methyl-3H-imidazo[4,5-b]pyridin-6-ol (892 mg, 5.98 mmol) was added to a stirred solution of 2-chloro-1-fluoro-4-nitrobenzene (1.05 g, 5.98 mmol) and $Cs_2CO_3$ (3.90 g, 12.0 mmol) in DMSO (60 mL) at 65° C. for 16 hours, then allowed to cool to room temperature. The reaction mixture was partitioned between water and EtOAc. The organic layer was dried over sodium sulfate, filtered, and concentrated in vacuo to give 6-(2-chloro-4-nitrophenoxy)-3-methyl-3H-imidazo[4,5-b]pyridine (1.75 g, 96%). m/z (APCI-pos) M+1=305.1.

Step B: $SnCl_2(H_2O)$ (3.7 g, 16 mmol) was added to a stirred solution of 6-(2-chloro-4-nitrophenoxy)-3-methyl-3H-imidazo[4,5-b]pyridine (1.0 g, 3.3 mmol) in methanol (33 mL) at 70° C. The mixture was stirred at 70° C. for 16 hours, then concentrated under reduced pressure. The resulting crude was taken up in EtOAc/1N aq. NaOH, organics isolated and dried over sodium sulfate, then concentrated under reduced pressure to give 3-chloro-4-((3-methyl-3H-imidazo[4,5-b]pyridin-6-yl)oxy)aniline (708 mg, 79%). m/z (APCI-pos) $M^{+}1$=275.0.

Step C: 3-Chloro-4-((3-methyl-3H-imidazo[4,5-b]pyridin-6-yl)oxy)aniline (91 mg, 0.33 mmol) was added to a stirred solution of 4,6-dichloropyrido[3,2-d]pyrimidine (66 mg, 0.33 mmol) in 2-propanol (3 mL) at 60° C. for 1.5 hours. The mixture was diluted with EtOAc, washed with 10% aq. k-carb, dried over sodium sulfate, and concentrated under reduced pressure to give 6-chloro-N-(3-chloro-4-((3-methyl-3H-imidazo[4,5-b]pyridin-6-yl)oxy)phenyl)pyrido[3,2-d]pyrimidin-4-amine (131 mg, 91%). m/z (APCI-pos) M+1=438.0.

Step D: tert-Butyl piperazine-1-carboxylate (96 mg, 0.51 mmol) was added to a stirred solution of 6-chloro-N-(3-chloro-4-((3-methyl-3H-imidazo[4,5-b]pyridin-6-yl)oxy)phenyl)pyrido[3,2-d]pyrimidin-4-amine (75 mg, 0.17 mmol) in DMSO (1.7 mL) at 100° C. for 20 hours, then allowed to cool to room temperature. The reaction was partitioned between water and EtOAc. The organic layer was dried over sodium sulfate, filtered, and concentrated in vacuo. Flash chromatography purification afforded tert-butyl 4-(4-((3-chloro-4-((3-methyl-3H-imidazo[4,5-b]pyridin-6-yl)oxy)phenyl)amino)pyrido[3,2-d]pyrimidin-6-yl)piperazine-1-carboxylate (74.3 mg, 74%). m/z (APCI-pos) M+1=588.3.

Step E: TFA (0.48 mL, 6.3 mmol) was added to a stirred solution of tert-butyl 4-(4-((3-chloro-4-((3-methyl-3H-imidazo[4,5-b]pyridin-6-yl)oxy)phenyl)amino)pyrido[3,2-d]pyrimidin-6-yl)piperazine-1-carboxylate (74 mg, 0.13 mmol) in DCM (1 mL) at 25° C. for 2 hours. The mixture was diluted with EtOAc, washed with 10% aq. k-carb, dried over sodium sulfate, and concentrated under reduced pressure to give N-(3-chloro-4-((3-methyl-3H-imidazo[4,5-b]pyridin-6-yl)oxy)phenyl)-6-(piperazin-1-yl)pyrido[3,2-d]pyrimidin-4-amine (56.3 mg, 92%). m/z (APCI-pos) M+1=488.2.

Step F: Acryloyl chloride (7.5 μL, 92 μmol) was added to a stirred solution of N-(3-chloro-4-((3-methyl-3H-imidazo[4,5-b]pyridin-6-yl)oxy)phenyl)-6-(piperazin-1-yl)pyrido[3,2-d]pyrimidin-4-amine (56 mg, 0.11 mmol) and DIEA (40 μL, 0.23 mmol) in DCM (1 mL) at 0° C. This mixture was stirred at 0° C. for 30 minutes. The mixture was diluted with EtOAc, washed with 10% aq. k-carb, dried over sodium sulfate, and concentrated under reduced pressure. Flash chromatography purification afforded 1-(4-(4-((3-chloro-4-((3-methyl-3H-imidazo[4,5-b]pyridin-6-yl)oxy)phenyl)amino)pyrido[3,2-d]pyrimidin-6-yl)piperazin-1-yl)prop-2-en-1-one (23 mg, 37%). $^1$H NMR (400 MHz, DMSO) δ 9.46 (s, 1H), 8.46 (s, 2H), 8.36 (d, J=2.6 Hz, 1H), 8.28 (d, J=2.5 Hz, 1H), 8.01-7.93 (m, 2H), 7.70 (d, J=2.5 Hz, 1H), 7.60 (d, J=9.4 Hz, 1H), 7.15 (d, J=8.9 Hz, 1H), 6.89 (dd, J=16.7, 10.5 Hz, 1H), 6.17 (dd, J=16.7, 2.3 Hz, 1H), 5.74 (dd, J=10.5, 2.3 Hz, 1H), 3.97-3.82 (m, 7H), 3.82-3.61 (m, 4H). m/z (APCI-pos) M+1=542.2.

Example 34

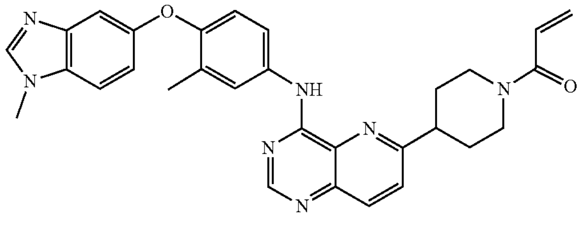 [SMILES: C=CC(=O)N1CCC(c2ccc3ncnc(Nc4ccc(Oc5ccc6c(c5)ncn6C)c(C)c4)c3n2)CC1]

1-(4-(4-((3-methyl-4-((1-methyl-1H-benzo[d]imidazol-5-yl)oxy)phenyl)amino)pyrido[3,2-d]pyrimidin-6-yl)piperidin-1-yl)prop-2-en-1-one Step A: A pressure tube equipped with a stir bar was charged with 6-chloro-N-(3-methyl-4-((1-methyl-1H-benzo[d]imidazol-5-yl)oxy)phenyl)pyrido[3,2-d]pyrimidin-4-amine (250 mg, 0.6 mmol), tert-butyl 4-(4,4,5,5-tetramethyl-1,3,2-dioxaborolan-2-yl)-3,6-dihydropyridine-1(2H)-carboxylate (556 mg, 1.8 mmol), dioxane (6 mL), 2M aq. k-carb (0.9 mL) and $Pd(PPh_3)_4$ (69.3 mg, 0.06 mmol). This mixture was purged with argon for a few minutes, tube sealed, and the mixture warmed to 100° C. overnight, then allowed to cool to room temperature. The mixture was diluted with EtOAc, washed with water/brine, dried over sodium sulfate, and concentrated under reduced pressure. Flash chromatography purification afforded tert-butyl 4-(4-((3-methyl-4-((1-methyl-1H-benzo[d]imidazol-5-yl)oxy)phenyl)amino)pyrido[3,2-d]pyrimidin-6-yl)-3,6-dihydropyridine-1(2H)-carboxylate (264 mg, 78%). m/z (APCI-pos) M+1=564.3.

Step B: A pressure tube containing tert-butyl 4-(4-((3-methyl-4-((1-methyl-1H-benzo[d]imidazol-5-yl)oxy)phenyl)amino)pyrido[3,2-d]pyrimidin-6-yl)-3,6-dihydropyridine-1(2H)-carboxylate (164 mg, 0.291 mmol) was charged with 3 mL of methanol and 150 mgs of Pearlman's catalyst. The tube was sealed, and the mixture was subjected to a balloon of hydrogen while warming to 45° C. After 3.5 hours, the mixture was allowed to cool to room temperature and purged with nitrogen. To the mixture was added methanol and Celite®, mixture stirred and filtered through GF/F filter paper. The filtrate was concentrated under reduced pressure to give tert-butyl 4-(4-((3-methyl-4-((1-methyl-1H-benzo[d]imidazol-5-yl)oxy)phenyl)amino)pyrido[3,2-d]pyrimidin-6-yl)piperidine-1-carboxylate (130 mg, 79%). m/z (APCI-pos) M+1=566.3.

Step C: A round bottom flask containing tert-butyl 4-(4-((3-methyl-4-((1-methyl-1H-benzo[d]imidazol-5-yl)oxy)phenyl)amino)pyrido[3,2-d]pyrimidin-6-yl)piperidine-1-carboxylate (130 mg, 0.23 mmol) was taken up in 2 mL of DCM. To this was added TFA (25 eq.) and the mixture was stirred at room temperature for 2 hours. The mixture was then diluted with EtOAc, washed with 10% aq. k-carb, dried over sodium sulfate, and concentrated under reduced pressure to give N-(3-methyl-4-((1-methyl-1H-benzo[d]imidazol-5-yl)oxy)phenyl)-6-(piperidin-4-yl)pyrido[3,2-d]pyrimidin-4-amine (93.4 mg, 87%). m/z (APCI-pos) M+1=466.3.

Step D: Acryloyl chloride (2.8 μL, 34 μmol) was added to a stirred solution of N-(3-methyl-4-((1-methyl-1H-benzo[d]imidazol-5-yl)oxy)phenyl)-6-(piperidin-4-yl)pyrido[3,2-d]pyrimidin-4-amine (20 mg, 43 μmol) and DIEA (15 μL, 86 μmol) in DCM (0.5 mL) at 0° C. The temperature was maintained at 0° C. for 30 minutes. The mixture was then diluted with EtOAc, washed with 10% aq. k-carb, dried over sodium sulfate, and concentrated under reduced pressure. Flash chromatography purification afforded 1-(4-(4-((3-methyl-4-((1-methyl-1H-benzo[d]imidazol-5-yl)oxy)phenyl)amino)pyrido[3,2-d]pyrimidin-6-yl)piperidin-1-yl)prop-2-en-1-one (9.6 mg). $^1$H NMR δ 1H NMR (400 MHz, DMSO) δ 9.78 (s, 1H), 8.60 (s, 1H), 8.19-8.10 (m, 2H), 7.91-7.83 (m, 2H), 7.78 (dd, J=8.7, 2.6 Hz, 1H), 7.57 (d, J=8.7 Hz, 1H), 7.10 (d, J=2.2 Hz, 1H), 7.00 (dd, J=8.7, 2.3 Hz, 1H), 6.96-6.79 (m, 2H), 6.13 (dd, J=16.7, 2.5 Hz, 1H), 5.69 (dd, J=10.5, 2.5 Hz, 1H), 4.65 (d, J=13.0 Hz, 1H), 4.25 (d, J=12.8 Hz, 1H), 3.84 (s, 3H), 3.29-3.18 (m, 2H), 2.80 (t, J=12.6 Hz, 1H), 2.26 (s, 3H), 2.07-1.97 (m, 2H), 1.97-1.80 (m, 2H). m/z (APCI-pos) M+1=520.3.

Example 35

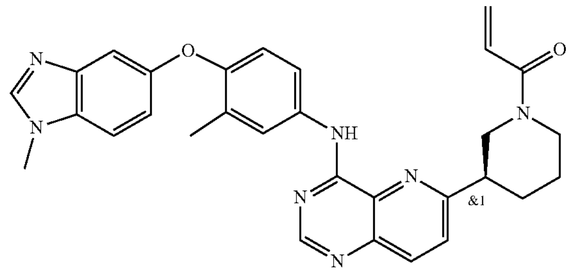 [SMILES: C=CC(=O)N1CCC[C@@H](c2ccc3ncnc(Nc4ccc(Oc5ccc6c(c5)ncn6C)c(C)c4)c3n2)C1]

1-(3-(4-((3-methyl-4-((1-methyl-1H-benzo[d]imidazol-5-yl)oxy)phenyl)amino)pyrido[3,2-d]pyrimidin-6-yl)piperidin-1-yl)prop-2-en-1-one Step A: A pressure tube containing 6-chloro-N-(3-methyl-4-((1-methyl-1H-benzo[d]imidazol-5-yl)oxy)phenyl)pyrido[3,2-d]pyrimidin-4-amine (100 mg, 0.24 mmol), tert-butyl 5-(4,4,5,5-tetramethyl-1,3,2-dioxaborolan-2-yl)-3,6-dihydropyridine-1(2H)-carboxylate (223 mg, 0.72 mmol), dioxane (2.4 mL), 3 eq. of 2M aq. k-carb, and $Pd(PPh_3)_4$ (27.7 mgs, 0.024 mmol). This mixture was purged with argon for a few minutes, tube sealed, and the mixture was warmed to 100° C. for 16 hours, then allowed to cool to room temperature. The mixture was diluted with EtOAc/water, extracted with EtOAc, extracts dried over sodium sulfate and concentrated under reduced pressure. Flash chromatography purification afforded tert-butyl 5-(4-((3-methyl-4-((1-methyl-1H-benzo[d]imidazol-5-yl)oxy)phenyl)amino)pyrido[3,2-d]pyrimidin-6-yl)-3,6-dihydropyridine-1(2H)-carboxylate (111 mg, 82%). m/z (APCI-pos) M+1=564.30.

Step B: Ammonium formate (90 mg, 1.4 mmol) was added to a stirred solution of tert-butyl 5-(4-((3-methyl-4-((1-methyl-1H-benzo[d]imidazol-5-yl)oxy)phenyl)amino)pyrido[3,2-d]pyrimidin-6-yl)-3,6-dihydropyridine-1(2H)-carboxylate (80 mg, 0.14 mmol) and 10% Pd/C (80 mgs) in MeOH (1.4 mL) at 75° C. in a pressure tube for 1 hour. The mixture was allowed to cool to room temperature. The mixture was diluted with methanol and filtered. The filtrate was concentrated under reduced pressure. The resulting material was triturated with $CHCl_3$ and filtered again to fully remove Pd solids. The filtrate was concentrated under reduced pressure to give tert-butyl 3-(4-((3-methyl-4-((1-methyl-1H-benzo[d]imidazol-5-yl)oxy)phenyl)amino)pyrido[3,2-d]pyrimidin-6-yl)piperidine-1-carboxylate (70 mg, 87%). m/z (APCI-pos) M+1=566.30.

Step C: TFA (0.19 mL, 2.5 mmol) was added to a stirred solution of tert-butyl 3-(4-((3-methyl-4-((1-methyl-1H-benzo[d]imidazol-5-yl)oxy)phenyl)amino)pyrido[3,2-d]pyrimidin-6-yl)piperidine-1-carboxylate (70 mg, 0.12 mmol) in DCM (1.2 mL) at 20° C. for 2 hours. The mixture was then diluted with EtOAc, washed with 10% aq. k-carb, dried over sodium sulfate, and concentrated under reduced pressure to give N-(3-methyl-4-((1-methyl-1H-benzo[d]imidazol-5-yl)oxy)phenyl)-6-(piperidin-3-yl)pyrido[3,2-d]pyrimidin-4-amine (49 mg, 85%). m/z (APCI-pos) M+1=466.25.

Step D: Acryloyl chloride (6.8 µL, 84 µmol) was added to a stirred solution of N-(3-methyl-4-((1-methyl-1H-benzo[d]imidazol-5-yl)oxy)phenyl)-6-(piperidin-3-yl)pyrido[3,2-d]pyrimidin-4-amine (49 mg, 0.11 mmol) and DIEA (27 mg, 0.21 mmol) in DCM (1.1 mL) at 0° C. under Nitrogen. After 30 minutes, the mixture was diluted with EtOAc, washed with 10% aq. k-carb, dried over sodium sulfate, and concentrated under reduced pressure. Flash chromatography purification afforded 1-(3-(4-((3-methyl-4-((1-methyl-1H-benzo[d]imidazol-5-yl)oxy)phenyl)amino)pyrido[3,2-d]pyrimidin-6-yl)piperidin-1-yl)prop-2-en-1-one (35 mg, 64%). $^1$H NMR (400 MHz, DMSO) δ 10.01-9.63 (m, 1H), 8.62 (d, J=4.2 Hz, 1H), 8.19-8.12 (m, 2H), 8.09-7.75 (m, 3H), 7.57 (d, J=8.7 Hz, 1H), 7.10 (d, J=2.2 Hz, 1H), 7.00 (dd, J=8.7, 2.3 Hz, 1H), 6.97-6.79 (m, 2H), 6.10 (dd, J=16.7, 2.4 Hz, 1H), 5.69-5.59 (m, 1H), 4.44-3.95 (m, 2H), 3.93-3.71 (m, 4H), 3.58-3.47 (m, 1H), 3.05-2.88 (m, 1H), 2.27 (s, 3H), 2.18-2.11 (m, 2H), 2.02-1.74 (m, 1H), 1.58-1.53 (m, 2H). m/z (APCI-pos) M+1=520.30.

Example 36

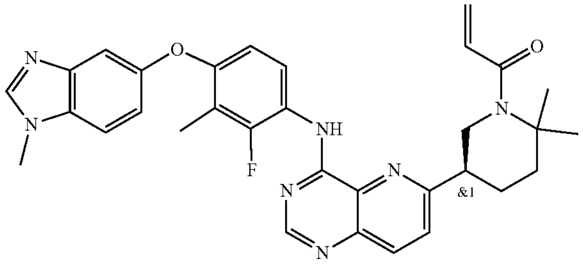 [SMILES: C=CC(=O)N1C[C@H](c2ccc3ncnc(Nc4ccc(Oc5ccc6c(c5)ncn6C)c(C)c4F)c3n2)CCC1(C)C]

1-(5-(4-((2-fluoro-3-methyl-4-((1-methyl-1H-benzo[d]imidazol-5-yl)oxy)phenyl)amino)pyrido[3,2-d]pyrimidin-6-yl)-2,2-dimethylpiperidin-1-yl)prop-2-en-1-one Step A: To an 8 mL vial containing $Irppy_2dtbbpy$ (1.3 mg, 1.4 µmol), $NiBr_2$ dtbbpy (3.4 mg, 6.9 µmol), quinuclidine (0.02 g, 0.2 mmol), and 6-chloro-N-(2-fluoro-3-methyl-4-((1-methyl-1H-benzo[d]imidazol-5-yl)oxy)phenyl)pyrido[3,2-d]pyrimidin-4-amine (40 mg, 92 µmol) were dissolved/suspended in DMA (1.0 mL). To a separate 8 mL vial containing 5,7-di-tert-butyl-3-phenyl-3-(tetrafluoro-15-boraneyl)-2,3-dihydrobenzo[d]oxazol-3-ium-2-ide (63 mg, 0.16 mmol) and tert-butyl 5-hydroxy-2,2-dimethylpiperidine-1-carboxylate (35 mg, 0.15 mmol) was added degassed MTBE (1.0 mL) under Nitrogen. After stirring for 1 minute, pyridine (12 µL, 0.15 mmol) was added through septum while vigorously stirring. After stirring for 10 minutes, the solution was taken up in a syringe and filtered through a syringe filter into the reaction vial containing nickel and iridium components. The vial was then capped and sparged with nitrogen for 10 minutes, parafilmed, and irradiated with 450 nm light in the integrated photoreactor for 4 hours (100% intensity, 1200 rpm stir, max fan speed). The reaction was concentrated in vacuo and the crude residue was purified over 12 g silica cartridge, eluting with a gradient of 1 to 10% MeOH in DCM to afford tert-butyl 5-(4-((2-fluoro-3-methyl-4-((1-methyl-1H-benzo[d]imidazol-5-yl)oxy)phenyl)amino)pyrido[3,2-d]pyrimidin-6-yl)-2,2-dimethylpiperidine-1-carboxylate (33.0 mg, 59%) as a solid. m/z (APCI-pos) M+1=612.30.

Step B: TFA (0.21 mL, 2.7 mmol) was added to a stirred solution of tert-butyl 5-(4-((2-fluoro-3-methyl-4-((1-methyl-1H-benzo[d]imidazol-5-yl)oxy)phenyl)amino)pyrido[3,2-d]pyrimidin-6-yl)-2,2-dimethylpiperidine-1-carboxylate (33 mg, 54 μmol) in DCM (0.54 mL). The reaction mixture was stirred for 2 hours. The reaction was partitioned between EtOAc and 10% $K_2CO_3$. The aqueous phase was extracted with EtOAc (×3). The organic layer was dried over sodium sulfate, filtered, and concentrated in vacuo. The product was used as is in the next reaction without further purification. 6-(6,6-dimethylpiperidin-3-yl)-N-(2-fluoro-3-methyl-4-((1-methyl-1H-benzo[d]imidazol-5-yl)oxy)phenyl)pyrido[3,2-d]pyrimidin-4-amine (25.4 mg, 92%) as a solid. m/z (APCI-pos) M+1=512.30.

Step C: Acryloyl chloride (75 μL, 0.5 molar $CH_2Cl_2$, 38 μmol) was added to a stirred solution of 6-(6,6-dimethylpiperidin-3-yl)-N-(2-fluoro-3-methyl-4-((1-methyl-1H-benzo[d]imidazol-5-yl)oxy)phenyl)pyrido[3,2-d]pyrimidin-4-amine (24 mg, 47 μmol) and DIPEA (16 μL, 94 μmol) in DCM at 0° C. The reaction was stirred for 30 minutes. The reaction was partitioned between DCM and 10% $K_2CO_3$. The aqueous phase was extracted with DCM (×3). The organic layer was dried over sodium sulfate, filtered, and concentrated in vacuo. The crude residue was purified over 4 g silica cartridge, eluting with a gradient of 1% to 10% MeOH in DCM to afford 1-(5-(4-((2-fluoro-3-methyl-4-((1-methyl-1H-benzo[d]imidazol-5-yl)oxy)phenyl)amino)pyrido[3,2-d]pyrimidin-6-yl)-2,2-dimethylpiperidin-1-yl)prop-2-en-1-one (13.5 mg, 51%) as a solid. $^1H$ NMR (400 MHz, $CDCl_3$) δ 9.37 (s, 1H), 8.76 (s, 1H), 8.51 (t, J=9.1 Hz, 1H), 8.18 (d, J=8.6 Hz, 1H), 8.05 (s, 1H), 7.67 (d, J=8.6 Hz, 1H), 7.41-7.32 (m, 2H), 7.10 (dd, J=8.7, 2.3 Hz, 1H), 6.82-6.74 (m, 1H), 6.50 (dd, J=16.9, 10.5 Hz, 1H), 6.20-6.11 (m, 1H), 5.60-5.52 (m, 1H), 4.03 (dd, J=14.2, 4.6 Hz, 1H), 3.90 (s, 3H), 3.62 (dd, J=14.2, 10.1 Hz, 1H), 3.40-3.28 (m, 1H), 2.30 (d, J=2.1 Hz, 3H), 2.24-2.01 (m, 2H), 1.98-1.71 (m, 2H), 1.70 (s, 3H), 1.56 (s, 3H); m/z (APCI-pos) M+1=566.2.

Example 37

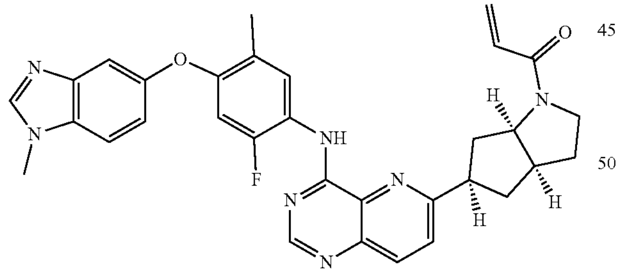

1-(5-(4-((2-fluoro-5-methyl-4-((1-methyl-1H-benzo[d]imidazol-5-yl)oxy)phenyl)amino)pyrido[3,2-d]pyrimidin-6-yl)hexahydrocyclopenta[b]pyrrol-1(2H)-yl)prop-2-en-1-one Step A: tert-Butyl 5-oxohexahydrocyclopenta[b]pyrrole-1(2H)-carboxylate (100 mg, 0.45 mmol) was added to anhydrous THF (2.2 mL) and cooled to 0° C. To this solution was added LiHMDS (0.488 mL, 0.49 mmol) as a 1M solution in THF followed by Comin's reagent (174 mg, 0.44 mmol) in two equal portions. After 60 minutes at 0° C., TLC analysis showed consumption of starting material. The reaction was quenched with brine and diluted with EtOAc and $H_2O$. The layers were separated, and the aqueous layer was extracted with EtOAc (3×). The combined organics were dried over sodium sulfate, filtered, and concentrated in vacuo to give an oil. The crude residue was purified via column chromatography, eluting with a gradient of 0% to 30% EtOAc in heptane to afford tert-butyl 5-(((trifluoromethyl)sulfonyl)oxy)-3,3a,6,6a-tetrahydrocyclopenta[b]pyrrole-1(2H)-carboxylate (138.6 mg, 87.4%), which was immediately carried forward.

Step B: tert-Butyl 5-(((trifluoromethyl)sulfonyl)oxy)-3,3a,6,6a-tetrahydrocyclopenta[b]pyrrole-1(2H)-carboxylate (138.6 mg, 387.9 μmol), 4,4,4',4',5,5,5',5'-octamethyl-2,2'-bi(1,3,2-dioxaborolane) (108.3 mg, 426.7 μmol), potassium acetate (114.2 mg, 1.164 mmol), 1,4-dioxane (3.879 mL), $PdCl_2$(dppf)-$CH_2Cl_2$ adduct (9.5 mg, 11.64 μmol), and dppf (6.45 mg, 11.64 μmol) were combined and the reaction purged with argon for 10 minutes. The reaction was sealed and stirred at 60° C. for 16 hours. The reaction was quenched with brine and partitioned between EtOAc and water. The aqueous phase was extracted with EtOAc (×3). The organic layer was dried over sodium sulfate, filtered, and concentrated in vacuo. The crude residue was purified over 12 g silica cartridge, eluting with a gradient of 0% to 60% EtOAc in heptane to afford tert-butyl 5-(4,4,5,5-tetramethyl-1,3,2-dioxaborolan-2-yl)-3,3a,6,6a-tetrahydrocyclopenta[b]pyrrole-1(2H)-carboxylate (126 mg, 376 μmol, 96.9%).

Step C: 6-Chloro-N-(2-fluoro-5-methyl-4-((1-methyl-1H-benzo[d]imidazol-5-yl)oxy)phenyl)pyrido[3,2-d]pyrimidin-4-amine (50 mg, 0.11 mmol), tert-butyl 5-(4,4,5,5-tetramethyl-1,3,2-dioxaborolan-2-yl)-3,3a,6,6a-tetrahydrocyclopenta[b]pyrrole-1(2H)-carboxylate (77 mg, 0.23 mmol), $Pd(Ph_3P)_4$ (13 mg, 11 μmol), and $K_2CO_3$ (0.17 mL, 2 molar Aq, 0.34 mmol) were dissolved in 1,4-dioxane (1.1 mL). The reaction mixture was sparged with argon for 15 minutes before the reaction vessel was sealed and stirred at 100° C. for 16 hours. The reaction was cooled to room temperature then partitioned between $CHCl_3$ and $H_2O$. The aqueous phase was extracted with $CHCl_3$ (×3). The organic layer was dried over sodium sulfate, filtered, and concentrated in vacuo. The crude residue was purified over 4 g silica cartridge, eluting with a gradient of 1% to 10% MeOH in DCM to afford tert-butyl 5-(4-((2-fluoro-5-methyl-4-((1-methyl-1H-benzo[d]imidazol-5-yl)oxy)phenyl)amino)pyrido[3,2-d]pyrimidin-6-yl)-3,3a,6,6a-tetrahydrocyclopenta[b]pyrrole-1(2H)-carboxylate (62.2 mg, 102 μmol, 89%). m/z (APCI-pos) M+1=608.2.

Step D: Pd/C (109 mg, 10% Wt, 102 μmol) and ammonium formate (64.5 mg, 1.02 mmol) were added to a stirred solution of tert-butyl 5-(4-((2-fluoro-5-methyl-4-((1-methyl-1H-benzo[d]imidazol-5-yl)oxy)phenyl)amino)pyrido[3,2-d]pyrimidin-6-yl)-3,3a,6,6a-tetrahydrocyclopenta[b]pyrrole-1(2H)-carboxylate (62.2 mg, 102 μmol) in methanol (1.02 mL) and stirred at 64° C. for 1 hour before cooling to room temperature. The reaction was filtered through celite and concentrated. The crude was dissolved in a minimal amount of $CHCl_3$ to precipitate any remaining ammonium formate and filtered. The product tert-butyl 5-(4-((2-fluoro-5-methyl-4-((1-methyl-1H-benzo[d]imidazol-5-yl)oxy)phenyl)amino)pyrido[3,2-d]pyrimidin-6-yl)hexahydrocyclopenta[b]pyrrole-1(2H)-carboxylate (50.5 mg, 81%) was used directly in the next reaction without further purification. m/z (APCI-pos) M+1=610.3.

Step E: TFA (0.13 mL, 1.6 mmol) was added to a stirred solution of tert-butyl 5-(4-((2-fluoro-5-methyl-4-((1-methyl-1H-benzo[d]imidazol-5-yl)oxy)phenyl)amino)pyrido[3,2-d]pyrimidin-6-yl)hexahydrocyclopenta[b]pyrrole-1(2H)-carboxylate (50 mg, 82 μmol) in DCM (0.82 mL). The reaction was stirred at room temperature for 2 hours. The reaction was quenched with 10% $K_2CO_3$ and extracted with EtOAc. The product N-(2-fluoro-5-methyl-4-((1-methyl-1H-benzo[d]imidazol-5-yl)oxy)phenyl)-6-(octahydrocyclopenta[b]pyrrol-5-yl)pyrido[3,2-d]pyrimidin-4-amine (36.3 mg, 87%) was used directly in the next reaction without further purification. m/z (APCI-pos) M+1=510.2.

Step F: Acryloyl chloride (0.12 mL, 0.4 molar, 47 μmol) was added to a stirred solution of N-(2-fluoro-5-methyl-4-((1-methyl-1H-benzo[d]imidazol-5-yl)oxy)phenyl)-6-(octahydrocyclopenta[b]pyrrol-5-yl)pyrido[3,2-d]pyrimidin-4-amine (30 mg, 59 μmol) and DIPEA (21 μL, 0.12 mmol) in DCM (0.59 mL) at 0° C. The reaction was stirred at this temperature for 30 minutes. The reaction was quenched with 10% $K_2CO_3$ and extracted with DCM. The organic layer was dried over sodium sulfate, filtered, and concentrated in vacuo. The crude residue was purified with reverse phase prep HPLC eluting with a gradient of 0% to 40% acetonitrile with 0.1% TFA in water with 0.1% TFA to afford 1-(5-(4-((2-fluoro-5-methyl-4-((1-methyl-1H-benzo[d]imidazol-5-yl)oxy)phenyl)amino)pyrido[3,2-d]pyrimidin-6-yl)hexahydrocyclopenta[b]pyrrol-1(2H)-yl)prop-2-en-1-one (4.8 mg, 8.5 μmol, 14%) as a solid. $^1H$ NMR (400 MHz, $CDCl_3$) δ 9.26-9.15 (m, 1H), 8.83-8.72 (m, 1H), 8.62-8.53 (m, 1H), 8.13-8.04 (m, 1H), 7.88 (s, 1H), 7.64-7.56 (m, 1H), 7.40-7.33 (m, 2H), 7.10-7.02 (m, 1H), 6.74-6.65 (m, 1H), 6.60-6.42 (m, 1H), 6.36 (ddd, J=19.0, 16.8, 2.2 Hz, 1H), 5.65 (ddd, J=12.2, 10.1, 2.2 Hz, 1H), 4.65-4.43 (m, 1H), 4.08-3.97 (m, 1H), 3.87 (s, 3H), 3.82-3.63 (m, 1H), 3.59-3.42 (m, 1H), 3.11-2.67 (m, 2H), 2.48-2.38 (m, 1H), 2.37 (s, 3H), 2.18-1.80 (m, 4H) [NMR indicates rotational isomers of the amide]; m/z (APCI-pos) M+1=564.2.

Example 38

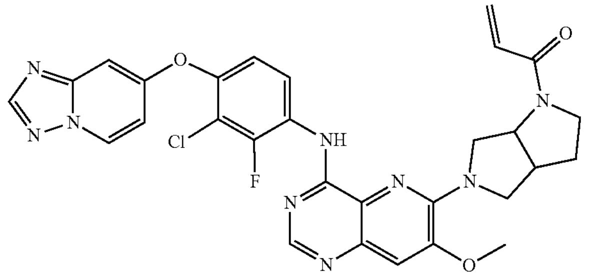 [SMILES: C=CC(=O)N1CCC2CN(c3nc4c(Nc5ccc(Oc6ccn7ncnc7c6)c(Cl)c5F)ncnc4cc3OC)CC21]

1-(5-(4-((4-([1,2,4]triazolo[1,5-a]pyridin-7-yloxy)-3-chloro-2-fluorophenyl)amino)-7-methoxypyrido[3,2-d]pyrimidin-6-yl)hexahydropyrrolo[3,4-b]pyrrol-1(2H)-yl)prop-2-en-1-one Step A: 4-Chloro-7-methoxy-6-(methylthio)pyrido[3,2-d]pyrimidine (0.15 g, 0.63 mmol), 4-([1,2,4]triazolo[1,5-a]pyridin-7-yloxy)-3-chloro-2-fluoroaniline (0.18 g, 0.63 mmol), and propan-2-01 (3.1 mL) were charged to a 25 mL round bottom flask. The mixture was stirred at 70° C. for 1 hour and then diluted with 25% IPA/CHCl3 and washed once with aqueous saturated sodium bicarbonate. Organics were dried over $Na_2SO_4$, filtered, and concentrated in vacuo, then purified by column chromatography (0 to 10% MeOH/DCM) to furnish N-(4-([1,2,4]triazolo[1,5-a]pyridin-7-yloxy)-3-chloro-2-fluorophenyl)-7-methoxy-6-(methylthio)pyrido[3,2-d]pyrimidin-4-amine (0.29 g, 95%). m/z (APCI-pos) $M^+1$=484.1.

Step B: N-(4-([1,2,4]Triazolo[1,5-a]pyridin-7-yloxy)-3-chloro-2-fluorophenyl)-7-methoxy-6-(methylthio)pyrido[3,2-d]pyrimidin-4-amine (0.16 g, 0.33 mmol) and DCM (3.3 mL, 0.33 mmol) were charged to a 25 mL round bottom flask and cooled to 0° C. with stirring. m-CPBA (70% wt in water, 94 mg, 0.38 mmol) was added to flask and the mixture was stirred at 0° C. for 90 minutes. The reaction was diluted with DCM and washed once with saturated aqueous sodium thiosulfate, and twice with saturated aqueous sodium bicarbonate. Organics were dried over $Na_2SO_4$, filtered, and concentrated in vacuo to furnish N-(4-([1,2,4]triazolo[1,5-a]pyridin-7-yloxy)-3-chloro-2-fluorophenyl)-7-methoxy-6-(methylsulfinyl)pyrido[3,2-d]pyrimidin-4-amine (0.19 g, 112%) as mixture of sulfone (25%), sulfoxide (75%), and impurities, used crude.

Step C: N-(4-([1,2,4]Triazolo[1,5-a]pyridin-7-yloxy)-3-chloro-2-fluorophenyl)-7-methoxy-6-(methylsulfinyl)pyrido[3,2-d]pyrimidin-4-amine (25 mg, 50 μmol), DMA (0.20 mL), Hunig's base (44 μL, 0.25 mmol) and tert-butyl hexahydropyrrolo[3,4-b]pyrrole-1(2H)-carboxylate, HCl (37 mg, 0.15 mmol) were charged to a dram vial equipped with a stir bar. The mixture was heated to 140° C. for 2 hours. The material was dry loaded onto silica gel and purified by column chromatography (0 to 10% MeOH/DCM) to furnish tert-butyl 5-(4-((4-([1,2,4]triazolo[1,5-a]pyridin-7-yloxy)-3-chloro-2-fluorophenyl)amino)-7-methoxypyrido[3,2-d]pyrimidin-6-yl)hexahydropyrrolo[3,4-b]pyrrole-1(2H)-carboxylate (8.4 mg, 26%). m/z (APCI-pos) $M^+1$=648.2.

Step D: tert-Butyl 5-(4-((4-([1,2,4]triazolo[1,5-a]pyridin-7-yloxy)-3-chloro-2-fluorophenyl)amino)-7-methoxypyrido[3,2-d]pyrimidin-6-yl)hexahydropyrrolo[3,4-b]pyrrole-1(2H)-carboxylate (8 mg, 12 μmol) and DCM (0.12 mL) were charged to a dram vial equipped with a stir bar. The mixture was cooled to 0° C. and TFA (19 μL, 0.25 mmol) was added to the stirring solution. The ice bath was removed, and the mixture was stirred at room temperature for 2 hours. The mixture was diluted with ethyl acetate and saturated aqueous sodium bicarbonate. Organics were dried over $Na_2SO_4$ and concentrated in vacuo to furnish N-(4-([1,2,4]triazolo[1,5-a]pyridin-7-yloxy)-3-chloro-2-fluorophenyl)-6-(hexahydropyrrolo[3,4-b]pyrrol-5(1H)-yl)-7-methoxypyrido[3,2-d]pyrimidin-4-amine (7 mg, 100%). m/z (APCI-pos) $M^+1$=548.2.

Step E: N-(4-([1,2,4]Triazolo[1,5-a]pyridin-7-yloxy)-3-chloro-2-fluorophenyl)-6-(hexahydropyrrolo[3,4-b]pyrrol-5(1H)-yl)-7-methoxypyrido[3,2-d]pyrimidin-4-amine (9 mg, 16 μmol), DCM (0.16 mL), and Hunig's base (3.4 μL, 20 μmol) were charged to a dram vial. The solution was stirred and cooled to 0° C. whereupon acryloyl chloride (12 μL, 12 μmol) was added dropwise. The mixture was warmed to room temperature and stirred for 4 hours. The reaction was dry loaded onto silica gel and purified by column chromatography (0 to 10% MeOH/DCM) to furnish 1-(5-(4-((4-([1,2,4]triazolo[1,5-a]pyridin-7-yloxy)-3-chloro-2-fluorophenyl)amino)-7-methoxypyrido[3,2-d]pyrimidin-6-yl)hexahydropyrrolo[3,4-b]pyrrol-1(2H)-yl)prop-2-en-1-one (1.42 mg, 13%). m/z (APCI-pos) $M^+1$=602.2. 1H NMR (400 MHz, cdcl3) δ 8.96-8.90 (m, 2H), 8.60 (d, J=9.0 Hz, 1H), 8.56-8.49 (m, 1H), 8.25 (s, 1H), 7.22 (d, J=15.1 Hz, 1H), 7.16-7.10 (m, 1H), 6.94-6.88 (m, 2H), 6.53-6.36 (m, 2H), 5.72 (dd, J=9.6, 2.8 Hz, 1H), 4.29-4.16 (m, 2H), 4.07-3.97

(m, 1H), 3.97-3.92 (m, 4H), 3.90-3.78 (m, 1H), 3.80-3.71 (m, 3H), 3.07 (d, J=6.6 Hz, 1H), 2.28-2.19 (m, 1H), 2.12-2.02 (m, 1H).

Example 39

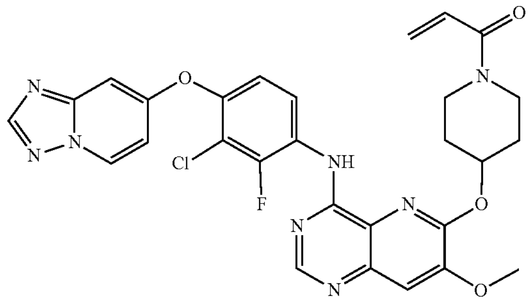 [SMILES: C=CC(=O)N1CCC(Oc2nc3c(Nc4ccc(Oc5ccn6ncnc6c5)c(Cl)c4F)ncnc3cc2OC)CC1]

1-(4-((4-((4-([1,2,4]triazolo[1,5-a]pyridin-7-yloxy)-3-chloro-2-fluorophenyl)amino)-7-methoxypyrido[3,2-d]pyrimidin-6-yl)oxy)piperidin-1-yl)prop-2-en-1-one Step A: N-(4-([1,2,4]Triazolo[1,5-a]pyridin-7-yloxy)-3-chloro-2-fluorophenyl)-7-methoxy-6-(methylsulfinyl) pyrido[3,2-d]pyrimidin-4-amine (25 mg, 50 μmol), DMA (0.20 mL) and tert-butyl 4-hydroxypiperidine-1-carboxylate (81 mg, 0.40 mmol) were charged to a dram vial equipped with a stir bar. The mixture was cooled to 0° C. and NaH (60% wt in mineral oil) (8.0 mg, 0.20 mmol) was added to the stirring solution. The ice bath was removed, and the mixture was stirred at 40° C. for 2 hours and then 50° C. for 1 hour. The material was dry loaded onto silica gel and purified by column chromatography (Redisep 12 g, 0 to 10% MeOH/DCM) to furnish tert-butyl 4-((4-((4-([1,2,4]triazolo [1,5-a]pyridin-7-yloxy)-3-chloro-2-fluorophenyl)amino)-7-methoxypyrido[3,2-d]pyrimidin-6-yl)oxy)piperidine-1-carboxylate (17 mg, 52%) m/z (APCI-pos) M+1=637.2.

Synthesized according to Example 38, Steps D-E, to furnish 1-(4-((4-((4-([1,2,4]triazolo[1,5-a]pyridin-7-yloxy)-3-chloro-2-fluorophenyl)amino)-7-methoxypyrido[3,2-d] pyrimidin-6-yl)oxy)piperidin-1-yl)prop-2-en-1-one (5.9 mg, 30%). m/z (APCI-pos) M+1=591.3. 1H NMR (400 MHz, cdcl3) δ 8.97 (t, J=8.9 Hz, 1H), 8.84-8.78 (m, 1H), 8.72 (s, 1H), 8.53 (dd, J=7.4, 0.8 Hz, 1H), 8.25 (s, 1H), 7.40 (s, 1H), 7.15 (dd, J=9.2, 2.0 Hz, 1H), 6.96-6.86 (m, 1H), 6.64 (dd, J=16.8, 10.6 Hz, 1H), 6.31 (dd, J=16.8, 1.9 Hz, 1H), 5.72 (dd, J=10.6, 1.9 Hz, 1H), 5.58-5.49 (m, 1H), 4.15 (s, 1H), 4.02 (s, 3H), 3.95 (s, 1H), 3.61 (s, 3H), 2.23 (s, 2H), 2.11-1.95 (m, 2H).

Example 40

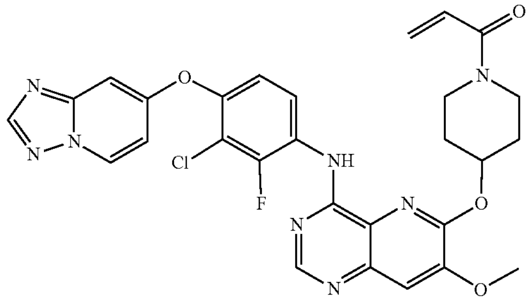 [SMILES: C=CC(=O)N1CCC(Oc2nc3c(Nc4ccc(Oc5ccn6ncnc6c5)c(Cl)c4F)ncnc3cc2OC)CC1]

1-(4-((4-((4-([1,2,4]triazolo[1,5-a]pyridin-7-yloxy)-2-fluoro-3-methylphenyl)amino)-7-methoxypyrido [3,2-d]pyrimidin-6-yl)oxy)piperidin-1-yl)prop-2-en-1-one Step A: 4,6-Dichloro-7-methoxypyrido[3,2-d]pyrimidine (98 mg, 043 mmol), IPA (2.1 mL), and 4-([1,2,4]triazolo[1,5-a]pyridin-7-yloxy)-2-fluoro-3-methylaniline (0.11 g, 0.43 mmol) were charged to a 25 mL round bottom flask equipped with a stir bar. The mixture was heated to 60° C. for 2 hours. The material was diluted with 25% IPA/$CHCl_3$, washed twice with saturated aqueous sodium bicarbonate, dried over $Na_2SO_4$, filtered and concentrated. The crude product was purified by column chromatography (0 to 10% MeOH/DCM) to furnish N-(4-([1,2,4]triazolo[1,5-a]pyridin-7-yloxy)-2-fluoro-3-methylphenyl)-6-chloro-7-methoxypyrido[3,2-d]pyrimidin-4-amine (0.19 g, 99%). m/z (APCI-pos) $M^+1$=452.1.

Synthesized according to Example 39, substituting N-(4-([1,2,4]triazolo[1,5-a]pyridin-7-yloxy)-2-fluoro-3-methylphenyl)-6-chloro-7-methoxypyrido[3,2-d]pyrimidin-4-amine for N-(4-([1,2,4]triazolo[1,5-a]pyridin-7-yloxy)-3-chloro-2-fluorophenyl)-7-methoxy-6-(methylsulfinyl) pyrido[3,2-d]pyrimidin-4-amine in Step A, to furnish 1-(4-((4-((4-([1,2,4]triazolo[1,5-a]pyridin-7-yloxy)-2-fluoro-3-methylphenyl)amino)-7-methoxypyrido[3,2-d]pyrimidin-6-yl)oxy)piperidin-1-yl)prop-2-en-1-one (3.8 mg, 45%). m/z (APCI-pos) $M^+1$=571.2. 1H NMR (400 MHz, CDCl3) δ 8.87-8.78 (m, 1H), 8.71 (s, 1H), 8.51 (dd, J=7.4, 0.8 Hz, 1H), 8.23 (s, 1H), 7.38 (s, 1H), 7.01 (dd, J=9.0, 1.8 Hz, 1H), 6.90 (dd, J=7.4, 2.6 Hz, 1H), 6.86 (dd, J=2.6, 0.8 Hz, 1H), 6.65 (dd, J=16.8, 10.6 Hz, 1H), 6.32 (dd, J=16.8, 1.9 Hz, 1H), 5.73 (dd, J=10.6, 1.9 Hz, 1H), 5.60-5.50 (m, 1H), 4.18 (s, 1H), 4.03 (s, 3H), 3.99-3.95 (m, 1H), 3.61 (s, 2H), 2.32-2.13 (m, 6H), 2.02 (d, J=8.8 Hz, 2H).

Example 41

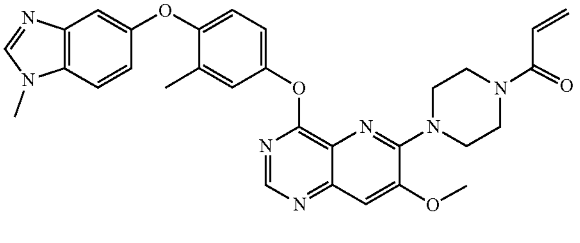 [SMILES: C=CC(=O)N1CCN(c2nc3c(Oc4ccc(Oc5ccc6c(c5)ncn6C)c(C)c4)ncnc3cc2OC)CC1]

1-(4-(7-methoxy-4-(3-methyl-4-((1-methyl-1H-benzo[d]imidazol-5-yl)oxy)phenoxy)pyrido[3,2-d]pyrimidin-6-yl)piperazin-1-yl)prop-2-en-1-one Step A: 4,6-Dichloro-7-methoxypyrido[3,2-d]pyrimidine (0.15 g, 0.65 mmol), 3-methyl-4-((1-methyl-1H-benzo[d]imidazol-5-yl)oxy)phenol (0.17 g, 0.65 mmol), DMA (3.3 mL), and $Cs_2CO_3$ (0.43 g, 1.3 mmol) were charged to a round bottom flask. The mixture was heated to 80° C. with stirring for 4 hours and then diluted with water. The resultant solid was collected via vacuum filtration to furnish 6-chloro-7-methoxy-4-(3-methyl-4-((1-methyl-1H-benzo[d]imidazol-5-yl)oxy)phenoxy)pyrido[3,2-d]pyrimidine (0.19 g, 63%). m/z (APCI-pos) M+1=448.2.

Synthesized according to Example 38, Steps C-E, substituting 6-chloro-7-methoxy-4-(3-methyl-4-((1-methyl-1H-benzo[d]imidazol-5-yl)oxy)phenoxy)pyrido[3,2-d]pyrimidine for N-(4-([1,2,4]triazolo[1,5-a]pyridin-7-yloxy)-3-chloro-2-fluorophenyl)-7-methoxy-6-(methylsulfinyl)pyrido[3,2-d]pyrimidin-4-amine to furnish 1-(4-(7-methoxy-4-(3-methyl-4-((1-methyl-1H-benzo[d]imidazol-5-yl)oxy)phenoxy)pyrido[3,2-d]pyrimidin-6-yl)piperazin-1-yl)prop-2-en-1-one (1.8 mg, 61%). m/z (APCI-pos) M+1=552.3. 1H NMR (400 MHz, cdcl3) δ 8.60 (s, 1H), 7.86 (s, 1H), 7.42-7.31 (m, 3H), 7.16 (d, J=2.8 Hz, 1H), 7.09 (dd, J=8.8, 2.3 Hz, 1H), 7.01 (dd, J=8.8, 2.9 Hz, 1H), 6.90 (d, J=8.8 Hz, 1H), 6.62 (dd, J=16.8, 10.6 Hz, 1H), 6.33 (dd, J=16.8, 1.9 Hz, 1H), 5.74 (dd, J=10.6, 1.9 Hz, 1H), 4.04 (s, 3H), 3.87-3.83 (m, 4H), 3.77-3.73 (m, 4H), 3.49 (s, 3H), 2.33 (s, 3H).

Example 42

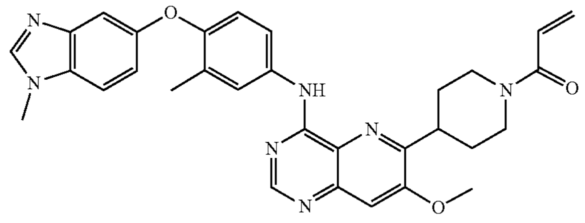 [SMILES: C=CC(=O)N1CCC(c2nc3c(Nc4ccc(Oc5ccc6c(c5)ncn6C)c(C)c4)ncnc3cc2OC)CC1]

1-(4-(7-methoxy-4-((3-methyl-4-((1-methyl-1H-benzo[d]imidazol-5-yl)oxy)phenyl)amino)pyrido[3,2-d]pyrimidin-6-yl)piperidin-1-yl)prop-2-en-1-one Step A: 3-Methyl-4-((1-methyl-1H-benzo[d]imidazol-5-yl)oxy)aniline (0.18 g, 0.72 mmol), 4,6-dichloro-7-methoxypyrido[3,2-d]pyrimidine (0.17 g, 0.72 mmol), and 2-propanol (3.6 mL) were charged to a 25 mL round bottom flask equipped with a stir bar. The mixture was stirred at 70° C. for 1 hour and then diluted with 25% IPA/$CHCl_3$. Organics were washed twice with 2M saturated aqueous sodium bicarbonate, dried over Na2SO4, filtered, and concentrated in vacuo to furnish 6-chloro-7-methoxy-N-(3-methyl-4-((1-methyl-1H-benzo[d]imidazol-5-yl)oxy)phenyl)pyrido[3,2-d]pyrimidin-4-amine (0.32 g, quant). m/z (APCI-pos) $M^+1$=447.2.

Step B: tert-Butyl 4-(4,4,5,5-tetramethyl-1,3,2-dioxaborolan-2-yl)-3,6-dihydropyridine-1(2H)-carboxylate (28 mg, 90 μmol), 6-chloro-7-methoxy-N-(3-methyl-4-((1-methyl-1H-benzo[d]imidazol-5-yl)oxy)phenyl)pyrido[3,2-d]pyrimidin-4-amine (20 mg, 45 μmol), 1,4-dioxane (0.45 mL), $K_2CO_3$ (19 mg, 0.13 mmol) and $Pd(PPh_3)_4$ (7.8 mg, 6.7 μmol) were charged to a conical glass microwave vessel. The mixture was sparged with argon and then heated to 100° C. for 16 hours. The material was purified directly by column chromatography (0 to 10% MeOH/DCM) to furnish tert-butyl 4-(7-methoxy-4-((3-methyl-4-((1-methyl-1H-benzo[d]imidazol-5-yl)oxy)phenyl)amino)pyrido[3,2-d]pyrimidin-6-yl)-3,6-dihydropyridine-1(2H)-carboxylate (19 mg, 72%). m/z (APCI-pos) $M^+1$=594.4.

Step C: tert-Butyl 4-(7-methoxy-4-((3-methyl-4-((1-methyl-1H-benzo[d]imidazol-5-yl)oxy)phenyl)amino)pyrido[3,2-d]pyrimidin-6-yl)-3,6-dihydropyridine-1(2H)-carboxylate (19 mg, 32 μmol), methanol (0.32 mL), ammonium formate (20 mg, 0.32 mmol) and palladium (10% wt on carbon, 34 mg, 32 μmol) were charged to a vial equipped with a stir bar. The mixture was heated to 70° C. for 1 hour. The material was diluted with DCM and filtered to furnish tert-butyl 4-(7-methoxy-4-((3-methyl-4-((1-methyl-1H-benzo[d]imidazol-5-yl)oxy)phenyl)amino)pyrido[3,2-d]pyrimidin-6-yl)piperidine-1-carboxylate (19 mg, 100%), which was carried on to the subsequent step without further purification. m/z (APCI-pos) $M^+1$=596.3.

Remaining steps were followed according to Example 38, Steps D-E, substituting tert-butyl 4-(7-methoxy-4-((3-methyl-4-((1-methyl-1H-benzo[d]imidazol-5-yl)oxy)phenyl)amino)pyrido[3,2-d]pyrimidin-6-yl)piperidine-1-carboxylate for tert-butyl 5-(4-((4-([1,2,4]triazolo[1,5-a]pyridin-7-yloxy)-3-chloro-2-fluorophenyl)amino)-7-methoxypyrido[3,2-d]pyrimidin-6-yl)hexahydropyrrolo[3,4-b]pyrrole-1(2H)-carboxylate, to furnish 1-(4-(7-methoxy-4-((3-methyl-4-((1-methyl-1H-benzo[d]imidazol-5-yl)oxy)phenyl)amino)pyrido[3,2-d]pyrimidin-6-yl)piperidin-1-yl)prop-2-en-1-one (1.3 mg, 28%). m/z (API-pos) M+1=550.3. 1H NMR (400 MHz, cdcl3) δ 8.77 (s, 1H), 8.67 (s, 1H), 7.84 (s, 1H), 7.75-7.66 (m, 2H), 7.38 (s, 1H), 7.35-7.29 (m, 2H), 7.05 (dd, J=8.8, 2.2 Hz, 1H), 6.94 (d, J=8.5 Hz, 1H), 6.67 (dd, J=16.8, 10.6 Hz, 1H), 6.33 (dd, J=16.8, 2.0 Hz, 1H), 5.72 (dd, J=10.5, 2.0 Hz, 1H), 4.90 (d, J=13.2 Hz, 1H), 4.19 (d, J=13.2 Hz, 1H), 4.00 (s, 3H), 3.84 (s, 3H), 3.58-3.47 (m, 2H), 3.29 (s, 1H), 2.86 (s, 13H), 2.35 (s, 3H), 2.03 (d, J=13.0 Hz, 3H).

Additional compounds of the invention were prepared by modifications of the methods exemplified above and are shown in Table 2 below. The method in Table 2 refers to the Example number procedure above in which the compound in the table was prepared in a similar procedure as the Example, changing the appropriate intermediate or reactant.

TABLE 2

| Example No. (Method) | Structure; IUPAC name | LCMS $M^{+}1$ | $^{1}H$ NMR (ppm); $^{19}F$ NMR (ppm); optical rotation; Chiral HPLC/SFC conditions |
|---|---|---|---|
| 43 (Ex. 25) | 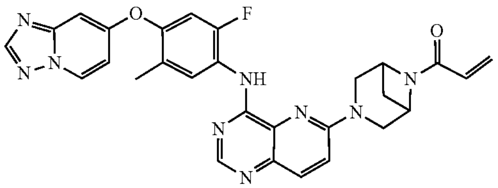 1-(3-(4-((4-([1,2,4]triazolo[1,5-a]pyridin-7-yloxy)-2-fluoro-5-methylphenyl)amino)pyrido[3,2-d]pyrimidin-6-yl)-3,6-diazabicyclo[3.1.1]heptan-6-yl)prop-2-en-1-one | 538.2 | $^{1}H$ NMR (400 MHz, DMSO) δ 9.24 (s, 1H), 8.96 (dd, J = 7.4, 0.7 Hz, 1H), 8.43 (d, J = 20.7 Hz, 2H), 8.32 (s, 1H), 8.00 (d, J = 9.3 Hz, 1H), 7.36 (dd, J = 17.5, 10.2 Hz, 2H), 7.05 (dd, J = 7.5, 2.6 Hz, 1H), 6.92 (dd, J = 2.6, 0.7 Hz, 1H), 6.48 (dd, J = 17.0, 10.3 Hz, 1H), 6.12 (dd, J = 16.9, 2.1 Hz, 1H), 5.69 (dd, J = 10.4, 2.0 Hz, 1H), 4.92 (s, 1H), 4.56 (s, 1H), 3.85 (s, 4H), 2.76 (q, J = 6.9 Hz, 1H), 2.20 (s, 3H), 1.70 (d, J = 8.7 Hz, 1H) |
| 44 (Ex. 25) | 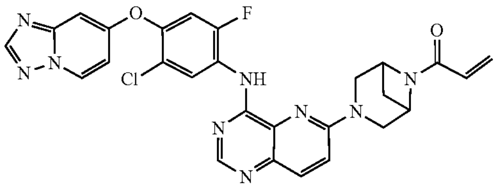 [SMILES: C=CC(=O)N1C2CC1CN(c1ccc3ncnc(Nc4cc(Cl)c(Oc5ccn6ncnc6c5)cc4F)c3n1)C2] 1-(3-(4-((4-([1,2,4]triazolo[1,5-a]pyridin-7-yloxy)-5-chloro-2-fluorophenyl)amino)pyrido[3,2-d]pyrimidin-6-yl)-3,6-diazabicyclo[3.1.1]heptan-6-yl)prop-2-en-1-one | 558.1 | $^{1}H$ NMR (400 MHz, $CDCl_3$) δ 9.30 (d, J = 8.4 Hz, 1H), 9.13 (d, J = 3.4 Hz, 1H), 8.70 (s, 1H), 8.53 (dd, J = 7.0, 1.1 Hz, 1H), 8.26 (s, 1H), 8.04 (d, J = 9.3 Hz, 1H), 7.18 (d, J = 9.3 Hz, 1H), 7.11 (d, J = 10.9 Hz, 1H), 6.95 - 6.87 (m, 2H), 6.37 (dd, J = 16.9, 2.0 Hz, 1H), 6.27 (dd, J = 16.9, 10.0 Hz, 1H), 5.72 (dd, J = 10.0, 2.0 Hz, 1H), 4.75 (s, 2H), 4.37 (d, J = 11.2 Hz, 1H), 3.98 (s, 2H), 3.78 (s, 1H), 2.96 - 2.86 (m, 1H), 1.77 (d, J = 8.9 Hz, 1H) |
| 45 (Ex. 25) | 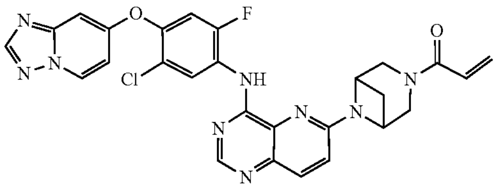 [SMILES: C=CC(=O)N1CC2CC(C1)N2c1ccc2ncnc(Nc3cc(Cl)c(Oc4ccn5ncnc5c4)cc3F)c2n1] 1-(6-(4-((4-([1,2,4]triazolo[1,5-a]pyridin-7-yloxy)-5-chloro-2-fluorophenyl)amino)pyrido[3,2-d]pyrimidin-6-yl)-3,6-diazabicyclo[3.1.1]heptan-3-yl)prop-2-en-1-one | 558.2 | $^{1}H$ NMR (400 MHz, $CDCl_3$) δ 9.25 (d, J = 8.3 Hz, 1H), 9.07 (d, J = 3.5 Hz, 1H), 8.72 (s, 1H), 8.53 (dd, J = 7.3, 0.9 Hz, 1H), 8.26 (s, 1H), 8.01 (d, J = 9.1 Hz, 1H), 7.10 (d, J = 10.9 Hz, 1H), 6.97 (d, J = 9.0 Hz, 1H), 6.96 - 6.87 (m, 2H), 6.46 (dd, J = 16.7, 10.2 Hz, 1H), 6.32 (dd, J = 16.7, 2.1 Hz, 1H), 5.68 (dd, J = 10.2, 2.1 Hz, 1H), 4.69 (d, J = 6.2 Hz, 2H), 4.38 (s, 1H), 4.16 (d, J = 13.9 Hz, 1H), 3.83 (d, J = 14.1 Hz, 1H), 3.77 (d, J = 11.3 Hz, 1H), 2.95 (q, J = 6.8 Hz, 1H), 1.74 (d, J = 8.8 Hz, 1H) |
| 46 (Ex. 25) | 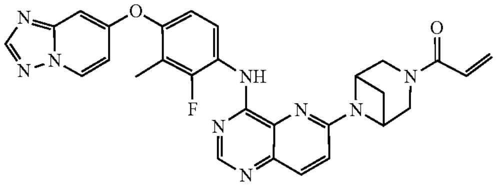 [SMILES: C=CC(=O)N1CC2CC(C1)N2c1ccc2ncnc(Nc3ccc(Oc4ccn5ncnc5c4)c(C)c3F)c2n1] 1-(6-(4-((4-([1,2,4]triazolo[1,5-a]pyridin-7-yloxy)-2-fluoro-3-methylphenyl)amino)pyrido[3,2-d]pyrimidin-6-yl)-3,6-diazabicyclo[3.1.1]heptan-3-yl)prop-2-en-1-one | 538.2 | $^{1}H$ NMR (400 MHz, $CDCl_3$) δ 9.07 (d, J = 3.5 Hz, 1H), 8.79 (t, J = 9.0 Hz, 1H), 8.66 (s, 1H), 8.54 - 8.48 (m, 1H), 8.24 (s, 1H), 7.99 (d, J = 9.0 Hz, 1H), 7.04 - 6.92 (m, 2H), 6.92 - 6.85 (m, 2H), 6.47 (dd, J = 16.7, 10.3 Hz, 1H), 6.32 (dd, J = 16.7, 2.1 Hz, 1H), 5.68 (dd, J = 10.3, 2.1 Hz, 1H), 4.69 (d, J = 6.1 Hz, 2H), 4.42 (d, J = 11.1 Hz, 1H), 4.17 (d, J = 14.0 Hz, 1H), 3.87 - 3.80 (m, 1H), 3.80 - 3.73 (m, 1H), 2.95 (q, J = 6.9 Hz, 1H), 2.20 (d, J = 2.1 Hz, 3H), 1.74 (d, J = 8.8 Hz, 1H) |

TABLE 2-continued

| Example No. (Method) | Structure; IUPAC name | LCMS $M^+1$ | $^1H$ NMR (ppm); $^{19}F$ NMR (ppm); optical rotation; Chiral HPLC/SFC conditions |
|---|---|---|---|
| 47 (Ex. 25) | 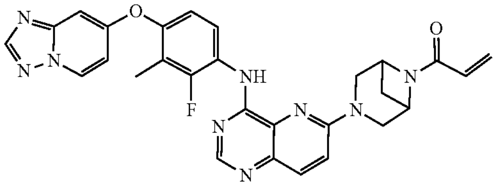 [SMILES: C=CC(=O)N1C2CC1CN(c1ccc3ncnc(Nc4ccc(Oc5ccn6ncnc6c5)c(C)c4F)c3n1)C2] 1-(3-(4-((4-([1,2,4]triazolo[1,5-a]pyridin-7-yloxy)-2-fluoro-3-methylphenyl)amino)pyrido[3,2-d]pyrimidin-6-yl)-3,6-diazabicyclo[3.1.1]heptan-6-yl)prop-2-en-1-one | 538.2 | $^1H$ NMR (400 MHz, $CDCl_3$) δ 9.13 (d, J = 3.6 Hz, 1H), 8.84 (t, J = 9.0 Hz, 1H), 8.65 (s, 1H), 8.51 (dd, J = 7.0, 1.2 Hz, 1H), 8.23 (s, 1H), 8.02 (d, J = 9.3 Hz, 1H), 7.16 (d, J = 9.3 Hz, 1H), 7.00 (dd, J = 9.0, 1.8 Hz, 1H), 6.93 - 6.85 (m, 2H), 6.38 (dd, J = 17.0, 2.1 Hz, 1H), 6.28 (dd, J = 16.9, 9.9 Hz, 1H), 5.72 (dd, J = 9.9, 2.1 Hz, 1H), 4.77 (d, J = 8.2 Hz, 2H), 4.37 (d, J = 11.2 Hz, 1H), 4.00 (s, 2H), 3.81 (s, 1H), 2.96 - 2.86 (m, 1H), 2.21 (d, J = 2.1 Hz, 3H), 1.78 (d, J = 8.8 Hz, 1H) |
| 48 (Ex. 25) | 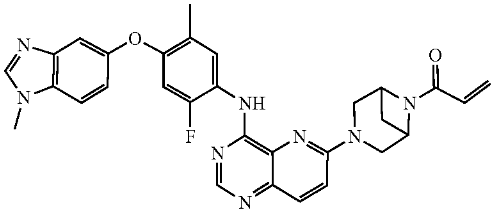 [SMILES: C=CC(=O)N1C2CC1CN(c1ccc3ncnc(Nc4cc(C)c(Oc5ccc6c(c5)ncn6C)cc4F)c3n1)C2] 1-(3-(4-((2-fluoro-5-methyl-4-((1-methyl-1H-benzo[d]imidazol-5-yl)oxy)phenyl)amino)pyrido[3,2-d]pyrimidin-6-yl)-3,6-diazabicyclo[3.1.1]heptan-6-yl)prop-2-en-1-one | 551.2 | $^1H$ NMR (400 MHz, $CDCl_3$) δ 8.89 (d, J = 2.7 Hz, 1H), 8.65 (d, J = 9.2 Hz, 1H), 8.63 (s, 1H), 8.00 (d, J = 9.3 Hz, 1H), 7.87 (s, 1H), 7.38 - 7.33 (m, 2H), 7.13 (d, J = 9.3 Hz, 1H), 7.06 (dd, J = 8.8, 2.2 Hz, 1H), 6.70 (d, J = 11.9 Hz, 1H), 6.35 (dd, J = 16.9, 2.0 Hz, 1H), 6.26 (dd, J = 16.9, 10.0 Hz, 1H), 5.70 (dd, J = 9.9, 2.1 Hz, 1H), 4.73 (t, J = 6.8 Hz, 2H), 4.33 (d, J = 11.2 Hz, 1H), 3.97 (s, 2H), 3.86 (s, 3H), 3.77 (s, 1H), 2.92 - 2.83 (m, 1H), 2.36 (s, 3H), 1.75 (d, J = 8.8 Hz, 1H) |
| 49 (Ex. 26) | 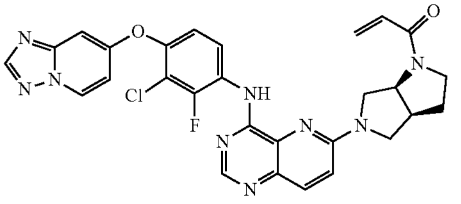 [SMILES: C=CC(=O)N1CC[C@H]2CN(c3ccc4ncnc(Nc5ccc(Oc6ccn7ncnc7c6)c(Cl)c5F)c4n3)C[C@H]21] 1-((3aS,6aS)-5-(4-((4-([1,2,4]triazolo[1,5-a]pyridin-7-yloxy)-3-chloro-2-fluorophenyl)amino)pyrido[3,2-d]pyrimidin-6-yl)hexahydropyrrolo[3,4-b]pyrrol-1(2H)-yl)prop-2-en-1-one | 572.2 | $^1H$ NMR (400 MHz, DMSO-$d_6$) δ 9.31 (s, 1H), 8.99 (d, J = 7.4 Hz, 1H), 8.48 - 8.35 (m, 3H), 7.95 (t, J = 9.6 Hz, 1H), 7.37 (d, J = 9.0 Hz, 1H), 7.28 (t, J = 9.8 Hz, 1H), 7.15 - 7.06 (m, 2H), 6.77 - 6.53 (m, 1H), 6.27 - 6.13 (m, 1H), 5.79 - 5.65 (m, 1H), 4.89 - 4.51 (m, 1H), 3.99 - 3.80 (m, 2H), 3.79 - 3.72 (m, 2H), 3.69 - 3.50 (m, 2H), 3.20 - 3.08 (m, 1H), 2.25 - 2.02 (m, 1H), 2.01 - 1.77 (m, 1H). |
| 50 (Ex. 26) | 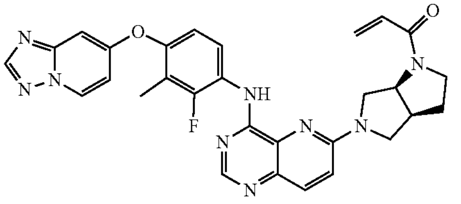 [SMILES: C=CC(=O)N1CC[C@H]2CN(c3ccc4ncnc(Nc5ccc(Oc6ccn7ncnc7c6)c(C)c5F)c4n3)C[C@H]21] 1-((3aS,6aS)-5-(4-((4-([1,2,4]triazolo[1,5-a]pyridin-7-yloxy)-2-fluoro-3-methylphenyl)amino)pyrido[3,2-d]pyrimidin-6-yl)hexahydropyrrolo[3,4-b]pyrrol-1(2H)-yl)prop-2-en-1-one | 552.39 | $^1H$ NMR (400 MHz, DMSO-$d_6$) δ 9.10 (s, 1H), 8.86 (d, J = 7.3 Hz, 1H), 8.52 - 8.41 (m, 2H), 8.32 (s, 1H), 7.94 (d, J = 9.2 Hz, 1H), 7.26 (d, J = 9.3 Hz, 1H), 7.11 (d, J = 9.1 Hz, 1H), 7.00 (d, J = 7.7 Hz, 1H), 6.97 (s, 1H), 6.73 - 6.52 (m, 1H), 6.19 (d, J = 16.5 Hz, 1H), 5.69 (d, J = 10.4 Hz, 1H), 4.83 - 4.59 (m, 1H), 4.08 - 3.96 (m, 1H), 3.88 (t, J = 9.9 Hz, 1H), 3.73 (s, 3H), 3.67 - 3.61 (m, 1H), 3.26 - 3.14 (m, 1H), 2.21 (s, 4H), 1.93 (s, 1H) |

TABLE 2-continued

| Example No. (Method) | Structure; IUPAC name | LCMS $M^+1$ | $^1H$ NMR (ppm); $^{19}F$ NMR (ppm); optical rotation; Chiral HPLC/SFC conditions |
|---|---|---|---|
| 51 (Ex. 26) | 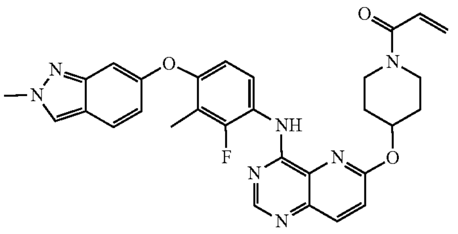 [SMILES: C=CC(=O)N1CCC(Oc2ccc3ncnc(Nc4ccc(Oc5ccc6cn(C)nc6c5)c(C)c4F)c3n2)CC1] 1-(4-((4-((2-fluoro-3-methyl-4-((2-methyl-2H-indazol-6-yl)oxy)phenyl)amino)pyrido[3,2-d]pyrimidin-6-yl)oxy)piperidin-1-yl)prop-2-en-1-one | 554.4 | $^1H$ NMR (400 MHz, DMSO-$d_6$) δ 9.40 (s, 1H), 8.51 (d, J = 2.6 Hz, 1H), 8.33 (s, 1H), 8.12 (d, J = 8.9 Hz, 1H), 7.88 - 7.78 (m, 1H), 7.75 (d, J = 9.5 Hz, 1H), 7.38 (d, J = 8.9 Hz, 1H), 6.96 - 6.80 (m, 4H), 6.12 (dd, J = 2.5, 16.7 Hz, 1H), 5.73 - 5.65 (m, 2H), 4.12 (s, 3H), 4.07 - 3.87 (m, 2H), 3.61 - 3.35 (m, 2H), 2.20 (s, 3H), 2.17 - 2.06 (m, 2H), 1.78 - 1.62 (m, 2H) |
| 52 (Ex. 26) | 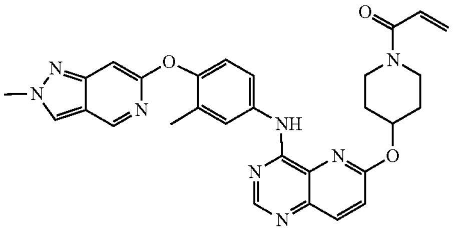 [SMILES: C=CC(=O)N1CCC(Oc2ccc3ncnc(Nc4ccc(Oc5cc6nn(C)cc6cn5)c(C)c4)c3n2)CC1] 1-(4-((4-((3-methyl-4-((2-methyl-2H-pyrazolo[4,3-c]pyridin-6-yl)oxy)phenyl)amino)pyrido[3,2-d]pyrimidin-6-yl)oxy)piperidin-1-yl)prop-2-en-1-one | 537.2 | $^1H$ NMR (400 MHz, Methanol-$d_4$) δ 8.93 (s, 1H), 8.53 (s, 2H), 8.07 (d, J = 9.1 Hz, 1H), 7.86 (s, 1H), 7.80 (d, J = 7.5 Hz, 1H), 7.36 (d, J = 9.1 Hz, 1H), 7.11 (d, J = 8.6 Hz, 1H), 6.84 (dd, J = 10.6, 16.7 Hz, 1H), 6.65 (s, 1H), 6.24 (d, J = 16.6 Hz, 1H), 5.87 (s, 1H), 5.77 (d, J = 9.8 Hz, 1H), 4.22 (s, 3H), 4.09 - 3.87 (m, 2H), 3.81 - 3.68 (m, 2H), 2.29 (s, 3H), 2.26 - 2.10 (m, 2H), 2.04 - 1.83 (m, 2H) |
| 53 (Ex. 26) | 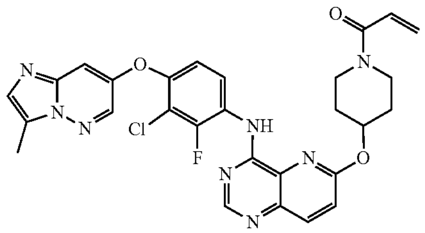 [SMILES: C=CC(=O)N1CCC(Oc2ccc3ncnc(Nc4ccc(Oc5cnn6c(C)cnc6c5)c(Cl)c4F)c3n2)CC1] 1-(4-((4-((3-chloro-2-fluoro-4-((3-methylimidazo[1,2-b]pyridazin-7-yl)oxy)phenyl)amino)pyrido[3,2-d]pyrimidin-6-yl)oxy)piperidin-1-yl)prop-2-en-1-one | 575.2 | $^1H$ NMR (400 MHz, DMSO-$d_6$) δ 12.51 - 12.09 (m, 2H), 9.55 (s, 1H), 8.53 (s, 1H), 8.14 (d, J = 9.0 Hz, 1H), 7.96 (t, J = 8.7 Hz, 1H), 7.43 - 7.32 (m, 2H), 7.01 (s, 1H), 6.86 (dd, J = 10.5, 16.7 Hz, 2H), 6.12 (dd, J = 2.4, 16.7 Hz, 1H), 5.75 - 5.65 (m, 2H), 4.07 - 3.83 (m, 2H), 3.61 - 3.36 (m, 2H), 2.21 (s, 3H), 2.16 - 2.05 (m, 2H), 1.78 - 1.64 (m, 2H) |
| 54 (Ex. 26) | 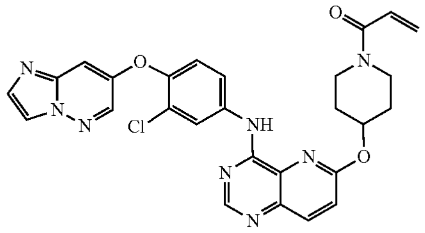 [SMILES: C=CC(=O)N1CCC(Oc2ccc3ncnc(Nc4ccc(Oc5cnn6ccnc6c5)c(Cl)c4)c3n2)CC1] 1-(4-((4-((3-chloro-4-(imidazo[1,2-b]pyridazin-7-yloxy)phenyl)amino)pyrido[3,2-d]pyrimidin-6-yl)oxy)piperidin-1-yl)prop-2-en-1-one | 543.3 | $^1H$ NMR (400 MHz, DMSO-$d_6$) δ 12.36 (s, 1H), 9.61 (s, 1H), 8.64 (s, 1H), 8.36 (d, J = 2.6 Hz, 1H), 8.15 (d, J = 9.0 Hz, 1H), 8.03 (dd, J = 2.6, 8.9 Hz, 1H), 7.50 (d, J = 8.9 Hz, 1H), 7.40 (d, J = 9.0 Hz, 1H), 7.37 - 7.25 (m, 1H), 7.22 - 7.11 (m, 1H), 6.93 - 6.79 (m, 2H), 6.12 (dd, J = 2.5, 16.7 Hz, 1H), 5.93 - 5.85 (m, 1H), 5.69 (dd, J = 2.5, 10.5 Hz, 1H), 4.04 - 3.80 (m, 2H), 3.74 - 3.40 (m, 2H), 2.22 - 1.99 (m, 2H), 1.80 - 1.62 (m, 2H) |

TABLE 2-continued

| Example No. (Method) | Structure; IUPAC name | LCMS $M^{+}1$ | $^{1}H$ NMR (ppm); $^{19}F$ NMR (ppm); optical rotation; Chiral HPLC/SFC conditions |
|---|---|---|---|
| 55 (Ex. 26) | 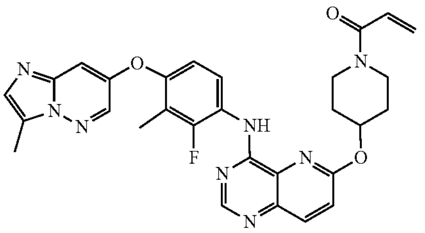 [SMILES: C=CC(=O)N1CCC(Oc2ccc3ncnc(Nc4ccc(Oc5cnn6c(C)cnc6c5)c(C)c4F)c3n2)CC1] 1-(4-((4-((2-fluoro-3-methyl-4-((3-methylimidazo[1,2-b]pyridazin-7-yl)oxy)phenyl)amino)pyrido[3,2-d]pyrimidin-6-yl)oxy)piperidin-1-yl)prop-2-en-1-one | 555.3 | $^{1}H$ NMR (400 MHz, DMSO-$d_6$) δ 12.23 (s, 1H), 9.41 (s, 1H), 8.51 (s, 1H), 8.13 (d, J = 9.1 Hz, 1H), 7.89 (t, J = 8.8 Hz, 1H), 7.38 (d, J = 9.0 Hz, 1H), 7.11 (d, J = 8.5 Hz, 1H), 6.92 - 6.81 (m, 2H), 6.12 (dd, J = 2.4, 16.8 Hz, 1H), 5.73 - 5.65 (m, 2H), 4.07 - 3.85 (m, 2H), 3.57 - 3.51 (m, 2H), 2.30 - 2.02 (m, 9H), 1.80 - 1.62 (m, 2H) |
| 56 (Ex. 26) | 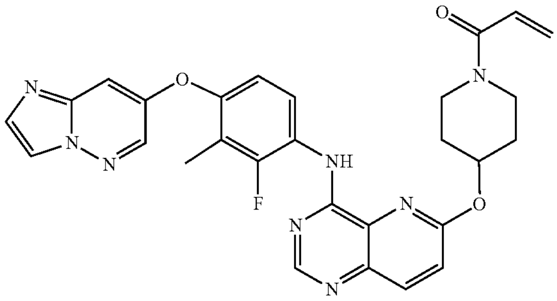 [SMILES: C=CC(=O)N1CCC(Oc2ccc3ncnc(Nc4ccc(Oc5cnn6ccnc6c5)c(C)c4F)c3n2)CC1] 1-(4-((4-((2-fluoro-4-(imidazo[1,2-b]pyridazin-7-yloxy)-3-methylphenyl)amino)pyrido[3,2-d]pyrimidin-6-yl)oxy)piperidin-1-yl)prop-2-en-1-one | 541.32 | $^{1}H$ NMR (400 MHz, Methanol-$d_4$) δ 8.54 (s, 1H), 8.31 (t, J = 8.9 Hz, 1H), 8.08 (d, J = 9.0 Hz, 1H), 7.36 (d, J = 9.1 Hz, 1H), 7.21 (s, 2H), 7.07 (d, J = 8.7 Hz, 1H), 6.89 - 6.77 (m, 2H), 6.22 (dd, J = 2.1, 16.9 Hz, 1H), 5.76 (dd, J = 2.0, 10.7 Hz, 1H), 5.70 - 5.61 (m, 1H), 4.12 - 3.90 (m, 2H), 3.65 (d, J = 8.9 Hz, 2H), 2.30 (s, 3H), 2.20 (s, 2H), 1.91 (s, 2H) |
| 57 (Ex. 26) | 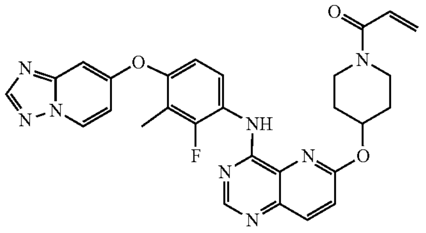 1-(4-((4-((4-([1,2,4]triazolo[1,5-a]pyridin-7-yloxy)-2-fluoro-3-methylphenyl)amino)pyrido[3,2-d]pyrimidin-6-yl)oxy)piperidin-1-yl)prop-2-en-1-one | 541.3 | $^{1}H$ NMR (400 MHz, DMSO-$d_6$) δ 9.41 (s, 1H), 8.98 (d, J = 7.5 Hz, 1H), 8.56 (s, 1H), 8.41 (s, 1H), 8.15 (d, J = 9.0 Hz, 1H), 8.04 (t, J = 8.8 Hz, 1H), 7.40 (d, J = 9.1 Hz, 1H), 7.17 (d, J = 8.9 Hz, 1H), 7.07 (dd, J = 2.7, 7.5 Hz, 1H), 6.96 - 6.81 (m, 2H), 6.13 (dd, J = 2.5, 16.7 Hz, 1H), 5.73 - 5.64 (m, 2H), 4.10 - 3.85 (m, 2H), 3.63 - 3.33 (m, 2H), 2.21 - 2.11 (m, 5H), 1.72 (s, 2H) |
| 58 (Ex. 26) | 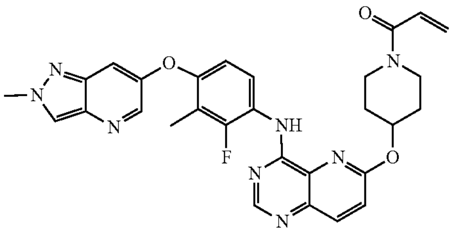 [SMILES: C=CC(=O)N1CCC(Oc2ccc3ncnc(Nc4ccc(Oc5cnc6cn(C)nc6c5)c(C)c4F)c3n2)CC1] 1-(4-((4-((2-fluoro-3-methyl-4-((2-methyl-2H-pyrazolo[4,3-b]pyridin-6-yl)oxy)phenyl)amino)pyrido[3,2-d]pyrimidin-6-yl)oxy)piperidin-1-yl)prop-2-en-1-one | 554.3 | $^{1}H$ NMR (400 MHz, DMSO-$d_6$) δ 9.42 (s, 1H), 8.67 (s, 1H), 8.52 (d, J = 3.0 Hz, 1H), 8.45 (d, J = 2.5 Hz, 1H), 8.13 (d, J = 9.0 Hz, 1H), 7.86 (t, J = 8.9 Hz, 1H), 7.39 (d, J = 9.0 Hz, 1H), 7.34 (d, J = 2.5 Hz, 1H), 6.98 - 6.81 (m, 2H), 6.13 (dd, J = 2.5, 16.7 Hz, 1H), 5.69 (dd, J = 2.6, 10.4 Hz, 2H), 4.17 (s, 3H), 4.09 - 3.86 (m, 2H), 3.60 - 3.48 (m, 1H), 3.46 - 3.35 (m, 1H), 2.23 (d, J = 2.0 Hz, 3H), 2.19 - 2.05 (m, 2H), 1.78 - 1.63 (m, 2H) |

TABLE 2-continued

| Example No. (Method) | Structure; IUPAC name | LCMS $M^+1$ | $^1H$ NMR (ppm); $^{19}F$ NMR (ppm); optical rotation; Chiral HPLC/SFC conditions |
|---|---|---|---|
| 59 (Ex. 28) | 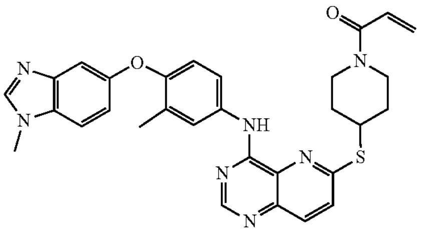 [SMILES: C=CC(=O)N1CCC(Sc2ccc3ncnc(Nc4ccc(Oc5ccc6c(c5)ncn6C)c(C)c4)c3n2)CC1] 1-(4-((4-((3-methyl-4-((1-methyl-1H-benzo[d]imidazol-5-yl)oxy)phenyl)amino)pyrido[3,2-d]pyrimidin-6-yl)thio)piperidin-1-yl)prop-2-en-1-one | 552.2 | $^1H$ NMR (400 MHz, $CDCl_3$) δ 8.72 (s, 1H), 8.71 (s, 1H), 7.95 (d, J = 8.9 Hz, 1H), 7.86 (s, 1H), 7.76 (d, J = 2.6 Hz, 1H), 7.57 - 7.49 (m, 2H), 7.34 (d, J = 8.7 Hz, 1H), 7.30 (d, J = 2.3 Hz, 1H), 7.07 (dd, J = 8.7, 2.3 Hz, 1H), 6.94 (d, J = 8.7 Hz, 1H), 6.61 (dd, J = 16.8, 10.6 Hz, 1H), 6.30 (dd, J = 16.8, 1.9 Hz, 1H), 5.71 (dd, J = 10.6, 1.9 Hz, 1H), 4.34 - 4.22 (m, 2H), 4.01 - 3.93 (m, 1H), 3.85 (s, 3H), 3.52 - 3.40 (m, 2H), 2.36 (s, 3H), 2.30 (ddd, J = 13.2, 6.0, 3.4 Hz, 2H), 1.90 (ddt, J = 14.2, 9.5, 4.7 Hz, 2H) |
| 60 (Ex. 28) | 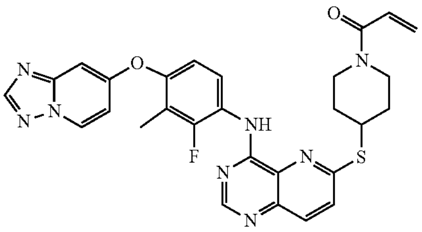 [SMILES: C=CC(=O)N1CCC(Sc2ccc3ncnc(Nc4ccc(Oc5ccn6ncnc6c5)c(C)c4F)c3n2)CC1] 1-(4-((4-((4-([1,2,4]triazolo[1,5-a]pyridin-7-yloxy)-2-fluoro-3-methylphenyl)amino)pyrido[3,2-d]pyrimidin-6-yl)thio)piperidin-1-yl)prop-2-en-1-one | 557.1 | $^1H$ NMR (400 MHz, $CDCl_3$) δ 9.27 (d, J = 3.8 Hz, 1H), 8.91 (t, J = 9.1 Hz, 1H), 8.78 (s, 1H), 8.52 (dd, J = 7.4, 0.7 Hz, 1H), 8.24 (s, 1H), 7.99 (d, J = 8.9 Hz, 1H), 7.54 (d, J = 8.8 Hz, 1H), 7.03 (dd, J = 9.0, 1.8 Hz, 1H), 6.90 (dd, J = 7.4, 2.6 Hz, 1H), 6.86 (dd, J = 2.6, 0.7 Hz, 1H), 6.63 (dd, J = 16.8, 10.6 Hz, 1H), 6.32 (dd, J = 16.8, 1.9 Hz, 1H), 5.72 (dd, J = 10.6, 1.9 Hz, 1H), 4.46 (d, J = 13.5 Hz, 1H), 4.35 - 4.25 (m, 1H), 4.03 (d, J = 13.7 Hz, 1H), 3.50 (t, J = 12.2 Hz, 1H), 3.35 (d, J = 11.9 Hz, 1H), 2.35 (d, J = 13.3 Hz, 2H), 2.22 (d, J = 2.1 Hz, 3H), 1.92 - 1.80 (m, 2H) |
| 61 (Ex. 28) | 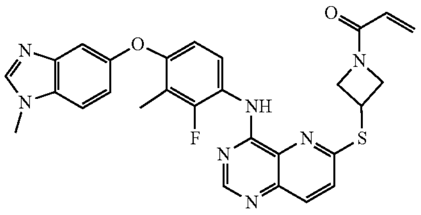 [SMILES: C=CC(=O)N1CC(Sc2ccc3ncnc(Nc4ccc(Oc5ccc6c(c5)ncn6C)c(C)c4F)c3n2)C1] 1-(3-((4-((2-fluoro-3-methyl-4-((1-methyl-1H-benzo[d]imidazol-5-yl)oxy)phenyl)amino)pyrido[3,2-d]pyrimidin-6-yl)thio)azetidin-1-yl)prop-2-en-1-one | 542.1 | $^1H$ NMR (400 MHz, $CDCl_3$) δ 9.06 (d, J = 3.4 Hz, 1H), 8.73 (s, 1H), 8.60 (t, J = 9.2 Hz, 1H), 8.00 (d, J = 8.8 Hz, 1H), 7.86 (s, 1H), 7.56 (d, J = 8.8 Hz, 1H), 7.39 - 7.31 (m, 2H), 7.07 (dd, J = 8.7, 2.3 Hz, 1H), 6.78 (dd, J = 9.1, 1.7 Hz, 1H), 6.39 (dd, J = 17.0, 1.9 Hz, 1H), 6.23 (dd, J = 17.0, 10.3 Hz, 1H), 5.73 (dd, J = 10.3, 1.8 Hz, 1H), 5.01 (t, J = 8.3 Hz, 1H), 4.79 - 4.59 (m, 2H), 4.30 (dd, J = 9.2, 4.9 Hz, 1H), 4.17 (dd, J = 10.6, 5.0 Hz, 1H), 3.86 (s, 3H), 2.31 (d, J = 2.1 Hz, 3H) |
| 62 (Ex. 28) | 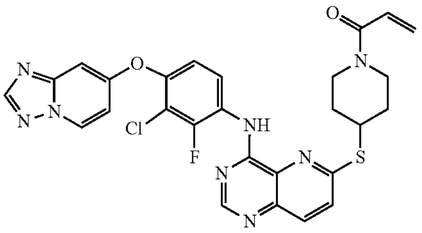 [SMILES: C=CC(=O)N1CCC(Sc2ccc3ncnc(Nc4ccc(Oc5ccn6ncnc6c5)c(Cl)c4F)c3n2)CC1] 1-(4-((4-((4-([1,2,4]triazolo[1,5-a]pyridin-7-yloxy)-3-chloro-2-fluorophenyl)amino)pyrido[3,2-d]pyrimidin-6-yl)thio)piperidin-1-yl)prop-2-en-1-one | 577.1 | $^1H$ NMR (400 MHz, $CDCl_3$) δ 9.28 (d, J = 3.5 Hz, 1H), 9.06 (t, J = 9.0 Hz, 1H), 8.80 (s, 1H), 8.54 (dd, J = 7.4, 0.8 Hz, 1H), 8.26 (s, 1H), 8.01 (d, J = 8.9 Hz, 1H), 7.56 (d, J = 8.9 Hz, 1H), 7.18 (dd, J = 9.2, 2.1 Hz, 1H), 6.93 (dd, J = 7.4, 2.6 Hz, 1H), 6.89 (dd, J = 2.7, 0.8 Hz, 1H), 6.63 (dd, J = 16.8, 10.6 Hz, 1H), 6.32 (dd, J = 16.8, 1.9 Hz, 1H), 5.72 (dd, J = 10.5, 1.9 Hz, 1H), 4.51 - 4.39 (m, 1H), 4.34 - 4.24 (m, 1H), 4.03 (d, J = 13.8 Hz, 1H), 3.51 (t, J = 12.0 Hz, 1H), 3.34 (t, J = 12.1 Hz, 1H), 2.35 (s, 2H), 1.94 - 1.79 (m, 2H) |

TABLE 2-continued

| Example No. (Method) | Structure; IUPAC name | LCMS $M^+1$ | $^1H$ NMR (ppm); $^{19}F$ NMR (ppm); optical rotation; Chiral HPLC/SFC conditions |
|---|---|---|---|
| 63 (Ex. 28) | 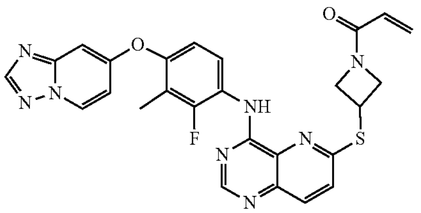 [SMILES: C=CC(=O)N1CC(Sc2ccc3ncnc(Nc4ccc(Oc5ccn6ncnc6c5)c(C)c4F)c3n2)C1] 1-(3-((4-((4-([1,2,4]triazolo[1,5-a]pyridin-7-yloxy)-2-fluoro-3-methylphenyl)amino)pyrido[3,2-d]pyrimidin-6-yl)thio)azetidin-1-yl)prop-2-en-1-one | 529.1 | $^1H$ NMR (400 MHz, $CDCl_3$) δ 9.17 (d, J = 3.4 Hz, 1H), 8.87 (t, J = 9.1 Hz, 1H), 8.79 (s, 1H), 8.52 (dd, J = 7.4, 0.8 Hz, 1H), 8.24 (s, 1H), 8.04 (d, J = 8.8 Hz, 1H), 7.59 (d, J = 8.9 Hz, 1H), 7.03 (dd, J = 9.0, 1.8 Hz, 1H), 6.93 - 6.84 (m, 2H), 6.39 (dd, J = 17.0, 1.8 Hz, 1H), 6.23 (dd, J = 17.0, 10.3 Hz, 1H), 5.73 (dd, J = 10.3, 1.8 Hz, 1H), 5.00 (t, J = 8.4 Hz, 1H), 4.81 - 4.72 (m, 1H), 4.68 (tt, J = 8.0, 5.0 Hz, 1H), 4.30 (dd, J = 9.1, 4.9 Hz, 1H), 4.18 (dd, J = 10.6, 5.0 Hz, 1H), 2.23 (d, J = 2.1 Hz, 3H) |
| 64 (Ex. 28) | 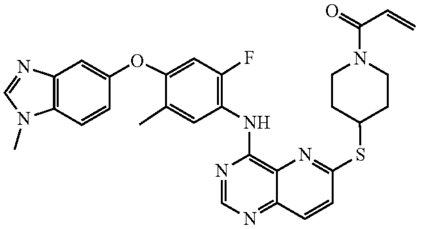 [SMILES: C=CC(=O)N1CCC(Sc2ccc3ncnc(Nc4cc(C)c(Oc5ccc6c(c5)ncn6C)cc4F)c3n2)CC1] 1-(4-((4-((2-fluoro-5-methyl-4-((1-methyl-1H-benzo[d]imidazol-5-yl)oxy)phenyl)amino)pyrido[3,2-d]pyrimidin-6-yl)thio)piperidin-1-yl)prop-2-en-1-one | 570.2 | $^1H$ NMR (400 MHz, $CDCl_3$) δ 9.11 (d, J = 3.3 Hz, 1H), 8.81 - 8.74 (m, 2H), 7.95 (d, J = 8.8 Hz, 1H), 7.87 (s, 1H), 7.50 (d, J = 8.8 Hz, 1H), 7.40 - 7.32 (m, 2H), 7.07 (dd, J = 8.7, 2.3 Hz, 1H), 6.69 (d, J = 12.3 Hz, 1H), 6.59 (dd, J = 16.8, 10.6 Hz, 1H), 6.27 (dd, J = 16.8, 2.0 Hz, 1H), 5.68 (dd, J = 10.6, 2.0 Hz, 1H), 4.49 (d, J = 13.6 Hz, 1H), 4.23 (tt, J = 10.4, 4.0 Hz, 1H), 4.00 (d, J = 13.7 Hz, 1H), 3.86 (s, 3H), 3.40 (t, J = 12.2 Hz, 1H), 3.17 (t, J = 12.3 Hz, 1H), 2.38 (s, 3H), 2.37 - 2.19 (m, 3H), 1.83 - 1.73 (m, 2H) |
| 65 (Ex. 29) | 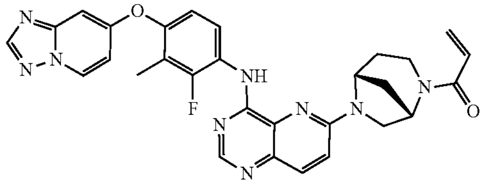 [SMILES: C=CC(=O)N1CC[C@@H]2C[C@H]1CN2c1ccc2ncnc(Nc3ccc(Oc4ccn5ncnc5c4)c(C)c3F)c2n1] 1-((1S,5R)-6-(4-((4-([1,2,4]triazolo[1,5-a]pyridin-7-yloxy)-2-fluoro-3-methylphenyl)amino)pyrido[3,2-d]pyrimidin-6-yl)-2,6-diazabicyclo[3.2.1]octan-2-yl)prop-2-en-1-one | 552.2 | $^1H$ NMR (400 MHz, $CDCl_3$) δ 9.17 (s, 1H), 8.84 (t, J = 9.0 Hz, 1H), 8.62 (s, 1H), 8.50 (dd, J = 7.2, 0.9 Hz, 1H), 8.23 (s, 1H), 7.97 (d, J = 9.2 Hz, 1H), 7.04 (d, J = 9.2 Hz, 1H), 7.00 (dd, J = 9.1, 1.8 Hz, 1H), 6.91 - 6.85 (m, 2H), 6.71 - 6.51 (m, 1H), 6.34 (d, J = 16.9 Hz, 1H), 5.81 - 5.70 (m, 1H), 5.00 - 4.45 (m, 2H), 3.99 - 3.83 (m, 2H), 3.68 (s, 1H), 3.36 - 2.85 (m, 1H), 2.35 - 2.12 (m, 2H), 2.20 (d, J = 2.1 Hz, 3H), 2.05 - 1.81 (m, 2H) |
| 66 (Ex. 29) | 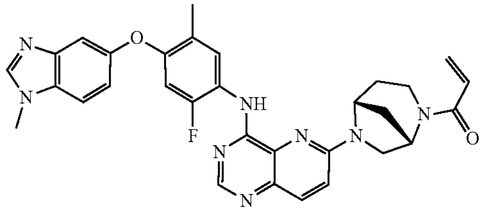 [SMILES: C=CC(=O)N1CC[C@@H]2C[C@H]1CN2c1ccc2ncnc(Nc3cc(C)c(Oc4ccc5c(c4)ncn5C)cc3F)c2n1] 1-((1S,5R)-6-(4-((2-fluoro-5-methyl-4-((1-methyl-1H-benzo[d]imidazol-5-yl)oxy)phenyl)amino)pyrido[3,2-d]pyrimidin-6-yl)-2,6-diazabicyclo[3.2.1]octan-2-yl)prop-2-en-1-one | 565.2 | $^1H$ NMR (400 MHz, $CDCl_3$) δ 8.92 (s, 1H), 8.66 (d, J = 9.2 Hz, 1H), 8.61 (s, 1H), 7.95 (d, J = 9.1 Hz, 1H), 7.86 (s, 1H), 7.35 (dd, J = 5.5, 3.2 Hz, 2H), 7.05 (dd, J = 8.7, 2.2 Hz, 1H), 7.00 (d, J = 9.2 Hz, 1H), 6.70 (d, J = 11.9 Hz, 1H), 6.53 (dd, J = 16.7, 10.5 Hz, 1H), 6.31 (d, J = 16.4 Hz, 1H), 5.78 - 5.68 (m, 1H), 4.95 - 4.42 (m, 2H), 3.86 (s, 3H), 3.78 - 3.53 (m, 2H), 3.32 - 2.86 (m, 2H), 2.36 (s, 3H), 2.31 - 2.07 (m, 2H), 2.01 - 1.77 (m, 2H) |

TABLE 2-continued

| Example No. (Method) | Structure; IUPAC name | LCMS $M^{+}1$ | $^{1}H$ NMR (ppm); $^{19}F$ NMR (ppm); optical rotation; Chiral HPLC/SFC conditions |
|---|---|---|---|
| 67 (Ex. 29) | 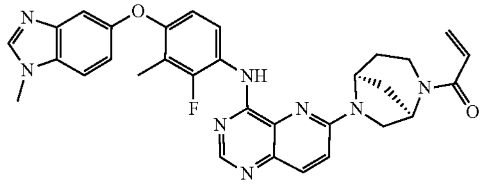 [SMILES: C=CC(=O)N1CC[C@H]2C[C@@H]1CN2c1ccc2ncnc(Nc3ccc(Oc4ccc5c(c4)ncn5C)c(C)c3F)c2n1] 1-((1R,5S)-6-(4-((2-fluoro-3-methyl-4-((1-methyl-1H-benzo[d]imidazol-5-yl)oxy)phenyl)amino)pyrido[3,2-d]pyrimidin-6-yl)-2,6-diazabicyclo[3.2.1]octan-2-yl)prop-2-en-1-one | 565.2 | $^{1}H$ NMR (400 MHz, $CDCl_3$) δ 9.04 (s, 1H), 8.60 - 8.52 (m, 2H), 7.95 (d, J = 9.1 Hz, 1H), 7.85 (s, 1H), 7.36 - 7.30 (m, 2H), 7.06 (dd, J = 8.8, 2.3 Hz, 1H), 7.01 (d, J = 9.1 Hz, 1H), 6.77 (dd, J = 9.0, 1.7 Hz, 1H), 6.70 - 6.51 (m, 1H), 6.35 - 6.29 (m, 1H), 5.79 - 5.70 (m, 1H), 4.93 - 4.45 (m, 2H), 3.93 - 3.85 (m, 2H), 3.85 (s, 3H), 3.75 - 3.58 (m, 1H), 3.35 - 2.86 (m, 1H), 2.28 (d, J = 2.1 Hz, 3H), 2.26 - 2.10 (m, 2H), 2.03 - 1.80 (m, 2H) |
| 68 (Ex. 29) | 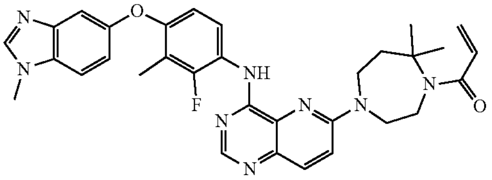 [SMILES: C=CC(=O)N1CCN(c2ccc3ncnc(Nc4ccc(Oc5ccc6c(c5)ncn6C)c(C)c4F)c3n2)CCC1(C)C] 1-(4-(4-((2-fluoro-3-methyl-4-((1-methyl-1H-benzo[d]imidazol-5-yl)oxy)phenyl)amino)pyrido[3,2-d]pyrimidin-6-yl)-7,7-dimethyl-1,4-diazepan-1-yl)prop-2-en-1-one | 581.2 | $^{1}H$ NMR (400 MHz, $CDCl_3$) δ 8.95 (d, J = 3.3 Hz, 1H), 8.59 - 8.52 (m, 2H), 7.94 (d, J = 9.3 Hz, 1H), 7.86 (s, 1H), 7.34 (d, J = 7.0 Hz, 1H), 7.33 (s, 1H), 7.24 (d, J = 9.4 Hz, 1H), 7.06 (dd, J = 8.6, 2.4 Hz, 1H), 6.78 (dd, J = 9.0, 1.7 Hz, 1H), 6.54 (dd, J = 16.8, 10.4 Hz, 1H), 6.13 (dd, J = 16.8, 1.8 Hz, 1H), 5.59 (dd, J = 10.4, 1.8 Hz, 1H), 4.04 (t, J = 5.0 Hz, 2H), 3.89 - 3.83 (obs m, 2H), 3.85 (s, 3H), 3.76 (t, J = 5.0 Hz, 2H), 2.29 (d, J = 2.1 Hz, 3H), 2.12 - 2.05 (m, 2H), 1.55 (s, 6H) |
| 69 (Ex. 29) | 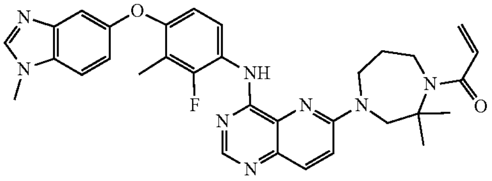 [SMILES: C=CC(=O)N1CCCN(c2ccc3ncnc(Nc4ccc(Oc5ccc6c(c5)ncn6C)c(C)c4F)c3n2)CC1(C)C] 1-(4-(4-((2-fluoro-3-methyl-4-((1-methyl-1H-benzo[d]imidazol-5-yl)oxy)phenyl)amino)pyrido[3,2-d]pyrimidin-6-yl)-2,2-dimethyl-1,4-diazepan-1-yl)prop-2-en-1-one | 581.2 | $^{1}H$ NMR (400 MHz, $CDCl_3$) δ 9.21 (s, 1H), 8.61 (s, 1H), 8.57 (t, J = 9.1 Hz, 1H), 8.13 (d, J = 9.3 Hz, 1H), 8.08 (s, 1H), 7.39 (d, J = 8.8 Hz, 1H), 7.35 - 7.28 (m, 2H), 7.11 (dd, J = 8.8, 2.3 Hz, 1H), 6.78 (dd, J = 9.0, 1.7 Hz, 1H), 6.51 (dd, J = 16.8, 10.4 Hz, 1H), 6.23 (dd, J = 16.8, 1.8 Hz, 1H), 5.64 (dd, J = 10.4, 1.8 Hz, 1H), 4.03 (s, 2H), 3.90 (s, 3H), 3.83 (t, J = 5.9 Hz, 2H), 3.69 (t, J = 5.7 Hz, 2H), 2.29 (d, J = 2.1 Hz, 3H), 2.14 - 2.02 (m, 2H), 1.61 (s, 6H) |
| 70 (Ex. 30) | 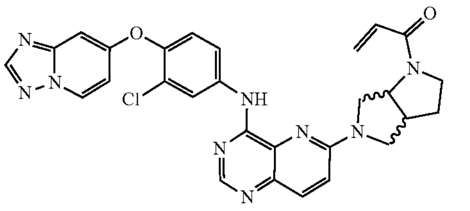 [SMILES: C=CC(=O)N1CCC2CN(c3ccc4ncnc(Nc5ccc(Oc6ccn7ncnc7c6)c(Cl)c5)c4n3)CC21] 1-(5-(4-((4-([1,2,4]triazolo[1,5-a]pyridin-7-yloxy)-3-chlorophenyl)amino)pyrido[3,2-d]pyrimidin-6-yl)hexahydropyrrolo[3,4-b]pyrrol-1(2H)-yl)prop-2-en-1-one | 554.2 | $^{1}H$ NMR (400 MHz, $CDCl_3$) δ 8.81 (m, 1H), 8.63 (m, 1H), 8.51 (m, 1H), 8.29 (s, 1H), 8.24 (s, 1H), 7.97 (m, 1H), 7.89 (m, 1H), 7.24 (s, 1H), 7.03 (d, J = 9.3 Hz, 1H), 6.91 (m, 2H), 6.47 (m, 2H), 5.75 (dd, J = 8.9, 3.3 Hz, 1H), 4.79 (m, 1H), 3.86 (m, 6H), 3.20 (m, 1H), 2.26 (m, 1H), 2.03 (s, 1H) |
| 71 (Ex. 30) | 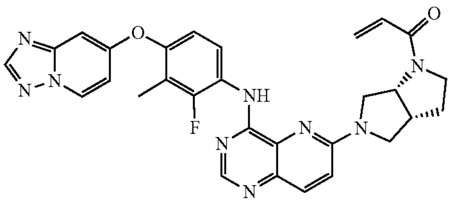 [SMILES: C=CC(=O)N1CC[C@@H]2CN(c3ccc4ncnc(Nc5ccc(Oc6ccn7ncnc7c6)c(C)c5F)c4n3)C[C@@H]21] | 552.3 | $^{1}H$ NMR (400 MHz, $CDCl_3$) δ 9.12 (d, J = 3.5 Hz, 1H), 8.80 (m, 1H), 8.62 (d, J = 8.7 Hz, 1H), 8.50 (m, 1H), 8.23 (s, 1H), 7.96 (m, 1H), 7.01 (m, 2H), 6.89 (m, 2H), 6.47 (m, 2H), 5.78 (m, 1H), 4.79 (m, 1H), 3.87 (m, 6H), 3.21 (m, 1H), 2.27 (m, 1H), 2.20 (d, J = 2.1 Hz, 3H), 2.08 (m, 1H) |

TABLE 2-continued

| Example No. (Method) | Structure; IUPAC name | LCMS $M^+1$ | $^1H$ NMR (ppm); $^{19}F$ NMR (ppm); optical rotation; Chiral HPLC/SFC conditions |
|---|---|---|---|
| | 1-((3aR,6aR)-5-(4-((4-([1,2,4]triazolo[1,5-a]pyridin-7-yloxy)-2-fluoro-3-methylphenyl)amino)pyrido[3,2-d]pyrimidin-6-yl)hexahydropyrrolo[3,4-b]pyrrol-1(2H)-yl)prop-2-en-1-one | | |
| 72 (Ex. 30) | 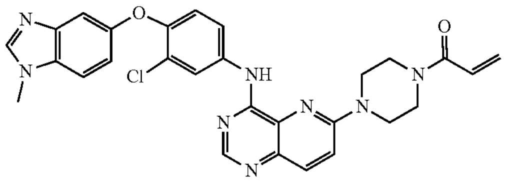 [SMILES: C=CC(=O)N1CCN(c2ccc3ncnc(Nc4ccc(Oc5ccc6c(c5)ncn6C)c(Cl)c4)c3n2)CC1] 1-(4-(4-((3-chloro-4-((1-methyl-1H-benzo[d]imidazol-5-yl)oxy)phenyl)amino)pyrido[3,2-d]pyrimidin-6-yl)piperazin-1-yl)prop-2-en-1-one | 541.3 | $^1H$ NMR (400 MHz, $CDCl_3$) δ 8.62 (s, 1H), 8.60 (s, 1H), 8.13 (d, J = 2.6 Hz, 1H), 8.00 (d, J = 9.3 Hz, 1H), 7.86 (s, 1H), 7.69 (dd, J = 8.9, 2.6 Hz, 1H), 7.37 (m, 2H), 7.28 (d, J = 9.3 Hz, 1H), 7.11 (dd, J = 8.7 Hz, 1H), 7.02 (m, J = 16.8, 10.6 Hz, 1H), 6.64 (dd, 16.8, 10.6 Hz, 1H), 6.38 (dd, J = 16.8, 1.9 Hz, 1H), 5.79 (dd, J = 10.5, 1.9 Hz, 1H), 3.91 (s, 2H), 3.86 (m, 3H), 3.82 (s, 6H) |
| 73 (Ex. 31) | 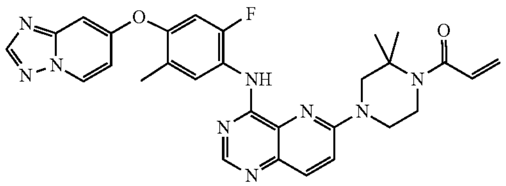 [SMILES: C=CC(=O)N1CCN(c2ccc3ncnc(Nc4cc(C)c(Oc5ccn6ncnc6c5)cc4F)c3n2)CC1(C)C] 1-(4-(4-((4-([1,2,4]triazolo[1,5-a]pyridin-7-yloxy)-2-fluoro-5-methylphenyl)amino)pyrido[3,2-d]pyrimidin-6-yl)-2,2-dimethylpiperazin-1-yl)prop-2-en-1-one | 554.3 | $^1H$ NMR (400 MHz, $CDCl_3$) δ 9.06 (d, J = 3.3 Hz, 1H), 8.89 (d, J = 9.1 Hz, 1H), 8.66 (s, 1H), 8.51 (m, 1H), 8.24 (s, 1H), 8.01 (d, J = 9.3 Hz, 1H), 7.16 (d, J = 9.3 Hz, 1H), 6.95 (d, J = 11.1 Hz, 1H), 6.88 (m, 2H), 6.57 (dd, J = 16.8, 10.6 Hz, 1H), 6.25 (dd, J = 16.8, 1.8 Hz, 1H), 5.68 (dd, J = 10.6, 1.8 Hz, 1H), 4.00 (t, J = 5.7 Hz, 2H), 3.91 (s, 2H), 3.84 (t, J = 5.7 Hz, 2H), 2.27 (d, 3H), 1.61 (s, 6H) |
| 74 (Ex. 31) | 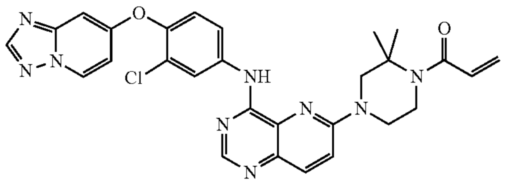 [SMILES: C=CC(=O)N1CCN(c2ccc3ncnc(Nc4ccc(Oc5ccn6ncnc6c5)c(Cl)c4)c3n2)CC1(C)C] 1-(4-(4-((4-([1,2,4]triazolo[1,5-a]pyridin-7-yloxy)-3-chlorophenyl)amino)pyrido[3,2-d]pyrimidin-6-yl)-2,2-dimethylpiperazin-1-yl)prop-2-en-1-one | 566.3 | $^1H$ NMR (400 MHz, $CDCl_3$) δ 8.74 (s, 1H), 8.65 (s, 1H), 8.51 (dd, J = 7.4, 0.8 Hz, 1H), 8.26 (d, J = 2.6 Hz, 1H), 8.24 (s, 1H), 8.01 (d, J = 9.3 Hz, 1H), 7.88 (dd, J = 8.8, 2.6 Hz, 1H), 7.18 (d, J = 9.4 Hz, 1H), 6.90 (m, 2H), 6.58 (dd, J = 16.8, 10.6 Hz, 1H), 6.26 (dd, 16.8, 10.6 Hz, 1H), 5.69 (dd, J = 10.6, 1.8 Hz, 1H), 5.69 (dd, J = 10.6, 1.8 Hz, 1H), 4.01 (t, J = 5.7 Hz, 2H), 3.87 (m, 4H), 1.63 (s, 6H) |
| 75 (Ex. 31) | 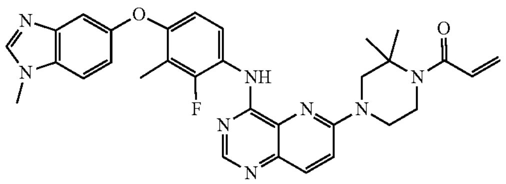 [SMILES: C=CC(=O)N1CCN(c2ccc3ncnc(Nc4ccc(Oc5ccc6c(c5)ncn6C)c(C)c4F)c3n2)CC1(C)C] 1-(4-(4-((2-fluoro-3-methyl-4-((1-methyl-1H-benzo[d]imidazol-5-yl)oxy)phenyl)amino)pyrido[3,2-d]pyrimidin-6-yl)-2,2-dimethylpiperazin-1-yl)prop-2-en-1-one | 567.3 | $^1H$ NMR (400 MHz, $CDCl_3$) δ 8.99 (d, J = 3.3 Hz, 1H), 8.57 (m, 2H), 7.98 (d, J = 9.3 Hz, 1H), 7.85 (s, 1H), 7.33 (m, 2H), 7.13 (d, J = 9.3 Hz, 1H), 7.06 (dd, J = 8.8, 2.2 Hz, 1H), 6.78 (m, 1H), 6.58 (dd, J = 16.8, 10.5 Hz, 1H), 6.26 (dd, J = 16.8, 1.8 Hz, 1H), 5.69 (dd, 10.6, 1.8 Hz, 1H), 4.00 (t, J = 5.7 Hz, 2H), 3.92 (s, 2H), 3.85 (m, 5H), 2.29 (d, J = 2.1 Hz, 3H), 1.62 (s, 6H) |

TABLE 2-continued

| Example No. (Method) | Structure; IUPAC name | LCMS $M^+1$ | $^1H$ NMR (ppm); $^{19}F$ NMR (ppm); optical rotation; Chiral HPLC/SFC conditions |
|---|---|---|---|
| 76 (Ex. 31) | 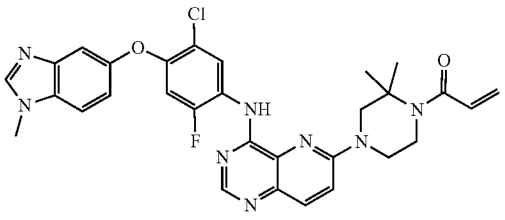 [SMILES: C=CC(=O)N1CCN(c2ccc3ncnc(Nc4cc(Cl)c(Oc5ccc6c(c5)ncn6C)cc4F)c3n2)CC1(C)C] 1-(4-(4-((5-chloro-2-fluoro-4-((1-methyl-1H-benzo[d]imidazol-5-yl)oxy)phenyl)amino)pyrido[3,2-d]pyrimidin-6-yl)-2,2-dimethylpiperazin-1-yl)prop-2-en-1-one | 587.3 | $^1H$ NMR (400 MHz, $CDCl_3$) δ 9.09 (d, J = 8.5 Hz, 1H), 8.94 (d, J = 3.2 Hz, 1H), 8.66 (s, 1H), 8.00 (d, J = 9.3 Hz, 1H), 7.89 (s, 1H), 7.40 (m, 2H), 7.12 (m, 2H), 6.79 (d, J = 11.8 Hz, 1H), 6.56 (dd, J = 16.8, 10.6 Hz, 1H), 6.24 (dd, J = 16.8, 1.8 Hz, 1H), 5.67 (dd, J = 10.6, 1.8 Hz, 1H), 3.98 (t, J = 5.7 Hz, 2H) 3.88 (s, 2H), 3.87 (s, 3H), 3.81 (t, J = 3.8 Hz, 2H), 1.59 (s, 6H) |
| 77 (Ex. 31) | 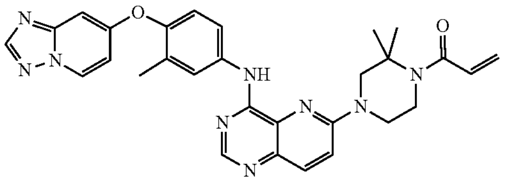 [SMILES: C=CC(=O)N1CCN(c2ccc3ncnc(Nc4ccc(Oc5ccn6ncnc6c5)c(C)c4)c3n2)CC1(C)C] 1-(4-(4-((4-([1,2,4]triazolo[1,5-a]pyridin-7-yloxy)-3-methylphenyl)amino)pyrido[3,2-d]pyrimidin-6-yl)-2,2-dimethylpiperazin-1-yl)prop-2-en-1-one | 536.2 | $^1H$ NMR (400 MHz, $CDCl_3$) δ 8.69 (s, 1H), 8.62 (s, 1H), 8.49 (d, J = 7.5 Hz, 1H), 8.22 (s, 1H), 8.00 (d, J = 9.3 Hz, 1H), 7.86 (d, J = 2.7 Hz, 1H), 7.81 (dd, J = 8.62, 2.7 Hz, 1H), 7.14 (dd, J = 17.2, 9.0 Hz, 1H), 6.87 (m, 2H), 6.58 (dd, J = 16.8, 10.6 Hz, 1H), 6.26 (16.8, 1.8 Hz, 1H), 5.69 (dd, J = 10.6, 1.8 Hz, 1H), 4.01 (m, 2H) 3.89 (s, 3H), 3.86 (m, 2H), 2.27 (s, 3H), 1.63 (s, 6H) |
| 78 (Ex. 30) | 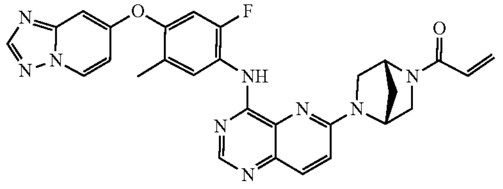 [SMILES: C=CC(=O)N1C[C@H]2C[C@@H]1CN2c1ccc2ncnc(Nc3cc(C)c(Oc4ccn5ncnc5c4)cc3F)c2n1] 1-((1R,4R)-5-(4-((4-([1,2,4]triazolo[1,5-a]pyridin-7-yloxy)-2-fluoro-5-methylphenyl)amino)pyrido[3,2-d]pyrimidin-6-yl)-2,5-diazabicyclo[2.2.1]heptan-2-yl)prop-2-en-1-one | 538.3 | $^1H$ NMR (400 MHz, $CDCl_3$) δ 9.05 (m, 1H), 8.88 (dd, J = 9.0, 4.2 Hz, 1H), 8.65 (s, 1H), 8.51 (m, 1H), 8.24 (s, 1H), 7.92 (dd, J = 9.2, 1.2 Hz, 1H), 6.96 (m, 2H), 6.88 (m, 2H), 6.41 (m, 1H), 6.28 (dd, J = 16.8, 10.2 Hz, 1H), 5.69 (dd, J = 10.3, 1.9 Hz, 1H), 3.76 (m, 4H) 3.64 (m, 1H), 2.27 (s, 3H), 2.11 (m, 3H) |
| 79 (Ex. 30) | 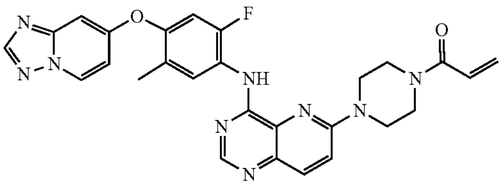 [SMILES: C=CC(=O)N1CCN(c2ccc3ncnc(Nc4cc(C)c(Oc5ccn6ncnc6c5)cc4F)c3n2)CC1] 1-(4-(4-((4-([1,2,4]triazolo[1,5-a]pyridin-7-yloxy)-2-fluoro-5-methylphenyl)amino)pyrido[3,2-d]pyrimidin-6-yl)piperazin-1-yl)prop-2-en-1-one | 526.2 | $^1H$ NMR (400 MHz, $CDCl_3$) δ 9.01 (d, J = 3.3 Hz, 1H), 8.88 (d, J = 9.0 Hz, 1H), 8.68 (s, 1H), 8.51 (m, 1H), 8.24 (s, 1H), 8.02 (d, J = 9.4 Hz, 1H), 7.31 (d, J = 9.4 Hz, 1H), 6.96 (d, J = 11.1 Hz, 1H), 6.88 (m, 2H), 6.64 (dd, J = 16.8, 10.5 Hz, 1H), 6.38 (dd, J = 16.8, 1.8 Hz, 1H), 5.79 (dd, J = 10.5, 1.8 Hz, 1H), 3.86 (m, 8H) 2.27 (s, 3H) |

TABLE 2-continued

| Example No. (Method) | Structure; IUPAC name | LCMS $M^{+}1$ | $^{1}H$ NMR (ppm); $^{19}F$ NMR (ppm); optical rotation; Chiral HPLC/SFC conditions |
|---|---|---|---|
| 80 (Ex. 30) | 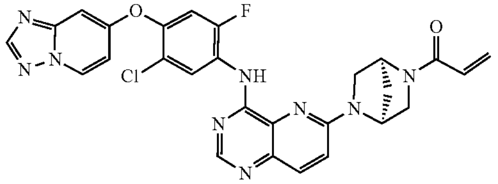 [SMILES: C=CC(=O)N1C[C@@H]2C[C@H]1CN2c1ccc2ncnc(Nc3cc(Cl)c(Oc4ccn5ncnc5c4)cc3F)c2n1] 1-((1S,4S)-5-(4-((4-([1,2,4]triazolo[1,5-a]pyridin-7-yloxy)-5-chloro-2-fluorophenyl)amino)pyrido[3,2-d]pyrimidin-6-yl)-2,5-diazabicyclo[2.2.1]heptan-2-yl)prop-2-en-1-one | 558.1 | $^{1}H$ NMR (400 MHz, $CDCl_3$) δ 9.29 (d, J = 8.4 Hz, 1H), 9.10 (d, J = 3.5 Hz, 1H), 8.69 (m, 1H), 8.53 (m, 1H), 8.26 (s, 1H), 7.99 (d, J = 8.2 Hz, 1H), 7.11 (m, 1H), 7.00 (m, 1H), 6.91 (m, 2H), 6.39 (dd, J = 16.8, 1.8 Hz, 1H), 6.41 (dd, J = 16.8, 2.0 Hz, 1H), 6.28 (dd, J = 16.8, 10.2 Hz, 1H), 5.73 (m, 1H), 3.77 (m, 4H) 2.14 (m, 3H) |
| 81 (Ex. 30) | 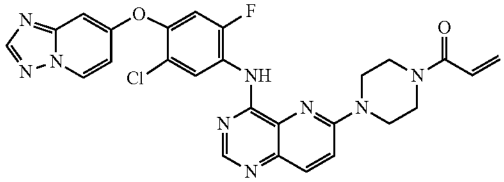 1-(4-(4-((4-([1,2,4]triazolo[1,5-a]pyridin-7-yloxy)-5-chloro-2-fluorophenyl)amino)pyrido[3,2-d]pyrimidin-6-yl)piperazin-1-yl)prop-2-en-1-one | 546.2 | $^{1}H$ NMR (400 MHz, $CDCl_3$) δ 9.29 (d, J = 8.4 Hz, 1H), 9.08 (m, 1H), 8.72 (s, 1H), 8.54 (m, 1H), 8.26 (s, 1H), 8.04 (d, J = 9.3 Hz, 1H), 7.32 (m, 1H), 7.12 (d, J = 10.9, 1H), 6.91 (m, 1H), 6.64 (dd, J = 16.8, 10.5 Hz, 1H), 6.39 (dd, J = 16.8, 1.8 Hz, 1H), 5.79 (dd, J = 10.5, 1.8 Hz, 1H), 3.82 (m, 8H) |
| 82 (Ex. 31) | 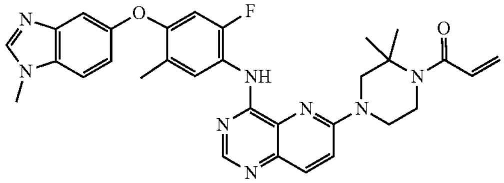 [SMILES: C=CC(=O)N1CCN(c2ccc3ncnc(Nc4cc(C)c(Oc5ccc6c(c5)ncn6C)cc4F)c3n2)CC1(C)C] 1-(4-(4-((2-fluoro-5-methyl-4-((1-methyl-1H-benzo[d]imidazol-5-yl)oxy)phenyl)amino)pyrido[3,2-d]pyrimidin-6-yl)-2,2-dimethylpiperazin-1-yl)prop-2-en-1-one | 567.3 | $^{1}H$ NMR (400 MHz, $CDCl_3$) δ 8.89 (d, J = 2.9 Hz, 1H), 8.63 (m, 2H), 7.98 (d, J = 9.3 Hz, 1H), 7.86 (s, 1H), 7.35 (m, 2H), 7.13 (d, J = 9.3 Hz, 1H) 7.05 (dd, J = 8.8, 2.2 Hz, 1H), 6.71 (d, J = 11.9 Hz, 1H), 6.56 (dd, J = 16.8, 10.6 Hz, 1H), 6.24 (dd, J = 16.8, 1.8 Hz, 1H), 5.67 (dd, J = 10.6, 1.8 Hz, 1H), 3.98 (t, J = 5.7 Hz, 2H), 3.87 (m, 5H), 3.81 (t, J = 5.7 Hz, 2H), 2.36 (s, 3H), 1.59 (s, 6H) |
| 83 (Ex. 30) | 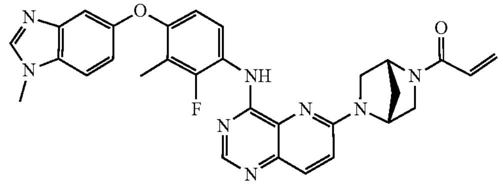 [SMILES: C=CC(=O)N1C[C@H]2C[C@@H]1CN2c1ccc2ncnc(Nc3ccc(Oc4ccc5c(c4)ncn5C)c(C)c3F)c2n1] 1-((1R,4R)-5-(4-((2-fluoro-3-methyl-4-((1-methyl-1H-benzo[d]imidazol-5-yl)oxy)phenyl)amino)pyrido[3,2-d]pyrimidin-6-yl)-2,5-diazabicyclo[2.2.1]heptan-2-yl)prop-2-en-1-one | 551.3 | $^{1}H$ NMR (400 MHz, DMSO-$d_6$) δ 9.24 (s, 1H), 8.35 (d, J = 2.3 Hz, 1H), 8.20 (s, 1H), 7.91 (m, 2H), 7.60 (d, J = 8.7 Hz, 1H), 7.19 (d, J = 2.3 Hz, 1H), 7.04 (dd, J = 8.5, 2.1 Hz, 1H), 6.82 (dd, J = 16.7, 10.3 Hz, 1H), 6.73 (d, J = 6.7 Hz, 1H), 6.42 (dd, J = 16.8, 10.4 Hz, 1H), 6.15 (m, 1H), 5.67 (ddd, J = 22.3, 10.1, 1.9 Hz, 1H), 5.01 (s, J = 1.1 Hz, 1H), 3.85 (s, 3H), 3.72 (m, 2H), 3.53 (m, 3H), 2.23 (d, J = 2.0 Hz, 3H), 2.06 (m, 2H) |

TABLE 2-continued

| Example No. (Method) | Structure; IUPAC name | LCMS $M^+1$ | $^1H$ NMR (ppm); $^{19}F$ NMR (ppm); optical rotation; Chiral HPLC/SFC conditions |
|---|---|---|---|
| 84 (Ex. 30) | 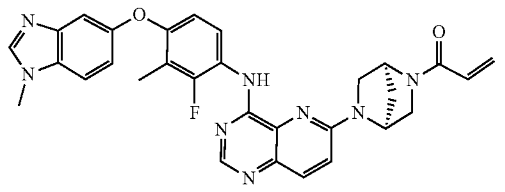 [SMILES: C=CC(=O)N1C[C@@H]2C[C@H]1CN2c1ccc2ncnc(Nc3ccc(Oc4ccc5c(c4)ncn5C)c(C)c3F)c2n1] 1-((1S,4S)-5-(4-((2-fluoro-3-methyl-4-((1-methyl-1H-benzo[d]imidazol-5-yl)oxy)phenyl)amino)pyrido[3,2-d]pyrimidin-6-yl)-2,5-diazabicyclo[2.2.1]heptan-2-yl)prop-2-en-1-one | 551.3 | $^1H$ NMR (400 MHz, DMSO-$d_6$) δ 9.24 (s, 1H), 8.35 (d, J = 2.3 Hz, 1H), 8.20 (s, 1H), 7.91 (m, 2H), 7.60 (d, J = 8.7 Hz, 1H), 7.19 (d, J = 2.3 Hz, 1H), 7.04 (dd, J = 8.5, 2.1 Hz, 1H), 6.82 (dd, J = 16.7, 10.3 Hz, 1H), 6.73 (d, J = 6.7 Hz, 1H), 6.42 (dd, J = 16.8, 10.4 Hz, 1H), 6.15 (m, 1H), 5.67 (ddd, J = 22.3, 10.1, 1.9 Hz, 1H), 5.01 (s, J = 1.1 Hz, 1H), 3.85 (s, 3H), 3.72 (m, 2H), 3.53 (m, 3H), 2.23 (d, J = 2.0 Hz, 3H), 2.06 (m, 2H) |
| 85 (Ex. 30) | 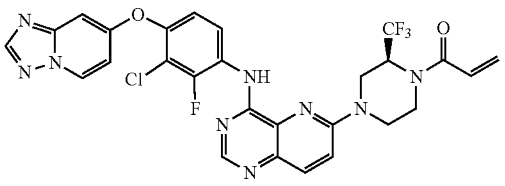 [SMILES: C=CC(=O)N1CCN(c2ccc3ncnc(Nc4ccc(Oc5ccn6ncnc6c5)c(Cl)c4F)c3n2)C[C@H]1C(F)(F)F] (S)-1-(4-(4-((4-([1,2,4]triazolo[1,5-a]pyridin-7-yloxy)-3-chloro-2-fluorophenyl)amino)pyrido[3,2-d]pyrimidin-6-yl)-2-(trifluoromethyl)piperazin-1-yl)prop-2-en-1-one | 614.1 | $^1H$ NMR (400 MHz, $CDCl_3$) δ 9.08 (d, J = 3.4 Hz, 1H), 9.00 (t, J = 8.9 Hz, 1H), 8.69 (s, 1H), 8.53 (m, 1H), 8.25 (s, 1H), 8.06 (d, J = 9.3 Hz, 1H), 7.32 (d, J = 9.3 Hz, 1H), 7.16 (dd, J = 9.2, 2.1 Hz, 1H), 6.92 (m, 1H), 6.63 (m, 1H), 6.45 (dd, J = 16.8, 1.7 Hz, 1H), 5.88 (d, J = 10.5 Hz, 1H), 5.53 (m, 1H), 4.64 (m, 3H), 3.57 (m, 4H) |
| 86 (Ex. 30) | 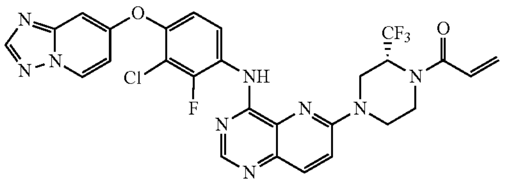 [SMILES: C=CC(=O)N1CCN(c2ccc3ncnc(Nc4ccc(Oc5ccn6ncnc6c5)c(Cl)c4F)c3n2)C[C@@H]1C(F)(F)F] (R)-1-(4-(4-((4-([1,2,4]triazolo[1,5-a]pyridin-7-yloxy)-3-chloro-2-fluorophenyl)amino)pyrido[3,2-d]pyrimidin-6-yl)-2-(trifluoromethyl)piperazin-1-yl)prop-2-en-1-one | 614.1 | $^1H$ NMR (400 MHz, $CDCl_3$) δ 9.08 (d, J = 3.4 Hz, 1H), 9.00 (t, J = 8.9 Hz, 1H), 8.69 (s, 1H), 8.53 (m, 1H), 8.25 (s, 1H), 8.06 (d, J = 9.3 Hz, 1H), 7.32 (d, J = 9.3 Hz, 1H), 7.16 (dd, J = 9.2, 2.1 Hz, 1H), 6.92 (m, 1H), 6.63 (m, 1H), 6.45 (dd, J = 16.8, 1.7 Hz, 1H), 5.88 (d, J = 10.5Hz, 1H), 5.53 (m, 1H), 4.64 (m, 3H), 3.57 (m, 4H) |
| 87 (Ex. 31) | 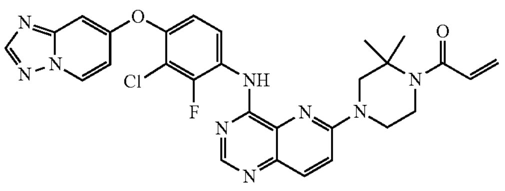 [SMILES: C=CC(=O)N1CCN(c2ccc3ncnc(Nc4ccc(Oc5ccn6ncnc6c5)c(Cl)c4F)c3n2)CC1(C)C] 1-(4-(4-((4-([1,2,4]triazolo[1,5-a]pyridin-7-yloxy)-3-chloro-2-fluorophenyl)amino)pyrido[3,2-d]pyrimidin-6-yl)-2,2-dimethylpiperazin-1-yl)prop-2-en-1-one | 574.2 | $^1H$ NMR (400 MHz, $CDCl_3$) δ 9.15 (d, J = 3.5 Hz, 1H), 9.01 (t, J = 8.9 Hz, 1H), 8.66 (s, 1H), 8.53 (m, 1H), 8.25 (s, 1H), 8.03 (d, J = 9.3 Hz, 1H), 7.17 (m, 2H), 6.92 (m, 2H), 6.58 (dd, J = 16.8, 10.6 Hz, 1H), 6.26 (dd, J = 16.8, 1.8 Hz, 1H), 5.70 (dd, J = 10.6, 1.8 Hz, 1H), 3.93 (m, 6H), 1.62 (s, 6H) |

TABLE 2-continued

| Example No. (Method) | Structure; IUPAC name | LCMS $M^+1$ | $^1H$ NMR (ppm); $^{19}F$ NMR (ppm); optical rotation; Chiral HPLC/SFC conditions |
|---|---|---|---|
| 88 (Ex. 30) | 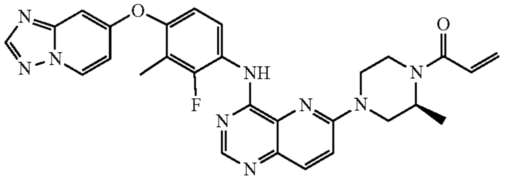 [SMILES: C=CC(=O)N1CCN(c2ccc3ncnc(Nc4ccc(Oc5ccn6ncnc6c5)c(C)c4F)c3n2)C[C@@H]1C] (S)-1-(4-(4-((4-([1,2,4]triazolo[1,5-a]pyridin-7-yloxy)-2-fluoro-3-methylphenyl)amino)pyrido[3,2-d]pyrimidin-6-yl)-2-methylpiperazin-1-yl)prop-2-en-1-one | 540.2 | $^1H$ NMR (400 MHz, $CDCl_3$) δ 9.08 (d, J = 3.6 Hz, 1H), 8.83 (t, J = 9.02 Hz, 1H), 8.65 (s, 1H), 8.51 (d, J = 7.3, 1H), 8.23 (s, 1H), 8.00 (d, J = 9.3 Hz, 1H), 7.28 (s, 1H), 7.01 (dd, J = 9.2, 1.8 Hz, 1H), 6.89 (m, 2H), 6.63 (dd, J = 16.7, 10.5 Hz, 1H), 6.39 (m, 1H), 5.77 (dd, J = 10.5, 1.9 Hz, 1H), 4.33 (m, 3H), 3.37 (m, 4H), 2.21 (d, J = 2.1 Hz, 3H), 1.35 (d, J = 6.7 Hz, 3H) |
| 89 (Ex. 30) | 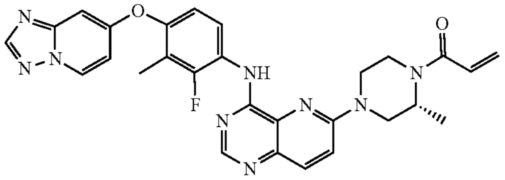 [SMILES: C=CC(=O)N1CCN(c2ccc3ncnc(Nc4ccc(Oc5ccn6ncnc6c5)c(C)c4F)c3n2)C[C@H]1C] (R)-1-(4-(4-((4-([1,2,4]triazolo[1,5-a]pyridin-7-yloxy)-2-fluoro-3-methylphenyl)amino)pyrido[3,2-d]pyrimidin-6-yl)-2-methylpiperazin-1-yl)prop-2-en-1-one | 540.3 | $^1H$ NMR (400 MHz, $CDCl_3$) δ 9.08 (d, J = 3.6 Hz, 1H), 8.83 (t, J = 9.02 Hz, 1H), 8.65 (s, 1H), 8.51 (d, J = 7.3, 1H), 8.23 (s, 1H), 8.00 (d, J = 9.3 Hz, 1H), 7.28 (s, 1H), 7.01 (dd, J = 9.2, 1.8 Hz, 1H), 6.89 (m, 2H), 6.63 (dd, J = 16.7, 10.5 Hz, 1H), 6.39 (m, 1H), 5.77 (dd, J = 10.5, 1.9 Hz, 1H), 4.33 (m, 3H), 3.37 (m, 4H), 2.21 (d, J = 2.1 Hz, 3H), 1.35 (d, J = 6.7 Hz, 3H) |
| 90 (Ex. 30) | 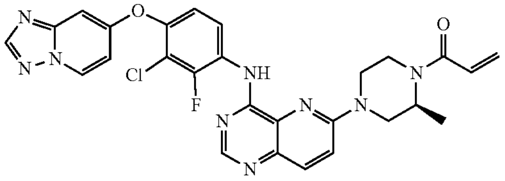 [SMILES: C=CC(=O)N1CCN(c2ccc3ncnc(Nc4ccc(Oc5ccn6ncnc6c5)c(Cl)c4F)c3n2)C[C@@H]1C] (S)-1-(4-(4-((4-([1,2,4]triazolo[1,5-a]pyridin-7-yloxy)-3-chloro-2-fluorophenyl)amino)pyrido[3,2-d]pyrimidin-6-yl)-2-methylpiperazin-1-yl)prop-2-en-1-one | 560.1 | $^1H$ NMR (400 MHz, $CDCl_3$) δ 9.11 (d, J = 3.4 Hz, 1H), 9.00 (t, J = 8.92 Hz, 1H), 8.66 (s, 1H), 8.53 (dd, J = 7.1, 1.2 Hz, 1H), 8.25 (s, 1H), 8.02 (d, J = 9.4 Hz, 1H), 7.29 (d, J = 9.4 Hz, 1H), 7.16 (dd, J = 9.2, 2.1 Hz, 1H), 6.92 (m, 2H), 6.63 (dd, J = 16.7, 10.5 Hz, 1H), 6.39 (m, 1H), 5.78 (dd, J = 10.5, 1.9 Hz, 1H), 4.35 (m, 3H), 3.41 (m, 4H), 1.35 (d, J = 6.7 Hz, 3H) |
| 91 (Ex. 30) | 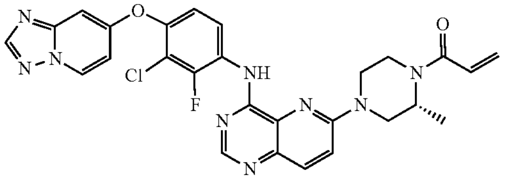 (R)-1-(4-(4-((4-([1,2,4]triazolo[1,5-a]pyridin-7-yloxy)-3-chloro-2-fluorophenyl)amino)pyrido[3,2-d]pyrimidin-6-yl)-2-methylpiperazin-1-yl)prop-2-en-1-one | 560.2 | $^1H$ NMR (400 MHz, $CDCl_3$) δ 9.11 (d, J = 3.4 Hz, 1H), 9.00 (t, J = 8.92 Hz, 1H), 8.66 (s, 1H), 8.53 (dd, J = 7.1, 1.2 Hz, 1H), 8.25 (s, 1H), 8.02 (d, J = 9.4 Hz, 1H), 7.29 (d, J = 9.4 Hz, 1H), 7.16 (dd, J = 9.2, 2.1 Hz, 1H), 6.92 (m, 2H), 6.63 (dd, J = 16.7, 10.5 Hz, 1H), 6.39 (m, 1H), 5.78 (dd, J = 10.5, 1.9 Hz, 1H), 4.35 (m, 3H), 3.41 (m, 4H), 1.35 (d, J = 6.7 Hz, 3H) |
| 92 (Ex. 30) | 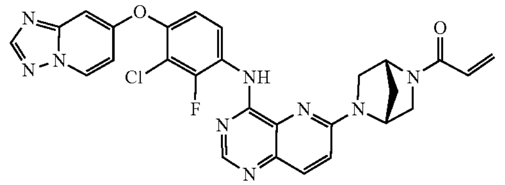 [SMILES: C=CC(=O)N1C[C@H]2C[C@@H]1CN2c1ccc2ncnc(Nc3ccc(Oc4ccn5ncnc5c4)c(Cl)c3F)c2n1] 1-((1R,4R)-5-(4-((4-([1,2,4]triazolo[1,5-a]pyridin-7-yloxy)-3-chloro-2-fluorophenyl)amino)pyrido[3,2- | 558.1 | 1H NMR (400 MHz, $CDCl_3$) δ 9.13 (m, 1H), 9.00 (t, J = 8.9 Hz, 1H), 8.65 (s, 1H), 8.53 (d, J = 8.2, 1.1 Hz, 1H), 8.25 (s, 1H), 7.99 (d, J = 9.2 Hz, 1H), 7.16 (m, 1H), 6.92 (m, 2H), 6.42 (dd, J = 16.8, 2.0 Hz, 1H), 6.29 (dd, J = 16.8, 10.2 Hz, 1H), 5.73 (m, 1H), 5.20 (s, 1H), 3.79 (m, 3H), 3.65 (m, 1H), 2.13 (m, 4H) |

TABLE 2-continued

| Example No. (Method) | Structure; IUPAC name | LCMS $M^{+}1$ | $^{1}H$ NMR (ppm); $^{19}F$ NMR (ppm); optical rotation; Chiral HPLC/SFC conditions |
|---|---|---|---|
| | d]pyrimidin-6-yl)-2,5-diazabicyclo[2.2.1]heptan-2-yl)prop-2-en-1-one | | |
| 93 (Ex. 30) | 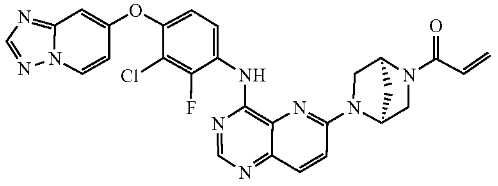 [SMILES: C=CC(=O)N1C[C@@H]2C[C@H]1CN2c1ccc2ncnc(Nc3ccc(Oc4ccn5ncnc5c4)c(Cl)c3F)c2n1] 1-((1S,4S)-5-(4-((4-([1,2,4]triazolo[1,5-a]pyridin-7-yloxy)-3-chloro-2-fluorophenyl)amino)pyrido[3,2-d]pyrimidin-6-yl)-2,5-diazabicyclo[2.2.1]heptan-2-yl)prop-2-en-1-one | 558.2 | 1H NMR (400 MHz, $CDCl_3$) δ 9.13 (m, 1H), 9.00 (t, J = 8.9 Hz, 1H), 8.65 (s, 1H), 8.53 (d, J = 8.2, 1.1 Hz, 1H), 8.25 (s, 1H), 7.99 (d, J = 9.2 Hz, 1H), 7.16 (m, 1H), 6.92 (m, 2H), 6.42 (dd, J = 16.8, 2.0 Hz, 1H), 6.29 (dd, J = 16.8, 10.2 Hz, 1H), 5.73 (m, 1H), 5.20 (s, 1H), 3.79 (m, 3H), 3.65 (m, 1H), 2.13 (m, 4H) |
| 94 (Ex. 30) | 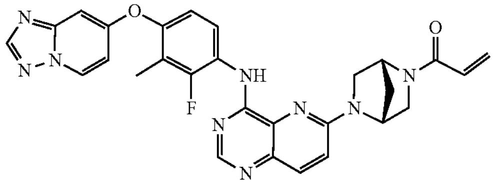 [SMILES: C=CC(=O)N1C[C@H]2C[C@@H]1CN2c1ccc2ncnc(Nc3ccc(Oc4ccn5ncnc5c4)c(C)c3F)c2n1] 1-((1R,4R)-5-(4-((4-([1,2,4]triazolo[1,5-a]pyridin-7-yloxy)-2-fluoro-3-methylphenyl)amino)pyrido[3,2-d]pyrimidin-6-yl)-2,5-diazabicyclo[2.2.1]heptan-2-yl)prop-2-en-1-one | 538.2 | $^{1}H$ NMR (400 MHz, $CDCl_3$) δ 9.11 (m, 1H), 8.83 (m, 1H), 8.63 (s, 1H), 8.51 (m, 1H), 8.23 (s, 1H), 7.97 (d, J = 9.3 Hz, 1H), 6.99 (m, 2H), 6.88 (m, 2H), 6.55 (dd, J = 16.8, 10.1 Hz, 1H), 6.41 (dd, J = 16.9, 2.0 Hz, 1H), 6.29 (d, J = 16.8, 10.1 Hz, 1H), 5.73 (m, 1H), 5.20 (s, 1H), 3.79 (m, 3H), 3.66 (m, 1H), 2.18 (m, 4H), 2.07 (m, 1H) |
| 95 (Ex. 30) | 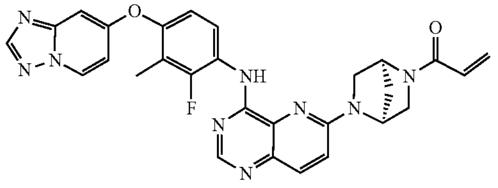 [SMILES: C=CC(=O)N1C[C@@H]2C[C@H]1CN2c1ccc2ncnc(Nc3ccc(Oc4ccn5ncnc5c4)c(C)c3F)c2n1] 1-((1S,4S)-5-(4-((4-([1,2,4]triazolo[1,5-a]pyridin-7-yloxy)-2-fluoro-3-methylphenyl)amino)pyrido[3,2-d]pyrimidin-6-yl)-2,5-diazabicyclo[2.2.1]heptan-2-yl)prop-2-en-1-one | 538.2 | $^{1}H$ NMR (400 MHz, $CDCl_3$) δ 9.11 (m, 1H), 8.83 (m, 1H), 8.63 (s, 1H), 8.51 (m, 1H), 8.23 (s, 1H), 7.97 (d, J = 9.3 Hz, 1H), 6.99 (m, 2H), 6.88 (m, 2H), 6.55 (dd, J = 16.8, 10.1 Hz, 1H), 6.41 (dd, J = 16.9, 2.0 Hz, 1H), 6.29 (d, J = 16.8, 10.1 Hz, 1H), 5.73 (m, 1H), 5.20 (s, 1H), 3.79 (m, 3H), 3.66 (m, 1H), 2.18 (m, 4H), 2.07 (m, 1H) |
| 96 (Ex. 30) | 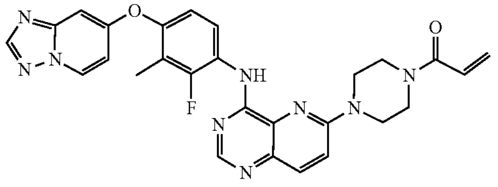 [SMILES: C=CC(=O)N1CCN(c2ccc3ncnc(Nc4ccc(Oc5ccn6ncnc6c5)c(C)c4F)c3n2)CC1] 1-(4-(4-((4-([1,2,4]triazolo[1,5-a]pyridin-7-yloxy)-2-fluoro-3-methylphenyl)amino)pyrido[3,2-d]pyrimidin-6-yl)piperazin-1-yl)prop-2-en-1-one | 526.2 | 1H NMR (400 MHz, $CDCl_3$) δ 9.08 (m, 1H), 8.81 (t, J = 9.0 Hz, 1H), 8.66 (s, 1H), 8.51 (dd, J = 7.3, 0.8 Hz, 1H), 8.02 (d, J = 9.3 Hz, 1H), 7.31 (d, J = 9.3 Hz, 1H), 7.02 (m, 1H), 6.89 (m, 2H), 6.65 (dd, J = 16.8, 10.5 Hz, 1H), 6.39 (dd, J = 16.8, 1.8 Hz, 1H), 5.79 (dd, J = 10.5, 1.8 Hz, 1H), (m, 1H), 3.85 (m, 8H), 2.21 (m, 3H); m/z (APCI-pos) M + 1 = 526.2 |

TABLE 2-continued

| Example No. (Method) | Structure; IUPAC name | LCMS $M^+1$ | $^1H$ NMR (ppm); $^{19}F$ NMR (ppm); optical rotation; Chiral HPLC/SFC conditions |
|---|---|---|---|
| 97 (Ex. 30) | 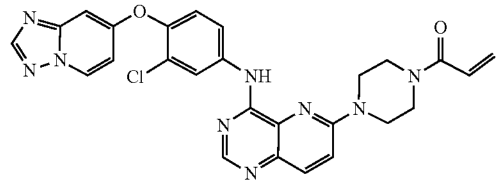 [SMILES: C=CC(=O)N1CCN(c2ccc3ncnc(Nc4ccc(Oc5ccn6ncnc6c5)c(Cl)c4)c3n2)CC1] 1-(4-(4-((4-([1,2,4]triazolo[1,5-a]pyridin-7-yloxy)-3-chlorophenyl)amino)pyrido[3,2-d]pyrimidin-6-yl)piperazin-1-yl)prop-2-en-1-one | 528.1 | $^1H$ NMR (400 MHz, $CDCl_3$) δ 8.73 (s, 1H), 8.67 (s, 1H), 8.52 (dd, J = 7.4, 0.8 Hz, 1H), 8.27 (d, J = 2.6 Hz, 1H), 8.24 (s, 1H), 8.03 (d, J = 9.4 Hz, 1H), 7.88 (dd, J = 8.8, 2.6 Hz, 1H), 7.31 (d, J = 9.4 Hz, 1H), 7.27 (d, J = 8.8 Hz, 1H), 6.92 (dd, J = 7.4, 2.6 Hz, 1H), 6.89 (dd, J = 2.6, 0.8 Hz, 1H), 3.88 (m, 8H) |
| 98 (Ex. 30) | 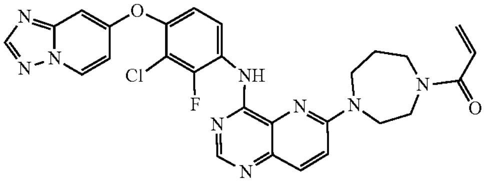 [SMILES: C=CC(=O)N1CCCN(c2ccc3ncnc(Nc4ccc(Oc5ccn6ncnc6c5)c(Cl)c4F)c3n2)CC1] 1-(4-(4-((4-([1,2,4]triazolo[1,5-a]pyridin-7-yloxy)-3-chloro-2-fluorophenyl)amino)pyrido[3,2-d]pyrimidin-6-yl)-1,4-diazepan-1-yl)prop-2-en-1-one | 560.1 | $^1H$ NMR (400 MHz, $CDCl_3$) δ 9.15 (m, 1H), 9.01 (m, 1H), 8.64 (s, 1H), 8.53 (m, 1H), 8.25 (s, 1H), 7.99 (d, J = 9.3 Hz, 1H), 7.23 (m, 1H), 7.16 (m, 1H), 6.92 (m, 2H), 6.58 (m, 1H), 6.40 (dd, J = 16.6, 2.0 Hz, 1H), 5.68 (m, 1H), 3.96 (m, 6H), 3.58 (m, 2H), 2.16 (m, 2H) |
| 99 (Ex. 30) | 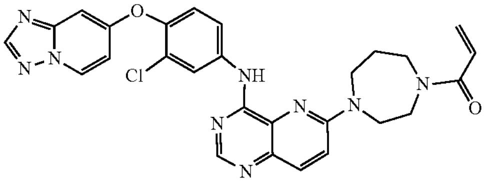 [SMILES: C=CC(=O)N1CCCN(c2ccc3ncnc(Nc4ccc(Oc5ccn6ncnc6c5)c(Cl)c4)c3n2)CC1] 1-(4-(4-((4-([1,2,4]triazolo[1,5-a]pyridin-7-yloxy)-3-chlorophenyl)amino)pyrido[3,2-d]pyrimidin-6-yl)-1,4-diazepan-1-yl)prop-2-en-1-one | 542.2 | $^1H$ NMR (400 MHz, DMSO-$d_6$) δ 9.43 (d, J = 7.9 Hz, 1H), 8.97 (m, 1H), 8.45 (m, 3H), 8.12 (m, 1H), 7.92 (m, 1H), 7.49 (m, 2H), 7.07 (m, 1H), 6.93 (m, 1H), 6.72 (m, 1H), 6.10 (dd, J = 16.6, 2.5 Hz, 1H), 5.65 (dd, J = 10.3, 2.5 Hz, 1H), 4.09 (m, 2H), 3.82 (m, 5H), 3.52 (m, 3H) |
| 100 (Ex. 30) | 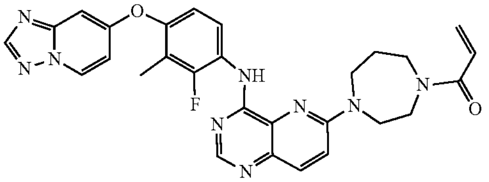 [SMILES: C=CC(=O)N1CCCN(c2ccc3ncnc(Nc4ccc(Oc5ccn6ncnc6c5)c(C)c4F)c3n2)CC1] 1-(4-(4-((4-([1,2,4]triazolo[1,5-a]pyridin-7-yloxy)-2-fluoro-3-methylphenyl)amino)pyrido[3,2-d]pyrimidin-6-yl)-1,4-diazepan-1-yl)prop-2-en-1-one | 540.3 | $^1H$ NMR (400 MHz, $CDCl_3$) δ 9.12 (m, 1H), 8.84 (m, 1H), 8.62 (s, 1H), 8.50 (m, 1H), 8.23 (s, 1H), 7.98 (m, 1H), 7.20 (m, 1H), 7.01 (m, 1H), 6.88 (m, 1H), 6.59 (m, 1H), 6.41 (m, 1H), 6.17 (m, 1H), 5.67 (m, 1H), 3.92 (m, 6H), 3.57 (m, 2H), 2.20 (m, 3H), 2.15 (m, 2H) |
| 101 | 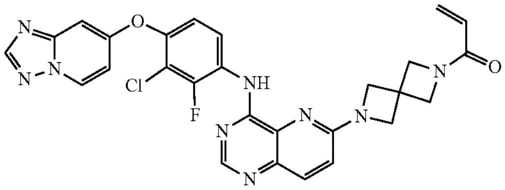 [SMILES: C=CC(=O)N1CC2(C1)CN(c1ccc3ncnc(Nc4ccc(Oc5ccn6ncnc6c5)c(Cl)c4F)c3n1)C2] | 558.2 | $^1H$ NMR (400 MHz, $CDCl_3$) δ 9.15 (m, 1H), 8.98 (t, J = 8.9 Hz, 1H), 8.66 (s, 1H), 8.53 (dd, J = 7.1, 1.1 Hz, 1H), 8.25 (s, 1H), 7.98 (d, J = 9.1 Hz, 1H), 7.15 (dd, J = 9.2, 2.1 Hz, 1H), 6.91 (m, 2H), 6.38 (dd, J = 17.0, 1.9 Hz, 1H), 6.21 (dd, J = 17.0, 10.3 Hz, 1H), 5.73 (dd, J = 10.4, 1.9 Hz, 1H), 4.41 (m, 8H) |

TABLE 2-continued

| Example No. (Method) | Structure; IUPAC name | LCMS $M^+1$ | $^1H$ NMR (ppm); $^{19}F$ NMR (ppm); optical rotation; Chiral HPLC/SFC conditions |
|---|---|---|---|
| | 1-(6-(4-((4-([1,2,4]triazolo[1,5-a]pyridin-7-yloxy)-3-chloro-2-fluorophenyl)amino)pyrido[3,2-d]pyrimidin-6-yl)-2,6-diazaspiro[3.3]heptan-2-yl)prop-2-en-1-one | | |
| 102 (Ex. 33) | 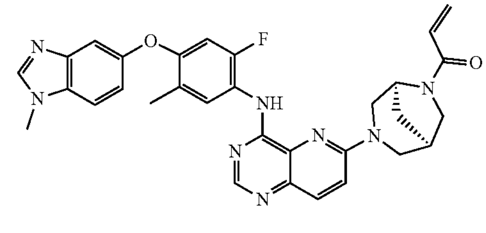 [SMILES: C=CC(=O)N1C[C@@H]2C[C@H]1CN(c1ccc3ncnc(Nc4cc(C)c(Oc5ccc6c(c5)ncn6C)cc4F)c3n1)C2] 1-((1R,5S)-3-(4-((2-fluoro-5-methyl-4-((1-methyl-1H-benzo[d]imidazol-5-yl)oxy)phenyl)amino)pyrido[3,2-d]pyrimidin-6-yl)-3,6-diazabicyclo[3.2.1]octan-6-yl)prop-2-en-1-one | 564.90 | $^1H$ NMR (400 MHz, $CDCl_3$) δ 8.84 (s, 1H), 8.68 – 8.55 (m, 2H), 7.98 – 7.89 (m, 1H), 7.87 (s, 1H), 7.39 – 7.32 (m, 2H), 7.23 – 7.12 (m, 1H), 7.05 (dd, J = 8.8, 2.1 Hz, 1H), 6.70 (d, J = 11.9 Hz, 1H), 6.61 – 6.33 (m, 2H), 5.77 – 5.63 (m, 1H), 4.79 (s, 1H), 4.55 – 4.08 (m, 2H), 3.86 (s, 3H), 3.77 – 3.28 (m, 3H), 3.25 – 3.11 (m, 1H), 2.98 – 2.71 (m, 1H), 2.35 (s, 3H), 2.25 – 2.01 (m, 1H), 2.01 – 1.81 (m, 1H). |
| 103 (Ex. 33) | 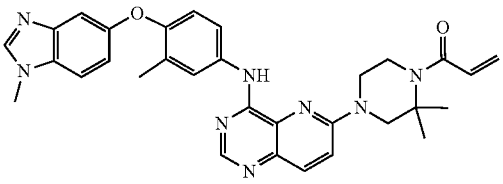 [SMILES: C=CC(=O)N1CCN(c2ccc3ncnc(Nc4ccc(Oc5ccc6c(c5)ncn6C)c(C)c4)c3n2)CC1(C)C] 1-(2,2-dimethyl-4-(4-((3-methyl-4-((1-methyl-1H-benzo[d]imidazol-5-yl)oxy)phenyl)amino)pyrido[3,2-d]pyrimidin-6-yl)piperazin-1-yl)prop-2-en-1-one | 549.30 | $^1H$ NMR (500 MHz, $CDCl_3$) δ 8.61 – 8.56 (m, 2H), 7.97 (d, J = 9.3 Hz, 1H), 7.84 (s, 1H), 7.73 (d, J = 2.5 Hz, 1H), 7.63 (dd, J = 8.7, 2.6 Hz, 1H), 7.35 – 7.29 (m, 2fH), 7.12 (d, J = 9.3 Hz, 1H), 7.06 (dd, J = 8.6, 2.3 Hz, 1H), 6.94 (d, J = 8.7 Hz, 1H), 6.57 (dd, J = 16.8, 10.6 Hz, 1H), 6.25 (dd, J = 16.8, 1.6 Hz, 1H), 5.68 (dd, J = 10.6, 1.7 Hz, 1H), 4.02 – 3.96 (m, 2H), 3.89 – 3.80 (m, 7H), 2.34 (s, 2H), 1.61 (s, 6H). |
| 104 (Ex. 33) | 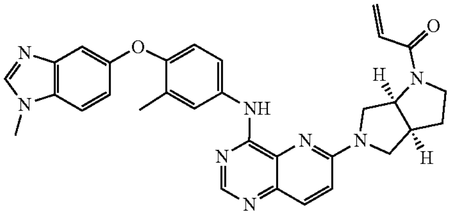 [SMILES: C=CC(=O)N1CC[C@H]2CN(c3ccc4ncnc(Nc5ccc(Oc6ccc7c(c6)ncn7C)c(C)c5)c4n3)C[C@H]21] rac-1-((3aR,6aR)-5-(4-((3-methyl-4-((1-methyl-1H-benzo[d]imidazol-5-yl)oxy)phenyl)amino)pyrido[3,2-d]pyrimidin-6-yl)hexahydropyrrolo[3,4-b]pyrrol-1(2H)-yl)prop-2-en-1-one | 547.30 | $^1H$ NMR (400 MHz, DMSO) δ 9.20 – 9.14 (m, 1H), 8.41 – 8.36 (m, 1H), 8.16 (s, 1H), 7.94 – 7.75 (m, 3H), 7.56 (d, J = 8.7 Hz, 1H), 7.21 (dd, J = 10.8, 9.3 Hz, 1H), 7.08 (d, J = 2.0 Hz, 1H), 6.99 (dd, J = 8.7, 2.3 Hz, 1H), 6.90 (d, J = 8.7 Hz, 1H), 6.76 – 6.56 (m, 1H), 6.26 – 6.13 (m, 1H), 5.79 – 5.66 (m, 1H), 4.83 – 4.49 (m, 1H), 4.21 – 3.79 (m, 5H), 3.79 – 3.47 (m, 3H), 3.29 – 3.00 (m, 2H), 2.25 (s, 3H), 2.21 – 2.03 (m, 1H), 2.01 – 1.78 (m, 1H). |
| 105 (Ex. 33) | 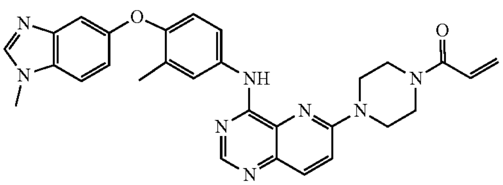 [SMILES: C=CC(=O)N1CCN(c2ccc3ncnc(Nc4ccc(Oc5ccc6c(c5)ncn6C)c(C)c4)c3n2)CC1] 1-(4-(4-((3-methyl-4-((1-methyl-1H-benzo[d]imidazol-5-yl)oxy)phenyl)amino)pyrido[3,2-d]pyrimidin-6-yl)piperazin-1-yl)prop-2-en-1-one | 521.30 | $^1H$ NMR (400 MHz, DMSO) δ 9.31 (s, 1H), 8.40 (s, 1H), 8.16 (s, 1H), 7.94 (d, J = 9.3 Hz, 1H), 7.84 (d, J = 2.5 Hz, 1H), 7.81 (d, J = 2.6 Hz, 1H), 7.79 (d, J = 2.6 Hz, 1H), 7.57 (dd, J = 9.0, 5.3 Hz, 2H), 7.08 (d, J = 2.1 Hz, 1H), 6.99 (dd, J = 8.7, 2.3 Hz, 1H), 6.93 – 6.84 (m, 2H), 6.17 (dd, J = 16.7, 2.3 Hz, 1H), 5.74 (dd, J = 10.5, 2.3 Hz, 1H), 3.91 – 3.81 (m, 7H), 3.78 – 3.67 (m, 4H), 2.25 (s, 3H). |

TABLE 2-continued

| Example No. (Method) | Structure; IUPAC name | LCMS $M^+1$ | $^1H$ NMR (ppm); $^{19}F$ NMR (ppm); optical rotation; Chiral HPLC/SFC conditions |
|---|---|---|---|
| 106 (Ex. 33) | 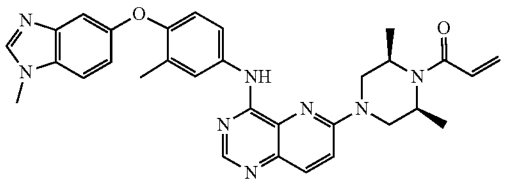 [SMILES: C=CC(=O)N1[C@H](C)CN(c2ccc3ncnc(Nc4ccc(Oc5ccc6c(c5)ncn6C)c(C)c4)c3n2)C[C@@H]1C] 1-((2S,6R)-2,6-dimethyl-4-(4-((3-methyl-4-((1-methyl-1H-benzo[d]imidazol-5-yl)oxy)phenyl)amino)pyrido[3,2-d]pyrimidin-6-yl)piperazin-1-yl)prop-2-en-1-one | 549.30 | $^1H$ NMR (500 MHz, $CDCl_3$) δ 8.61 - 8.56 (m, 2H), 7.97 (d, J = 9.3 Hz, 1H), 7.84 (s, 1H), 7.73 (d, J = 2.6 Hz, 1H), 7.63 (dd, J = 8.7, 2.7 Hz, 1H), 7.34 - 7.27 (m, 2H), 7.06 (dd, J = 8.6, 2.3 Hz, 1H), 6.95 (d, J = 8.7 Hz, 1H), 6.64 (dd, J = 16.7, 10.5 Hz, 1H), 6.40 (dd, J = 16.7, 1.9 Hz, 1H), 5.76 (dd, J = 10.5, 1.9 Hz, 1H), 4.36 (d, J = 12.4 Hz, 2H), 3.85 (s, 3H), 3.34 (dd, J = 13.3, 4.4 Hz, 2H), 2.35 (s, 2H), 1.41 (d, J = 6.9 Hz, 6H). |
| 107 (Ex. 33) | 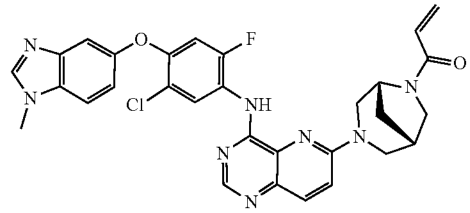 [SMILES: C=CC(=O)N1C[C@H]2C[C@@H]1CN(c1ccc3ncnc(Nc4cc(Cl)c(Oc5ccc6c(c5)ncn6C)cc4F)c3n1)C2] 1-((1S,5R)-3-(4-((5-chloro-2-fluoro-4-((1-methyl-1H-benzo[d]imidazol-5-yl)oxy)phenyl)amino)pyrido[3,2-d]pyrimidin-6-yl)-3,6-diazabicyclo[3.2.1]octan-6-yl)prop-2-en-1-one | 585.30 | $^1H$ NMR (400 MHz, $CDCl_3$) δ 9.12 - 9.02 (m, 1H), 8.92 - 8.85 (m, 1H), 8.69 - 8.63 (m, 1H), 8.03 - 7.84 (m, 2H), 7.49 - 7.34 (m, 2H), 7.25 - 7.14 (m, 1H), 7.10 (dd, J = 8.7, 2.3 Hz, 1H), 6.79 (d, J = 11.7 Hz, 1H), 6.63 - 6.28 (m, 2H), 5.77 - 5.63 (m, 1H), 4.92-4.08 (m, 3H), 3.87 (s, 3H), 3.78 - 3.49 (m, 2H), 3.39 - 3.31 (m, 1H), 3.25 - 3.11 (m, 1H), 2.94 - 2.72 (m, 1H), 2.28 - 1.80 (m, 2H). |
| 108 (Ex. 33) | 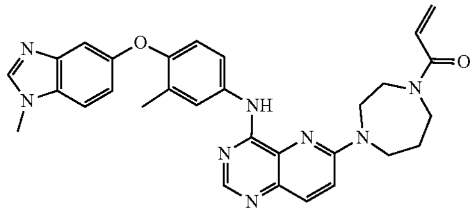 [SMILES: C=CC(=O)N1CCCN(c2ccc3ncnc(Nc4ccc(Oc5ccc6c(c5)ncn6C)c(C)c4)c3n2)CC1] 1-(4-(4-((3-methyl-4-((1-methyl-1H-benzo[d]imidazol-5-yl)oxy)phenyl)amino)pyrido[3,2-d]pyrimidin-6-yl)-1,4-diazepan-1-yl)prop-2-en-1-one | 535.3 | 1H NMR (400 MHz, DMSO) δ 9.20 (d, J = 5.2 Hz, 1H), 8.36 (d, J = 5.9 Hz, 1H), 8.16 (s, 1H), 7.92 - 7.72 (m, 3H), 7.56 (d, J = 8.7 Hz, 1H), 7.48 - 7.38 (m, 1H), 7.07 (s, 1H), 6.99 (dt, J = 8.7, 2.1 Hz, 1H), 6.91 (dd, J = 8.7, 1.7 Hz, 1H), 6.81 - 6.63 (m, 1H), 6.10 (dd, J = 16.6, 2.4 Hz, 0.5H), 5.85 (d, J = 16.5 Hz, 0.5H), 5.65 (dd, J = 10.4, 2.4 Hz, 0.5H), 5.45 (d, J = 11.8 Hz, 0.5H), 4.16 - 3.95 (m, 2H), 3.93 - 3.81 (m, 5H), 3.77 (t, J = 5.4 Hz, 1H), 3.51 (dt, J = 18.0, 6.0 Hz, 2H), 2.25 (d, J = 2.0 Hz, 3H), 1.98 - 1.79 (m, 3H). |
| 109 (Ex. 33) | 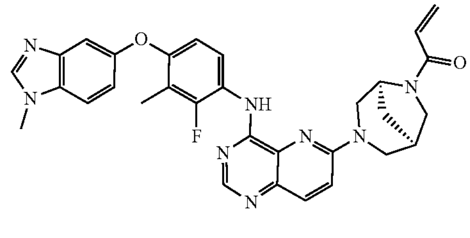 [SMILES: C=CC(=O)N1C[C@@H]2C[C@H]1CN(c1ccc3ncnc(Nc4ccc(Oc5ccc6c(c5)ncn6C)c(C)c4F)c3n1)C2] 1-((1R,5S)-3-(4-((2-fluoro-3-methyl-4-((1-methyl-1H-benzo[d]imidazol-5-yl)oxy)phenyl)amino)pyrido[3,2-d]pyrimidin-6-yl)-3,6-diazabicyclo[3.2.1]octan-6-yl)prop-2-en-1-one | 565.30 | $^1H$ NMR (400 MHz, $CDCl_3$) δ 8.98 - 8.91 (m, 1H), 8.60 - 8.56 (m, 1H), 8.56 - 8.47 (m, 1H), 7.98 - 7.89 (m, 1H), 7.86 (s, 1H), 7.37 - 7.29 (m, 2H), 7.23 - 7.13 (m, 1H), 7.06 (dd, J = 8.8, 2.2 Hz, 1H), 6.76 (dd, J = 9.0, 1.5 Hz, 1H), 6.66 - 6.31 (m, 2H), 5.86 - 5.53 (m, 1H), 4.81 (s, 1H), 4.63 - 4.11 (m, 3H), 3.85 (s, 3H), 3.80 - 3.33 (m, 3H), 3.28 - 3.13 (m, 1H), 2.97 - 2.73 (m, 1H), 2.32 - 2.26 (m, 3H), 2.25 - 2.03 (m, 1H), 2.02 - 1.85 (m, 1H). |

TABLE 2-continued

| Example No. (Method) | Structure; IUPAC name | LCMS $M^{+}1$ | $^{1}$H NMR (ppm); $^{19}$F NMR (ppm); optical rotation; Chiral HPLC/SFC conditions |
|---|---|---|---|
| 110 (Ex. 33) | 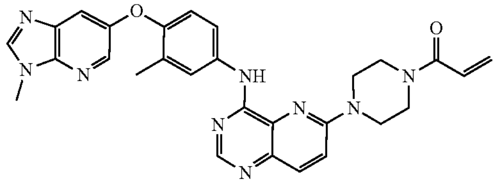 [SMILES: C=CC(=O)N1CCN(c2ccc3ncnc(Nc4ccc(Oc5cnc6c(c5)ncn6C)c(C)c4)c3n2)CC1] 1-(4-(4-((3-methyl-4-((3-methyl-3H-imidazo[4,5-b]pyridin-6-yl)oxy)phenyl)amino)pyrido[3,2-d]pyrimidin-6-yl)piperazin-1-yl)prop-2-en-1-one | 521.75 | $^{1}$H NMR (400 MHz, DMSO) δ 9.32 (s, 1H), 8.43 (s, 1H), 8.41 (s, 1H), 8.24 (d, J = 2.5 Hz, 1H), 7.94 (d, J = 9.3 Hz, 1H), 7.88 (d, J = 2.4 Hz, 1H), 7.82 (dd, J = 8.7, 2.6 Hz, 1H), 7.61 - 7.54 (m, 2H), 6.95 - 6.83 (m, 2H), 6.17 (dd, J = 16.7, 2.3 Hz, 1H), 5.74 (dd, J = 10.4, 2.3 Hz, 1H), 3.89 - 3.83 (m, 7H), 3.75 - 3.71 (m, 4H), 2.29 (s, 3H). |
| 111 (Ex. 33) | 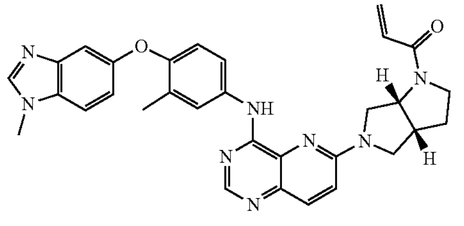 [SMILES: C=CC(=O)N1CC[C@@H]2CN(c3ccc4ncnc(Nc5ccc(Oc6ccc7c(c6)ncn7C)c(C)c5)c4n3)C[C@@H]21] 1-((3aR,6aR)-5-(4-((3-methyl-4-((1-methyl-1H-benzo[d]imidazol-5-yl)oxy)phenyl)amino)pyrido[3,2-d]pyrimidin-6-yl)hexahydropyrrolo[3,4-b]pyrrol-1(2H)-yl)prop-2-en-1-one | 547.30 | $^{1}$H NMR (400 MHz, DMSO) δ 9.20 - 9.14 (m, 1H), 8.41 - 8.36 (m, 1H), 8.16 (s, 1H), 7.94 - 7.75 (m, 3H), 7.56 (d, J = 8.7 Hz, 1H), 7.21 (dd, J = 10.8, 9.3 Hz, 1H), 7.08 (d, J = 2.0 Hz, 1H), 6.99 (dd, J = 8.7, 2.3 Hz, $^{1}$H), 6.90 (d, J = 8.7 Hz, 1H), 6.76 - 6.56 (m, 1H), 6.26 - 6.13 (m, 1H), 5.79 - 5.66 (m, 1H), 4.87 - 4.49 (m, 1H), 4.22 - 3.80 (m, 5H), 3.80 - 3.47 (m, 4H), 3.25 - 3.03 (m, 1H), 2.25 (s, 3H), 2.21 2.03 (m, 1H), 1.97 - 1.75 (m, 1H). |
| 112 (Ex. 33) | 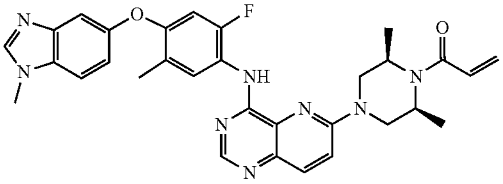 [SMILES: C=CC(=O)N1[C@H](C)CN(c2ccc3ncnc(Nc4cc(C)c(Oc5ccc6c(c5)ncn6C)cc4F)c3n2)C[C@@H]1C] 1-((2S,6R)-4-(4-((2-fluoro-5-methyl-4-((1-methyl-1H-benzo[d]imidazol-5-yl)oxy)phenyl)amino)pyrido[3,2-d]pyrimidin-6-yl)-2,6-dimethylpiperazin-1-yl)prop-2-en-1-one | 567.30 | $^{1}$H NMR (500 MHz, $CDCl_3$) δ 8.88 (d, J = 2.5 Hz, 1H), 8.67 (d, J = 9.2 Hz, 1H), 8.64 (s, 1H), 7.97 (d, J = 9.3 Hz, 1H), 7.87 (s, 1H), 7.38 - 7.33 (m, 2H), 7.28 (d, J = 9.4 Hz, 1H), 7.06 (dd, J = 8.8, 2.1 Hz, 1H), 6.71 (d, J = 12.0 Hz, 1H), 6.63 (dd, J = 16.7, 10.5 Hz, 1H), 6.38 (dd, J = 16.7, 1.9 Hz, 1H), 5.75 (dd, J = 10.5, 1.8 Hz, 1H), 4.40 (s, 2H), 3.86 (s, 3H), 3.33 (dd, J = 13.4, 4.4 Hz, 2H), 2.36 (s, 3H), 1.38 (d, J = 6.9 Hz, 6H). |
| 113 (Ex. 33) | 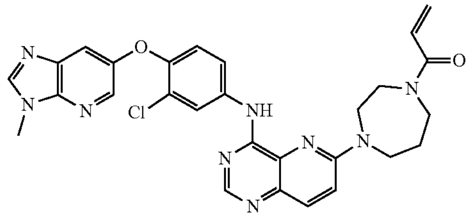 [SMILES: C=CC(=O)N1CCCN(c2ccc3ncnc(Nc4ccc(Oc5cnc6c(c5)ncn6C)c(Cl)c4)c3n2)CC1] 1-(4-(4-((3-chloro-4-((3-methyl-3H-imidazo[4,5-b]pyridin-6-yl)oxy)phenyl)amino)pyrido[3,2-d]pyrimidin-6-yl)-1,4-diazepan-1-yl)prop-2-en-1-one | 556.15 | $^{1}$H NMR (400 MHz, DMSO) δ 9.36 (d, J = 7.2 Hz, 1H), 8.47 (s, 1H), 8.43 (d, J = 4.9 Hz, 1H), 8.34 (dd, J = 8.7, 2.6 Hz, 1H), 8.31 - 8.26 (m, 1H), 7.99 - 7.86 (m, 2H), 7.70 (t, J = 2.4 Hz, 1H), 7.46 (t, J = 9.6 Hz, 1H), 7.17 (dd, J = 8.9, 1.2 Hz, 1H), 6.72 (ddd, J = 26.8, 16.7, 10.4 Hz, 1H), 6.10 (dd, J = 16.6, 2.4 Hz, 0.5H), 5.84 (d, J = 16.8 Hz, 0.5H), 5.65 (dd, J = 10.4, 2.4 Hz, 0.5H), 5.44 (d, J = 10.7 Hz, 0.5iH), 4.08-3.99 (m, 2H), 3.89 - 3.84 (m, 5H), 3.77 (t, J = 5.4 Hz, 1H), 3.51 (dt, J = 18.4, 6.0 Hz, 2H), 1.95 - 1.82 (m, 2H). |

TABLE 2-continued

| Example No. (Method) | Structure; IUPAC name | LCMS $M^{+}1$ | $^{1}H$ NMR (ppm); $^{19}F$ NMR (ppm); optical rotation; Chiral HPLC/SFC conditions |
|---|---|---|---|
| 114 (Ex. 33) | 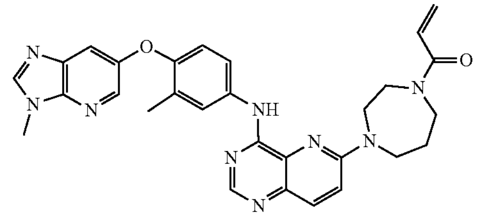 [SMILES: C=CC(=O)N1CCCN(c2ccc3ncnc(Nc4ccc(Oc5cnc6c(c5)ncn6C)c(C)c4)c3n2)CC1] 1-(4-(4-((3-methyl-4-((3-methyl-3H-imidazo[4,5-b]pyridin-6-yl)oxy)phenyl)amino)pyrido[3,2-d]pyrimidin-6-yl)-1,4-diazepan-1-yl)prop-2-en-1-one | 536.30 | $^{1}H$ NMR (400 MHz, DMSO) δ 9.24-9.18 (m, 1H), 8.43 (s, 1H), 8.37 (d, J = 5.8 Hz, 1H), 8.26 – 8.21 (m, 1H), 7.92 – 7.74 (m, 3H), 7.61 – 7.55 (m, 1H), 7.48 – 7.38 (m, 1H), 6.93 (d, J = 8.7 Hz, 1H), 6.81 – 6.63 (m, 1H), 6.10 (dd, J = 16.6, 2.4 Hz, 0.5 H), 5.84 (dd, J = 16.7, 2.1 Hz, 0.5H), 5.65 (dd, J = 10.4, 2.4 Hz, 0.5H), 5.45 (d, J = 10.7 Hz, 0.5H), 4.14 – 3.95 (m, 2H), 3.91 – 3.81 (m, 5H), 3.77 (t, J = 5.4 Hz, 1H), 3.51 (dt, J = 17.9, 6.0 Hz, 3H), 2.32 – 2.27 (m, 3H), 1.96 – 1.82 (m, 2H). |
| 115 (Ex. 33) | 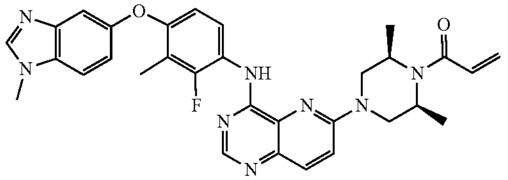 [SMILES: C=CC(=O)N1[C@H](C)CN(c2ccc3ncnc(Nc4ccc(Oc5ccc6c(c5)ncn6C)c(C)c4F)c3n2)C[C@@H]1C] 1-((2S,6R)-4-(4-((2-fluoro-3-methyl-4-((1-methyl-1H-benzo[d]imidazol-5-yl)oxy)phenyl)amino)pyrido[3,2-d]pyrimidin-6-yl)-2,6-dimethylpiperazin-1-yl)prop-2-en-1-one | 567.30 | $^{1}H$ NMR (500 MHz, $CDCl_3$) δ 8.99 (d, J = 2.6 Hz, 1H), 8.61 – 8.54 (m, 2H), 7.97 (d, J = 9.3 Hz, 1H), 7.86 (s, 1H), 7.35 – 7.27 (m, 2H), 7.06 (dd, J = 8.6, 2.3 Hz, 1H), 6.78 (d, J = 9.0 Hz, 1H), 6.65 (dd, J = 16.7, 10.5 Hz, 1H), 6.40 (dd, J = 16.7, 1.8 Hz, 1H), 5.76 (dd, J = 10.5, 1.8 Hz, 1H), 4.43 (s, 2H), 3.86 (s, 3H), 3.35 (dd, J = 13.4, 4.4 Hz, 2H), 2.29 (d, J = 1.9 Hz, 3H), 1.41 (d, J = 6.8 Hz, 6H). |
| 116 (Ex. 33) | 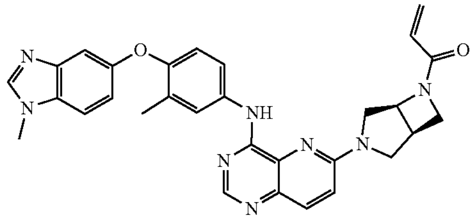 [SMILES: C=CC(=O)N1C[C@H]2CN(c3ccc4ncnc(Nc5ccc(Oc6ccc7c(c6)ncn7C)c(C)c5)c4n3)C[C@H]21] 1-((1R,5S)-3-(4-((3-methyl-4-((1-methyl-1H-benzo[d]imidazol-5-yl)oxy)phenyl)amino)pyrido[3,2-d]pyrimidin-6-yl)-3,6-diazabicyclo[3.2.0]heptan-6-yl)prop-2-en-1-one | 533.20 | $^{1}H$ NMR (400 MHz, DMSO) δ 9.30 – 9.24 (m, 1H), 8.41 (d, 1H), 8.16 (s, 1H), 7.98 – 7.89 (m, 1H), 7.89 – 7.76 (m, 2H), 7.56 (d, J = 8.7 Hz, 1H),7.41 (dd, J = 9.2, 8.0 Hz, 1H), 7.08 (d, J = 2.0 Hz, 1H), 6.99 (dd, J = 8.7, 2.3 Hz, 1H), 6.90 (dd, J = 8.7, 4.9 Hz, 1H), 6.51 (dd, J = 16.9, 10.3 Hz, 0.5H), 6.27 (dd, J = 17.0, 10.2 Hz, 0.5H), 6.13 (ddd, J = 21.0, 16.9, 2.2 Hz, 1H), 5.81 – 5.57 (m, 0.5H), 5.25 – 5.18 (m, 0.5H), 5.01 – 4.93 (m, 0.5H), 4.50 – 4.26 (m, 2.5H), 4.15 – 4.07 (m, 0.5H), 3.92 (d, 0.5H), 3.83 (s, 3H), 3.59 (dd, J = 10.2, 3.7 Hz, 0.5H), 3.42 – 3.23 (m, 3H), 2.25 (s, 3H). |
| 117 (Ex. 33) | 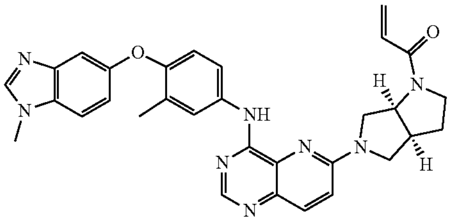 [SMILES: C=CC(=O)N1CC[C@H]2CN(c3ccc4ncnc(Nc5ccc(Oc6ccc7c(c6)ncn7C)c(C)c5)c4n3)C[C@H]21] 1-((3aS,6aS)-5-(4-((3-methyl-4-((1-methyl-1H-benzo[d]imidazol-5-yl)oxy)phenyl)amino)pyrido[3,2-d]pyrimidin-6-yl)hexahydropyrrolo[3,4-b]pyrrol-1(2H)-yl)prop-2-en-1-one | 547.30 | $^{1}H$ NMR (400 MHz, DMSO) δ 9.19 (s, 1H), 8.39 (s, 1H), 8.18 (s, 1H), 7.98 – 7.69 (m, 3H), 7.60 – 7.53 (m, 1H), 7.28 – 6.82 (m, 4H), 6.79 – 6.51 (m, 1H), 6.32 – 6.07 (m, 1H), 5.86 – 5.57 (m, 1H), 4.88 – 4.48 (m, 1H), 4.25 – 3.52 (m, 8H), 2.33 – 1.66 (m, 4H). |

TABLE 2-continued

| Example No. (Method) | Structure; IUPAC name | LCMS $M^{+}1$ | $^{1}H$ NMR (ppm); $^{19}F$ NMR (ppm); optical rotation; Chiral HPLC/SFC conditions |
|---|---|---|---|
| 118 (Ex. 33) | 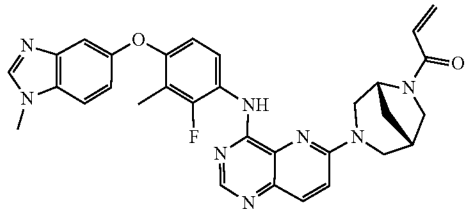 [SMILES: C=CC(=O)N1C[C@H]2C[C@@H]1CN(c1ccc3ncnc(Nc4ccc(Oc5ccc6c(c5)ncn6C)c(C)c4F)c3n1)C2] 1-((1S,5R)-3-(4-((2-fluoro-3-methyl-4-((1-methyl-1H-benzo[d]imidazol-5-yl)oxy)phenyl)amino)pyrido[3,2-d]pyrimidin-6-yl)-3,6-diazabicyclo[3.2.1]octan-6-yl)prop-2-en-1-one | 565.30 | $^{1}H$ NMR (400 MHz, $CDCl_3$) δ 8.96 - 8.92 (m, 1H), 8.61 - 8.44 (m, 2H), 7.97 - 7.89 (m, 1H), 7.86 (s, 1H), 7.37 - 7.30 (m, 2H), 7.23 - 7.12 (m, 1H), 7.06 (dd, J = 8.8, 2.1 Hz, 1H), 6.77 (d, J = 9.0 Hz, 1H), 6.66 - 6.33 (m, 2H), 5.82 - 5.60 (m, 1H), 4.84 - 4.83 (m, 1H), 4.57 - 4.12 (m, 2H), 3.85 (s, 3H), 3.79 - 3.50 (m, 2H), 3.38 (d, J = 12.6 Hz, 1H), 3.28 - 3.12 (m, 1H), 2.98 - 2.75 (m, 1H), 2.29 (s, 3H), 2.26 - 2.03 (m, 1H), 2.02 - 1.81 (m, 1H). |
| 119 (Ex. 33) | 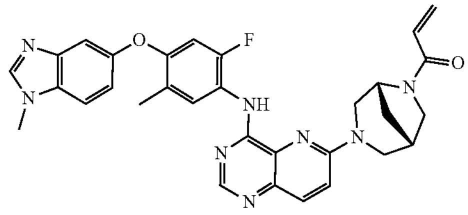 [SMILES: C=CC(=O)N1C[C@H]2C[C@@H]1CN(c1ccc3ncnc(Nc4cc(C)c(Oc5ccc6c(c5)ncn6C)cc4F)c3n1)C2] 1-((1S,5R)-3-(4-((2-fluoro-5-methyl-4-((1-methyl-1H-benzo[d]imidazol-5-yl)oxy)phenyl)amino)pyrido[3,2-d]pyrimidin-6-yl)-3,6-diazabicyclo[3.2.1]octan-6-yl)prop-2-en-1-one | 565.3 | $^{1}H$ NMR (500 MHz, $CDCl_3$) δ 8.84 (s, 1H), 8.67 - 8.57 (m, 2H), 7.97 - 7.90 (m, 1H), 7.87 (s, 1H), 7.38 - 7.32 (m, 2H), 7.22 - 7.13 (m, 1H), 7.05 (dd, J = 8.7, 2.1 Hz, 1H), 6.70 (d, J = 11.9 Hz, 1H), 6.61 - 6.31 (m, 2H), 5.79 - 5.61 (m, 1H), 4.79 (s, 1jH), 4.54 - 4.25 (m. 2H), 3.86 (s, 3H), 3.74 - 3.63 (m, 1H), 3.62 - 3.53 (m, 1H), 3.40 - 3.31 (m, 1H), 3.26 - 3.07 (m, 1H), 2.91 - 2.73 (m, 1H), 2.35 (s, 3H), 2.25 - 2.01 (m, 1H), 1.99 - 1.84 (m, 1H). |
| 120 (Ex. 34) | 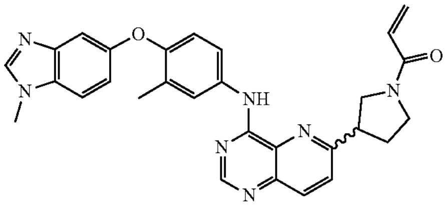 [SMILES: C=CC(=O)N1CCC(c2ccc3ncnc(Nc4ccc(Oc5ccc6c(c5)ncn6C)c(C)c4)c3n2)C1] rac-(R)-1-(3-(4-((3-methyl-4-((1-methyl-1H-benzo[d]imidazol-5-yl)oxy)phenyl)amino)pyrido[3,2-d]pyrimidin-6-yl)pyrrolidin-1-yl)prop-2-en-1-one | 506.3 | $^{1}H$ NMR δ 1H NMR (400 MHz, DMSO) δ 9.71 (s, 1H), 8.62 (d, J = 1.6 Hz, 1H), 8.21 - 8.13 (m, 2H), 7.97 - 7.72 (m, 3H), 7.57 (d, J = 8.7 Hz, 1H), 7.10 (d, J = 2.0 Hz, 1H), 7.00 (dd, J = 8.7, 2.1 Hz, 1H), 6.90 (d, J = 8.7 Hz, 1H), 6.69 (ddd, J = 29.4, 16.7, 10.3 Hz, 1H), 6.18 (dd, J = 16.7, 2.3 Hz, 1H), 5.69 (dd, J = 10.3, 2.2 Hz, 1H), 4.10 (d, J = 7.9 Hz, 1H), 4.05 - 3.60 (m, 6H), 3.53 - 3.43 (m, 1H), 2.48 - 2.35 (m, 2H), 2.27 (s, 3H). |
| 121 (Ex. 34) | 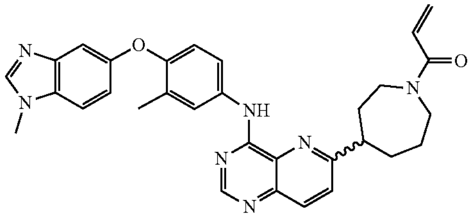 [SMILES: C=CC(=O)N1CCCC(c2ccc3ncnc(Nc4ccc(Oc5ccc6c(c5)ncn6C)c(C)c4)c3n2)CC1] 1-(4-(4-((3-methyl-4-((1-methyl-1H-benzo[d]imidazol-5-yl)oxy)phenyl)amino)pyrido[3,2-d]pyrimidin-6-yl)azepan-1-yl)prop-2-en-1-one | 534.20 | $^{1}H$ NMR (400 MHz, DMSO) δ 9.78 - 9.70 (m, 1H), 8.59 (s, 1H), 8.17 (s, 1H), 8.12 (dd, J = 8.6, 2.1 Hz, 1H), 7.94 - 7.75 (m, 3H), 7.57 (d, J = 8.7 Hz, 1H), 7.10 (d, J = 2.2 Hz, 1H), 7.00 (dd, J = 8.7, 2.3 Hz, 1H), 6.93 - 6.72 (m, 2H), 6.15 (ddd, J = 16.6, 5.3, 2.5 Hz, 1H), 5.78 - 5.63 (m, 1H), 4.42 - 4.28 (m, 1H), 3.96 - 3.44 (m, 7H), 2.26 (s, 3H), 2.23 - 1.64 (m, 6H). |

TABLE 2-continued

| Example No. (Method) | Structure; IUPAC name | LCMS $M^{+}1$ | $^{1}H$ NMR (ppm); $^{19}F$ NMR (ppm); optical rotation; Chiral HPLC/SFC conditions |
|---|---|---|---|
| 122 (Ex. 35) | 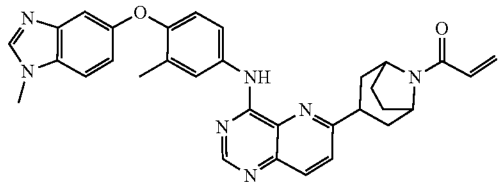 [SMILES: C=CC(=O)N1C2CCC1CC(c1ccc3ncnc(Nc4ccc(Oc5ccc6c(c5)ncn6C)c(C)c4)c3n1)C2] 1-(3-(4-((3-methyl-4-((1-methyl-1H-benzo[d]imidazol-5-yl)oxy)phenyl)amino)pyrido[3,2-d]pyrimidin-6-yl)-8-azabicyclo[3.2.1]octan-8-yl)prop-2-en-1-one | 546.30 | $^{1}H$ NMR (400 MHz, DMSO) δ 9.78 - 9.64 (m, 1H), 8.63 - 8.57 (m, 1H), 8.24 - 7.97 (m, 2H), 7.88 - 7.81 (m, 2H), 7.75 (dd, J = 8.7, 2.6 Hz, 1H), 7.57 (d, J = 8.7 Hz, 1H), 7.10 (d, J = 2.2 Hz, 1H), 7.00 (dd, J = 8.7, 2.3 Hz, 1H), 6.95 - 6.86 (m, 1H), 6.84 - 6.71 (m, 1H), 6.26 - 6.15 (m, 1H), 5.78 - 5.66 (m, 1H), 4.77 - 4.45 (m, 2H), 3.84 (s, 3H), 3.70 - 3.58 (m, 1H), 2.26 (s, 3H), 2.14 - 1.87 (m, 8H) |
| 123 (Ex. 35) | 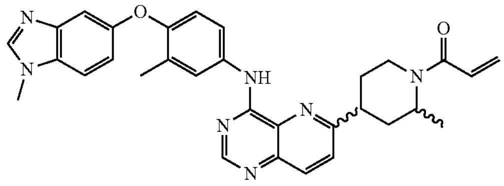 [SMILES: C=CC(=O)N1CCC(c2ccc3ncnc(Nc4ccc(Oc5ccc6c(c5)ncn6C)c(C)c4)c3n2)CC1C] 1-(2-methyl-4-(4-((3-methyl-4-((1-methyl-1H-benzo[d]imidazol-5-yl)oxy)phenyl)amino)pyrido[3,2-d]pyrimidin-6-yl)piperidin-1-yl)prop-2-en-1-one | 533.90 | $^{1}H$ NMR (400 MHz, $CDCl_3$) δ 9.04 - 8.97 (m, 1H), 8.76 - 8.71 (m, 1H), 8.11 (dd, J = 8.6, 1.5 Hz, 1H), 7.85 (s, 1H), 7.80 - 7.75 (m, 1H), 7.75 - 7.66 (m, 1H), 7.65 - 7.58 (m, 1H), 7.38 - 7.30 (m, 2H), 7.07 (dd, J = 8.4, 2.1 Hz, 1H), 6.95 (d, J = 8.7 Hz, 1H), 6.72 - 6.58 (m, 1H), 6.44 - 6.26 (m, 1H), 5.80 - 5.64 (m, 1H), 5.30 - 3.93 (m, 2H), 3.85 (s, 3H), 3.49 - 3.35 (m, 1H), 3.28 - 2.94 (m, 1H), 2.42 - 1.74 (m, 7H), 1.51 - 1.20 (m, 3H). |
| 124 (Ex. 35) | 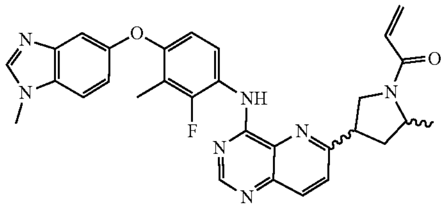 [SMILES: C=CC(=O)N1CC(c2ccc3ncnc(Nc4ccc(Oc5ccc6c(c5)ncn6C)c(C)c4F)c3n2)CC1C] 1-(4-(4-((2-fluoro-3-methyl-4-((1-methyl-1H-benzo[d]imidazol-5-yl)oxy)phenyl)amino)pyrido[3,2-d]pyrimidin-6-yl)-2-methylpyrrolidin-1-yl)prop-2-en-1-one | 538.30 | $^{1}H$ NMR (500 MHz, $CDCl_3$) δ 9.37 - 9.14 (m, 1H), 8.78 - 8.72 (m, 1H), 8.56 - 8.30 (m, 1H), 8.17 - 8.11 (m, 1H), 7.87 (s, 1H), 7.66 (d, J = 8.6 Hz, 1H), 7.35 (d, J = 8.5 Hz, 3H), 7.07 (d, J = 8.6 Hz, 1H), 6.77 (d, J = 8.9 Hz, 1H), 6.63 - 6.31 (m, 2H), 5.78 - 5.68 (m, 1H), 4.65 - 3.90 (m, 3H), 3.86 (s, 3H), 3.76 - 3.64 (m, 1H), 2.96 - 2.38 (m, 2H), 2.31 (s, 3H), 2.27 - 1.97 (m, 2H), 1.49 - 1.40 (m, 3H). |
| 125 (Ex. 35) | 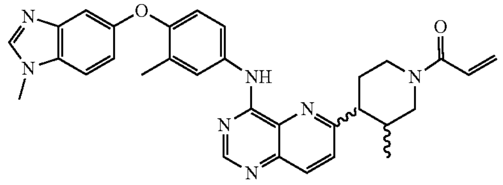 [SMILES: C=CC(=O)N1CCC(c2ccc3ncnc(Nc4ccc(Oc5ccc6c(c5)ncn6C)c(C)c4)c3n2)C(C)C1] 1-((3RS,4R*)3-methyl-4-(4-((3-methyl-4-((1-methyl-1H-benzo[d]imidazol-5-yl)oxy)phenyl)amino)pyrido[3,2-d]pyrimidin-6-yl)piperidin-1-yl)prop-2-en-1-one | 534.30 | $^{1}H$ NMR (400 MHz, $CDCl_3$) δ 9.03 - 8.97 (m, 1H), 8.77 - 8.71 (m, 1H), 8.15 - 8.07 (m, 1H), 7.85 (s, 1H), 7.80 - 7.65 (m, 2H), 7.65 - 7.48 (m, 1H), 7.36 - 7.30 (m, 2H), 7.07 (dd, J = 8.8, 2.2 Hz, 1H), 6.95 (d, J = 8.7 Hz, 1H), 6.86 - 6.48 (m, 1H), 6.39 - 6.29 (m, 1H), 5.78 - 5.67 (m, 1H), 5.08 - 4.56 (m, 1H), 4.38 - 3.94 (m, 1H), 3.85 (s, 3H), 3.61 - 3.06 (m, 2H), 3.01 - 2.69 (m, 1H), 2.64 - 2.25 (m, 6H), 2.12 - 1.82 (m, 1H), 0.92 - 0.63 (m, 3H). |
| 126 (Ex. 35) | 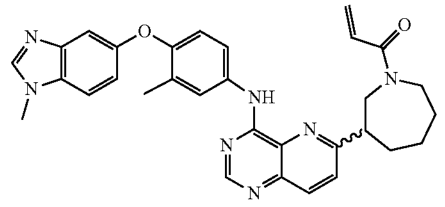 [SMILES: C=CC(=O)N1CCCCC(c2ccc3ncnc(Nc4ccc(Oc5ccc6c(c5)ncn6C)c(C)c4)c3n2)C1] | 534.30 | 1H NMR (500 MHz, $CDCl_3$) δ 9.34 - 8.88 (m, 1H), 8.77 - 8.71 (m, 1H), 8.16 - 8.06 (m, 1H), 7.93 - 7.53 (m, 4H), 7.35 - 7.30 (m, 2H), 7.09 - 7.03 (m, 1H), 6.97 - 6.92 (m, 1H), 6.69 - 6.60 (m, 1H), 6.45 - 6.38 (m, 1H), 5.77 - 5.68 (m, 1H), 4.35 - 4.05 (m,1H), 3.96 - 3.58 (m, 5H), 3.57 - 3.19 (m, 1H), 2.36 (s, 3H), 2.23 - 1.46 (m, 7H). |

TABLE 2-continued

| Example No. (Method) | Structure; IUPAC name | LCMS $M^{+}1$ | $^{1}H$ NMR (ppm); $^{19}F$ NMR (ppm); optical rotation; Chiral HPLC/SFC conditions |
|---|---|---|---|
| | 1-(3-(4-((3-methyl-4-((1-methyl-1H-benzo[d]imidazol-5-yl)oxy)phenyl)amino)pyrido[3,2-d]pyrimidin-6-yl)azepan-1-yl)prop-2-en-1-one | | |
| 127 (Ex. 35) | 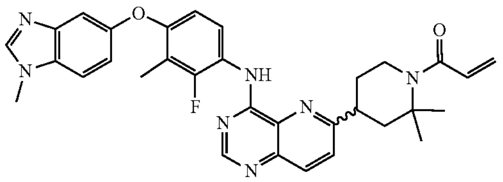 [SMILES: C=CC(=O)N1CCC(c2ccc3ncnc(Nc4ccc(Oc5ccc6c(c5)ncn6C)c(C)c4F)c3n2)CC1(C)C] 1-(4-(4-((2-fluoro-3-methyl-4-((1-methyl-1H-benzo[d]imidazol-5-yl)oxy)phenyl)amino)pyrido[3,2-d]pyrimidin-6-yl)-2,2-dimethylpiperidin-1-yl)prop-2-en-1-one | 566.30 | $^{1}H$ NMR (500 MHz, $CDCl_3$) δ 9.34 (s, 1H), 8.75 (s, 1H), 8.49 (t, J = 9.0 Hz, 1H), 8.12 (d, J = 8.6 Hz, 1H), 7.87 (s, 1H), 7.64 (d, J = 8.6 Hz, 1H), 7.38 - 7.32 (m, 2H), 7.07 (dd, J = 8.8, 2.0 Hz, 1H), 6.77 (d, J = 8.9 Hz, 1H), 6.58 (dd, J = 16.9, 10.5 Hz, 1H), 6.20 (dd, J = 16.9, 1.6 Hz, 1H), 5.62 (dd, J = 10.5, 1.5 Hz, 1H), 3.97 - 3.79 (m, 4H), 3.47 (ddd, J = 13.6, 8.7, 3.8 Hz, 1H), 3.35 (ddt, J = 13.0, 9.7, 4.8 Hz, 1H), 2.31 (s, 3H), 2.25 - 2.17 (m, 1H), 2.16 - 2.05 (m, 2H), 1.85 (dd, J = 13.8, 2.7 Hz, 1H), 1.69 (s, 3H), 1.61 (s, 3H). |
| 128 (Ex. 35) | 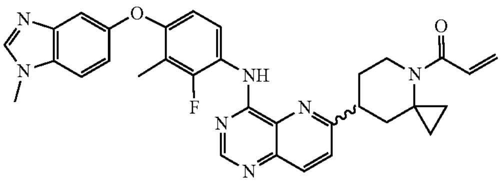 [SMILES: C=CC(=O)N1CCC(c2ccc3ncnc(Nc4ccc(Oc5ccc6c(c5)ncn6C)c(C)c4F)c3n2)CC12CC2] 1-(7-(4-((2-fluoro-3-methyl-4-((1-methyl-1H-benzo[d]imidazol-5-yl)oxy)phenyl)amino)pyrido[3,2-d]pyrimidin-6-yl)-4-azaspiro[2.5]octan-4-yl)prop-2-en-1-one | 564.30 | $^{1}H$ NMR (500 MHz, $CDCl_3$) δ 9.26 (s, 1H), 8.73 (s, 1H), 8.42 (t, J = 9.0 Hz, 1H), 8.10 (d, J = 8.7 Hz, 1H), 7.86 (s, 1H), 7.61 (d, J = 8.7 Hz, 1H), 7.37 - 7.32 (m, 2H), 7.07 (dd, J = 8.7, 2.3 Hz, 1H), 6.98 - 6.89 (m, 1H), 6.75 (d, J = 9.1 Hz, 1H), 6.41 (d, J = 16.9 Hz, 1H), 5.74 (d, J = 9.5 Hz, 1H), 4.80 (s, 1H), 3.86 (s, 3H), 3.47 (t, J = 11.8 Hz, 1H), 3.09 (s, 1H), 2.49 - 2.35 (m, 1H), 2.33 - 2.29 (m, 3H), 2.14 - 2.08 (m, 1H), 2.01 - 1.84 (m, 1H), 1.54 - 1.33 (m, 3H), 1.21 - 1.09 (m, 1H), 0.86 - 0.74 (m, 2H). |
| 129 (Ex. 37) | 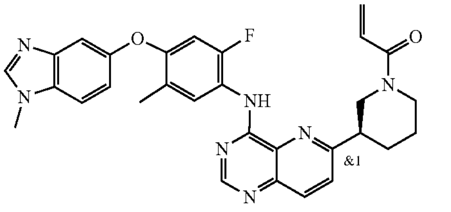 [SMILES: C=CC(=O)N1CCC[C@@H](c2ccc3ncnc(Nc4cc(C)c(Oc5ccc6c(c5)ncn6C)cc4F)c3n2)C1] rac-(R)-1-(3-(4-((2-fluoro-5-methyl-4-((1-methyl-1H-benzo[d]imidazol-5-yl)oxy)phenyl)amino)pyrido[3,2-d]pyrimidin-6-yl)piperidin-1-yl)prop-2-en-1-one | 538.1 | $^{1}H$ NMR (400 MHz, $CDCl_3$) δ 10.28 - 9.35 (m, 1H), 9.07 - 8.66 (m, 2H), 8.66 - 8.46 (m, 1H), 8.41 - 8.10 (m, 1H), 7.84 - 7.65 (m, 1H), 7.54 - 7.47 (m, 1H), 7.47 - 7.33 (m, 1H), 7.25 - 7.20 (m, 1H), 6.77 - 6.68 (m, 1H), 6.67 - 6.56 (m, 1H), 6.42 - 6.08 (m, 1H), 5.76 - 5.60 (m, 1H), 4.80 - 4.16 (m, 1H), 4.05 (s, 3H), 3.85 - 3.43 (m, 2H), 3.37 - 2.80 (m, 2H), 2.33 (s, 3H), 2.31 - 2.23 (m, 2H), 2.23 - 2.11 (m, 1H), 2.05 - 1.83 (m, 1H). |
| 130 (Ex. 37) | 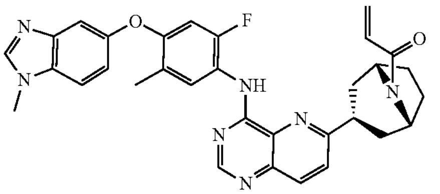 rac-1-((1R,5S)-3-(4-((2-fluoro-5-methyl-4-((1-methyl-1H-benzo[d]imidazol-5-yl)oxy)phenyl)amino)pyrido[3,2-d]pyrimidin-6-yl)-8-azabicyclo[3.2.1]octan-8-yl)prop-2-en-1-one | 564.2 | $^{1}H$ NMR (400 MHz, $CDCl_3$) δ 9.53 - 9.37 (m, 1H), 8.86 - 8.78 (m, 1H), 8.72 - 8.47 (m, 1H), 8.44 - 8.28 (m, 1H), 7.84 - 7.65 (m, 1H), 7.53 - 7.47 (m, 1H), 7.42 - 7.32 (m, 1H), 7.25 - 7.21 (m, 1H), 6.83 - 6.72 (m, 1H), 6.63 - 6.51 (m, 1H), 6.49 - 6.34 (m, 1H), 5.83 - 5.66 (m, 1H), 5.04 - 4.78 (m, 1H), 4.61 - 4.36 (m, 1H), 4.05 (d, J = 4.6 Hz, 3H), 3.71 - 3.23 (m, 1H), 2.74 - 2.39 (m, 1H), 2.32 (s, 4H), 2.26 - 2.15 (m, 1H), 2.15 - 2.05 (m, 2H), 2.05 - 1.89 (m, 3H). |

TABLE 2-continued

| Example No. (Method) | Structure; IUPAC name | LCMS $M^{+}1$ | $^{1}H$ NMR (ppm); $^{19}F$ NMR (ppm); optical rotation; Chiral HPLC/SFC conditions |
|---|---|---|---|
| 131 (Ex. 37) | 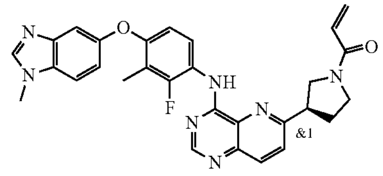 [SMILES: C=CC(=O)N1CC[C@@H](c2ccc3ncnc(Nc4ccc(Oc5ccc6c(c5)ncn6C)c(C)c4F)c3n2)C1] rac-(R)-1-(3-(4-((2-fluoro-3-methyl-4-((1-methyl-1H-benzo[d]imidazol-5-yl)oxy)phenyl)amino)pyrido[3,2-d]pyrimidin-6-yl)pyrrolidin-1-yl)prop-2-en-1-one | 524.2 | $^{1}H$ NMR (400 MHz, $CDCl_3$) δ 9.24 (s, 1H), 8.78 - 8.72 (m, 1H), 8.44 (td, J = 9.0, 4.8 Hz, 1H), 8.15 (dd, J = 8.6, 7.0 Hz, 1H), 7.86 (s, 1H) 7.67 (dd, J = 8.6, 4.6 Hz, 1H), 7.39 - 7.30 (m, 2H), 7.10 - 7.03 (m, 1H), 6.75 (ddd, J = 9.0, 3.5, 1.7 Hz, 1H), 6.55 (ddd, J = 16.8, 10.0, 4.6 Hz, 1H), 6.43 (dt, J = 16.8, 2.4 Hz, 1H), 5.73 (dt, J = 10.0, 2.4 Hz, 1H), 4.24 - 4.09 (m, 1H), 4.07 - 3.88 (m, 2H), 3.86 (s, 3H), 3.83 - 3.64 (m, 1H), 2.60 - 2.43 (m, 2H), 2.38 - 2.18 (m, 4H). |
| 132 (Ex. 37) | 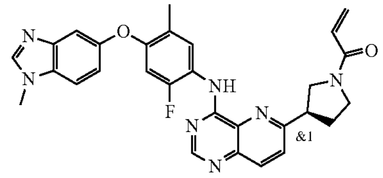 [SMILES: C=CC(=O)N1CC[C@@H](c2ccc3ncnc(Nc4cc(C)c(Oc5ccc6c(c5)ncn6C)cc4F)c3n2)C1] rac-(R)-1-(3-(4-((2-fluoro-5-methyl-4-((1-methyl-1H-benzo[d]imidazol-5-yl)oxy)phenyl)amino)pyrido[3,2-d]pyrimidin-6-yl)pyrrolidin-1-yl)prop-2-en-1-one | 524.2 | $^{1}H$ NMR (400 MHz, $CDCl_3$) δ 9.12 (s, 1H), 8.84 - 8.77 (m, 1H), 7.86 (s, 1H), 8.57 - 8.48 (m, 1H), 8.15 (dd, J = 8.6, 7.1 Hz, 1H), 7.66 (dd, J = 8.6, 5.0 Hz, 1H), 7.41 - 7.33 (m, 2H), 7.10 - 7.03 (m, 1H), 6.72 - 6.64 (m, 1H), 6.51 (ddd, J = 16.8, 10.1, 4.3 Hz, 1H), 6.40 (ddd, J = 16.8, 2.3, 1.1 Hz, 1H), 5.70 (dd, J = 10.1, 2.3 Hz, 1H), 4.20 - 4.06 (m, 1H), 4.04 - 3.87 (m, 2H), 3.87 (s, 3H), 3.85 - 3.62 (m, 2H), 2.59 - 2.40 (m, 1H), 2.40 - 2.35 (m, 3H), 2.35 - 2.23 (m, 1H). |
| 133 (Ex. 37) | 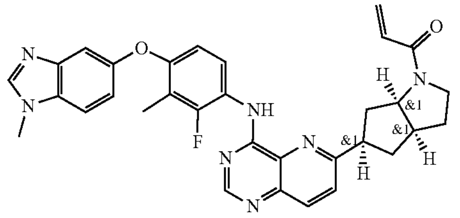 [SMILES: C=CC(=O)N1CC[C@H]2C[C@@H](c3ccc4ncnc(Nc5ccc(Oc6ccc7c(c6)ncn7C)c(C)c5F)c4n3)C[C@H]21] rac-1-((3aR,5R,6aR)-5-(4-((2-fluoro-3-methyl-4-((1-methyl-1H-benzo[d]imidazol-5-yl)oxy)phenyl)amino)pyrido[3,2-d]pyrimidin-6-yl)hexahydrocyclopenta[b]pyrrol-1(2H)-yl)prop-2-en-1-one | 564.2 | $^{1}H$ NMR (400 MHz, $CDCl_3$) δ 9.38 - 9.28 (m, 1H), 8.76 - 8.70 (m, 1H), 8.54 - 8.43 (m. 1H), 8.12 - 8.03 (m, 1H), 7.86 (s, 1H), 7.64 - 7.57 (m, 1H), 7.38 - 7.28 (m, 2H), 7.10 - 7.02 (m, 1H), 6.80 - 6.72 (m, 1H), 6.61 - 6.32 (m, 2H), 5.73 - 5.63 (m, 1H), 4.75 - 4.42 (m, 1H), 4.19 - 3.96 (m, 1H), 3.86 (s, 3H), 3.84 - 3.67 (m. 1H), 3.63 - 3.43 (m, 1H), 3.08 - 2.67 (m, 2H), 2.50 - 2.33 (m, 1H), 2.30 (d, J = 2.2 Hz, 3H), 2.24 - 1.85 (m, 4H). |
| 134 (Ex. 37) | 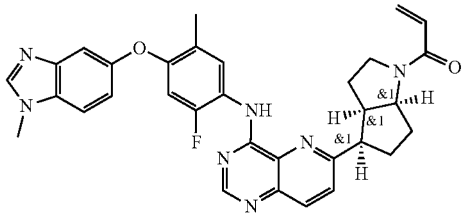 [SMILES: C=CC(=O)N1CC[C@@H]2[C@H](c3ccc4ncnc(Nc5cc(C)c(Oc6ccc7c(c6)ncn7C)cc5F)c4n3)CC[C@@H]21] rac-1-((3aR,4R,6aS)-4-(4-((2-fluoro-5-methyl-4-((1-methyl-1H-benzo[d]imidazol-5-yl)oxy)phenyl)amino)pyrido[3,2-d]pyrimidin-6-yl)hexahydrocyclopenta[b]pyrrol-1(2H)-yl)prop-2-en-1-one | 564.2 | $^{1}H$ NMR (400 MHz, $CDCl_3$) δ 9.27 - 9.21 (m, 1H), 8.80 (s, 1H), 8.66 - 8.56 (m, 1H), 8.12 (dd, J = 8.6, 1.5 Hz, 1H), 7.86 (s, 1H), 7.68 - 7.60 (m, 1H), 7.40 - 7.33 (m, 2H), 7.11 - 7.02 (m, 1H), 6.74 - 6.66 (m, 1H), 6.57 - 6.32 (m, 2H), 5.74 - 5.61 (m, 1H), 4.73 - 4.48 (m, 1H), 3.87 (s, 3H), 3.75 - 3.59 (m, 2H), 3.58 - 3.43 (m, 1H), 3.39 - 3.17 (m, 1H), 2.57 - 2.26 (m, 4H), 2.23 - 2.07 (m, 2H), 2.05 - 1.95 (m, 1H), 1.79 - 1.50 (m, 2H). |

TABLE 2-continued

| Example No. (Method) | Structure; IUPAC name | LCMS $M^{+}1$ | $^{1}$H NMR (ppm); $^{19}$F NMR (ppm); optical rotation; Chiral HPLC/SFC conditions |
|---|---|---|---|
| 135 (Ex. 36) | 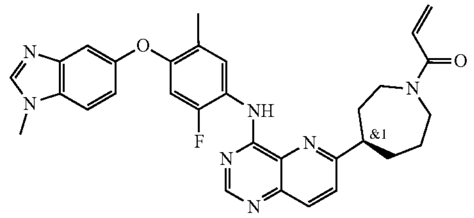 [SMILES: C=CC(=O)N1CCC[C@@H](c2ccc3ncnc(Nc4cc(C)c(Oc5ccc6c(c5)ncn6C)cc4F)c3n2)CC1] rac-(R)-1-(4-(4-((2-fluoro-5-methyl-4-((1-methyl-1H-benzo[d]imidazol-5-yl)oxy)phenyl)amino)pyrido[3,2-d]pyrimidin-6-yl)azepan-1-yl)prop-2-en-1-one | 552.2 | 1H NMR (400 MHz, $CDCl_3$) δ 9.42 - 9.19 (m, 1H), 8.75 (d, J = 7.1 Hz, 1H), 8.50 (td, J = 9.1, 7.0 Hz, 1H), 8.13 (dd, J = 16.5, 8.6 Hz, 1H), 7.86 (s, 1H), 7.69 (dd, J = 42.0, 8.6 Hz, 1H), 7.35 (dt, J = 5.8, 2.2 Hz, 2H), 7.11 - 7.03 (m, 1H), 6.81 - 6.74 (m, 1H), 6.71 - 6.61 (m, 1H), 6.48 - 6.36 (m, 1H), 5.78 - 5.70 (m, 1H), 4.55 - 4.46 (m, 1H), 4.30 - 4.14 (m, 1H), 3.98 - 3.88 (m, 1H), 3.86 (s, 3H), 3.81 - 3.70 (m, 1H), 3.59 - 3.48 (m, 1H), 3.48 - 3.39 (m, 1H), 3.38 - 3.25 (m, 1H), 2.31 (t, J = 2.0 Hz, 3H), 2.23 - 1.95 (m, 3H), 1.95 - 1.76 (m, 1H). |
| 136 (Ex. 36) | 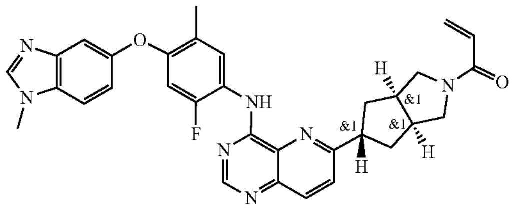 [SMILES: C=CC(=O)N1C[C@H]2C[C@H](c3ccc4ncnc(Nc5cc(C)c(Oc6ccc7c(c6)ncn7C)cc5F)c4n3)C[C@H]2C1] 1-((3aR,5s,6aS)-5-(4-((2-fluoro-5-methyl-4-((1-methyl-1H-benzo[d]imidazol-5-yl)oxy)phenyl)amino)pyrido[3,2-d]pyrimidin-6-yl)hexahydrocyclopenta[c]pyrrol-2(1H)-yl)prop-2-en-1-one | 564.2 | $^{1}$H NMR (500 MHz, $CDCl_3$) δ 9.32 - 9.15 (m, 1H), 8.81 - 8.76 (m, 1H), 8.62 - 8.55 (m, 1H), 8.12 - 8.06 (m, 1H), 7.89 - 7.85 (m, 1H), 7.65 - 7.58 (m, 1H), 7.39 - 7.33 (m, 2H), 7.10 - 7.03 (m, 1H), 6.73 - 6.66 (m, 1H), 6.53 - 6.42 (m, 1H), 6.38 - 6.28 (m, 1H), 5.72 - 5.59 (m, 1H), 3.92 - 3.78 (m, 1H), 3.76 - 3.43 (m, 5H), 3.17 - 2.78 (m, 2H), 2.54 - 2.23 (m, 6H), 2.17 - 1.76 (m, 3H). |
| 137 (Ex. 36) | 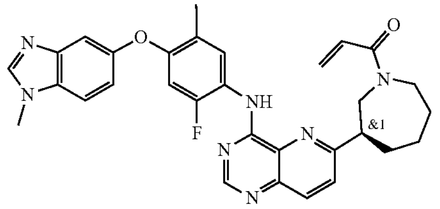 [SMILES: C=CC(=O)N1CCCC[C@@H](c2ccc3ncnc(Nc4cc(C)c(Oc5ccc6c(c5)ncn6C)cc4F)c3n2)C1] rac-(R)-1-(3-(4-((2-fluoro-5-methyl-4-((1-methyl-1H-benzo[d]imidazol-5-yl)oxy)phenyl)amino)pyrido[3,2-d]pyrimidin-6-yl)azepan-1-yl)prop-2-en-1-one | 552.2 | $^{1}$H NMR (500 MHz, $CDCl_3$) δ 9.37 - 9.14 (m, 1H), 8.82 - 8.77 (m, 1H), 8.63 - 8.55 (m, 1H), 8.18 - 8.08 (m, 1H), 7.89 - 7.86 (m, 1H), 7.78 - 7.60 (m, 1H), 7.39 - 7.33 (m, 2H), 7.10 - 7.03 (m, 1H), 6.73 - 6.59 (m, 2H), 6.51 - 6.32 (m, 1H), 5.87 - 5.60 (m, 1H), 4.50 - 4.43 (m, 1H), 4.26-4.12 (m, 1H), 3.91 - 3.68 (m, 4H), 3.55 - 3.37 (m, 2H), 3.37 - 3.16 (m, 1H), 2.40 - 2.35 (m, 3H), 2.17 - 1.93 (m, 4H), 1.93 - 1.74 (m, 1H). |
| 138 (Ex. 36) | 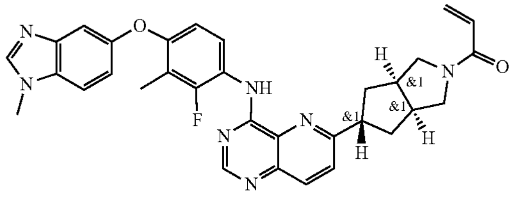 [SMILES: C=CC(=O)N1C[C@H]2C[C@H](c3ccc4ncnc(Nc5ccc(Oc6ccc7c(c6)ncn7C)c(C)c5F)c4n3)C[C@H]2C1] 1-((3aR,5s,6aS)-5-(4-((2-fluoro-3-methyl-4-((1-methyl-1H-benzo[d]imidazol-5-yl)oxy)phenyl)amino)pyrido[3,2-d]pyrimidin-6-yl)hexahydrocyclopenta[c]pyrrol-2(1H)-yl)prop-2-en-1-one | 564.2 | $^{1}$H NMR (500 MHz, $CDCl_3$) δ 9.36 (s, 1H), 8.73 (s, 1H), 8.55 - 8.48 (m, 1H), 8.09 (d, J = 8.6 Hz, 1H), 7.86 (s, 1H), 7.61 (d, J = 8.6 Hz, 1H), 7.37 - 7.32 (m, 2H), 7.09 - 7.03 (m, 1H), 6.80 - 6.74 (m, 1H), 6.55 - 6.46 (m, 1H), 6.44 - 6.34 (m, 1H), 5.74 - 5.64 (m, 1H), 4.07 - 3.82 (m, 5H), 3.79 - 3.41 (m, 3H), 3.15 - 2.86 (m, 1H), 2.61 - 2.21 (m, 5H), 2.16 - 1.80 (m, 3H). |

TABLE 2-continued

| Example No. (Method) | Structure; IUPAC name | LCMS $M^+1$ | $^1H$ NMR (ppm); $^{19}F$ NMR (ppm); optical rotation; Chiral HPLC/SFC conditions |
|---|---|---|---|
| 139 (Ex. 36) | 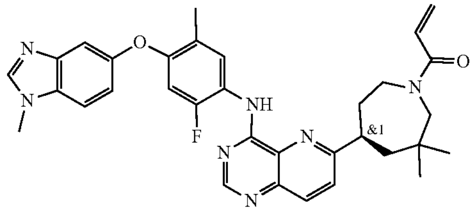 [SMILES: C=CC(=O)N1CC[C@H](c2ccc3ncnc(Nc4cc(C)c(Oc5ccc6c(c5)ncn6C)cc4F)c3n2)CC(C)(C)C1]<br>rac-(R)-1-(5-(4-((2-fluoro-5-methyl-4-((1-methyl-1H-benzo[d]imidazol-5-yl)oxy)phenyl)amino)pyrido[3,2-d]pyrimidin-6-yl)-3,3-dimethylazepan-1-yl)prop-2-en-1-one | 580.2 | $^1H$ NMR (400 MHz, $CDCl_3$) δ 9.24 (s, 1H), 8.81 - 8.76 (m, 1H), 8.61 - 8.51 (m, 1H), 8.14 (dd, J = 8.7, 2.6 Hz, 1H), 7.98 (s, 1H), 7.58 (dd, J = 8.7, 3.3 Hz, 1H), 7.42 - 7.34 (m, 2H), 7.13 - 7.06 (m, 1H), 6.75 - 6.60 (m, 2H), 6.39 (ddd, J = 16.7, 8.6, 2.1 Hz, 1H), 5.72 (ddd, J = 10.5, 4.8, 2.1 Hz, 1H), 3.97 - 3.88 (m, 4H), 3.88 - 3.68 (m, 2H), 3.59 - 3.33 (m, 1H), 3.32 - 3.16 (m, 1H), 2.36 (s, 3H), 2.32 - 2.06 (m, 2H), 1.98 - 1.62 (m, 4H), 1.11 (d, J = 3.3 Hz, 3H), 1.06 (d, J = 7.4 Hz, 3H). |
| 140 (Ex. 36) | 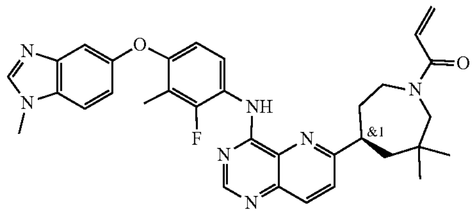 [SMILES: C=CC(=O)N1CC[C@H](c2ccc3ncnc(Nc4ccc(Oc5ccc6c(c5)ncn6C)c(C)c4F)c3n2)CC(C)(C)C1]<br>rac-(R)-1-(5-(4-((2-fluoro-3-methyl-4-((1-methyl-1H-benzo[d]imidazol-5-yl)oxy)phenyl)amino)pyrido[3,2-d]pyrimidin-6-yl)-3,3-dimethylazepan-1-yl)prop-2-en-1-one | 580.2 | $^1H$ NMR (400 MHz, $CDCl_3$) δ 9.31 (s, 1H), 8.76 - 8.70 (m, 1H), 8.52 - 8.42 (m, 1H), 8.10 (dd, J = 8.6, 6.1 Hz, 1H), 7.86 (s, 1H), 7.57 (dd, J = 8.6, 4.6 Hz, 1H), 7.38 - 7.31 (m, 2H), 7.11 - 7.03 (m, 1H), 6.80 - 6.62 (m, 2H), 6.41 (ddd, J = 16.8, 7.3, 2.1 Hz, 1H), 5.74 (ddd, J = 10.0, 7.3, 2.1 Hz, 1H), 3.99 - 3.67 (m, 5H), 3.60 - 3.35 (m, 1H), 3.33 - 3.17 (m, 1H), 2.45 - 2.30 (m, 5H), 2.27 - 2.04 (m, 1H), 1.98 - 1.66 (m, 2H), 1.13 (d, J = 2.6 Hz, 3H), 1.08 (d, J = 6.0 Hz, 3H). |
| 141 (Ex. 36) | 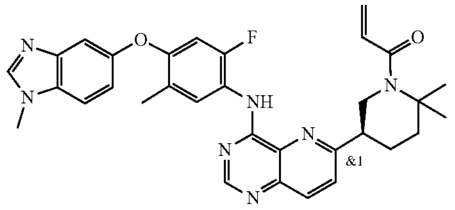 [SMILES: C=CC(=O)N1C[C@H](c2ccc3ncnc(Nc4cc(C)c(Oc5ccc6c(c5)ncn6C)cc4F)c3n2)CCC1(C)C]<br>rac-(R)-1-(5-(4-((2-fluoro-5-methyl-4-((1-methyl-1H-benzo[d]imidazol-5-yl)oxy)phenyl)amino)pyrido[3,2-d]pyrimidin-6-yl)-2,2-dimethylpiperidin-1-yl)prop-2-en-1-one | 566.2 | $^1H$ NMR (400 MHz, $CDCl_3$) δ 9.26 (s, 1H), 8.80 (s, 1H), 8.60 (d, J = 9.0 Hz, 1H), 8.18 (d, J = 8.6 Hz, 1H), 8.00 (s, 1H), 7.67 (d, J = 8.6 Hz, 1H), 7.42 - 7.34 (m, 2H), 7.09 (dd, J = 8.7, 2.3 Hz, 1H), 6.71 (d, J = 11.8 Hz, 1H), 6.47 (dd, J = 16.9, 10.5 Hz, 1H), 6.13 (dd, J = 16.9, 1.8 Hz, 1H), 5.53 (dd, J = 10.5, 1.8 Hz, 1H), 4.01 (dd, J = 14.2, 4.7 Hz, 1H), 3.89 (s, 3H), 3.61 (dd, J = 14.2, 10.0 Hz, 1H), 3.37 - 3.25 (m, 1H), 2.37 (s, 3H), 2.22 - 1.98 (m, 2H), 1.98 - 1.73 (m, 2H), 1.67 (s, 3H), 1.53 (s, 3H). |
| 142 (Ex. 37) | 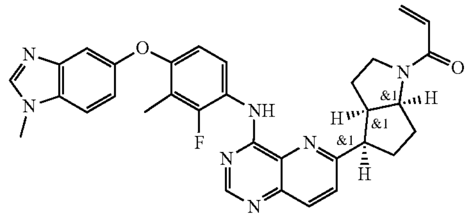 [SMILES: C=CC(=O)N1CC[C@@H]2[C@H](c3ccc4ncnc(Nc5ccc(Oc6ccc7c(c6)ncn7C)c(C)c5F)c4n3)CC[C@@H]21]<br>rac-1-((3aR,4R,6aS)-4-(4-((2-fluoro-3-methyl-4-((1-methyl-1H-benzo[d]imidazol-5-yl)oxy)phenyl)amino)pyrido[3,2-d]pyrimidin-6-yl)hexahydrocyclopenta[b]pyrrol-1(2H)-yl)prop-2-en-1-one | 564.2 | $^1H$ NMR (400 MHz, $CDCl_3$) δ 9.39 - 9.34 (m, 1H), 8.75 (s, 1H), 8.58 - 8.47 (m, 1H), 8.15 - 8.08 (m, 1H), 7.69 - 7.61 (m, 1H), 7.38 - 7.31 (m, 2H), 7.11 - 7.02 (m, 1H), 6.81 - 6.74 (m, 1H), 6.68 - 6.28 (m, 2H), 5.75 - 5.64 (m, 1H), 4.81 - 4.52 (m, 1H), 3.86 (s, 3H), 3.78 - 3.59 (m, 2H), 3.59 - 3.45 (m, 1H), 3.43 - 3.17 (m, 1H), 2.56 - 2.28 (m, 4H), 2.27 - 2.08 (m, 2H), 2.08 - 1.94 (m, 1H), 1.84 - 1.59 (m, 2H). |

TABLE 2-continued

| Example No. (Method) | Structure; IUPAC name | LCMS $M^+1$ | $^1$H NMR (ppm); $^{19}$F NMR (ppm); optical rotation; Chiral HPLC/SFC conditions |
|---|---|---|---|
| 143 (Ex. 37) | 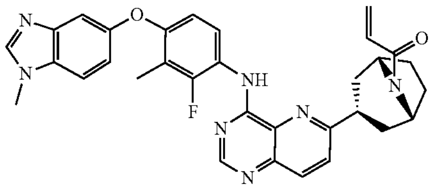 rac-1-((1R,5S)-3-(4-((2-fluoro-3-methyl-4-((1-methyl-1H-benzo[d]imidazol-5-yl)oxy)phenyl)amino)pyrido[3,2-d]pyrimidin-6-yl)-8-azabicyclo[3.2.1]octan-8-yl)prop-2-en-1-one | 564.2 | 1H NMR (400 MHz, $CDCl_3$) δ 9.40 – 9.18 (m, 1H), 8.86 – 8.62 (m, 1H), 8.61 – 8.36 (m, 1H), 8.19 – 7.96 (m, 1H), 7.84 – 7.56 (m, 1H), 7.38 – 7.29 (m, 2H), 7.11 – 7.03 (m, 1H), 6.82 – 6.71 (m, 1H), 6.66 – 6.54 (m, 1H), 6.50 – 6.41 (m, 1H), 5.75 (dd, J = 10.2, 2.2 Hz, 1H), 5.03 – 4.80 (m, 1H), 4.67 – 4.43 (m, 1H), 3.86 (d, J = 0.9 Hz, 3H), 3.68 – 3.25 (m, 1H), 2.79 – 2.58 (m, 1H), 2.45 – 2.37 (m, 1H), 2.31 (dd, J = 4.1, 2.2 Hz, 4H), 2.28 – 2.17 (m, 1H), 2.13 – 2.06 (m, 1H), 2.06 – 1.93 (m, 2H), 1.94 – 1.76 (m, 1H). |
| 144 (Ex. 37) | 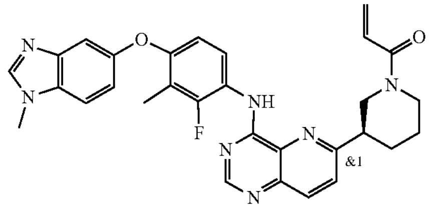 [SMILES: C=CC(=O)N1CCC[C@@H](c2ccc3ncnc(Nc4ccc(Oc5ccc6c(c5)ncn6C)c(C)c4F)c3n2)C1] rac-(R)-1-(3-(4-((2-fluoro-3-methyl-4-((1-methyl-1H-benzo[d]imidazol-5-yl)oxy)phenyl)amino)pyrido[3,2-d]pyrimidin-6-yl)piperidin-1-yl)prop-2-en-1-one | 538.1 | $^1$H NMR (400 MHz, $CDCl_3$) δ 9.78 – 9.33 (m, 1H), 8.79 – 8.72 (m, 1H), 8.61 – 8.06 (m, 2H), 7.75 – 7.63 (m, 1H), 7.47 – 7.32 (m, 2H), 7.15 (d, J = 8.8 Hz, 1H), 6.83 – 6.73 (m, 1H), 6.70 – 6.58 (m, 1H), 6.30 (t, J = 15.4 Hz, 1H), 5.71 (dd, J = 10.6, 1.9 Hz, 1H), 4.80 – 4.26 (m, 1H), 3.94 (s, 3H), 3.69 – 3.35 (m, 2H), 3.28 – 2.76 (m, 2H), 2.29 (d, J = 2.1 Hz, 3H), 2.18 – 1.89 (m, 2H), 1.89 – 1.61 (m, 2H). |
| 145 (Ex. 36) | 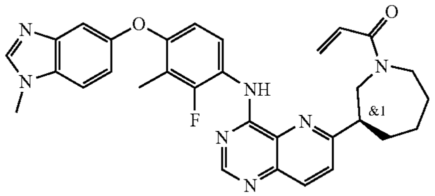 [SMILES: C=CC(=O)N1CCCC[C@@H](c2ccc3ncnc(Nc4ccc(Oc5ccc6c(c5)ncn6C)c(C)c4F)c3n2)C1] rac-(R)-1-(3-(4-((2-fluoro-3-methyl-4-((1-methyl-1H-benzo[d]imidazol-5-yl)oxy)phenyl)amino)pyrido[3,2-d]pyrimidin-6-yl)azepan-1-yl)prop-2-en-1-one | 552.2 | $^1$H NMR (400 MHz, $CDCl_3$) δ 9.43 – 9.19 (m, 1H), 8.75 (d, J = 7.1 Hz, 1H), 8.50 (td, J = 9.1, 7.0 Hz, 1H), 8.13 (dd, J = 16.5, 8.6 Hz, 1H), 7.86 (s, 1H), 7.69 (dd, J = 42.0, 8.6 Hz, 1H), 7.35 (dt, J = 5.8, 2.2 Hz, 2H), 7.11 – 7.03 (m, 1H), 6.81 – 6.74 (m, 1H), 6.72 – 6.61 (m, 1H), 6.49 – 6.36 (m, 1H), 5.78 – 5.70 (m, 1H), 4.55 – 4.46 (m, 1H), 4.31 – 4.14 (m, 1H), 3.98 – 3.88 (m, 1H), 3.86 (s, 3H), 3.81 – 3.70 (m, 1H), 3.60 – 3.49 (m, 1H), 3.48 – 3.39 (m, 1H), 3.38 – 3.25 (m, 1H), 2.31 (t, J = 2.0 Hz, 3H), 2.23 – 1.95 (m, 3H), 1.95 – 1.77 (m, 1H). |
| 146 (Ex. 37) | 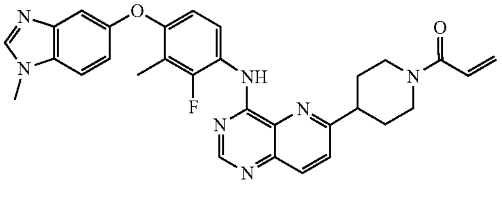 [SMILES: C=CC(=O)N1CCC(c2ccc3ncnc(Nc4ccc(Oc5ccc6c(c5)ncn6C)c(C)c4F)c3n2)CC1] 1-(4-(4-((2-fluoro-3-methyl-4-((1-methyl-1H-benzo[d]imidazol-5-yl)oxy)phenyl)amino)pyrido[3,2-d]pyrimidin-6-yl)piperidin-1-yl)prop-2-en-1-one | 538.1 | $^1$H NMR (400 MHz, $CDCl_3$) δ 9.30 (s, 1H), 8.74 (s, 1H), 8.46 (t, J = 9.1 Hz, 1H), 8.13 (d, J = 8.6 Hz, 1H), 7.86 (s, 1H), 7.63 (d, J = 8.6 Hz, 1H), 7.38 – 7.31 (m, 2H), 7.07 (dd, J = 8.8, 2.3 Hz, 1H), 6.79 – 6.73 (m, 1H), 6.68 (dd, J = 16.9, 10.6 Hz, 1H), 6.33 (dd, J = 16.9, 2.0 Hz, 1H), 5.73 (dd, J = 10.6, 2.0 Hz, 1H), 4.91 – 4.83 (m, 1H), 4.26 – 4.18 (m, 1H), 3.86 (s, 3H), 3.36 – 3.26 (m, 1H), 3.21 (tt, J = 11.7, 3.8 Hz, 1H), 2.95 – 2.84 (m, 1H), 2.31 (d, J = 2.2 Hz, 3H), 2.22 – 2.09 (m, 2H), 2.05 – 1.85 (m, 2H). |

TABLE 2-continued

| Example No. (Method) | Structure; IUPAC name | LCMS $M^+1$ | $^1H$ NMR (ppm); $^{19}F$ NMR (ppm); optical rotation; Chiral HPLC/SFC conditions |
|---|---|---|---|
| 147 (Ex. 37) | 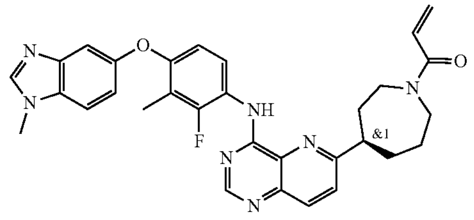 [SMILES: C=CC(=O)N1CCC[C@@H](c2ccc3ncnc(Nc4ccc(Oc5ccc6c(c5)ncn6C)c(C)c4F)c3n2)CC1] rac-(R)-1-(4-(4-((2-fluoro-3-methy-4-((1-methyl-1H-benzo[d]imidazol-5-yl)oxy)phenyl)amino)pyrido[3,2-d]pyrimidin-6-yl)azepan-1-yl)prop-2-en-1-one | 552.2 | $^1H$ NMR (400 MHz, $CDCl_3$) δ 9.30 (s, 1H), 8.73 (d, J = 2.7 Hz, 1H), 8.52 - 8.40 (m, 1H), 8.09 (dd, J = 8.6, 5.2 Hz, 1H), 7.86 (s, 1H), 7.59 (d, J = 8.6 Hz, 1H), 7.38 - 7.29 (m, 2H), 7.10 - 7.03 (m, 1H), 6.76 (d, J = 8.8 Hz, 1H), 6.66 (ddd, J = 16.9, 10.4, 6.8 Hz, 1H), 6.41 (ddd, J = 16.9, 6.8, 2.0 Hz, 1H), 5.74 (dt, J = 10.4, 2.0 Hz, 1H), 3.99 - 3.88 (m, 1H), 3.86 (s, 3H), 3.85 - 3.52 (m, 3H), 3.18 - 3.08 (m, 1H), 2.38 - 2.21 (m, 4H), 2.20 - 2.06 (m, 3H), 2.02 - 1.80 (m, 2H). |
| 148 (Ex. 38) | 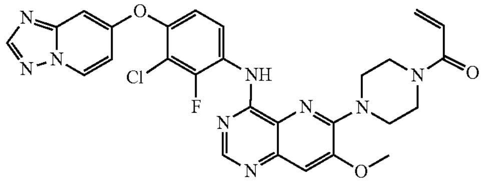 [SMILES: C=CC(=O)N1CCN(c2nc3c(Nc4ccc(Oc5ccn6ncnc6c5)c(Cl)c4F)ncnc3cc2OC)CC1] 1-(4-(4-((4-([1,2,4]triazolo[1,5-a]pyridin-7-yloxy)-3-chloro-2-fluorophenyl)amino)-7-methoxypyrido[3,2-d]pyrimidin-6-yl)piperazin-1-yl)prop-2-en-1-one | 576.1 | 1H NMR (400 MHz, $CDCl_3$) δ 9.01 - 8.92 (m, 2H), 8.68 (s, 1H), 8.54 (dd, J = 6.9, 1.3 Hz, 1H), 8.25 (s, 1H), 7.39 (s, 1H), 7.15 (dd, J = 9.2, 2.0 Hz, 1H), 6.96 - 6.89 (m, 2H), 6.66 (dd, J = 16.8, 10.6 Hz, 1H), 6.37 (dd, J = 16.9, 1.9 Hz, 1H), 5.78 (dd, J = 10.5, 1.9 Hz, 1H), 4.05 (s, 3H), 3.94 - 3.89 (m, 2H), 3.85 - 3.80 (m, 2H), 3.74 - 3.67 (m, 4H). |
| 149 (Ex. 39) | 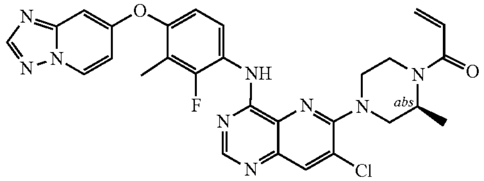 [SMILES: C=CC(=O)N1CCN(c2nc3c(Nc4ccc(Oc5ccn6ncnc6c5)c(C)c4F)ncnc3cc2Cl)C[C@@H]1C] (S)-1-(4-(4-((4-([1,2,4]triazolo[1,5-a]pyridin-7-yloxy)-2-fluoro-3-methylphenyl)amino)-7-chloropyrido[3,2-d]pyrimidin-6-yl)-2-methylpiperazin-1-yl)prop-2-en-1-one | 574.1 | 1H NMR (400 MHz, DMSO) δ 9.44 (s, 1H), 8.98 (dd, J = 7.4, 0.7 Hz, 1H), 8.54 (s, 1H), 8.41 (s, 1H), 8.33 (s, 1H), 8.06 (t, J = 8.9 Hz, 1H), 7.16 (dd, J = 8.9, 1.6 Hz, 1H), 7.07 (dd, J = 7.5, 2.6 Hz, 1H), 6.93 (dd, J = 2.7, 0.7 Hz, 1H), 6.87 (dd, J = 16.7, 10.5 Hz, 1H), 6.16 (dd, J = 16.7, 2.4 Hz, 1H), 5.73 (dd, J = 10.5, 2.4 Hz, 1H), 4.88 - 4.23 (m, 2H), 4.10 - 3.97 (m, 2H), 3.64 - 3.54 (m, 1H), 3.15 (d, J = 12.8 Hz, 1H), 3.07 - 3.02 (m, 1H), 2.17 (d, J = 2.0 Hz, 3H). |
| 150 (Ex. 38) | 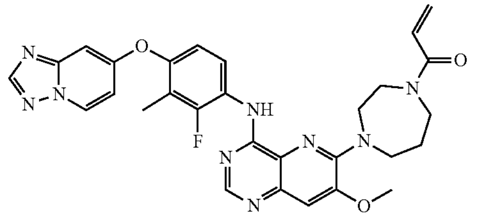 [SMILES: C=CC(=O)N1CCCN(c2nc3c(Nc4ccc(Oc5ccn6ncnc6c5)c(C)c4F)ncnc3cc2OC)CC1] 1-(4-(4-((4-([1,2,4]triazolo[1,5-a]pyridin-7-yloxy)-2-fluoro-3-methylphenyl)amino)-7-methoxypyrido[3,2-d]pyrimidin-6-yl)-1,4-diazepan-1-yl)prop-2-en-1-one | 570.3 | 1H NMR (400 MHz, $CDCl_3$) δ 8.92 (dd, J = 18.9, 3.7 Hz, 1H), 8.87 - 8.78 (m, 1H), 8.61 (d, J = 1.2 Hz, 1H), 8.50 (dt, J = 7.0, 1.1 Hz, 1H), 8.23 (s, 1H), 7.29 (s, 1H), 6.99 (dt, J = 9.1, 2.5 Hz, 1H), 6.94 - 6.84 (m, 2H), 6.67 - 6.55 (m, 1H), 6.47 - 6.19 (m, 1H), 5.78 - 5.62 (m, 1H), 4.11 - 4.04 (m, 1H), 4.04 - 3.90 (m, 8H), 3.67 (t, J = 6.2 Hz, 1H), 3.60 (t, J = 6.3 Hz, 1H), 2.20 (t, J = 2.6 Hz, 3H), 2.16 - 2.08 (m, 2H). |

TABLE 2-continued

| Example No. (Method) | Structure; IUPAC name | LCMS $M^+1$ | $^1$H NMR (ppm); $^{19}$F NMR (ppm); optical rotation; Chiral HPLC/SFC conditions |
|---|---|---|---|
| 151 (Ex. 40) | 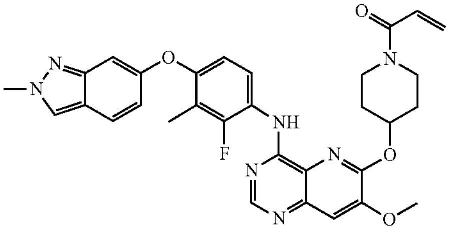 [SMILES: C=CC(=O)N1CCC(Oc2nc3c(Nc4ccc(Oc5ccc6cn(C)nc6c5)c(C)c4F)ncnc3cc2OC)CC1] 1-(4-((4-((2-fluoro-3-methyl-4-((2-methyl-2H-indazol-6-yl)oxy)phenyl)amino)-7-methoxypyrido[3,2-d]pyrimidin-6-yl)oxy)piperidin-1-yl)prop-2-en-1-one | 583.3 | $^1$H NMR (400 MHz, $CDCl_3$) δ 8.71 (d, J = 3.6 Hz, 1H), 8.67 (s, 1H), 8.61 (t, J = 9.1 Hz, 1H), 7.84 (s, 1H), 7.60 (dd, J = 9.0, 0.7 Hz, 1H), 7.36 (s, 1H), 6.98 – 6.93 (m, 1H), 6.93 – 6.85 (m, 2H), 6.65 (dd, J = 16.8, 10.6 Hz, 1H), 6.31 (dd, J = 16.8, 1.9 Hz, 1H), 5.72 (dd, J = 10.6, 1.9 Hz, 1H), 5.59 – 5.50 (m, 1H), 4.18 – 4.14 (m, 4H), 4.03 – 3.99 (m, 4H), 3.62 – 3.58 (m, 2H), 2.30 – 2.22 (m, 5H), 2.07 – 1.94 (m, 2H). |
| 152 (Ex. 38) | 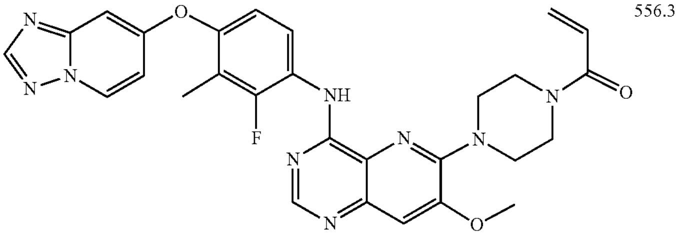 1-(4-(4-((4-([1,2,4]triazolo[1,5-a]pyridin-7-yloxy)-2-fluoro-3-methylphenyl)amino)-7-methoxypyrido[3,2-d]pyrimidin-6-yl)piperazin-1-yl)prop-2-en-1-one | 556.3 | 1H NMR (400 MHz, $CDCl_3$) δ 8.95 (d, J = 3.6 Hz, 1H), 8.79 (t, J = 9.0 Hz, 1H), 8.66 (s, 1H), 8.50 (dd, J = 7.3, 0.9 Hz, 1H), 8.23 (s, 1H), 7.37 (s, 1H), 6.99 (d, J = 9.3 Hz, 1H), 6.92 – 6.84 (m, 2H), 6.65 (dd, J = 16.8, 10.6 Hz, 1H), 6.36 (dd, J = 16.8, 1.9 Hz, 1H), 5.77 (dd, J = 10.5, 1.9 Hz, 1H), 4.04 (s, 3H), 3.95 – 3.90 (m, 2H), 3.84 – 3.79 (m, 2H), 3.73 – 3.66 (m, 4H), 2.20 (s, 3H). |
| 153 (Ex. 38) | 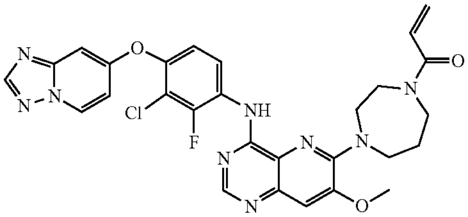 [SMILES: C=CC(=O)N1CCCN(c2nc3c(Nc4ccc(Oc5ccn6ncnc6c5)c(Cl)c4F)ncnc3cc2OC)CC1] 1-(4-(4-((4-([1,2,4]triazolo[1,5-a]pyridin-7-yloxy)-3-chloro-2-fluorophenyl)amino)-7-methoxypyrido[3,2-d]pyrimidin-6-yl)-1,4-diazepan-1-yl)prop-2-en-1-one | 590.2 | 1H NMR (400 MHz, $CDCl_3$) δ 8.98 (q, J = 9.6 Hz, 1H), 8.63 (d, J = 2.5 Hz, 1H), 8.56 – 8.50 (m, 1H), 8.26 (s, 1H), 8.10 – 7.92 (m, 1H), 7.59 – 7.35 (m, 1H), 7.36 (s, 1H), 7.17 – 7.11 (m, 1H), 6.94 – 6.89 (m, 2H), 6.66 – 6.54 (m, 1H), 6.42 – 6.21 (m, 1H), 5.76 – 5.62 (m, 1H), 4.12 – 4.06 (m, 1H), 4.06 – 3.98 (m, 3H), 3.98 – 3.88 (m, 5H), 3.74 – 3.55 (m, 2H), 2.16 – 2.08 (m, 2H). |
| 154 (Ex. 38) | 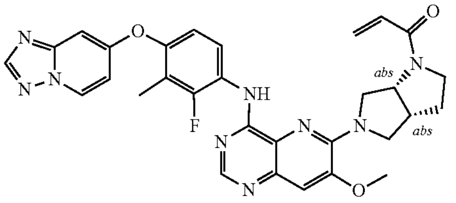 [SMILES: C=CC(=O)N1CC[C@@H]2CN(c3nc4c(Nc5ccc(Oc6ccn7ncnc7c6)c(C)c5F)ncnc4cc3OC)C[C@@H]21] 1-((3aR,6aR)-5-(4-((4-([1,2,4]triazolo[1,5-a]pyridin-7-yloxy)-2-fluoro-3-methylphenyl)amino)-7-methoxypyrido[3,2-d]pyrimidin-6-yl)hexahydropyrrolo[3,4-d]pyrrol-1(2H)-yl)prop-2-en-1-one | 582.3 | 1H NMR (400 MHz, $CDCl_3$) δ 8.92 – 8.86 (m, 1H), 8.86 – 8.72 (m, 1H), 8.59 (d, J = 8.7 Hz, 1H), 8.54 – 8.47 (m, 1H), 8.23 (s, 1H), 7.27 – 7.20 (m, 1H), 7.02 – 6.95 (m, 1H), 6.95 – 6.85 (m, 2H), 6.58 – 6.36 (m, 2H), 5.83 – 5.68 (m, 1H), 4.75 – 4.55 (m, 1H), 4.26 – 4.14 (3.78 (m, 1H), 3.81 – 3.70 (m,m, 2H), 4.12 – 3.92 (m, 4H), 3.90 – 2H), 3.25 – 3.01 (m, 1H), 2.30 – 2.15 (m, 4H), 2.17 – 1.84 (m, 1H). |

TABLE 2-continued

| Example No. (Method) | Structure; IUPAC name | LCMS $M^+1$ | $^1H$ NMR (ppm); $^{19}F$ NMR (ppm); optical rotation; Chiral HPLC/SFC conditions |
|---|---|---|---|
| 155 (Ex. 42) | 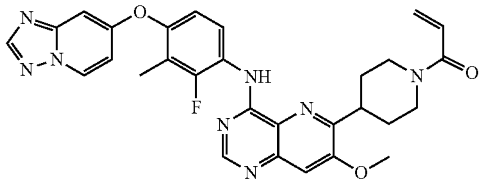 [SMILES: C=CC(=O)N1CCC(c2nc3c(Nc4ccc(Oc5ccn6ncnc6c5)c(C)c4F)ncnc3cc2OC)CC1] 1-(4-(4-((4-([1,2,4]triazolo[1,5-a]pyridin-7-yloxy)-2-fluoro-3-methylphenyl)amino)-7-methoxypyrido[3,2-d]pyrimidin-6-yl)piperidin-1-yl)prop-2-en-1-one | 555.3 | $^1H$ NMR (400 MHz, $CDCl_3$) δ 9.17 - 9.01 (m, 1H), 8.51 (dd, J = 7.4, 0.8 Hz, 1H), 8.23 (s, 1H), 7.47 (s, 1H), 7.13 - 7.00 (m, 1H), 6.94 - 6.80 (m, 3H), 6.51 (dd, J = 16.8, 1.6 Hz, 1H), 6.25 (dd, J = 16.8, 10.3 Hz, 1H), 5.69 (dd, J = 10.3, 1.6 Hz, 1H), 4.04 (s, 3H), 3.52 - 3.46 (m, 2H), 3.38 - 3.33 (m, 1H), 2.85 - 2.81 (m, 2H), 2.24 - 2.17 (m, 3H), 1.80 - 1.76 (m, 2H), 1.61 - 1.53 (m, 2H). |
| 156 (Ex. 40) | 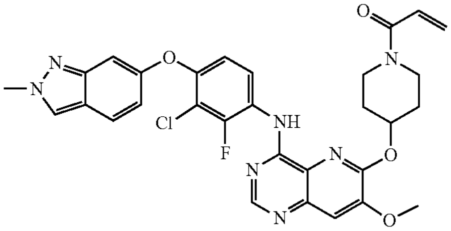 [SMILES: C=CC(=O)N1CCC(Oc2nc3c(Nc4ccc(Oc5ccc6cn(C)nc6c5)c(Cl)c4F)ncnc3cc2OC)CC1] 1-(4-((4-((3-chloro-2-fluoro-4-((2-methyl-2H-indazol-6-yl)oxy)phenyl)amino)-7-methoxypyrido[3,2-d]pyrimidin-6-yl)oxy)piperidin-1-yl)prop-2-en-1-one | 604.2 | 1H NMR (400 MHz, $CDCl_3$) δ 8.74 (t, J = 9.0 Hz, 1H), 8.70 (d, J = 3.4 Hz, 1H), 8.68 (s, 1H), 7.88 (s, 1H), 7.64 (d, J = 9.0 Hz, 1H), 7.37 (s, 1H), 7.07 (d, J = 2.1 Hz, 1H), 7.01 - 6.87 (m, 2H), 6.65 (dd, J = 16.8, 10.6 Hz, 1H), 6.31 (dd, J = 16.9, 1.9 Hz, 1H), 5.76 - 5.69 (m, 1H), 5.60 - 5.50 (m, 1H), 4.21 - 4.09 (m, 4H), 4.04 - 3.91 (m, 4H), 3.67 - 3.59 (m, 2H), 2.25 - 2.21 (m, 2H), 2.08 - 1.95 (m, 2H). |
| 157 (Ex. 40) | 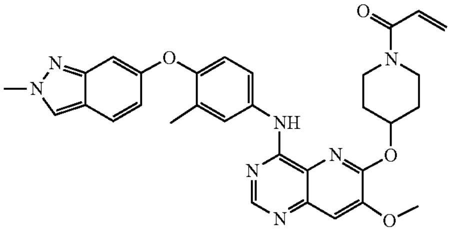 [SMILES: C=CC(=O)N1CCC(Oc2nc3c(Nc4ccc(Oc5ccc6cn(C)nc6c5)c(C)c4)ncnc3cc2OC)CC1] 1-(4-((7-methoxy-4-((3-methyl-4-((2-methyl-2H-indazol-6-yl)oxy)phenyl)amino)pyrido[3,2-d]pyrimidin-6-yl)oxy)piperidin-1-yl)prop-2-en-1-one | 566.3 | 1H NMR (400 MHz, $CDCl_3$) δ 8.64 (s, 1H), 8.25 (s, 1H), 7.83 (s, 1H), 7.69 (d, J = 2.7 Hz, 1H), 7.64 - 7.55 (m, 2H), 7.34 (s, 1H), 7.02 (d, J = 8.6 Hz, 1H), 6.96 - 6.87 (m, 1H), 6.63 (dd, J = 16.8, 10.6 Hz, 1H), 6.30 (dd, J = 16.8, 1.9 Hz, 1H), 5.71 (dd, J = 10.6, 2.0 Hz, 1H), 5.63 - 5.55 (m, 1H), 4.15 (s, 3H), 4.00 (s, 3H), 4.00 - 3.78 (m, 4H), 3.66 - 3.61 (m, 1H), 3.48 (s, 2H), 2.30 (s, 3H), 2.18 - 1.95 (m, 4H). |
| 158 | 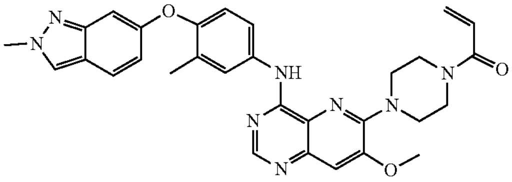 [SMILES: C=CC(=O)N1CCN(c2nc3c(Nc4ccc(Oc5ccc6cn(C)nc6c5)c(C)c4)ncnc3cc2OC)CC1] 1-(4-(7-methoxy-4-((3-methyl-4-((2-methyl-2H-indazol-6-yl)oxy)phenyl)amino)pyrido[3,2-d]pyrimidin-6-yl)piperazin-1-yl)prop-2-en-1-one | 551.3 | 1H NMR (400 MHz, $CDCl_3$) δ 8.60 (s, 1H), 8.48 (s, 1H), 7.82 (s, 1H), 7.71 (d, J = 2.7 Hz, 1H), 7.66 (dd, J = 8.5, 2.8 Hz, 1H), 7.58 (dd, J = 8.9, 0.8 Hz, 1H), 7.33 (s, 1H), 7.02 (d, J = 8.6 Hz, 1H), 6.98 - 6.87 (m, 2H), 6.64 (dd, J = 16.8, 10.5 Hz, 1H), 6.35 (dd, J = 16.8, 1.9 Hz, 1H), 5.75 (dd, J = 10.6, 1.9 Hz, 1H), 4.14 (s, 3H), 4.01 (s, 3H), 3.94 - 3.89 (m, 2H), 3.82 - 3.77 (m, 2H), 3.66 - 3.59 (m, 4H), 2.30 (s, 3H). |

TABLE 2-continued

| Example No. (Method) | Structure; IUPAC name | LCMS $M^{+}1$ | $^{1}H$ NMR (ppm); $^{19}F$ NMR (ppm); optical rotation; Chiral HPLC/SFC conditions |
|---|---|---|---|
| 159 (Ex. 38) | 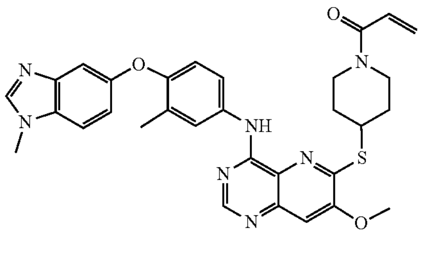 [SMILES: C=CC(=O)N1CCC(Sc2nc3c(Nc4ccc(Oc5ccc6c(c5)ncn6C)c(C)c4)ncnc3cc2OC)CC1] 1-(4-((7-methoxy-4-((3-methyl-4-((1-methyl-1H-benzo[d]imidazol-5-yl)oxy)phenyl)amino)pyrido[3,2-d]pyrimidin-6-yl)thio)piperidin-1-yl)prop-2-en-1-one | 582.3 | 1H NMR (400 MHz, $CDCl_3$) δ 8.66 (s, 1H), 8.56 (s, 1H), 7.85 (s, 1H), 7.74 (dd, J = 2.8, 0.8 Hz, 1H), 7.51 (dd, J = 8.6, 2.7 Hz, 1H), 7.33 (dd, J = 8.7, 0.6 Hz, 1H), 7.31 - 7.25 (m, 2H), 7.07 (dd, J = 8.7, 2.3 Hz, 1H), 6.94 (d, J = 8.7 Hz, 1H), 6.61 (dd, J = 16.8, 10.6 Hz, 1H), 6.30 (dd, J = 16.8, 1.9 Hz, 1H), 5.71 (dd, J = 10.6, 1.9 Hz, 1H), 4.32 - 4.20 (m, 1H), 4.04 (s, 3H), 3.85 (s, 3H), 2.37 - 2.26 (m, 5H), 1.90 (dtd, J = 13.1, 9.1, 3.7 Hz, 2H), 1.71 - 1.35 (m, 4H). |
| 160 (Ex. 38) | 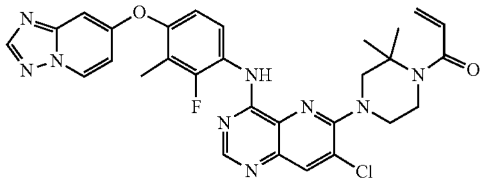 [SMILES: C=CC(=O)N1CCN(c2nc3c(Nc4ccc(Oc5ccn6ncnc6c5)c(C)c4F)ncnc3cc2Cl)CC1(C)C] 1-(4-(4-((4-([1,2,4]triazolo[1,5-a]pyridin-7-yloxy)-2-fluoro-3-methylphenyl)amino)-7-chloropyrido[3,2-d]pyrimidin-6-yl)-2,2-dimethylpiperazin-1-yl)prop-2-en-1-one | 588.3 | 1H NMR (400 MHz, $CDCl_3$) δ 9.01 (d, J = 3.6 Hz, 1H), 8.79 (t, J = 9.0 Hz, 1H), 8.68 (s, 1H), 8.51 (d, J = 7.4 Hz, 1H), 8.23 (s, 1H), 8.12 (s, 1H), 7.00 (dd, J = 9.1, 1.7 Hz, 1H), 6.92 - 6.83 (m, 2H), 6.57 (dd, J = 16.8, 10.5 Hz, 1H), 6.25 (dd, J = 16.8, 1.8 Hz, 1H), 5.67 (dd, J = 10.5, 1.9 Hz, 1H), 3.89 - 3.82 (m, 4H), 3.66 (s, 2H), 2.20 (d, J = 2.1 Hz, 3H), 1.65 (s, 6H). |

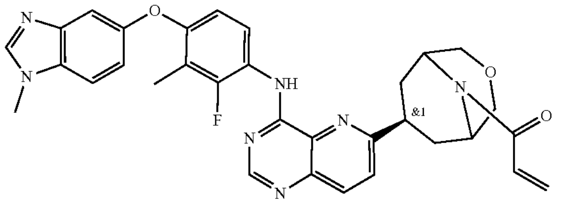

Example 161

1-(7-(4-((2-fluoro-3-methyl-4-((1-methyl-1H-benzo[d]imidazol-5-yl)oxy)phenyl)amino)pyrido[3,2-d]pyrimidin-6-yl)-3-oxa-9-azabicyclo[3.3.1]nonan-9-yl)prop-2-en-1-one Step A: A pressure tube containing 6-chloro-N-(2-fluoro-3-methyl-4-((1-methyl-1H-benzo[d]imidazol-5-yl)oxy)phenyl)pyrido[3,2-d]pyrimidin-4-amine (100 mg, 0.23 mmol) was charged with tert-butyl 7-(4,4,5,5-tetramethyl-1,3,2-dioxaborolan-2-yl)-3-oxa-9-azabicyclo[3.3.1]non-6-ene-9-carboxylate (121 mg, 0.345 mmol), dioxane (2.3 mL), 2M aqueous k-carb (0.345 mL, 3 eq.) and $Pd(PPh_3)_4$ (26.6 mg, 0.023 mmol). The mixture was purged with argon for a few minutes, and the tube was sealed. The mixture warmed to 100° C. for 16 hours, then allowed to cool to room temperature. The mixture was then diluted with EtOAc/water, extracted with EtOAc, extracts dried over sodium sulfate and concentrated under reduced pressure. Column chromatography (DCM to 10% MeOH-DCM) afforded tert-butyl 7-(4-((2-fluoro-3-methyl-4-((1-methyl-1H-benzo[d]imidazol-5-yl)oxy)phenyl)amino)pyrido[3,2-d]pyrimidin-6-yl)-3-oxa-9-azabicyclo[3.3.1]non-6-ene-9-carboxylate (91.3 mg, 64%). m/z (APCI-pos) M+1=624.30.

Step B: A pressure tube containing tert-butyl 7-(4-((2-fluoro-3-methyl-4-((1-methyl-1H-benzo[d]imidazol-5-yl)oxy)phenyl)amino)pyrido[3,2-d]pyrimidin-6-yl)-3-oxa-9-azabicyclo[3.3.1]non-6-ene-9-carboxylate (91.3 mg, 0.146 mmol) was charged with methanol (1.5 mL), ammonium formate (92.3 mg, 1.46 mmol) and 10% Pd/C (90 mg). The tube was sealed, and the mixture warmed to 75° C. for 1.5 hours, then allowed to cool to room temperature. The mixture was diluted with MeOH, filtered through an acrodisc filter attached to the end of a syringe, and the filtrate concentrated under reduced pressure. The resulting crude product was taken up in EtOAc/10% aqueous potassium carbonate, dried over sodium sulfate and concentrated under reduced pressure to give tert-butyl 7-(4-((2-fluoro-3-methyl-4-((1-methyl-1H-benzo[d]imidazol-5-yl)oxy)phenyl)amino)pyrido[3,2-d]pyrimidin-6-yl)-3-oxa-9-azabicyclo[3.3.1]nonane-9-carboxylate (61 mg, 67%). m/z (APCI-pos) M+1=626.35.

Step C: TFA (0.22 g, 20 Eq, 1.9 mmol) was added to a stirred solution of tert-butyl 7-(4-((2-fluoro-3-methyl-4-((1-methyl-1H-benzo[d]imidazol-5-yl)oxy)phenyl)amino)pyrido[3,2-d]pyrimidin-6-yl)-3-oxa-9-azabicyclo[3.3.1]nonane-9-carboxylate (61 mg, 97 μmol) in DCM (1 mL) at 20° C. for 2 hours. The mixture was then diluted with EtOAc, washed with 10% aqueous potassium carbonate, dried over sodium sulfate, and concentrated under reduced pressure to give 6-(3-oxa-9-azabicyclo[3.3.1]nonan-7-yl)-N-(2-fluoro-3-methyl-4-((1-methyl-1H-benzo[d]imidazol-5-yl)oxy)phenyl)pyrido[3,2-d]pyrimidin-4-amine (43.1 mg, 84%). m/z (APCI-pos) M+1=526.30.

Step D: Acryloyl chloride (5.9 mg, 0.8 Eq, 65 μmol) was added to a stirred solution of 6-(3-oxa-9-azabicyclo[3.3.1]nonan-7-yl)-N-(2-fluoro-3-methyl-4-((1-methyl-1H-benzo[d]imidazol-5-yl)oxy)phenyl)pyrido[3,2-d]pyrimidin-4-amine (43 mg, 1 Eq, 82 μmol) and DIEA (21 mg, 2 Eq, 0.16 mmol) in DCM (0.8 mL) at 0° C. under nitrogen for 30 minutes. The mixture was diluted with EtOAc, washed with 10% aqueous potassium carbonate, dried over sodium sulfate, and concentrated under reduced pressure. Flash chromatography (DCM to 10% MeOH-DCM) afforded 1-(7-(4-((2-fluoro-3-methyl-4-((1-methyl-1H-benzo[d]imidazol-5-yl)oxy)phenyl)amino)pyrido[3,2-d]pyrimidin-6-yl)-3-oxa-9-azabicyclo[3.3.1]nonan-9-yl)prop-2-en-1-one (45 mg, 95%). $^1$H NMR (400 MHz, $CDCl_3$) δ 9.35-9.27 (m, 1H), 8.76-8.71 (m, 1H), 8.50-8.39 (m, 1H), 8.11 (d, J=8.7 Hz, 1H), 7.90 (s, 1H), 7.72-7.62 (m, 1H), 7.39-7.32 (m, 2H), 7.08 (dd, J=8.8, 2.1 Hz, 1H), 6.76 (d, J=9.0 Hz, 1H), 6.70-6.57 (m, 1H), 6.48-6.39 (m, 1H), 5.85-5.76 (m, 1H), 5.02-4.77 (m, 1H), 4.64-4.05 (m, 2H), 4.02-3.56 (m, 7H), 3.03-2.90 (m, 1H), 2.59-2.39 (m, 2H), 2.35-2.23 (m, 5H). m/z (APCI-pos) M+1=580.35.

Example 162

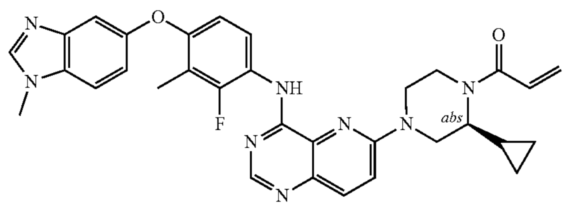 [SMILES: C=CC(=O)N1CCN(c2ccc3ncnc(Nc4ccc(Oc5ccc6c(c5)ncn6C)c(C)c4F)c3n2)C[C@@H]1C1CC1]

(S)-1-(2-cyclopropyl-4-(4-((2-fluoro-3-methyl-4-((1-methyl-1H-benzo[d]imidazol-5-yl)oxy)phenyl)amino)pyrido[3,2-d]pyrimidin-6-yl)piperazin-1-yl)prop-2-en-1-one Step A: tert-Butyl (S)-2-cyclopropylpiperazine-1-carboxylate (59 mg, 1.5 Eq, 0.26 mmol) was added to a stirred solution of 6-chloro-N-(2-fluoro-3-methyl-4-((1-methyl-1H-benzo[d]imidazol-5-yl)oxy)phenyl)pyrido[3,2-d]pyrimidin-4-amine (75 mg, 1 Eq, 0.17 mmol) and DIEA (67 mg, 3 Eq, 0.52 mmol) in DMSO (1.7 mL) at 100° C. for 16 hours, then allowed to cool to room temperature. The reaction was partitioned between water and EtOAc. The organic layer was dried over sodium sulfate, filtered, and concentrated in vacuo. Flash chromatography afforded tert-butyl (S)-2-cyclopropyl-4-(4-((2-fluoro-3-methyl-4-((1-methyl-1H-benzo[d]imidazol-5-yl)oxy)phenyl)amino)pyrido[3,2-d]pyrimidin-6-yl)piperazine-1-carboxylate (67 mg, 62%). m/z (APCI-pos) M+1=625.30.

Step B: TFA (0.24 g, 20 Eq, 2.1 mmol) was added to a stirred solution of tert-butyl (S)-2-cyclopropyl-4-(4-((2-fluoro-3-methyl-4-((1-methyl-1H-benzo[d]imidazol-5-yl)oxy)phenyl)amino)pyrido[3,2-d]pyrimidin-6-yl)piperazine-1-carboxylate (67 mg, 1 Eq, 0.11 mmol) in DCM (1.1 mL) at 20° C. for 2 hours. The mixture was diluted with EtOAc, washed with 10% aqueous potassium carbonate, dried over sodium sulfate, and concentrated under reduced pressure to give (S)-6-(3-cyclopropylpiperazin-1-yl)-N-(2-fluoro-3-methyl-4-((1-methyl-1H-benzo[d]imidazol-5-yl)oxy)phenyl)pyrido[3,2-d]pyrimidin-4-amine (35.5 mg, 63%). m/z (APCI-pos) M+1=525.30.

Step C: Acryloyl chloride (4.9 mg, 0.8 Eq, 54 μmol) was added to a stirred solution of (S)-6-(3-cyclopropylpiperazin-1-yl)-N-(2-fluoro-3-methyl-4-((1-methyl-1H-benzo[d]imidazol-5-yl)oxy)phenyl)pyrido[3,2-d]pyrimidin-4-amine (36 mg, 1 Eq, 68 μmol) and DIEA (26 mg, 3 Eq, 0.20 mmol) in DCM (0.8 mL) at 0° C. under nitrogen for 30 minutes. The mixture was diluted with EtOAc, washed with 10% aqueous potassium carbonate, dried over sodium sulfate, and concentrated under reduced pressure. Flash chromatography afforded (S)-1-(2-cyclopropyl-4-(4-((2-fluoro-3-methyl-4-((1-methyl-1H-benzo[d]imidazol-5-yl)oxy)phenyl)amino)pyrido[3,2-d]pyrimidin-6-yl)piperazin-1-yl)prop-2-en-1-one (21.8 mg). $^1$H NMR (400 MHz, $CDCl_3$) δ 8.99 (s, 1H), 8.68-8.42 (m, 2H), 7.97 (d, J=9.3 Hz, 1H), 7.86 (s, 1H), 7.37-7.28 (m, 3H), 7.06 (dd, J=8.7, 2.1 Hz, 1H), 6.77 (d, J=8.8 Hz, 1H), 6.63-6.58 (m, 1H), 6.36 (d, J=16.4 Hz, 1H), 5.76 (d, J=10.6 Hz, 1H), 4.88-2.89 (m, 7H), 3.85 (s, 3H), 2.30 (s, 3H), 1.40-1.16 (m, 1H), 0.74-0.30 (m, 4H). m/z (APCI-pos) M+1=579.30.

Example 163

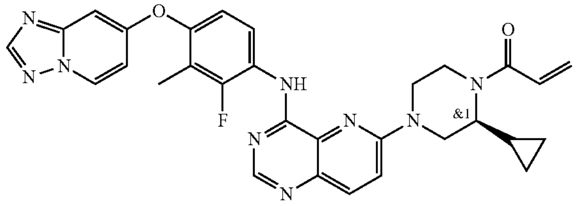 [SMILES: C=CC(=O)N1CCN(c2ccc3ncnc(Nc4ccc(Oc5ccn6ncnc6c5)c(C)c4F)c3n2)C[C@@H]1C1CC1]

rac-1-(4-(4-((4-([1,2,4]triazolo[1,5-a]pyridin-7-yloxy)-2-fluoro-3-methylphenyl)amino)pyrido[3,2-d]pyrimidin-6-yl)-2-cyclopropylpiperazin-1-yl)prop-2-en-1-one Step A: tert-Butyl 2-cyclopropylpiperazine-1-carboxylate (132 mg, 2 Eq, 585 μmol) was added to a stirred solution of N-(4-([1,2,4]triazolo[1,5-a]pyridin-7-yloxy)-2-fluoro-3-methylphenyl)-6-chloropyrido[3,2-d]pyrimidin-4-amine, HCl (134 mg, 1 Eq, 292 μmol) and DIEA (151 mg, 4 Eq, 1.17 mmol) in DMSO (3 mL) at 100° C. for 16 hours, then allowed to cool to room temperature. The mixture was diluted with EtOAc, washed with brine/water, dried over sodium sulfate, and concentrated under reduced pressure. Flash chromatography afforded rac-tert-butyl (R)-4-(4-((4-([1,2,4]triazolo[1,5-a]pyridin-7-yloxy)-2-fluoro-3-methylphenyl)amino)pyrido[3,2-d]pyrimidin-6-yl)-2-cyclopropylpiperazine-1-carboxylate product (106 mg, 59%). m/z (APCI-pos) M+1=612.30.

Step B: TFA (395 mg, 20 Eq, 3.47 mmol) was added to a stirred solution of tert-butyl 4-(4-((4-([1,2,4]triazolo[1,5-a]pyridin-7-yloxy)-2-fluoro-3-methylphenyl)amino)pyrido[3,2-d]pyrimidin-6-yl)-2-cyclopropylpiperazine-1-carboxylate (106 mg, 1 Eq, 173 μmol) in DCM (1.7 mL) at 20° C. for 2 hours. The mixture was diluted with EtOAc, washed with 10% aqueous k-carb, dried over sodium sulfate, and concentrated under reduced pressure to give rac-N-(4-([1,2,4]triazolo[1,5-a]pyridin-7-yloxy)-2-fluoro-3-methylphenyl)-6-(3-cyclopropylpiperazin-1-yl)pyrido[3,2-d]pyrimidin-4-amine (79 mg, 89%). m/z (APCI-pos) M+1=512.20.

Step C: Acryloyl chloride (6.49 mg, 1 Eq, 71.7 μmol) was added to a stirred solution of N-(4-([1,2,4]triazolo[1,5-a]pyridin-7-yloxy)-2-fluoro-3-methylphenyl)-6-(3-cyclopropylpiperazin-1-yl)pyrido[3,2-d]pyrimidin-4-amine (36.7 mg, 1 Eq, 71.7 μmol) and DIEA (27.8 mg, 3 Eq, 215 μmol) in DCM (0.7 mL) at 0° C. under nitrogen for 30 minutes. The mixture was diluted with EtOAc, washed with 10% aqueous potassium carbonate, dried over sodium sulfate, and concentrated under reduced pressure. Flash chromatography (DCM to 10% MeOH-DCM) afforded rac-1-(4-(4-((4-([1,2,4]triazolo[1,5-a]pyridin-7-yloxy)-2-fluoro-3-methylphenyl)amino)pyrido[3,2-d]pyrimidin-6-yl)-2-cyclopropylpiperazin-1-yl)prop-2-en-1-one (24.6 mg). $^1$H NMR (400 MHz, $CDCl_3$) δ 9.11 (d, J=3.4 Hz, 1H), 8.84 (t, J=9.0 Hz, 1H), 8.65 (s, 1H), 8.51 (dd, J=7.3, 0.7 Hz, 1H), 8.24 (s, 1H), 8.00 (d, J=9.3 Hz, 1H), 7.34 (d, J=9.4 Hz, 1H), 7.01 (dd, J=9.0, 1.5 Hz, 1H), 6.93-6.85 (m, 2H), 6.67-6.56 (m, 1H), 6.37 (dd, J=16.7, 1.5 Hz, 1H), 5.76 (dd, J=10.5, 1.7 Hz, 1H), 4.60-4.55 (m, 2H), 3.35 (dd, J=13.1, 3.6 Hz, 1H), 3.19 (td, J=12.7, 3.5 Hz, 1H), 2.21 (s, 3H), 1.43-1.17 (m, 1H), 0.77-0.36 (m, 4H). m/z (APCI-pos) M+1=566.20.

Example 164

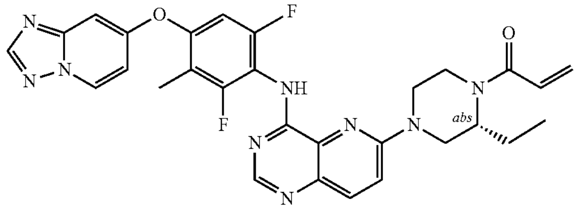 [SMILES: C=CC(=O)N1CCN(c2ccc3ncnc(Nc4c(F)cc(Oc5ccn6ncnc6c5)c(C)c4F)c3n2)C[C@H]1CC]

(R)-1-(4-(4-((4-([1,2,4]triazolo[1,5-a]pyridin-7-yloxy)-2-fluoro-5-methylphenyl)amino)pyrido[3,2-d]pyrimidin-6-yl)-2-ethylpiperazin-1-yl)prop-2-en-1-one Step A: tert-Butyl (R)-2-ethylpiperazine-1-carboxylate (76 mg, 2 Eq, 0.36 mmol) was added to a stirred solution of N-(4-([1,2,4]triazolo[1,5-a]pyridin-7-yloxy)-2-fluoro-5-methylphenyl)-6-chloropyrido[3,2-d]pyrimidin-4-amine (75 mg, 1 Eq, 0.18 mmol) and DIEA (92 mg, 4 Eq, 0.71 mmol) in DMSO (1.7 mL) at 100° C. for 16 hours, then allowed to cool to room temperature. The mixture was diluted with EtOAc, washed with water/brine, dried over sodium sulfate, and concentrated under reduced pressure. Flash chromatography (DCM to 10% MeOH-DCM) afforded tert-butyl (R)-4-(4-((4-([1,2,4]triazolo[1,5-a]pyridin-7-yloxy)-2-fluoro-5-methylphenyl)amino)pyrido[3,2-d]pyrimidin-6-yl)-2-ethylpiperazine-1-carboxylate (74 mg, 69%). m/z (APCI-pos) M+1=600.30.

Step B: TFA (0.42 g, 30 Eq, 3.7 mmol) was added to a stirred solution of tert-butyl (R)-4-(4-((4-([1,2,4]triazolo[1,5-a]pyridin-7-yloxy)-2-fluoro-5-methylphenyl)amino)pyrido[3,2-d]pyrimidin-6-yl)-2-ethylpiperazine-1-carboxylate (74 mg, 1 Eq, 0.12 mmol) in DCM (1.2 mL) at 20° C. for 16 hours. The mixture was diluted with EtOAc, washed with 10% aqueous potassium carbonate, dried over sodium sulfate, and concentrated under reduced pressure to give (R)—N-(4-([1,2,4]triazolo[1,5-a]pyridin-7-yloxy)-2-fluoro-5-methylphenyl)-6-(3-ethylpiperazin-1-yl)pyrido[3,2-d]pyrimidin-4-amine (62 mg, 100%). m/z (APCI-pos) M+1=500.30.

Step C: Acryloyl chloride (11 mg, 1 Eq, 0.12 mmol) was added to a stirred solution of (R)—N-(4-([1,2,4]triazolo[1,5-a]pyridin-7-yloxy)-2-fluoro-5-methylphenyl)-6-(3-ethylpiperazin-1-yl)pyrido[3,2-d]pyrimidin-4-amine (62 mg, 1 Eq, 0.12 mmol) and DIEA (48 mg, 3 Eq, 0.37 mmol) in DCM (1.2 mL) at 0° C. for 30 minutes. The mixture was diluted with EtOAc, washed with 10% aqueous potassium carbonate, dried over sodium sulfate, and concentrated under reduced pressure. Flash chromatography (DCM to 10% MeOH-DCM) afforded (R)-1-(4-(4-((4-([1,2,4]triazolo[1,5-a]pyridin-7-yloxy)-2-fluoro-5-methylphenyl)amino)pyrido[3,2-d]pyrimidin-6-yl)-2-ethylpiperazin-1-yl)prop-2-en-1-one (41.5 mg, 60%). $^1$H NMR (400 MHz, $CDCl_3$) δ 9.02 (d, J=3.0 Hz, 1H), 8.89 (d, J=9.1 Hz, 1H), 8.67 (s, 1H), 8.51 (dd, J=6.6, 1.6 Hz, 1H), 8.24 (s, 1H), 8.00 (d, J=9.3 Hz, 1H), 7.26 (d, 1H), 6.95 (d, J=11.1 Hz, 1H), 6.92-6.85 (m, 2H), 6.64 (dd, J=16.7, 10.5 Hz, 1H), 6.38 (d, J=16.8 Hz, 1H), 5.77 (dd, J=10.5, 1.8 Hz, 1H), 5.04-3.79 (m, 4H), 3.68-2.98 (m, 3H), 2.27 (s, 3H), 1.76 (s, 2H), 0.98 (t, J=7.4 Hz, 3H). m/z (APCI-pos) M+1=554.30.

Example 165

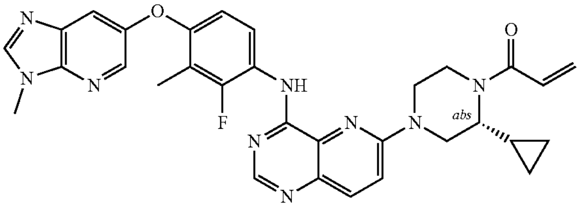 [SMILES: C=CC(=O)N1CCN(c2ccc3ncnc(Nc4ccc(Oc5cnc6c(c5)ncn6C)c(C)c4F)c3n2)C[C@H]1C1CC1]

(R)-1-(2-cyclopropyl-4-(4-((2-fluoro-3-methyl-4-((3-methyl-3H-imidazo[4,5-b]pyridin-6-yl)oxy)phenyl)amino)pyrido[3,2-d]pyrimidin-6-yl)piperazin-1-yl)prop-2-en-1-one Step A: tert-Butyl (R)-2-cyclopropylpiperazine-1-carboxylate hydrochloride (90 mg, 2 Eq, 0.34 mmol) was added to a stirred solution of 6-chloro-N-(2-fluoro-3-methyl-4-((3-methyl-3H-imidazo[4,5-b]pyridin-6-yl)oxy)phenyl)pyrido[3,2-d]pyrimidin-4-amine (75 mg, 1 Eq, 0.17 mmol) and DIEA (89 mg, 4 Eq, 0.69 mmol) in DMSO (1.7 mL) at 100° C. for 16 hours, then allowed to cool to room temperature. The mixture was diluted with EtOAc, washed with brine/water, dried over sodium sulfate, and concentrated under reduced pressure. Flash chromatography (DCM to 10% MeOH-DCM) afforded tert-butyl (R)-2-cyclopropyl-4-(4-((2-fluoro-3-methyl-4-((3-methyl-3H-imidazo[4,5-b]pyridin-6-yl)oxy)phenyl)amino)pyrido[3,2-d]pyrimidin-6-yl)piperazine-1-carboxylate (48.3 mg, 45%). m/z (APCI-pos) M+1=626.35.

Step B: TFA (264 mg, 30 Eq, 2.32 mmol) was added to a stirred solution of tert-butyl (R)-2-cyclopropyl-4-(4-((2-fluoro-3-methyl-4-((3-methyl-3H-imidazo[4,5-b]pyridin-6-yl)oxy)phenyl)amino)pyrido[3,2-d]pyrimidin-6-yl)piperazine-1-carboxylate (48.3 mg, 1 Eq, 77.2 μmol) in DCM (0.8 mL) at 20° C. for 16 hours. The mixture was diluted with EtOAc, washed with 10% aqueous potassium carbonate, dried over sodium sulfate, and concentrated under reduced pressure to give (R)-6-(3-cyclopropylpiperazin-1-yl)-N-(2-fluoro-3-methyl-4-((3-methyl-3H-imidazo[4,5-b]pyridin-6-yl)oxy)phenyl)pyrido[3,2-d]pyrimidin-4-amine (34.5 mg, 85%). This material was carried directly onto the next step.

Step C: Acryloyl chloride (5.94 mg, 1 Eq, 65.6 μmol) was added to a stirred solution of (R)-6-(3-cyclopropylpiperazin-1-yl)-N-(2-fluoro-3-methyl-4-((3-methyl-3H-imidazo[4,5-b]pyridin-6-yl)oxy)phenyl)pyrido[3,2-d]pyrimidin-4-amine (34.5 mg, 1 Eq, 65.6 μmol) and DIEA (25.5 mg, 3 Eq, 197 μmol) in DCM (0.7 mL) at 0° C. under nitrogen for 30 minutes. The mixture was diluted with EtOAc, washed with 10% aqueous potassium carbonate, dried over sodium sulfate, and concentrated under reduced pressure. Flash chromatography (DCM to 10% MeOH-DCM) afforded (R)-1-(2-cyclopropyl-4-(4-((2-fluoro-3-methyl-4-((3-methyl-3H-imidazo[4,5-b]pyridin-6-yl)oxy)phenyl)amino)pyrido[3,2-d]pyrimidin-6-yl)piperazin-1-yl)prop-2-en-1-one (24.4 mg, 64%). $^1$H NMR (400 MHz, $CDCl_3$) δ 9.03-8.98 (m, 1H), 8.66-8.57 (m, 2H), 8.30 (d, J=2.3 Hz, 1H), 8.04 (s, 1H), 7.97 (d, J=9.3 Hz, 1H), 7.61 (d, J=2.4 Hz, 1H), 7.32 (d, J=9.3 Hz, 1H), 6.76 (d, J=8.9 Hz, 1H), 6.67-6.56 (m, 1H), 6.36 (d, J=16.6 Hz, 1H), 5.76 (d, J=11.2 Hz, 1H), 5.02-3.00 (m, 7H), 3.94 (s, 3H), 2.31 (s, 3H), 1.45-1.13 (m, 1H), 0.77-0.33 (m, 4H). m/z (APCI-pos) M+1=580.30.

Example 166

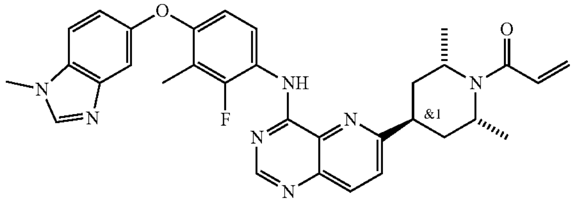 [SMILES: C=CC(=O)N1[C@H](C)C[C@@H](c2ccc3ncnc(Nc4ccc(Oc5ccc6c(c5)ncn6C)c(C)c4F)c3n2)C[C@@H]1C]

1-((2R,4SR,6S)-4-(4-((2-fluoro-3-methyl-4-((1-methyl-1H-benzo[d]imidazol-5-yl)oxy)phenyl)amino)pyrido[3,2-d]pyrimidin-6-yl)-2,6-dimethylpiperidin-1-yl)prop-2-en-1-one Step A: An 8 mL vial containing (4,4'-Di-t-butyl-2,2'-bipyridine)bis[2-(2-pyridinyl-kN)phenyl-kC]iridium(III) hexafluorophosphate (1.6 mg, 1.7 μmol), (SP-4-2)-[4,4'-bis(1,1-dimethylethyl)-2,2'-bipyridine-κN1,κN1']dibromo-Nickel (4.2 mgs, 8.6 μmol), quinuclidine (26 mg, 0.23 mmol), phthalimide (3.8 mg, 0.026 mmol), and 6-chloro-N-(2-fluoro-3-methyl-4-((1-methyl-1H-benzo[d]imidazol-5-yl)oxy)phenyl)pyrido[3,2-d]pyrimidin-4-amine (50 mg, 0.11 mmol) was taken up in DMA (1 mL). To a separate 8 ml vial was added 5,7-di-tert-butyl-3-phenyl-3-(tetrafluoro-15-boraneyl)-2,3-dihydrobenzo[d]oxazol-3-ium-2-ide (95 mg, 0.24 mmol), tert-butyl (2S,4r,6R)-4-hydroxy-2,6-dimethylpiperidine-1-carboxylate (53 mg, 0.23 mmol), and dry MTBE (1 mL) under nitrogen. After 1 minutes of stirring, pyridine (19 μL, 0.23 mmol) was added, and the mixture stirred vigorously for 5 minutes. This mixture was the taken up in a syringe and filtered through an acrodisc into the first vial. This vial was capped, purged with nitrogen for a few minutes, parafilmed and irradiated with 450 nm light in the photoreactor for 4 hours (100% intensity, 750 rpm stir, max speed fan). The mixture was diluted with EtOAc, washed several times with brine, dried over sodium sulfate and concentrated under reduced pressure. Flash chromatography (DCM to 10% MeOH-DCM) afforded tert-butyl (2R,4SR,6S)-4-(4-((2-fluoro-3-methyl-4-((1-methyl-1H-benzo[d]imidazol-5-yl)oxy)phenyl)amino)pyrido[3,2-d]pyrimidin-6-yl)-2,6-dimethylpiperidine-1-carboxylate (32 mg, 45%). m/z (APCI-pos) M+1=612.40.

Step B: TFA (0.17 g, 30 Eq, 1.5 mmol) was added to a stirred solution of tert-butyl (2R,4SR,6S)-4-(4-((2-fluoro-3-methyl-4-((1-methyl-1H-benzo[d]imidazol-5-yl)oxy)phenyl)amino)pyrido[3,2-d]pyrimidin-6-yl)-2,6-dimethylpiperidine-1-carboxylate (30 mg, 1 Eq, 49 μmol) in DCM (0.5 mL) at 20° C. for 5 hours. The mixture was then diluted with EtOAc, washed with 10% aqueous potassium carbonate, dried over sodium sulfate, and concentrated under reduced pressure to give 6-((2R,4SR,6S)-2,6-dimethylpiperidin-4-yl)-N-(2-fluoro-3-methyl-4-((1-methyl-1H-benzo[d]imidazol-5-yl)oxy)phenyl)pyrido[3,2-d]pyrimidin-4-amine (24 mg, 96%). m/z (APCI-pos) M+1=512.30.

Step C: Acryloyl chloride (3.4 mg, 0.8 Eq, 38 μmol) was added to a stirred solution of 6-((2R,4SR,6S)-2,6-dimethylpiperidin-4-yl)-N-(2-fluoro-3-methyl-4-((1-methyl-1H-benzo[d]imidazol-5-yl)oxy)phenyl)pyrido[3,2-d]pyrimidin-4-amine (24 mg, 1 Eq, 47 μmol) and DIEA (18 mg, 3 Eq, 0.14 mmol) in DCM (0.5 mL) at 0° C. under nitrogen for 30 minutes. The mixture was diluted with EtOAc, washed with 10% aqueous potassium carbonate, dried over sodium sulfate, and concentrated under reduced pressure. Flash chromatography (DCM to 10% MeOH-DCM) afforded 1-((2R,4SR,6S)-4-(4-((2-fluoro-3-methyl-4-((1-methyl-1H-benzo[d]imidazol-5-yl)oxy)phenyl)amino)pyrido[3,2-d]pyrimidin-6-yl)-2,6-dimethylpiperidin-1-yl)prop-2-en-1-one (12 mg, 45%). $^1$H NMR (400 MHz, $CDCl_3$) δ 9.42-9.25 (m, 1H), 8.74 (s, 1H), 8.56-8.43 (m, 1H), 8.17-8.08 (m, 1H), 7.86 (s, 1H), 7.71-7.58 (m, 1H), 7.38-7.32 (m, 2H), 7.11-7.03 (m, 1H), 6.80-6.62 (m, 2H), 6.43-6.31 (m, 1H), 5.76-5.68 (m, 1H), 5.21-4.32 (m, 2H), 3.86 (s, 3H), 3.68-2.99 (m, 1H), 2.57-1.90 (m, 5H), 2.32 (s, 3H), 1.54-1.38 (m, 6H). m/z (APCI-pos) M+1=566.30. This material was a 6:1 ratio of diastereomers.

Example 167

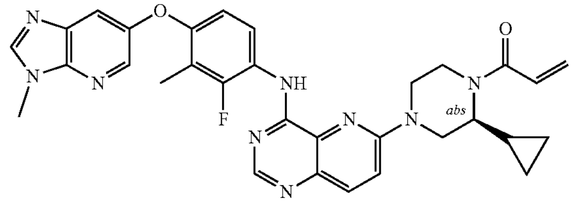 [SMILES: C=CC(=O)N1CCN(c2ccc3ncnc(Nc4ccc(Oc5cnc6c(c5)ncn6C)c(C)c4F)c3n2)C[C@@H]1C1CC1]

(S)-1-(2-cyclopropyl-4-(4-((2-fluoro-3-methyl-4-((3-methyl-3H-imidazo[4,5-b]pyridin-6-yl)oxy)phenyl)amino)pyrido[3,2-d]pyrimidin-6-yl)piperazin-1-yl)prop-2-en-1-one Step A: (S)-2-Cyclopropylpiperazine hydrochloride (86 mg, 2.5 Eq, 0.43 mmol) was added to a stirred solution of 6-chloro-N-(2-fluoro-3-methyl-4-((3-methyl-3H-imidazo[4,5-b]pyridin-6-yl)oxy)phenyl)pyrido[3,2-d]pyrimidin-4-amine (75 mg, 1 Eq, 0.17 mmol) and DIEA (0.11 g, 5 Eq, 0.86 mmol) in DMSO (1.7 mL) at 100° C. for 16 hours, then allowed to cool to room temperature. The mixture was diluted with EtOAc, washed with brine/water, then 10% aqueous k-carb (2×), dried over sodium sulfate and concentrated under reduced pressure. Flash chromatography (DCM to 20% MeOH/DCM) afforded (S)-6-(3-cyclopropylpiperazin-1-yl)-N-(2-fluoro-3-methyl-4-((3-methyl-3H-imidazo[4,5-b]pyridin-6-yl)oxy)phenyl)pyrido[3,2-d]pyrimidin-4-amine (34.3 mg, 38%). m/z (APCI-pos) M+1=526.20.

Step B: Acryloyl chloride (5.91 mg, 1 Eq, 65.3 μmol) was added to a stirred solution of (S)-6-(3-cyclopropylpiperazin-1-yl)-N-(2-fluoro-3-methyl-4-((3-methyl-3H-imidazo[4,5-b]pyridin-6-yl)oxy)phenyl)pyrido[3,2-d]pyrimidin-4-amine (34.3 mg, 1 Eq, 65.3 μmol) and DIEA (25.3 mg, 3 Eq, 196 μmol) in DCM (0.7 mL) at 0° C. under Nitrogen for 30 minutes. The mixture was diluted with EtOAc, washed with 10% aqueous potassium carbonate, dried over sodium sulfate, and concentrated under reduced pressure. Flash chromatography (DCM to 10% MEOH/DCM) afforded (S)-1-(2-cyclopropyl-4-(4-((2-fluoro-3-methyl-4-((3-methyl-3H-imidazo[4,5-b]pyridin-6-yl)oxy)phenyl)amino)pyrido[3,2-d]pyrimidin-6-yl)piperazin-1-yl)prop-2-en-1-one (20 mg, 53%). $^1$H NMR (400 MHz, $CDCl_3$) δ 9.01 (s, 1H), 8.66-8.57 (m, 2H), 8.30 (s, 1H), 8.04 (s, 1H), 7.98 (d, J=9.2 Hz, 1H), 7.61 (s, 1H), 7.35-7.28 (m, 1H), 6.76 (d, J=8.8 Hz, 1H), 6.67-6.56 (m, 1H), 6.36 (d, J=16.6 Hz, 1H), 5.76 (d, J=10.3 Hz, 1H), 4.95-2.94 (m, 7H), 3.93 (s, 3H), 2.31 (s, 3H), 1.45-1.11 (m, 2H), 0.75-0.32 (m, 4H). m/z (APCI-pos) M+1=580.3.

Example 168

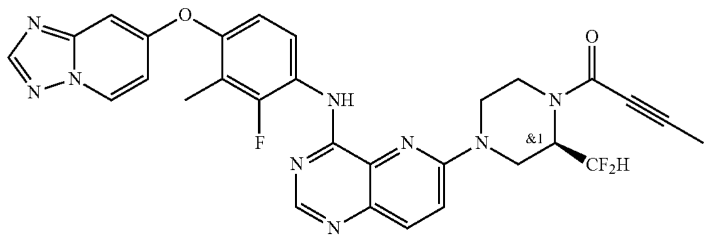 [SMILES: CC#CC(=O)N1CCN(c2ccc3ncnc(Nc4ccc(Oc5ccn6ncnc6c5)c(C)c4F)c3n2)C[C@@H]1C(F)F]

rac-1-(4-(4-((4-([1,2,4]triazolo[1,5-a]pyridin-7-yloxy)-2-fluoro-3-methylphenyl)amino)pyrido[3,2-d]pyrimidin-6-yl)-2-(difluoromethyl)piperazin-1-yl) but-2-yn-1-one Step A: rac-tert-Butyl (R)-2-(difluoromethyl)piperazine-1-carboxylate (140 mg, 2 Eq, 593 μmol) was added to a stirred solution of N-(4-([1,2,4]triazolo[1,5-a]pyridin-7-yloxy)-2-fluoro-3-methylphenyl)-6-chloropyrido[3,2-d]pyrimidin-4-amine (125 mg, 1 Eq, 296 μmol) and DIEA (153 mg, 4 Eq, 1.19 mmol) in DMSO (2.4 mL) at 100° C. for 16 hours. Another 1 equivalent of the piperazine and 2 equivalents of DIEA were added, and the mixture stirred at 100° C. for another 24 hours, then allowed to cool to room temperature. The mixture was diluted with EtOAc, washed with water/brine, dried over sodium sulfate, and concentrated under reduced pressure. Flash chromatography (DCM to 10% MeOH/DCM) afforded rac-tert-butyl (R)-4-(4-((4-([1,2,4]triazolo[1,5-a]pyridin-7-yloxy)-2-fluoro-3-methylphenyl)amino)pyrido[3,2-d]pyrimidin-6-yl)-2-(difluoromethyl)piperazine-1-carboxylate (128 mg, 70%). m/z (APCI-pos) M+1=622.3.

Step B: TFA (0.27 g, 30 Eq, 2.4 mmol) was added to a stirred solution of rac-tert-butyl (R)-4-(4-((4-([1,2,4]triazolo[1,5-a]pyridin-7-yloxy)-2-fluoro-3-methylphenyl)amino)pyrido[3,2-d]pyrimidin-6-yl)-2-(difluoromethyl)piperazine-1-carboxylate (49 mg, 1 Eq, 79 μmol) in DCM (0.8 mL) at 20° C. for 16 hours. The mixture was diluted with EtOAc, washed 2× with 10% aqueous potassium carbonate, dried over sodium sulfate and concentrated under reduced pressure to give rac-(R)—N-(4-([1,2,4]triazolo[1,5-a]pyridin-7-yloxy)-2-fluoro-3-methylphenyl)-6-(3-(difluoromethyl)piperazin-1-yl)pyrido[3,2-d]pyrimidin-4-amine (41 mg, 100%). m/z (APCI-pos) M+1=522.20.

Step C: 2,4,6-Tripropyl-1,3,5,2,4,6-trioxatriphosphinane 2,4,6-trioxide (0.13 g, 50% Wt, 2.5 Eq, 0.20 mmol) was added to a stirred solution of rac-(R)—N-(4-([1,2,4]triazolo[1,5-a]pyridin-7-yloxy)-2-fluoro-3-methylphenyl)-6-(3-(difluoromethyl)piperazin-1-yl)pyrido[3,2-d]pyrimidin-4-amine (41 mg, 1 Eq, 79 μmol), but-2-ynoic acid (9.9 mg, 1.5 Eq, 0.12 mmol), and DIEA (51 mg, 0.39 mmol) in DMF (0.8 mL) at 20° C. for 16 hours. The mixture was diluted with EtOAc, washed with water/brine (3×), 10% aqueous k-carb (1×), dried over sodium sulfate and concentrated under reduced pressure. Flash chromatography (DCM to 10% MeOH/DCM) afforded rac-1-(4-(4-((4-([1,2,4]triazolo[1,5-a]pyridin-7-yloxy)-2-fluoro-3-methylphenyl)amino)pyrido[3,2-d]pyrimidin-6-yl)-2-(difluoromethyl)piperazin-1-yl) but-2-yn-1-one (32 mg, 69%). $^1$H NMR (400 MHz, $CDCl_3$) δ 9.05 (s, 1H), 8.82 (t, J=9.0 Hz, 1H), 8.67 (d, J=4.4 Hz, 1H), 8.54-8.47 (m, 1H), 8.24 (s, 1H), 8.04 (dd, J=9.3, 4.9 Hz, 1H), 7.31 (dd, J=11.1, 9.3 Hz, 1H), 7.01 (dd, J=9.3, 1.7 Hz, 1H), 6.93-6.85 (m, 2H), 6.26-5.82 (m, 1H), 5.09-4.78 (m, 1H), 4.70 (dd, J=13.9, 7.9 Hz, 1H), 4.59-4.29 (m, 1H), 3.74-3.62 (m, 1H), 3.56 (ddd, J=14.3, 4.9, 2.4 Hz, 1H), 3.45-3.28 (m, 1H), 3.25-3.05 (m, 1H), 2.21 (t, J=1.7 Hz, 3H), 2.09 (d, J=1.6 Hz, 3H). m/z (APCI-pos) M+1=588.20.

Example 169

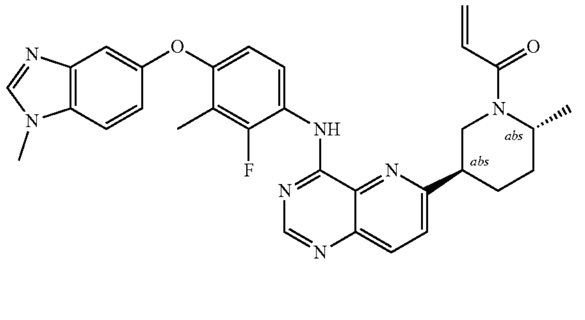 [SMILES: C=CC(=O)N1C[C@H](c2ccc3ncnc(Nc4ccc(Oc5ccc6c(c5)ncn6C)c(C)c4F)c3n2)CC[C@H]1C]

1-((2R,5R)-5-(4-((2-fluoro-3-methyl-4-((1-methyl-1H-benzo[d]imidazol-5-yl)oxy)phenyl)amino)pyrido[3,2-d]pyrimidin-6-yl)-2-methylpiperidin-1-yl)prop-2-en-1-one Step A: A pressure tube containing 6-chloro-N-(2-fluoro-3-methyl-4-((1-methyl-1H-benzo[d]imidazol-5-yl)oxy)phenyl)pyrido[3,2-d]pyrimidin-4-amine (100 mg, 0.23 mmol) was charged with tert-butyl (R)-2-methyl-5-(4,4,5,5-tetramethyl-1,3,2-dioxaborolan-2-yl)-3,6-dihydropyridine-1(2H)-carboxylate (149 mg, 0.460 mmol), dioxane (2.3 mL), 2M aqueous k-carb (0.345 mL, 3 eq.) and $Pd(PPh_3)_4$ (26.6 mg, 0.023 mmol). The mixture was purged with argon for a few minutes, tube sealed, and the mixture warmed to 100° C. for 16 hours, then allowed to cool to room temperature. The mixture was then diluted with EtOAc/water, extracted with EtOAc, extracts dried over sodium sulfate and concentrated under reduced pressure. Flash chromatography (DCM to 10% MeOH/DCM) afforded tert-butyl (R)-5-(4-((2-fluoro-3-methyl-4-((1-methyl-1H-benzo[d]imidazol-5-yl)oxy)phenyl)amino)pyrido[3,2-d]pyrimidin-6-yl)-2-methyl-3,6-dihydropyridine-1(2H)-carboxylate (79.5 mg, 58%). m/z (APCI-pos) M+1=596.30.

Step B: A pressure tube containing tert-butyl (R)-5-(4-((2-fluoro-3-methyl-4-((1-methyl-1H-benzo[d]imidazol-5-yl)oxy)phenyl)amino)pyrido[3,2-d]pyrimidin-6-yl)-2-methyl-3,6-dihydropyridine-1(2H)-carboxylate (79.5 mg, 0.133 mmol) was charged with methanol (1.3 mL), ammonium formate (84.2 mg, 1.33 mmol) and 10% Pd/C (80 mg). The tube was sealed, and the mixture warmed to 75° C. for 2 hours, then allowed to cool to room temperature. The mixture was diluted with methanol, filtered through an acrodisc filter attached to the end of a syringe, and the filtrate concentrated under reduced pressure. The resulting crude product was taken up in EtOAc/10% aqueous potassium carbonate, dried over sodium sulfate and concentrated under reduced pressure to give the diastereomeric mixture (56.1 mg). Chiral OD-H chromatography (MeOH:IPA:DEA, 80:20:0.01, 5%-70% over 16 minutes) separated the diastereomers to give tert-butyl (2R,5R)-5-(4-((2-fluoro-3-methyl-4-((1-methyl-1H-benzo[d]imidazol-5-yl)oxy)phenyl)amino)pyrido[3,2-d]pyrimidin-6-yl)-2-methylpiperidine-1-carboxylate (20.7 mg, peak 1) and tert-butyl (2R,5S)-5-(4-((2-fluoro-3-methyl-4-((1-methyl-1H-benzo[d]imidazol-5-yl)oxy)phenyl)amino)pyrido[3,2-d]pyrimidin-6-yl)-2-methylpiperidine-1-carboxylate (17.7 mg, peak 2, 70% overall). m/z (APCI-pos) M+1=598.40 for peak 1 and m/z (APCI-pos) M+1=598.35 for peak 2.

Step C: TFA (79.0 mg, 53.4 μL, 20 Eq, 693 μmol) was added to a stirred solution of tert-butyl (2R,5R)-5-(4-((2-fluoro-3-methyl-4-((1-methyl-1H-benzo[d]imidazol-5-yl)oxy)phenyl)amino)pyrido[3,2-d]pyrimidin-6-yl)-2-methylpiperidine-1-carboxylate (20.7 mg, 0.1 molar, 1 Eq, 34.6 μmol) in DCM (0.4 mL) at 20° C. for 2 hours. The mixture was diluted with EtOAc, washed with 10% aqueous potassium carbonate, dried over sodium sulfate, and concentrated under reduced pressure to give N-(2-fluoro-3-methyl-4-((1-methyl-1H-benzo[d]imidazol-5-yl)oxy)phenyl)-6-((3R,6R)-6-methylpiperidin-3-yl)pyrido[3,2-d]pyrimidin-4-amine (12.7 mg, 74%). m/z (APCI-pos) M+1=498.30.

Step D: Acryloyl chloride (1.85 mg, 0.8 Eq, 20.4 μmol) was added to a stirred solution of N-(2-fluoro-3-methyl-4-((1-methyl-1H-benzo[d]imidazol-5-yl)oxy)phenyl)-6-((3R,6R)-6-methylpiperidin-3-yl)pyrido[3,2-d]pyrimidin-4-amine (12.7 mg, 1 Eq, 25.5 μmol) and DIEA (9.90 mg, 3 Eq, 76.6 μmol) in DCM (0.3 mL) at 0° C. under nitrogen for 30 minutes. The mixture was diluted with EtOAc, washed with 10% aqueous potassium carbonate, dried over sodium sulfate, and concentrated under reduced pressure. Flash chromatography (DCM to 10% MeOH/DCM) afforded 1-((2R,5R)-5-(4-((2-fluoro-3-methyl-4-((1-methyl-1H-benzo[d]imidazol-5-yl)oxy)phenyl)amino)pyrido[3,2-d]pyrimidin-6-yl)-2-methylpiperidin-1-yl)prop-2-en-1-one (7.2 mg, 51%). $^1H$ NMR (400 MHz, $CDCl_3$) δ 9.56 (s, 1H), 8.68 (s, 1H), 8.08 (d, J=8.7 Hz, 1H), 8.00-7.82 (m, 2H), 7.73 (d, J=8.7 Hz, 1H), 7.40 (d, J=2.2 Hz, 1H), 7.35 (d, J=8.7 Hz, 1H), 7.07 (dd, J=8.7, 2.2 Hz, 1H), 6.70 (d, J=8.9 Hz, 1H), 6.55 (dd, J=16.7, 10.6 Hz, 1H), 6.13 (dd, J=16.7, 1.9 Hz, 1H), 5.59-5.52 (m, 1H), 4.43 (s, 1H), 3.86 (s, 3H), 3.47-3.24 (m, 2H), 2.43-2.22 (m, 5H), 1.91-1.42 (m, 2H), 1.35 (d, J=6.8 Hz, 3H). m/z (APCI-pos) M+1=552.30.

Example 170

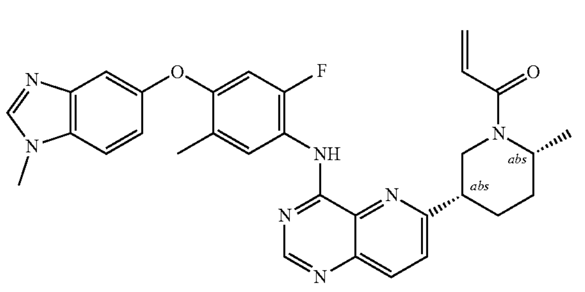 [SMILES: C=CC(=O)N1C[C@@H](c2ccc3ncnc(Nc4cc(C)c(Oc5ccc6c(c5)ncn6C)cc4F)c3n2)CC[C@H]1C]

1-((2R,5S)-5-(4-((2-fluoro-5-methyl-4-((1-methyl-1H-benzo[d]imidazol-5-yl)oxy)phenyl)amino)pyrido[3,2-d]pyrimidin-6-yl)-2-methylpiperidin-1-yl)prop-2-en-1-one Step A: TFA (76.7 mg, 30 Eq, 673 μmol) was added to a stirred solution of tert-butyl (2R,5S)-5-(4-((2-fluoro-5-methyl-4-((1-methyl-1H-benzo[d]imidazol-5-yl)oxy)phenyl)amino)pyrido[3,2-d]pyrimidin-6-yl)-2-methylpiperidine-1-carboxylate (13.4 mg, 1 Eq, 22.4 μmol, Example 169, Step B) in DCM (0.2 mL) at 20° C. for 2 hours. The mixture was diluted with EtOAc, washed with 10% aqueous potassium carbonate, dried over sodium sulfate, and concentrated under reduced pressure to give N-(2-fluoro-5-methyl-4-((1-methyl-1H-benzo[d]imidazol-5-yl)oxy)phenyl)-6-((3S,6R)-6-methylpiperidin-3-yl)pyrido[3,2-d]pyrimidin-4-amine (7.8 mg, 70%). m/z (APCI-pos) M+1=498.30.

Step B: Acryloyl chloride (1.1 mg, 0.8 Eq, 13 μmol) was added to a stirred solution of N-(2-fluoro-5-methyl-4-((1-methyl-1H-benzo[d]imidazol-5-yl)oxy)phenyl)-6-((3S,6R)-6-methylpiperidin-3-yl)pyrido[3,2-d]pyrimidin-4-amine (7.8 mg, 1 Eq, 16 μmol) and DIEA (6.1 mg, 3 Eq, 47 μmol) in DCM (0.16 mL) at 0° C. under nitrogen for 30 minutes. The mixture was diluted with EtOAc, washed with 10% aqueous potassium carbonate, dried over sodium sulfate, and concentrated under reduced pressure. Flash chromatography (DCM to 10% MeOH/DCM) afforded (2.4 mg, 28%). $^1H$ NMR (400 MHz, $CDCl_3$) δ 9.25 (s, 1H), 8.80 (s, 1H), 8.67-8.52 (m, 1H), 8.21-8.03 (m, 1H), 7.88 (s, 1H), 7.66 (d, J=8.6 Hz, 1H), 7.40-7.33 (m, 2H), 7.07 (d, J=8.6 Hz, 1H), 6.74-6.59 (m, 2H), 6.34-6.22 (m, 1H), 5.74-5.64 (m, 1H), 5.20-4.77 (m, 1H), 4.49-4.07 (m, 1H), 3.87 (s, 3H), 3.71-2.93 (m, 2H), 2.38 (s, 3H), 2.26-1.71 (m, 4H), 1.47-1.22 (m, 3H). m/z (APCI-pos) M+1=552.25.

Example 171

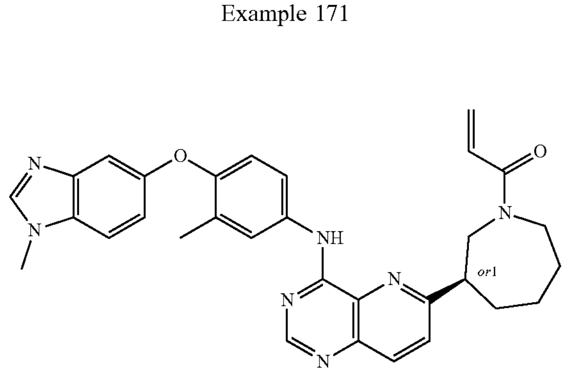

rel-(R)-1-(3-(4-((3-methyl-4-((1-methyl-1H-benzo[d]imidazo-5-yl)oxy)phenyl)amino)pyrido[3,2-d]pyrimidin-6-yl)azepan-1-yl)prop-2-en-1-one Step A: A pressure tube containing 6-chloro-N-(3-methyl-4-((1-methyl-1H-benzo[d]imidazol-5-yl)oxy)phenyl)pyrido[3,2-d]pyrimidin-4-amine (110 mg, 0.264 mmol) was charged with tert-butyl 6-(4,4,5,5-tetramethyl-1,3,2-dioxaborolan-2-yl)-2,3,4,7-tetrahydro-1H-azepine-1-carboxylate (128 mg, 0.396 mmol), dioxane (2.6 mL) aqueous k-carb (3 eq. of a 2M solution) and $Pd(PPh_3)_4$ (30.5 mg, 0.0264 mmol). This mixture was purged with argon for a few minutes, tube sealed, and the mixture warmed to 100° C. for 16 hours then allowed to cool to room temperature. The mixture was diluted with EtOAc, washed with water/brine, dried over sodium sulfate, and concentrated under reduced pressure. Flash chromatography (DCM to 10% MeOH/DCM) afforded rel-(R)-1-(3-(4-((3-methyl-4-((1-methyl-1H-benzo[d]imidazol-5-yl)oxy)phenyl)amino)pyrido[3,2-d]pyrimidin-6-yl)azepan-1-yl)prop-2-en-1-one (101 mg, 66%). m/z (APCI-pos) M+1=578.30.

Step B: A pressure tube containing tert-butyl 6-(4-((3-methyl-4-((1-methyl-1H-benzo[d]imidazol-5-yl)oxy)phenyl)amino)pyrido[3,2-d]pyrimidin-6-yl)-2,3,4,7-tetrahydro-1H-azepine-1-carboxylate (101 mg, 0.175 mmol) was charged with methanol (1.75 mL), ammonium formate (110 mg, 1.75 mmol) and 10% Pd/C (100 mg). The tube was sealed, and the mixture warmed to 75° C. for 1 hour, then allowed to cool to room temperature. The mixture was diluted with MeOH, filtered through an acrodisc filter attached to a syringe, and the filtrate concentrated under reduced pressure. The resulting crude material was taken up in EtOAc/10% aqueous potassium carbonate, extracted with EtOAc, extracts dried over sodium sulfate and concentrated under reduced pressure to give rac-tert-butyl-3-(4-((3-methyl-4-((1-methyl-1H-benzo[d]imidazol-5-yl)oxy)phenyl)amino)pyrido[3,2-d]pyrimidin-6-yl)azepane-1-carboxylate (67.4 mg, 67%). m/z (APCI-pos) M+1=580.30. Chiral separation ((AS-H (2×25 cm) 20% methanol (0.1% DEA)/$CO_2$, 100 bar 60 mL/min, 220 nm inj. vol.: 0.5 mL, 2 mg/mL DCM:methanol) afforded rel-tert-butyl-(R)-3-(4-((3-methyl-4-((1-methyl-1H-benzo[d]imidazol-5-yl)oxy)phenyl)amino)pyrido[3,2-d]pyrimidin-6-yl)azepane-1-carboxylate (29 mg) and rel-tert-butyl-(S)-3-(4-((3-methyl-4-((1-methyl-1H-benzo[d]imidazol-5-yl)oxy)phenyl)amino)pyrido[3,2-d]pyrimidin-6-yl)azepane-1-carboxylate (27 mg). m/z (APCI-pos) M+1=580.30 for both isomers.

Step C: TFA (0.17 g, 30 Eq, 1.5 mmol) was added to a stirred solution of rel-tert-butyl (R)-3-(4-((3-methyl-4-((1-methyl-1H-benzo[d]imidazol-5-yl)oxy)phenyl)amino)pyrido[3,2-d]pyrimidin-6-yl)azepane-1-carboxylate (29 mg, 1 Eq, 50 μmol) in DCM (0.5 mL) at 20° C. for 2 hours. The mixture was diluted with EtOAc, washed with 10% aqueous potassium carbonate, dried over sodium sulfate, and concentrated under reduced pressure to give rel-(R)-6-(azepan-3-yl)-N-(3-methyl-4-((1-methyl-1H-benzo[d]imidazol-5-yl)oxy)phenyl)pyrido[3,2-d]pyrimidin-4-amine (20.8 mg, 87%). m/z (APCI-pos) M+1=480.30.

Step D: Acryloyl chloride (3.93 mg, 1 Eq, 43.4 μmol) was added to a stirred solution of rel-(R)-6-(azepan-3-yl)-N-(3-methyl-4-((1-methyl-1H-benzo[d]imidazol-5-yl)oxy)phenyl)pyrido[3,2-d]pyrimidin-4-amine (20.8 mg, 1 Eq, 43.4 μmol) and DIEA (16.8 mg, 3 Eq, 130 μmol) in DCM (0.5 mL) at 0° C. under nitrogen for 30 minutes. The mixture was diluted with EtOAc, washed with 10% aqueous potassium carbonate, dried over sodium sulfate, and concentrated under reduced pressure. Flash chromatography (DCM to 10% MeOH/DCM) afforded rel-(R)-1-(3-(4-((3-methyl-4-((1-methyl-1H-benzo[d]imidazol-5-yl)oxy)phenyl)amino)pyrido[3,2-d]pyrimidin-6-yl)azepan-1-yl)prop-2-en-1-one (11.3 mg, 49%). $^1$H NMR (400 MHz, $CDCl_3$) δ 9.29-8.90 (m, 1H), 8.78-8.71 (m, 1H), 8.17-8.05 (m, 1H), 7.87-7.81 (m, 2H), 7.81-7.57 (m, 2H), 7.37-7.29 (m, 2H), 7.11-7.03 (m, 1H), 6.99-6.91 (m, 1H), 6.71-6.59 (m, 1H), 6.46-6.37 (m, 1H), 5.78-5.67 (m, 1H), 4.34-4.10; 3.83-3.60; 3.52-3.22 (m, 5H), 3.88-3.83 (m, 3H), 2.39-2.33 (m, 3H), 2.22-1.76 (m, 5H), 1.69-1.48 (m, 1H). m/z (APCI-pos) $M^+1$=534.30.

Example 172

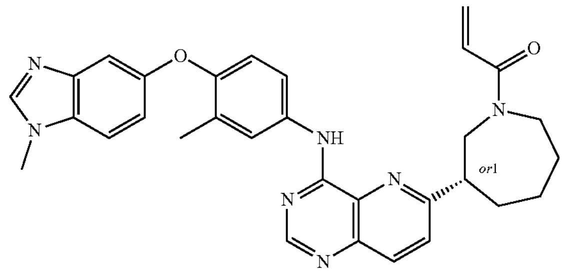 [SMILES: C=CC(=O)N1CCCC[C@H](c2ccc3ncnc(Nc4ccc(Oc5ccc6c(c5)ncn6C)c(C)c4)c3n2)C1]

rel-(S)-1-(3-(4-((3-methyl-4-((1-methyl-1H-benzo[d]imidazol-5-yl)oxy)phenyl)amino)pyrido[3,2-d]pyrimidin-6-yl)azepan-1-yl)prop-2-en-1-one Step A: TFA (0.16 g, 30 Eq, 1.4 mmol) was added to a stirred solution of rel-tert-butyl (R)-3-(4-((3-methyl-4-((1-methyl-1H-benzo[d]imidazol-5-yl)oxy)phenyl)amino)pyrido[3,2-d]pyrimidin-6-yl)azepane-1-carboxylate (27 mg, 1 Eq, 47 μmol, Example 171, Step B) in DCM (0.4 mL) at 20° C. for 2 hours. The mixture was diluted with EtOAc, washed with 10% aqueous potassium carbonate, dried over sodium sulfate, and concentrated under reduced pressure to give rel-(S)-6-(azepan-3-yl)-N-(3-methyl-4-((1-methyl-1H-benzo[d]imidazol-5-yl)oxy)phenyl)pyrido[3,2-d]pyrimidin-4-amine (20 mg, 90%). m/z (APCI-pos) M+1=480.30.

Step B: Acryloyl chloride (3.8 mg, 1 Eq, 42 μmol) was added to a stirred solution of rel-(R)-6-(azepan-3-yl)-N-(3-methyl-4-((1-methyl-1H-benzo[d]imidazol-5-yl)oxy)phenyl)pyrido[3,2-d]pyrimidin-4-amine (20 mg, 1 Eq, 42 μmol) and DIEA (16 mg, 3 Eq, 0.13 mmol) in DCM (0.5 mL) at 0° C. under nitrogen for 30 minutes. The mixture was diluted with EtOAc, washed with 10% aqueous potassium carbonate, dried over sodium sulfate, and concentrated under reduced pressure. Flash chromatography (DCM to 10% MeOH/DCM) afforded rel-(S)-1-(3-(4-((3-methyl-4-((1-methyl-1H-benzo[d]imidazol-5-yl)oxy)phenyl)amino)pyrido[3,2-d]pyrimidin-6-yl)azepan-1-yl)prop-2-en-1-one (11.7 mg, 53%). $^1$H NMR (400 MHz, $CDCl_3$) δ 9.29-8.90 (m, 1H), 8.78-8.71 (m, 1H), 8.17-8.05 (m, 1H), 7.87-7.81 (m, 2H), 7.80-7.58 (m, 2H), 7.37-7.29 (m, 2H), 7.11-7.02 (m, 1H), 6.99-6.91 (m, 1H), 6.71-6.59 (m, 1H), 6.46-6.37 (m, 1H), 5.78-5.67 (m, 1H), 4.34-4.10; 3.83-3.60; 3.52-3.22 (m, 5H), 3.87-3.83 (m, 3H), 2.39-2.34 (m, 3H), 2.23-1.75 (m, 5H), 1.70-1.49 (m, 1H). m/z (APCI-pos) M+1=534.30.

Example 173

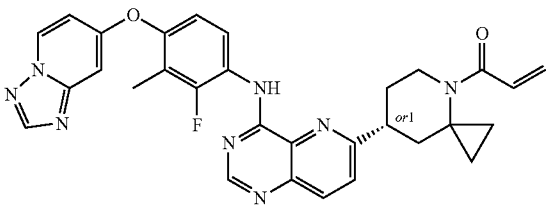 [SMILES: C=CC(=O)N1CC[C@@H](c2ccc3ncnc(Nc4ccc(Oc5ccn6ncnc6c5)c(C)c4F)c3n2)CC12CC2]

rel-(R)-1-(7-(4-((4-([1,2,4]triazolo[1,5-a]pyridin-7-yloxy)-2-fluoro-3-methylphenyl)amino)pyrido[3,2-d]pyrimidin-6-yl)-4-azaspiro[2.5]octan-4-yl)prop-2-en-1-one Step A: An 8 mL vial containing (4,4'-di-tert-butyl-2,2'-bipyridine)bis[(2-pyridinyl)phenyl]iridium(III) hexafluorophosphate (6.51 mg, 0.0071 mmol), (SP-4-2)-[4,4'-bis(1,1-dimethylethyl)-2,2'-bipyridine-κN1,κN1']dibromo-nickel (17.3 mg, 0.0356 mmol), quinuclidine (105 mgs, 0.948 mmol), phthalimide (15.7 mg, 0.107 mmol), and N-(4-([1,2,4]triazolo[1,5-a]pyridin-7-yloxy)-2-fluoro-3-methylphenyl)-6-chloropyrido[3,2-d]pyrimidin-4-amine (200 mgs, 0.474 mmol) was taken up in DMA (2.0 mL). To a separate 8 ml vial was added 5,7-di-tert-butyl-3-phenyl-3-(tetrafluoro-15-boraneyl)-2,3-dihydrobenzo[d]oxazol-3-ium-2-ide (394 mg, 0.996 mmol), tert-butyl 7-hydroxy-4-azaspiro[2.5]octane-4-carboxylate (216 mg, 0.948 mmol), and dry MTBE (3.0 mL) under nitrogen. After 1 minute of stirring, pyridine (76.4 μL, 0.948 mmol) was added, and the mixture stirred vigorously for 5 minutes. This mixture was the taken up in a syringe and filtered through an acrodisc into the first vial. This vial was capped, purged with nitrogen for a few minutes, parafilmed and irradiated with 450 nm light in the photoreactor for 8 hours (100% intensity, 750 rpm stir, max speed fan). The mixture was diluted with EtOAc, washed several times with brine, dried over sodium sulfate and concentrated under reduced pressure. Flash chromatography (DCM to 10% MeOH/DCM) afforded rel-tert-butyl (R)-7-(4-((4-([1,2,4]triazolo[1,5-a]pyridin-7-yloxy)-2-fluoro-3-methylphenyl)amino)pyrido[3,2-d]pyrimidin-6-yl)-4-azaspiro[2.5]octane-4-carboxylate (83 mg, 29%). m/z (APCI-pos) M+1=597.20. Chiral separation of this material (ChiralTech Chiralcel® OD-H, 250 (L)×20 (ID) mm, 40% i-PrOH (0.1% DEA) with CO2) afforded rel-tert-butyl (R)-7-(4-((4-([1,2,4]triazolo[1,5-a]pyridin-7-yloxy)-2-fluoro-3-methylphenyl)amino)pyrido[3,2-d]pyrimidin-6-yl)-4-azaspiro[2.5]octane-4-carboxylate (34 mg) and rel-tert-butyl (S)-7-(4-((4-([1,2,4]triazolo[1,5-a]pyridin-7-yloxy)-2-fluoro-3-methylphenyl)amino)pyrido[3,2-d]pyrimidin-6-yl)-4-azaspiro[2.5]octane-4-carboxylate (35 mg).

Step B: TFA (0.19 g, 30 Eq, 1.7 mmol) was added to a stirred solution of rel-tert-butyl (R)-7-(4-((4-([1,2,4]triazolo[1,5-a]pyridin-7-yloxy)-2-fluoro-3-methylphenyl)amino)pyrido[3,2-d]pyrimidin-6-yl)-4-azaspiro[2.5]octane-4-carboxylate (34 mg, 1 Eq, 57 μmol) in DCM (0.6 mL) at 20° C. for 16 hours. The mixture was diluted with EtOAc, washed 2× with 10% aqueous potassium carbonate, dried over sodium sulfate and concentrated under reduced pressure to give rel-(R)—N-(4-([1,2,4]triazolo[1,5-a]pyridin-7-yloxy)-2-fluoro-3-methylphenyl)-6-(4-azaspiro[2.5]octan-7-yl)pyrido[3,2-d]pyrimidin-4-amine (21.2 mg, 75%). m/z (APCI-pos) M+1=497.25.

Step C: Acryloyl chloride (3.86 mg, 1 Eq, 42.7 μmol) was added to a stirred solution of rel-(R)—N-(4-([1,2,4]triazolo[1,5-a]pyridin-7-yloxy)-2-fluoro-3-methylphenyl)-6-(4-azaspiro[2.5]octan-7-yl)pyrido[3,2-d]pyrimidin-4-amine (21.2 mg, 1 Eq, 42.7 μmol) and DIEA (16.6 mg, 3 Eq, 128 μmol) in DCM (0.5 mL) at 0° C. under nitrogen for 30 minutes. The mixture was diluted with EtOAc, washed with 10% aqueous potassium carbonate, dried over sodium sulfate, and concentrated under reduced pressure. Flash chromatography (DCM to 10% MeOH/DCM) afforded rel-(R)-1-(7-(4-((4-([1,2,4]triazolo[1,5-a]pyridin-7-yloxy)-2-fluoro-3-methylphenyl)amino)pyrido[3,2-d]pyrimidin-6-yl)-4-azaspiro[2.5]octan-4-yl)prop-2-en-1-one (16.1 mg, 69%). $^1$H NMR (400 MHz, $CDCl_3$) δ 9.41 (d, J=3.3 Hz, 1H), 8.80 (s, 1H), 8.75 (t, J=9.0 Hz, 1H), 8.56-8.48 (m, 1H), 8.24 (s, 1H), 8.14 (d, J=8.7 Hz, 1H), 7.64 (d, J=8.7 Hz, 1H), 7.01 (dd, J=9.1, 1.8 Hz, 1H), 6.95-6.86 (m, 2H), 6.41 (d, J=16.8 Hz, 1H), 5.74 (dd, J=10.4, 2.1 Hz, 1H), 4.93-4.70 (m, 1H), 3.60-3.38 (m, 1H), 3.20-2.99 (m, 1H), 2.54-2.31 (m, 1H), 2.22 (d, J=2.1 Hz, 3H), 2.17-1.85 (m, 2H), 1.52-1.05 (m, 3H), 0.93-0.69 (m, 2H). m/z (APCI-pos) M+1=551.20.

Example 174

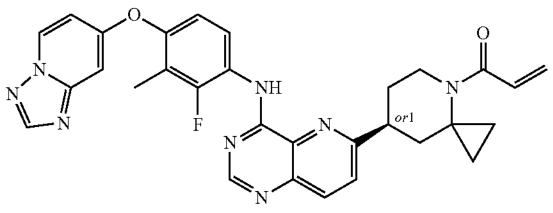 [SMILES: C=CC(=O)N1CC[C@H](c2ccc3ncnc(Nc4ccc(Oc5ccn6ncnc6c5)c(C)c4F)c3n2)CC12CC2]

rel-(S)-1-(7-(4-((4-([1,2,4]triazolo[1,5-a]pyridin-7-yloxy)-2-fluoro-3-methylphenyl)amino)pyrido[3,2-d]pyrimidin-6-yl)-4-azaspiro[2.5]octan-4-yl)prop-2-en-1-one Step A: TFA (0.20 g, 30 Eq, 1.8 mmol) was added to a stirred solution of rel-tert-butyl (R)-7-(4-((4-([1,2,4]triazolo[1,5-a]pyridin-7-yloxy)-2-fluoro-3-methylphenyl)amino)pyrido[3,2-d]pyrimidin-6-yl)-4-azaspiro[2.5]octane-4-carboxylate (35 mg, 1 Eq, 59 μmol) in DCM (0.6 mL) at 20° C. for 16 hours. The mixture was diluted with EtOAc, washed 2× with washed with 10% aqueous potassium carbonate, dried over sodium sulfate, and concentrated under reduced pressure to give rel-(S)—N-(4-([1,2,4]triazolo[1,5-a]pyridin-7-yloxy)-2-fluoro-3-methylphenyl)-6-(4-azaspiro[2.5]octan-7-yl)pyrido[3,2-d]pyrimidin-4-amine (20.2 mg, 69%). m/z (APCI-pos) M+1=497.30.

Step B: Acryloyl chloride (3.68 mg, 1 Eq, 40.7 μmol) was added to a stirred solution of rel-(S)—N-(4-([1,2,4]triazolo[1,5-a]pyridin-7-yloxy)-2-fluoro-3-methylphenyl)-6-(4-azaspiro[2.5]octan-7-yl)pyrido[3,2-d]pyrimidin-4-amine (20.2 mg, 1 Eq, 40.7 μmol) and DIEA (15.8 mg, 3 Eq, 122 μmol) in DCM (0.5 mL) at 0° C. under nitrogen for 30 minutes. The mixture was diluted with EtOAc, washed with 10% aqueous k-carb, dried over sodium sulfate, and concentrated under reduced pressure. Flash chromatography (DCM to 10% MeOH/DCM) afforded rel-(S)-1-(7-(4-((4-([1,2,4]triazolo[1,5-a]pyridin-7-yloxy)-2-fluoro-3-methylphenyl)amino)pyrido[3,2-d]pyrimidin-6-yl)-4-azaspiro[2.5]octan-4-yl)prop-2-en-1-one (16.5 mg). $^1$H NMR (400 MHz, $CDCl_3$) δ 9.41 (d, J=3.2 Hz, 1H), 8.80 (s, 1H), 8.75 (t, J=8.9 Hz, 1H), 8.55-8.48 (m, 1H), 8.24 (s, 1H), 8.14 (d, J=8.7 Hz, 1H), 7.64 (d, J=8.7 Hz, 1H), 7.01 (dd, J=9.0, 1.8 Hz, 1H), 6.97-6.82 (m, 2H), 6.41 (d, J=16.8 Hz, 1H), 5.74 (dd, J=10.3, 2.1 Hz, 1H), 4.92-4.68 (m, 1H), 3.60-3.36 (m, 1H), 3.22-2.95 (m, 1H), 2.51-2.32 (m, 1H), 2.22 (d, J=2.1 Hz, 3H), 2.16-1.83 (m, 2H), 1.52-1.07 (m, 3H), 0.91-0.69 (m, 2H). m/z (APCI-pos) M+1=551.30.

Example 175

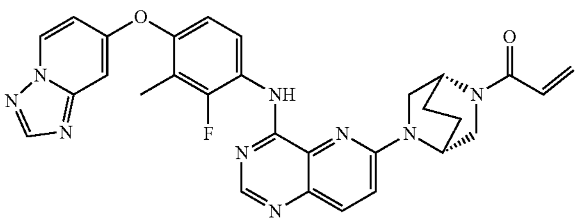 [SMILES: C=CC(=O)N1C[C@H]2CC[C@@H]1CN2c1ccc2ncnc(Nc3ccc(Oc4ccn5ncnc5c4)c(C)c3F)c2n1]

1-((1R,4R)-5-(4-((4-([1,2,4]triazolo[1,5-a]pyridin-7-yloxy)-2-fluoro-3-methylphenyl)amino)pyrido[3,2-d]pyrimidin-6-yl)-2,5-diazabicyclo[2.2.2]octan-2-yl)prop-2-en-1-one Step A: To a vial was added N-(4-([1,2,4]triazolo[1,5-a]pyridin-7-yloxy)-2-fluoro-3-methylphenyl)-6-chloropyrido[3,2-d]pyrimidin-4-amine (35 mg, 83 μmol) and (1R,4R)-tert-Butyl 2,5-diazabicyclo[2.2.2]octane-2-carboxylate (35 mg, 0.17 mmol) followed by DMSO (0.83 mL) and N,N-diisopropylethylamine (22 μL, 0.12 mmol). The mixture was then warmed to 100° C. where it stirred for 4 hours. The mixture was then cooled to ambient temperature and diluted with water. The mixture was then extracted with $CHCl_3$ (3×), and the combined extracts were dried over $Na_2SO_4$, filtered and concentrated. The crude product was then purified via column chromatography (1-8% MeOH/$CHCl_3$) to afford tert-butyl (1R,4R)-5-(4-((4-([1,2,4]triazolo[1,5-a]pyridin-7-yloxy)-2-fluoro-3-methylphenyl)amino)pyrido[3,2-d]pyrimidin-6-yl)-2,5-diazabicyclo[2.2.2]octane-2-carboxylate (42 mg, 85%) as a solid. m/z (APCI-pos) M+1=598.2.

Step B: To a vial containing tert-butyl (1R,4R)-5-(4-((4-([1,2,4]triazolo[1,5-a]pyridin-7-yloxy)-2-fluoro-3-methylphenyl)amino)pyrido[3,2-d]pyrimidin-6-yl)-2,5-diazabicyclo[2.2.2]octane-2-carboxylate (42 mg, 70 μmol) was added $CH_2Cl_2$ (1.4 mL), and the solution was treated with TFA (0.11 mL, 1.4 mmol). The mixture was then stirred at ambient temperature for 1 hour. The mixture was neutralized with saturated aqueous $NaHCO_3$, and the resulting mixture was extracted with 20% IPA/$CHCl_3$ (3×). The combined extracts were then dried over $Na_2SO_4$, filtered and concentrated. The crude product (32 mg) was used directly in the subsequent step. m/z (APCI-pos) M+1=498.2.

Step C: The crude product was then dissolved in $CH_2Cl_2$ (1.4 mL) and N,N-diisopropylethylamine (24 μL, 0.14 mmol). The mixture was cooled to 0° C. in an ice/water bath and then acryloyl chloride (5.7 μL, 70 μmol) was added. The mixture was then stirred at 0° C. for 0.5 hour. The mixture was then treated with saturated aqueous $NaHCO_3$, and the mixture was extracted with $CHCl_3$ (3×). The combined organic extracts were dried over $Na_2SO_4$, filtered and concentrated. The crude product was then purified via column chromatography (2 to 8% MeOH/$CH_2Cl_2$) to afford 1-((1R,4R)-5-(4-((4-([1,2,4]triazolo[1,5-a]pyridin-7-yloxy)-2-fluoro-3-methylphenyl)amino)pyrido[3,2-d]pyrimidin-6-yl)-2,5-diazabicyclo[2.2.2]octan-2-yl)prop-2-en-1-one (26 mg, 59% for two steps) as a solid. $^1$H NMR (400 MHz, $CDCl_3$) δ 9.07 (s, 1H), 8.82 (td, J=9.0, 2.2 Hz, 1H), 8.63 (s, 1H), 8.53-8.47 (m, 1H), 8.23 (s, 1H), 7.99 (dd, J=9.3, 3.1 Hz, 1H), 7.06 (d, J=9.2 Hz, 1H), 7.03-6.97 (m, 1H), 6.92-6.84 (m, 2H), 6.64-6.36 (m, 2H), 5.80-5.73 (m, 1H), 4.76 (d, J=260.6 Hz, 2H), 4.02-3.68 (m, 4H), 2.25-2.13 (m, 5H), 2.09-1.92 (m, 2H). (Amide rotational isomers present in NMR) m/z (APCI-pos) M+1=552.2.

Example 176

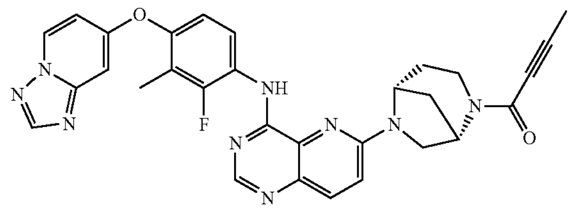 [SMILES: CC#CC(=O)N1CC[C@@H]2C[C@H]1CN2c1ccc2ncnc(Nc3ccc(Oc4ccn5ncnc5c4)c(C)c3F)c2n1]

1-((1 S,5R)-6-(4-((4-([1,2,4]triazolo[1,5-a]pyridin-7-yloxy)-2-fluoro-3-methylphenyl)amino)pyrido[3,2-d]pyrimidin-6-yl)-2,6-diazabicyclo[3.2.1]octan-2-yl)but-2-yn-1-one Step A: To a vial was added N-(4-([1,2,4]triazolo[1,5-a]pyridin-7-yloxy)-2-fluoro-3-methylphenyl)-6-chloropyrido[3,2-d]pyrimidin-4-amine (100 mg, 237 μmol) and (1S,5R)-2,6-Diaza-bicyclo[3.2.1]octane-2-carboxylic acid tert-butyl ester (101 mg, 474 μmol) followed by DMSO (1.58 mL). Then N,N-diisopropylethylamine (82.6 μL, 474 μmol) was added, and the mixture was then warmed to 100° C. where it stirred for 3 hours. The mixture was then cooled to ambient temperature and diluted with water. The solid was isolated by vacuum filtration and washed with water. The solid was then dissolved in $CH_2Cl_2$, and the filtrate was dried over $Na_2SO_4$, filtered and concentrated. The crude product was then purified via column chromatography (1-8% MeOH/$CHCl_3$) to afford tert-butyl (1S,5R)-6-(4-((4-([1,2,4]triazolo[1,5-a]pyridin-7-yloxy)-2-fluoro-3-methylphenyl)amino)pyrido[3,2-d]pyrimidin-6-yl)-2,6-diazabicyclo[3.2.1]octane-2-carboxylate (135 mg, 95%) as a solid. m/z (APCI-pos) M+1=598.3.

Step B: To a vial containing tert-butyl (1S,5R)-6-(4-((4-([1,2,4]triazolo[1,5-a]pyridin-7-yloxy)-2-fluoro-3-methylphenyl)amino)pyrido[3,2-d]pyrimidin-6-yl)-2,6-diazabicyclo[3.2.1]octane-2-carboxylate (135 mg, 226 μmol) was added $CH_2Cl_2$ (4.52 mL), and the solution was treated with TFA (348 μL, 4.52 mmol). The mixture was then stirred at ambient temperature for 1 hour.

The mixture was neutralized with saturated aqueous $NaHCO_3$, and the resulting mixture was extracted with 20% $IPA/CHCl_3$ (3×). The combined extracts were then dried over $Na_2SO_4$, filtered and concentrated. The crude product (118 mg) was used directly in the subsequent step. m/z (APCI-pos) M+1=498.2.

Step C: The crude product was then dissolved in $CH_2Cl_2$ (4.52 mL) and N,N-diisopropylethylamine (157 μL, 904 μmol). To the mixture was then added but-2-ynoic acid (22.8 mg, 271 μmol) followed by HATU (94.5 mg, 248 μmol). The mixture was then stirred for 0.5 hour. The mixture was then treated with 1:1 water:saturated aqueous $NaHCO_3$, and the mixture was extracted with $CHCl_3$ (3×). The combined organic extracts were dried over $Na_2SO_4$, filtered and concentrated. The crude product was then purified via column chromatography (2 to 8% $MeOH/CH_2Cl_2$) to afford 1-((1S, 5R)-6-(4-((4-([1,2,4]triazolo[1,5-a]pyridin-7-yloxy)-2-fluoro-3-methylphenyl)amino)pyrido[3,2-d]pyrimidin-6-yl)-2,6-diazabicyclo[3.2.1]octan-2-yl)but-2-yn-1-one (108 mg, 97% for 2 steps) as a solid. $^1H$ NMR (400 MHz, $CDCl_3$) δ 9.16 (dd, J=7.9, 3.6 Hz, 1H), 8.84 (t, J=9.0 Hz, 1H), 8.62 (d, J=0.9 Hz, 1H), 8.53-8.48 (m, 1H), 8.23 (s, 1H), 7.98 (dd, J=9.2, 2.5 Hz, 1H), 7.07-6.98 (m, 2H), 6.92-6.85 (m, 2H), 5.52-5.30 (m, 1H), 4.79 (br s, 1H), 4.38 (ddd, J=66.0, 14.0, 6.4 Hz, 1H), 3.91 (dd, J=26.0, 10.8 Hz, 1H), 3.70 (br s, 1H), 3.32-2.80 (m, 1H), 2.36-2.10 (obs m, 2H), 2.22-2.18 (m, 3H), 2.05 (d, J=30 Hz, 3H), 2.00-1.78 (m, 2H). (Amide rotational isomers present in NMR) m/z (APCI-pos) M+1=564.2.

Example 177

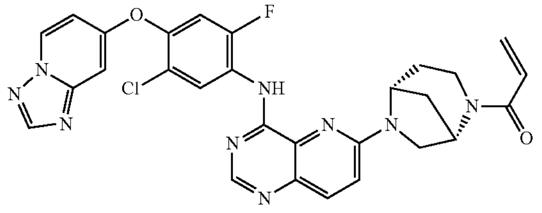 [SMILES: C=CC(=O)N1CC[C@@H]2C[C@H]1CN2c1ccc2ncnc(Nc3cc(Cl)c(Oc4ccn5ncnc5c4)cc3F)c2n1]

1-((1 S,5R)-6-(4-((4-([1,2,4]triazolo[1,5-a]pyridin-7-yloxy)-5-chloro-2-fluorophenyl)amino)pyrido[3,2-d]pyrimidin-6-yl)-2,6-diazabicyclo[3.2.1]octan-2-yl)prop-2-en-1-one Step A: To a vial was added N-(4-([1,2,4]triazolo[1,5-a]pyridin-7-yloxy)-5-chloro-2-fluorophenyl)-6-chloropyrido[3,2-d]pyrimidin-4-amine (35 mg, 79 μmol) and tert-butyl (1S,5R)-2,6-diazabicyclo[3.2.1]octane-2-carboxylate (30 mg, 0.14 mmol) and DMSO (0.53 mL) followed by N,N-diisopropylethylamine (21 μL, 0.12 mmol). The mixture was then warmed to 100° C. where it stirred for 5 hours. The mixture was then cooled to ambient temperature and diluted with water. The solid was isolated by vacuum filtration and washed with water. The solid was then dissolved in $CH_2Cl_2$, and the filtrate was dried over $Na_2SO_4$, filtered and concentrated. The crude product was then purified via column chromatography (1-8% $MeOH/CH_2Cl_2$) to afford tert-butyl (1S,5R)-6-(4-((4-([1,2,4]triazolo[1,5-a]pyridin-7-yloxy)-5-chloro-2-fluorophenyl)amino)pyrido[3,2-d]pyrimidin-6-yl)-2,6-diazabicyclo[3.2.1]octane-2-carboxylate (49 mg, quant) as a solid. m/z (APCI-pos) M+1=618.2.

Step B: To a vial containing tert-butyl (1S,5R)-6-(4-((4-([1,2,4]triazolo[1,5-a]pyridin-7-yloxy)-5-chloro-2-fluorophenyl)amino)pyrido[3,2-d]pyrimidin-6-yl)-2,6-diazabicyclo[3.2.1]octane-2-carboxylate (49 mg, 79 μmol) was added $CH_2Cl_2$ (1.6 mL), and the solution was treated with TFA (0.12 mL, 1.6 mmol). The mixture was then stirred at ambient temperature for 1 hour. The mixture was neutralized with saturated aqueous $NaHCO_3$, and the resulting mixture was extracted with 20% $IPA/CHCl_3$ (3×). The combined extracts were then dried over $Na_2SO_4$, filtered and concentrated. The crude product (40 mg) was used directly in the subsequent step. m/z (APCI-pos) M+1=518.2.

Step C: The crude product was then dissolved in $CH_2Cl_2$ (1.6 mL) and N,N-diisopropylethylamine (28 μL, 0.16 mmol). The mixture was cooled to 0° C. in an ice/water bath, and then acryloyl chloride (6.4 μL, 79 μmol) was added. The mixture was then stirred at 0° C. for 0.5 hour. The mixture was then treated with saturated aqueous $NaHCO_3$ and was extracted with $CHCl_3$ (3×). The combined organic extracts were dried over $Na_2SO_4$, filtered and concentrated. The crude product was then purified via column chromatography (2 to 8% $MeOH/CH_2Cl_2$) to afford 1-((1 S,5R)-6-(4-((4-([1,2,4]triazolo[1,5-a]pyridin-7-yloxy)-5-chloro-2-fluorophenyl)amino)pyrido[3,2-d]pyrimidin-6-yl)-2,6-diazabicyclo[3.2.1]octan-2-yl)prop-2-en-1-one (36 mg, 75% over 2 steps) as a solid. $^1H$ NMR (400 MHz, $CDCl_3$) δ 9.29 (d, J=8.3 Hz, 1H), 9.16 (s, 1H), 8.68 (s, 1H), 8.54-8.51 (m, J=8.3 Hz, 1H), 8.25 (s, 1H), 7.99 (d, J=9.3 Hz, 1H), 7.11 (d, J=10.8 Hz, 1H), 7.06 (d, J=9.2 Hz, 1H), 6.94-6.88 (m, 2H), 6.71-6.49 (m, 1H), 6.33 (d, J=16.6 Hz, 1H), 5.78-5.71 (m, 1H), 5.61-4.88 (m, 1H), 4.77 (br s, 1H), 4.53-3.85 (m, 2H), 3.68 (br s, 1H), 3.36-2.86 (m, 1H), 2.26-2.11 (m, 2H), 2.06-1.81 (m, 2H). (Amide rotational isomers present in NMR) m/z (APCI-pos) M+1=572.2.

Example 178

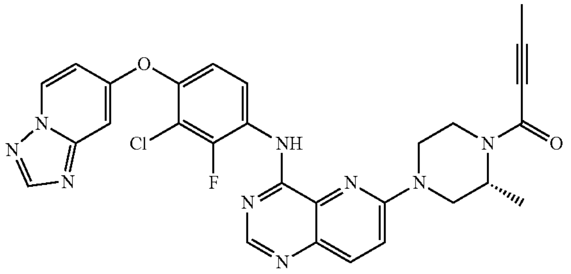 [SMILES: CC#CC(=O)N1CCN(c2ccc3ncnc(Nc4ccc(Oc5ccn6ncnc6c5)c(Cl)c4F)c3n2)C[C@H]1C]

(R)-1-(4-(4-((4-([1,2,4]triazolo[1,5-a]pyridin-7-yloxy)-3-chloro-2-fluorophenyl)amino)pyrido[3,2-d]pyrimidin-6-yl)-2-methylpiperazin-1-yl)but-2-yn-1-one Step A: To a vial was added N-(4-([1,2,4]triazolo[1,5-a]pyridin-7-yloxy)-3-chloro-2-fluorophenyl)-6-chloropyrido[3,2-d]pyrimidin-4-amine (50 mg, 0.11 mmol), tert-butyl (2R)-2-methyl-1-piperazinecarboxylate (45 mg, 0.23 mmol) and DMSO (0.75 mL), followed by N,N-diisopropylethylamine (30 μL, 0.17 mmol). The mixture was then warmed to 90° C. where it stirred for 16 hours. The mixture was then cooled to ambient temperature and diluted with water, and the solid was isolated by vacuum filtration. The solid was then dissolved in $CH_2Cl_2$, and the filtrate was dried over $Na_2SO_4$, filtered and concentrated. Crude tert-butyl (R)-4-(4-((4-([1,2,4]triazolo[1,5-a]pyridin-7-yloxy)-3-chloro-2-fluorophenyl)amino)pyrido[3,2-d]pyrimidin-6-yl)-2-methylpiperazine-1-carboxylate (68 mg, 99%) was sufficiently pure to move to the subsequent step without further purification. m/z (APCI-pos) M+1=606.2.

Step B: To a vial containing tert-butyl (R)-4-(4-((4-([1,2,4]triazolo[1,5-a]pyridin-7-yloxy)-3-chloro-2-fluorophenyl)amino)pyrido[3,2-d]pyrimidin-6-yl)-2-methylpiperazine-1-carboxylate (68 mg, 0.11 mmol) was added $CH_2Cl_2$ (2.2 mL), and the solution was treated with TFA (0.17 mL, 2.2 mmol). The mixture was then stirred at ambient temperature for 2 hours. The mixture was neutralized with saturated aqueous $NaHCO_3$, and the resulting mixture was extracted with 20% IPA/$CHCl_3$ (3×). The combined extracts were then dried over $Na_2SO_4$, filtered and concentrated. The crude product was used directly in the subsequent step. m/z (APCI-pos) M+1=506.1.

Step C: The crude product was then dissolved in DMF (0.56 mL) and N,N-diisopropylethylamine (98 μL). To the mixture was then added 2-butynoicacid (15 μL, 0.17 mmol) followed by propylphosphonic anhydride (0.17 mL, 50% Wt, 0.28 mmol). The mixture was then stirred for 5 hours. The mixture was then treated with saturated aqueous $NaHCO_3$, and the mixture was extracted with $CHCl_3$ (3×). The combined organic extracts were dried over $Na_2SO_4$, filtered and concentrated. The crude product was then purified via column chromatography (2 to 8% MeOH/$CH_2Cl_2$) followed by Reverse Phase chromatography (10 to 70% ACN/$H_2O$ with 0.1% TFA buffer). The fractions containing clean product were then concentrated, treated with saturated aqueous $NaHCO_3$, then extracted with $CHCl_3$ (3×). The combined organic extracts were dried over $Na_2SO_4$, filtered, and concentrated to afford (R)-1-(4-(4-((4-([1,2,4]triazolo[1,5-a]pyridin-7-yloxy)-3-chloro-2-fluorophenyl)amino)pyrido[3,2-d]pyrimidin-6-yl)-2-methylpiperazin-1-yl)but-2-yn-1-one (24 mg, 35% over two steps) as a solid. $^1H$ NMR (400 MHz, $CDCl_3$) δ 9.10 (d, J=3.4 Hz, 1H), 9.01 (t, J=8.9 Hz, 1H), 8.67 (s, 1H), 8.54 (dd, J=7.2, 1.0 Hz, 1H), 8.25 (s, 1H), 8.02 (dd, J=9.4, 1.4 Hz, 1H), 7.30 (dd, J=9.4, 6.9 Hz, 1H), 7.16 (dd, J=9.2, 2.0 Hz, 1H), 6.95-6.89 (m, 2H), 4.95-4.78 (m, 1H), 4.60-4.12 (m, 3H), 3.67-3.16 (m, 3H), 2.08 (d, J=4.3 Hz, 3H), 1.33 (dd, J=38.3, 6.8 Hz, 3H). m/z (APCI-pos) M+1=572.2.

Example 179

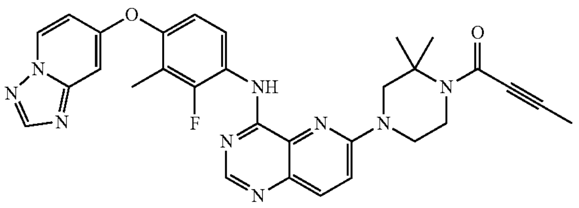 [SMILES: CC#CC(=O)N1CCN(c2ccc3ncnc(Nc4ccc(Oc5ccn6ncnc6c5)c(C)c4F)c3n2)CC1(C)C]

1-(4-(4-((4-([1,2,4]triazolo[1,5-a]pyridin-7-yloxy)-2-fluoro-3-methylphenyl)amino)pyrido[3,2-d]pyrimidin-6-yl)-2,2-dimethylpiperazin-1-yl)but-2-yn-1-one Step A: DIPEA (0.11 g, 0.87 mmol) was added to a stirred solution of N-(4-([1,2,4]triazolo[1,5-a]pyridin-7-yloxy)-2-fluoro-3-methylphenyl)-6-chloropyrido[3,2-d]pyrimidin-4-amine hydrochloride (0.080 g, 0.17 mmol) and tert-butyl 2,2-dimethylpiperazine-1-carboxylate (0.11 g, 0.52 mmol) in DMSO (1.5 mL) at 100° C. under sealed tube. The reaction was partitioned between water and $CH_2Cl_2$. The organic layer was dried over sodium sulfate, filtered, and concentrated in vacuo. The crude residue was purified over 12 g silica cartridge, eluting with a gradient of 0% to 50%, 20% MeOH in $CH_2Cl_2$ in $CH_2Cl_2$ to afford tert-butyl-4-(4-((4-([1,2,4]triazolo[1,5-a]pyridin-7-yloxy)-2-fluoro-3-methylphenyl)amino)pyrido[3,2-d]pyrimidin-6-yl)-2,2-dimethylpiperazine-1-carboxylate (0.078 g, 0.13 mmol, 75%). m/z (APCI-pos) M+1=600.3.

Step B: Trifluoroacetic acid (0.30 g, 2.6 mmol) was added to a stirred solution of tert-butyl-4-(4-((4-([1,2,4]triazolo[1,5-a]pyridin-7-yloxy)-2-fluoro-3-methylphenyl)amino)pyrido[3,2-d]pyrimidin-6-yl)-2,2-dimethylpiperazine-1-carboxylate (0.078 g, 0.13 mmol) in DCM. The reaction mixture was diluted with DCM and quenched via the addition of saturated $NaHCO_3$. After 10 minutes of stirring, the aqueous and organic phases were separated, and the aqueous layer was extracted with DCM, the combined organic layers were dried over $Na_2SO_4$ and concentrated to afford N-(4-([1,2,4]triazolo[1,5-a]pyridin-7-yloxy)-2-fluoro-3-methylphenyl)-6-(3,3-dimethylpiperazin-1-yl)pyrido[3,2-d]pyrimidin-4-amine (58.7 mg, 118 μmol, 90%). m/z (APCI-pos) M+1=500.2.

Step C: 2,4,6-Tripropyl-1,3,5,2,4,6-trioxatriphosphinane 2,4,6-trioxide (0.16 g, 0.15 mL, 50% Wt, 2.5 Eq, 0.25 mmol) was added to a stirred solution of DIPEA (65 mg, 0.50 mmol), N-(4-([1,2,4]triazolo[1,5-a]pyridin-7-yloxy)-2-fluoro-3-methylphenyl)-6-(3,3-dimethylpiperazin-1-yl)pyrido[3,2-d]pyrimidin-4-amine (0.050 g, 0.10 mmol), but-2-ynoic acid (13 mg, 0.15 mmol) in DMF (1.5 mL). After 16 hours, the reaction mixture was diluted with water and EtOAc. The aqueous and organic layers were separated. The aqueous layer was extracted with EtOAc. The combined organic layers were washed with brine, dried over $Na_2SO_4$, and concentrated. The resulting crude oil was purified via normal phase chromatography (12 g, $SiO_2$) using a gradient of 0% to 50%, 20% MeOH in $CH_2Cl_2$ in $CH_2Cl_2$ to afford 1-(4-(4-((4-([1,2,4]triazolo[1,5-a]pyridin-7-yloxy)-2-fluoro-3-methylphenyl)amino)pyrido[3,2-d]pyrimidin-6-yl)-2,2-dimethylpiperazin-1-yl)but-2-yn-1-one (9.1 mg, 16 μmol, 16%). $^1H$ NMR (400 MHz, $CDCl_3$) δ 9.11 (d, J=3.6 Hz, 1H), 8.84 (t, J=9.1 Hz, 1H), 8.64 (s, 1H), 8.51 (dd, J=7.2, 1.0 Hz, 1H), 8.23 (s, 1H), 8.01 (d, J=9.3 Hz, 1H), 7.15 (d, J=9.3 Hz, 1H), 7.01 (m, 1H), 6.89 (m, 2H), 4.25 (t, J=5.7 Hz, 1H), 3.92 (s, 2H), 3.85 (t, J=5.7 Hz, 2H), 2.21 (d, J=2.1 Hz, 3H), 2.04 (s, 3H), 1.55 (s, 6H). m/z (esi) M+1=566.2.

Example 180

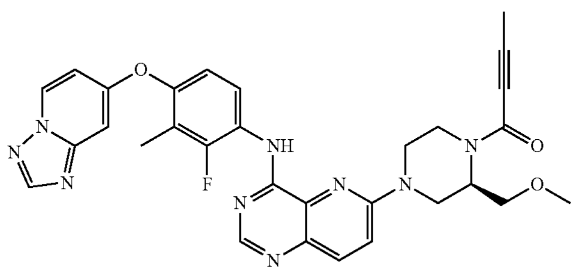 [SMILES: CC#CC(=O)N1CCN(c2ccc3ncnc(Nc4ccc(Oc5ccn6ncnc6c5)c(C)c4F)c3n2)C[C@@H]1COC]

(R)-1-(4-(4-((4-([1,2,4]triazolo[1,5-a]pyridin-7-yloxy)-2-fluoro-3-methylphenyl)amino)pyrido[3,2-d]pyrimidin-6-yl)-2-(methoxymethyl)piperazin-1-yl)but-2-yn-1-one Step A: N-Ethyl-N-isopropylpropan-2-amine (46 mg, 0.36 mmol) was added to a stirred solution of N-(4-([1,2,4]triazolo[1,5-a]pyridin-7-yloxy)-2-fluoro-3-methylphenyl)-6-chloropyrido[3,2-d]pyrimidin-4-amine (0.050 g, 0.12 mmol) and tert-butyl (R)-2-(methoxymethyl)piperazine-1-carboxylate (55 mg, 0.24 mmol) in DMSO (1 mL) at 100° C. under sealed tube. The reaction was partitioned between water and EtOAc. The organic layer was dried over sodium sulfate, filtered, and concentrated in vacuo. The crude residue was purified over 12 g silica cartridge, eluting with a gradient of 5% to 50%, 20% MeOH in $CH_2Cl_2$ in $CH_2Cl_2$ to afford tert-butyl (R)-4-(4-((4-([1,2,4]triazolo[1,5-a]pyridin-7-yloxy)-2-fluoro-3-methylphenyl)amino)pyrido[3,2-d]pyrimidin-6-yl)-2-(methoxymethyl)piperazine-1-carboxylate (57 mg, 93 μmol, 78%). m/z (esi) M+1=616.3.

Step B: Trifluoroacetic acid (0.21 g, 1.9 mmol) was added to a stirred solution of tert-butyl (R)-4-(4-((4-([1,2,4]triazolo[1,5-a]pyridin-7-yloxy)-2-fluoro-3-methylphenyl)amino)pyrido[3,2-d]pyrimidin-6-yl)-2-(methoxymethyl)piperazine-1-carboxylate (57 mg, 93 μmol) in DCM (1 mL). The reaction was partitioned between saturated $NaHCO_3$ and $CH_2Cl_2$. The organic layer was dried over sodium sulfate, filtered, and concentrated in vacuo to afford (R)—N-(4-([1,2,4]triazolo[1,5-a]pyridin-7-yloxy)-2-fluoro-3-methylphenyl)-6-(3-(methoxymethyl)piperazin-1-yl)pyrido[3,2-d]pyrimidin-4-amine (45 mg, 94%). m/z (esi) M+1=516.2.

Step C: 2,4,6-Tripropyl-1,3,5,2,4,6-trioxatriphosphinane 2,4,6-trioxide (0.14 g, 0.22 mmol) was added to a stirred solution of but-2-ynoic acid (11 mg, 0.13 mmol), DIPEA (56 mg, 0.44 mmol), and (R)—N-(4-([1,2,4]triazolo[1,5-a]pyridin-7-yloxy)-2-fluoro-3-methylphenyl)-6-(3-(methoxymethyl)piperazin-1-yl)pyrido[3,2-d]pyrimidin-4-amine (45 mg, 87 μmol) in DCM (1 mL). The reaction was partitioned between water and EtOAc. The organic layer was dried over sodium sulfate, filtered, and concentrated in vacuo. The crude residue was purified over 12 g silica cartridge, eluting with a gradient of 5% to 50%, 20% MeOH in $CH_2Cl_2$ in $CH_2Cl_2$ to afford (R)-1-(4-(4-((4-([1,2,4]triazolo[1,5-a]pyridin-7-yloxy)-2-fluoro-3-methylphenyl)amino)pyrido[3,2-d]pyrimidin-6-yl)-2-(methoxymethyl)piperazin-1-yl)but-2-yn-1-one (13.3 mg, 22.9 μmol, 26%). $^1H$ NMR (400 MHz, CDCl3) δ 9.08 (dd, J=6.3, 3.6 Hz, 1H), 8.82 (td, J=9.0, 3.2 Hz, 1H), 8.65 (s, 1H), 8.51 (d, J=7.3 Hz, 1H), 8.24 (s, 1H), 8.00 (dd, J=9.3, 3.0 Hz, 1H), 7.32 (d, J=9.4 Hz, 1H), 7.01 (m, 1H), 6.89 (m, 2H), 4.58 (m, 4H), 3.49 (m, 2H), 3.33 (m, 4H), 3.13 (m, 1H), 2.21 (d, J=2.2 Hz, 3H), 2.07 (d, J=1.5 Hz, 3H). m/z (esi) M+1=582.2.

Example 181

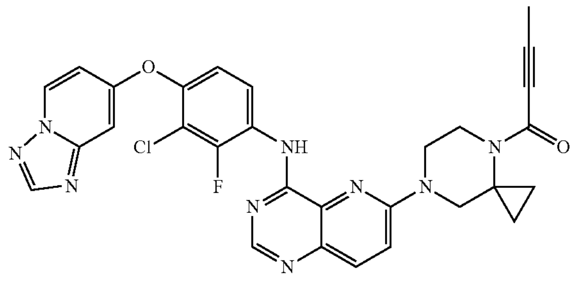 [SMILES: CC#CC(=O)N1CCN(c2ccc3ncnc(Nc4ccc(Oc5ccn6ncnc6c5)c(C)c4F)c3n2)CC12CC2]

1-(7-(4-((4-([1,2,4]triazolo[1,5-a]pyridin-7-yloxy)-3-chloro-2-fluorophenyl)amino)pyrido[3,2-d]pyrimidin-6-yl)-4,7-diazaspiro[2.5]octan-4-yl)but-2-yn-1-one Step A: N-Ethyl-N-isopropylpropan-2-amine (0.07 g, 0.5 mmol) was added to a stirred solution of N-(4-([1,2,4]triazolo[1,5-a]pyridin-7-yloxy)-3-chloro-2-fluorophenyl)-6-chloropyrido[3,2-d]pyrimidin-4-amine hydrochloride (0.05 g, 0.1 mmol) and tert-butyl 4,7-diazaspiro[2.5]octane-4-carboxylate (0.07 g, 0.3 mmol) in DMSO (1.5 mL) at 100° C. under sealed tube. The reaction was partitioned between water and EtOAc. The organic layer was washed with brine, dried over sodium sulfate, filtered, and concentrated in vacuo. The crude residue was purified over 12 g silica cartridge, eluting with a gradient of 5% to 50%, 20% MeOH in $CH_2Cl_2$ in $CH_2Cl_2$ to afford tert-butyl-7-(4-((4-([1,2,4]triazolo[1,5-a]pyridin-7-yloxy)-3-chloro-2-fluorophenyl)amino)pyrido[3,2-d]pyrimidin-6-yl)-4,7-diazaspiro[2.5]octane-4-carboxylate (59 mg, 95 μmol, 90%). m/z (esi) M+1=618.2.

Step B: Trifluoroacetic acid (0.16 g, 1.4 mmol) was added to a stirred solution of tert-butyl 7-(4-((4-([1,2,4]triazolo[1,5-a]pyridin-7-yloxy)-3-chloro-2-fluorophenyl)amino)pyrido[3,2-d]pyrimidin-6-yl)-4,7-diazaspiro[2.5]octane-4-carboxylate (0.059 g, 95 μmol) in DCM (1 mL). After 45 minutes, the reaction mixture was diluted with DCM and quenched via the addition of saturated $NaHCO_3$. After 10 minutes of stirring, the aqueous and organic layers were separated, and the aqueous layer was extracted with DCM. The combined organic layers were dried over $Na_2SO_4$ and concentrated to afford N-(4-([1,2,4]triazolo[1,5-a]pyridin-7-yloxy)-3-chloro-2-fluorophenyl)-6-(4,7-diazaspiro[2.5]octan-7-yl)pyrido[3,2-d]pyrimidin-4-amine (48 mg, 93 μmol, 97%). m/z (esi) M+1=518.2.

Step C: 2,4,6-Tripropyl-1,3,5,2,4,6-trioxatriphosphinane 2,4,6-trioxide (0.15 g, 0.23 mmol) was added to a stirred solution of but-2-ynoic acid (12 mg, 1.5 Eq, 0.14 mmol), N-ethyl-N-isopropylpropan-2-amine (60 mg, 0.46 mmol) and N-(4-([1,2,4]triazolo[1,5-a]pyridin-7-yloxy)-3-chloro-2-fluorophenyl)-6-(4,7-diazaspiro[2.5]octan-7-yl)pyrido[3,2-d]pyrimidin-4-amine (48 mg, 93 μmol) in DMF (1 mL). The reaction was partitioned between water and EtOAc. The organic layer was washed with brine (2×), dried over sodium sulfate, filtered, and concentrated in vacuo. The crude residue was purified over 12 g silica cartridge, eluting with a gradient of 5% to 50%, 20% MeOH in $CH_2Cl_2$ in $CH_2Cl_2$ to afford 1-(7-(4-((4-([1,2,4]triazolo[1,5-a]pyridin-7-yloxy)-3-chloro-2-fluorophenyl)amino)pyrido[3,2-d]pyrimidin-6-yl)-4,7-diazaspiro[2.5]octan-4-yl)but-2-yn-1-one (9.6 mg, 16 μmol, 18%). $^1H$ NMR (400 MHz, $CDCl_3$) δ 9.01 (m, 2H), 8.66 (d, J=1.0 Hz, 1H), 8.53 (dd, J=7.1, 1.1 Hz, 1H), 8.25 (s, 1H), 8.00 (dd, J=9.3, 2.3 Hz, 1H), 7.27 (m, 1H), 7.15 (dd, J=9.2, 2.0 Hz, 1H), 6.92 (m, 2H), 4.06 (m, 1H), 3.95 (m, 2H), 3.82 (m, 1H), 3.75 (s, 1H), 3.63 (s, 1H), 2.09 (s, 3H), 1.34 (m, 1H), 1.23 (m, 1H), 1.11 (m, 1H) 1.02 (m, 1H). m/z (esi) M+1=584.2.

Example 182

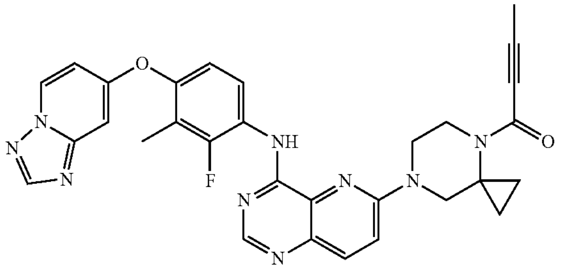

1-(7-(4-((4-([1,2,4]triazolo[1,5-a]pyridin-7-yloxy)-2-fluoro-3-methylphenyl)amino)pyrido[3,2-d]pyrimidin-6-yl)-4,7-diazaspiro[2.5]octan-4-yl)but-2-yn-1-one Step A: DIEPA (0.07 g, 0.5 mmol) was added to a stirred solution of N-(4-([1,2,4]triazolo[1,5-a]pyridin-7-yloxy)-2-fluoro-3-methylphenyl)-6-chloropyrido[3,2-d]pyrimidin-4-amine hydrochloride (0.05 g, 0.1 mmol) and tert-butyl 4,7-diazaspiro[2.5]octane-4-carboxylate (0.07 g, 0.3 mmol) in DMSO (1 mL) at 100° C. under sealed tube. The reaction was partitioned between water and EtOAc. The organic layer was washed with brine, dried over sodium sulfate, filtered, and concentrated in vacuo. The crude residue was purified over 12 g silica cartridge, eluting with a gradient of 5% to 50%, 20% MeOH in $CH_2Cl_2$ in $CH_2Cl_2$ to afford tert-butyl-7-(4-((4-([1,2,4]triazolo[1,5-a]pyridin-7-yloxy)-2-fluoro-3-methylphenyl)amino)pyrido[3,2-d]pyrimidin-6-yl)-4,7-diazaspiro[2.5]octane-4-carboxylate (57 mg, 95 μmol, 90%). m/z (esi) M+1=598.3.

Step B: Trifluoroacetic acid (0.16 g, 1.4 mmol) was added to a stirred solution of tert-butyl 7-(4-((4-([1,2,4]triazolo[1,5-a]pyridin-7-yloxy)-2-fluoro-3-methylphenyl)amino)pyrido[3,2-d]pyrimidin-6-yl)-4,7-diazaspiro[2.5]octane-4-carboxylate (0.057 g, 95 μmol) in DCM (1 mL). The reaction was partitioned between saturated $NaHCO_3$ and $CH_2Cl_2$. The organic layer was dried over sodium sulfate, filtered, and concentrated in vacuo to afford N-(4-([1,2,4]triazolo[1,5-a]pyridin-7-yloxy)-2-fluoro-3-methylphenyl)-6-(4,7-diazaspiro[2.5]octan-7-yl)pyrido[3,2-d]pyrimidin-4-amine (39 mg, 78 μmol, 82%). m/z (esi) M+1=498.2.

Step C: 2,4,6-Tripropyl-1,3,5,2,4,6-trioxatriphosphinane 2,4,6-trioxide (0.12 g, 0.20 mmol) was added to a stirred solution of but-2-ynoic acid (9.9 mg, 0.12 mmol), N-ethyl-N-isopropylpropan-2-amine (51 mg, 0.39 mmol) and N-(4-([1,2,4]triazolo[1,5-a]pyridin-7-yloxy)-2-fluoro-3-methylphenyl)-6-(4,7-diazaspiro[2.5]octan-7-yl)pyrido[3,2-d]pyrimidin-4-amine (39 mg, 78 μmol) in DMF (1 mL). The reaction was partitioned between water and EtOAc. The organic layer was dried over sodium sulfate, filtered, and concentrated in vacuo. The crude residue was purified over 12 g silica cartridge, eluting with a gradient of 5% to 50%, 20% MeOH in $CH_2Cl_2$ in $CH_2Cl_2$ to afford 1-(7-(4-((4-([1,2,4]triazolo[1,5-a]pyridin-7-yloxy)-2-fluoro-3-methylphenyl)amino)pyrido[3,2-d]pyrimidin-6-yl)-4,7-diazaspiro[2.5]octan-4-yl)but-2-yn-1-one (11.9 mg, 21.1 μmol, 27%). $^1$H NMR (400 MHz, CDC13) δ 9.03 (m, 1H), 8.82 (t, J=9.0 Hz, 1H), 8.64 (s, 1H), 8.51 (dd, J=7.3, 0.9 Hz, 1H), 8.23 (s, 1H), 7.98 (d, J=9.4 Hz, 1H), 7.23 (m, 1H), 7.00 (dd, J=9.1, 1.8 Hz, 1H), 6.88 (m, 2H), 4.06 (m, 1H) 3.94 (m, 2H), 3.83 (m, 1H), 3.73 (s, 1H), 3.65 (m, 1H), 2.21 (d, J=2.1 Hz, 3H), 2.09 (s, 3H), 1.34 (m, 1H), 1.23 (m, 1H), 1.10 (m, 1H), 1.03 (m, 1H). m/z (esi) M+1=564.2.

Example 183

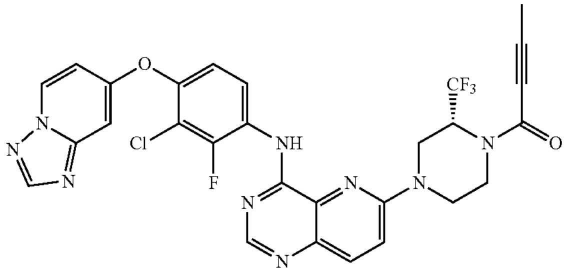 [SMILES: CC#CC(=O)N1CCN(c2ccc3ncnc(Nc4ccc(Oc5ccn6ncnc6c5)c(Cl)c4F)c3n2)C[C@@H]1C(F)(F)F]

(R)-1-(4-(4-((4-([1,2,4]triazolo[1,5-a]pyridin-7-yloxy)-3-chloro-2-fluorophenyl)amino)pyrido[3,2-d]pyrimidin-6-yl)-2-(trifluoromethyl)piperazin-1-yl)but-2-yn-1-one Step A: DIPEA (0.09 g, 0.7 mmol) was added to a stirred solution of (R)-2-(trifluoromethyl)piperazine dihydrochloride (0.05 g, 0.2 mmol) and N-(4-([1,2,4]triazolo[1,5-a]pyridin-7-yloxy)-3-chloro-2-fluorophenyl)-6-chloropyrido[3,2-d]pyrimidin-4-amine (0.05 g, 0.1 mmol) in DMSO (1 mL) at 100° C. under sealed tube. The reaction was partitioned between water and EtOAc. The organic layer was washed with brine, dried over sodium sulfate, filtered, and concentrated in vacuo. The crude residue was purified over 12 g silica cartridge, eluting with a gradient of 5% to 50%, 20% MeOH in $CH_2Cl_2$ in $CH_2Cl_2$ to afford (R)—N-(4-([1,2,4]triazolo[1,5-a]pyridin-7-yloxy)-3-chloro-2-fluorophenyl)-6-(3-(trifluoromethyl)piperazin-1-yl)pyrido[3,2-d]pyrimidin-4-amine (50.7 mg, 90.6 μmol, 80%). m/z (esi) M+1=560.2.

Step B: 2,4,6-Tripropyl-1,3,5,2,4,6-trioxatriphosphinane 2,4,6-trioxide (144 mg, 226 μmol) was added to a stirred solution of but-2-ynoic acid (11.4 mg, 136 μmol), DIPEA (58.5 mg, 453 μmol) and (R)—N-(4-([1,2,4]triazolo[1,5-a]pyridin-7-yloxy)-3-chloro-2-fluorophenyl)-6-(3-(trifluoromethyl)piperazin-1-yl)pyrido[3,2-d]pyrimidin-4-amine (0.0507 g, 90.6 μmol) in DMF (1 mL). The reaction mixture was partitioned between water and EtOAc, the aqueous layer was extracted with EtOAc, the combined organic layers were dried over $Na_2SO_4$, and concentrated. The crude residue was purified over 12 g silica cartridge, eluting with a gradient of 5% to 50%, 20% MeOH in $CH_2Cl_2$ in $CH_2Cl_2$ to afford (R)-1-(4-(4-((4-([1,2,4]triazolo[1,5-a]pyridin-7-yloxy)-3-chloro-2-fluorophenyl)amino)pyrido[3,2-d]pyrimidin-6-yl)-2-(trifluoromethyl)piperazin-1-yl)but-2-yn-1-one (5.1 mg, 8.1 μmol, 9.0%). $^1$H NMR (400 MHz, $CDCl_3$) δ 9.11 (m, 1H), 9.03 (m, 1H), 8.71 (s, 1H), 8.28 (s, 1H), 8.10 (dd, J=9.3, 0.8 Hz, 1H), 7.34 (dd, J=9.4, 2.8 Hz, 1H), 7.19 (m, 1H), 6.92 (m, 2H), 5.35 (m, 1H), 5.15 (m, 1H), 4.88 (m, 1H), 4.72 (m, 1H), 4.62 (m, 1H), 3.49 (m, 1H), 3.26 (m, 1H), 2.13 (d, J=4.8 Hz, 3H). m/z (esi) M+1=626.2.

Example 184

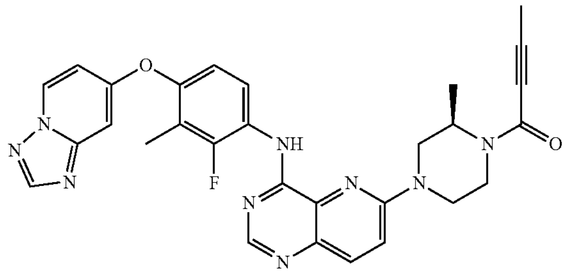 [SMILES: CC#CC(=O)N1CCN(c2ccc3ncnc(Nc4ccc(Oc5ccn6ncnc6c5)c(C)c4F)c3n2)C[C@H]1C]

(R)-1-(4-(4-((4-([1,2,4]triazolo[1,5-a]pyridin-7-yloxy)-2-fluoro-3-methylphenyl)amino)pyrido[3,2-d]pyrimidin-6-yl)-2-methylpiperazin-1-yl)but-2-yn-1-one Step A: N-Ethyl-N-isopropylpropan-2-amine (212 mg, 1.64 mmol) was added to a stirred solution of N-(4-([1,2,4]triazolo[1,5-a]pyridin-7-yloxy)-2-fluoro-3-methylphenyl)-6-chloropyrido[3,2-d]pyrimidin-4-amine hydrochloride (0.150 g, 327 μmol) and tert-butyl (R)-2-methylpiperazine-1-carboxylate (197 mg, 982 μmol) in DMSO (3 mL) at 100° C. under sealed tube. The reaction was partitioned between water and $CH_2Cl_2$. The aqueous layer was extracted with DCM, the combined organic layer was dried over sodium sulfate, filtered, and concentrated in vacuo. The crude residue was purified over 12 g silica cartridge, eluting with a gradient of 0% to 50%, 20% MeOH in $CH_2Cl_2$ in $CH_2Cl_2$ to afford tert-butyl (R)-4-(4-((4-([1,2,4]triazolo[1,5-a]pyridin-7-yloxy)-2-fluoro-3-methylphenyl)amino)pyrido[3,2-d]pyrimidin-6-yl)-2-methylpiperazine-1-carboxylate (129 mg, 220 μmol, 67.3%). m/z (esi) M+1=586.3.

Step B: Trifluoroacetic acid (502 mg, 4.41 mmol) was added to a stirred solution of tert-butyl-(R)-4-(4-((4-([1,2,4]triazolo[1,5-a]pyridin-7-yloxy)-2-fluoro-3-methylphenyl)amino)pyrido[3,2-d]pyrimidin-6-yl)-2-methylpiperazine-1-carboxylate (129 mg, 220 μmol) in DCM (2 mL). The reaction was diluted with DCM and quenched with saturated $NaHCO_3$. After 10 minutes of stirring, the aqueous and organic layers were separated, the aqueous layer was extracted with DCM, the combined organic layers were dried over sodium sulfate, filtered, and concentrated in vacuo to afford (R)—N-(4-([1,2,4]triazolo[1,5-a]pyridin-7-yloxy)-2-fluoro-3-methylphenyl)-6-(3-methylpiperazin-1-yl)pyrido[3,2-d]pyrimidin-4-amine (86 mg, 0.18 mmol, 80%). m/z (esi) M+1=486.3.

Step C: 2,4,6-Tripropyl-1,3,5,2,4,6-trioxatriphosphinane 2,4,6-trioxide (0.13 g, 0.20 mmol) was added to a stirred solution of N-ethyl-N-isopropylpropan-2-amine (87 mg, 0.67 mmol), but-2-ynoic acid (28 mg, 0.33 mmol) and (R)—N-(4-([1,2,4]triazolo[1,5-a]pyridin-7-yloxy)-2-fluoro-3-methylphenyl)-6-(3-methylpiperazin-1-yl)pyrido[3,2-d]pyrimidin-4-amine (65 mg, 0.13 mmol) in DMF (1 mL). The reaction was partitioned between water and EtOAc. The organic layer was dried over sodium sulfate, filtered, and concentrated in vacuo. The crude residue was purified over 12 g silica cartridge, eluting with a gradient of 5% to 50%, 20% MeOH in $CH_2Cl_2$ in $CH_2Cl_2$ to afford (R)-1-(4-(4-((4-([1,2,4]triazolo[1,5-a]pyridin-7-yloxy)-2-fluoro-3-methylphenyl)amino)pyrido[3,2-d]pyrimidin-6-yl)-2-methylpiperazin-1-yl)but-2-yn-1-one (13.4 mg, 24.3 μmol, 18%). $^1$H NMR (400 MHz, $CDCl_3$) δ 9.08 (d, J=3.6 Hz, 1H), 8.84 (t, J=8.8 Hz, 1H), 8.66 (s, 1H), 8.53 (dd, J=7.4, 0.9 Hz, 1H), 8.23 (s, 1H), 7.30 (m, 1H), 7.02 (dd, J=9.0, 1.8 Hz, 1H), 6.90 (m, 2H), 4.89 (m, 1H), 4.55 (m, 1H), 4.41 (m, 1H), 4.22 (m, 1H), 3.64 (m, 1H), 3.42 (m, 1H), 3.22 (m, 1H), 2.23 (d, J=2.1 Hz, 3H), 2.09 (d, J=4.2 Hz, 3H), 1.35 (d, J=6.8 Hz, 3H). m/z (esi) M+1=552.2.

Example 185

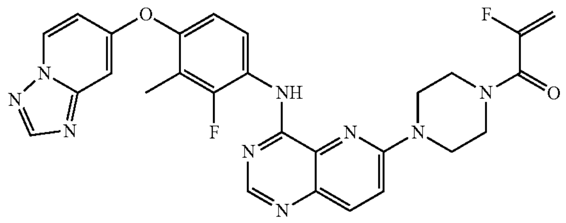 [SMILES: C=C(F)C(=O)N1CCN(c2ccc3ncnc(Nc4ccc(Oc5ccn6ncnc6c5)c(C)c4F)c3n2)CC1]

1-(4-(4-((4-([1,2,4]triazolo[1,5-a]pyridin-7-yloxy)-2-fluoro-3-methylphenyl)amino)pyrido[3,2-d]pyrimidin-6-yl)piperazin-1-yl)-2-fluoroprop-2-en-1-one Step A: DIPEA (212 mg, 1.64 mmol) was added to a stirred solution of N-(4-([1,2,4]triazolo[1,5-a]pyridin-7-yloxy)-2-fluoro-3-methylphenyl)-6-chloropyrido[3,2-d]pyrimidin-4-amine hydrochloride (0.150 g, 327 μmol) and tert-butyl piperazine-1-carboxylate (183 mg, 982 μmol) in DMSO (3.5 mL) at 100° C. under sealed tube. The reaction was partitioned between water and $CH_2Cl_2$. The organic layer was washed with brine, dried over sodium sulfate, filtered, and concentrated in vacuo. The crude residue was purified over 24 g silica cartridge, eluting with a gradient of 0% to 50%, 20% MeOH in $CH_2Cl_2$ in $CH_2Cl_2$ to afford tert-butyl 4-(4-((4-([1,2,4]triazolo[1,5-a]pyridin-7-yloxy)-2-fluoro-3-methylphenyl)amino)pyrido[3,2-d]pyrimidin-6-yl)piperazine-1-carboxylate (0.100 g, 175 μmol, 53.4%). m/z (esi) M+1=572.3.

Step B: Trifluoroacetic acid (399 mg, 3.50 mmol) was added to a stirred solution of tert-butyl 4-(4-((4-([1,2,4]triazolo[1,5-a]pyridin-7-yloxy)-2-fluoro-3-methylphenyl)amino)pyrido[3,2-d]pyrimidin-6-yl)piperazine-1-carboxylate (0.100 g, 175 μmol) in DCM (1.5 mL). The reaction was diluted with DCM and quenched via the addition of saturated $NaHCO_3$. After 10 minutes of stirring, the aqueous and organic layers were separated, the aqueous layer was extracted with DCM, and the combined organic layers were dried over sodium sulfate, filtered, and concentrated in vacuo to afford N-(4-([1,2,4]triazolo[1,5-a]pyridin-7-yloxy)-2-fluoro-3-methylphenyl)-6-(piperazin-1-yl)pyrido[3,2-d]pyrimidin-4-amine (68 mg, 0.14 mmol, 82%). m/z (esi) M+1=472.2.

Step C: 2-Fluoroacrylic acid (41 mg, 0.46 mmol) was added to a stirred solution of 2,4,6-tripropyl-1,3,5,2,4,6-trioxatriphosphinane 2,4,6-trioxide (0.58 g, 0.91 mmol), N-(4-([1,2,4]triazolo[1,5-a]pyridin-7-yloxy)-2-fluoro-3-methylphenyl)-6-(piperazin-1-yl)pyrido[3,2-d]pyrimidin-4-amine (0.043 g, 91 μmol) and N-ethyl-N-isopropylpropan-2-amine (0.24 g, 1.8 mmol) in DCM (1 mL). After 20 minutes, the reaction mixture was heated to 50° C. After 40 minutes, the reaction mixture was diluted with EtOAc and water. The aqueous and organic layers were separated, the organic layer was washed with brine, dried over $Na_2SO_4$, and concentrated. The crude material was purified via normal phase chromatography (12 g, $SiO_2$) using a gradient of 5 to 50%, 20% MeOH in $CH_2Cl_2$ in $CH_2Cl_2$ to afford 1-(4-(4-((4-([1,2,4]triazolo[1,5-a]pyridin-7-yloxy)-2-fluoro-3-methylphenyl)amino)pyrido[3,2-d]pyrimidin-6-yl) piperazin-1-yl)-2-fluoroprop-2-en-1-one (0.9 mg, 2 μmol, 2%). $^1$H NMR (400 MHz, $CDCl_3$) δ 9.09 (d, J=3.6 Hz, 1H), 8.85 (t, J=9.0 Hz, 1H), 8.69 (s, 1H), 8.53 (dd, J=7.3, 0.9 Hz, 1H), 8.26 (s, 1H), 8.05 (d, J=9.3 Hz, 1H), 7.33 (d, J=9.3 Hz, 1H), 7.03 (dd, J=9.2, 1.7 Hz, 1H), 6.91 (m, 2H), 5.41 (dd, J=47.5, 3.6 Hz, 1H), 5.25 (dd, J=16.8, 3.6 Hz, 1H) 3.88 (s, 8H), 2.23 (d, J=2.1 Hz, 3H). m/z (esi) M+1=544.2.

Example 186

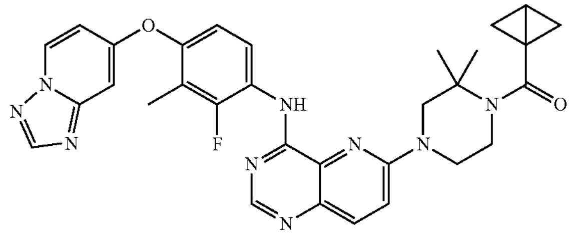 [SMILES: Cc1c(Oc2ccn3ncnc3c2)ccc(Nc2ncnc3ccc(N4CCN(C(=O)C56CC5C6)C(C)(C)C4)nc23)c1F]

(4-(4-((4-([1,2,4]triazolo[1,5-a]pyridin-7-yloxy)-2-fluoro-3-methylphenyl)amino)pyrido[3,2-d]pyrimidin-6-yl)-2,2-dimethylpiperazin-1-yl)(bicyclo[1.1.0]butan-1-yl)methanone Step A: DIPEA (0.11 g, 0.87 mmol) was added to a stirred solution of N-(4-([1,2,4]triazolo[1,5-a]pyridin-7-yloxy)-2-fluoro-3-methylphenyl)-6-chloropyrido[3,2-d]pyrimidin-4-amine hydrochloride (0.080 g, 0.17 mmol) and tert-butyl-2,2-dimethylpiperazine-1-carboxylate (0.11 g, 0.52 mmol) in DMSO (1.5 mL) at 100° C. under sealed tube. The reaction was partitioned between water and $CH_2Cl_2$. The organic layer was dried over sodium sulfate, filtered, and concentrated in vacuo. The crude residue was purified over 12 g silica cartridge, eluting with a gradient of 0% to 50%, 20% MeOH in $CH_2Cl_2$ in $CH_2Cl_2$ to afford tert-butyl-4-(4-((4-([1,2,4]triazolo[1,5-a]pyridin-7-yloxy)-2-fluoro-3-methylphenyl)amino)pyrido[3,2-d]pyrimidin-6-yl)-2,2-dimethylpiperazine-1-carboxylate (0.078 g, 0.13 mmol, 75%). m/z (esi) M+1=600.3.

Step B: Trifluoroacetic acid (0.30 g, 2.6 mmol) was added to a stirred solution of tert-butyl 4-(4-((4-([1,2,4]triazolo[1,5-a]pyridin-7-yloxy)-2-fluoro-3-methylphenyl)amino) pyrido[3,2-d]pyrimidin-6-yl)-2,2-dimethylpiperazine-1-carboxylate (0.078 g, 0.13 mmol) in DCM. The reaction mixture was diluted with DCM and quenched via the addition of saturated $NaHCO_3$. After 10 minutes of stirring, the aqueous and organic phases were separated, and the aqueous layer was extracted with DCM. The combined organic layers were dried over $Na_2SO_4$ and concentrated to afford N-(4-([1,2,4]triazolo[1,5-a]pyridin-7-yloxy)-2-fluoro-3-methylphenyl)-6-(3,3-dimethylpiperazin-1-yl) pyrido[3,2-d]pyrimidin-4-amine (58.7 mg, 118 μmol, 90%). m/z (esi) M+1=500.2.

Step C: 2,4,6-Tripropyl-1,3,5,2,4,6-trioxatriphosphinane 2,4,6-trioxide (80 mg, 0.25 mmol) was added to a stirred solution of N-(4-([1,2,4]triazolo[1,5-a]pyridin-7-yloxy)-2-fluoro-3-methylphenyl)-6-(3,3-dimethylpiperazin-1-yl) pyrido[3,2-d]pyrimidin-4-amine (50 mg, 0.10 mmol), N-ethyl-N-isopropylpropan-2-amine (65 mg, 0.50 mmol) and potassium bicyclo[1.1.0]butane-1-carboxylate (20 mg, 0.15 mmol) in DMF (1 mL). The reaction mixture was concentrated and the crude residue was purified via normal phase chromatography (12 g, $SiO_2$) using a gradient of 5 to 50%, 20% MeOH in $CH_2Cl_2$ in $CH_2Cl_2$ to afford (4-(4-((4-([1,2,4]triazolo[1,5-a]pyridin-7-yloxy)-2-fluoro-3-methylphenyl)amino)pyrido[3,2-d]pyrimidin-6-yl)-2,2-dimethylpiperazin-1-yl)(bicyclo[1.1.0]butan-1-yl)methanone (5.3 mg, 9.1 μmol, 9.1%). $^1$H NMR (400 MHz, $CDCl_3$) δ 9.15 (d, J=3.3 Hz, 1H), 8.86 (t, J=9.1 Hz, 1H), 8.66 (s, 1H), 8.53 (dd, J=7.2, 0.9 Hz, 1H), 8.25 (s, 1H), 8.03 (d, J=9.3 Hz, 1H), 7.19 (d, J=9.3 Hz, 1H), 7.03 (m, 1H), 6.91 (m, 2H), 4.32 (m, 2H), 3.92 (s, 2H), 3.88 (m, 2H), 2.28 (d, J=3.5 Hz, 2H), 2.23 (d, J=2.1 Hz, 3H), 2.04 (m, 2H), 1.61 (s, 6H). m/z (esi) M+1=580.3.

Example 187

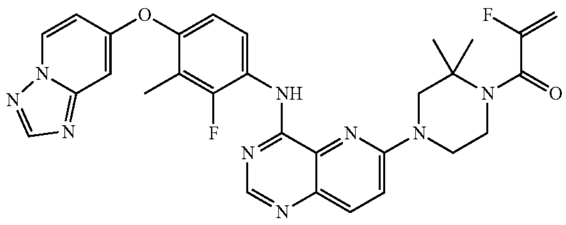 [SMILES: C=C(F)C(=O)N1CCN(c2ccc3ncnc(Nc4ccc(Oc5ccn6ncnc6c5)c(C)c4F)c3n2)CC1(C)C]

1-(4-(4-((4-([1,2,4]triazolo[1,5-a]pyridin-7-yloxy)-2-fluoro-3-methylphenyl)amino)pyrido[3,2-d]pyrimidin-6-yl)-2,2-dimethylpiperazin-1-yl)-2-fluoroprop-2-en-1-one Step A: DIPEA (0.11 g, 0.87 mmol) was added to a stirred solution of N-(4-([1,2,4]triazolo[1,5-a]pyridin-7-yloxy)-2-fluoro-3-methylphenyl)-6-chloropyrido[3,2-d]pyrimidin-4-amine hydrochloride (0.080 g, 0.17 mmol) and tert-butyl-2,2-dimethylpiperazine-1-carboxylate (0.11 g, 0.52 mmol) in DMSO (1.5 mL) at 100° C. under sealed tube. The reaction was partitioned between water and $CH_2Cl_2$. The organic layer was dried over sodium sulfate, filtered, and concentrated in vacuo. The crude residue was purified over 12 g silica cartridge, eluting with a gradient of 0% to 50%, 20% MeOH in $CH_2Cl_2$ in $CH_2Cl_2$ to afford tert-butyl-4-(4-((4-([1,2,4]triazolo[1,5-a]pyridin-7-yloxy)-2-fluoro-3-methylphenyl)amino)pyrido[3,2-d]pyrimidin-6-yl)-2,2-dimethylpiperazine-1-carboxylate (0.078 g, 0.13 mmol, 75%). m/z (esi) M+1=600.3.

Step B: Trifluoroacetic acid (0.30 g, 2.6 mmol) was added to a stirred solution of tert-butyl 4-(4-((4-([1,2,4]triazolo[1,5-a]pyridin-7-yloxy)-2-fluoro-3-methylphenyl)amino) pyrido[3,2-d]pyrimidin-6-yl)-2,2-dimethylpiperazine-1-carboxylate (0.078 g, 0.13 mmol) in DCM. The reaction mixture was diluted with DCM and quenched via the addition of saturated $NaHCO_3$. After 10 minutes of stirring, the aqueous and organic phases were separated. The aqueous layer was extracted with DCM, and the combined organic layers were dried over $Na_2SO_4$ and concentrated to afford N-(4-([1,2,4]triazolo[1,5-a]pyridin-7-yloxy)-2-fluoro-3-methylphenyl)-6-(3,3-dimethylpiperazin-1-yl)pyrido[3,2-d] pyrimidin-4-amine (58.7 mg, 118 μmol, 90%). m/z (esi) M+1=500.2.

Step C: 2-Fluoroacrylic acid (0.05 g, 0.5 mmol) was added to a stirred solution of N-(4-([1,2,4]triazolo[1,5-a]pyridin-7-yloxy)-2-fluoro-3-methylphenyl)-6-(3,3-dimethylpiperazin-1-yl)pyrido[3,2-d]pyrimidin-4-amine (0.05 g, 0.1 mmol), N-ethyl-N-isopropylpropan-2-amine (0.3 g, 2 mmol), 2,4,6-tripropyl-1,3,5,2,4,6-trioxatriphosphinane 2,4,6-trioxide (0.6 g, 1 mmol) in DMF (2 mL) at 50° C. After 1 hour, the reaction was partitioned between water 25% IPA/$CHCl_3$. The combined organic layers were washed with brine, dried over $Na_2SO_4$, and concentrated. The resulting crude material was purified via normal phase chromatography (12 g, $SiO_2$) eluting with a gradient of 0% to 50%, 20% MeOH in $CH_2Cl_2$ in $CH_2Cl_2$ to afford 1-(4-(4-((4-([1,2,4]triazolo[1,5-a]pyridin-7-yloxy)-2-fluoro-3-methylphenyl)amino)pyrido[3,2-d]pyrimidin-6-yl)-2,2-dimethylpiperazin-1-yl)-2-fluoroprop-2-en-1-one (10.8 mg, 18.9 μmol, 20%). $^1$H NMR (400 MHz, CDCl3) δ 9.17 (d, J=3.6 Hz, 1H), 8.86 (t, J=8.9 Hz, 1H), 8.66 (s, 1H), 8.53 (dd, J=7.3, 0.9 Hz, 1H), 8.25 (s, 1H), 8.03 (d, J=9.3 Hz, 1H), 7.18 (d, J=9.3 Hz, 1H), 7.03 (dd, J=9.0, 1.8 Hz, 1H), 6.91 (m, 2H), 5.31 (dd, J=47.7, 3.5 Hz, 1H), 5.15 (dd, J=16.9, 3.5 Hz, 1H), 3.95 (m, 4H), 3.87 (m, 2H) 2.23 (d, J=2.1 Hz, 3H), 1.63 (s, 6H). m/z (esi) M+1=572.2.

Example 188

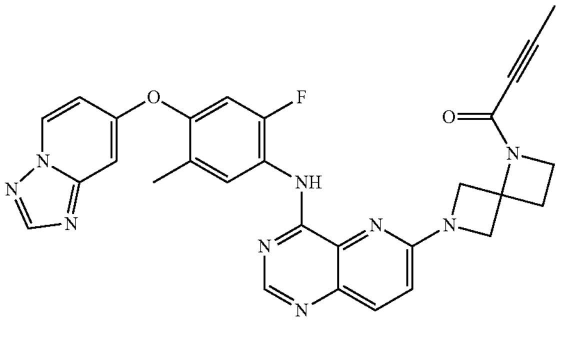 [SMILES: CC#CC(=O)N1CCC12CN(c1ccc3ncnc(Nc4cc(C)c(Oc5ccn6ncnc6c5)cc4F)c3n1)C2]

1-(6-(4-((4-([1,2,4]triazolo[1,5-a]pyridin-7-yloxy)-2-fluoro-5-methylphenyl)amino)pyrido[3,2-d]pyrimidin-6-yl)-1,6-diazaspiro[3.3]heptan-1-yl)but-2-yn-1-one Step A: tert-Butyl 1,6-diazaspiro[3.3]heptane-1-carboxylate (50 mg, 0.25 mmol) was added to a stirred solution of N-(4-([1,2,4]triazolo[1,5-a]pyridin-7-yloxy)-2-fluoro-5-methylphenyl)-6-chloropyrido[3,2-d]pyrimidin-4-amine (0.053 g, 0.13 mmol) and DIPEA (49 mg, 0.38 mmol) in DMSO (1.5 mL) at 100° C. under sealed tube. The reaction was partitioned between water and EtOAc. The organic layer was washed with brine, dried over sodium sulfate, filtered, and concentrated in vacuo. The crude residue was purified over 12 g silica cartridge, eluting with a gradient of 5% to 50%, 20% MeOH in $CH_2Cl_2$ in $CH_2Cl_2$ to afford tert-butyl-6-(4-((4-([1,2,4]triazolo[1,5-a]pyridin-7-yloxy)-2-fluoro-5-methylphenyl)amino)pyrido[3,2-d]pyrimidin-6-yl)-1,6-diazaspiro[3.3]heptane-1-carboxylate (46.6 mg, 79.8 μmol, 64%). m/z (esi) M+1=584.3.

Step B: Trifluoroacetic acid (182 mg, 1.60 mmol) was added to a stirred solution of tert-butyl-6-(4-((4-([1,2,4]triazolo[1,5-a]pyridin-7-yloxy)-2-fluoro-5-methylphenyl)amino)pyrido[3,2-d]pyrimidin-6-yl)-1,6-diazaspiro[3.3]heptane-1-carboxylate (46.6 mg, 1 Eq, 79.8 μmol) in DCM (1 mL). The reaction was partitioned between saturated $NaHCO_3$ and EtOAc. The organic layer was dried over sodium sulfate, filtered, and concentrated in vacuo to afford N-(4-([1,2,4]triazolo[1,5-a]pyridin-7-yloxy)-2-fluoro-5-methylphenyl)-6-(1,6-diazaspiro[3.3]heptan-6-yl)pyrido[3,2-d]pyrimidin-4-amine (37.5 mg, 77.6 μmol, 97.1%). m/z (esi) M+1=484.2.

Step C: 2,4,6-Tripropyl-1,3,5,2,4,6-trioxatriphosphinane 2,4,6-trioxide (123 mg, 194 μmol) was added to a stirred solution of but-2-ynoic acid (9.78 mg, 116 μmol), N-(4-([1,2,4]triazolo[1,5-a]pyridin-7-yloxy)-2-fluoro-5-methylphenyl)-6-(1,6-diazaspiro[3.3]heptan-6-yl)pyrido[3,2-d]pyrimidin-4-amine (37.5 mg, 77.6 μmol) and DIPEA (50.1 mg, 388 μmol) in DMF (1 mL). The reaction was partitioned between water and EtOAc. The organic layer was dried over sodium sulfate, filtered, and concentrated in vacuo. The crude residue was purified over 12 g silica cartridge, eluting with a gradient of 5% to 50%, 20% MeOH in $CH_2Cl_2$ in $CH_2Cl_2$ to afford 1-(6-(4-((4-([1,2,4]triazolo[1,5-a]pyridin-7-yloxy)-2-fluoro-5-methylphenyl)amino)pyrido[3,2-d]pyrimidin-6-yl)-1,6-diazaspiro[3.3]heptan-1-yl)but-2-yn-1-one (20.2 mg, 36.8 μmol, 47.4%). $^1$H NMR (400 MHz, CDCl3) δ 9.08 (d, J=3.1 Hz, 1H), 8.87 (d, J=9.1 Hz, 1H), 8.65 (d, J=8.7 Hz, 1H), 8.51 (m, 1H), 8.24 (s, 1H), 7.96 (m, 1H), 6.91 (m, 4H), 4.97 (m, 1H), 4.41 (dd, J=9.6, 1.3 Hz, 1H), 4.24 (d, J=9.0 Hz, 1H), 4.13 (m, 1H), 4.02 (m, 1H), 2.65 (m, 2H) 2.27 (d, J=3.1 Hz, 3H), 1.36 (s, 3H). m/z (esi) M+1=550.2.

Example 189

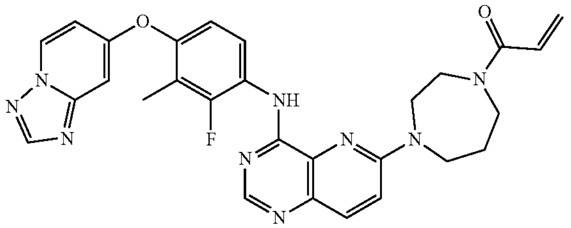 [SMILES: C=CC(=O)N1CCCN(c2ccc3ncnc(Nc4ccc(Oc5ccn6ncnc6c5)c(C)c4F)c3n2)CC1]

1-(4-(4-((4-([1,2,4]triazolo[1,5-a]pyridin-7-yloxy)-2-fluoro-3-methylphenyl)amino)pyrido[3,2-d]pyrimidin-6-yl)azepan-1-yl)prop-2-en-1-one Step A: To a 8 mL vial containing (4,4'-di-tert-butyl-2,2'-bipyridine)bis[(2-pyridinyl)phenyl]iridium(III) hexafluorophosphate (1.3 mg, 1.4 μmol), (SP-4-2)-[4,4'-bis(1,1-dimethylethyl)-2,2'-bipyridine-κN1,κN1']dibromo-nickel (3.5 mg, 7.1 μmol), quinuclidine (21 mg, 0.19 mmol), phthalimide (3.1 mg, 0.02 mmol), and N-(4-([1,2,4]triazolo[1,5-a]pyridin-7-yloxy)-2-fluoro-3-methylphenyl)-6-chloropyrido[3,2-d]pyrimidin-4-amine (40 mg, 0.10 mmol) were dissolved/suspended in DMA (1.0 mL). To a separate 8 mL vial containing 5,7-di-tert-butyl-3-phenyl-3-(tetrafluoro-15-boraneyl)-2,3-dihydrobenzo[d]oxazol-3-ium-2-ide (79 mg, 0.20 mmol) and tert-butyl 4-hydroxyazepane-1-carboxylate (41 mg, 0.19 mmol) was added degassed MTBE (1.0 mL) under nitrogen. After stirring for 5 minutes, pyridine (15 μL, 0.19 mmol) was added. After stirring for an additional 10 minutes, the solution was taken up in a syringe and filtered through a syringe filter into the reaction vial containing nickel and iridium components. The vial was then capped and sparged with nitrogen for 10 minutes, parafilmed, and irradiated with 450 nm light in the integrated photoreactor for 6 hours (100% intensity, 1200 rpm stir, max fan speed). The reaction was concentrated in vacuo, and the crude residue was purified over 12 g silica cartridge, eluting with a gradient of 1-10% MeOH/DCM to afford tert-butyl 4-(4-((4-([1,2,4]triazolo[1,5-a]pyridin-7-yloxy)-2-fluoro-3-methylphenyl)amino)pyrido[3,2-d]pyrimidin-6-yl)azepane-1-carboxylate (16.4 mg, 30%) as a mixture of enantiomers. m/z (esi) M+1=585.2.

Step B: Trifluoroacetic acid (43 μL, 0.56 mmol) was added to a stirred solution of tert-butyl 4-(4-((4-([1,2,4]triazolo[1,5-a]pyridin-7-yloxy)-2-fluoro-3-methylphenyl)amino)pyrido[3,2-d]pyrimidin-6-yl)azepane-1-carboxylate (16.4 mg, 0.04 μmol) in DCM (0.4 mL). The reaction was stirred at 23° C. for 2 hours before diluting with EtOAc and quenching with 10% $K_2CO_3$. The aqueous phase was extracted with EtOAc (3×), and the combined organic layers were washed with 10% $K_2CO_3$. The organic layer was then dried over sodium sulfate, filtered, and concentrated in vacuo to afford N-(4-([1,2,4]triazolo[1,5-a]pyridin-7-yloxy)-2-fluoro-3-methylphenyl)-6-(azepan-4-yl)pyrido[3,2-d]pyrimidin-4-amine (12.0 mg, 88%), which was used directly in the next reaction without further purification. m/z (esi) M+1=485.2.

Step C: Acryloyl chloride (40 μL, 0.02 mmol) as a 0.5M solution in DCM was added to a stirred solution of afford N-(4-([1,2,4]triazolo[1,5-a]pyridin-7-yloxy)-2-fluoro-3-methylphenyl)-6-(azepan-4-yl)pyrido[3,2-d]pyrimidin-4-amine (12.0 mg, 0.03 mmol) and DIPEA (8.6 μL, 0.05 mmol) in DCM (0.4 mL) at 0° C. The reaction mixture was stirred for 10 minutes at this temperature before partitioning between 10% $K_2CO_3$ and DCM. The aqueous phase was extracted with DCM (3×). The combined organic layers were then dried over sodium sulfate, filtered, and concentrated in vacuo, and the crude residue was purified over 4 g silica cartridge, eluting with a gradient of 1-10% MeOH/DCM to afford 1-(4-(4-((4-([1,2,4]triazolo[1,5-a]pyridin-7-yloxy)-2-fluoro-3-methylphenyl)amino)pyrido[3,2-d]pyrimidin-6-yl)azepan-1-yl)prop-2-en-1-one (4.9 mg, 37%). $^1H$ NMR (400 MHz, $CDCl_3$) δ 9.44 (s, 1H), 8.83-8.72 (m, 2H), 8.55-8.48 (m, 1H), 8.24 (s, 1H), 8.17-8.09 (m, 1H), 7.66-7.59 (m, 1H), 7.05-6.98 (m, 1H), 6.93-6.85 (m, 2H), 6.73-6.60 (m, 1H), 6.47-6.36 (m, 1H), 5.78-5.70 (m, 1H), 4.00-3.53 (m, 4H), 3.20-3.10 (m, 1H), 2.36-2.25 (m, 1H), 2.24-2.20 (m, 3H), 2.21-2.05 (m, 3H), 2.03-1.80 (m, 2H). m/z (esi) M+1=539.2.

Example 190

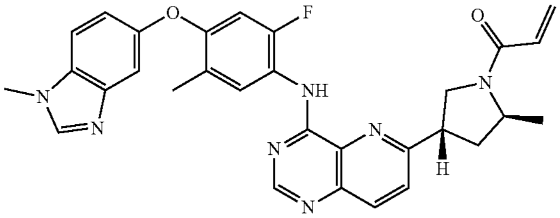 [SMILES: C=CC(=O)N1C[C@@H](c2ccc3ncnc(Nc4cc(C)c(Oc5ccc6c(c5)ncn6C)cc4F)c3n2)C[C@@H]1C]

1-((2S,4S)-4-(4-((2-fluoro-5-methyl-4-((1-methyl-1H-benzo[d]imidazol-5-yl)oxy)phenyl)amino)pyrido[3,2-d]pyrimidin-6-yl)-2-methylpyrrolidin-1-yl)prop-2-en-1-one Prepared according to the procedure for Example 189, using 6-chloro-N-(2-fluoro-5-methyl-4-((1-methyl-1H-benzo[d]imidazol-5-yl)oxy)phenyl)pyrido[3,2-d]pyrimidin-4-amine in place of N-(4-([1,2,4]triazolo[1,5-a]pyridin-7-yloxy)-2-fluoro-3-methylphenyl)-6-chloropyrido[3,2-d]pyrimidin-4-amine and tert-butyl (2S,4S)-4-hydroxy-2-methylpyrrolidine-1-carboxylate in place of tert-butyl 4-hydroxyazepane-1-carboxylate to yield 1-((2S,4S)-4-(4-((2-fluoro-5-methyl-4-((1-methyl-1H-benzo[d]imidazol-5-yl)oxy)phenyl)amino)pyrido[3,2-d]pyrimidin-6-yl)-2-methylpyrrolidin-1-yl)prop-2-en-1-one (10.2 mg, 52%). $^1H$ NMR (500 MHz, $CDCl_3$) δ 9.26-9.04 (m, 1H), 8.82-8.76 (m, 1H), 8.50-8.41 (m, 1H), 8.17-8.11 (m, 1H), 7.88 (s, 1H), 7.68-7.63 (m, 1H), 7.41-7.34 (m, 2H), 7.10-7.04 (m, 1H), 6.73-6.65 (m, 1H), 6.59-6.33 (m, 2H), 5.76-5.65 (m, 1H), 4.62-4.32 (m, 1H), 4.22-3.94 (m, 2H), 3.93-3.60 (m, 4H), 2.85-2.40 (m, 1H), 2.39-2.35 (m, 4H), 2.29-1.95 (m, 1H), 1.46-1.38 (m, 3H). m/z (esi) M+1=538.2.

Example 191

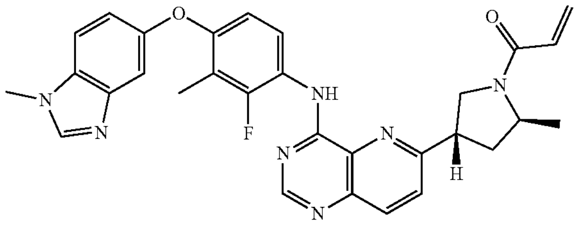 [SMILES: C=CC(=O)N1C[C@@H](c2ccc3ncnc(Nc4ccc(Oc5ccc6c(c5)ncn6C)c(C)c4F)c3n2)C[C@@H]1C]

1-((2S,4S)-4-(4-((2-fluoro-3-methyl-4-((1-methyl-1H-benzo[d]imidazol-5-yl)oxy)phenyl)amino)pyrido[3,2-d]pyrimidin-6-yl)-2-methylpyrrolidin-1-yl)prop-2-en-1-one Prepared according to the procedure for Example 189, using 6-chloro-N-(2-fluoro-3-methyl-4-((1-methyl-1H-benzo[d]imidazol-5-yl)oxy)phenyl)pyrido[3,2-d]pyrimidin-4-amine in place of N-(4-([1,2,4]triazolo[1,5-a]pyridin-7-yloxy)-2-fluoro-3-methylphenyl)-6-chloropyrido[3,2-d]pyrimidin-4-amine and tert-butyl (2S,4S)-4-hydroxy-2-methylpyrrolidine-1-carboxylate in place of tert-butyl 4-hydroxyazepane-1-carboxylate to yield 1-((2S,4S)-4-(4-((2-fluoro-3-methyl-4-((1-methyl-1H-benzo[d]imidazol-5-yl)oxy)phenyl)amino)pyrido[3,2-d]pyrimidin-6-yl)-2-methylpyrrolidin-1-yl)prop-2-en-1-one (16.2 mg, 66%). $^1H$ NMR (500 MHz, $CDCl_3$) δ 9.38-9.14 (m, 1H), 8.77-8.72 (m, 1H), 8.56-8.32 (m, 1H), 8.17-8.11 (m, 1H), 7.86 (s, 1H), 7.69-7.63 (m, 1H), 7.39-7.32 (m, 2H), 7.10-7.04 (m, 1H), 6.79-6.71 (m, 1H), 6.66-6.32 (m, 2H), 5.78-5.68 (m, 1H), 4.66-4.32 (m, 1H), 4.23-3.95 (m, 2H), 3.94-3.63 (m, 4H), 2.88-2.39 (m, 1H), 2.36-2.28 (m, 3H), 2.28-1.94 (m, 1H), 1.51-1.37 (m, 3H). m/z (esi) M+1=538.1.

Example 192

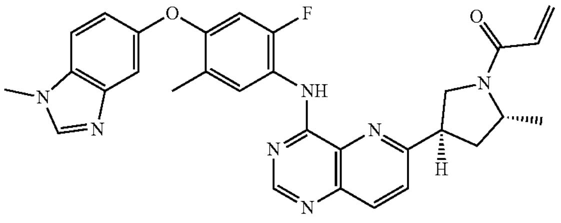 [SMILES: C=CC(=O)N1C[C@H](c2ccc3ncnc(Nc4cc(C)c(Oc5ccc6c(c5)ncn6C)cc4F)c3n2)C[C@H]1C]

1-((2R,4R)-4-(4-((2-fluoro-5-methyl-4-((1-methyl-1H-benzo[d]imidazol-5-yl)oxy)phenyl)amino)pyrido[3,2-d]pyrimidin-6-yl)-2-methylpyrrolidin-1-yl)prop-2-en-1-one Prepared according to the procedure for Example 189, using 6-chloro-N-(2-fluoro-5-methyl-4-((1-methyl-1H-benzo[d]imidazol-5-yl)oxy)phenyl)pyrido[3,2-d]pyrimidin-4-amine in place of N-(4-([1,2,4]triazolo[1,5-a]pyridin-7-yloxy)-2-fluoro-3-methylphenyl)-6-chloropyrido[3,2-d]pyrimidin-4-amine and tert-butyl (2R,4R)-4-hydroxy-2-methylpyrrolidine-1-carboxylate in place of tert-butyl 4-hydroxyazepane-1-carboxylate to yield 1-((2R,4R)-4-(4-((2-fluoro-5-methyl-4-((1-methyl-1H-benzo[d]imidazol-5-yl)oxy)phenyl)amino)pyrido[3,2-d]pyrimidin-6-yl)-2-methylpyrrolidin-1-yl)prop-2-en-1-one (14.7 mg, 66%). $^1$H NMR (500 MHz, $CDCl_3$) δ 9.26-9.04 (m, 1H), 8.82-8.76 (m, 1H), 8.50-8.41 (m, 1H), 8.17-8.11 (m, 1H), 7.88 (s, 1H), 7.68-7.63 (m, 1H), 7.41-7.34 (m, 2H), 7.10-7.04 (m, 1H), 6.73-6.65 (m, 1H), 6.59-6.33 (m, 2H), 5.76-5.65 (m, 1H), 4.62-4.32 (m, 1H), 4.22-3.94 (m, 2H), 3.93-3.60 (m, 4H), 2.85-2.40 (m, 1H), 2.39-2.35 (m, 4H), 2.29-1.95 (m, 1H), 1.46-1.38 (m, 3H). m/z (esi) M+1=538.2.

Example 193

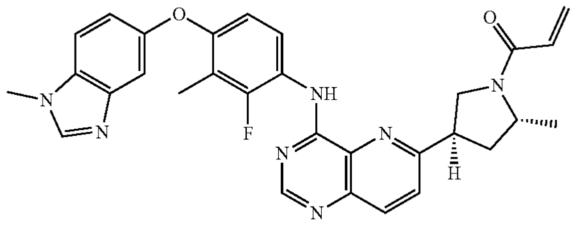 [SMILES: C=CC(=O)N1C[C@H](c2ccc3ncnc(Nc4ccc(Oc5ccc6c(c5)ncn6C)c(C)c4F)c3n2)C[C@H]1C]

1-((2R,4R)-4-(4-((2-fluoro-3-methyl-4-((1-methyl-1H-benzo[d]imidazol-5-yl)oxy)phenyl)amino)pyrido[3,2-d]pyrimidin-6-yl)-2-methylpyrrolidin-1-yl)prop-2-en-1-one Prepared according to the procedure for Example 189, using 6-chloro-N-(2-fluoro-3-methyl-4-((1-methyl-1H-benzo[d]imidazol-5-yl)oxy)phenyl)pyrido[3,2-d]pyrimidin-4-amine in place of N-(4-([1,2,4]triazolo[1,5-a]pyridin-7-yloxy)-2-fluoro-3-methylphenyl)-6-chloropyrido[3,2-d]pyrimidin-4-amine and tert-butyl (2R,4R)-4-hydroxy-2-methylpyrrolidine-1-carboxylate in place of tert-butyl 4-hydroxyazepane-1-carboxylate to yield 1-((2R,4R)-4-(4-((2-fluoro-3-methyl-4-((1-methyl-1H-benzo[d]imidazol-5-yl)oxy)phenyl)amino)pyrido[3,2-d]pyrimidin-6-yl)-2-methylpyrrolidin-1-yl)prop-2-en-1-one (12.6 mg, 58%). $^1$H NMR (500 MHz, $CDCl_3$) δ 9.38-9.14 (m, 1H), 8.77-8.72 (m, 1H), 8.56-8.32 (m, 1H), 8.17-8.11 (m, 1H), 7.86 (s, 1H), 7.69-7.63 (m, 1H), 7.39-7.32 (m, 2H), 7.10-7.04 (m, 1H), 6.79-6.71 (m, 1H), 6.66-6.32 (m, 2H), 5.78-5.68 (m, 1H), 4.66-4.32 (m, 1H), 4.23-3.95 (m, 2H), 3.94-3.63 (m, 4H), 2.88-2.39 (m, 1H), 2.36-2.28 (m, 3H), 2.28-1.94 (m, 1H), 1.51-1.37 (m, 3H). m/z (esi) M+1=538.1.

Example 194

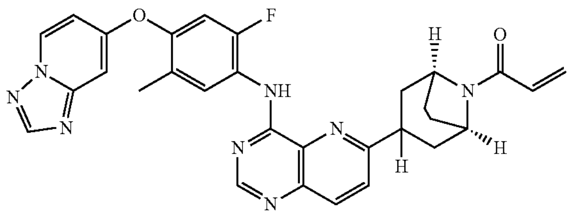 [SMILES: C=CC(=O)N1[C@@H]2CC[C@H]1CC(c1ccc3ncnc(Nc4cc(C)c(Oc5ccn6ncnc6c5)cc4F)c3n1)C2]

1-((1R,5S)-3-(4-((4-([1,2,4]triazolo[1,5-a]pyridin-7-yloxy)-2-fluoro-5-methylphenyl)amino)pyrido[3,2-d]pyrimidin-6-yl)-8-azabicyclo[3.2.1]octan-8-yl)prop-2-en-1-one Step A: A vial equipped with a stir bar was charged with N-(4-[1,2,4]triazolo[1,5-a]pyridine-7-yloxy)-2-fluoro-5-methylphenyl)-6-chloropyrido[3,2-d]pyrimidin-4-amine (50 mg, 0.12 mmol), tert-butyl 3-(4,4,5,5-tetramethyl-1,3,2-dioxaborolan-2-yl)-8-azabicyclo[3.2.1]oct-2-ene-8-carboxylate (79 mg, 0.24 mmol), $Pd(Ph_3P)_4$ (14 mg, 0.01 mmol), 2M aqueous $K_2CO_3$ (0.18 mL, 0.36 mmol), and 1,4-dioxane (1.2 mL). This mixture was purged with argon for 10 minutes, and the tube was sealed. The mixture was warmed to 100° C. for 16 hours, then allowed to cool to room temperature. The mixture was diluted with water/DCM, extracted with DCM, combined extracts dried over sodium sulfate and concentrated under reduced pressure. The crude residue was purified over 12 g silica cartridge, eluting with a gradient of 1-10% MeOH/DCM to afford tert-butyl (1R,5S)-3-(4-((4-([1,2,4]triazolo[1,5-a]pyridin-7-yloxy)-2-fluoro-5-methylphenyl)amino)pyrido[3,2-d]pyrimidin-6-yl)-8-azabicyclo[3.2.1]oct-2-ene-8-carboxylate (55.2 mg, 78%). m/z (esi) M+1=595.2.

Step B: 10% Pd/C (98 mg, 0.09 mmol) and ammonium formate (58 mg, 0.92 mmol) were added to a stirred solution of tert-butyl (1R,5S)-3-(4-((4-([1,2,4]triazolo[1,5-a]pyridin-7-yloxy)-2-fluoro-5-methylphenyl)amino)pyrido[3,2-d]pyrimidin-6-yl)-8-azabicyclo[3.2.1]oct-2-ene-8-carboxylate (55 mg, 0.09 mmol) in MeOH (1.0 mL). The reaction was stirred at 64° C. for 1 hour before cooling to room temperature. The reaction was filtered and concentrated. To remove excess ammonium formate, the residue was dissolved in the minimal amount of $CHCl_3$, filtered, and concentrated. The product, tert-butyl (1R,5S)-3-(4-((4-([1,2,4]triazolo[1,5-a]pyridin-7-yloxy)-2-fluoro-5-methylphenyl)amino)pyrido[3,2-d]pyrimidin-6-yl)-8-azabicyclo[3.2.1]octane-8-carboxylate (16.9 mg, 31%), was used directly without further purification. m/z (esi) M+1=597.2.

Step C: Trifluoroacetic acid (45 μL, 0.57 mmol) was added to a stirred tert-butyl (1R,5S)-3-(4-((4-([1,2,4]triazolo[1,5-a]pyridin-7-yloxy)-2-fluoro-5-methylphenyl)amino)pyrido[3,2-d]pyrimidin-6-yl)-8-azabicyclo[3.2.1]octane-8-carboxylate (16.9 mg, 0.03 mmol) in DCM (0.4 mL). The reaction was stirred at 23° C. for 2 hours before diluting with EtOAc and quenching with 10% $K_2CO_3$. The aqueous phase was extracted with EtOAc (3×), and the combined organic layers were washed with 10% $K_2CO_3$. The organic layer was then dried over sodium sulfate, filtered and concentrated in vacuo to afford N-(4-([1,2,4]triazolo[1,5-a]pyridin-7-yloxy)-2-fluoro-5-methylphenyl)-6-((1R,5S)-8-azabicyclo[3.2.1]octan-3-yl)pyrido[3,2-d]pyrimidin-4-amine (13.7 mg, 97%), which was used directly in the next reaction without further purification. m/z (esi) M+1=497.2.

Step D: Acryloyl chloride (42 μL, 0.02 mmol) as a 0.5M solution in DCM was added to a stirred solution of afford N-(4-([1,2,4]triazolo[1,5-a]pyridin-7-yloxy)-2-fluoro-5-methylphenyl)-6-((1R,5S)-8-azabicyclo[3.2.1]octan-3-yl)pyrido[3,2-d]pyrimidin-4-amine (13.0 mg, 0.03 mmol) and DIPEA (9.1 μL, 0.05 mmol) in DCM (0.5 mL) at 0° C. The reaction mixture was stirred for 10 minutes at this temperature before partitioning between 10% $K_2CO_3$ and DCM. The aqueous phase was extracted with DCM (3×). The combined organic layers were then dried over sodium sulfate, filtered, and concentrated in vacuo, and the crude residue was purified over 4 g silica cartridge, eluting with a gradient of 1-10% MeOH/DCM to afford 1-((1R,5S)-3-(4-((4-([1,2,4]triazolo[1,5-a]pyridin-7-yloxy)-2-fluoro-5-methylphenyl)amino)pyrido[3,2-d]pyrimidin-6-yl)-8-azabicyclo[3.2.1]octan-8-yl)prop-2-en-1-one (5.4 mg, 37%). $^1$H NMR (400 MHz, $CDCl_3$) δ 9.50-9.24 (m, 1H), 8.92-8.76 (m, 2H), 8.55-8.47 (m, 1H), 8.24 (s, 1H), 8.15 (t, J=8.5 Hz, 1H), 7.88-7.58 (m, 1H), 7.02-6.93 (m, 1H), 6.93-6.84 (m, 2H), 6.65-6.57 (m, 1H), 6.48-6.40 (m, 1H), 5.79-5.70 (m, 1H), 5.01-4.81 (m, 1H), 4.58-4.42 (m, 1H), 3.70-3.25 (m, 1H), 2.73-2.35 (m, 2H), 2.28 (d, J=5.3 Hz, 3H), 2.26-1.77 (m, 6H). m/z (esi) M+1=551.2.

Example 195

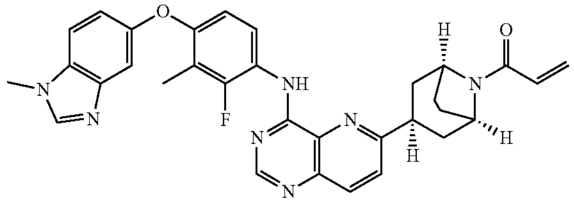 [SMILES: C=CC(=O)N1[C@@H]2CC[C@H]1C[C@H](c1ccc3ncnc(Nc4ccc(Oc5ccc6c(c5)ncn6C)c(C)c4F)c3n1)C2]

1-((1R,3s,5S)-3-(4-((2-fluoro-3-methyl-4-((1-methyl-1H-benzo[d]imidazol-5-yl)oxy)phenyl)amino)pyrido[3,2-d]pyrimidin-6-yl)-8-azabicyclo[3.2.1]octan-8-yl)prop-2-en-1-one Step A: A vial equipped with a stir bar was charged with 6-chloro-N-(2-fluoro-3-methyl-4-((1-methyl-1H-benzo[d]imidazol-5-yl)oxy)phenyl)pyrido[3,2-d]pyrimidin-4-amine (150 mg, 0.35 mmol), tert-butyl 3-(4,4,5,5-tetramethyl-1,3,2-dioxaborolan-2-yl)-8-azabicyclo[3.2.1]oct-2-ene-8-carboxylate (231 mg, 0.69 mmol), $Pd(Ph_3P)_4$ (40 mg, 0.04 mmol), 2M aqueous $K_2CO_3$ (0.52 mL, 1.0 mmol), and 1,4-dioxane (3.5 mL). This mixture was purged with argon for 10 minutes, the tube sealed, and the mixture was warmed to 100° C. for 16 hours, then allowed to cool to room temperature. The mixture was diluted with water/DCM, extracted with DCM, combined extracts dried over sodium sulfate and concentrated under reduced pressure. The crude residue was purified over 12 g silica cartridge, eluting with a gradient of 1-10% MeOH/DCM to afford tert-butyl (1R,5S)-3-(4-((2-fluoro-3-methyl-4-((1-methyl-1H-benzo[d]imidazol-5-yl)oxy)phenyl)amino)pyrido[3,2-d]pyrimidin-6-yl)-8-azabicyclo[3.2.1]oct-2-ene-8-carboxylate (180.7 mg, 86%). m/z (esi) M+1=608.2.

Step B: 10% Pd/C (316 mg, 0.30 mmol) and ammonium formate (188 mg, 3.0 mmol) were added to a stirred solution of tert-butyl (1R,5S)-3-(4-((2-fluoro-3-methyl-4-((1-methyl-1H-benzo[d]imidazol-5-yl)oxy)phenyl)amino)pyrido[3,2-d]pyrimidin-6-yl)-8-azabicyclo[3.2.1]oct-2-ene-8-carboxylate (180.7 mg, 3.0 mmol) in MeOH (3.0 mL). The reaction was stirred at 64° C. for 1 hour before cooling to room temperature. The reaction was filtered and concentrated. To remove excess ammonium formate, the residue was dissolved in the minimal amount of $CHCl_3$, filtered, and concentrated. The product tert-butyl (1R,3sr,5S)-3-(4-((2-fluoro-3-methyl-4-((1-methyl-1H-benzo[d]imidazol-5-yl)oxy)phenyl)amino)pyrido[3,2-d]pyrimidin-6-yl)-8-azabicyclo[3.2.1]octane-8-carboxylate (166.5 mg, 92%) was used directly without further purification. m/z (esi) M+1=610.2.

Step C: Trifluoroacetic acid (0.4 mL, 5.2 mmol) was added to a stirred tert-butyl (1R,3sr,5S)-3-(4-((2-fluoro-3-methyl-4-((1-methyl-1H-benzo[d]imidazol-5-yl)oxy)phenyl)amino)pyrido[3,2-d]pyrimidin-6-yl)-8-azabicyclo[3.2.1]octane-8-carboxylate (160 mg, 0.26 mmol) in DCM (2.7 mL). The reaction was stirred at 23° C. for 2 hours before diluting with EtOAc and quenching with 10% $K_2CO_3$. The aqueous phase was extracted with EtOAc (3×), and the combined organic layers were washed with 10% $K_2CO_3$. The organic layer was then dried over sodium sulfate, filtered, and concentrated in vacuo. The crude residue was purified using HPLC eluting with a gradient of 0% to 50% acetonitrile with 0.1% TFA in water with 0.1% TFA to afford minor diastereomer 6-((1R,3,2,5S)-8-azabicyclo[3.2.1]octan-3-yl)-N-(2-fluoro-3-methyl-4-((1-methyl-1H-benzo[d]imidazol-5-yl)oxy)phenyl)pyrido[3,2-d]pyrimidin-4-amine (7.3 mg, 5.5%). m/z (esi) M+1=510.2.

Step D: Acryloyl chloride (28 μL, 0.01 μmol) as a 0.5M solution in DCM was added to a stirred solution of afford 6-((1R,3,2,5S)-8-azabicyclo[3.2.1]octan-3-yl)-N-(2-fluoro-3-methyl-4-((1-methyl-1H-benzo[d]imidazol-5-yl)oxy)phenyl)pyrido[3,2-d]pyrimidin-4-amine (7.3 mg, 0.01 mmol) and DIPEA (4.9 μL, 0.03 mmol) in DCM (0.4 mL) at 0° C. The reaction mixture was stirred for 10 minutes at this temperature before partitioning between 10% $K_2CO_3$ and DCM. The aqueous phase was extracted with DCM (3×). The combined organic layers were then dried over sodium sulfate, filtered, and concentrated in vacuo, and the crude residue was purified over 4 g silica cartridge, eluting with a gradient of 1-10% MeOH/DCM to 1-((1R,3s,5S)-3-(4-((2-fluoro-3-methyl-4-((1-methyl-1H-benzo[d]imidazol-5-yl)oxy)phenyl)amino)pyrido[3,2-d]pyrimidin-6-yl)-8-azabicyclo[3.2.1]octan-8-yl)prop-2-en-1-one (6.4 mg, 80%). $^1$H NMR (400 MHz, $CDCl_3$) δ 9.50-9.24 (m, 1H), 8.92-8.76 (m, 2H), 8.55-8.47 (m, 1H), 8.24 (s, 1H), 8.15 (t, J=8.5 Hz, 1H), 7.88-7.58 (m, 1H), 7.02-6.93 (m, 1H), 6.93-6.84 (m, 2H), 6.65-6.57 (m, 1H), 6.48-6.40 (m, 1H), 5.79-5.70 (m, 1H), 5.01-4.81 (m, 1H), 4.58-4.42 (m, 1H), 3.70-3.25 (m, 1H), 2.73-2.35 (m, 2H), 2.28 (d, J=5.3 Hz, 3H), 2.26-1.77 (m, 6H). m/z (esi) M+1=564.2.

Example 196

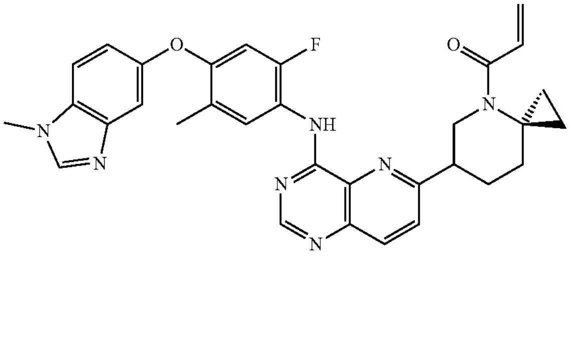

1-(6-(4-((2-fluoro-5-methyl-4-((1-methyl-1H-benzo[d]imidazol-5-yl)oxy)phenyl)amino)pyrido[3,2-d]pyrimidin-6-yl)-4-azaspiro[2.5]octan-4-yl)prop-2-en-1-one Prepared according to the procedure for Example 189, using 6-chloro-N-(2-fluoro-5-methyl-4-((1-methyl-1H-benzo[d]imidazol-5-yl)oxy)phenyl)pyrido[3,2-d]pyrimidin-4-amine in place of N-(4-([1,2,4]triazolo[1,5-a]pyridin-7-yloxy)-2-fluoro-3-methylphenyl)-6-chloropyrido[3,2-d]pyrimidin-4-amine and tert-butyl 6-hydroxy-4-azaspiro[2.5]octane-4-carboxylate in place of tert-butyl 4-hydroxyazepane-1-carboxylate to yield 1-(6-(4-((2-fluoro-5-methyl-4-((1-methyl-1H-benzo[d]imidazol-5-yl)oxy)phenyl)amino)pyrido[3,2-d]pyrimidin-6-yl)-4-azaspiro[2.5]octan-4-yl)prop-2-en-1-one (9.3 mg, 70%). $^1$H NMR (400 MHz, $CDCl_3$) δ 9.37-9.21 (m, 1H), 8.78 (s, 1H), 8.60-8.40 (m, 1H), 8.15-8.08 (m, 1H), 7.87 (s, 1H), 7.70-7.63 (m, 1H), 7.41-7.33 (m, 2H), 7.10-7.03 (m, 1H), 6.95-6.79 (m, 1H), 6.74-6.66 (m, 1H), 6.40-6.32 (m, 1H), 5.73-5.66 (m, 1H), 4.80 (s, 1H), 3.86 (s, 3H), 3.20 (s, 2H), 2.37 (s, 3H), 2.31-1.92 (m, 3H), 1.28 (d, J=18.2 Hz, 2H), 1.11 (s, 1H), 0.92-0.68 (m, 2H). m/z (esi) M+1=564.2.

Example 197

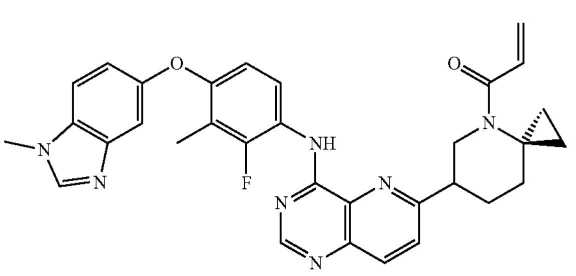

1-(6-(4-((2-fluoro-3-methyl-4-((1-methyl-1H-benzo[d]imidazol-5-yl)oxy)phenyl)amino)pyrido[3,2-d]pyrimidin-6-yl)-4-azaspiro[2.5]octan-4-yl)prop-2-en-1-one Prepared according to the procedure for Example 189, using 6-chloro-N-(2-fluoro-3-methyl-4-((1-methyl-1H-benzo[d]imidazol-5-yl)oxy)phenyl)pyrido[3,2-d]pyrimidin-4-amine in place of N-(4-([1,2,4]triazolo[1,5-a]pyridin-7-yloxy)-2-fluoro-3-methylphenyl)-6-chloropyrido[3,2-d]pyrimidin-4-amine and tert-butyl 6-hydroxy-4-azaspiro[2.5]octane-4-carboxylate in place of tert-butyl 4-hydroxyazepane-1-carboxylate to yield 1-(6-(4-((2-fluoro-3-methyl-4-((1-methyl-1H-benzo[d]imidazol-5-yl)oxy)phenyl)amino)pyrido[3,2-d]pyrimidin-6-yl)-4-azaspiro[2.5]octan-4-yl)prop-2-en-1-one (14.0 mg, 70%). $^1$H NMR (400 MHz, $CDCl_3$) δ 9.41 (s, 1H), 8.74 (s, 1H), 8.47-8.43 (m, 1H), 8.15-8.08 (m, 1H), 7.86 (s, 1H), 7.71-7.64 (m, 1H), 7.38-7.31 (m, 2H), 7.10-7.03 (m, 1H), 6.98-6.87 (m, 1H), 6.80-6.73 (m, 1H), 6.42-6.34 (m, 1H), 5.75-5.68 (m, 1H), 5.00-4.66 (m, 1H), 3.86 (s, 3H), 3.47-3.05 (m, 2H), 2.31 (d, J=2.1 Hz, 3H), 2.26 (s, 3H), 1.44-1.28 (m, 2H), 1.19-1.04 (m, 1H), 0.94-0.67 (m, 2H). m/z (esi) M+1=564.2.

Example 198

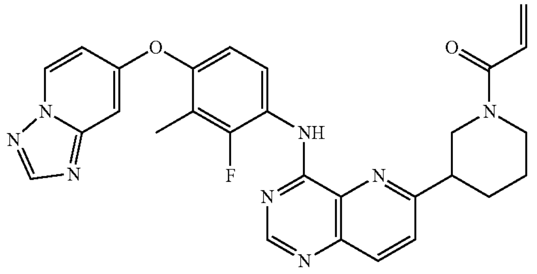 [SMILES: C=CC(=O)N1CCCC(c2ccc3ncnc(Nc4ccc(Oc5ccn6ncnc6c5)c(C)c4F)c3n2)C1]

1-(3-(4-((4-([1,2,4]triazolo[1,5-a]pyridin-7-yloxy)-2-fluoro-3-methylphenyl)amino)pyrido[3,2-d]pyrimidin-6-yl)piperidin-1-yl)prop-2-en-1-one Prepared according to the procedure for Example 189, using tert-butyl 3-hydroxypiperidine-1-carboxylate in place of tert-butyl 4-hydroxyazepane-1-carboxylate to yield 1-(3-(4-((4-([1,2,4]triazolo[1,5-a]pyridin-7-yloxy)-2-fluoro-3-methylphenyl)amino)pyrido[3,2-d]pyrimidin-6-yl)piperidin-1-yl)prop-2-en-1-one (12.3 mg 54%). $^1$H NMR (400 MHz, $CDCl_3$) δ 9.63-9.39 (m, 1H), 8.87-8.66 (m, 2H), 8.55-8.49 (m, 1H), 8.24 (s, 1H), 8.20-8.13 (m, 1H), 7.74-7.65 (m, 1H), 7.05-6.98 (m, 1H), 6.94-6.87 (m, 2H), 6.72-6.60 (m, 1H), 6.36-6.27 (m, 1H), 5.75-5.68 (m, 1H), 4.91-4.67 (m, 1H), 4.44-3.96 (m, 1H), 3.65-3.25 (m, 1H), 3.23-2.77 (m, 2H), 2.44-2.15 (m, 4H), 2.13-1.82 (m, 2H), 1.83-1.62 (m, 1H). m/z (esi) M+1=525.2.

Example 199

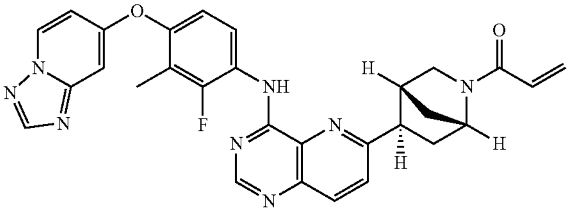 [SMILES: C=CC(=O)N1C[C@@H]2C[C@H]1C[C@H]2c1ccc2ncnc(Nc3ccc(Oc4ccn5ncnc5c4)c(C)c3F)c2n1]

rac-1-((1 S,4R,5R)-5-(4-((4-([1,2,4]triazolo[1,5-a]pyridin-7-yloxy)-2-fluoro-3-methylphenyl)amino)pyrido[3,2-d]pyrimidin-6-yl)-2-azabicyclo[2.2.1]heptan-2-yl)prop-2-en-1-one Prepared according to the procedure for Example 189, using tert-butyl 5-hydroxy-2-azabicyclo[2.2.1]heptane-2-carboxylate in place of tert-butyl 4-hydroxyazepane-1-carboxylate to yield rac-1-((1 S,4R,5R)-5-(4-((4-([1,2,4]triazolo[1,5-a]pyridin-7-yloxy)-2-fluoro-3-methylphenyl)amino)pyrido[3,2-d]pyrimidin-6-yl)-2-azabicyclo[2.2.1]heptan-2-yl)prop-2-en-1-one (16.6 mg, 60%). $^1$H NMR (400 MHz, $CDCl_3$) δ 9.46 (s, 1H), 8.88-8.77 (m, 2H), 8.55-8.48 (m, 1H), 8.24 (s, 1H), 8.22-8.11 (m, 1H), 7.88-7.57 (m, 1H), 7.11-6.83 (m, 3H), 6.70-6.32 (m, 2H), 5.79-5.71 (m, 1H), 4.96-4.63 (m, 1H), 3.66-3.47 (m, 2H), 3.45-3.33 (m, 1H), 2.95-2.86 (m, 1H), 2.75-2.30 (m, 1H), 2.25-2.19 (m, 3H), 2.16-1.93 (m, 2H), 1.89-1.64 (m, 1H). m/z (esi) M+1=537.2.

Example 200

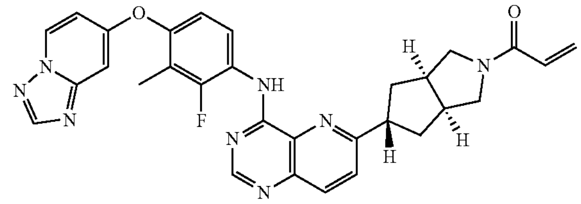 [SMILES: C=CC(=O)N1C[C@H]2C[C@H](c3ccc4ncnc(Nc5ccc(Oc6ccn7ncnc7c6)c(C)c5F)c4n3)C[C@H]2C1]

1-((3aR,5s,6aS)-5-(4-((4-([1,2,4]triazolo[1,5-a]pyridin-7-yloxy)-2-fluoro-3-methylphenyl)amino)pyrido[3,2-d]pyrimidin-6-yl)hexahydrocyclopenta[c]pyrrol-2(1H)-yl)prop-2-en-1-one Prepared according to the procedure for Example 189, using tert-butyl 5-hydroxyhexahydrocyclopenta[c]pyrrole-2(1H)-carboxylate in place of tert-butyl 4-hydroxyazepane-1-carboxylate to yield 1-((3aR,5s,6aS)-5-(4-((4-([1,2,4]triazolo[1,5-a]pyridin-7-yloxy)-2-fluoro-3-methylphenyl)amino)pyrido[3,2-d]pyrimidin-6-yl)hexahydrocyclopenta[c]pyrrol-2(1H)-yl)prop-2-en-1-one (6.8 mg, 25%). $^{1}$H NMR (400 MHz, $CDCl_3$) δ 9.52-9.47 (m, 1H), 8.86-8.76 (m, 2H), 8.55-8.48 (m, 1H), 8.24 (s, 1H), 8.16-8.09 (m, 1H), 7.68-7.61 (m, 1H), 7.06-6.98 (m, 1H), 6.94-6.85 (m, 2H), 6.58-6.45 (m, 1H), 6.45-6.33 (m, 1H), 5.75-5.63 (m, 1H), 3.95-3.48 (m, 5H), 3.18-3.01 (m, 2H), 2.59-2.26 (m, 2H), 2.22 (t, J=2.5 Hz, 3H), 2.20-1.87 (m, 2H). m/z (esi) M+1=551.1.

Example 201

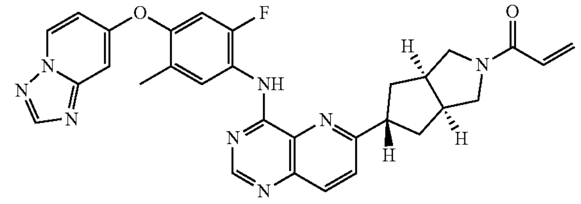 [SMILES: C=CC(=O)N1C[C@H]2C[C@H](c3ccc4ncnc(Nc5cc(C)c(Oc6ccn7ncnc7c6)cc5F)c4n3)C[C@H]2C1]

1-((3aR,5s,6aS)-5-(4-((4-([1,2,4]triazolo[1,5-a]pyridin-7-yloxy)-2-fluoro-5-methylphenyl)amino)pyrido[3,2-d]pyrimidin-6-yl)hexahydrocyclopenta[c]pyrrol-2(1H)-yl)prop-2-en-1-one Prepared according to the procedure for Example 189, using N-(4-[1,2,4]triazolo[1,5-a]pyridine-7-yloxy)-2-fluoro-5-methylphenyl)-6-chloropyrido[3,2-d]pyrimidin-4-amine in place of N-(4-([1,2,4]triazolo[1,5-a]pyridin-7-yloxy)-2-fluoro-3-methylphenyl)-6-chloropyrido[3,2-d]pyrimidin-4-amine and tert-butyl 5-hydroxyhexahydrocyclopenta[c]pyrrole-2(1H)-carboxylate in place of tert-butyl 4-hydroxyazepane-1-carboxylate to yield 1-((3aR,5s,6aS)-5-(4-((4-([1,2,4]triazolo[1,5-a]pyridin-7-yloxy)-2-fluoro-5-methylphenyl)amino)pyrido[3,2-d]pyrimidin-6-yl)hexahydrocyclopenta[c]pyrrol-2(1H)-yl)prop-2-en-1-one (15.1 mg, 50%). $^{1}$H NMR (400 MHz, $CDCl_3$) δ 9.46-9.39 (m, 1H), 8.90-8.80 (m, 2H), 8.56-8.48 (m, 1H), 8.24 (s, 1H), 8.18-8.09 (m, 1H), 7.68-7.61 (m, 1H), 7.01-6.93 (m, 1H), 6.93-6.85 (m, 2H), 6.56-6.33 (m, 2H), 5.74-5.62 (m, 1H), 3.99-3.45 (m, 4H), 3.20-2.98 (m, 2H), 2.61-2.29 (m, 2H), 2.30-2.24 (m, 3H), 2.19-2.03 (m, 2H), 2.02-1.84 (m, 1H). m/z (esi) M+1=551.

Example 202

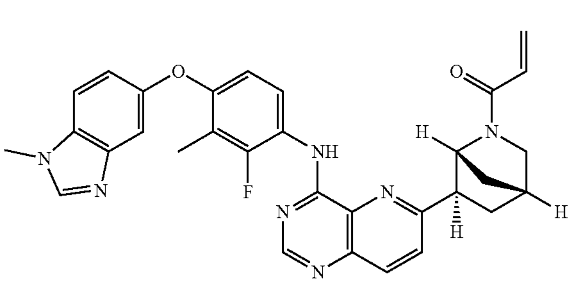 [SMILES: C=CC(=O)N1C[C@H]2C[C@@H]1[C@H](c1ccc3ncnc(Nc4ccc(Oc5ccc6c(c5)ncn6C)c(C)c4F)c3n1)C2]

rac-1-((1R,4R,6R)-6-(4-((2-fluoro-3-methyl-4-((1-methyl-1H-benzo[d]imidazol-5-yl)oxy)phenyl)amino)pyrido[3,2-d]pyrimidin-6-yl)-2-azabicyclo[2.2.1]heptan-2-yl)prop-2-en-1-one Prepared according to the procedure for Example 189, using 6-chloro-N-(2-fluoro-3-methyl-4-((1-methyl-1H-benzo[d]imidazol-5-yl)oxy)phenyl)pyrido[3,2-d]pyrimidin-4-amine in place of N-(4-([1,2,4]triazolo[1,5-a]pyridin-7-yloxy)-2-fluoro-3-methylphenyl)-6-chloropyrido[3,2-d]pyrimidin-4-amine and tert-butyl 6-hydroxy-2-azabicyclo[2.2.1]heptane-2-carboxylate in place of tert-butyl 4-hydroxyazepane-1-carboxylate to yield rac-1-((1R,4R,6R)-6-(4-((2-fluoro-3-methyl-4-((1-methyl-1H-benzo[d]imidazol-5-yl)oxy)phenyl)amino)pyrido[3,2-d]pyrimidin-6-yl)-2-azabicyclo[2.2.1]heptan-2-yl)prop-2-en-1-one (8.7 mg, 50%). $^{1}$H NMR (500 MHz, $CDCl_3$) δ 9.35-9.30 (m, 1H), 8.77-8.73 (m, 1H), 8.57-8.48 (m, 1H), 8.15-8.09 (m, 1H), 7.88 (s, 1H), 7.69-7.61 (m, 1H), 7.38-7.31 (m, 2H), 7.10-7.04 (m, 1H), 6.81-6.74 (m, 1H), 6.63-6.32 (m, 2H), 5.76-5.69 (m, 1H), 4.97-4.52 (m, 1H), 3.86 (s, 3H), 3.71-3.42 (m, 2H), 3.37-3.29 (m, 1H), 3.10-2.90 (m, 1H), 2.52-2.21 (m, 6H), 2.20-2.08 (m, 1H), 1.84-1.73 (m, 1H). m/z (esi) M+1=550.2.

Example 203

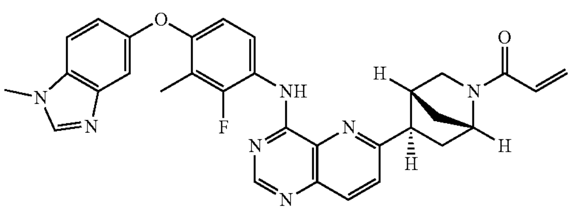 [SMILES: C=CC(=O)N1C[C@@H]2C[C@H]1C[C@H]2c1ccc2ncnc(Nc3ccc(Oc4ccc5c(c4)ncn5C)c(C)c3F)c2n1]

rac-1-((1S,4R,5R)-5-(4-((2-fluoro-3-methyl-4-((1-methyl-1H-benzo[d]imidazol-5-yl)oxy)phenyl)amino)pyrido[3,2-d]pyrimidin-6-yl)-2-azabicyclo[2.2.1]heptan-2-yl)prop-2-en-1-one Prepared according to the procedure for Example 189, using 6-chloro-N-(2-fluoro-3-methyl-4-((1-methyl-1H-benzo[d]imidazol-5-yl)oxy)phenyl)pyrido[3,2-d]pyrimidin-4-amine in place of N-(4-([1,2,4]triazolo[1,5-a]pyridin-7-yloxy)-2-fluoro-3-methylphenyl)-6-chloropyrido[3,2-d]pyrimidin-4-amine and tert-butyl 5-hydroxy-2-azabicyclo[2.2.1]heptane-2-carboxylate in place of tert-butyl 4-hydroxyazepane-1-carboxylate to yield rac-1-((1 S,4R,5R)-5-(4-((2-fluoro-3-methyl-4-((1-methyl-1H-benzo[d]imidazol-5-yl)oxy)phenyl)amino)pyrido[3,2-d]pyrimidin-6-yl)-2-azabicyclo[2.2.1]heptan-2-yl)prop-2-en-1-one (12.3 mg, 51%). $^{1}$H NMR (500 MHz, $CDCl_3$) δ 9.35-9.31 (m, 1H), 8.78-8.73 (m, 1H), 8.57-8.48 (m, 1H), 8.17-8.08 (m, 1H), 7.88 (s, 1H), 7.81-7.59 (m, 1H), 7.38-7.32 (m, 2H), 7.11-7.04 (m, 1H), 6.81-6.74 (m, 1H), 6.68-6.34 (m, 2H), 5.78-5.71 (m, 1H), 4.93-4.63 (m, 1H), 3.86 (s, 3H), 3.70-3.45 (m, 2H), 3.44-3.32 (m, 1H), 2.96-2.85 (m, 1H), 2.72-2.33 (m, 1H), 2.34-2.28 (m, 3H), 2.16-1.92 (m, 2H), 1.85-1.59 (m, 1H). m/z (esi) M+1=550.2.

Example 204

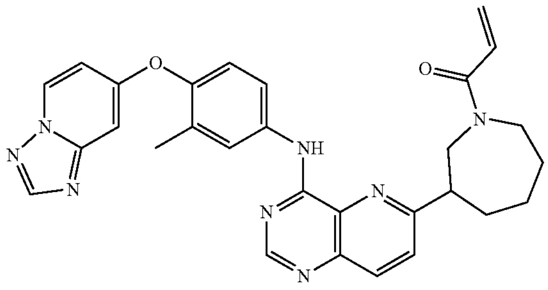 [SMILES: C=CC(=O)N1CCCCC(c2ccc3ncnc(Nc4ccc(Oc5ccn6ncnc6c5)c(C)c4)c3n2)C1]

1-(3-(4-((4-([1,2,4]triazolo[1,5-a]pyridin-7-yloxy)-3-methylphenyl)amino)pyrido[3,2-d]pyrimidin-6-yl)azepan-1-yl)prop-2-en-1-one Prepared according to the procedure for Example 189, using N-(4-([1,2,4]triazolo[1,5-a]pyridin-7-yloxy)-3-methylphenyl)-6-chloropyrido[3,2-d]pyrimidin-4-amine in place of N-(4-([1,2,4]triazolo[1,5-a]pyridin-7-yloxy)-2-fluoro-3-methylphenyl)-6-chloropyrido[3,2-d]pyrimidin-4-amine and tert-butyl 3-hydroxyazepane-1-carboxylate in place of tert-butyl 4-hydroxyazepane-1-carboxylate to yield 1-(3-(4-((4-([1,2,4]triazolo[1,5-a]pyridin-7-yloxy)-3-methylphenyl)amino)pyrido[3,2-d]pyrimidin-6-yl)azepan-1-yl)prop-2-en-1-one (18.1 mg, 67%). $^{1}$H NMR (400 MHz, $CDCl_3$) δ 9.57-9.00 (m, 1H), 8.82-8.75 (m, 1H), 8.53-8.46 (m, 1H), 8.22 (s, 1H), 8.20-8.11 (m, 1H), 8.05-7.83 (m, 2H), 7.77-7.59 (m, 1H), 7.19-7.10 (m, 1H), 6.94-6.83 (m, 2H), 6.71-6.59 (m, 1H), 6.47-6.37 (m, 1H), 5.78-5.67 (m, 1H), 4.27-3.93 (m, 2H), 3.85-3.64 (m, 2H), 3.57-3.21 (m, 1H), 2.28 (d, J=3.9 Hz, 3H), 2.21-1.78 (m, 5H), 1.66-1.59 (m, 1H). m/z (esi) M+1=521.2.

Example 205

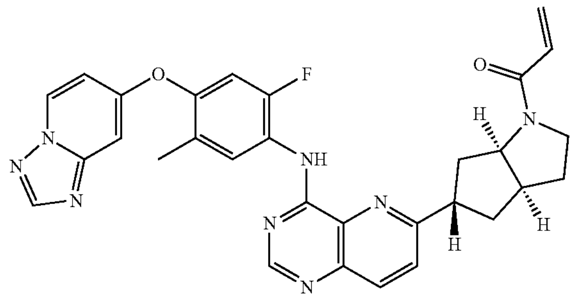 [SMILES: C=CC(=O)N1CC[C@H]2C[C@H](c3ccc4ncnc(Nc5cc(C)c(Oc6ccn7ncnc7c6)cc5F)c4n3)C[C@H]21]

rac-1-((3aR,5S,6aR)-5-(4-((4-([1,2,4]triazolo[1,5-a]pyridin-7-yloxy)-2-fluoro-5-methylphenyl)amino)pyrido[3,2-d]pyrimidin-6-yl)hexahydrocyclopenta[b]pyrrol-1(2H)-yl)prop-2-en-1-one Prepared according to the procedure for Example 189, using N-(4-[1,2,4]triazolo[1,5-a]pyridine-7-yloxy)-2-fluoro-5-methylphenyl)-6-chloropyrido[3,2-d]pyrimidin-4-amine in place of N-(4-([1,2,4]triazolo[1,5-a]pyridin-7-yloxy)-2-fluoro-3-methylphenyl)-6-chloropyrido[3,2-d]pyrimidin-4-amine and tert-butyl (3aS,6aR)-5-hydroxyhexahydrocyclopenta[b]pyrrole-1(2H)-carboxylate in place of tert-butyl 4-hydroxyazepane-1-carboxylate to yield rac-1-((3aR,5S,6aR)-5-(4-((4-([1,2,4]triazolo[1,5-a]pyridin-7-yloxy)-2-fluoro-5-methylphenyl)amino)pyrido[3,2-d]pyrimidin-6-yl)hexahydrocyclopenta[b]pyrrol-1 (2H)-yl)prop-2-en-1-one (29.0 mg, 74%). $^{1}$H NMR (400 MHz, $CDCl_3$) δ 9.43-9.39 (m, 1H), 8.91-8.79 (m, 2H), 8.55-8.48 (m, 1H), 8.24 (s, 1H), 8.17-8.08 (m, 1H), 7.68-7.61 (m, 1H), 7.02-6.93 (m, 1H), 6.93-6.86 (m, 2H), 6.64-6.48 (m, 1H), 6.46-6.34 (m, 1H), 5.74-5.66 (m, 1H), 4.71-4.59 (m, 1H), 4.02-3.91 (m, 1H), 3.84-3.45 (m, 2H), 3.22-2.96 (m, 1H), 2.60-2.26 (m, 6H), 2.25-1.99 (m, 2H), 1.97-1.77 (m, 1H). m/z (esi) M+1=551.2.

Example 206

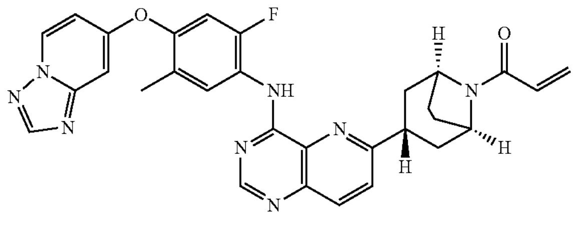 [SMILES: C=CC(=O)N1[C@@H]2CC[C@H]1C[C@@H](c1ccc3ncnc(Nc4cc(C)c(Oc5ccn6ncnc6c5)cc4F)c3n1)C2]

1-((1R,3r,5S)-3-(4-((4-([1,2,4]triazolo[1,5-a]pyridin-7-yloxy)-2-fluoro-5-methylphenyl)amino)pyrido[3,2-d]pyrimidin-6-yl)-8-azabicyclo[3.2.1]octan-8-yl)prop-2-en-1-one Prepared according to the procedure for Example 189, using N-(4-[1,2,4]triazolo[1,5-a]pyridine-7-yloxy)-2-fluoro-5-methylphenyl)-6-chloropyrido[3,2-d]pyrimidin-4-amine in place of N-(4-([1,2,4]triazolo[1,5-a]pyridin-7-yloxy)-2-fluoro-3-methylphenyl)-6-chloropyrido[3,2-d]

pyrimidin-4-amine and tert-butyl 3-hydroxy-8-azabicyclo[3.2.1]octane-8-carboxylate in place of tert-butyl 4-hydroxyazepane-1-carboxylate to yield 1-((1R,3r,5S)-3-(4-((4-([1,2,4]triazolo[1,5-a]pyridin-7-yloxy)-2-fluoro-5-methylphenyl)amino)pyrido[3,2-d]pyrimidin-6-yl)-8-azabicyclo[3.2.1]octan-8-yl)prop-2-en-1-one (15.3 mg, 68%). $^1$H NMR (400 MHz, $CDCl_3$) δ 9.33 (d, J=2.9 Hz, 1H), 8.84-8.76 (m, 2H), 8.55-8.48 (m, 1H), 8.24 (s, 1H), 8.14 (d, J=8.7 Hz, 1H), 7.64 (d, J=8.7 Hz, 1H), 6.97 (d, J=10.9 Hz, 1H), 6.92-6.83 (m, 2H), 6.59 (dd, J=16.8, 10.2 Hz, 1H), 6.44 (dd, J=16.8, 2.1 Hz, 1H), 5.74 (dd, J=10.2, 2.1 Hz, 1H), 4.99-4.92 (m, 1H), 4.56-4.50 (m, 1H), 3.65-3.52 (m, 1H), 2.27 (s, 3H), 2.26-2.06 (m, 5H), 2.06-1.90 (m, 3H). m/z (esi) M+1=551.2.

Example 207

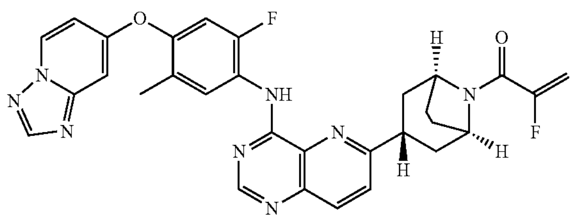 [SMILES: C=C(F)C(=O)N1[C@@H]2CC[C@H]1C[C@@H](c1ccc3ncnc(Nc4cc(C)c(Oc5ccn6ncnc6c5)cc4F)c3n1)C2]

1-((1R,3r,5S)-3-(4-((4-([1,2,4]triazolo[1,5-a]pyridin-7-yloxy)-2-fluoro-5-methylphenyl)amino)pyrido[3,2-d]pyrimidin-6-yl)-8-azabicyclo[3.2.1]octan-8-yl)-2-fluoroprop-2-en-1-one Step A: To a 40 mL vial containing $Ir(dtbbpy)(ppy)_2$ (6.5 mg, 7.1 μmol), $NiBr_2$ dtbbpy (17.3 mg, 36 μmol), quinuclidine (105 mg, 0.95 mmol), phthalimide (15.7 mg, 0.11 mmol), and N-(4-([1,2,4]triazolo[1,5-a]pyridin-7-yloxy)-2-fluoro-5-methylphenyl)-6-chloropyrido[3,2-d] pyrimidin-4-amine (200 mg, 0.47 mmol) were dissolved/suspended in DMA (4.8 mL). To a separate 40 mL vial containing 5,7-di-tert-butyl-3-phenyl-3-(tetrafluoro-15-boraneyl)-2,3-dihydrobenzo[d]oxazol-3-ium-2-ide (394 mg, 1.0 mmol), tert-butyl 3-hydroxy-8-azabicyclo[3.2.1]octane-8-carboxylate (216 mg, 0.95 mmol) was added degassed MTBE (4.8 mL) under nitrogen. After stirring for 5 minutes, pyridine (76 μL, 0.95 mmol) was added. After stirring for an additional 10 minutes, the solution was taken up in a syringe and filtered through a syringe filter into the reaction vial containing nickel and iridium components. The vial was then capped and sparged with nitrogen for 10 minutes, parafilmed, and irradiated with 450 nm light in the integrated photoreactor for 12 hours (100% intensity, 750 rpm stir, max fan speed). The reaction was concentrated in vacuo, and the crude residue was purified over 40 g silica cartridge, eluting with a gradient of 1-10% MeOH/DCM to afford tert-butyl (1R,3r,5S)-3-(4-((4-([1,2,4]triazolo[1,5-a]pyridin-7-yloxy)-2-fluoro-5-methylphenyl)amino)pyrido[3,2-d]pyrimidin-6-yl)-8-azabicyclo[3.2.1]octane-8-carboxylate (105.4 mg, 37%). m/z (esi) M+1=597.2.

Step B: Trifluoroacetic acid (262 μL, 3.4 mmol) was added to a stirred solution of tert-butyl (1R,3r,5S)-3-(4-((4-([1,2,4]triazolo[1,5-a]pyridin-7-yloxy)-2-fluoro-5-methylphenyl)amino)pyrido[3,2-d]pyrimidin-6-yl)-8-azabicyclo[3.2.1]octane-8-carboxylate (101.5 mg, 0.17 mmol) in DCM (1.7 mL). The reaction was stirred at 23° C. for 2 hours before diluting with EtOAc and quenching with 10% $K_2CO_3$. The aqueous phase was extracted with EtOAc (3×), and the combined organic layers were washed with 10% $K_2CO_3$. The organic layer was then dried over sodium sulfate, filtered and concentrated in vacuo to afford N-(4-([1,2,4]triazolo[1,5-a]pyridin-7-yloxy)-2-fluoro-5-methylphenyl)-6-((1R,3r,5S)-8-azabicyclo[3.2.1]octan-3-yl)pyrido[3,2-d]pyrimidin-4-amine (84.3 mg, 100%), which was used directly in the next reaction without further purification. m/z (esi) M+1=497.2.

Step C: 2,4,6-Tripropy;-1,3,5,2,4,6-trioxatriphosphinane 2,4,6-trioxide (50 wt %) in DMF (240 μL, 0.40 mmol) was added to a stirred solution of DIPEA (0.14 mL, 0.81 mmol), N-(4-([1,2,4]triazolo[1,5-a]pyridin-7-yloxy)-2-fluoro-5-methylphenyl)-6-((1R,3r,5S)-8-azabicyclo[3.2.1]octan-3-yl)pyrido[3,2-d]pyrimidin-4-amine (20 mg, 0.04 mmol), and 2-fluoroacrylic acid (18 mg, 0.20 mmol) in DMF (0.75 mL) at 23° C. under air. After 1 hour at 50° C., the reaction mixture was cooled to room temperature, diluted with water and EtOAc, and the aqueous layer was extracted with EtOAc (3×). The combined organic layers were washed with brine (3×), dried over sodium sulfate, and concentrated in vacuo. The crude residue was purified over 4 g silica cartridge, eluting with a gradient of 1-10% MeOH/DCM to afford 1-((1R,3r,5S)-3-(4-((4-([1,2,4]triazolo[1,5-a]pyridin-7-yloxy)-2-fluoro-5-methylphenyl)amino)pyrido[3,2-d]pyrimidin-6-yl)-8-azabicyclo[3.2.1]octan-8-yl)-2-fluoroprop-2-en-1-one (5.0 mg, 22%). $^1$H NMR (400 MHz, $CDCl_3$) δ 9.36 (d, J=3.0 Hz, 1H), 8.84-8.78 (m, 2H), 8.55-8.48 (m, 1H), 8.24 (s, 1H), 8.15 (d, J=8.7 Hz, 1H), 7.66 (d, J=8.7 Hz, 1H), 6.98 (d, J=10.9 Hz, 1H), 6.92-6.86 (m, 2H), 5.51 (dd, J=47.3, 3.2 Hz, 1H), 5.17 (dd, J=16.5, 3.2 Hz, 1H), 4.96-4.92 (m, 1H), 4.76-4.71 (m, 1H), 3.57 (tt, J=11.8, 5.4 Hz, 1H), 2.27 (s, 3H), 2.26-2.13 (m, 3H), 2.13-1.90 (m, 5H). 19F NMR (376 MHz, CDCl3) 5-109.05 (dd, J=47.2, 16.6 Hz, 1F), -130.09 (t, J=10.0 Hz, 1F). m/z (esi) M+1=569.2.

Example 208

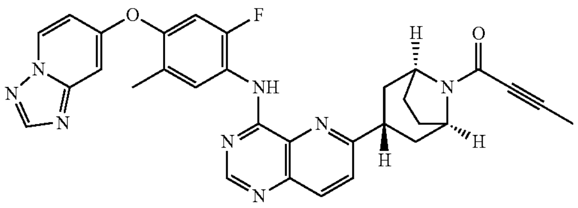 [SMILES: CC#CC(=O)N1[C@@H]2CC[C@H]1C[C@@H](c1ccc3ncnc(Nc4cc(C)c(Oc5ccn6ncnc6c5)cc4F)c3n1)C2]

1-((1R,3r,5S)-3-(4-((4-([1,2,4]triazolo[1,5-a]pyridin-7-yloxy)-2-fluoro-5-methylphenyl)amino)pyrido[3,2-d]pyrimidin-6-yl)-8-azabicyclo[3.2.1]octan-8-yl)but-2-yn-1-one Prepared according to the procedure for Example 207, using but-2-ynoic acid in place of 2-fluoroacrylic acid to yield 1-((1R,3r,5S)-3-(4-((4-([1,2,4]triazolo[1,5-a]pyridin-7-yloxy)-2-fluoro-5-methylphenyl)amino)pyrido[3,2-d]pyrimidin-6-yl)-8-azabicyclo[3.2.1]octan-8-yl)but-2-yn-1-one (7.5 mg, 33%). $^1$H NMR (400 MHz, $CDCl_3$) δ 9.35 (d, J=2.8 Hz, 1H), 8.82 (s, 1H), 8.79 (d, J=8.9 Hz, 1H), 8.52 (dd, J=6.8, 1.4 Hz, 1H), 8.24 (s, 1H), 8.14 (d, J=8.7 Hz, 1H), 7.66 (d, J=8.7 Hz, 1H), 6.97 (d, J=10.8 Hz, 1H), 6.92-6.85 (m, 2H), 4.85 (dt, J=6.3, 2.9 Hz, 1H), 4.70 (dt, J=6.3, 2.9 Hz, 1H), 3.57 (tt, J=11.7, 5.4 Hz, 1H), 2.27 (s, 3H), 2.26-2.06 (m, 5H), 2.02 (s, 3H), 2.01-1.89 (m, 3H). m/z (esi) M+1=563.2.

Example 209

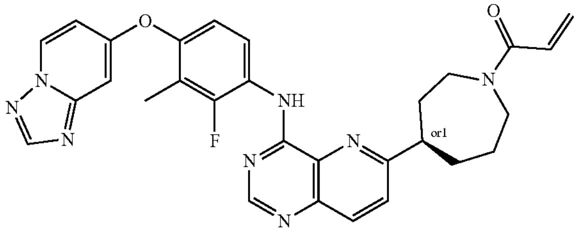 [SMILES: C=CC(=O)N1CCC[C@@H](c2ccc3ncnc(Nc4ccc(Oc5ccn6ncnc6c5)c(C)c4F)c3n2)CC1]

rel-(R)-1-(4-(4-((4-([1,2,4]triazolo[1,5-a]pyridin-7-yloxy)-2-fluoro-3-methylphenyl)amino)pyrido[3,2-d]pyrimidin-6-yl)azepan-1-yl)prop-2-en-1-one Step A: In a 40 mL vial containing (4,4'-di-tert-butyl-2,2'-bipyridine)bis[(2-pyridinyl)phenyl]iridium(III) hexafluorophosphate (6.5 mg, 7.1 μmol), (SP-4-2)-[4,4'-bis(1,1-dimethylethyl)-2,2'-bipyridine-κN1,κN1']dibromo-Nickel (17.2 mg, 36 μmol), quinuclidine (105 mg, 0.95 mmol), phthalimide (15.7 mg, 0.11 mmol), and N-(4-([1,2,4]triazolo[1,5-a]pyridin-7-yloxy)-2-fluoro-3-methylphenyl)-6-chloropyrido[3,2-d]pyrimidin-4-amine (Intermediate S, 200 mg, 0.47 mmol) were dissolved/suspended in DMA (4.8 mL). To a separate 20 mL vial containing 5,7-di-tert-butyl-3-phenyl-3-(tetrafluoro-15-boraneyl)-2,3-dihydrobenzo[d]oxazol-3-ium-2-ide (394 mg, 1.0 mmol) and tert-butyl 4-hydroxyazepane-1-carboxylate (204 mg, 0.95 mmol) was added degassed MTBE (4.8 mL) under nitrogen. After stirring for 5 minutes, pyridine (76 μL, 0.95 mmol) was added. After stirring for an additional 10 minutes, the solution was taken up in a syringe and filtered through a syringe filter into the reaction vial containing nickel and iridium components. The vial was then capped and sparged with nitrogen for 10 minutes, parafilmed, and irradiated with 450 nm light in the integrated photoreactor for 12 hours (100% intensity, 750 rpm stir, max fan speed). The reaction was concentrated in vacuo, and the crude residue was purified over 40 g silica cartridge, eluting with a gradient of 1-10% MeOH/DCM to afford rac-tert-butyl (R)-4-(4-((4-([1,2,4]triazolo[1,5-a]pyridin-7-yloxy)-2-fluoro-3-methylphenyl)amino)pyrido[3,2-d]pyrimidin-6-yl)azepane-1-carboxylate. The mixture of enantiomers was subsequently separated by chiral Prep-SFC (30% EtOH/$CO_2$, 60 mL/min; 100 bar outlet pressure with a 2 cm×25 cm Whelk-01 RR column) to afford rel-tert-butyl (R)-4-(4-((4-([1,2,4]triazolo[1,5-a]pyridin-7-yloxy)-2-fluoro-3-methylphenyl)amino)pyrido[3,2-d]pyrimidin-6-yl)azepane-1-carboxylate (38 mg, 14%). m/z (esi) M+1=585.3.

Step B: Trifluoroacetic acid (0.10 mL, 1.3 mmol) was added to a stirred solution of rel-tert-butyl (R)-4-(4-((4-([1,2,4]triazolo[1,5-a]pyridin-7-yloxy)-2-fluoro-3-methylphenyl)amino)pyrido[3,2-d]pyrimidin-6-yl)azepane-1-carboxylate (38 mg, 0.07 mmol) in DCM (0.7 mL). The reaction was stirred at 23° C. for 2 hours before diluting with EtOAc and quenching with 10% $K_2CO_3$. The aqueous phase was extracted with EtOAc (3×), and the combined organic layers were washed with 10% $K_2CO_3$. The organic layer was then dried over sodium sulfate, filtered, and concentrated in vacuo to afford rel-(R)—N-(4-([1,2,4]triazolo[1,5-a]pyridin-7-yloxy)-2-fluoro-3-methylphenyl)-6-(azepan-4-yl)pyrido[3,2-d]pyrimidin-4-amine (19.9 mg, 63%), which was used directly in the next reaction without further purification. m/z (esi) M+1=485.2. $[\alpha]_D^{33}=-4.6$.

Step C: Acryloyl chloride (25 μL, 0.01 mmol) as a 0.5M solution in DCM was added to a stirred solution of rel-(R)—N-(4-([1,2,4]triazolo[1,5-a]pyridin-7-yloxy)-2-fluoro-3-methylphenyl)-6-(azepan-4-yl)pyrido[3,2-d]pyrimidin-4-amine (7.6 mg, 0.02 mmol) and DIPEA (5.5 μL, 0.03 mmol) in DCM (0.4 mL) at 0° C. The reaction mixture was stirred for 10 minutes at this temperature before partitioning between 10% $K_2CO_3$ and DCM. The aqueous phase was extracted with DCM (3×). The combined organic layers were then dried over sodium sulfate, filtered, and concentrated in vacuo, and the crude residue was purified over 4 g silica cartridge, eluting with a gradient of 1-10% MeOH/DCM to afford rel-(R)-1-(4-(4-((4-([1,2,4]triazolo[1,5-a]pyridin-7-yloxy)-2-fluoro-3-methylphenyl)amino)pyrido[3,2-d]pyrimidin-6-yl)azepan-1-yl)prop-2-en-1-one (5.6 mg, 66%). $^1$H NMR (400 MHz, $CDCl_3$) δ 9.44 (s, 1H), 8.83-8.72 (m, 2H), 8.55-8.48 (m, 1H), 8.24 (s, 1H), 8.17-8.09 (m, 1H), 7.66-7.59 (m, 1H), 7.05-6.98 (m, 1H), 6.94-6.85 (m, 2H), 6.73-6.60 (m, 1H), 6.47-6.36 (m, 1H), 5.78-5.70 (m, 1H), 4.00-3.53 (m, 4H), 3.20-3.10 (m, 1H), 2.39-2.24 (m, 1H), 2.22 (d, J=2.1 Hz, 3H), 2.20-2.05 (m, 3H), 2.03-1.75 (m, 2H). m/z (esi) M+1=539.2.

Example 210

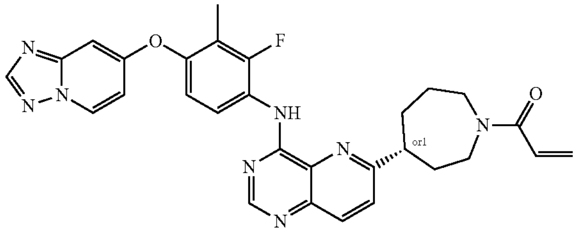 [SMILES: C=CC(=O)N1CCC[C@@H](c2ccc3ncnc(Nc4ccc(Oc5ccn6ncnc6c5)c(C)c4F)c3n2)CC1]

rel-(S)-1-(4-(4-((4-([1,2,4]triazolo[1,5-a]pyridin-7-yloxy)-2-fluoro-3-methylphenyl)amino)pyrido[3,2-d]pyrimidin-6-yl)azepan-1-yl)prop-2-en-1-one Step A: In a 40 mL vial containing (4,4'-di-tert-butyl-2,2'-bipyridine)bis[(2-pyridinyl)phenyl]iridium(III) hexafluorophosphate (6.5 mg, 7.1 μmol), (SP-4-2)-[4,4'-bis(1,1-dimethylethyl)-2,2'-bipyridine-κN1,κN1']dibromo-Nickel (17.2 mg, 36 μmol), quinuclidine (105 mg, 0.95 mmol), phthalimide (15.7 mg, 0.11 mmol), and N-(4-([1,2,4]triazolo[1,5-a]pyridin-7-yloxy)-2-fluoro-3-methylphenyl)-6-chloropyrido[3,2-d]pyrimidin-4-amine (200 mg, 0.47 mmol) were dissolved/suspended in DMA (4.8 mL). To a separate 20 mL vial containing 5,7-di-tert-butyl-3-phenyl-3-(tetrafluoro-15-boraneyl)-2,3-dihydrobenzo[d]oxazol-3-ium-2-ide (394 mg, 1.0 mmol) and tert-butyl 4-hydroxyazepane-1-carboxylate (204 mg, 0.95 mmol) was added degassed MTBE (4.8 mL) under nitrogen. After stirring for 5 minutes, pyridine (76 μL, 0.95 mmol) was added. After stirring for an additional 10 minutes, the solution was taken up in a syringe and filtered through a syringe filter into the reaction vial containing nickel and iridium components. The vial was then capped and sparged with nitrogen for 10 minutes, parafilmed, and irradiated with 450 nm light in the integrated photoreactor for 12 hours (100% intensity, 750 rpm stir, max fan speed). The reaction was concentrated in vacuo, and the crude residue was purified over 40 g silica cartridge, eluting with a gradient of 1-10% MeOH/DCM to afford rac-tert-butyl (S)-4-(4-((4-([1,2,4]triazolo[1,5-a]pyridin-7-yloxy)-2-fluoro-3-methylphenyl)amino)pyrido[3,2-d]pyrimidin-6-yl) azepane-1-carboxylate. The purified mixture of enantiomers was subsequently separated by chiral Prep-SFC (30% EtOH/$CO_2$, 60 mL/min; 100 bar outlet pressure with a 2 cm×25 cm Whelk-01 RR column) to afford rel-tert-butyl (S)-4-(4-((4-([1,2,4]triazolo[1,5-a]pyridin-7-yloxy)-2-fluoro-3-methylphenyl)amino)pyrido[3,2-d]pyrimidin-6-yl)azepane-1-carboxylate (42 mg, 15%). m/z (esi) M+1=585.3.

Step B: Trifluoroacetic acid (0.11 mL, 1.4 mmol) was added to a stirred solution of rel-tert-butyl (S)-4-(4-((4-([1,2,4]triazolo[1,5-a]pyridin-7-yloxy)-2-fluoro-3-methylphenyl)amino)pyrido[3,2-d]pyrimidin-6-yl)azepane-1-carboxylate (40 mg, 0.07 mmol) in DCM (0.7 mL). The reaction was stirred at 23° C. for 2 hours before diluting with EtOAc and quenching with 10% $K_2CO_3$. The aqueous phase was extracted with EtOAc (3×), and the combined organic layers were washed with 10% $K_2CO_3$. The organic layer was then dried over sodium sulfate, filtered, and concentrated in vacuo to afford rel-(S)—N-(4-([1,2,4]triazolo[1,5-a]pyridin-7-yloxy)-2-fluoro-3-methylphenyl)-6-(azepan-4-yl)pyrido[3,2-d]pyrimidin-4-amine (29.1 mg, 88%), which was used directly in the next reaction without further purification. m/z (esi) M+1=485.2. $[\alpha]_D^{23}$=+6.4.

Step C: Acryloyl chloride (33 μL, 0.02 mmol) as a 0.5M solution in DCM was added to a stirred solution of rel-(S)—N-(4-([1,2,4]triazolo[1,5-a]pyridin-7-yloxy)-2-fluoro-3-methylphenyl)-6-(azepan-4-yl)pyrido[3,2-d]pyrimidin-4-amine (10 mg, 0.02 mmol) and DIPEA (7.2 μL, 0.04 mmol) in DCM (0.4 mL) at 0° C. The reaction mixture was stirred for 10 minutes at this temperature before partitioning between 10% $K_2CO_3$ and DCM. The aqueous phase was extracted with DCM (3×). The combined organic layers were then dried over sodium sulfate, filtered, and concentrated in vacuo, and the crude residue was purified over 4 g silica cartridge, eluting with a gradient of 1-10% MeOH/DCM to afford rel-(S)-1-(4-(4-((4-([1,2,4]triazolo[1,5-a]pyridin-7-yloxy)-2-fluoro-3-methylphenyl)amino)pyrido[3,2-d]pyrimidin-6-yl)azepan-1-yl)prop-2-en-1-one (5.2 mg, 47%). $^1H$ NMR (400 MHz, $CDCl_3$) δ 9.44 (s, 1H), 8.83-8.72 (m, 2H), 8.55-8.48 (m, 1H), 8.24 (s, 1H), 8.17-8.09 (m, 1H), 7.66-7.59 (m, 1H), 7.05-6.98 (m, 1H), 6.94-6.85 (m, 2H), 6.73-6.60 (m, 1H), 6.47-6.36 (m, 1H), 5.78-5.70 (m, 1H), 4.00-3.53 (m, 4H), 3.20-3.10 (m, 1H), 2.39-2.24 (m, 1H), 2.22 (d, J=2.1 Hz, 3H), 2.20-2.05 (m, 3H), 2.03-1.75 (m, 2H). m/z (esi) M+1=539.2.

Example 211

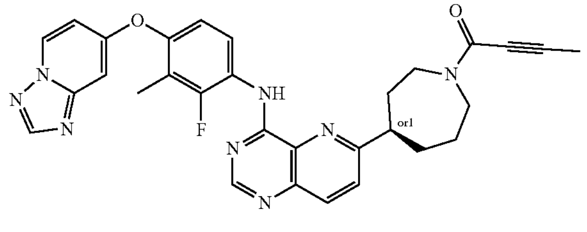 [SMILES: CC#CC(=O)N1CCC[C@@H](c2ccc3ncnc(Nc4ccc(Oc5ccn6ncnc6c5)c(C)c4F)c3n2)CC1]

rel-(R)-1-(4-(4-((4-([1,2,4]triazolo[1,5-a]pyridin-7-yloxy)-2-fluoro-3-methylphenyl)amino)pyrido[3,2-d]pyrimidin-6-yl)azepan-1-yl)but-2-yn-1-one Step A: In a 40 mL vial containing (4,4'-di-tert-butyl-2,2'-bipyridine)bis[(2-pyridinyl)phenyl]iridium(III) hexafluorophosphate (6.5 mg, 7.1 μmol), (SP-4-2)-[4,4'-bis(1,1-dimethylethyl)-2,2'-bipyridine-κN1,κN1']dibromo-Nickel (17.2 mg, 36 μmol), quinuclidine (105 mg, 0.95 mmol), phthalimide (15.7 mg, 0.11 mmol), and N-(4-([1,2,4]triazolo[1,5-a]pyridin-7-yloxy)-2-fluoro-3-methylphenyl)-6-chloropyrido[3,2-d]pyrimidin-4-amine (200 mg, 0.47 mmol) were dissolved/suspended in DMA (4.8 mL). To a separate 20 mL vial containing 5,7-di-tert-butyl-3-phenyl-3-(tetrafluoro-15-boraneyl)-2,3-dihydrobenzo[d]oxazol-3-ium-2-ide (394 mg, 1.0 mmol) and tert-butyl 4-hydroxyazepane-1-carboxylate (204 mg, 0.95 mmol) was added degassed MTBE (4.8 mL) under nitrogen. After stirring for 5 minutes, pyridine (76 μL, 0.95 mmol) was added. After stirring for an additional 10 minutes, the solution was taken up in a syringe and filtered through a syringe filter into the reaction vial containing nickel and iridium components. The vial was then capped and sparged with nitrogen for 10 minutes, parafilmed, and irradiated with 450 nm light in the integrated photoreactor for 12 hours (100% intensity, 750 rpm stir, max fan speed). The reaction was concentrated in vacuo, and the crude residue was purified over 40 g silica cartridge, eluting with a gradient of 1-10% MeOH/DCM to afford rac-tert-butyl (R)-4-(4-((4-([1,2,4]triazolo[1,5-a]pyridin-7-yloxy)-2-fluoro-3-methylphenyl)amino)pyrido[3,2-d]pyrimidin-6-yl) azepane-1-carboxylate. The mixture of enantiomers was subsequently separated by chiral Prep-SFC (30% EtOH/$CO_2$, 60 mL/min; 100 bar outlet pressure with a 2 cm×25 cm Whelk-01 RR column) to afford rel-tert-butyl (R)-4-(4-((4-([1,2,4]triazolo[1,5-a]pyridin-7-yloxy)-2-fluoro-3-methylphenyl)amino)pyrido[3,2-d]pyrimidin-6-yl)azepane-1-carboxylate (38 mg, 14%). m/z (esi) M+1=585.3.

Step B: Trifluoroacetic acid (0.1 mL, 1.3 mmol) was added to a stirred solution of rel-tert-butyl (R)-4-(4-((4-([1,2,4]triazolo[1,5-a]pyridin-7-yloxy)-2-fluoro-3-methylphenyl)amino)pyrido[3,2-d]pyrimidin-6-yl)azepane-1-carboxylate (38 mg, 0.07 mmol) in DCM (0.7 mL). The reaction was stirred at 23° C. for 2 hours before diluting with EtOAc and quenching with 10% $K_2CO_3$. The aqueous phase was extracted with EtOAc (3×), and the combined organic layers were washed with 10% $K_2CO_3$. The organic layer was then dried over sodium sulfate, filtered, and concentrated in vacuo to afford rel-(R)—N-(4-([1,2,4]triazolo[1,5-a]pyridin-7-yloxy)-2-fluoro-3-methylphenyl)-6-(azepan-4-yl)pyrido[3,2-d]pyrimidin-4-amine (19.9 mg, 63%), which was used directly in the next reaction without further purification. m/z (esi) M+1=485.2. $[\alpha]_D^{23}$=−4.6.

Step C: 2,4,6-Tripropy;-1,3,5,2,4,6-trioxatriphosphinane 2,4,6-trioxide (50 wt %) in DMF (23 μL, 0.04 mmol) was added to a stirred solution of DIPEA (14 μL, 0.08 mmol), rel-(R)—N-(4-([1,2,4]triazolo[1,5-a]pyridin-7-yloxy)-2-fluoro-3-methylphenyl)-6-(azepan-4-yl)pyrido[3,2-d]pyrimidin-4-amine (7.7 mg, 0.02 mmol), and but-2-ynoic acid (2.0 mg, 0.02 mmol) in DMF (0.75 mL) at 23° C. under air. After 2 hours, the reaction mixture was diluted with water and EtOAc, and the aqueous layer was extracted with EtOAc (3×). The combined organic layers were washed with brine (3×), dried over sodium sulfate, and concentrated in vacuo. The crude residue was purified over 4 g silica cartridge, eluting with a gradient of 1-10% MeOH/DCM to afford rel-(R)-1-(4-(4-((4-([1,2,4]triazolo[1,5-a]pyridin-7-yloxy)-2-fluoro-3-methylphenyl)amino)pyrido[3,2-d]pyrimidin-6-yl)azepan-1-yl)but-2-yn-1-one (2.2 mg, 25%). $^1$H NMR (400 MHz, $CDCl_3$) δ 9.45 (s, 1H), 8.84-8.72 (m, 2H), 8.55-8.48 (m, 1H), 8.24 (s, 1H), 8.18-8.10 (m, 1H), 7.68-7.59 (m, 1H), 7.06-6.98 (m, 1H), 6.91-6.87 (m, 2H), 4.18-3.84 (m, 2H), 3.82-3.62 (m, 2H), 3.17-3.09 (m, 1H), 2.39-2.25 (m, 1H), 2.22 (d, J=2.1 Hz, 3H), 2.20-2.06 (m, 3H), 2.07-2.01 (m, 3H), 2.00-1.83 (m, 2H). m/z (esi) M+1=551.2.

Example 212

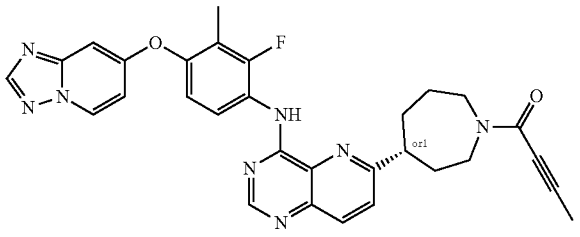 [SMILES: CC#CC(=O)N1CCC[C@@H](c2ccc3ncnc(Nc4ccc(Oc5ccn6ncnc6c5)c(C)c4F)c3n2)CC1]

rel-(S)-1-(4-(4-((4-([1,2,4]triazolo[1,5-a]pyridin-7-yloxy)-2-fluoro-3-methylphenyl)amino)pyrido[3,2-d]pyrimidin-6-yl)azepan-1-yl)but-2-yn-1-one Step A: In a 40 mL vial containing (4,4'-di-tert-butyl-2,2'-bipyridine)bis[(2-pyridinyl)phenyl]iridium(III) hexafluorophosphate (6.5 mg, 7.1 μmol), (SP-4-2)-[4,4'-bis(1,1-dimethylethyl)-2,2'-bipyridine-κN1,κN1']dibromo-Nickel (17.2 mg, 36 μmol), quinuclidine (105 mg, 0.95 mmol), phthalimide (15.7 mg, 0.11 mmol), and N-(4-([1,2,4]triazolo[1,5-a]pyridin-7-yloxy)-2-fluoro-3-methylphenyl)-6-chloropyrido[3,2-d]pyrimidin-4-amine (200 mg, 0.47 mmol) were dissolved/suspended in DMA (4.8 mL). To a separate 20 mL vial containing 5,7-di-tert-butyl-3-phenyl-3-(tetrafluoro-15-boraneyl)-2,3-dihydrobenzo[d]oxazol-3-ium-2-ide (394 mg, 1.0 mmol) and tert-butyl 4-hydroxyazepane-1-carboxylate (204 mg, 0.95 mmol) was added degassed MTBE (4.8 mL) under nitrogen. After stirring for 5 minutes, pyridine (76 μL, 0.95 mmol) was added. After stirring for an additional 10 minutes, the solution was taken up in a syringe and filtered through a syringe filter into the reaction vial containing nickel and iridium components. The vial was then capped and sparged with nitrogen for 10 minutes, parafilmed, and irradiated with 450 nm light in the integrated photoreactor for 12 hours (100% intensity, 750 rpm stir, max fan speed). The reaction was concentrated in vacuo, and the crude residue was purified over 40 g silica cartridge, eluting with a gradient of 1-10% MeOH/DCM to afford rac-tert-butyl (S)-4-(4-((4-([1,2,4]triazolo[1,5-a]pyridin-7-yloxy)-2-fluoro-3-methylphenyl)amino)pyrido[3,2-d]pyrimidin-6-yl)azepane-1-carboxylate. The purified mixture of enantiomers was subsequently separated by chiral Prep-SFC (30% EtOH/$CO_2$, 60 mL/min; 100 bar outlet pressure with a 2 cm×25 cm Whelk-01 RR column) to afford rel-tert-butyl (S)-4-(4-((4-([1,2,4]triazolo[1,5-a]pyridin-7-yloxy)-2-fluoro-3-methylphenyl)amino)pyrido[3,2-d]pyrimidin-6-yl)azepane-1-carboxylate (42 mg, 15% yield, 99% purity). m/z (esi) M+1=585.3.

Step B: Trifluoroacetic acid (0.11 mL, 1.4 mmol) was added to a stirred solution of rel-tert-butyl (S)-4-(4-((4-([1,2,4]triazolo[1,5-a]pyridin-7-yloxy)-2-fluoro-3-methylphenyl)amino)pyrido[3,2-d]pyrimidin-6-yl)azepane-1-carboxylate (40 mg, 0.07 mmol) in DCM (0.7 mL). The reaction was stirred at 23° C. for 2 hours before diluting with EtOAc and quenching with 10% $K_2CO_3$. The aqueous phase was extracted with EtOAc (3×), and the combined organic layers were washed with 10% $K_2CO_3$. The organic layer was then dried over sodium sulfate, filtered, and concentrated in vacuo to afford rel-(S)—N-(4-([1,2,4]triazolo[1,5-a]pyridin-7-yloxy)-2-fluoro-3-methylphenyl)-6-(azepan-4-yl)pyrido[3,2-d]pyrimidin-4-amine (29.1 mg, 88%), which was used directly in the next reaction without further purification. m/z (esi) M+1=485.2. $[\alpha]_D^{23}$=+6.4.

Step C: 2,4,6-Tripropy;-1,3,5,2,4,6-trioxatriphosphinane 2,4,6-trioxide (50 wt %) in DMF (32 μL, 0.06 mmol) was added to a stirred solution of DIPEA (19 μL, 0.11 mmol), rel-(S)—N-(4-([1,2,4]triazolo[1,5-a]pyridin-7-yloxy)-2-fluoro-3-methylphenyl)-6-(azepan-4-yl)pyrido[3,2-d]pyrimidin-4-amine (10.7 mg, 0.02 mmol), and but-2-ynoic acid (2.8 mg, 0.03 mmol) in DMF (0.75 mL) at 23° C. under air. After 2 hours, the reaction mixture was diluted with water and EtOAc, and the aqueous layer was extracted with EtOAc (3×). The combined organic layers were washed with brine (3×), dried over sodium sulfate, and concentrated in vacuo. The crude residue was purified over 4 g silica cartridge, eluting with a gradient of 1-10% MeOH/DCM to afford rel-(S)-1-(4-(4-((4-([1,2,4]triazolo[1,5-a]pyridin-7-yloxy)-2-fluoro-3-methylphenyl)amino)pyrido[3,2-d]pyrimidin-6-yl)azepan-1-yl)but-2-yn-1-one (4.3 mg, 35%). $^1$H NMR (400 MHz, $CDCl_3$) δ 9.45 (s, 1H), 8.84-8.72 (m, 2H), 8.55-8.48 (m, 1H), 8.24 (s, 1H), 8.18-8.10 (m, 1H), 7.68-7.59 (m, 1H), 7.06-6.98 (m, 1H), 6.91-6.87 (m, 2H), 4.18-3.84 (m, 2H), 3.82-3.62 (m, 2H), 3.17-3.09 (m, 1H), 2.39-2.25 (m, 1H), 2.22 (d, J=2.1 Hz, 3H), 2.20-2.06 (m, 3H), 2.07-2.01 (m, 3H), 2.00-1.83 (m, 2H). m/z (esi) M+1=551.2.

Example 213

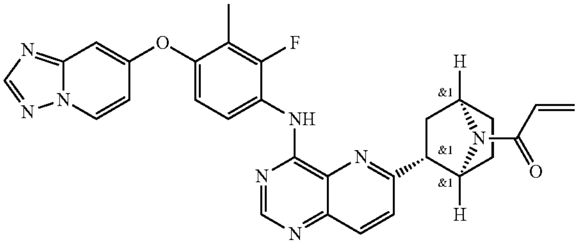 [SMILES: C=CC(=O)N1[C@@H]2CC[C@H]1[C@H](c1ccc3ncnc(Nc4ccc(Oc5ccn6ncnc6c5)c(C)c4F)c3n1)C2]

rac-1-((1 S,2R,4R)-2-(4-((4-([1,2,4]triazolo[1,5-a]pyridin-7-yloxy)-2-fluoro-3-methylphenyl)amino)pyrido[3,2-d]pyrimidin-6-yl)-7-azabicyclo[2.2.1]heptan-7-yl)prop-2-en-1-one Prepared according to the procedure for Example 189, using tert-butyl 2-hydroxy-7-azabicyclo[2.2.1]heptane-7-carboxylate in place of tert-butyl 4-hydroxyazepane-1-carboxylate to yield rac-1-((1 S,2R,4R)-2-(4-((4-([1,2,4]triazolo[1,5-a]pyridin-7-yloxy)-2-fluoro-3-methylphenyl)amino)pyrido[3,2-d]pyrimidin-6-yl)-7-azabicyclo[2.2.1]heptan-7-yl)prop-2-en-1-one (6.0 mg, 54%). $^1$H NMR (400 MHz, $CDCl_3$) δ 9.79-9.25 (m, 1H), 8.76-8.71 (m, 1H), 8.55-8.48 (m, 1H), 8.48-8.29 (m, 1H), 8.24 (s, 1H), 8.14-8.07 (m, 1H), 7.67-7.58 (m, 1H), 7.02-6.86 (m, 3H), 6.56-6.25 (m, 1H), 6.20-6.03 (m, 1H), 5.76-5.35 (m, 1H), 5.28-4.95 (m, 1H), 4.62-4.45 (m, 1H), 3.48-3.38 (m, 1H), 2.58-2.18 (m, 5H), 2.15-1.61 (m, 4H). m/z (esi) M+1=537.2.

Example 214

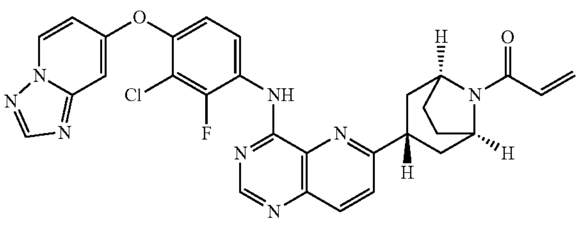 [SMILES: C=CC(=O)N1[C@@H]2CC[C@H]1C[C@@H](c1ccc3ncnc(Nc4ccc(Oc5ccn6ncnc6c5)c(Cl)c4F)c3n1)C2]

1-((1R,3r,5S)-3-(4-((4-([1,2,4]triazolo[1,5-a]pyridin-7-yloxy)-3-chloro-2-fluorophenyl)amino)pyrido[3,2-d]pyrimidin-6-yl)-8-azabicyclo[3.2.1]octan-8-yl)prop-2-en-1-one Prepared according to the procedure for Example 189, using N-(4-([1,2,4]triazolo[1,5-a]pyridin-7-yloxy)-3-chloro-2-fluorophenyl)-6-chloropyrido[3,2-d]pyrimidin-4-amine in place of N-(4-([1,2,4]triazolo[1,5-a]pyridin-7-yloxy)-2-fluoro-3-methylphenyl)-6-chloropyrido[3,2-d]pyrimidin-4-amine and tert-butyl 3-hydroxy-8-azabicyclo[3.2.1]octane-8-carboxylate in place of tert-butyl 4-hydroxyazepane-1-carboxylate to yield 1-((1R,3r,5S)-3-(4-((4-([1,2,4]triazolo[1,5-a]pyridin-7-yloxy)-3-chloro-2-fluorophenyl)amino)pyrido[3,2-d]pyrimidin-6-yl)-8-azabicyclo[3.2.1]octan-8-yl)prop-2-en-1-one (6.8 mg, 54%). $^{1}H$ NMR (400 MHz, $CDCl_3$) δ 9.43 (d, J=3.1 Hz, 1H), 8.92 (dd, J=9.1, 8.5 Hz, 1H), 8.82 (s, 1H), 8.57-8.51 (m, 1H), 8.26 (s, 1H), 8.16 (d, J=8.7 Hz, 1H), 7.67 (d, J=8.7 Hz, 1H), 7.16 (dd, J=9.1, 2.1 Hz, 1H), 6.96-6.89 (m, 2H), 6.60 (dd, J=16.8, 10.2 Hz, 1H), 6.47 (dd, J=16.8, 2.2 Hz, 1H), 5.77 (dd, J=10.2, 2.2 Hz, 1H), 4.99-4.93 (m, 1H), 4.58-4.52 (m, 1H), 3.60 (tt, J=12.0, 6.3 Hz, 1H), 2.37-1.86 (m, 8H). m/z (esi) M+1=571.2.

Example 215

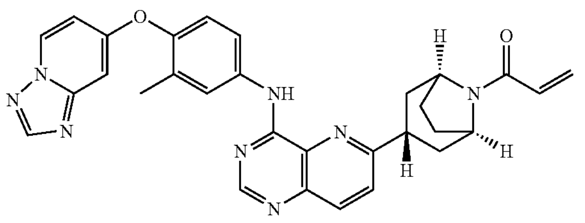 [SMILES: C=CC(=O)N1[C@@H]2CC[C@H]1C[C@@H](c1ccc3ncnc(Nc4ccc(Oc5ccn6ncnc6c5)c(C)c4)c3n1)C2]

1-((1R,3r,5S)-3-(4-((4-([1,2,4]triazolo[1,5-a]pyridin-7-yloxy)-3-methylphenyl)amino)pyrido[3,2-d]pyrimidin-6-yl)-8-azabicyclo[3.2.1]octan-8-yl)prop-2-en-1-one Prepared according to the procedure for Example 189, using N-(4-([1,2,4]triazolo[1,5-a]pyridin-7-yloxy)-3-methylphenyl)-6-chloropyrido[3,2-d]pyrimidin-4-amine in place of N-(4-([1,2,4]triazolo[1,5-a]pyridin-7-yloxy)-2-fluoro-3-methylphenyl)-6-chloropyrido[3,2-d]pyrimidin-4-amine and tert-butyl 3-hydroxy-8-azabicyclo[3.2.1]octane-8-carboxylate in place of tert-butyl 4-hydroxyazepane-1-carboxylate to yield 1-((1R,3r,5S)-3-(4-((4-([1,2,4]triazolo[1,5-a]pyridin-7-yloxy)-3-methylphenyl)amino)pyrido[3,2-d]pyrimidin-6-yl)-8-azabicyclo[3.2.1]octan-8-yl)prop-2-en-1-one (24.1 mg, 74%). $^{1}H$ NMR (400 MHz, $CDCl_3$) δ 9.08 (s, 1H), 8.77 (s, 1H), 8.50 (dd, J=7.4, 0.8 Hz, 1H), 8.22 (s, 1H), 8.11 (d, J=8.7 Hz, 1H), 7.93-7.85 (m, 2H), 7.62 (d, J=8.7 Hz, 1H), 7.17-7.10 (m, 1H), 6.93-6.84 (m, 2H), 6.60 (dd, J=16.8, 10.2 Hz, 1H), 6.46 (dd, J=16.8, 2.2 Hz, 1H), 5.75 (dd, J=10.2, 2.2 Hz, 1H), 5.01-4.95 (m, 1H), 4.57-4.50 (m, 1H), 3.58 (tt, J=11.6, 5.5 Hz, 1H), 2.38-2.26 (m, 4H), 2.26-1.90 (m, 7H). m/z (esi) M+1=533.2.

Example 216

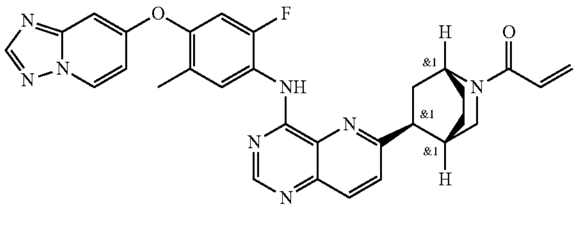 [SMILES: C=CC(=O)N1C[C@H]2CC[C@@H]1C[C@@H]2c1ccc2ncnc(Nc3cc(C)c(Oc4ccn5ncnc5c4)cc3F)c2n1]

rac-1-((1R,4S,5S)-5-(4-((4-([1,2,4]triazolo[1,5-a]pyridin-7-yloxy)-2-fluoro-5-methylphenyl)amino)pyrido[3,2-d]pyrimidin-6-yl)-2-azabicyclo[2.2.2]octan-2-yl)prop-2-en-1-one Prepared according to the procedure for Example 189, using N-(4-([1,2,4]triazolo[1,5-a]pyridin-7-yloxy)-2-fluoro-5-methylphenyl)-6-chloropyrido[3,2-d]pyrimidin-4-amine in place of N-(4-([1,2,4]triazolo[1,5-a]pyridin-7-yloxy)-2-fluoro-3-methylphenyl)-6-chloropyrido[3,2-d]pyrimidin-4-amine and tert-butyl 5-hydroxy-2-azabicyclo[2.2.2]octane-2-carboxylate in place of tert-butyl 4-hydroxyazepane-1-carboxylate to yield rac-1-((1R,4S,5S)-5-(4-((4-([1,2,4]triazolo[1,5-a]pyridin-7-yloxy)-2-fluoro-5-methylphenyl)amino)pyrido[3,2-d]pyrimidin-6-yl)-2-azabicyclo[2.2.2]octan-2-yl)prop-2-en-1-one (6.4 mg, 64%). $^{1}H$ NMR (400 MHz, $CDCl_3$) δ 9.53-9.47 (m, 1H), 8.96-8.84 (m, 2H), 8.55-8.49 (m, 1H), 8.24 (s, 1H), 8.21-8.14 (m, 1H), 7.74-7.66 (m, 1H), 7.00-6.83 (m, 3H), 6.67-6.52 (m, 1H), 6.50-6.31 (m, 1H), 5.81-5.66 (m, 1H), 4.93-4.20 (m, 1H), 3.94-3.45 (m, 3H), 2.81-2.53 (m, 1H), 2.43-2.24 (m, 5H), 2.06-1.68 (m, 4H). m/z (esi) M+1=551.2.

Example 217

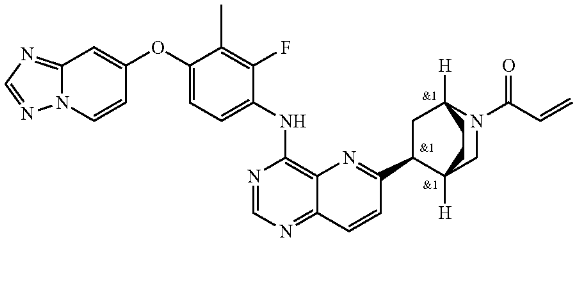 [SMILES: C=CC(=O)N1C[C@H]2CC[C@@H]1C[C@@H]2c1ccc2ncnc(Nc3ccc(Oc4ccn5ncnc5c4)c(C)c3F)c2n1]

rac-1-((1R,4S,5S)-5-(4-((4-([1,2,4]triazolo[1,5-a]pyridin-7-yloxy)-2-fluoro-3-methylphenyl)amino)pyrido[3,2-d]pyrimidin-6-yl)-2-azabicyclo[2.2.2]octan-2-yl)prop-2-en-1-one Prepared according to the procedure for Example 189, using tert-butyl 5-hydroxy-2-azabicyclo[2.2.2]octane-2-carboxylate in place of tert-butyl 4-hydroxyazepane-1-carboxylate to yield rac-1-((1R,4S,5S)-5-(4-((4-([1,2,4]triazolo[1,5-a]pyridin-7-yloxy)-2-fluoro-3-methylphenyl)amino)pyrido[3,2-d]pyrimidin-6-yl)-2-azabicyclo[2.2.2]octan-2-yl)prop-2-en-1-one (9.1 mg, 63%). $^1$H NMR (400 MHz, $CDCl_3$) δ 9.58-9.53 (m, 1H), 8.93-8.81 (m, 2H), 8.55-8.48 (m, 1H), 8.24 (s, 1H), 8.21-8.14 (m, 1H), 7.74-7.66 (m, 1H), 7.07-6.99 (m, 1H), 6.94-6.84 (m, 2H), 6.68-6.53 (m, 1H), 6.52-6.30 (m, 1H), 5.84-5.65 (m, 1H), 5.00-4.20 (m, 1H), 3.93-3.82 (m, 2H), 3.79-3.65 (m, 1H), 3.55-3.48 (m, 1H), 2.89-2.58 (m, 1H), 2.49-2.29 (m, 2H), 2.23 (s, 3H), 2.14-1.87 (m, 2H), 1.86-1.57 (m, 1H). m/z (esi) M+1=551.2.

Example 218

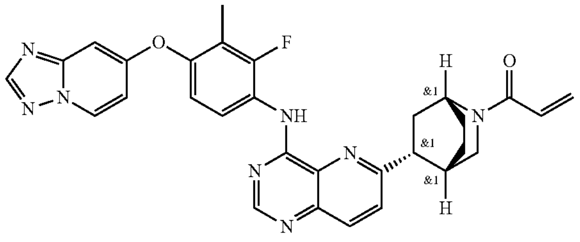 [SMILES: C=CC(=O)N1C[C@H]2CC[C@@H]1C[C@H]2c1ccc2ncnc(Nc3ccc(Oc4ccn5ncnc5c4)c(C)c3F)c2n1]

rac-1-((1R,4S,5R)-5-(4-((4-([1,2,4]triazolo[1,5-a]pyridin-7-yloxy)-2-fluoro-3-methylphenyl)amino)pyrido[3,2-d]pyrimidin-6-yl)-2-azabicyclo[2.2.2]octan-2-yl)prop-2-en-1-one Prepared according to the procedure for Example 189, using tert-butyl 5-hydroxy-2-azabicyclo[2.2.2]octane-2-carboxylate in place of tert-butyl 4-hydroxyazepane-1-carboxylate to yield rac-1-((1R,4S,5R)-5-(4-((4-([1,2,4]triazolo[1,5-a]pyridin-7-yloxy)-2-fluoro-3-methylphenyl)amino)pyrido[3,2-d]pyrimidin-6-yl)-2-azabicyclo[2.2.2]octan-2-yl)prop-2-en-1-one (5.2 mg, 64%). $^1$H NMR (400 MHz, $CDCl_3$) δ 9.39-9.34 (m, 1H), 8.83-8.77 (m, 1H), 8.74-8.60 (m, 1H), 8.55-8.48 (m, 1H), 8.26-8.22 (m, 1H), 8.19-8.11 (m, 1H), 7.71-7.63 (m, 1H), 7.04-6.96 (m, 1H), 6.95-6.84 (m, 2H), 6.69-6.25 (m, 2H), 5.70-5.59 (m, 1H), 4.95-4.18 (m, 1H), 3.89-3.60 (m, 1H), 3.53-3.41 (m, 2H), 2.81-2.67 (m, 1H), 2.51-2.22 (m, 2H), 2.22-2.16 (m, 3H), 2.14-1.79 (m, 4H). m/z (esi) M+1=551.2.

Example 219

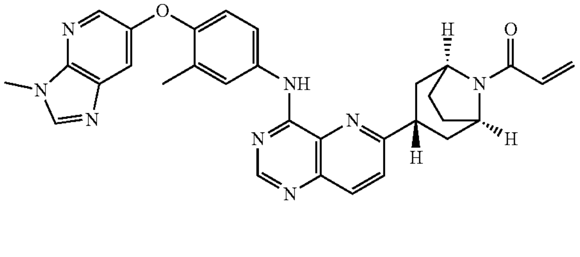 [SMILES: C=CC(=O)N1[C@@H]2CC[C@H]1C[C@@H](c1ccc3ncnc(Nc4ccc(Oc5cnc6c(c5)ncn6C)c(C)c4)c3n1)C2]

1-((1R,3r,5S)-3-(4-((3-methyl-4-((3-methyl-3H-imidazo[4,5-b]pyridin-6-yl)oxy)phenyl)amino)pyrido[3,2-d]pyrimidin-6-yl)-8-azabicyclo[3.2.1]octan-8-yl)prop-2-en-1-one Prepared according to the procedure for Example 189, using 6-chloro-N-(3-methyl-4-((3-methyl-3H-imidazo[4,5-b]pyridin-6-yl)oxy)phenyl)pyrido[3,2-d]pyrimidin-4-amine in place of N-(4-([1,2,4]triazolo[1,5-a]pyridin-7-yloxy)-2-fluoro-3-methylphenyl)-6-chloropyrido[3,2-d]pyrimidin-4-amine and tert-butyl 3-hydroxy-8-azabicyclo[3.2.1]octane-8-carboxylate in place of tert-butyl 4-hydroxyazepane-1-carboxylate to yield 1-((1R,3r,5S)-3-(4-((3-methyl-4-((3-methyl-3H-imidazo[4,5-b]pyridin-6-yl)oxy)phenyl)amino)pyrido[3,2-d]pyrimidin-6-yl)-8-azabicyclo[3.2.1]octan-8-yl)prop-2-en-1-one (9.1 mg, 59%). $^1$H NMR (400 MHz, $CDCl_3$) δ 8.99 (s, 1H), 8.73 (s, 1H), 8.30 (d, J=2.4 Hz, 1H), 8.09 (d, J=8.7 Hz, 1H), 8.02 (s, 1H), 7.80 (d, J=2.7 Hz, 1H), 7.73 (dd, J=8.7, 2.7 Hz, 1H), 7.63-7.57 (m, 2H), 6.92 (d, J=8.7 Hz, 1H), 6.59 (dd, J=16.8, 10.2 Hz, 1H), 6.46 (dd, J=16.8, 2.2 Hz, 1H), 5.75 (dd, J=10.2, 2.2 Hz, 1H), 5.00-4.94 (m, 1H), 4.56-4.50 (m, 1H), 3.93 (s, 3H), 3.57 (tt, J=11.6, 5.6 Hz, 1H), 2.37 (s, 3H), 2.33-1.88 (m, 8H). m/z (esi) M+1=547.3.

Example 220

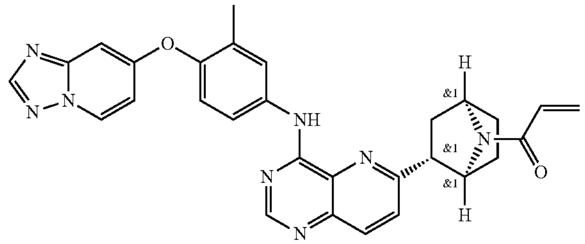 [SMILES: C=CC(=O)N1[C@@H]2CC[C@H]1[C@H](c1ccc3ncnc(Nc4ccc(Oc5ccn6ncnc6c5)c(C)c4)c3n1)C2]

rac-1-((1 S,2R,4R)-2-(4-((4-([1,2,4]triazolo[1,5-a]pyridin-7-yloxy)-3-methylphenyl)amino)pyrido[3,2-d]pyrimidin-6-yl)-7-azabicyclo[2.2.1]heptan-7-yl)prop-2-en-1-one Prepared according to the procedure for Example 189, using N-(4-([1,2,4]triazolo[1,5-a]pyridin-7-yloxy)-3-methylphenyl)-6-chloropyrido[3,2-d]pyrimidin-4-amine in place of N-(4-([1,2,4]triazolo[1,5-a]pyridin-7-yloxy)-2-fluoro-3-methylphenyl)-6-chloropyrido[3,2-d]pyrimidin-4-amine and tert-butyl 2-hydroxy-7-azabicyclo[2.2.1]heptane-7-carboxylate in place of tert-butyl 4-hydroxyazepane-1-carboxylate to yield rac-1-((1 S,2R,4R)-2-(4-((4-([1,2,4]triazolo[1,5-a]pyridin-7-yloxy)-3-methylphenyl)amino)pyrido[3,2-d]pyrimidin-6-yl)-7-azabicyclo[2.2.1]heptan-7-yl)prop-2-en-1-one (13.4 mg, 62%). $^1$H NMR (400 MHz, $CDCl_3$) δ 10.34-9.39 (m, 1H), 8.73 (s, 1H), 8.52-8.45 (m, 1H), 8.39-8.23 (m, 2H), 8.22 (s, 1H), 8.09-8.01 (m, 1H), 7.61-7.40 (m, 1H), 7.18-7.09 (m, 1H), 6.93-6.85 (m, 2H), 6.57-5.85 (m, 2H), 5.73-5.49 (m, 1H), 5.28-4.99 (m, 1H), 4.63-4.16 (m, 1H), 3.44-3.32 (m, 1H), 2.74-2.30 (m, 1H), 2.30-2.25 (m, 3H), 2.18-1.89 (m, 3H), 1.89-1.60 (m, 2H). m/z (esi) M+1=519.2.

Example 221

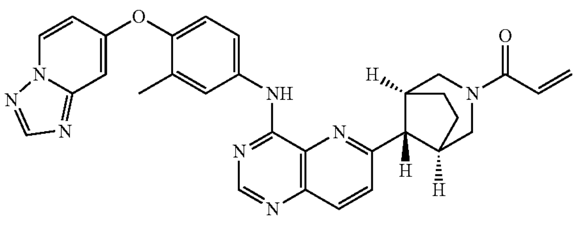 [SMILES: C=CC(=O)N1C[C@H]2CC[C@@H](C1)[C@@H]2c1ccc2ncnc(Nc3ccc(Oc4ccn5ncnc5c4)c(C)c3)c2n1]

1-((1R,5S,8r)-8-(4-((4-([1,2,4]triazolo[1,5-a]pyridin-7-yloxy)-3-methylphenyl)amino)pyrido[3,2-d]pyrimidin-6-yl)-3-azabicyclo[3.2.1]octan-3-yl)prop-2-en-1-one Prepared according to the procedure for Example 189, using N-(4-([1,2,4]triazolo[1,5-a]pyridin-7-yloxy)-3-methylphenyl)-6-chloropyrido[3,2-d]pyrimidin-4-amine in place of N-(4-([1,2,4]triazolo[1,5-a]pyridin-7-yloxy)-2-fluoro-3-methylphenyl)-6-chloropyrido[3,2-d]pyrimidin-4-amine and tert-butyl (1R,5S,8r)-8-hydroxy-3-azabicyclo[3.2.1]octane-3-carboxylate in place of tert-butyl 4-hydroxyazepane-1-carboxylate to yield 1-((1R,5S,8r)-8-(4-((4-([1,2,4]triazolo[1,5-a]pyridin-7-yloxy)-3-methylphenyl)amino)pyrido[3,2-d]pyrimidin-6-yl)-3-azabicyclo[3.2.1]octan-3-yl)prop-2-en-1-one (4.9 mg, 51%). $^1$H NMR (400 MHz, CDCl3) δ 9.09 (s, 1H), 8.79 (s, 1H), 8.50 (dd, J=7.4, 0.7 Hz, 1H), 8.23 (s, 1H), 8.15 (d, J=8.7 Hz, 1H), 7.91-7.82 (m, 2H), 7.73 (d, J=8.7 Hz, 1H), 7.15 (d, J=8.4 Hz, 1H), 6.93-6.83 (m, 2H), 6.65 (dd, J=16.8, 10.6 Hz, 1H), 6.34 (dd, J=16.8, 1.9 Hz, 1H), 5.73 (dd, J=10.6, 1.9 Hz, 1H), 4.69 (d, J=13.1 Hz, 1H), 4.02 (d, J=12.3 Hz, 1H), 3.49 (d, J=12.3 Hz, 1H), 3.30 (s, 1H), 3.06 (d, J=13.1 Hz, 1H), 2.97 (s, 2H), 2.28 (s, 3H), 1.91-1.73 (m, 2H), 1.73-1.57 (m, 2H). m/z (esi) M+1=533.3.

Example 222

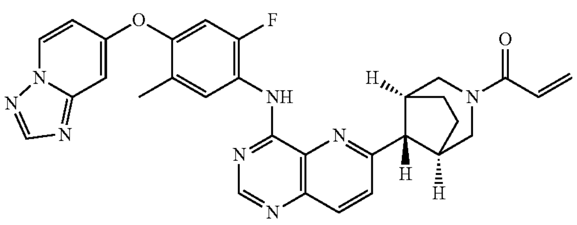 [SMILES: C=CC(=O)N1C[C@H]2CC[C@@H](C1)[C@@H]2c1ccc2ncnc(Nc3cc(C)c(Oc4ccn5ncnc5c4)cc3F)c2n1]

1-((1R,5S,8r)-8-(4-((4-([1,2,4]triazolo[1,5-a]pyridin-7-yloxy)-2-fluoro-5-methylphenyl)amino)pyrido[3,2-d]pyrimidin-6-yl)-3-azabicyclo[3.2.1]octan-3-yl)prop-2-en-1-one Prepared according to the procedure for Example 189, using N-(4-([1,2,4]triazolo[1,5-a]pyridin-7-yloxy)-2-fluoro-5-methylphenyl)-6-chloropyrido[3,2-d]pyrimidin-4-amine in place of N-(4-([1,2,4]triazolo[1,5-a]pyridin-7-yloxy)-2-fluoro-3-methylphenyl)-6-chloropyrido[3,2-d]pyrimidin-4-amine and tert-butyl (1R,5S,8r)-8-hydroxy-3-azabicyclo[3.2.1]octane-3-carboxylate in place of tert-butyl 4-hydroxyazepane-1-carboxylate to yield 1-((1R,5S,8r)-8-(4-((4-([1,2,4]triazolo[1,5-a]pyridin-7-yloxy)-2-fluoro-5-methylphenyl)amino)pyrido[3,2-d]pyrimidin-6-yl)-3-azabicyclo[3.2.1]octan-3-yl)prop-2-en-1-one (2.0 mg, 33%). $^1$H NMR (400 MHz, $CDCl_3$) δ 9.43 (d, J=3.2 Hz, 1H), 8.91-8.82 (m, 2H), 8.52 (dd, J=7.0, 1.1 Hz, 1H), 8.24 (s, 1H), 8.17 (d, J=8.7 Hz, 1H), 7.75 (d, J=8.7 Hz, 1H), 7.01-6.94 (m, 1H), 6.92-6.85 (m, 2H), 6.65 (dd, J=16.8, 10.6 Hz, 1H), 6.33 (dd, J=16.8, 1.9 Hz, 1H), 5.72 (dd, J=10.6, 1.9 Hz, 1H), 4.71-4.64 (m, 1H), 4.01 (d, J=12.2 Hz, 1H), 3.47 (d, J=12.2 Hz, 1H), 3.30 (s, 1H), 3.05 (d, J=13.2 Hz, 1H), 2.98-2.87 (m, 2H), 2.28 (s, 3H), 1.95-1.73 (m, 2H), 1.71-1.57 (m, 2H). m/z (esi) M+1=551.3.

Example 223

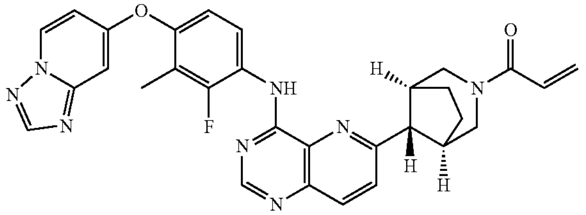 [SMILES: C=CC(=O)N1C[C@H]2CC[C@@H](C1)[C@@H]2c1ccc2ncnc(Nc3ccc(Oc4ccn5ncnc5c4)c(C)c3F)c2n1]

1-((1R,5S,8r)-8-(4-((4-([1,2,4]triazolo[1,5-a]pyridin-7-yloxy)-2-fluoro-3-methylphenyl)amino)pyrido[3,2-d]pyrimidin-6-yl)-3-azabicyclo[3.2.1]octan-3-yl)prop-2-en-1-one Prepared according to the procedure for Example 189, using tert-butyl (1R,5S,8r)-8-hydroxy-3-azabicyclo[3.2.1]octane-3-carboxylate in place of tert-butyl 4-hydroxyazepane-1-carboxylate to yield 1-((1R,5S,8r)-8-(4-((4-([1,2,4]triazolo[1,5-a]pyridin-7-yloxy)-2-fluoro-3-methylphenyl)amino)pyrido[3,2-d]pyrimidin-6-yl)-3-azabicyclo[3.2.1]octan-3-yl)prop-2-en-1-one (1.7 mg, 27%). $^1$H NMR (400 MHz, $CDCl_3$) δ 9.49 (d, J=3.5 Hz, 1H), 8.88-8.79 (m, 2H), 8.55-8.48 (m, 1H), 8.24 (s, 1H), 8.17 (d, J=8.7 Hz, 1H), 7.75 (d, J=8.7 Hz, 1H), 7.06-6.98 (m, 1H), 6.93-6.85 (m, 2H), 6.66 (dd, J=16.8, 10.6 Hz, 1H), 6.33 (dd, J=16.8, 1.9 Hz, 1H), 5.72 (dd, J=10.6, 2.0 Hz, 1H), 4.72-4.64 (m, 1H), 4.06-3.99 (m, 1H), 3.48 (d, J=12.3 Hz, 1H), 3.31 (s, 1H), 3.10-3.02 (m, 1H), 2.99-2.90 (m, 2H), 2.22 (d, J=2.1 Hz, 3H), 2.01-1.76 (m, 2H), 1.71-1.60 (m, 2H). m/z (esi) M+1=551.3.

Example 224

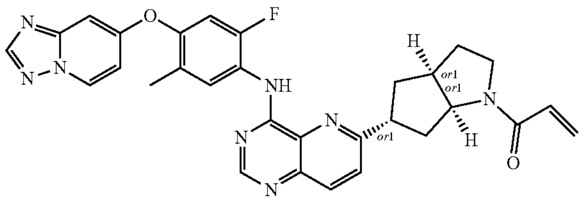 [SMILES: C=CC(=O)N1CC[C@@H]2C[C@@H](c3ccc4ncnc(Nc5cc(C)c(Oc6ccn7ncnc7c6)cc5F)c4n3)C[C@@H]21]

rel-1-((3aR,5S,6aR)-5-(4-((4-([1,2,4]triazolo[1,5-a]pyridin-7-yloxy)-2-fluoro-5-methylphenyl)amino)pyrido[3,2-d]pyrimidin-6-yl)hexahydrocyclopenta[b]pyrrol-1(2H)-yl)prop-2-en-1-one Step A: In a 40 mL vial containing (4,4'-di-tert-butyl-2,2'-bipyridine)bis[(2-pyridinyl)phenyl]iridium(III) hexafluorophosphate (6.5 mg, 7.1 μmol), (SP-4-2)-[4,4'-bis(1,1-dimethylethyl)-2,2'-bipyridine-κN1,κN1']dibromo-nickel (17.3 mg, 36 μmol), quinuclidine (105 mg, 0.95 mmol), phthalimide (15.7 mg, 0.11 mmol), and N-(4-([1,2,4]triazolo[1,5-a]pyridin-7-yloxy)-2-fluoro-5-methylphenyl)-6-chloropyrido[3,2-d] pyrimidin-4-amine (200 mg, 0.47 mmol) were dissolved/suspended in DMA (4.8 mL). To a separate 40 mL vial containing 5,7-di-tert-butyl-3-phenyl-3-(tetrafluoro-15-boraneyl)-2,3-dihydrobenzo[d]oxazol-3-ium-2-ide (394 mg, 1.0 mmol) and rac-tert-butyl (3aS,6aR)-5-hydroxyhexahydrocyclopenta[b]pyrrole-1(2H)-carboxylate (216 mg, 0.95 mmol) was added degassed MTBE (4.8 mL) under nitrogen. After stirring for 5 minutes, pyridine (77 μL, 0.95 mmol) was added. After stirring for an additional 10 minutes, the solution was taken up in a syringe and filtered through a syringe filter into the reaction vial containing nickel and iridium components. The vial was then capped and sparged with nitrogen for 10 minutes, parafilmed, and irradiated with 450 nm light in the integrated photoreactor for 12 hours (100% intensity, 750 rpm stir, max fan speed). The reaction was concentrated in vacuo, and the crude residue was purified over 40 g silica cartridge, eluting with a gradient of 1-10% MeOH/DCM to afford rac-tert-butyl (3aR,5S,6aR)-5-(4-((4-([1,2,4]triazolo[1,5-a]pyridin-7-yloxy)-2-fluoro-5-methylphenyl)amino)pyrido[3,2-d]pyrimidin-6-yl)hexahydrocyclopenta[b]pyrrole-1(2H)-carboxylate. The mixture of enantiomers was then separated using chiral Prep-SFC (50% EtOH/$CO_2$, 50 mL/min, 35° C.; 100 bar outlet pressure with a 30 mm×250 mm AD-H column) to give rel-tert-butyl (3aR,5S,6aR)-5-(4-((4-([1,2,4]triazolo[1,5-a]pyridin-7-yloxy)-2-fluoro-5-methylphenyl)amino)pyrido[3,2-d]pyrimidin-6-yl)hexahydrocyclopenta[b]pyrrole-1(2H)-carboxylate (22 mg, 7.8%). m/z (esi) M+1=597.3.

Step B: Trifluoroacetic acid (57 μL, 0.74 mmol) was added to a stirred solution of rel-tert-butyl (3aR,5S,6aR)-5-(4-((4-([1,2,4]triazolo[1,5-a]pyridin-7-yloxy)-2-fluoro-5-methylphenyl)amino)pyrido[3,2-d]pyrimidin-6-yl)hexahydrocyclopenta[b]pyrrole-1(2H)-carboxylate (22 mg, 0.04 mmol) in DCM (0.5 mL). The reaction was stirred at 23° C. for 2 hours before diluting with EtOAc and quenching with 10% $K_2CO_3$. The aqueous phase was extracted with EtOAc (3×), and the combined organic layers were washed with 10% $K_2CO_3$. The organic layer was then dried over sodium sulfate, filtered and concentrated in vacuo to afford rel-N-(4-([1,2,4]triazolo[1,5-a]pyridin-7-yloxy)-2-fluoro-5-methylphenyl)-6-((3aR,5S,6aR)-octahydrocyclopenta[b]pyrrol-5-yl)pyrido[3,2-d]pyrimidin-4-amine (14.3 mg, 78%), which was used directly in the next reaction without further purification. m/z (esi) M+1=497.2.

Step C: Acryloyl chloride (46 μL, 0.02 mmol) as a 0.5M solution in DCM was added to a stirred solution of rel-N-(4-([1,2,4]triazolo[1,5-a]pyridin-7-yloxy)-2-fluoro-5-methylphenyl)-6-((3aR,5S,6aR)-octahydrocyclopenta[b]pyrrol-5-yl)pyrido[3,2-d]pyrimidin-4-amine (14.3 mg, 0.03 mmol) and DIPEA (0.01 mL, 0.06 mmol) in DCM (0.5 mL) at 0° C. The reaction mixture was stirred for 10 minutes at this temperature before partitioning between 10% $K_2CO_3$ and DCM. The aqueous phase was extracted with DCM (3×). The combined organic layers were then dried over sodium sulfate, filtered, and concentrated in vacuo, and the crude residue was purified over 4 g silica cartridge, eluting with a gradient of 1-10% MeOH/DCM to afford rel-1-((3aR,5S,6aR)-5-(4-((4-([1,2,4]triazolo[1,5-a]pyridin-7-yloxy)-2-fluoro-5-methylphenyl)amino)pyrido[3,2-d]pyrimidin-6-yl)hexahydrocyclopenta[b]pyrrol-1(2H)-yl)prop-2-en-1-one (10.2 mg, 64%). The stereochemistry of this single enantiomer was arbitrarily assigned. $^1$H NMR (400 MHz, $CDCl_3$) δ 9.43-9.39 (m, 1H), 8.91-8.79 (m, 2H), 8.55-8.48 (m, 1H), 8.24 (s, 1H), 8.17-8.08 (m, 1H), 7.68-7.61 (m, 1H), 7.02-6.93 (m, 1H), 6.93-6.86 (m, 2H), 6.64-6.48 (m, 1H), 6.46-6.34 (m, 1H), 5.74-5.66 (m, 1H), 4.71-4.59 (m, 1H), 4.02-3.91 (m, 1H), 3.84-3.45 (m, 2H), 3.22-2.96 (m, 1H), 2.60-2.26 (m, 6H), 2.25-1.99 (m, 2H), 1.97-1.77 (m, 1H). m/z (esi) M+1=551.2. $[\alpha]_D^{23}$=+38.600.

Example 225

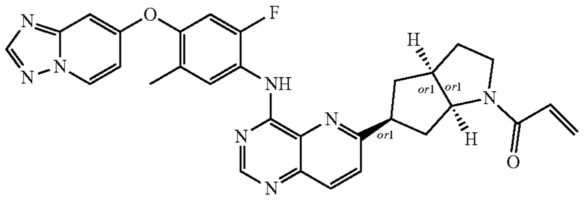 [SMILES: C=CC(=O)N1CC[C@@H]2C[C@H](c3ccc4ncnc(Nc5cc(C)c(Oc6ccn7ncnc7c6)cc5F)c4n3)C[C@@H]21]

rel-1-((3aS,5R,6aS)-5-(4-((4-([1,2,4]triazolo[1,5-a]pyridin-7-yloxy)-2-fluoro-5-methylphenyl)amino)pyrido[3,2-d]pyrimidin-6-yl)hexahydrocyclopenta[b]pyrrol-1(2H)-yl)prop-2-en-1-one Prepared according to the procedure for Example 224 using the remaining enantiomer after chiral prep-SFC. The stereochemistry of this single enantiomer was arbitrarily assigned. $^1$H NMR (400 MHz, $CDCl_3$) δ 9.43-9.39 (m, 1H), 8.91-8.79 (m, 2H), 8.55-8.48 (m, 1H), 8.24 (s, 1H), 8.17-8.08 (m, 1H), 7.68-7.61 (m, 1H), 7.02-6.93 (m, 1H), 6.93-6.86 (m, 2H), 6.64-6.48 (m, 1H), 6.46-6.34 (m, 1H), 5.74-5.66 (m, 1H), 4.71-4.59 (m, 1H), 4.02-3.91 (m, 1H), 3.84-3.45 (m, 2H), 3.22-2.96 (m, 1H), 2.60-2.26 (m, 6H), 2.25-1.99 (m, 2H), 1.97-1.77 (m, 1H). m/z (esi) M+1=551.2. $[\alpha]_D^{23}$=−32.59°.

Example 226

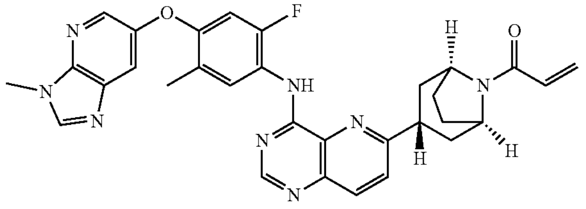 [SMILES: C=CC(=O)N1[C@@H]2CC[C@H]1C[C@@H](c1ccc3ncnc(Nc4cc(C)c(Oc5cnc6c(c5)ncn6C)cc4F)c3n1)C2]

1-((1R,3r,5S)-3-(4-((2-fluoro-5-methyl-4-((3-methyl-3H-imidazo[4,5-b]pyridin-6-yl)oxy)phenyl)amino)pyrido[3,2-d]pyrimidin-6-yl)-8-azabicyclo[3.2.1]octan-8-yl)prop-2-en-1-one Prepared according to the procedure for Example 189, using and 6-chloro-N-(2-fluoro-5-methyl-4-((3-methyl-3H-imidazo[4,5-b]pyridin-6-yl)oxy)phenyl)pyrido[3,2-d]pyrimidin-4-amine in place of N-(4-([1,2,4]triazolo[1,5-a]pyridin-7-yloxy)-2-fluoro-3-methylphenyl)-6-chloropyrido[3,2-d]pyrimidin-4-amine and tert-butyl 3-hydroxy-8-azabicyclo[3.2.1]octane-8-carboxylate in place of tert-butyl 4-hydroxyazepane-1-carboxylate to yield 1-((1R,3r,5S)-3-

(4-((2-fluoro-5-methyl-4-((3-methyl-3H-imidazo[4,5-b]pyridin-6-yl)oxy)phenyl)amino)pyrido[3,2-d]pyrimidin-6-yl)-8-azabicyclo[3.2.1]octan-8-yl)prop-2-en-1-one (22.1 mg, 74%). $^{1}$H NMR (400 MHz, $CDCl_3$) δ 9.17 (d, J=2.5 Hz, 1H), 8.78 (s, 1H), 8.60 (d, J=8.8 Hz, 1H), 8.30 (d, J=2.5 Hz, 1H), 8.11 (d, J=8.8 Hz, 1H), 8.05 (s, 1H), 7.68-7.58 (m, 2H), 6.68 (d, J=11.5 Hz, 1H), 6.57 (dd, J=16.8, 10.2 Hz, 1H), 6.42 (dd, J=16.8, 2.1 Hz, 1H), 5.72 (dd, J=10.2, 2.1 Hz, 1H), 4.97-4.91 (m, 1H), 4.55-4.48 (m, 1H), 3.94 (s, 3H), 3.63-3.50 (m, 1H), 2.38 (d, J=1.0 Hz, 3H), 2.29-1.85 (m, 6H). m/z (esi) M+1=565.2.

Example 227

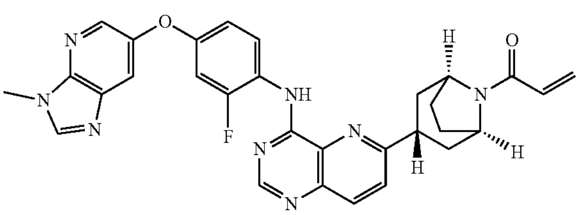 [SMILES: C=CC(=O)N1[C@@H]2CC[C@H]1C[C@@H](c1ccc3ncnc(Nc4ccc(Oc5cnc6c(c5)ncn6C)cc4F)c3n1)C2]

1-((1R,3r,5S)-3-(4-((2-fluoro-3-methyl-4-((3-methyl-3H-imidazo[4,5-b]pyridin-6-yl)oxy)phenyl)amino)pyrido[3,2-d]pyrimidin-6-yl)-8-azabicyclo[3.2.1]octan-8-yl)prop-2-en-1-one Prepared according to the procedure for Example 189, using 6-chloro-N-(2-fluoro-3-methyl-4-((3-methyl-3H-imidazo[4,5-b]pyridin-6-yl)oxy)phenyl)pyrido[3,2-d]pyrimidin-4-amine in place of N-(4-([1,2,4]triazolo[1,5-a]pyridin-7-yloxy)-2-fluoro-3-methylphenyl)-6-chloropyrido[3,2-d]pyrimidin-4-amine and tert-butyl 3-hydroxy-8-azabicyclo[3.2.1]octane-8-carboxylate in place of tert-butyl 4-hydroxyazepane-1-carboxylate to yield 1-((1R,3r,5S)-3-(4-((2-fluoro-3-methyl-4-((3-methyl-3H-imidazo[4,5-b]pyridin-6-yl)oxy)phenyl)amino)pyrido[3,2-d]pyrimidin-6-yl)-8-azabicyclo[3.2.1]octan-8-yl)prop-2-en-1-one (10.0 mg, 44%). $^{1}$H NMR (400 MHz, $CDCl_3$) δ 9.29 (d, J=2.9 Hz, 1H), 8.73 (s, 1H), 8.49 (t, J=9.0 Hz, 1H), 8.30 (d, J=2.5 Hz, 1H), 8.10 (d, J=8.6 Hz, 1H), 8.04 (s, 1H), 7.66-7.58 (m, 2H), 6.73 (dd, J=9.0, 1.7 Hz, 1H), 6.60 (dd, J=16.8, 10.2 Hz, 1H), 6.46 (dd, J=16.8, 2.2 Hz, 1H), 5.75 (dd, J=10.2, 2.2 Hz, 1H), 5.00-4.93 (m, 1H), 4.57-4.51 (m, 1H), 3.94 (s, 3H), 3.64-3.51 (m, 1H), 2.32 (d, J=2.1 Hz, 3H), 2.26-1.89 (m, 6H). m/z (esi) M+1=565.2.

Example 228

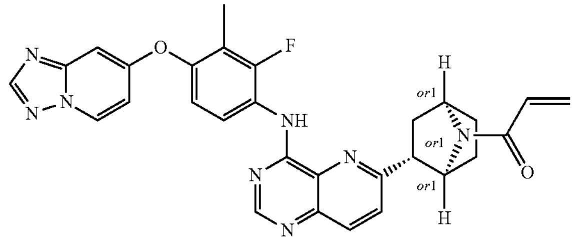 [SMILES: C=CC(=O)N1[C@@H]2CC[C@H]1[C@H](c1ccc3ncnc(Nc4ccc(Oc5ccn6ncnc6c5)c(C)c4F)c3n1)C2]

rel-1-((1 S,2R,4R)-2-(4-((4-([1,2,4]triazolo[1,5-a]pyridin-7-yloxy)-2-fluoro-3-methylphenyl)amino)pyrido[3,2-d]pyrimidin-6-yl)-7-azabicyclo[2.2.1]heptan-7-yl)prop-2-en-1-one Step A: In a 8 mL vial containing (4,4'-di-tert-butyl-2,2'-bipyridine)bis[(2-pyridinyl)phenyl]iridium(III) hexafluorophosphate (1.3 mg, 1.4 μmol), (SP-4-2)-[4,4'-bis(1,1-dimethylethyl)-2,2'-bipyridine-κN1,κN1']dibromo-Nickel (3.5 mg, 7.1 μmol), quinuclidine (21 mg, 0.19 mmol), phthalimide (3.1 mg, 0.02 mmol), and N-(4-([1,2,4]triazolo[1,5-a]pyridin-7-yloxy)-2-fluoro-3-methylphenyl)-6-chloropyrido[3,2-d]pyrimidin-4-amine (Intermediate S, 40 mg, 0.10 mol) were dissolved/suspended in DMA (1.0 mL). To a separate 8 mL vial containing 5,7-di-tert-butyl-3-phenyl-3-(tetrafluoro-15-boraneyl)-2,3-dihydrobenzo[d]oxazol-3-ium-2-ide (79 mg, 0.20 mmol) and tert-butyl 2-hydroxy-7-azabicyclo[2.2.1]heptane-7-carboxylate (43 mg, 0.19 mmol) was added degassed MTBE (1.0 mL) under nitrogen. After stirring for 5 minutes, pyridine (15 μL, 0.19 mmol) was added. After stirring for an additional 10 minutes, the solution was taken up in a syringe and filtered through a syringe filter into the reaction vial containing nickel and iridium components. The vial was then capped and sparged with nitrogen for 10 minutes, parafilmed, and irradiated with 450 nm light in the integrated photoreactor for 12 hours (100% intensity, 1200 rpm stir, max fan speed). Four reactions were run in parallel to obtain the desired amount of product after chiral separation. The reactions were combined and concentrated in vacuo, and the crude residue was purified over 40 g silica cartridge, eluting with a gradient of 1-10% MeOH/DCM to afford rac-tert-butyl (1S,2R,4R)-2-(4-((4-([1,2,4]triazolo[1,5-a]pyridin-7-yloxy)-2-fluoro-3-methylphenyl)amino)pyrido[3,2-d]pyrimidin-6-yl)-7-azabicyclo[2.2.1]heptane-7-carboxylate. The mixture of enantiomers was subsequently separated by chiral Prep-SFC (40% EtOH (0.1% DEA)/$CO_2$, 85 mL/min, 35° C.; 100 bar outlet pressure with a 30 mm×250 mm Regis Whelk-01 RR column) to afford rel-tert-butyl (1S,2R,4R)-2-(4-((4-([1,2,4]triazolo[1,5-a]pyridin-7-yloxy)-2-fluoro-3-methylphenyl)amino)pyrido[3,2-d]pyrimidin-6-yl)-7-azabicyclo[2.2.1]heptane-7-carboxylate (26 mg, 12%). m/z (esi) M+1=583.2.

Step B: Trifluoroacetic acid (69 μL, 0.89 mmol) was added to a stirred solution of rel-tert-butyl (1S,2R,4R)-2-(4-((4-([1,2,4]triazolo[1,5-a]pyridin-7-yloxy)-2-fluoro-3-methylphenyl)amino)pyrido[3,2-d]pyrimidin-6-yl)-7-azabicyclo[2.2.1]heptane-7-carboxylate (26 mg, 0.04 mmol) in DCM (0.5 mL). The reaction was stirred at 23° C. for 2 hours before diluting with EtOAc and quenching with 10% $K_2CO_3$. The aqueous phase was extracted with EtOAc (3×), and the combined organic layers were washed with 10% $K_2CO_3$. The organic layer was then dried over sodium sulfate, filtered and concentrated in vacuo to afford rel-N-(4-([1,2,4]triazolo[1,5-a]pyridin-7-yloxy)-2-fluoro-3-methylphenyl)-6-((1S,2R,4R)-7-azabicyclo[2.2.1]heptan-2-yl)pyrido[3,2-d]pyrimidin-4-amine (18.8 mg, 87%), which was used directly in the next reaction without further purification. m/z (esi) M+1=483.2.

Step C: Acryloyl chloride (44 μL, 0.02 mmol) as a 0.5M solution in DCM was added to a stirred solution of rel-N-(4-([1,2,4]triazolo[1,5-a]pyridin-7-yloxy)-2-fluoro-3-methylphenyl)-6-((1S,2R,4R)-7-azabicyclo[2.2.1]heptan-2-yl)pyrido[3,2-d]pyrimidin-4-amine (13.2 mg, 0.03 mmol) and DIPEA (9.5 μL, 0.06 mmol) in DCM (0.4 mL) at 0° C. The reaction mixture was stirred for 10 minutes at this temperature before partitioning between 10% $K_2CO_3$ and DCM. The aqueous phase was extracted with DCM (3×). The combined organic layers were then dried over sodium sulfate, filtered, and concentrated in vacuo, and the crude residue was purified over 4 g silica cartridge, eluting with a gradient of 1-10% MeOH/DCM to afford rel-1-((1S,2R,4R)-2-(4-((4-([1,2,4]triazolo[1,5-a]pyridin-7-yloxy)-2-fluoro-3-methylphenyl)amino)pyrido[3,2-d]pyrimidin-6-yl)-7-azabicyclo[2.2.1]heptan-7-yl)prop-2-en-1-one (8.1 mg, 55%). The stereochemistry of this single enantiomer was arbitrarily assigned. $^1$H NMR (400 MHz, $CDCl_3$) δ 9.79-9.25 (m, 1H), 8.76-8.71 (m, 1H), 8.55-8.48 (m, 1H), 8.48-8.29 (m, 1H), 8.24 (s, 1H), 8.14-8.07 (m, 1H), 7.67-7.58 (m, 1H), 7.02-6.86 (m, 3H), 6.56-6.25 (m, 1H), 6.20-6.03 (m, 1H), 5.76-5.35 (m, 1H), 5.28-4.95 (m, 1H), 4.62-4.45 (m, 1H), 3.48-3.38 (m, 1H), 2.58-2.18 (m, 5H), 2.15-1.61 (m, 4H). m/z (esi) M+1=537.2. $[\alpha]_D^{23}$=−86.67°.

Example 229

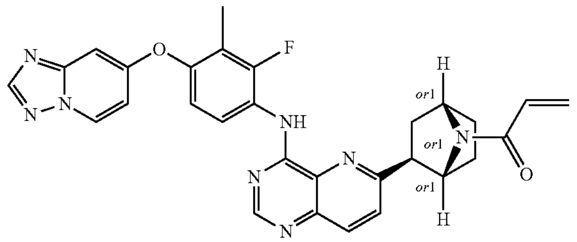 [SMILES: C=CC(=O)N1[C@H]2CC[C@@H]1[C@@H](c1ccc3ncnc(Nc4ccc(Oc5ccn6ncnc6c5)c(C)c4F)c3n1)C2]

rel-1-((1R,2S,4S)-2-(4-((4-([1,2,4]triazolo[1,5-a]pyridin-7-yloxy)-2-fluoro-3-methylphenyl)amino)pyrido[3,2-d]pyrimidin-6-yl)-7-azabicyclo[2.2.1]heptan-7-yl)prop-2-en-1-one Prepared according to the procedure for Example 228, using the remaining enantiomer after chiral prep-SFC. The stereochemistry of this single enantiomer was arbitrarily assigned. $^1$H NMR (400 MHz, $CDCl_3$) δ 9.79-9.25 (m, 1H), 8.76-8.71 (m, 1H), 8.55-8.48 (m, 1H), 8.48-8.29 (m, 1H), 8.24 (s, 1H), 8.14-8.07 (m, 1H), 7.67-7.58 (m, 1H), 7.02-6.86 (m, 3H), 6.56-6.25 (m, 1H), 6.20-6.03 (m, 1H), 5.76-5.35 (m, 1H), 5.28-4.95 (m, 1H), 4.62-4.45 (m, 1H), 3.48-3.38 (m, 1H), 2.58-2.18 (m, 5H), 2.15-1.61 (m, 4H). m/z (esi) M+1=537.2. $[\alpha]_D^{23}$=+112.00°.

Example 230

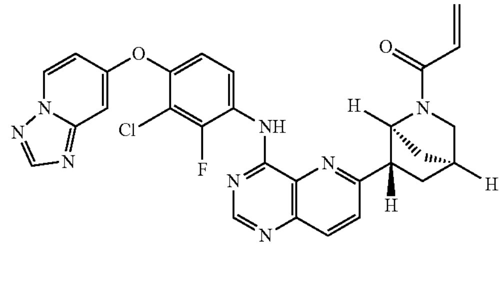 [SMILES: C=CC(=O)N1C[C@H]2C[C@H](c3ccc4ncnc(Nc5ccc(Oc6ccn7ncnc7c6)c(Cl)c5F)c4n3)[C@@H]1C2]

1-((1 S,4S,6S)-6-(4-((4-([1,2,4]triazolo[1,5-a]pyridin-7-yloxy)-3-chloro-2-fluorophenyl)amino)pyrido[3,2-d]pyrimidin-6-yl)-2-azabicyclo[2.2.1]heptan-2-yl)prop-2-en-1-one Prepared according to the procedure for Example 189, N-(4-([1,2,4]triazolo[1,5-a]pyridin-7-yloxy)-3-chloro-2-fluorophenyl)-6-chloropyrido[3,2-d]pyrimidin-4-amine in place of N-(4-([1,2,4]triazolo[1,5-a]pyridin-7-yloxy)-2-fluoro-3-methylphenyl)-6-chloropyrido[3,2-d]pyrimidin-4-amine and (1S,4R,6S)-6-hydroxy-2-azabicyclo[2.2.1]heptane-2-carboxylate in place of tert-butyl 4-hydroxyazepane-1-carboxylate to yield 1-((1S,4S,6S)-6-(4-((4-([1,2,4]triazolo[1,5-a]pyridin-7-yloxy)-3-chloro-2-fluorophenyl)amino)pyrido[3,2-d]pyrimidin-6-yl)-2-azabicyclo[2.2.1]heptan-2-yl)prop-2-en-1-one (6.1 mg, 56%). $^1$H NMR (400 MHz, $CDCl_3$) δ 9.52-9.44 (m, 1H), 9.04-8.94 (m, 1H), 8.88-8.82 (m, 1H), 8.58-8.51 (m, 1H), 8.26 (s, 1H), 8.24-8.14 (m, 1H), 7.91-7.61 (m, 1H), 7.22-7.14 (m, 1H), 6.97-6.88 (m, 2H), 6.71-6.31 (m, 2H), 5.80-5.71 (m, 1H), 4.95-4.64 (m, 1H), 3.67-3.47 (m, 2H), 3.45-3.33 (m, 1H), 2.95-2.86 (m, 1H), 2.71-2.29 (m, 1H), 2.20-1.92 (m, 2H), 1.87-1.64 (m, 1H). m/z (esi) M+1=557.1.

Example 231

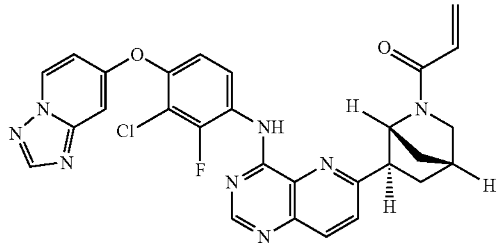 [SMILES: C=CC(=O)N1C[C@H]2C[C@@H]1[C@H](c1ccc3ncnc(Nc4ccc(Oc5ccn6ncnc6c5)c(Cl)c4F)c3n1)C2]

1-((1R,4R,6R)-6-(4-((4-([1,2,4]triazolo[1,5-a]pyridin-7-yloxy)-3-chloro-2-fluorophenyl)amino)pyrido[3,2-d]pyrimidin-6-yl)-2-azabicyclo[2.2.1]heptan-2-yl)prop-2-en-1-one Prepared according to the procedure for Example 189, N-(4-([1,2,4]triazolo[1,5-a]pyridin-7-yloxy)-3-chloro-2-fluorophenyl)-6-chloropyrido[3,2-d]pyrimidin-4-amine in place of N-(4-([1,2,4]triazolo[1,5-a]pyridin-7-yloxy)-2-fluoro-3-methylphenyl)-6-chloropyrido[3,2-d]pyrimidin-4-amine and tert-butyl (1R,4S,6R)-6-hydroxy-2-azabicyclo[2.2.1]heptane-2-carboxylate in place of tert-butyl 4-hydroxyazepane-1-carboxylate to yield 1-((1R,4R,6R)-6-(4-((4-([1,2,4]triazolo[1,5-a]pyridin-7-yloxy)-3-chloro-2-fluorophenyl)amino)pyrido[3,2-d]pyrimidin-6-yl)-2-azabicyclo[2.2.1]heptan-2-yl)prop-2-en-1-one (6.3 mg, 57%). $^1$H NMR (400 MHz, $CDCl_3$) δ 9.52-9.44 (m, 1H), 9.04-8.94 (m, 1H), 8.88-8.82 (m, 1H), 8.58-8.51 (m, 1H), 8.26 (s, 1H), 8.24-8.14 (m, 1H), 7.91-7.61 (m, 1H), 7.22-7.14 (m, 1H), 6.97-6.88 (m, 2H), 6.71-6.31 (m, 2H), 5.80-5.71 (m, 1H), 4.95-4.64 (m, 1H), 3.67-3.47 (m, 2H), 3.45-3.33 (m, 1H), 2.95-2.86 (m, 1H), 2.71-2.29 (m, 1H), 2.20-1.92 (m, 2H), 1.87-1.64 (m, 1H). m/z (esi) M+1=557.1.

Example 232

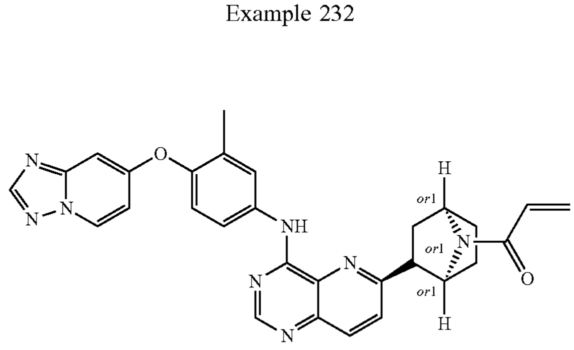

rel-1-((1S,2R,4R)-2-(4-((4-([1,2,4]triazolo[1,5-a]pyridin-7-yloxy)-3-methylphenyl)amino)pyrido[3,2-d]pyrimidin-6-yl)-7-azabicyclo[2.2.1]heptan-7-yl)prop-2-en-1-one Step A: In a 8 mL vial containing (4,4'-di-tert-butyl-2,2'-bipyridine)bis[(2-pyridinyl)phenyl]iridium(III) hexafluorophosphate (1.4 mg, 1.5 μmol), (SP-4-2)-[4,4'-bis(1,1-dimethylethyl)-2,2'-bipyridine-κN1,κN1']dibromo-Nickel (3.6 mg, 7.4 μmol), quinuclidine (22 mg, 0.20 mmol), phthalimide (3.3 mg, 0.02 mmol), and N-(4-([1,2,4]triazolo[1,5-a]pyridin-7-yloxy)-3-methylphenyl)-6-chloropyrido[3,2-d]pyrimidin-4-amine (Intermediate Y, 40 mg, 0.10 mmol) were dissolved/suspended in DMA (1.0 mL). To a separate 8 mL vial containing 5,7-di-tert-butyl-3-phenyl-3-(tetrafluoro-15-boraneyl)-2,3-dihydrobenzo[d]oxazol-3-ium-2-ide (82 mg, 0.21 mmol) and tert-butyl 2-hydroxy-7-azabicyclo[2.2.1]heptane-7-carboxylate (42 mg, 0.2 mmol) was added degassed MTBE (1.0 mL) under nitrogen. After stirring for 5 minutes, pyridine (16 μL, 0.20 mmol) was added. After stirring for an additional 10 minutes, the solution was taken up in a syringe and filtered through a syringe filter into the reaction vial containing nickel and iridium components. The vial was then capped and sparged with nitrogen for 10 minutes, parafilmed, and irradiated with 450 nm light in the integrated photoreactor for 12 hours (100% intensity, 1200 rpm stir, max fan speed). Three reactions were run in parallel to obtain the desired amount of product after chiral separation. The reactions were combined and concentrated in vacuo, and the crude residue was purified over 24 g silica cartridge, eluting with a gradient of 1-10% MeOH/DCM to afford rac-tert-butyl (1S,2R,4R)-2-(4-((4-([1,2,4]triazolo[1,5-a]pyridin-7-yloxy)-3-methylphenyl)amino)pyrido[3,2-d]pyrimidin-6-yl)-7-azabicyclo[2.2.1]heptane-7-carboxylate. The mixture of enantiomers was subsequently separated by chiral Prep-SFC (40% iPrOH (0.1% DEA)/$CO_2$, 70 mL/min; 100 bar outlet pressure with a 30 mm×250 mm AD-H column) to afford rel-tert-butyl (1S,2R,4R)-2-(4-((4-([1,2,4]triazolo[1,5-a]pyridin-7-yloxy)-3-methylphenyl)amino)pyrido[3,2-d]pyrimidin-6-yl)-7-azabicyclo[2.2.1]heptane-7-carboxylate (32 mg, 19%). m/z (esi) M+1=565.2.

Step B: Trifluoroacetic acid (87 μL, 1.1 mmol) was added to a stirred solution of rel-tert-butyl (1S,2R,4R)-2-(4-((4-([1,2,4]triazolo[1,5-a]pyridin-7-yloxy)-3-methylphenyl)amino)pyrido[3,2-d]pyrimidin-6-yl)-7-azabicyclo[2.2.1]heptane-7-carboxylate (32 mg, 0.06 mmol) in DCM (0.6 mL). The reaction was stirred at 23° C. for 2 hours before diluting with EtOAc and quenching with 10% $K_2CO_3$. The aqueous phase was extracted with EtOAc (3×), and the combined organic layers were washed with 10% $K_2CO_3$. The organic layer was then dried over sodium sulfate, filtered and concentrated in vacuo to afford rel-N-(4-([1,2,4]triazolo[1,5-a]pyridin-7-yloxy)-3-methylphenyl)-6-((1S,2R,4R)-7-azabicyclo[2.2.1]heptan-2-yl)pyrido[3,2-d]pyrimidin-4-amine (22.3 mg, 85%), which was used directly in the next reaction without further purification. m/z (esi) M+1=465.2.

Step C: Acryloyl chloride (96 μL, 0.05 mmol) as a 0.5M solution in DCM was added to a stirred solution of rel-N-(4-([1,2,4]triazolo[1,5-a]pyridin-7-yloxy)-2-fluoro-3-methylphenyl)-6-((1S,4R,5R)-2-azabicyclo[2.2.2]octan-5-yl)pyrido[3,2-d]pyrimidin-4-amine (22.3 mg, 0.05 mmol) and DIPEA (15.7 μL, 0.10 mmol) in DCM (0.5 mL) at 0° C. The reaction mixture was stirred for 10 minutes at this temperature before partitioning between 10% $K_2CO_3$ and DCM. The aqueous phase was extracted with DCM (3×). The combined organic layers were then dried over sodium sulfate, filtered, and concentrated in vacuo, and the crude residue was purified over 4 g silica cartridge, eluting with a gradient of 1-10% MeOH/DCM to afford rel-1-((1S,2R,4R)-2-(4-((4-([1,2,4]triazolo[1,5-a]pyridin-7-yloxy)-3-methylphenyl)amino)pyrido[3,2-d]pyrimidin-6-yl)-7-azabicyclo[2.2.1]heptan-7-yl)prop-2-en-1-one (18.0 mg, 72%). The stereochemistry of this single enantiomer was arbitrarily assigned. $^1H$ NMR (400 MHz, $CDCl_3$) δ 10.28-9.38 (m, 1H), 8.77-8.71 (m, 1H), 8.52-8.45 (m, 1H), 8.41-8.23 (m, 2H), 8.22 (s, 1H), 8.09-8.01 (m, 1H), 7.63-7.41 (m, 1H), 7.20-7.06 (m, 1H), 6.93-6.85 (m, 2H), 6.54-5.85 (m, 2H), 5.73-4.95 (m, 2H), 4.61-4.17 (m, 1H), 3.44-3.32 (m, 1H), 2.80-2.31 (m, 1H), 2.31-2.25 (m, 3H), 2.16-1.88 (m, 2H), 1.87-1.61 (m, 3H). m/z (esi) M+1=519.2. $[\alpha]_D^{23}$=+123.97°.

Example 233

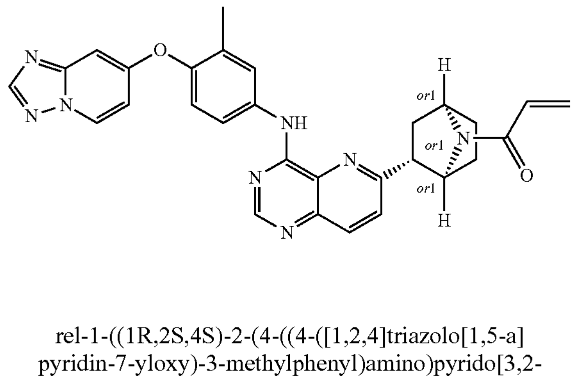

rel-1-((1R,2S,4S)-2-(4-((4-([1,2,4]triazolo[1,5-a]pyridin-7-yloxy)-3-methylphenyl)amino)pyrido[3,2-d]pyrimidin-6-yl)-7-azabicyclo[2.2.1]heptan-7-yl)prop-2-en-1-one Prepared according to the procedure for Example 232, using the remaining enantiomer after chiral prep-SFC. The stereochemistry of this single enantiomer was arbitrarily assigned. $^1H$ NMR (400 MHz, $CDCl_3$) δ 10.28-9.38 (m, 1H), 8.77-8.71 (m, 1H), 8.52-8.45 (m, 1H), 8.41-8.23 (m, 2H), 8.22 (s, 1H), 8.09-8.01 (m, 1H), 7.63-7.41 (m, 1H), 7.20-7.06 (m, 1H), 6.93-6.85 (m, 2H), 6.54-5.85 (m, 2H), 5.73-4.95 (m, 2H), 4.61-4.17 (m, 1H), 3.44-3.32 (m, 1H), 2.80-2.31 (m, 1H), 2.31-2.25 (m, 3H), 2.16-1.88 (m, 2H), 1.87-1.61 (m, 3H). m/z (esi) M+1=519.2. $[\alpha]_D^{23}$=−66.85°.

Example 234

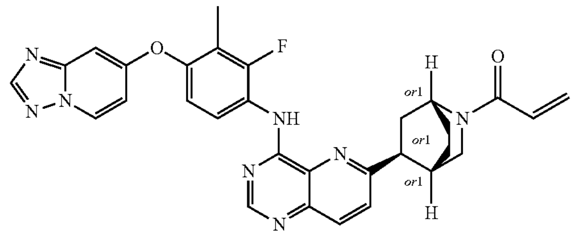 [SMILES: C=CC(=O)N1C[C@H]2CC[C@@H]1C[C@@H]2c1ccc2ncnc(Nc3ccc(Oc4ccn5ncnc5c4)c(C)c3F)c2n1]

rel-1-((1R,4S,5S)-5-(4-((4-([1,2,4]triazolo[1,5-a]pyridin-7-yloxy)-2-fluoro-3-methylphenyl)amino)pyrido[3,2-d]pyrimidin-6-yl)-2-azabicyclo[2.2.2]octan-2-yl)prop-2-en-1-one Step A: In a 8 mL vial containing (4,4'-di-tert-butyl-2,2'-bipyridine)bis[(2-pyridinyl)phenyl]iridium(III) hexafluorophosphate (1.3 mg, 1.4 μmol), (SP-4-2)-[4,4'-bis(1,1-dimethylethyl)-2,2'-bipyridine-κN1,κN1']dibromo-Nickel (3.5 mg, 7.1 μmol), quinuclidine (21 mg, 0.19 mmol), phthalimide (3.1 mg, 0.02 mmol), and N-(4-([1,2,4]triazolo[1,5-a]pyridin-7-yloxy)-2-fluoro-3-methylphenyl)-6-chloropyrido[3,2-d]pyrimidin-4-amine (40 mg, 0.10 mmol) were dissolved/suspended in DMA (1.0 mL). To a separate 8 mL vial containing 5,7-di-tert-butyl-3-phenyl-3-(tetrafluoro-15-boraneyl)-2,3-dihydrobenzo[d]oxazol-3-ium-2-ide (79 mg, 0.20 mmol) and tert-butyl 5-hydroxy-2-azabicyclo[2.2.2]octane-2-carboxylate (43 mg, 0.19 mmol) was added degassed MTBE (1.0 mL) under nitrogen. After stirring for 5 minutes, pyridine (15 μL, 0.19 mmol) was added. After stirring for an additional 10 minutes, the solution was taken up in a syringe and filtered through a syringe filter into the reaction vial containing nickel and iridium components. The vial was then capped and sparged with nitrogen for 10 minutes, parafilmed, and irradiated with 450 nm light in the integrated photoreactor for 12 hours (100% intensity, 1200 rpm stir, max fan speed). Four reactions were run in parallel to obtain the desired amount of product after chiral separation. The reactions were combined and concentrated in vacuo, and the crude residue was purified over 40 g silica cartridge, eluting with a gradient of 1-10% MeOH/DCM to afford rac-tert-butyl (1R,4S,5S)-5-(4-((4-([1,2,4]triazolo[1,5-a]pyridin-7-yloxy)-2-fluoro-3-methylphenyl)amino)pyrido[3,2-d]pyrimidin-6-yl)-2-azabicyclo[2.2.2]octane-2-carboxylate. The mixture of enantiomers was subsequently separated by chiral Prep-SFC (30% MeOH (0.1% DEA)/$CO_2$, 60 mL/min; 100 bar outlet pressure with a 30 mm×250 mm OD-H column) to afford rel-tert-butyl (1R,4S,5S)-5-(4-((4-([1,2,4]triazolo[1,5-a]pyridin-7-yloxy)-2-fluoro-3-methylphenyl)amino)pyrido[3,2-d]pyrimidin-6-yl)-2-azabicyclo[2.2.2]octane-2-carboxylate (23 mg, 10%). m/z (esi) M+1=597.2.

Step B: Trifluoroacetic acid (59 μL, 0.77 mmol) was added to a stirred solution of rel-tert-butyl (1R,4S,5S)-5-(4-((4-([1,2,4]triazolo[1,5-a]pyridin-7-yloxy)-2-fluoro-3-methylphenyl)amino)pyrido[3,2-d]pyrimidin-6-yl)-2-azabicyclo[2.2.2]octane-2-carboxylate (23 mg, 0.04 mmol) in DCM (0.4 mL). The reaction was stirred at 23° C. for 2 hours before diluting with EtOAc and quenching with 10% $K_2CO_3$. The aqueous phase was extracted with EtOAc (3×), and the combined organic layers were washed with 10% $K_2CO_3$. The organic layer was then dried over sodium sulfate, filtered and concentrated in vacuo to afford rel-N-(4-([1,2,4]triazolo[1,5-a]pyridin-7-yloxy)-2-fluoro-3-methylphenyl)-6-((1R,4S,5S)-2-azabicyclo[2.2.2]octan-5-yl)pyrido[3,2-d]pyrimidin-4-amine (17.1 mg, 89%), which was used directly in the next reaction without further purification. m/z (esi) M+1=497.1.

Step C: Acryloyl chloride (69 μL, 0.03 mmol) as a 0.5M solution in DCM was added to a stirred solution of rel-N-(4-([1,2,4]triazolo[1,5-a]pyridin-7-yloxy)-2-fluoro-3-methylphenyl)-6-((1R,4S,5S)-2-azabicyclo[2.2.2]octan-5-yl)pyrido[3,2-d]pyrimidin-4-amine (17.1 mg, 0.03 mmol) and DIPEA (11.1 μL, 0.07 mmol) in DCM (0.4 mL) at 0° C. The reaction mixture was stirred for 10 minutes at this temperature before partitioning between 10% $K_2CO_3$ and DCM. The aqueous phase was extracted with DCM (3×). The combined organic layers were then dried over sodium sulfate, filtered, and concentrated in vacuo, and the crude residue was purified over 4 g silica cartridge, eluting with a gradient of 1-10% MeOH/DCM to afford rel-1-((1R,4S,5S)-5-(4-((4-([1,2,4]triazolo[1,5-a]pyridin-7-yloxy)-2-fluoro-3-methylphenyl)amino)pyrido[3,2-d]pyrimidin-6-yl)-2-azabicyclo[2.2.2]octan-2-yl)prop-2-en-1-one (15.0 mg, 79%). The stereochemistry of this single enantiomer was arbitrarily assigned. $^1$H NMR (400 MHz, $CDCl_3$) δ 9.58-9.53 (m, 1H), 8.93-8.81 (m, 2H), 8.55-8.48 (m, 1H), 8.24 (s, 1H), 8.21-8.14 (m, 1H), 7.74-7.66 (m, 1H), 7.07-6.99 (m, 1H), 6.94-6.84 (m, 2H), 6.68-6.53 (m, 1H), 6.52-6.30 (m, 1H), 5.84-5.65 (m, 1H), 5.00-4.20 (m, 1H), 3.93-3.82 (m, 2H), 3.79-3.65 (m, 1H), 3.55-3.48 (m, 1H), 2.89-2.58 (m, 1H), 2.49-2.29 (m, 2H), 2.23 (s, 3H), 2.14-1.87 (m, 2H), 1.86-1.57 (m, 1H). m/z (esi) M+1=551.2. $[\alpha]_D^{23}$=+26.48°.

Example 235

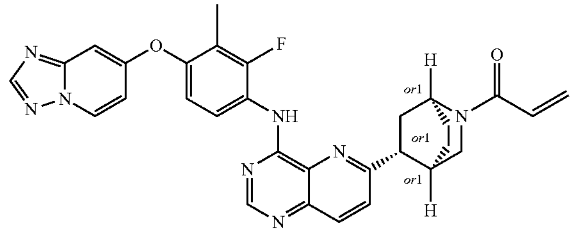 [SMILES: C=CC(=O)N1C[C@@H]2CC[C@H]1C[C@H]2c1ccc2ncnc(Nc3ccc(Oc4ccn5ncnc5c4)c(C)c3F)c2n1]

rel-1-((1 S,4R,5R)-5-(4-((4-([1,2,4]triazolo[1,5-a]pyridin-7-yloxy)-2-fluoro-3-methylphenyl)amino)pyrido[3,2-d]pyrimidin-6-yl)-2-azabicyclo[2.2.2]octan-2-yl)prop-2-en-1-one Prepared according to the procedure for Example 234, using the remaining enantiomer after chiral prep-SFC. The stereochemistry of this single enantiomer was arbitrarily assigned. $^1$H NMR (400 MHz, $CDCl_3$) δ 9.58-9.53 (m, 1H), 8.93-8.81 (m, 2H), 8.55-8.48 (m, 1H), 8.24 (s, 1H), 8.21-8.14 (m, 1H), 7.74-7.66 (m, 1H), 7.07-6.99 (m, 1H), 6.94-6.84 (m, 2H), 6.68-6.53 (m, 1H), 6.52-6.30 (m, 1H), 5.84-5.65 (m, 1H), 5.00-4.20 (m, 1H), 3.93-3.82 (m, 2H), 3.79-3.65 (m, 1H), 3.55-3.48 (m, 1H), 2.89-2.58 (m, 1H), 2.49-2.29 (m, 2H), 2.23 (s, 3H), 2.14-1.87 (m, 2H), 1.86-1.57 (m, 1H). m/z (esi) M+1=551.2. $[\alpha]_D^{23}$=−10.76°.

Example 236

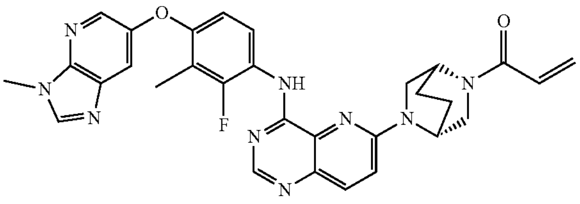

1-((1R,4R)-5-(4-((2-fluoro-3-methyl-4-((3-methyl-3H-imidazo[4,5-b]pyridin-6-yl)oxy)phenyl)amino)pyrido[3,2-d]pyrimidin-6-yl)-2,5-diazabicyclo[2.2.2]octan-2-yl)prop-2-en-1-one Step A: To a vial was added 6-chloro-N-(2-fluoro-3-methyl-4-((3-methyl-3H-imidazo[4,5-b]pyridin-6-yl)oxy)phenyl)pyrido[3,2-d]pyrimidin-4-amine (Intermediate HH, 30 mg, 0.07 mmol) and (1R,4R)-tert-Butyl 2,5-diazabicyclo[2.2.2]octane-2-carboxylate (29 mg, 0.14 mmol) followed by DMSO (0.46 mL) and DIPEA (24 μL, 0.14 mmol). The mixture was then warmed to 100° C. where it stirred for 6 hours. The mixture was then cooled to ambient temperature and diluted with water and saturated aqueous $NaHCO_3$. The resulting solid was isolated by vacuum filtration, and the solid was washed with water then dissolved in $CHCl_3$ and dried over $Na_2SO_4$, filtered and concentrated. The crude product was then purified via column chromatography (12 G RediSep, 2 to 8% $MeOH/CH_2Cl_2$) to afford tert-butyl (1R,4R)-5-(4-((2-fluoro-3-methyl-4-((3-methyl-3H-imidazo[4,5-b]pyridin-6-yl)oxy)phenyl)amino)pyrido[3,2-d]pyrimidin-6-yl)-2,5-diazabicyclo[2.2.2]octane-2-carboxylate (38 mg, 90%) as a solid. m/z (esi) M+1=612.2.

Step B: Trifluoroacetic acid (91 μL, 1.2 mmol) was added to a stirred solution tert-butyl (1R,4R)-5-(4-((2-fluoro-3-methyl-4-((3-methyl-3H-imidazo[4,5-b]pyridin-6-yl)oxy)phenyl)amino)pyrido[3,2-d]pyrimidin-6-yl)-2,5-diazabicyclo[2.2.2]octane-2-carboxylate (36.1 mg, 0.06 mmol) in DCM (1.2 mL). The reaction was stirred at 23° C. for 1 hour before diluting with EtOAc and quenching with 10% $K_2CO_3$. The aqueous phase was extracted with EtOAc (3×), and the combined organic layers were washed with 10% $K_2CO_3$. The organic layer was then dried over sodium sulfate, filtered and concentrated in vacuo to afford 6-((1R,4R)-2,5-diazabicyclo[2.2.2]octan-2-yl)-N-(2-fluoro-3-methyl-4-((3-methyl-3H-imidazo[4,5-b]pyridin-6-yl)oxy)phenyl)pyrido[3,2-d]pyrimidin-4-amine (29.0 mg, 96%), which was used directly in the next reaction without further purification. m/z (esi) M+1=512.2.

Step C: Acryloyl chloride (0.11 mL, 0.06 mmol) as a 0.5M solution in DCM was added to a stirred solution 6-((1R,4R)-2,5-diazabicyclo[2.2.2]octan-2-yl)-N-(2-fluoro-3-methyl-4-((3-methyl-3H-imidazo[4,5-b]pyridin-6-yl)oxy)phenyl)pyrido[3,2-d]pyrimidin-4-amine (29.0 mg, 0.06 mmol) and DIPEA (19.7 μL, 0.11 mmol) in DCM (0.6 mL) at 0° C. The reaction mixture was stirred for 10 minutes at this temperature before partitioning between 10% $K_2CO_3$ and DCM. The aqueous phase was extracted with DCM (3×). The combined organic layers were then dried over sodium sulfate, filtered, and concentrated in vacuo, and the crude residue was purified over 4 g silica cartridge, eluting with a gradient of 1-10% MeOH/DCM to afford 1-((1R,4R)-5-(4-((2-fluoro-3-methyl-4-((3-methyl-3H-imidazo[4,5-b]

pyridin-6-yl)oxy)phenyl)amino)pyrido[3,2-d]pyrimidin-6-yl)-2,5-diazabicyclo[2.2.2]octan-2-yl)prop-2-en-1-one (25.8 mg, 81%). $^1H$ NMR (400 MHz, $CDCl_3$) δ 8.97 (s, 1H), 8.63-8.53 (m, 2H), 8.32-8.27 (m, 1H), 8.14-7.94 (m, 2H), 7.63-7.58 (m, 1H), 7.10-7.01 (m, 1H), 6.79-6.72 (m, 1H), 6.66-6.35 (m, 2H), 5.81-5.72 (m, 1H), 5.11-4.38 (m, 1H), 4.04-3.96 (m, 1H), 3.93 (s, 3H), 3.90-3.79 (m, 1H), 3.76-3.58 (m, 2H), 3.14-3.03 (m, 2H), 2.33-2.28 (m, 3H), 2.27-2.10 (m, 2H), 2.09-1.90 (m, 2H). m/z (esi) M+1=566.2.

Example 237

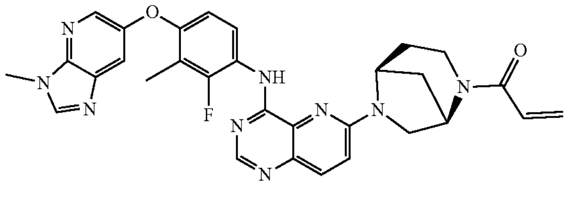 [SMILES: C=CC(=O)N1CC[C@H]2C[C@@H]1CN2c1ccc2ncnc(Nc3ccc(Oc4cnc5c(c4)ncn5C)c(C)c3F)c2n1]

1-((1R,5S)-6-(4-((2-fluoro-3-methyl-4-((3-methyl-3H-imidazo[4,5-b]pyridin-6-yl)oxy)phenyl)amino)pyrido[3,2-d]pyrimidin-6-yl)-2,6-diazabicyclo[3.2.1]octan-2-yl)prop-2-en-1-one Step A: To a vial was added 6-chloro-N-(2-fluoro-3-methyl-4-((3-methyl-3H-imidazo[4,5-b]pyridin-6-yl)oxy)phenyl)pyrido[3,2-d]pyrimidin-4-amine (34 mg, 0.08 mmol) and (1R,5S)-2,6-diaza-bicyclo[3.2.1]octane-2-carboxylic acid tert-butyl ester (33 mg, 0.16 mmol), followed by DMSO (0.52 mL) and DIPEA (20 μL, 0.12 mmol). The mixture was then warmed to 100° C. where it stirred for 6 hours. The mixture was then cooled to ambient temperature and diluted with water and saturated aqueous $NaHCO_3$. The resulting solid was isolated by vacuum filtration, and the solid was washed with water, dissolved in $CHCl_3$, and dried over $Na_2SO_4$, filtered and concentrated. The crude product was then purified via column chromatography (12 G RediSep, 2 to 8% MeOH/CH2Cl2) to afford tert-butyl (1R,5S)-6-(4-((2-fluoro-3-methyl-4-((3-methyl-3H-imidazo[4,5-b]pyridin-6-yl)oxy)phenyl)amino)pyrido[3,2-d]pyrimidin-6-yl)-2,6-diazabicyclo[3.2.1]octane-2-carboxylate (45.9 mg, 96%) as a solid. m/z (esi) M+1=612.3.

Step B: Trifluoroacetic acid (0.12 mL, 1.5 mmol) was added to a stirred solution tert-butyl (1R,5S)-6-(4-((2-fluoro-3-methyl-4-((3-methyl-3H-imidazo[4,5-b]pyridin-6-yl)oxy)phenyl)amino)pyrido[3,2-d]pyrimidin-6-yl)-2,6-diazabicyclo[3.2.1]octane-2-carboxylate (45.9 mg, 0.08 mmol) in DCM (1.5 mL). The reaction was stirred at 23° C. for 1 hour before diluting with EtOAc and quenching with 10% $K_2CO_3$. The aqueous phase was extracted with EtOAc (3×), and the combined organic layers were washed with 10% $K_2CO_3$. The organic layer was then dried over sodium sulfate, filtered and concentrated in vacuo to 6-((1R,5S)-2,6-diazabicyclo[3.2.1]octan-6-yl)-N-(2-fluoro-3-methyl-4-((3-methyl-3H-imidazo[4,5-b]pyridin-6-yl)oxy)phenyl)pyrido[3,2-d]pyrimidin-4-amine (36.5 mg, 95%), which was used directly in the next reaction without further purification. m/z (esi) M+1=512.2.

Step C: Acryloyl chloride (0.14 mL, 0.07 mmol) as a 0.5M solution in DCM was added to a stirred solution 6-((1R,5S)-2,6-diazabicyclo[3.2.1]octan-6-yl)-N-(2-fluoro-3-methyl-4-((3-methyl-3H-imidazo[4,5-b]pyridin-6-yl)oxy)

phenyl)pyrido[3,2-d]pyrimidin-4-amine (36.5 mg, 0.07 mmol) and DIPEA (24.9 μL, 0.14 mmol) in DCM (0.8 mL) at 0° C. The reaction mixture was stirred for 10 minutes at this temperature before partitioning between 10% $K_2CO_3$ and DCM. The aqueous phase was extracted with DCM (3×). The combined organic layers were then dried over sodium sulfate, filtered, and concentrated in vacuo, and the crude residue was purified over 4 g silica cartridge, eluting with a gradient of 1-10% MeOH/DCM to afford 1-((1R,5S)-6-(4-((2-fluoro-3-methyl-4-((3-methyl-3H-imidazo[4,5-b]pyridin-6-yl)oxy)phenyl)amino)pyrido[3,2-d]pyrimidin-6-yl)-2,6-diazabicyclo[3.2.1]octan-2-yl)prop-2-en-1-one (37.5 mg, 92%). $^1H$ NMR (400 MHz, $CDCl_3$) δ 9.08 (s, 1H), 8.65-8.56 (m, 2H), 8.32-8.26 (m, 1H), 8.03 (s, 1H), 8.00-7.93 (m, 1H), 7.62-7.57 (m, 1H), 7.05-6.98 (m, 1H), 6.82-6.72 (m, 1H), 6.71-6.47 (m, 1H), 6.37-6.29 (m, 1H), 5.81-5.69 (m, 1H), 5.64-4.84 (m, 1H), 4.57-3.84 (m, 4H), 3.73-3.58 (m, 2H), 3.42-3.21 (m, 1H), 3.14-3.03 (m, 3H), 2.32-2.27 (m, 3H), 2.21-2.12 (m, 1H), 2.04-1.82 (m, 2H). m/z (esi) M+1=566.2.

Example 238

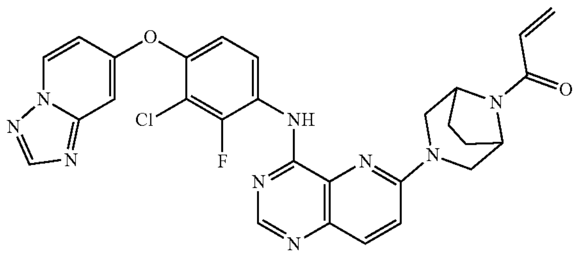 [SMILES: C=CC(=O)N1C2CCC1CN(c1ccc3ncnc(Nc4ccc(Oc5ccn6ncnc6c5)c(Cl)c4F)c3n1)C2]

1-(3-(4-((4-([1,2,4]triazolo[1,5-a]pyridin-7-yloxy)-3-chloro-2-fluorophenyl)amino)pyrido[3,2-d]pyrimidin-6-yl)-3,8-diazabicyclo[3.2.1]octan-8-yl)prop-2-en-1-one Step A: N-(4-([1,2,4]Triazolo[1,5-a]pyridin-7-yloxy)-3-chloro-2-fluorophenyl)-6-chloropyrido[3,2-d]pyrimidin-4-amine hydrochloride (40 mg, 0.084 mmol), 3,8-diazabicyclo[3.2.1]octane-8-carboxylic acid tert-butyl ester (53 mg, 0.25 mmol), DMSO (0.5 mL), and DIPEA (73 μL, 0.42 mmol) were combined in a vial. The mixture was stirred at 120° C. for 16 hours, then cooled to ambient temperature. The reaction mixture was poured into water (10 mL) and extracted twice with DCM (10 mL). The combined organic layers were washed with brine (10 mL), dried over $MgSO_4$, filtered, and concentrated. The crude material was purified by silica gel column chromatography (0 to 16% MeOH in DCM) to yield a solid, tert-butyl 3-(4-((4-([1,2,4]triazolo[1,5-a]pyridin-7-yloxy)-3-chloro-2-fluorophenyl)amino)pyrido[3,2-d]pyrimidin-6-yl)-3,8-diazabicyclo[3.2.1]octane-8-carboxylate (43 mg, 82%). m/z (esi) M+1=618.2.

Step B: To a stirred solution of tert-butyl 3-(4-((4-([1,2,4]triazolo[1,5-a]pyridin-7-yloxy)-3-chloro-2-fluorophenyl)amino)pyrido[3,2-d]pyrimidin-6-yl)-3,8-diazabicyclo[3.2.1]octane-8-carboxylate (43 mg, 0.069 mmol) in DCM (1 mL), trifluoroacetic acid (0.11 mL) was added. The reaction mixture was stirred for 30 minutes, then quenched with aqueous $K_2CO_3$ solution. The mixture was extracted with 3:1 $CHCl_3$/IPA solution. The combined organic layers were dried over $MgSO_4$, filtered, and concentrated to a solid, N-(4-([1,2,4]triazolo[1,5-a]pyridin-7-yloxy)-3-chloro-2-fluorophenyl)-6-(3,8-diazabicyclo[3.2.1]octan-3-yl)pyrido[3,2-d]pyrimidin-4-amine, which was used without further purification in the next step, assuming quantitative yield (36 mg, 100%). m/z (esi) M+1=518.1.

Step C: To a stirred solution of N-(4-([1,2,4]triazolo[1,5-a]pyridin-7-yloxy)-3-chloro-2-fluorophenyl)-6-(3,8-diazabicyclo[3.2.1]octan-3-yl)pyrido[3,2-d]pyrimidin-4-amine (36 mg, 0.069 mmol) in DCM (1 mL), DIPEA (36 μL, 0.21 mmol) was added. The solution was cooled to 0° C., and acryloyl chloride (2.2 μL total) was added. After 1 hour stirring at 0° C., the reaction mixture was concentrated under reduced pressure. The crude material was purified by silica gel column chromatography (0 to 16% MeOH in DCM) to yield the product as a solid, 1-(3-(4-((4-([1,2,4]triazolo[1,5-a]pyridin-7-yloxy)-3-chloro-2-fluorophenyl)amino)pyrido[3,2-d]pyrimidin-6-yl)-3,8-diazabicyclo[3.2.1]octan-8-yl)prop-2-en-1-one (9.9 mg, 25%). $^1H$ NMR (400 MHz, $CDCl_3$) δ 9.10 (d, J=3.4 Hz, 1H), 8.99 (t, J=8.9 Hz, 1H), 8.67 (s, 1H), 8.54 (dd, J=7.1, 1.1 Hz, 1H), 8.25 (s, 1H), 8.02 (d, J=9.4 Hz, 1H), 7.26 (d, J=9.4 Hz, 1H), 7.16 (dd, J=9.1, 2.0 Hz, 1H), 6.96-6.88 (m, 2H), 6.60 (dd, J=16.8, 10.2 Hz, 1H), 6.46 (dd, J=16.8, 2.0 Hz, 1H), 5.80 (dd, J=10.2, 2.0 Hz, 1H), 5.03 (d, J=4.9 Hz, 1H), 4.59 (d, J=4.9 Hz, 1H), 4.35 (d, J=12.3 Hz, 1H), 4.07 (d, J=11.9 Hz, 1H), 3.45 (d, J=11.8 Hz, 1H), 3.27 (d, J=12.3 Hz, 1H), 2.19-1.84 (m, 4H). m/z (esi) M+1=572.2.

Example 239

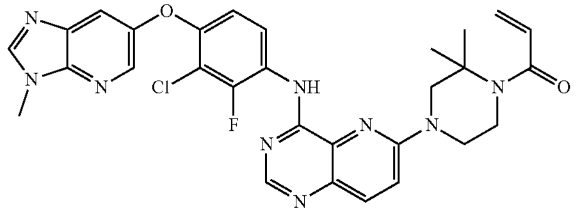 [SMILES: C=CC(=O)N1CCN(c2ccc3ncnc(Nc4ccc(Oc5cnc6c(c5)ncn6C)c(Cl)c4F)c3n2)CC1(C)C]

1-(4-(4-((3-chloro-2-fluoro-4-((3-methyl-3H-imidazo[4,5-b]pyridin-6-yl)oxy)phenyl)amino)pyrido[3,2-d]pyrimidin-6-yl)-2,2-dimethylpiperazin-1-yl)prop-2-en-1-one Step A: A scintillation vial was charged with 4,6-dichloropyrido[3,2-d]pyrimidine (22.3 mg, 0.11 mmol), 3-chloro-2-fluoro-4-((3-methyl-3H-imidazo[4,5-b]pyridin-6-yl)oxy)aniline (Intermediate LL, 32.6 mg, 0.11 mmol), and 2-propanol (1.1 mL). The mixture was stirred at 70° C. for 1.5 hours, then cooled to ambient temperature and diluted with water and extracted three times with DCM. The combined organic layers were washed with brine, dried over $MgSO_4$, filtered, and concentrated to an orange solid. The crude material was purified by silica gel chromatography (0 to 16% MeOH in DCM) to obtain the product as an orange solid, 6-chloro-N-(3-chloro-2-fluoro-4-((3-methyl-3H-imidazo[4,5-b]pyridin-6-yl)oxy)phenyl)pyrido[3,2-d]pyrimidin-4-amine (24.4 mg, 48.0%). m/z (esi) M+1=456.1.

Step B: A 4 mL vial was charged with tert-butyl 2,2-dimethylpiperazine-1-carboxylate (34.4 mg, 0.16 mmol), 6-chloro-N-(3-chloro-2-fluoro-4-((3-methyl-3H-imidazo[4,5-b]pyridin-6-yl)oxy)phenyl)pyrido[3,2-d]pyrimidin-4-amine (24.4 mg, 0.053 μmol), DMSO (0.5 mL), and DIPEA (0.047 mL, 0.27 mmol) and stirred at 100° C. for 18 hours. The reaction mixture was cooled to ambient temperature and diluted with water. The mixture was extracted three times with DCM. The combined organic layers were washed with brine, dried over MgSO4, filtered, and concentrated to an oil, which was used without further purification in the next step assuming a quantitative yield (34 mg, 100%). m/z (esi) M+1=634.2.

Step C: To a stirred solution tert-butyl 4-(4-((3-chloro-2-fluoro-4-((3-methyl-3H-imidazo[4,5-b]pyridin-6-yl)oxy) phenyl)amino)pyrido[3,2-d]pyrimidin-6-yl)-2,2-dimethylpiperazine-1-carboxylate (34 mg, 0.053 mmol) in DCM (1 mL) was added trifluoroacetic acid (0.08 mL). The reaction mixture was stirred for 3 hours, then quenched with aqueous $K_2CO_3$ solution. The mixture was extracted with DCM. The combined organic layers were washed with brine, dried over $MgSO_4$, filtered, and concentrated. The crude material was purified by silica gel chromatography (0 to 16% MeOH in DCM) to yield N-(3-chloro-2-fluoro-4-((3-methyl-3H-imidazo[4,5-b]pyridin-6-yl)oxy)phenyl)-6-(3,3-dimethylpiperazin-1-yl)pyrido[3,2-d]pyrimidin-4-amine (11.9 mg, 42%). m/z (esi) M+1=534.2.

Step D: To a stirred solution of N-(3-chloro-2-fluoro-4-((3-methyl-3H-imidazo[4,5-b]pyridin-6-yl)oxy)phenyl)-6-(3,3-dimethylpiperazin-1-yl)pyrido[3,2-d]pyrimidin-4-amine (11.9 mg, 22 μmol) in DCM (1 mL), DIPEA (12 μL, 67 μmol) was added. The solution was cooled to 0° C. and acryloyl chloride (1.5 μL) was added. After 15 minutes stirring at 0° C., the reaction mixture was concentrated under reduced pressure. The crude material was purified by silica gel column chromatography (0 to 16% MeOH in DCM) to yield the product, 1-(4-(4-((3-chloro-2-fluoro-4-((3-methyl-3H-imidazo[4,5-b]pyridin-6-yl)oxy)phenyl)amino)pyrido [3,2-d]pyrimidin-6-yl)-2,2-dimethylpiperazin-1-yl)prop-2-en-1-one (7.3 mg, 56%). $^1$H NMR (400 MHz, $CDCl_3$) δ 9.02 (d, J=3.1 Hz, 1H), 8.77 (t, J=9.0 Hz, 1H), 8.59 (s, 1H), 8.33 (d, J=2.5 Hz, 1H), 8.06 (s, 1H), 7.99 (d, J=9.3 Hz, 1H), 7.67 (d, J=2.5 Hz, 1H), 7.16 (d, J=9.3 Hz, 1H), 6.86 (dd, J=9.3, 2.1 Hz, 1H), 6.58 (dd, J=16.8, 10.6 Hz, 1H), 6.26 (dd, J=16.8, 1.8 Hz, 1H), 5.69 (dd, J=10.5, 1.8 Hz, 1H), 4.00 (t, J=5.7 Hz, 2H), 3.94 (s, 3H), 3.90 (s, 2H) 3.84 (t, J=6.4, 4.9 Hz, 2H), 1.62 (s, 6H). m/z (esi) M+1=588.2.

Example 240

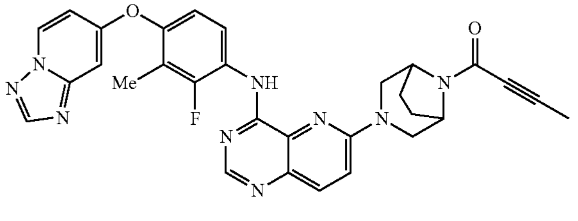 [SMILES: CC#CC(=O)N1C2CCC1CN(c1ccc3ncnc(Nc4ccc(Oc5ccn6ncnc6c5)c(C)c4F)c3n1)C2]

1-(3-(4-((4-([1,2,4]triazolo[1,5-a]pyridin-7-yloxy)-2-fluoro-3-methylphenyl)amino)pyrido[3,2-d]pyrimidin-6-yl)-3,8-diazabicyclo[3.2.1]octan-8-yl)but-2-yn-1-one A flask was charged with N-(4-([1,2,4]triazolo[1,5-a]pyridin-7-yloxy)-2-fluoro-3-methylphenyl)-6-(3,8-diazabicyclo [3.2.1]octan-3-yl)pyrido[3,2-d]pyrimidin-4-amine (9.1 mg, 18 μmol), DMF (0.18 mL), 2-butynoicacid (2.3 mg, 27 μmol), and DIPEA (16 μL, 91 μmol). Propylphosphonic anhydride (27 μL of 50% wt solution in EtOAc, 46 μmol) was then added. The mixture was stirred 2 hours at room temperature, then diluted with EtOAc and washed with water. The aqueous layer was extracted twice with EtOAc. The combined organic layers were washed with brine, dried over $MgSO_4$, filtered, and concentrated. The crude material was purified by silica gel chromatography (0 to 16% MeOH in DCM), to yield a solid, 1-(3-(4-((4-([1,2,4]triazolo[1,5-a]pyridin-7-yloxy)-2-fluoro-3-methylphenyl)amino)pyrido [3,2-d]pyrimidin-6-yl)-3,8-diazabicyclo[3.2.1]octan-8-yl) but-2-yn-1-one (6.3 mg, 61%). $^1$H NMR (400 MHz, $CDCl_3$) δ 9.06 (d, J=3.6 Hz, 1H), 8.82 (t, J=9.0 Hz, 1H), 8.65 (s, 1H), 8.51 (dd, J=7.3, 0.9 Hz, 1H), 8.24 (s, 1H), 8.00 (d, J=9.4 Hz, 1H), 7.24 (d, J=9.4 Hz, 1H), 7.01 (dd, J=8.8, 1.8 Hz, 1H), 6.93-6.85 (m, 2H), 4.93 (d, J=6.2 Hz, 1H), 4.75 (d, J=6.2 Hz, 1H), 4.32 (d, J=12.3 Hz, 1H), 4.17-4.09 (m, 1H), 3.36 (dt, J=12.4, 3.0 Hz, 2H), 2.21 (d, J=2.1 Hz, 3H), 2.13-2.00 (m, 5H), 1.98-1.85 (m, 2H). m/z (esi) M+1=564.2.

Example 241

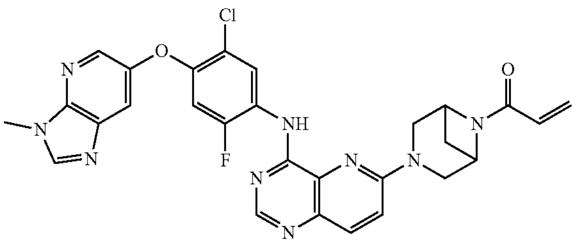 [SMILES: C=CC(=O)N1C2CC1CN(c1ccc3ncnc(Nc4cc(Cl)c(Oc5cnc6c(c5)ncn6C)cc4F)c3n1)C2]

1-(3-(4-((5-chloro-2-fluoro-4-((3-methyl-3H-imidazo[4,5-b]pyridin-6-yl)oxy)phenyl)amino)pyrido[3,2-d]pyrimidin-6-yl)-3,6-diazabicyclo[3.1.1]heptan-6-yl)prop-2-en-1-one Step A: 3-Methyl-3H-imidazo[4,5-b]pyridin-6-ol (0.54 g, 3.6 mmol), 1-chloro-2,4-difluoro-5-nitrobenzene (0.70 g, 3.6 mmol), $Cs_2CO_3$ (1.4 g, 4.3 mmol), and DMSO (18 mL) were charged to a 50 mL round bottom flask. The mixture was stirred at room temperature overnight and then diluted with ethyl acetate and washed with brine (10×). Organics were dried over $Na_2SO_4$, dry loaded onto silica gel, and purified by column chromatography (Redisep 40 g, 0-10% MeOH/DCM) to furnish 6-(2-chloro-5-fluoro-4-nitrophenoxy)-3-methyl-3H-imidazo[4,5-b]pyridine and 6-(4-chloro-5-fluoro-2-nitrophenoxy)-3-methyl-3H-imidazo[4,5-b]pyridine (0.85 g, 73%) as an inseparable mixture. m/z (esi) M+1=323.1.

Step B: A mixture of 6-(4-chloro-5-fluoro-2-nitrophenoxy)-3-methyl-3H-imidazo[4,5-b]pyridine and 6-(2-chloro-5-fluoro-4-nitrophenoxy)-3-methyl-3H-imidazo[4,5-b]pyridine (0.85 g, 2.6 mmol), tetrahydrofuran (13 mL), saturated aqueous ammonium chloride (13 mL), and zinc (1.7 g, 26 mmol) were charged to a 50 mL recovery flask. The mixture was stirred at room temperature overnight, diluted with ethyl acetate and filtered through GF/F paper. Organics were dry loaded onto silica gel and purified by column chromatography (Redisep 40 g, 100% ethyl acetate) to furnish 5-chloro-2-fluoro-4-((3-methyl-3H-imidazo[4,5-b]pyridin-6-yl)oxy)aniline (0.29 g, 37%). m/z (esi) M+1=293.1.

Step C: 4,6-Dichloropyrido[3,2-d]pyrimidine (0.18 g, 0.90 mmol), IPA (9.0 mL), and 5-chloro-2-fluoro-4-((3-methyl-3H-imidazo[4,5-b]pyridin-6-yl)oxy)aniline (0.29 g, 0.90 mmol) were charged to a 50 mL recovery flask. The mixture was stirred at 70° C. for 1 hour and then diluted with 25% IPA/$CHCl_3$ and washed once with 2M aqueous $K_2CO_3$. Organics were dried over $Na_2SO_4$ and concentrated in vacuo to furnish 6-chloro-N-(5-chloro-2-fluoro-4-((3-methyl-3H-imidazo[4,5-b]pyridin-6-yl)oxy)phenyl)pyrido[3,2-d]pyrimidin-4-amine (0.41 g, 100%). m/z (esi) M+1=456.0.

Step D: Synthesized according to Example 239, Steps A-C substituting 6-chloro-N-(5-chloro-2-fluoro-4-((3-methyl-3H-imidazo[4,5-b]pyridin-6-yl)oxy)phenyl)pyrido[3,2-d]pyrimidin-4-amine in place of N-(4-([1,2,4]triazolo[1,5-a]pyridin-7-yloxy)-2-fluoro-5-methylphenyl)-6-chloropyrido[3,2-d]pyrimidin-4-amine and tert-butyl 3,6-diazabicyclo[3.1.1]heptane-6-carboxylate in place of tert-butyl (3aS,6aS)-hexahydropyrrolo[3,4-b]pyrrole-1(2H)-carboxylate to furnish 1-(3-(4-((5-chloro-2-fluoro-4-((3-methyl-3H-imidazo[4,5-b]pyridin-6-yl)oxy)phenyl)amino)pyrido[3,2-d]pyrimidin-6-yl)-3,6-diazabicyclo[3.1.1]heptan-6-yl)prop-2-en-1-one (10 mg, 40%). m/z (esi) M+1=572.2. $^1H$ NMR (400 MHz, MeOD) δ 8.70 (s, 2H), 8.41 (d, J=2.5 Hz, 1H), 8.36 (d, J=7.8 Hz, 1H), 8.05 (d, J=9.4 Hz, 1H), 7.79 (d, J=2.5 Hz, 1H), 7.56 (d, J=9.5 Hz, 1H), 7.11 (d, J=10.9 Hz, 1H), 6.48 (dd, J=17.0, 10.4 Hz, 1H), 6.26 (dd, J=16.9, 1.8 Hz, 1H), 5.75 (dd, J=10.4, 1.8 Hz, 1H), 4.96-4.90 (m, 1H), 4.72-4.68 (m, 1H), 4.25 (s, 1H), 4.11-3.88 (m, 6H), 2.98-2.88 (m, 1H), 1.79 (d, J=9.1 Hz, 1H).

Example 242

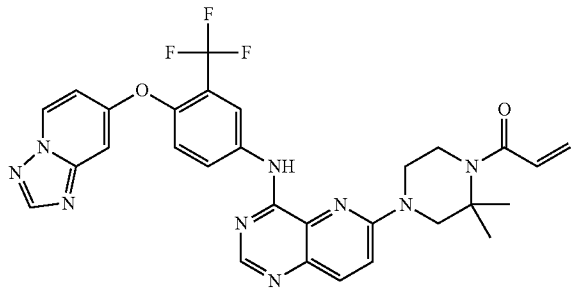 [SMILES: C=CC(=O)N1CCN(c2ccc3ncnc(Nc4ccc(Oc5ccn6ncnc6c5)c(C(F)(F)F)c4)c3n2)CC1(C)C]

1-(4-(4-((4-([1,2,4]triazolo[1,5-a]pyridin-7-yloxy)-3-(trifluoromethyl)phenyl)amino)pyrido[3,2-d]pyrimidin-6-yl)-2,2-dimethylpiperazin-1-yl)prop-2-en-1-one Step A: 1-Fluoro-4-nitro-2-(trifluoromethyl)benzene (0.20 g, 0.96 mmol), [1,2,4]triazolo[1,5-a]pyridin-7-ol (0.11 g, 0.80 mmol), DMSO (4.0 mL), and $Cs_2CO_3$ (0.31 g, 0.96 mmol) were charged to a 20 mL vial equipped with a stir bar. The mixture was heated to 80° C. for 45 minutes and then 100° C. for 1 hour. The mixture was diluted with ethyl acetate and washed with brine (10×). Organics were dry loaded onto silica gel and purified by column chromatography (Redisep 24 g, 30-80% ethyl acetate/heptane) to furnish 7-(4-nitro-2-(trifluoromethyl)phenoxy)-[1,2,4]triazolo[1,5-a]pyridine (0.20 g, 76%). m/z (esi) M+1=325.1.

Step B: Prepared according to Example 241, Steps B-C substituting 7-(4-nitro-2-(trifluoromethyl)phenoxy)-[1,2,4]triazolo[1,5-a]pyridine in place of a mixture of 6-(4-chloro-5-fluoro-2-nitrophenoxy)-3-methyl-3H-imidazo[4,5-b]pyridine and 6-(2-chloro-5-fluoro-4-nitrophenoxy)-3-methyl-3H-imidazo[4,5-b]pyridine to furnish N-(4-([1,2,4]triazolo[1,5-a]pyridin-7-yloxy)-3-(trifluoromethyl)phenyl)-6-chloropyrido[3,2-d]pyrimidin-4-amine (84 mg, 100%). m/z (esi) M+1=458.1.

Step C: Prepared according to Example 238, Steps A-C substituting N-(4-([1,2,4]triazolo[1,5-a]pyridin-7-yloxy)-3-(trifluoromethyl)phenyl)-6-chloropyrido[3,2-d]pyrimidin-4-amine in place of N-(4-([1,2,4]triazolo[1,5-a]pyridin-7-yloxy)-2-fluoro-5-methylphenyl)-6-chloropyrido[3,2-d]pyrimidin-4-amine and tert-butyl 2,2-dimethylpiperazine-1-carboxylate in place of tert-butyl (3aS,6aS)-hexahydropyrrolo[3,4-b]pyrrole-1(2H)-carboxylate to furnish 1-(4-(4-((4-([1,2,4]triazolo[1,5-a]pyridin-7-yloxy)-3-(trifluoromethyl)phenyl)amino)pyrido[3,2-d]pyrimidin-6-yl)-2,2-dimethylpiperazin-1-yl)prop-2-en-1-one (12 mg, 70%). m/z (esi) M+1=590.2. $^1H$ NMR (400 MHz, $CDCl_3$) δ 8.81 (s, 1H), 8.64 (s, 1H), 8.53 (dd, J=7.5, 0.7 Hz, 1H), 8.32-8.23 (m, 3H), 8.02 (d, J=9.3 Hz, 1H), 7.26 (d, J=8.7 Hz, 1H), 7.19 (d, J=9.3 Hz, 1H), 6.99 (dd, J=2.6, 0.7 Hz, 1H), 6.92 (dd, J=7.5, 2.6 Hz, 1H), 6.58 (dd, J=16.8, 10.6 Hz, 1H), 6.26 (dd, J=16.8, 1.8 Hz, 1H), 5.70 (dd, J=10.5, 1.8 Hz, 1H), 4.05-3.98 (m, 2H), 3.91-3.84 (m, 4H), 1.62 (s, 6H).

Example 243

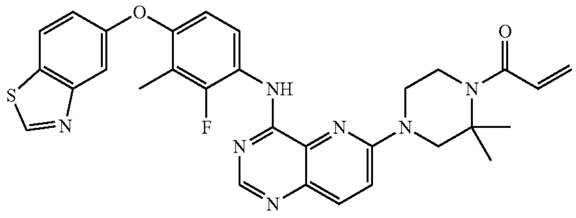 [SMILES: C=CC(=O)N1CCN(c2ccc3ncnc(Nc4ccc(Oc5ccc6scnc6c5)c(C)c4F)c3n2)CC1(C)C]

1-(4-(4-((4-(benzo[d]thiazol-5-yloxy)-2-fluoro-3-methylphenyl)amino)pyrido[3,2-d]pyrimidin-6-yl)-2,2-dimethylpiperazin-1-yl)prop-2-en-1-one Synthesized according to Example 242, Steps A-C, substituting 1,3-difluoro-2-methyl-4-nitrobenzene in place of 1-fluoro-4-nitro-2-(trifluoromethyl)benzene and benzo[d]thiazol-5-ol in place of [1,2,4]triazolo[1,5-a]pyridin-7-ol in step A to furnish 1-(4-(4-((4-(benzo[d]thiazol-5-yloxy)-2-fluoro-3-methylphenyl)amino)pyrido[3,2-d]pyrimidin-6-yl)-2,2-dimethylpiperazin-1-yl)prop-2-en-1-one (9.6 mg, 58%). m/z (esi) M+1=570.2. $^1H$ NMR (400 MHz, $CDCl_3$) δ 9.05 (d, J=3.4 Hz, 1H), 9.00 (s, 1H), 8.69 (t, J=9.1 Hz, 1H), 8.58 (s, 1H), 7.99 (dd, J=9.3, 2.4 Hz, 1H), 7.88 (d, J=8.8 Hz, 1H), 7.59 (d, J=2.3 Hz, 1H), 7.19 (dd, J=8.5, 2.2 Hz, 1H), 7.16-7.09 (m, 1H), 6.91 (dd, J=9.0, 1.7 Hz, 1H), 6.58 (dd, J=16.8, 10.5 Hz, 1H), 6.26 (dd, J=16.8, 1.8 Hz, 1H), 5.69 (dd, J=10.5, 1.8 Hz, 1H), 4.04-3.97 (m, 2H), 3.92 (s, 2H), 3.87-3.77 (m, 2H), 2.26 (d, J=2.1 Hz, 3H), 1.62 (s, 6H).

Example 244

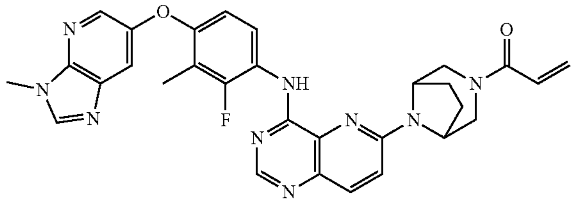 [SMILES: C=CC(=O)N1CC2CCC(C1)N2c1ccc2ncnc(Nc3ccc(Oc4cnc5c(c4)ncn5C)c(C)c3F)c2n1]

1-(8-(4-((2-fluoro-3-methyl-4-((3-methyl-3H-imidazo[4,5-b]pyridin-6-yl)oxy)phenyl)amino)pyrido[3,2-d]pyrimidin-6-yl)-3,8-diazabicyclo[3.2.1]octan-3-yl)prop-2-en-1-one Step A: 4,6-Dichloropyrido[3,2-d]pyrimidine (0.32 g, 1.6 mmol), 2-fluoro-3-methyl-4-((3-methyl-3H-imidazo[4,5-b]pyridin-6-yl)oxy)aniline (0.43 g, 1.6 mmol), and 2-propanol (16 mL) were charged to 50 mL recovery flask. The mixture was stirred for 20 minutes at 70° C. and then diluted with 25% IPA/$CHCl_3$ and 2M aqueous $K_2CO_3$. Organics were dried over $Na_2SO_4$ and concentrated in vacuo to furnish 6-chloro-N-(2-fluoro-3-methyl-4-((3-methyl-3H-imidazo[4,5-b]pyridin-6-yl)oxy)phenyl)pyrido[3,2-d]pyrimidin-4-amine (0.59 g, 85%), carried on crude.

Step B: Synthesized according to Example 238, Steps A-C, substituting 6-chloro-N-(2-fluoro-3-methyl-4-((3-methyl-3H-imidazo[4,5-b]pyridin-6-yl)oxy)phenyl)pyrido[3,2-d]pyrimidin-4-amine in place of N-(4-([1,2,4]triazolo[1,5-a]pyridin-7-yloxy)-2-fluoro-5-methylphenyl)-6-chloropyrido[3,2-d]pyrimidin-4-amine and tert-butyl 3,8-diazabicyclo[3.2.1]octane-8-carboxylate in place of tert-butyl (3aS,6aS)-hexahydropyrrolo[3,4-b]pyrrole-1(2H)-carboxylate to furnish 1-(8-(4-((2-fluoro-3-methyl-4-((3-methyl-3H-imidazo[4,5-b]pyridin-6-yl)oxy)phenyl)amino)pyrido[3,2-d]pyrimidin-6-yl)-3,8-diazabicyclo[3.2.1]octan-3-yl)prop-2-en-1-one (8.1 mg, 41%). m/z (esi) M+1=566.3. $^1$H NMR (400 MHz, $CDCl_3$) δ 9.00 (d, J=3.4 Hz, 1H), 8.60 (t, J=11.0 Hz, 1H), 8.30 (d, J=2.5 Hz, 1H), 8.04 (s, 1H), 7.98 (d, J=9.2 Hz, 1H), 7.61 (d, J=2.5 Hz, 1H), 7.21 (d, J=9.3 Hz, 1H), 6.75 (dd, J=9.1, 1.7 Hz, 1H), 6.56 (dd, J=16.8, 10.5 Hz, 1H), 6.33 (dd, J=16.8, 1.9 Hz, 1H), 5.74 (dd, J=10.5, 1.9 Hz, 1H), 4.88-4.83 (m, 1H), 4.74-4.69 (m, 1H), 4.54 (d, J=13.4 Hz, 1H), 3.93 (s, 3H), 3.81 (d, J=12.5 Hz, 1H), 3.68 (d, J=12.6 Hz, 1H), 3.14 (d, J=13.3 Hz, 1H), 2.31 (d, J=2.1 Hz, 3H), 2.17-2.12 (m, 2H), 2.01-1.93 (m, 1H), 1.93-1.85 (m, 1H).

Example 245

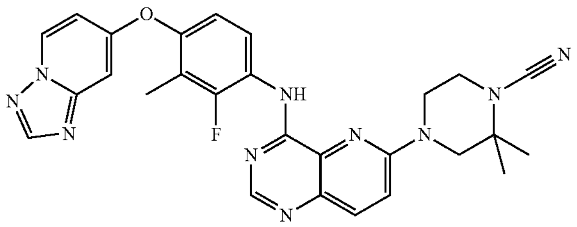 [SMILES: Cc1c(Oc2ccn3ncnc3c2)ccc(Nc2ncnc3ccc(N4CCN(C#N)C(C)(C)C4)nc23)c1F]

4-(4-((4-([1,2,4]triazolo[1,5-a]pyridin-7-yloxy)-2-fluoro-3-methylphenyl)amino)pyrido[3,2-d]pyrimidin-6-yl)-2,2-dimethylpiperazine-1-carbonitrile N-(4-([1,2,4]Triazolo[1,5-a]pyridin-7-yloxy)-2-fluoro-3-methylphenyl)-6-(3,3-dimethylpiperazin-1-yl)pyrido[3,2-d]pyrimidin-4-amine (20 mg, 40 μmol) was added to DMF (0.40 mL) with $Cs_2CO_3$ (52 mg, 0.16 mmol) and cyanic bromide (8.5 mg, 80 μmol). The mixture was stirred at room temperature for 20 minutes, and then the mixture was dry loaded onto silica gel and purified by column chromatography (Redisep 12 g, 0-16% MeOH/DCM) to furnish 4-(4-((4-([1,2,4]triazolo[1,5-a]pyridin-7-yloxy)-2-fluoro-3-methylphenyl)amino)pyrido[3,2-d]pyrimidin-6-yl)-2,2-dimethylpiperazine-1-carbonitrile (9.5 mg, 45%). m/z (esi) M+1=525.3. $^1$H NMR (400 MHz, $CDCl_3$) δ 9.03 (d, J=3.6 Hz, 1H), 8.82 (t, J=9.0 Hz, 1H), 8.65 (s, 1H), 8.51 (dd, J=7.4, 0.8 Hz, 1H), 8.23 (s, 1H), 8.01 (d, J=9.3 Hz, 1H), 7.25 (d, J=9.3 Hz, 1H), 7.01 (dd, J=9.0, 1.8 Hz, 1H), 6.90 (dd, J=7.4, 2.6 Hz, 1H), 6.86 (dd, J=2.6, 0.7 Hz, 1H), 3.94-3.87 (m, 2H), 3.69 (s, 2H), 3.55-3.47 (m, 3H), 2.21 (d, J=2.1 Hz, 3H), 1.46 (s, 6H).

Example 246

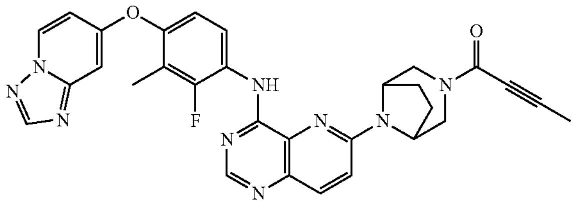 [SMILES: CC#CC(=O)N1CC2CCC(C1)N2c1ccc2ncnc(Nc3ccc(Oc4ccn5ncnc5c4)c(C)c3F)c2n1]

1-(8-(4-((4-([1,2,4]triazolo[1,5-a]pyridin-7-yloxy)-2-fluoro-3-methylphenyl)amino)pyrido[3,2-d]pyrimidin-6-yl)-3,8-diazabicyclo[3.2.1]octan-3-yl)but-2-yn-1-one Step A: Synthesized according to Example 238, Steps A-B, substituting tert-butyl 3,8-diazabicyclo[3.2.1]octane-3-carboxylate in place of tert-butyl (3aS,6aS)-hexahydropyrrolo[3,4-b]pyrrole-1(2H)-carboxylate and N-(4-([1,2,4]triazolo[1,5-a]pyridin-7-yloxy)-2-fluoro-3-methylphenyl)-6-chloropyrido[3,2-d]pyrimidin-4-amine in place of N-(4-([1,2,4]triazolo[1,5-a]pyridin-7-yloxy)-2-fluoro-5-methylphenyl)-6-chloropyrido[3,2-d]pyrimidin-4-amine in Step A to furnish N-(4-([1,2,4]triazolo[1,5-a]pyridin-7-yloxy)-2-fluoro-3-methylphenyl)-6-(3,8-diazabicyclo[3.2.1]octan-8-yl)pyrido[3,2-d]pyrimidin-4-amine (5.4 mg, 100%). m/z (esi) M+1=498.3.

Step B: 2,4,6-Tripropyl-1,3,5,2,4,6-trioxatriphosphinane 2,4,6-trioxide (50% wt in 2-methyltetrahydrofuran) (17 mg, 27 μmol), but-2-ynoic acid (1.4 mg, 16 μmol), N-(4-([1,2,4]triazolo[1,5-a]pyridin-7-yloxy)-2-fluoro-3-methylphenyl)-6-(3,8-diazabicyclo[3.2.1]octan-8-yl)pyrido[3,2-d]pyrimidin-4-amine (5.4 mg, 11 μmol), Hunig's base (7.0 mg, 54 μmol) and DMF (0.11 mL) were charged to a dram vial. The mixture was stirred at 100° C. overnight. The mixture was dry loaded onto silica gel and purified by column chromatography (Redisep 12 g, 0 to 14% MeOH/DCM) to furnish 1-(8-(4-((4-([1,2,4]triazolo[1,5-a]pyridin-7-yloxy)-2-fluoro-3-methylphenyl)amino)pyrido[3,2-d]pyrimidin-6-yl)-3,8-diazabicyclo[3.2.1]octan-3-yl)but-2-yn-1-one (1.1 mg, 18%). m/z (esi) M+1=564.3. $^{1}$H NMR (400 MHz, $CDCl_3$) δ 9.09 (d, J=3.6 Hz, 1H), 8.82 (t, J=9.0 Hz, 1H), 8.65 (s, 1H), 8.51 (dd, J=7.2, 0.9 Hz, 1H), 8.24 (s, 1H), 8.01 (d, J=9.2 Hz, 1H), 7.22 (d, J=9.3 Hz, 1H), 7.04-6.97 (m, 1H), 6.93-6.85 (m, 2H), 4.84 (d, J=5.9 Hz, 1H), 4.72 (d, J=5.9 Hz, 1H), 4.43 (d, J=13.1 Hz, 1H), 4.25 (d, J=12.9 Hz, 1H), 3.61 (d, J=12.8 Hz, 1H), 3.16 (d, J=13.2 Hz, 1H), 2.21 (d, J=2.2 Hz, 3H), 2.16 (s, 2H), 2.03-1.88 (m, 2H), 1.56 (s, 3H).

Example 247

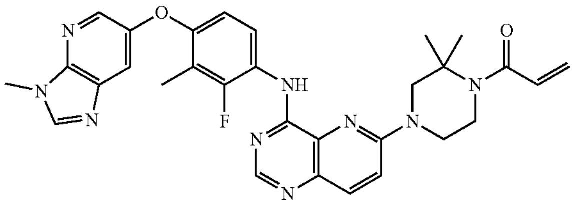 [SMILES: C=CC(=O)N1CCN(c2ccc3ncnc(Nc4ccc(Oc5cnc6c(c5)ncn6C)c(C)c4F)c3n2)CC1(C)C]

1-(4-(4-((2-fluoro-3-methyl-4-((3-methyl-3H-imidazo[4,5-b]pyridin-6-yl)oxy)phenyl)amino)pyrido[3,2-d]pyrimidin-6-yl)-2,2-dimethylpiperazin-1-yl)prop-2-en-1-one Synthesized according to Example 244, substituting tert-butyl 2,2-dimethylpiperazine-1-carboxylate in place of tert-butyl 3,8-diazabicyclo[3.2.1]octane-8-carboxylate in Step B to furnish 1-(4-(4-((2-fluoro-3-methyl-4-((3-methyl-3H-imidazo[4,5-b]pyridin-6-yl)oxy)phenyl)amino)pyrido[3,2-d]pyrimidin-6-yl)-2,2-dimethylpiperazin-1-yl)prop-2-en-1-one (6.0 mg, 59%). m/z (esi) M+1=568.2. H NMR (400 MHz, $CDCl_3$) δ 9.02 (d, J=3.4 Hz, 1H), 8.661-8.55 (m, 2H), 8.29 (d, J=2.4 Hz, 1H), 8.04 (m, 1H), 7.99 (d, J=9.3 Hz, 1H), 7.60 (d, J=2.5 Hz, 1H), 7.14 (d, J=9.3 Hz, 1H), 6.76 (dd, J=9.0, 1.7 Hz, 1H), 6.58 (dd, J=16.8, 10.5 Hz, 1H), 6.26 (dd, J=16.8, 1.8 Hz, 1H), 5.69 (dd, J=10.6, 1.8 Hz, 1H), 4.00 (t, J=5.7 Hz, 2H), 3.93 (s, 3H), 3.92 (4, 2H), 3.84 (t, 2H), 2.30 (d, J=2.1 Hz, 3H), 1.62 (5, 6H).

Additional compounds of the invention were prepared by modifications of the methods exemplified above and are shown in Table 3 below. The method in Table 3 refers to the Example number procedure above in which the compound in the table was prepared in a similar procedure as the Example, changing the appropriate intermediate or reactant.

TABLE 3

| Example No. (Method) | Structure; IUPAC name | LCMS $M^{+1}$ | $^{1}$H NMR (ppm); $^{19}$F NMR (ppm); optical rotation; Chiral HPLC/SFC conditions |
|---|---|---|---|
| 248 (Ex 162) | 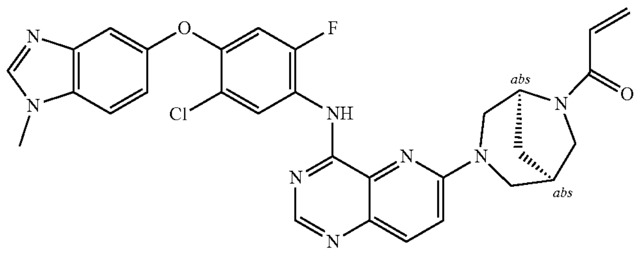 1-((1R,5S)-3-(4-((5-chloro-2-fluoro-4-((1-methyl-1H-benzo[d]imidazol-5-yl)oxy)phenyl)amino)pyrido[3,2-d]pyrimidin-6-yl)-3,6-diazabicyclo[3.2.1]octan-6-yl)prop-2-en-1-one | 585.25 | $^{1}$H NMR (400 MHz, $CDCl_3$) δ 9.12-9.02 (m, 1H), 8.93-8.86 (m, 1H), 8.69-8.63 (m, 1H), 8.06-7.80 (m, 2H), 7.51-7.32 (m, 2H), 7.25-7.14 (m, 1H), 7.11 (dd, J = 8.7, 2.3 Hz, 1H), 6.79 (d, J = 11.7 Hz, 1H), 6.60-6.31 (m, 2H), 5.77-5.66 (m, 1H), 4.82-4.77 (m, 1H), 4.51-4.09 (m, 2H), 3.87 (s, 3H), 3.76-3.49 (m, 2H), 3.39-3.31 (m, 1H), 3.27-3.08 (m, 1H), 2.93-2.73 (m, 1H), 2.28-1.79 (m, 2H). |
| 249 (Ex 162) | 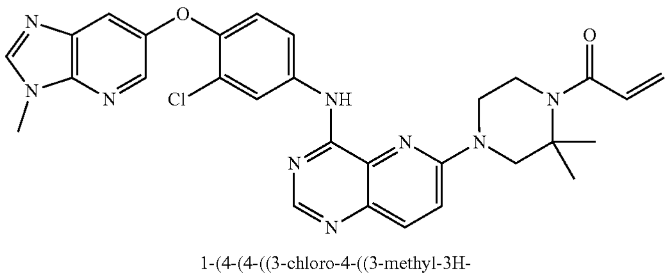 1-(4-(4-((3-chloro-4-((3-methyl-3H-imidazo[4,5-b]pyridin-6-yl)oxy)phenyl)amino)pyrido[3,2-d]pyrimidin-6-yl)-2,2-dimethylpiperazin-1-yl)prop-2-en-1-one | 570.30 | $^{1}$H NMR (400 MHz, $CDCl_3$) δ 8.65 (s, 1H), 8.61 (s, 1H), 8.33 (d, J = 2.5 Hz, 1H), 8.16 (d, J = 2.6 Hz, 1H), 8.04 (s, 1H), 8.00 (d, J = 9.3 Hz, 1H), 7.74 (dd, J = 8.9, 2.6 Hz, 1H), 7.63 (d, J = 2.5 Hz, 1H), 7.16 (d, J = 9.3 Hz, 1H), 7.04 (d, J = 8.8 Hz, 1H), 6.57 (dd, J = 16.8, 10.6 Hz, 1H), 6.25 (dd, J = 16.8, 1.8 Hz, 1H), 5.69 (dd, J = 10.6, 1.8 Hz, 1H), 4.04-3.96 (m, 2H), 3.93 (s, 3H), 3.89-3.81 (m, 4H), 1.62 (s, 6H). |

TABLE 3-continued

| Example No. (Method) | Structure; IUPAC name | LCMS $M^{+1}$ | $^{1}H$ NMR (ppm); $^{19}F$ NMR (ppm); optical rotation; Chiral HPLC/SFC conditions |
|---|---|---|---|
| 250 (Ex 162) | 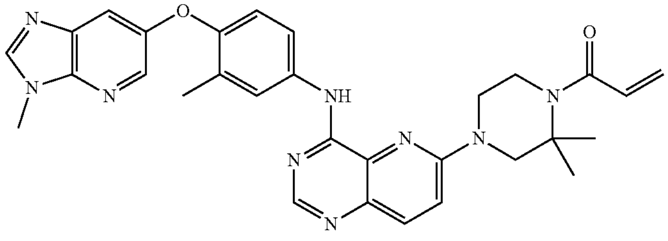 1-(2,2-dimethyl-4-(4-((3-methyl-4-((3-methyl-3H-imidazo[4,5-b]pyridin-6-yl)oxy)phenyl)amino)pyrido[3,2-d]pyrimidin-6-yl)piperazin-1-yl)prop-2-en-1-one | 550.30 | 1H NMR (400 MHz, CDCl3) δ 8.62 (s, 1H), 8.59 (s, 1H), 8.30 (d, J = 2.5 Hz, 1H), 8.02 (s, 1H), 7.99 (d, J = 9.3 Hz, 1H), 7.77 (d, J = 2.5 Hz, 1H), 7.67 (dd, J = 8.7, 2.7 Hz, 1H), 7.58 (d, J = 2.5 Hz, 1H), 7.14 (d, J = 9.3 Hz, 1H), 6.93 (d, J = 8.7 Hz, 1H), 6.57 (dd, J = 16.8, 10.6 Hz, 1H), 6.25 (dd, J = 16.8, 1.8 Hz, 1H), 5.69 (dd, J = 10.6, 1.8 Hz, 1H), 4.03-3.96 (m, 2H), 3.93 (s, 3H), 3.90-3.80 (m, 4H), 2.36 (s, 3H), 1.62 (s, 6H). |
| 251 (Ex 162) | 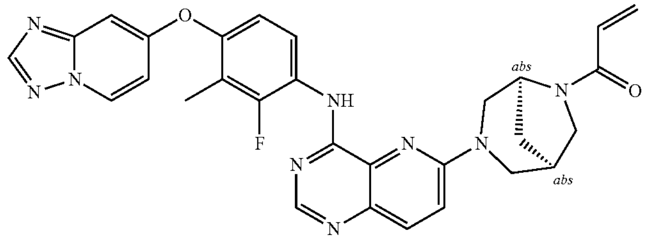 1-((1R,5S)-3-(4-((4-([1,2,4]triazolo[1,5-a]pyridin-7-yloxy)-2-fluoro-3-methylphenyl)amino)pyrido[3,2-d]pyrimidin-6-yl)-3,6-diazabicyclo[3.2.1]octan-6-yl)prop-2-en-1-one | 552.25 | $^{1}H$ NMR (400 MHz, $CDCl_3$) δ 9.11-9.04 (m, 1H), 8.87-8.75 (m, 1H), 8.63 (s, 1H), 8.51 (d, J = 6.7 Hz, 1H), 8.23 (s, 1H), 8.01-7.92 (m, 1H), 7.26-7.15 (m, 2H), 7.00 (d, J = 8.4 Hz, 1H), 6.92-6.86 (m, 2H), 6.49-6.36 (m, 2H), 5.84-5.57 (m, 1H), 4.82 (s, 1H), 4.57-4.13 (m, 2H), 3.82-3.49 (m, 2H), 3.48-3.08 (m, 2H), 2.96-2.74 (m, 1H), 2.31-1.59 (m, 5H). |
| 252 (Ex 162) | 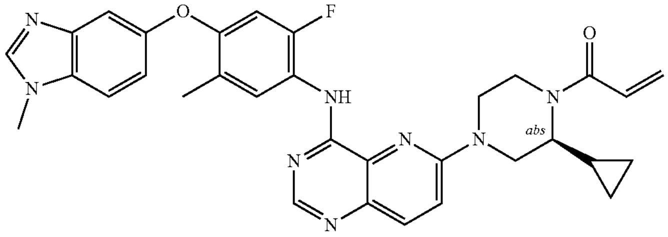 (S)-1-(2-cyclopropyl-4-(4-((2-fluoro-5-methyl-4-((1-methyl-1H-benzo[d]imidazol-5-yl)oxy)phenyl)amino)pyrido[3,2-d]pyrimidin-6-yl)piperazin-1-yl)prop-2-en-1-one | 579.30 | $^{1}H$ NMR (400 MHz, $CDCl_3$) δ 8.89 (s, 1H), 8.70-8.62 (m, 2H), 7.98 (d, J = 9.3 Hz, 1H), 7.88 (s, 1H), 7.39-7.28 (m, 3H), 7.07 (dd, J = 8.8, 1.9 Hz, 1H), 6.71 (d, J = 11.9 Hz, 1H), 6.64-6.54 (m, 1H), 6.35 (d, J = 17.1 Hz, 1H), 5.74 (d, J = 11.3 Hz, 1H), 4.81-2.90 (m, 7H), 3.86 (s, 3H), 2.36 (s, 3H), 1.41-1.14 (m, 1H), 0.71-0.31 (m, 4H). |

TABLE 3-continued

| Example No. (Method) | Structure; IUPAC name | LCMS $M^{+1}$ | $^{1}H$ NMR (ppm); $^{19}F$ NMR (ppm); optical rotation; Chiral HPLC/SFC conditions |
|---|---|---|---|
| 253 (Ex 162) | 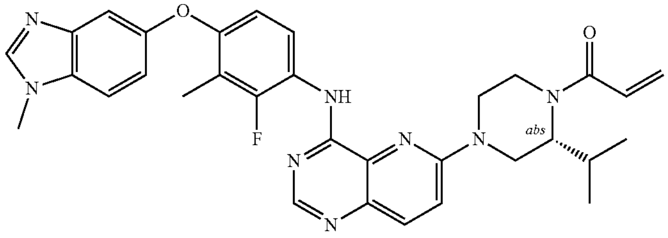 (R)-1-(4-(4-((2-fluoro-5-methyl-4-((1-meethyl-1H-benzo[d]imidazol-5-yl)oxy)phenyl)amino)pyrido[3,2-d]pyrimidin-6-yl)-2-isopropylpiperazin-1-yl)prop-2-en-1-one | 581.30 | $^{1}H$ NMR (400 MHz, $CDCl_3$) δ 8.98-8.93 (m, 1H), 8.63-8.51 (m, 2H), 7.97 (d, J = 9.3 Hz, 1H), 7.86 (s, 1H), 7.37-7.30 (m, 2H), 7.26-7.21 (m, 1H), 7.06 (dd, J = 8.7, 2.3 Hz, 1H), 6.77 (dd, J = 9.0, 1.4 Hz, 1H), 6.72-6.61 (m, 1H), 6.46-6.29 (m, 1H), 5.77 (d, J = 10.4 Hz, 1H), 4.98-4.72 (m, 1H), 4.71-4.40 (m, 1H), 4.35-3.95 (m, 1H), 3.86 (s, 3H), 3.81-3.36 (m, 1H), 3.27-2.92 (m, 3H), 2.37-2.00 (m, 4H), 1.23-1.15 (m, 3H), 0.93-0.87 (m, 3H). |
| 254 (Ex 162) | 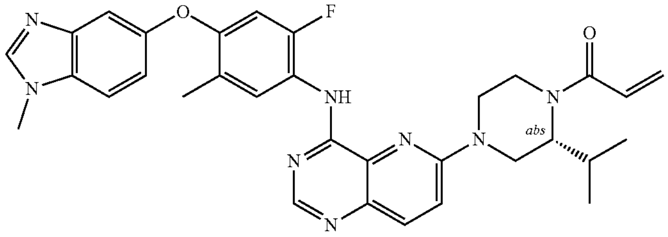 (R)-1-(4-(4-((2-fluoro-5-methyl-4-((1-methyl-1H-benzo[d]imidazol-5-yl)oxy)phenyl)amino)pyrido[3,2-d]pyrimidin-6-yl)-2-isopropylpiperazin-1-yl)prop-2-en-1-one | 543.30 | $^{1}H$ NMR (400 MHz, $CDCl_3$) δ 8.85 (s, 1H), 8.74-8.59 (m, 2H), 7.98 (d, J = 9.3 Hz, 1H), 7.88 (s, 1H), 7.39-7.32 (m, 2H), 7.27-7.21 (m, 1H), 7.06 (dd, J = 8.8, 2.2 Hz, 1H), 6.78-6.57 (m, 2H), 6.46-6.26 (m, 1H), 5.76 (d, J = 10.4 Hz, 1H), 4.94-4.17 (m, 1H), 4.69-4.36 (m, 1H), 4.33-3.93 (m, 1H), 3.86 (s, 3H), 3.79-3.35 (m, 1H), 3.27-2.90 (m, 3H), 2.36 (s, 3H), 2.27-1.98 (m, 1H), 1.31 (d, J = 6.5 Hz, 3H), 0.88 (d, J = 6.8 Hz, 3H). |
| 255 (Ex 162) | 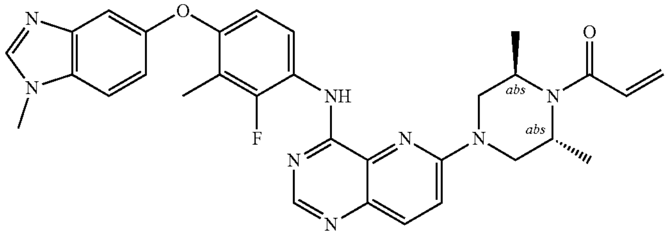 1-((2R,6R)-4-(4-((2-fluoro-3-methyl-4-((1-methyl-1H-benzo[d]imidazol-5-yl)oxy)phenyl)amino)pyrido[3,2-d]pyrimidin-6-yl)-2,6-dimethylpiperazin-1-yl)prop-2-en-1-one | 567.30 | $^{1}H$ NMR (400 MHz, $CDCl_3$) δ 9.01 (d, J = 2.8 Hz, 1H), 8.66-8.49 (m, 2H), 8.01 (d, J = 9.3 Hz, 1H), 7.87 (s, 1H), 7.37-7.31 (m, 2H), 7.15 (d, J = 9.3 Hz, 1H), 7.06 (dd, J = 8.6, 2.4 Hz, 1H), 6.78 (dd, J = 9.0, 1.5 Hz, 1H), 6.65 (dd, J = 16.6, 10.2 Hz, 1H), 6.50 (dd, J = 16.6, 2.1 Hz, 1H), 5.79 (dd, J = 10.2, 2.1 Hz, 1H), 4.94-3.72 (m, 9H), 2.29 (d, J = 2.1 Hz, 3H), 1.41 (d, J = 6.4 Hz, 6H). |
| 256 (Ex 162) | 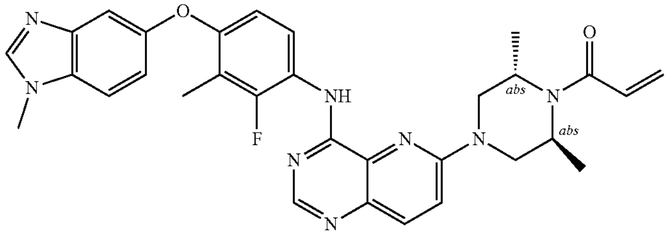 1-((2S,6S)-4-(4-((2-fluoro-3-methyl-4-((1-methyl-1H-benzo[d]imidazol-5-yl)oxy)phenyl)amino)pyrido[3,2-d]pyrimidin-6-yl)-2,6-dimethylpiperazin-1-yl)prop-2-en-1-one | 567.30 | $^{1}H$ NMR (400 MHz, $CDCl_3$) δ 9.00 (d, J = 2.9 Hz, 1H), 8.65-8.48 (m, 2H), 8.01 (d, J = 9.3 Hz, 1H), 7.86 (s, 1H), 7.37-7.31 (m, 2H), 7.15 (d, J = 9.3 Hz, 1H), 7.06 (dd, J = 8.8, 2.2 Hz, 1H), 6.78 (dd, J = 9.0, 1.5 Hz, 1H), 6.65 (dd, J = 16.6, 10.2 Hz, 1H), 6.50 (dd, J = 16.6, 2.1 Hz, 1H), 4.93-3.89 (s, 6H), 3.86 (s, 3H), 2.29 (d, J = 2.0 Hz, 3H), 1.41 (d, J = 6.4 Hz, 6H). |

TABLE 3-continued

| Example No. (Method) | Structure; IUPAC name | LCMS $M^{+1}$ | $^1H$ NMR (ppm); $^{19}F$ NMR (ppm); optical rotation; Chiral HPLC/SFC conditions |
|---|---|---|---|
| 257 (Ex 162) | 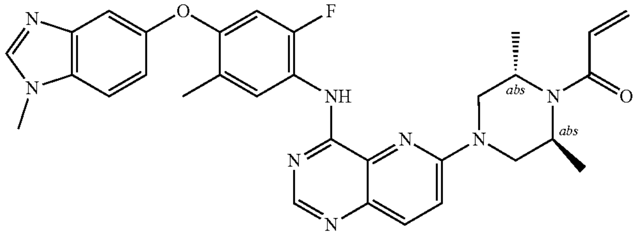 1-((2S,6S)-4-(4-((2-fluoro-5-methyl-4-((1-methyl-1H-benzo[d]imidazol-5-yl)oxy)phenyl)amino)pyrido[2,3-d]pyrimidin-6-yl)-2,6-dimethylpiperazin-1-yl)prop-2-en-1-one | 567.30 | $^1H$ NMR (400 MHz, $CDCl_3$) δ 8.88 (d, J = 2.4 Hz, 1H), 8.68-8.61 (m, 2H), 8.01 (d, J = 9.3 Hz, 1H), 7.87 (s, 1H), 7.36 (dd, J = 5.5, 2.9 Hz, 2H), 7.14 (d, J = 9.3 Hz, 1H), 7.06 (dd, J = 8.8, 2.2 Hz, 1H), 6.71 (d, J = 11.9 Hz, 1H), 6.63 (dd, J = 16.6, 10.2 Hz, 1H), 6.48 (dd, J = 16.6, 2.1 Hz, 1H), 5.78 (dd, J = 10.2, 2.1 Hz, 1H), 4.91-4.26 (m, 2H), 4.21-3.74 (m, 7H), 2.36 (s, 3H), 1.39 (d, J = 6.5 Hz, 6H). |
| 258 (Ex 162) | 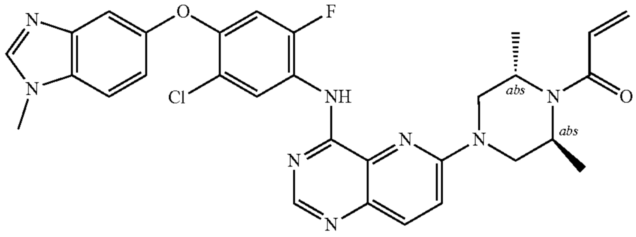 1-((2S,6S)-4-(4-((5-chloro-2-fluoro-4-((1-methyl-1H-benzo[d]imidazol-5-yl)oxy)phenyl)amino)pyrido[3,2-d]pyrimidin-6-yl)-2,6-dimethylpiperazin-1-yl)prop-2-en-1-one | 587.20 | $^1H$ NMR (400 MHz, $CDCl_3$) δ 9.10 (d, J = 8.5 Hz, 1H), 8.68 (s, 1H), 7.89 (s, 1H), 7.43 (d, J = 2.2 Hz, 1H), 7.39 (d, J = 8.7 Hz, 1H), 7.16 (d, J = 9.3 Hz, 1H), 7.11 (dd, J = 8.7, 2.3 Hz, 1H), 6.80 (d, J = 11.8 Hz, 1H), 6.63 (dd, J = 16.6, 10.2 Hz, 1H), 6.48 (dd, J = 16.6, 2.1 Hz, 1H), 5.78 (dd, J = 10.2, 2.1 Hz, 1H), 4.95-4.24 (m, 2H), 4.21-3.76 (m, 7H), 1.39 (d, J = 6.5 Hz, 6H). |
| 259 (Ex 162) | 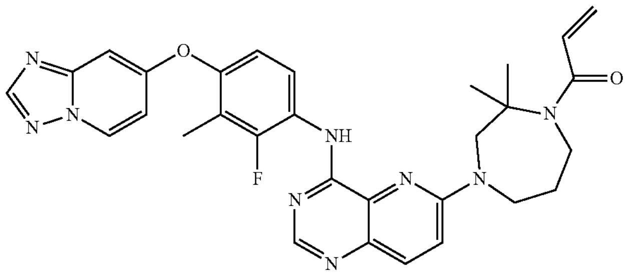 1-(4-(4-((4-([1,2,4]triazol[1,5-a]pyridin-7-yloxy)-2-fluoro-3-methylphenyl)amino)pyrido[3,2-d]pyrimidin-6-yl)-2,2-dimethyl-1,4-diazepan-1-yl)prop-2-en-1-one | 568.30 | $^1H$ NMR (400 MHz, $CDCl_3$) δ 9.13 (d, J = 3.4 Hz, 1H), 8.87 (t, J = 9.1 Hz, 1H), 8.62 (s, 1H), 8.50 (dd, J = 6.6, 1.6 Hz, 1H), 8.23 (s, 1H), 7.96 (d, J = 9.4 Hz, 1H), 7.35-7.27 (m, 1H), 7.00 (dd, J = 9.0, 1.5 Hz, 1H), 6.92-6.85 (m, 2H), 6.51 (dd, J = 16.8, 10.5 Hz, 1H), 6.23 (dd, J = 16.8, 1.8 Hz, 1H), 5.63 (dd, J = 10.4, 1.8 Hz, 1H), 4.04 (s, 2H), 3.86-3.79 (m, 2H), 3.73-3.66 (m, 2H), 2.21 (d, J = 1.9 Hz 3H), 2.13-2.03 (m, 2H), 1.61 (s, 6H). |

TABLE 3-continued

| Example No. (Method) | Structure; IUPAC name | LCMS $M^{+1}$ | $^{1}H$ NMR (ppm); $^{19}F$ NMR (ppm); optical rotation; Chiral HPLC/SFC conditions |
|---|---|---|---|
| 260 (Ex 162) | 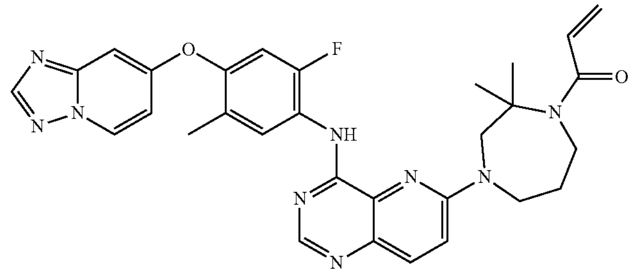 1-(4-(4-((4-([1,2,4]triazolo[1,5-a]pyridin-7-yloxy)-2-fluoro-5-methylphenyl)amino)pyrido[3,2-d]pyrimidin-6-yl)-2,2-dimethyl-1,4-diazepan-1-yl)prop-2-en-1-one | 568.20 | $^{1}H$ NMR (400 MHz, $CDCl_3$) δ 9.09 (d, J = 3.2 Hz, 1H), 8.92 (d, J = 9.1 Hz, 1H), 8.65 (s, 1H), 8.54-8.47 (m, 1H), 8.24 (s, 1H), 7.96 (d, J = 9.4 Hz, 1H), 7.33-7.26 (m, 1H), 6.95 (d, J = 11.1 Hz, 1H), 6.88 (dq, J = 4.4, 2.6 Hz, 2H), 6.50 (dd, J = 16.8, 10.4 Hz, 1H), 6.22 (dd, J = 16.8, 1.7 Hz, 1H), 5.63 (dd, J = 10.5, 1.7 Hz, 1H), 4.02 (s, 1H), 3.85-3.78 (m, 2H), 3.72-3.65 (m, 2H), 2.27 (s, 3H), 2.12-2.03 (m, 2H), 1.60 (s, 6H). |
| 261 (Ex 162) | 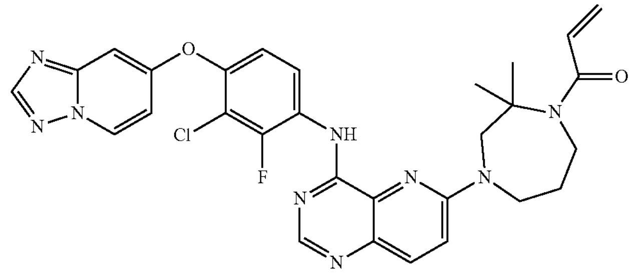 1-(4-(4-((4-([1,2,4]triazolo[1,5-a]pyridin-7-yloxy)-3-chloro-2-fluorophenyl)amino)pyrido[3,2-d]pyrimidin-6-yl)-2,2-dimethyl-1,4-diazepan-1-yl)prop-2-en-1-one | 588.20 | $^{1}H$ NMR (400 MHz, $CDCl_3$) δ 9.15 (d, J = 3.1 Hz, 1H), 9.03 (t, J = 8.9 Hz, 1H), 8.64 (s, 1H), 8.56-8.50 (m, 1H), 8.25 (s, 1H), 7.97 (d, J = 9.4 Hz, 1H), 7.32 (d, J = 9.4 Hz, 1H), 7.15 (dd, J = 9.2, 2.0 Hz, 1H), 6.95-6.88 (m, 2H), 6.51 (dd, J = 16.8, 10.4 Hz, 1H), 6.23 (dd, J = 16.8, 1.8 Hz, 1H), 5.64 (dd, J = 10.5, 1.7 Hz, 1H), 4.02 (s, 2H), 3.88-3.80 (m, 2H), 3.73-3.66 (m, 2H), 2.14-2.04 (m, 2H), 1.61 (s, 6H). |
| 262 (Ex 162) | 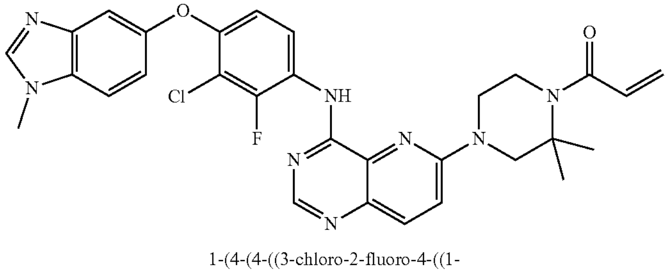 1-(4-(4-((3-chloro-2-fluoro-4-((1-methyl-1H-benzo[d]imidazol-5-yl)oxy)phenyl)amino)pyrido[3,2-d]pyrimidin-6-yl)-2,2-dimethylpiperazin-1-yl)prop-2-en-1-one | 587.20 | $^{1}H$ NMR (400 MHz, $CDCl_3$) δ 9.00 (s, 1H), 8.69 (t, J = 9.0 Hz, 1H), 8.59 (s, 1H), 8.00 (d, J = 9.3 Hz, 1H), 7.90 (s, 1H), 7.41 (d, J = 2.2 Hz, 1H), 7.37 (d, J = 8.7 Hz, 1H), 7.16 (d, J = 9.3 Hz, 1H), 7.11 (dd, J = 8.7, 2.3 Hz, 1H), 6.85 (dd, J = 9.2, 1.9 Hz, 1H), 6.58 (dd, J = 16.8, 10.6 Hz, 1H), 6.26 (dd, J = 16.8, 1.7 Hz, 1H), 5.69 (dd, J = 10.6, 1.8 Hz, 1H), 4.04-3.97 (m, 2H), 3.93-3.80 (m, 7H), 1.62 (s, 6H). |

TABLE 3-continued

| Example No. (Method) | Structure; IUPAC name | LCMS $M^{+1}$ | $^1$H NMR (ppm); $^{19}$F NMR (ppm); optical rotation; Chiral HPLC/SFC conditions |
|---|---|---|---|
| 263 (Ex 162) | 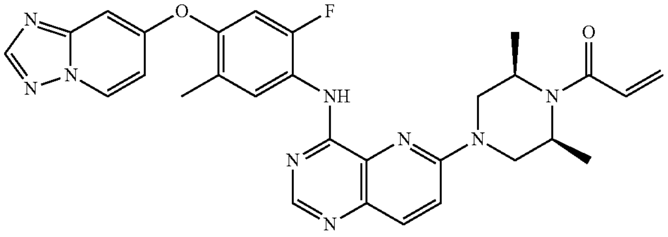 1-((2S,6R)-4-(4-((4-([1,2,4]triazolo[1,5-a]pyridin-7-yloxy)-2-fluoro-4-methylphenyl)amino)pyrido[3,2-d]pyrimidin-6-yl)-2,6-dimethylpiperazin-1-yl)prop-2-en-1-one | 554.30 | $^1$H NMR (400 MHz, $CDCl_3$) δ 9.05 (d, J = 2.9 Hz, 1H), 8.90 (d, J = 9.1 Hz, 1H), 8.67 (s, 1H), 8.51 (dd, J = 6.8, 1.4 Hz, 1H), 8.24 (s, 1H), 8.00 (d, J = 9.3 Hz, 1H), 7.31 (d, J = 9.4 Hz, 1H), 6.96 (d, J = 11.1 Hz, 1H), 6.92-6.85 (m, 2H), 6.64 (dd, J = 16.7, 10.5 Hz, 1H), 6.40 (dd, J = 16.7, 1.8 Hz, 1H), 5.76 (dd, J = 10.5, 1.8 Hz, 1H), 4.98-4.18 (m, 4H), 3.36 (dd, J = 13.4, 4.4 Hz, 2H), 2.27 (s, 3H), 1.50-1.32 (m, 6H). |
| 264 (Ex 162) | 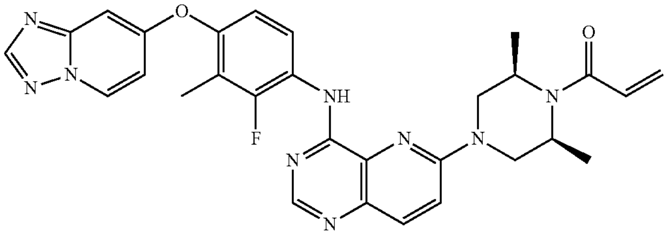 1-((2S,6R)-4-(4-((4-([1,2,4]triazolo[1,5-a]pyridin-7-yloxy)-2-fluoro-3-methylphenyl)amino)pyrido[3,2-d]pyrimidin-6-yl)-2,6-dimethylpiperazin-1-yl)prop-2-en-1-one | 554.20 | $^1$H NMR (400 MHz, $CDCl_3$) δ 9.11 (d, J = 3.3 Hz, 1H), 8.85 (t, J = 9.0 Hz, 1H), 8.64 (s, 1H), 8.51 (d, J = 7.3 Hz, 1H), 8.23 (s, 1H), 8.00 (d, J = 9.3 Hz, 1H), 7.31 (d, J = 9.4 Hz, 1H), 7.01 (d, J = 8.8 Hz, 1H), 6.96-6.84 (m, 2H), 6.65 (dd, J = 16.7, 10.5 Hz, 1H), 6.40 (dd, J = 16.7, 1.8 Hz, 1H), 5.76 (dd, J = 10.5, 1.8 Hz, 1H), 5.02-4.23 (m, 4H), 3.37 (dd, J = 13.4, 4.4 Hz, 2H), 2.21 (d, J = 1.8 Hz, 3H), 1.44-1.38 (m, 6H). |
| 265 (Ex 162) | 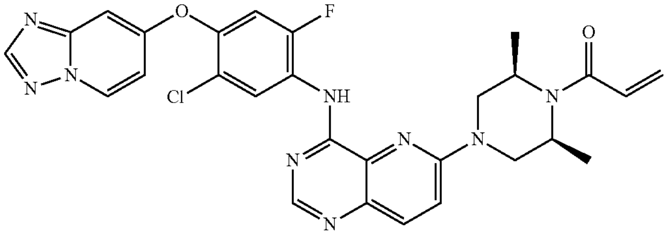 1-((2S,6R)-4-(4-((4-([1,2,4]triazolo[1,5-a]pyridin-7-yloxy)-5-chloro-2-fluorophenyl)amino)pyrido[3,2-d]pyrimidin-6-yl)-2,6-dimethylpiperazin-1-yl)prop-2-en-1-one | 574.20 | $^1$H NMR (400 MHz, $CDCl_3$) δ 9.29 (d, J = 8.4 Hz, 1H), 9.12 (d, J = 3.3 Hz, 1H), 8.69 (s, 1H), 8.57-8.50 (m, 1H), 8.26 (s, 1H), 8.03 (d, J = 9.3 Hz, 1H), 7.18 (d, J = 9.4 Hz, 1H), 7.11 (d, J = 10.9 Hz, 1H), 6.95-6.87 (m, 2H), 6.57 (dd, J = 16.8, 10.6 Hz, 1H), 6.26 (dd, J = 16.8, 1.8 Hz, 1H), 5.69 (dd, J = 10.6, 1.8 Hz, 1H), 4.04-3.96 (m, 2H), 3.91 (s, 2H), 3.88-3.80 (m, 2H), 1.61 (s, 6H). |

TABLE 3-continued

| Example No. (Method) | Structure; IUPAC name | LCMS $M^{+1}$ | $^1H$ NMR (ppm); $^{19}F$ NMR (ppm); optical rotation; Chiral HPLC/SFC conditions |
|---|---|---|---|
| 266 (Ex 162) | 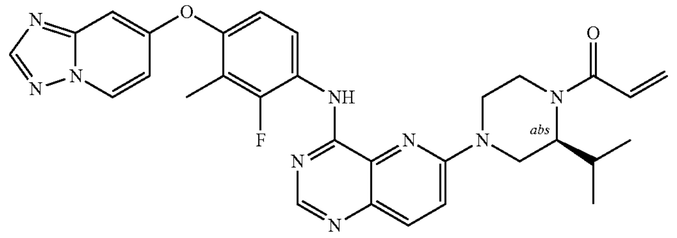 (S)-1-(4-(4-((4-([1,2,4]triazolo[1,5-a]pyridin-7-yloxy)-2-fluoro-3-methylphenyl)amino)pyrido[3,2-d]pyrimidin-6-yl)-2-isopropylpiperazin-1-yl)prop-2-en-1-one | 568.30 | $^1H$ NMR (400 MHz, $CDCl_3$) δ 9.07 (d, J = 3.4 Hz, 1H), 8.85 (t, J = 9.0 Hz, 1H), 8.64 (s, 1H), 8.51 (dd, J = 7.4, 0.7 Hz, 1H), 8.23 (s, 1H), 8.00 (d, J = 9.3 Hz, 1H), 7.27 (d, J = 8.7 Hz, 1H), 7.01 (dd, J = 9.0, 1.6 Hz, 1H), 6.93-6.84 (m, 2H), 6.67 (dd, J = 16.4, 10.7 Hz, 1H), 6.47-6.29 (m, 1H), 5.77 (d, J = 10.5 Hz, 1H), 4.98-4.74 (m, 1H), 4.70-4.58 (m, 1H), 4.54-4.22 (m, 1H), 4.13-3.68 (m, 1H), 3.60-2.92 (m, 3H), 2.40-2.00 (m, 4H), 1.18 (d, J = 5.9 Hz, 3H), 0.90 (d, J = 6.7 Hz, 3H). |
| 267 (Ex 162) | 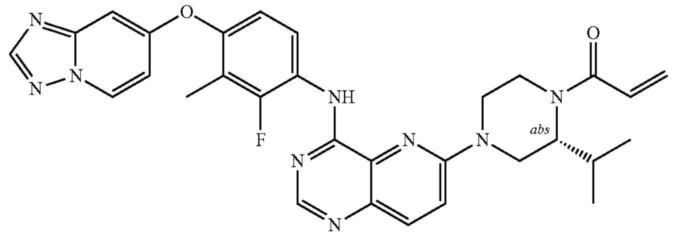 (R)-1-(4-(4-((4-([1,2,4]triazolo[1,5-a]pyridin-7-yloxy)-2-fluoro-3-methylphenyl)amino)pyrido[3,2-d]pyrimidin-6-yl)-2-isopropylpiperazin-1-yl)prop-2-en-1-one | 568.30 | $^1H$ NMR (400 MHz, $CDCl_3$) δ 9.07 (d, J = 3.4 Hz, 1H), 8.85 (t, J = 8.9 Hz, 1H), 8.64 (s, 1H), 8.51 (dd, J = 7.4, 0.8 Hz, 1H), 8.23 (s, 1H), 8.00 (d, J = 9.3 Hz, 1H), 7.27 (d, J = 8.88 Hz, 1H), 7.01 (dd, J = 8.9, 1.7 Hz, 1H), 6.93-6.84 (m, 2H), 6.72-6.61 (m, 1H), 6.46-6.28 (m, 1H), 5.77 (d, J = 10.5 Hz, 1H), 5.01-4.74 (m, 1H), 4.74-4.56 (m, 1H), 4.55-4.21 (m, 1H), 4.11-3.71 (m, 1H), 3.58-2.90 (m, 3H), 2.35-1.98 (m, 4H), 1.18 (d, J = 5.8 Hz, 3H), 0.90 (d, J = 6.7 Hz, 3H). |
| 268 (Ex 162) | 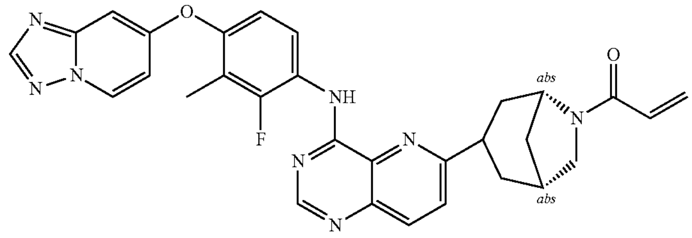 1-((1S,5R)-3-(4-((4-([1,2,4]triazolo[1,5-a]pyridin-7-yloxy)-2-fluoro-3-methylphenyl)amino)pyrido[3,2-d]pyrimidin-6-yl)-3,6-diazabicyclo[3.2.1]octan-6-yl)prop-2-en-1-one | 552.20 | $^1H$ NMR (400 MHz, $CDCl_3$) δ 9.12-9.04 (m, 1H), 8.88-8.76 (m, 1H), 8.66-8.61 (m, 1H), 8.54-8.47 (m, 1H), 8.23 (s, 1H), 8.01-7.92 (m, 1H), 7.26-7.16 (m, 1H), 7.04-6.96 (m, 1H), 6.93-6.86 (m, 2H), 6.68-6.32 (m, 2H), 5.84-5.63 (m, 1H), 4.89-4.13 (m, 3H), 3.82-3.52 (m, 2H), 3.48-3.08 (m, 2H), 2.98-2.76 (m, 1H), 2.23-2.18 (m, 3H), 2.15-1.86 (m, 2H). |
| 269 (Ex 162) | 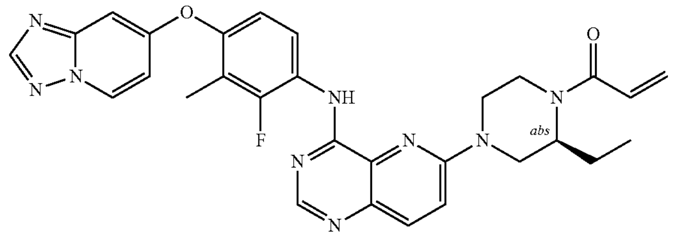 (S)-1-(4-(4-((4-([1,2,4]triazolo[1,5-a]pyridin-7-yloxy)-2-fluoro-3-methylphenyl)amino)pyrido[3,2-d]pyrimidin-6-yl)-2-ethylpiperazin-1-yl)prop-2-en-1-one | 554.30 | $^1H$ NMR (400 MHz, $CDCl_3$) δ 9.08 (d, J = 3.3 Hz, 1H), 8.84 (t, J = 9.0 Hz, 1H), 8.65 (s, 1H), 8.51 (dd, J = 7.4, 0.8 Hz, 1H), 8.23 (s, 1H), 8.00 (d, J = 9.3 Hz, 1H), 7.26 (d, 1H), 7.01 (dd, J = 9.2, 1.5 Hz, 1H), 6.93-6.84 (m, 2H), 6.65 (dd, J = 16.8, 10.5 Hz, 1H), 6.43-6.34 (m, 1H), 5.78 (dd, J = 10.5, 1.8 Hz, 1H), 4.96-3.84 (m, 4H), 3.71-3.06 (m, 3H), 2.21 (d, J = 2.0 Hz, 3H), 1.91-1.65 (m, 2H), 0.99 (t, J = 7.4 Hz, 3H). |

TABLE 3-continued

| Example No. (Method) | Structure; IUPAC name | LCMS $M^{+1}$ | $^1H$ NMR (ppm); $^{19}F$ NMR (ppm); optical rotation; Chiral HPLC/SFC conditions |
|---|---|---|---|
| 270 (Ex 162) | 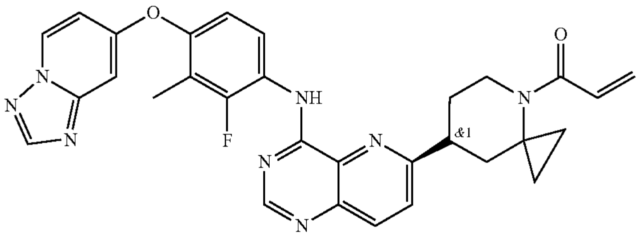 rac-(R)-1-(7-(4-((4-([1,2,4]triazolo[1,5-a]pyridin-7-yloxy)-2-fluoro-3-methylphenyl)amino)pyrido[3,2-d]pyrimidin-6-yl)-4-azaspiro[2.5]octan-4-yl)prop-2-en-1-one | 551.20 | $^1H$ NMR (400 MHz, $CDCl_3$) δ 9.41 (s, 1H), 8.82-8.70 (m, 2H), 8.52 (d, J = 7.8 Hz, 1H), 8.24 (s, 1H), 8.14 (d, J = 8.6 Hz, 1H), 7.64 (d, J = 8.7 Hz, 1H), 7.10-6.80 (m, 4H), 6.41 (d, J = 16.2 Hz, 1H), 5.74 (d, J = 10.5 Hz, 1H), 4.94-4.71 (m, 1H), 3.62-2.91 (m, 2H), 2.54-1.82 (m, 5H), 1.54-1.08 (m, 2H), 0.91-0.70 (m, 4H). |
| 271 (Ex 162) | 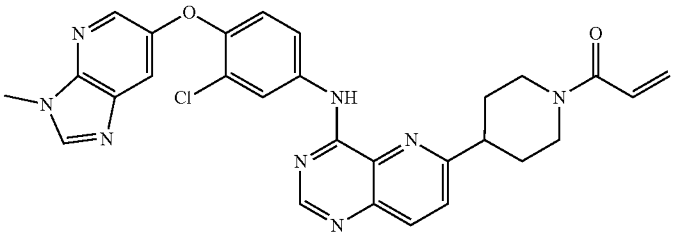 1-(4-(4-((3-chloro-4-((3-methyl-3H-imidazo[4,5-b]pyridin-6-yl)oxy)phenyl)amino)pyrido[3,2-d]pyrimidin-6-yl)piperazin-1-yl)prop-2-en-1-one | 541.10 | $^1H$ NMR (400 MHz, $CDCl_3$) δ 9.05 (s, 1H), 8.78 (s, 1H), 8.34 (d, J = 2.4 Hz, 1H), 8.26 (d, J = 2.5 Hz, 1H), 8.15 (d, J = 8.7 Hz, 1H), 8.05 (s, 1H), 7.76 (dd, J = 8.8, 2.5 Hz, 1H), 7.68-7.61 (m, 2H), 7.04 (d, J = 8.8 Hz, 1H), 6.34 (dd, J = 16.8, 1.7 Hz, 1H), 5.74 (dd, J = 10.5, 1.7 Hz, 1H), 4.92 (d, J = 12.2 Hz, 1H), 4.22 (d, J = 12.0 Hz, 1H), 3.94 (s, 3H), 3.40-3.11 (m, 2H), 2.90-2.80 (m, 1H), 2.22-2.05 (m, 3H), 1.99-1.85 (m, 2H), 1.57 (s, 3H). |
| 272 (Ex 166) | 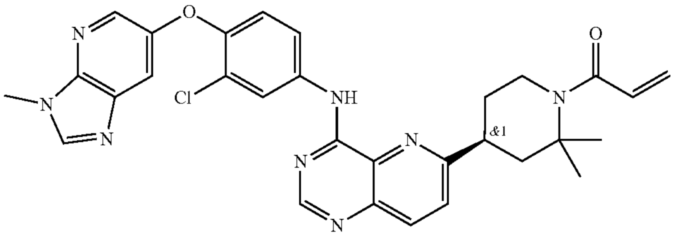 rac-(R)-1-(4-(4-((3-chloro-4-((3-methyl-3H-imidazo[4,5-b]pyridin-6-yl)oxy)phenyl)amino)pyrido[3,2-d]pyrimidin-6-yl)-2,2-dimethylpiperidin-1-yl)prop-2-en-1-one | 569.20 | $^1H$ NMR (400 MHz, $CDCl_3$) δ 9.07 (s, 1H), 8.78 (s, 1H), 8.34 (s, 1H), 8.24 (s, 1H), 8.15 (d, J = 8.6 Hz, 1H), 8.05 (s, 1H), 7.76 (d, J = 8.4 Hz, 1H), 7.70-7.62 (m, 2H), 7.05 (d, J = 8.8 Hz, 1H), 6.57 (dd, J = 16.8, 10.5 Hz, 1H), 6.19 (d, J = 16.8 Hz, 1H), 5.62 (d, J = 10.4 Hz, 1H), 4.00-3.80 (m, 4H), 3.49-3.29 (m, 2H), 2.92-1.97 (m, 3H), 1.87-1.77 (m, 1H), 1.69 (s, 3H), 1.60 (s, 3H). |
| 273 (Ex 166) | 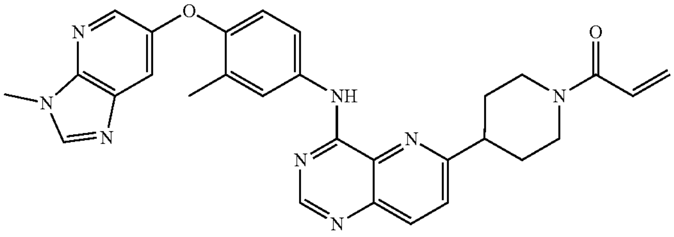 1-(4-(4-((3-methyl-4-((3-methyl-3H-imidazo[4,5-b]pyridin-6-yl)oxy)phenyl)amino)pyrido[3,2-d]pyrimidin-6-yl)piperidin-1-yl)prop-2-en-1-one | 521.30 | $^1H$ NMR (400 MHz, $CDCl_3$) δ 9.02 (s, 1H), 8.74 (s, 1H), 8.31 (d, J = 2.5 Hz, 1H), 8.12 (d, J = 8.6 Hz, 1H), 8.03 (s, 1H), 7.81 (d, J = 2.5 Hz, 1H), 7.75 (dd, J = 8.7, 2.7 Hz, 1H), 7.65-7.57 (m, 2H), 6.93 (d, J = 8.7 Hz, 1H), 6.34 (dd, J = 16.8, 1.9 Hz, 1H), 5.74 (dd, J = 10.6, 1.9 Hz, 1H), 4.92 (d, J = 12.8 Hz, 1H), 4.22 (d, J = 12.9 Hz, 1H), 3.93 (s, 3H), 3.37-3.10 (m, 2H), 2.91-2.80 (m, 1H), 2.38 (s, 3H), 2.15-2.07 (m, 2H), 2.01-1.86 (m, 2H). |

TABLE 3-continued

| Example No. (Method) | Structure; IUPAC name | LCMS $M^{+1}$ | $^{1}H$ NMR (ppm); $^{19}F$ NMR (ppm); optical rotation; Chiral HPLC/SFC conditions |
| --- | --- | --- | --- |
| 274 (Ex 162) | 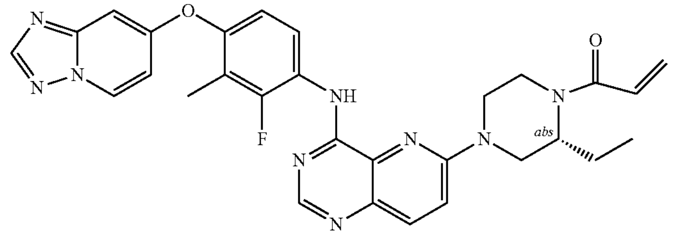 (R)-1-(4-(4-((4-([1,2,4]triazolo[1,5-a]pyridin-7-yloxy)-2-fluoro-3-methylphenyl)amino)pyrido[3,2-d]pyrimidin-6-yl)-2-ethylpiperazin-1-yl)prop-2-en-1-one | 554.30 | $^{1}H$ NMR (400 MHz, $CDCl_3$) δ 9.08 (d, J = 3.3 Hz, 1H), 8.84 (t, J = 9.0 Hz, 1H), 8.64 (s, 1H), 8.51 (dd, J = 7.4, 0.7 Hz, 1H), 8.23 (s, 1H), 8.00 (d, J = 9.3 Hz, 1H), 7.31-7.26 (m, 1H), 7.01 (dd, J = 9.0, 1.6 Hz, 1H), 6.93-6.84 (m, 2H), 6.65 (dd, J = 16.8, 10.5 Hz, 1H), 6.43-6.34 (m, 1H), 5.78 (dd, J = 10.5, 1.8 Hz, 1H), 5.06-3.79 (m, 4H), 3.72-3.00 (m, 3H), 2.21 (d, J = 2.0 Hz, 3H), 1.79-1.74 (m, 2H), 0.99 (t, J = 7.4 Hz, 3H). |
| 275 (Ex 162) | 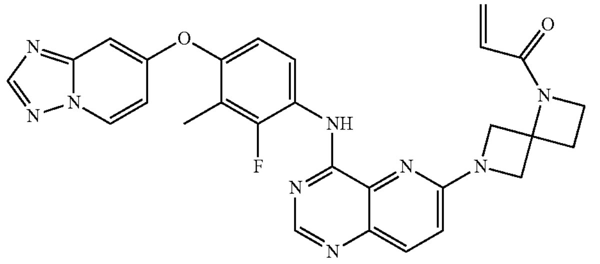 1-(6-(4-((4-([1,2,4]triazolo[1,5-a]pyridin-7-yloxy)-2-fluoro-3-methylphenyl)amino)pyrido[3,2-d]pyrimidin-6-yl)-1,6-diazaspiro[3.3]heptan-1-yl)prop-2-en-1-one | 538.20 | $^{1}H$ NMR (400 MHz, $CDCl_3$) δ 9.19-9.10 (m, 1H), 8.87-8.78 (m, 1H), 8.68-8.59 (m, 1H), 8.54-8.47 (m, 1H), 8.23 (s, 1H), 8.04-7.88 (m, 1H), 7.03-6.85 (m, 4H), 6.61-6.31 (m, 1H), 6.17 (dd, J = 16.9, 10.3 Hz, 1H), 5.78-5.63 (m, 1H), 5.07 (d, J = 9.5 Hz, 2H), 4.73-4.40 (m, 1H), 4.33-3.98 (m, 3H), 2.72-2.57 (m, 2H), 2.22-2.16 (m, 3H). |
| 276 (Ex 162) | 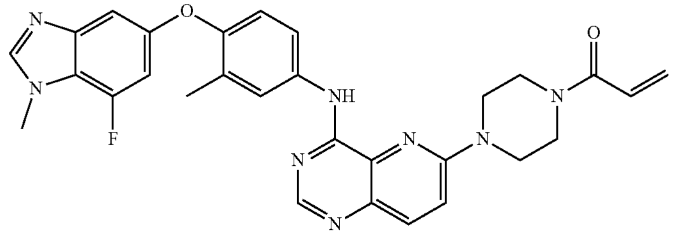 1-(4-(4-((4-((7-fluoro-1-methyl-1H-benzo[d]imidazol-5-yl)oxy)-3-methylphenyl)amino)pyrido[3,2-d]pyrimidin-6-yl)piperazin-1-yl)prop-2-en-1-one | 539.30 | $^{1}H$ NMR (400 MHz, $CDCl_3$) δ 8.62-8.58 (m, 2H), 7.99 (d, J = 9.3 Hz, 1H), 7.77-7.73 (m, 2H), 7.70 (dd, J = 8.6, 2.7 Hz, 1H), 7.31-7.26 (m, 1H), 7.04 (d, J = 2.0 Hz, 1H), 7.00 (d, J = 8.6 Hz, 1H), 6.75 (dd, J = 12.2, 2.0 Hz, 1H), 6.64 (dd, J = 16.8, 10.5 Hz, 1H), 6.38 (dd, J = 16.8, 1.8 Hz, 1H), 5.79 (dd, J = 10.5, 1.8 Hz, 1H), 4.00 (s, 3H), 3.96-3.66 (m, 8H), 2.31 (s, 2H). |
| 277 (Ex 162) | 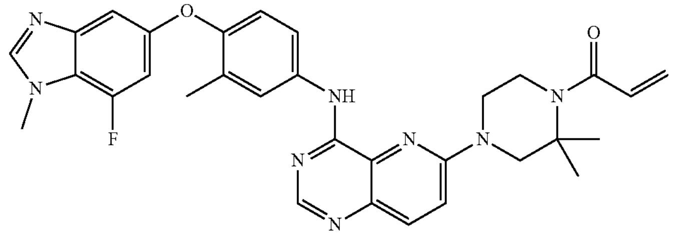 1-(4-(4-((4-((7-fluoro-1-methyl-1H-benzo[d]imidazol-5-yl)oxy)-3-methylphenyl)amino)pyrido[3,2-d]pyrimidin-6-yl)-2,2-dimethylpiperazin-1-yl)prop-2-en-1-one | 567.30 | $^{1}H$ NMR (400 MHz, $CDCl_3$) δ 8.64-8.57 (m, 2H), 7.98 (d, J = 9.3 Hz, 1H), 7.78-7.72 (m, 2H), 7.68 (dd, J = 8.6, 2.7 Hz, 1H), 7.13 (d, J = 9.3 Hz, 1H), 7.04 (d, J = 2.0 Hz, 1H), 7.00 (d, J = 8.7 Hz, 1H), 6.75 (dd, J = 12.2, 2.0 Hz, 1H), 6.57 (dd, J = 16.8, 10.6 Hz, 1H), 6.25 (dd, J = 16.8, 1.8 Hz, 1H), 5.69 (dd, J = 10.6, 1.8 Hz, 1H), 4.03-3.96 (m, 5H), 3.90-3.80 (m, 4H), 2.31 (s, 3H), 1.62 (s, 6H). |

TABLE 3-continued

| Example No. (Method) | Structure; IUPAC name | LCMS $M^{+1}$ | $^{1}H$ NMR (ppm); $^{19}F$ NMR (ppm); optical rotation; Chiral HPLC/SFC conditions |
|---|---|---|---|
| 278 (Ex 162) | 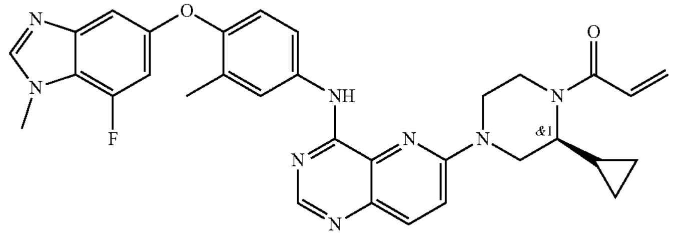 Rac-1-(2-cyclopropyl-4-(4-((4-((7-fluoro-1-methyl-1H-benzo[d]imidazol-5-yl)oxy)-3-methylphenyl)amino)pyrido[3,2-d]pyrimidin-6-yl)piperazin-1-yl)prop-2-en-1-one | 579.30 | $^{1}H$ NMR (400 MHz, $CDCl_3$) δ 8.65-8.56 (m, 2H), 7.97 (d, J = 9.3 Hz, 1H), 7.80-7.73 (m, 2H), 7.69 (dd, J = 8.7, 2.7 Hz, 1H), 7.32 (d, J = 9.4 Hz, 1H), 7.04 (d, J = 2.0 Hz, 1H), 7.00 (d, J = 8.7 Hz, 1H), 6.75 (dd, J = 12.2, 2.0 Hz, 1H), 6.65-6.54 (m, 1H), 6.36 (d, J = 15.3 Hz, 1H), 5.76 (dd, J = 10.5, 1.7 Hz, 1H), 4.59 (d, J = 12.1 Hz, 1H), 4.48 (d, J = 12.3 Hz, 1H), 4.40-3.40 (m, 3H), 4.00 (d, J = 0.9 Hz, 3H), 3.32 (dd, J = 13.0, 3.6 Hz, 1H), 3.16 (td, J = 12.7, 3.6 Hz, 1H), 2.31 (s, 3H), 1.35 (s, 1H), 0.72-0.38 (m, 4H). |
| 279 (Ex 166) | 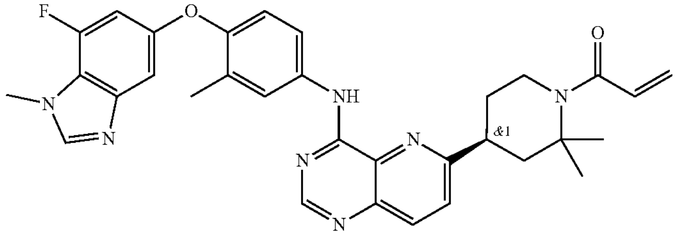 rac-1-(4-(4-((4-((7-fluoro-1-methyl-1H-benzo[d]imidazol-5-yl)oxy)-3-methylphenyl)amino)pyrido[3,2-d]pyrimidin-6-yl)-2,2-dimethylpiperidin-1-yl)prop-2-en-1-one | 566.30 | $^{1}H$ NMR (400 MHz, $CDCl_3$) δ 9.04 (s, 1H), 8.75 (s, 1H), 8.12 (d, J = 8.6 Hz, 1H), 7.81 (d, J = 2.2 Hz, 1H), 7.78-7.70 (m, 2H), 7.64 (d, J = 8.6 Hz, 1H), 7.05 (d, J = 1.9 Hz, 1H), 7.01 (d, J = 8.7 Hz, 1H), 6.76 (dd, J = 12.2, 1.8 Hz, 1H), 6.57 (dd, J = 16.9, 10.5 Hz, 1H), 6.20 (dd, J = 16.9, 1.7 Hz, 1H), 5.62 (dd, J = 10.5, 1.7 Hz, 1H), 4.00 (s, 3H), 3.95-3.84 (m, 1H), 3.49-3.28 (m, 2H), 2.33 (s, 3H), 2.24-2.14 (m, 1H), 2.12-1.99 (m, 2H), 1.91-1.79 (m, 1H), 1.69 (s, 3H), 1.60 (s, 3H). |
| 280 (Ex 166) | 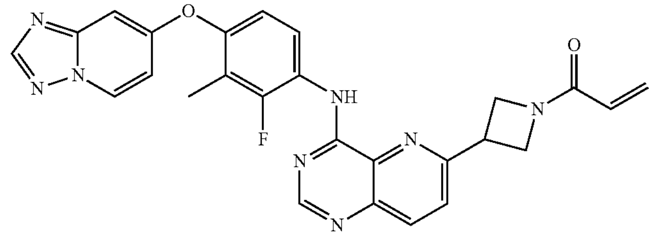 1-(3-(4-((4-([1,2,4]triazolo[1,5-a]pyridin-7-yloxy)-2-fluoro-3-methylphenyl)amino)propyl[3,2-d]pyrimidin-6-yl)azetidin-1-yl)prop-2-en-1-one | 497.20 | $^{1}H$ NMR (400 MHz, $CDCl_3$) δ 9.42 (d, J = 2.8 Hz, 1H), 8.83 (s, 1H), 8.76 (t, J = 8.9 Hz, 1H), 8.55-8.49 (m, 1H), 8.26-8.18 (m, 2H), 7.70 (d, J = 8.6 Hz, 1H), 7.02 (dd, J = 9.0, 1.5 Hz, 1H), 6.93-6.87 (m, 2H), 6.43 (dd, J = 17.0, 2.1 Hz, 1H), 6.32 (dd, J = 17.0, 10.1 Hz, 1H), 5.75 (dd, J = 10.1, 2.1 Hz, 1H), 4.90-4.53 (m, 3H), 4.44 (dd, J = 10.0, 6.0 Hz, 1H), 4.23 (tt, J = 8.8, 5.9 Hz, 1H), 2.21 (d, J = 2.0 Hz, 3H). |
| 281 (Ex 162) | 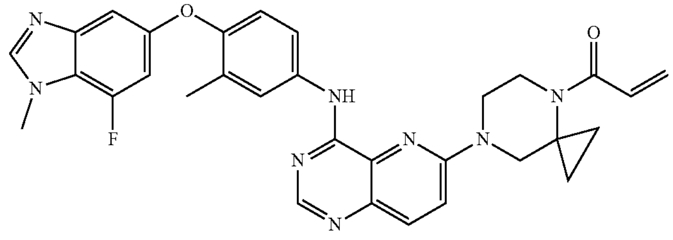 1-(7-(4-((4-((7-fluoro-1-methyl-1H-benzo[d]imidazol-5-yl)oxy)-3-methylphenyl)amino)pyrido[3,2-d]pyrimidin-6-yl)-4,7-diazaspiro[2.5]octan-4-yl)prop-2-en-1-one | 565.30 | $^{1}H$ NMR (400 MHz, $CDCl_3$) δ 8.60 (s, 1H), 8.54 (s, 1H), 7.96 (d, J = 9.3 Hz, 1H), 7.77-7.71 (m, 2H), 7.67 (dd, J = 8.6, 2.7 Hz, 1H), 7.24-7.18 (m, 1H), 7.04 (d, J = 2.0 Hz, 1H), 7.00 (d, J = 8.6 Hz, 1H), 6.75 (dd, J = 12.2, 2.0 Hz, 1H), 6.42 (d, J = 15.5 Hz, 1H), 5.77 (dd, J = 10.4, 1.8 Hz, 1H), 4.08-3.93 (m, 5H), 3.85-3.80 (m, 2H), 3.62 (s, 2H), 2.31 (s, 3H), 1.19-1.11 (m, 4H). |

TABLE 3-continued

| Example No. (Method) | Structure; IUPAC name | LCMS $M^{+1}$ | $^{1}H$ NMR (ppm); $^{19}F$ NMR (ppm); optical rotation; Chiral HPLC/SFC conditions |
|---|---|---|---|
| 282 (Ex 162) | 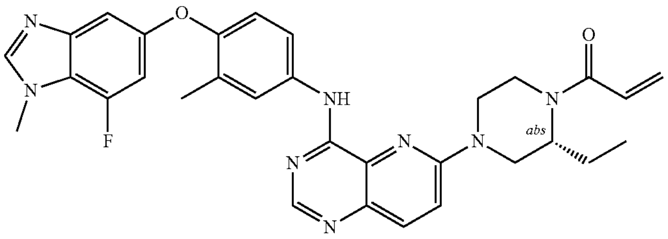 (R)-1-(2-ethyl-4-(4-((4-((7-fluoro-1-methyl-1H-benzo[d]imidazol-5-yl)oxy)-3-methylphenyl)amino)pyrido[3,2-d]pyrimidin-6-yl)piperazin-1-yl)prop-2-en-1-one | 567.30 | $^{1}H$ NMR (400 MHz, $CDCl_3$) δ 8.62-8.57 (m, 2H), 7.97 (d, J = 9.3 Hz, 1H), 7.78-7.73 (m, 2H), 7.68 (dd, J = 8.6, 2.6 Hz, 1H), 7.26 (d, 1H), 7.04 (d, J = 2.0 Hz, 1H), 7.00 (d, J = 8.7 Hz, 1H), 6.75 (dd, J = 12.2, 2.0 Hz, 1H), 6.64 (dd, J = 16.8, 10.5 Hz, 1H), 6.43-6.35 (m, 1H), 5.77 (dd, J = 10.5, 1.9 Hz, 1H), 4.94-4.05 (m, 4H), 4.00 (s, 3H), 2.31 (s, 3H), 1.91-1.60 (m, 2H), 0.98 (t, J = 7.4 Hz, 3H). |
| 283 (Ex 162) | 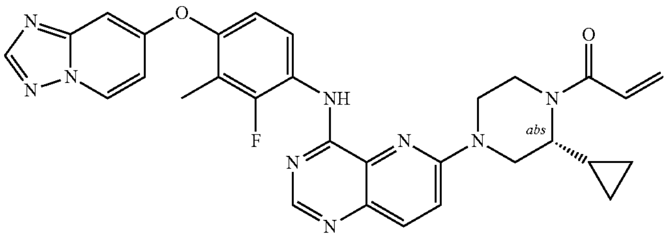 (R)-1-(4-(4-((4-([1,2,4]triazolo[1,5-a]pyridin-7-yloxy)-2-fluoro-3-methylphenyl)amino)pyrido[3,2-d]pyrimidin-6-yl)-2-cyclopropylpiperazin-1-yl)prop-2-en-1-one | 566.25 | $^{1}H$ NMR (400 MHz, $CDCl_3$) δ 9.11 (d, J = 3.3 Hz, 1H), 8.84 (t, J = 9.0 Hz, 1H), 8.65 (s, 1H), 8.51 (dd, J = 7.3, 0.7 Hz, 1H), 8.24 (s, 1H), 8.00 (d, J = 9.3 Hz, 1H), 7.34 (d, J = 9.4 Hz, 1H), 7.05-6.98 (m, 1H), 6.93-6.85 (m, 2H), 6.69-6.53 (m, 1H), 6.37 (d, J = 15.2 Hz, 1H), 5.80-5.73 (m, 1H), 4.58 (s, 2H), 3.35 (dd, J = 13.1, 3.6 Hz, 1H), 3.24-3.14 (m, 1H), 2.21 (s, 3H), 1.40-1.18 (m, 1H), 0.71-0.44 (m, 4H). |
| 284 (Ex 162) | 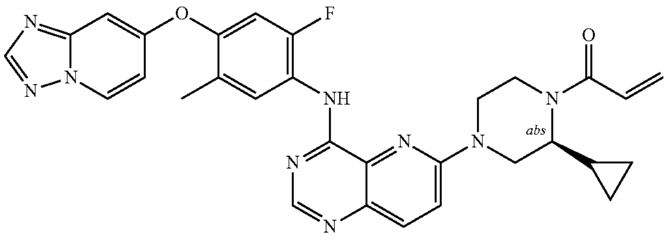 (S)-1-(4-(4-((4-([1,2,4]triazolo[1,5-a]pyridin-7-yloxy)-2-fluoro-5-methylphenyl)amino)pyrido[3,2-d]pyrimidin-6-yl)-2-cyclopropylpiperazin-1-yl)prop-2-en-1-one | 566.25 | $^{1}H$ NMR (400 MHz, $CDCl_3$) δ 9.05 (d, J = 3.0 Hz, 1H), 8.90 (d, J = 9.1 Hz, 1H), 8.67 (s, 1H), 8.55-8.48 (m, 1H), 8.24 (s, 1H), 8.00 (d, J = 9.3 Hz, 1H), 7.37-7.29 (m, 1H), 6.96 (d, J = 11.1 Hz, 1H), 6.90-6.86 (m, 2H), 6.66-6.55 (m, 1H), 6.36 (dd, J = 16.7, 1.5 Hz, 1H), 5.76 (dd, J = 10.5, 1.8 Hz, 1H), 4.66-4.43 (m, 2H), 3.34 (dd, J = 13.1, 3.7 Hz, 1H), 3.18 (td, J = 12.7, 3.5 Hz, 1H), 2.27 (s, 3H), 1.37-1.24 (m, 1H), 0.73-0.40 (m, 4H). |
| 285 (Ex 162) | 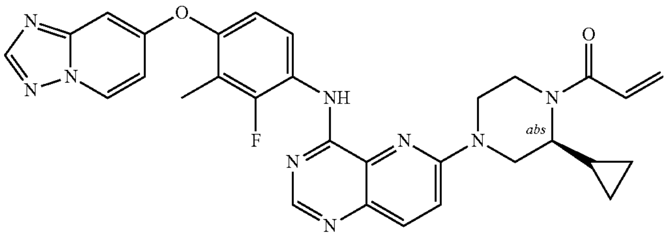 (S)-1-(4-(4-((4-([1,2,4]triazolo[1,5-a]pyridin-7-yloxy)-2-fluoro-3-methylphenyl)amino)pyrido[3,2-d]pyrimidin-6-yl)-2-cyclopropylpiperazin-1-yl)prop-2-en-1-one | 566.25 | $^{1}H$ NMR (400 MHz, $CDCl_3$) δ 9.11 (d, J = 3.3 Hz, 1H), 8.84 (t, J = 9.0 Hz, 1H), 8.65 (s, 1H), 8.51 (dd, J = 7.3, 0.8 Hz, 1H), 8.24 (s, 1H), 8.00 (d, J = 9.3 Hz, 1H), 7.34 (d, J = 9.4 Hz, 1H), 7.01 (dd, J = 8.8, 1.5 Hz, 1H), 6.93-6.85 (m, 2H), 6.67-6.56 (m, 1H), 6.37 (dd, J = 16.7, 1.6 Hz, 1H), 5.76 (dd, J = 10.5, 1.7 Hz, 1H), 4.68-4.44 (m, 2H), 3.35 (dd, J = 13.1, 3.6 Hz, 1H), 3.19 (td, J = 12.6, 3.4 Hz, 1H), 2.21 (s, 3H), 1.41-1.23 (m, 1H), 0.72-0.40 (m, 4H). |

TABLE 3-continued

| Example No. (Method) | Structure; IUPAC name | LCMS $M^{+1}$ | $^1H$ NMR (ppm); $^{19}F$ NMR (ppm); optical rotation; Chiral HPLC/SFC conditions |
|---|---|---|---|
| 286 (Ex 162) | 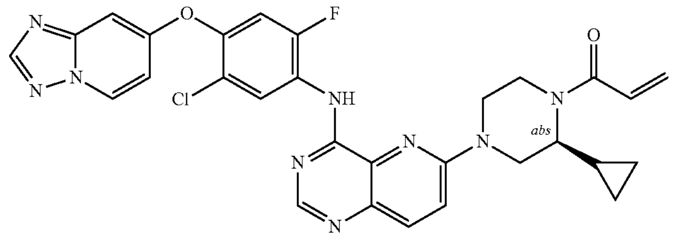 (S)-1-(4-(4-((4-([1,2,4]triazolo[1,5-a]pyridin-7-yloxy)-5-chloro-2-fluorophenyl)amino)pyrido[3,2-d]pyrimidin-6-yl)-2-cyclopropylpiperazin-1-yl)prop-2-en-1-one | 586.10 | $^1H$ NMR (400 MHz, $CDCl_3$) δ 9.30 (d, J = 8.4 Hz, 1H), 9.11 (d, J = 3.4 Hz, 1H), 8.71 (s, 1H), 8.57-8.50 (m, 1H), 8.26 (s, 1H), 8.02 (d, J = 9.4 Hz, 1H), 7.36 (d, J = 9.4 Hz, 1H), 7.12 (d, J = 10.9 Hz, 1H), 6.95-6.88 (m, 2H), 6.66-6.54 (m, 1H), 6.36 (dd, J = 16.8, 1.6 Hz, 1H), 5.76 (dd, J = 10.5, 1.7 Hz, 1H), 4.65-4.45 (m, 2H), 3.35 (dd, J = 13.2, 3.7 Hz, 1H), 3.19 (td, J = 12.7, 3.5 Hz, 1H), 1.39-1.21 (m, 1H), 0.71-0.36 (m, 4H). |
| 287 (Ex 162) | 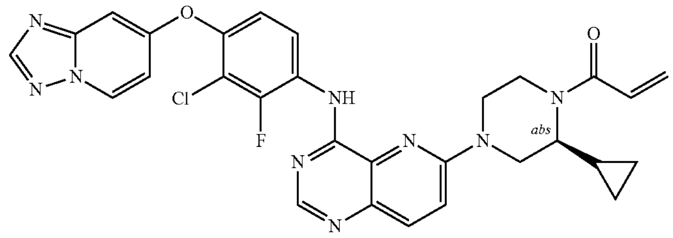 (S)-1-(4-(4-((4-([1,2,4]triazolo[1,5-a]pyridin-7-yloxy)-3-chloro-2-fluorophenyl)amino)pyrido[3,2-d]pyrimidin-6-yl)-2-cyclopropylpiperazin-1-yl)prop-2-en-1-one | 586.20 | $^1H$ NMR (400 MHz, $CDCl_3$) δ 9.13 (d, J = 3.0 Hz, 1H), 9.01 (t, J = 8.9 Hz, 1H), 8.66 (s, 1H), 8.54 (dd, J = 7.2, 0.8 Hz, 1H), 8.25 (s, 1H), 8.02 (d, J = 9.4 Hz, 1H), 7.36 (d, J = 9.4 Hz, 1H), 7.16 (dd, J = 9.2, 1.9 Hz, 1H), 6.96-6.88 (m, 2H), 6.69-6.53 (m, 1H), 6.37 (d, J = 15.5 Hz, 1H), 5.81-5.73 (m, 1H), 4.79-4.36 (m, 2H), 3.35 (dd, J = 13.1, 3.7 Hz, 1H), 3.23-3.15 (m, 1H), 1.40-1.19 (m, 1H), 0.71-0.42 (m, 4H). |
| 288 (Ex 162) | 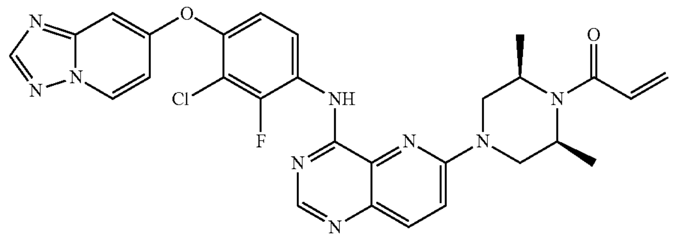 1-((2S,6R)-4-(4-((4-([1,2,4]triazolo[1,5-a]pyridin-7-yloxy)-3-chloro-2-fluorophenyl)amino)pyrido[3,2-d]pyrimidin-6-yl)-2,6-dimethylpiperazin-1-yl)prop-2-en-1-one | 574.20 | 1H NMR (400 MHz, CDCl3) δ 9.13 (d, J = 3.2 Hz, 1H), 9.01 (t, J = 8.9 Hz, 1H), 8.66 (s, 1H), 8.53 (dd, J = 7.2, 1.0 Hz, 1H), 8.25 (s, 1H), 8.02 (d, J = 9.4 Hz, 1H), 7.33 (d, J = 9.4 Hz, 1H), 7.16 (dd, J = 9.2, 2.0 Hz, 1H), 6.96-6.88 (m, 2H), 6.65 (dd, J = 16.7, 10.5 Hz, 1H), 6.40 (dd, J = 16.7, 1.9 Hz, 1H), 5.77 (dd, J = 10.5, 1.9 Hz, 1H), 4.88-4.08 (m, 4H), 3.38 (dd, J = 13.4, 4.4 Hz, 2H), 1.41 (d, J = 6.9 Hz, 6H). |

TABLE 3-continued

| Example No. (Method) | Structure; IUPAC name | LCMS $M^{+1}$ | $^1H$ NMR (ppm); $^{19}F$ NMR (ppm); optical rotation; Chiral HPLC/SFC conditions |
|---|---|---|---|
| 289 (ex 162) | 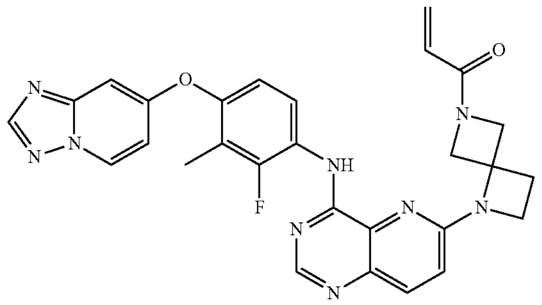 1-(1-(4-((4-([1,2,4]triazolo[1,5-a]pyridin-7-yloxy)-2-fluoro-3-methylphenyl)amino)pyrido[3,2-d]pyrimidin-6-yl)-1,6-diazaspiro[3.3]heptan-6-yl)prop-2-en-1-one | 538.20 | $^1H$ NMR (400 MHz, $CDCl_3$) δ 9.02 (d, J = 2.9 Hz, 1H), 8.70 (t, J = 9.0 Hz, 1H), 8.62 (s, 1H), 8.49 (dd, J = 7.3, 0.8 Hz, 1H), 8.23 (s, 1H), 7.99 (d, J = 9.1 Hz, 1H), 6.96 (dd, J = 9.0, 1.6 Hz, 1H), 6.90-6.79 (m, 3H), 6.44-6.27 (m, 2H), 5.70 (dd, J = 9.0, 3.3 Hz, 1H), 5.30 (s, 1H), 5.06 (d, J = 11.0 Hz, 1H), 4.30 (dd, J = 20.4, 10.1 Hz, 2H), 4.12 (q, J = 6.4 Hz, 2H), 2.73 (t, J = 7.1 Hz, 2H), 2.11 (d, J = 1.9 Hz, 3H). |
| 290 (Ex 162) | 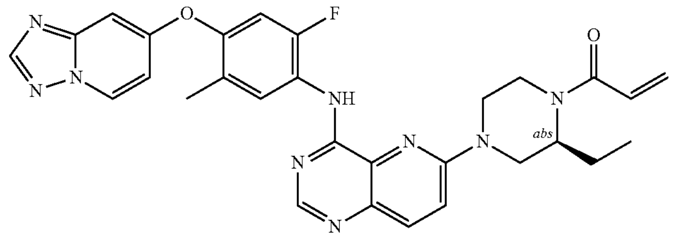 (S)-1-(4-(4-((4-([1,2,4]triazolo[1,5-a]pyridin-7-yloxy)-2-fluoro-5-methylphenyl)amino)pyrido[3,2-d]pyrimidin-6-yl)-2-ethylpiperazin-1-yl)prop-2-en-1-one | 554.30 | $^1H$ NMR (400 MHz, $CDCl_3$) δ 9.02 (d, J = 3.0 Hz, 1H), 8.89 (d, J = 9.1 Hz, 1H), 8.67 (s, 1H), 8.51 (dd, J = 6.6, 1.6 Hz, 1H), 8.24 (s, 1H), 8.00 (d, J = 9.3 Hz, 1H), 7.26 (d, 1H), 6.95 (d, J = 11.1 Hz, 1H), 6.92-6.85 (m, 2H), 6.64 (dd, J = 16.8, 10.5 Hz, 1H), 6.42-6.34 (m, 1H), 5.77 (dd, J = 10.5, 1.8 Hz, 1H), 5.05-3.87 (m, 4H), 3.64-3.15 (m, 3H), 2.27 (s, 3H), 1.89-1.66 (m, 2H), 0.98 (t, J = 7.4 Hz, 3H). |
| 291 (Ex 162) | 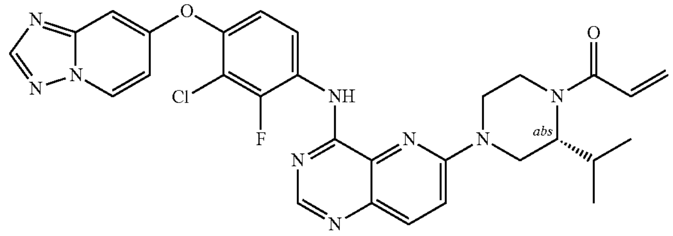 (R)-1-(4-(4-((4-([1,2,4]triazolo[1,5-a]pyridin-7-yloxy)-3-chloro-2-fluorophenyl)amino)pyrido[3,2-d]pyrimidin-6-yl)-2-isopropylpiperazin-1-yl)prop-2-en-1-one | 588.20 | $^1H$ NMR (400 MHz, $CDCl_3$) δ 9.09 (d, J = 3.0 Hz, 1H), 9.02 (t, J = 8.8 Hz, 1H), 8.66 (s, 1H), 8.53 (d, J = 7.3 Hz, 1H), 8.25 (s, 1H), 8.01 (d, J = 9.4 Hz, 1H), 7.26 (d, 1H), 7.16 (dd, J = 9.2, 1.8 Hz, 1H), 6.96-6.88 (m, 2H), 6.66 (dd, J = 16.2, 10.4 Hz, 1H), 6.48-6.30 (m, 1H), 5.78 (d, J = 10.5 Hz, 1H), 5.00-4.74 (m, 1H), 4.69-4.41 (m, 1H), 4.35-3.96 (m, 1H), 3.87-3.38 (m, 1H), 3.33-2.92 (m, 3H), 2.37-1.99 (m, 1H), 1.22-1.15 (m, 3H), 0.94-0.87 (m, 3H). |

TABLE 3-continued

| Example No. (Method) | Structure; IUPAC name | LCMS $M^{+1}$ | $^1$H NMR (ppm); $^{19}$F NMR (ppm); optical rotation; Chiral HPLC/SFC conditions |
|---|---|---|---|
| 292 (Ex 162) | 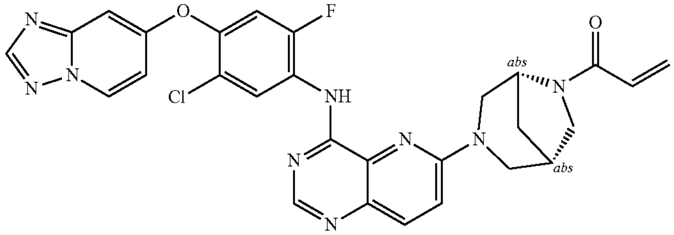 1-((1S,5R)-3-(4-((4-([1,2,4]triazolo[1,5-a]pyridin-7-yloxy)-5-chloro-2-fluorophenyl)amino)pyrido[3,2-d]pyrimidin-6-yl)-3,6-diazabicyclo[3.2.1]octan-6-yl)prop-2-en-1-one | 572.20 | $^1$H NMR (400 MHz, $CDCl_3$) δ 9.32-9.23 (m, 1H), 9.12-9.04 (m, 1H), 8.72-8.66 (m, 1H), 8.57-8.50 (m, 1H), 8.26 (s, 1H), 8.03-7.94 (m, 1H), 7.28-7.17 (m, 1H), 7.10 (d, J = 10.8 Hz, 1H), 6.95-6.87 (m, 2H), 6.65-6.33 (m, 2H), 5.85-5.57 (m, 1H), 4.84-4.78 (m, 1H), 4.57-4.12 (m, 2H), 3.83-3.48 (m, 2H), 3.40 (d, J = 12.4 Hz, 1H), 3.29-3.14 (m, 1H), 2.96-2.75 (m, 1H), 2.32-1.83 (m, 2H). |
| 293 (Ex 162) | 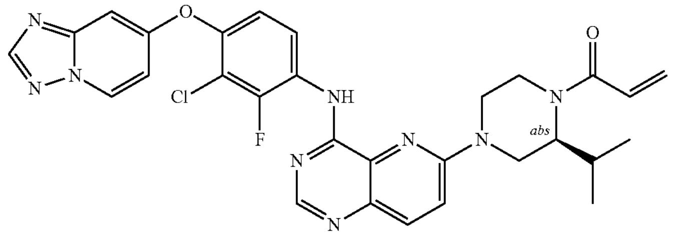 (S)-1-(4-(4-((4-([1,2,4]triazolo[1,5-a]pyridin-7-yloxy)-3-chloro-2-fluorophenyl)amino)pyrido[3,2-d]pyrimidin-6-yl)-2-isopropylpiperazin-1-yl)prop-2-en-1-one | 588.20 | $^1$H NMR (400 MHz, $CDCl_3$) δ 9.09 (d, J = 3.1 Hz, 1H), 9.02 (t, J = 8.9 Hz, 1H), 8.66 (s, 1H), 8.53 (dd, J = 7.3, 0.9 Hz, 1H), 8.25 (s, 1H), 8.01 (d, J = 9.4 Hz, 1H), 7.26 (d, 1H), 7.16 (dd, J = 9.2, 2.0 Hz, 1H), 6.96-6.88 (m, 2H), 6.66 (dd, J = 16.4, 10.5 Hz, 1H), 6.44-6.35 (m, 1H), 5.78 (d, J = 10.4 Hz, 1H), 5.03-4.70 (m, 1H), 4.70-4.42 (m, 1H), 4.36-3.95 (m, 1H), 3.86-3.41 (m, 1H), 3.33-2.90 (m, 3H), 2.34-2.03 (m, 1H), 1.21-1.16 (m, 3H), 0.90 (d, J = 6.7 Hz, 3H). |
| 294 (Ex 162) | 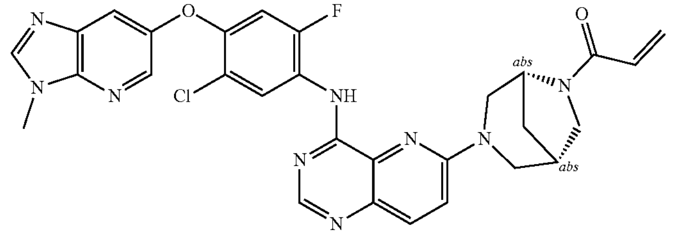 1-((1S,5R)-3-(4-((5-chloro-2-fluoro-4-((3-methyl-3H-imidazo[4,5-b]pyridin-6-yl)oxy)phenyl)amino)pyrido[3,2-d]pyrimidin-6-yl)-3,6-diazabicyclo[3.2.1]octan-6-yl)prop-2-en-1-one | 586.20 | $^1$H NMR (400 MHz, $CDCl_3$) δ 9.19-9.09 (m, 1H), 8.97-8.92 (m, 1H), 8.69-8.63 (m, 1H), 8.36-8.35 (m, 1H), 8.09-8.04 (m, 1H), 8.02-7.91 (m, 1H), 7.71-7.66 (m, 1H), 7.25-7.19 (m, 1H), 6.85-6.78 (m, 1H), 6.66-6.26 (m, 2H), 5.77-5.63 (m, 1H), 4.82-4.78 (m, 1H), 4.55-4.08 (m, 3H), 3.95 (s, 3H), 3.80-3.47 (m, 2H), 3.47-3.06 (m, 2H), 2.95-2.70 (m, 1H), 2.35-1.79 (m, 2H). |

TABLE 3-continued

| Example No. (Method) | Structure; IUPAC name | LCMS $M^{+1}$ | $^1H$ NMR (ppm); $^{19}F$ NMR (ppm); optical rotation; Chiral HPLC/SFC conditions |
|---|---|---|---|
| 295 (Ex 167) | 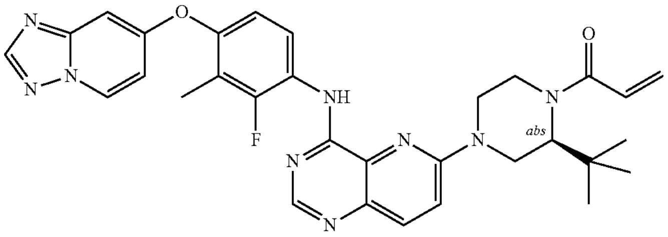 (S)-1-(4-(4-((4-([1,2,4]triazolo[1,5-a]pyridin-7-yloxy)-2-fluoro-3-methylphenyl)amino)pyrido[3,2-d]pyrimidin-6-yl)-2-(tert-butyl)piperazin-1-yl)prop-2-en-1-one | 582.30 | $^1H$ NMR (400 MHz, $CDCl_3$) δ 9.14-9.09 (m, 1H), 8.88 (q, J = 8.8 Hz, 1H), 8.64 (s, 1H), 8.51 (d, J = 7.0 Hz, 1H), 8.23 (s, 1H), 7.99 (d, J = 9.3 Hz, 1H), 7.20 (dd, J = 9.3, 6.9 Hz, 1H), 7.01 (d, J = 8.9 Hz, 1H), 6.95-6.84 (m, 2H), 6.69 (ddd, J = 16.8, 10.6, 2.9 Hz, 1H), 6.36-6.34 (m, 1H), 5.74 (ddd, J = 14.9, 10.5, 1.7 Hz, 1H), 4.98-4.70 (m, 1H), 4.43-3.68 (m, 4H), 3.53-3.22 (m, 2H), 2.23-2.14 (m, 3H), 1.12 (d, J = 11.5 Hz, 9H). |
| 296 (Ex 166) | 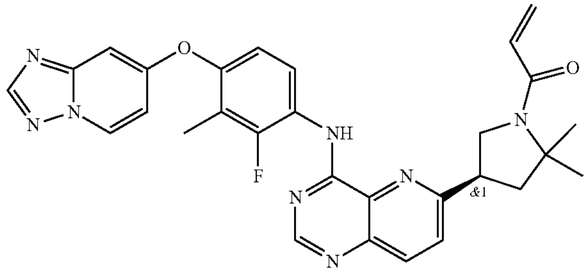 rac-(R)-1-(4-(4-((4-([1,2,4]triazolo[1,5-a]pyridin-7-yloxy)-2-fluoro-3-methylphenyl)amino)pyrido[3,2-d]pyrimidin-6-yl)-2,2-dimethylpyrrolidin-1-yl)prop-2-en-1-one | 539.20 | $^1H$ NMR (400 MHz, $CDCl_3$) δ 9.44-9.39 (m, 1H), 8.85-8.70 (m, 2H), 8.52 (d, J = 7.5 Hz, 1H), 8.24 (s, 1H), 8.19 (d, J = 8.6 Hz, 1H), 7.71 (d, J = 8.6 Hz, 1H), 7.06-6.99 (m, 1H), 6.94-6.85 (m, 2H), 6.53 (dd, J = 16.7, 10.1 Hz, 1H), 6.39 (dd, J = 16.7, 2.2 Hz, 1H), 5.68 (dd, J = 10.2, 2.1 Hz, 1H), 4.24-4.15 (m, 1H), 4.05 (t, J = 10.2 Hz, 1H), 3.86 (ddd, J = 18.2, 10.9, 7.7 Hz, 1H), 2.33 (dd, J = 9.2, 4.7 Hz, 3H), 2.23 (d, J = 1.9 Hz, 2H), 1.72 (s, 3H), 1.64 (s, 3H). |
| 297 (Ex 162) | 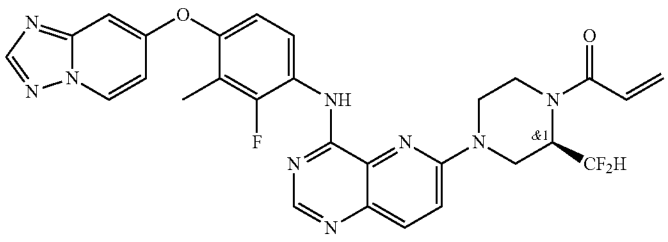 rac-(R)-1-(4-(4-((4-([1,2,4]triazolo[1,5-a]pyridin-7-yloxy)-2-fluoro-3-methylphenyl)amino)pyrido[3,2-d]pyrimidin-6-yl)-2-(difluoromethyl)piperazin-1-yl)prop-2-en-1-one | 576.20 | $^1H$ NMR (400 MHz, $CDCl_3$) δ 9.06 (d, J = 3.0 Hz, 1H), 8.83 (t, J = 9.0 Hz, 1H), 8.67 (s, 1H), 8.51 (dd, J = 7.1, 1.0 Hz, 1H), 8.24 (s, 1H), 8.04 (d, J = 9.3 Hz, 1H), 7.35-7.28 (m, 1H), 7.01 (dd, J = 8.9, 1.6 Hz, 1H), 6.94-6.85 (m, 2H), 6.66 (dd, J = 16.8, 10.6 Hz, 1H), 6.42 (dd, J = 16.8, 1.5 Hz, 1H), 6.07 (t, J = 55.7 Hz, 1H), 5.85 (d, J = 11.1 Hz, 1H), 5.19-4.56 (m, 2H), 4.42-4.37 (m, 1H), 4.21-4.02 (m, 1H), 3.84-2.99 (m, 3H), 2.21 (d, J = 2.0 Hz, 3H). |

TABLE 3-continued

| Example No. (Method) | Structure; IUPAC name | LCMS $M^{+1}$ | $^1H$ NMR (ppm); $^{19}F$ NMR (ppm); optical rotation; Chiral HPLC/SFC conditions |
|---|---|---|---|
| 298 (Ex 166) | 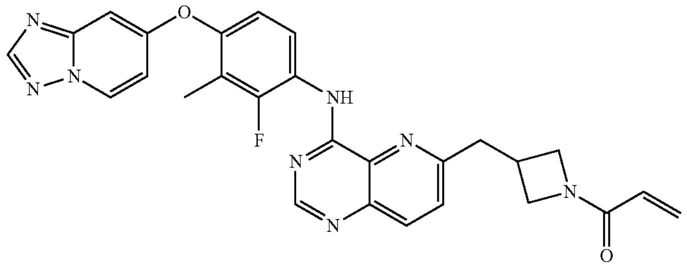 1-(3-((4-((4-([1,2,4]triazolo[1,5-a]pyridin-7-yloxy)-2-fluoro-3-methylphenyl)amino)pyrido[3,2-d]pyrimidin-6-yl)methyl)azetidin-1-yl)prop-2-en-1-one | 511.20 | $^1H$ NMR (400 MHz, $CDCl_3$) δ 9.40 (d, J = 3.1 Hz, 1H), 8.88-8.79 (m, 2H), 8.52 (dd, J = 7.2, 0.9 Hz, 1H), 8.24 (s, 1H), 8.15 (d, J = 8.6 Hz, 1H), 7.63 (d, J = 8.6 Hz, 1H), 7.06-6.99 (m, 1H), 6.94-6.86 (m, 2H), 6.37 (dd, J = 17.0, 2.0 Hz, 1H), 6.25 (dd, J = 17.0, 10.2 Hz, 1H), 5.69 (dd, J = 10.2, 2.0 Hz, 1H), 4.56 (t, J = 7.9 Hz, 1H), 4.44-4.35 (m, 1H), 4.14 (dd, J = 8.5, 4.6 Hz, 1H), 3.97 (dd, J = 10.3, 4.6 Hz, 1H), 3.46-3.31 (m, 3H), 2.23 (d, J = 2.0 Hz, 3H). |
| 299 (Ex 162) | 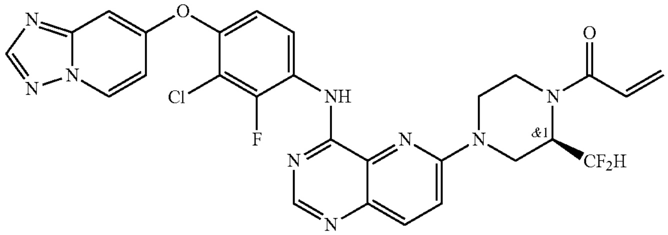 rac-(R)-1-(4-(4-((4-([1,2,4]triazolo[1,5-a]pyridin-7-yloxy)-3-chloro-2-fluorophenyl)amino)propyl[3,2-d]pyrimidin-6-yl)-2-(difluoromethyl)piperazin-1-yl)prop-2-en-1-one | 596.15 | $^1H$ NMR (400 MHz, $CDCl_3$) δ 9.09 (s, 1H), 8.99 (t, J = 8.9 Hz, 1H), 8.69 (s, 1H), 8.57-8.50 (m, 1H), 8.25 (s, 1H), 8.06 (d, J = 9.3 Hz, 1H), 7.33 (d, J = 9.2 Hz, 1H), 7.16 (dd, J = 9.2, 2.0 Hz, 1H), 6.96-6.90 (m, 2H), 6.66 (dd, J = 16.8, 10.6 Hz, 1H), 6.43 (dd, J = 16.8, 1.5 Hz, 2H), 6.06 (t, J = 55.8 Hz, 1H), 5.85 (d, J = 11.3 Hz, 2H), 5.18-4.57 (m, 2H), 4.55-3.96 (m, 2H), 3.84-3.00 (m, 3H). |
| 300 (Ex 162) | 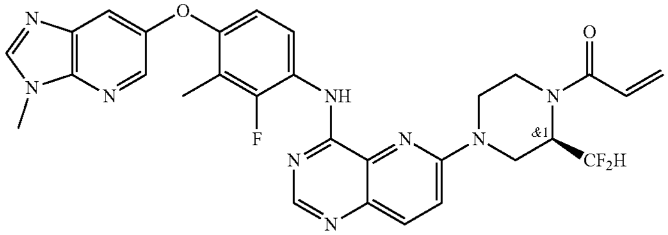 rac-(R)-1-(2-(difluoromethyl)-4-(4-((2-fluoro-3-methyl-4-((3-methyl-3H-imidazo[4,5-b]pyridin-6-yl)oxy)phenyl)amino)pyrido[3,2-d]pyrimidin-6-yl)piperazin-1-yl)prop-2-en-1-one | 590.30 | $^1H$ NMR (400 MHz, $CDCl_3$) δ 8.96 (s, 1H), 8.64-8.55 (m, 2H), 8.30 (d, J = 2.5 Hz, 1H), 8.06-7.99 (m, 2H), 7.61 (d, J = 2.5 Hz, 1H), 7.33-7.26 (m, 1H), 6.75 (d, J = 9.1 Hz, 1H), 6.66 (dd, J = 16.7, 10.5 Hz, 1H), 6.42 (d, J = 16.6 Hz, 1H), 6.26-5.89 (m, 1H), 5.85 (d, J = 10.7 Hz, 1H), 5.20-4.56 (m, 2H), 4.51-4.02 (m, 2H), 3.94 (s, 3H), 3.82-3.02 (m, 3H), 2.31 (d, J = 1.8 Hz, 3H). |

TABLE 3-continued

| Example No. (Method) | Structure; IUPAC name | LCMS $M^{+1}$ | $^1H$ NMR (ppm); $^{19}F$ NMR (ppm); optical rotation; Chiral HPLC/SFC conditions |
|---|---|---|---|
| 301 (Ex 166) | 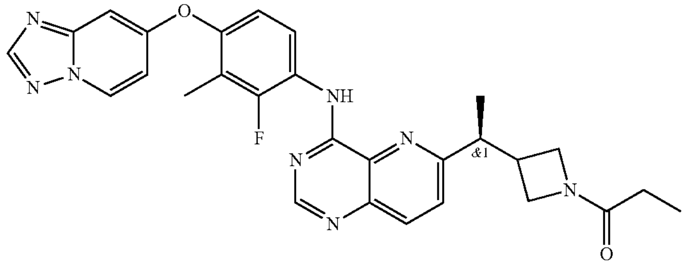 rac-(R)-1-(3-(1-(4-((4-([1,2,4]triazolo[1,5-a]pyridin-7-yloxy)-2-fluoro-3-methylphenyl)amino)pyrido[3,2-d]pyrimidin-6-yl)ethyl)azetidin-1-yl)prop-2-en-1-one | 525.30 | $^1H$ NMR (400 MHz, $CDCl_3$) δ 9.42 (s, 1H), 8.87-8.78 (m, 2H), 8.52 (d, J = 7.1 Hz, 1H), 8.24 (s, 1H), 8.21-8.14 (m, 1H), 7.66 (t, J = 9.0 Hz, 1H), 7.03 (d, J = 8.6 Hz, 1H), 6.89 (d, J = 10.6 Hz, 2H), 6.49-6.01 (m, 2H), 5.67 (dd, J = 21.8, 9.7 Hz, 1H), 4.59-4.11 (m, 2H), 4.06-3.71 (m, 2H), 3.46-3.15 (m, 2H), 2.23 (s, 3H), 1.42 (d, J = 5.7 Hz, 3H). |
| 302 (Ex 166) | 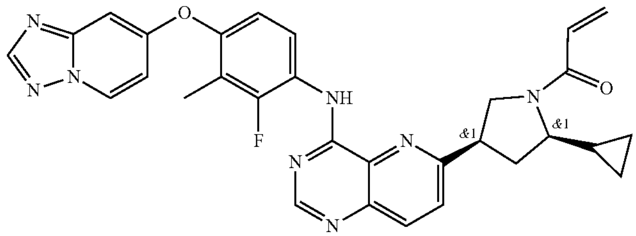 rac-1-(-4-(4-((4-([1,2,4]triazolo[1,5-a]pyridin-7-yloxy)-2-fluoro-3-methylphenyl)amino)pyrido[3,2-d]pyrimidin-6-yl)-2-cyclopropylpyrrolidin-1-yl)prop-2-en-1-one | 551.25 | $^1H$ NMR (400 MHz, $CDCl_3$) δ 9.52-9.30 (m, 1H), 8.85-8.78 (m, 1H), 8.69 (t, J = 8.9 Hz, 1H), 8.52 (d, J = 8.0 Hz, 1H), 8.24 (s, 1H), 8.18 (dd, J = 8.5, 4.8 Hz, 1H), 7.70 (dd, J = 8.6, 3.6 Hz, 1H), 7.01 (d, J = 9.3 Hz, 1H), 6.94-6.87 (m, 2H), 6.68-6.49 (m, 1H), 6.42 (dd, J = 16.7, 5.1 Hz, 1H), 5.77-5.67 (m, 1H), 4.30-3.52 (m, 4H), 2.85-2.30 (m, 2H), 2.22 (s, 3H), 1.22-0.98 (m, 1H), 0.98-0.23 (m, 4H). Mixture of diastereomers |
| 303 (Ex 167) | 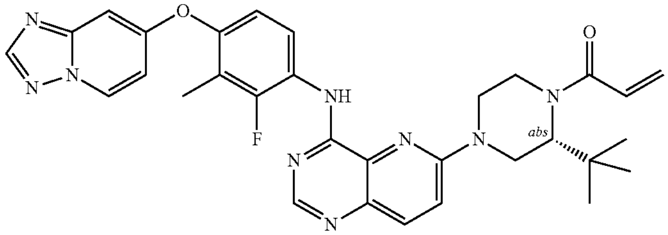 (R)-1-(4-(4-((4-([1,2,4]triazolo[1,5-a]pyridin-7-yloxy)-2-fluoro-3-methylphenyl)amino)pyrido[3,2-d]pyrimidin-6-yl)-2-(tert-butyl)piperazin-1-yl)prop-2-en-1-one | 582.30 | $^1H$ NMR (400 MHz, $CDCl_3$) δ 9.15-9.09 (m, 1H), 8.88 (q, J = 8.88 Hz, 1H), 8.64 (s, 1H), 8.51 (dd, J = 6.9, 1.4 Hz, 1H), 8.23 (s, 1H), 7.99 (d, J = 9.3 Hz, 1H), 7.20 (dd, J = 9.3. 6.8 Hz, 1H), 7.01 (d, J = 8.5 Hz, 1H), 6.95-6.84 (m, 2H), 6.69 (ddd, J = 16.8, 10.6, 2.9 Hz, 1H), 6.34 (ddd, J = 27.4, 16.7, 1.8 Hz, 1H), 5.74 (ddd, J = 14.9, 10.5, 1.8 Hz, 1H), 4.99-4.69 (m, 1H), 4.44-3.64 (m, 6H), 3.50-3.23 (m, 1H), 2.20 (d, J = 2.0 Hz, 3H), 1.12 (d, J = 11.5 Hz, 9H). |

TABLE 3-continued

| Example No. (Method) | Structure; IUPAC name | LCMS $M^{+1}$ | $^1H$ NMR (ppm); $^{19}F$ NMR (ppm); optical rotation; Chiral HPLC/SFC conditions |
|---|---|---|---|
| 304 (Ex 162) | 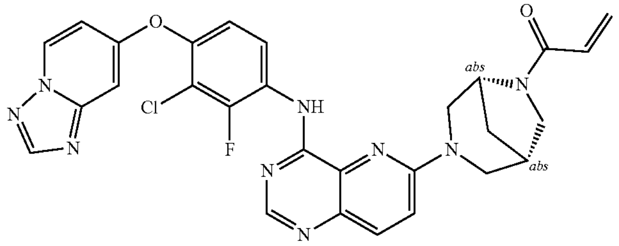 1-((1S,5R)-3-(4-((4-([1,2,4]triazolo[1,5-a]pyridin-7-yloxy)-3-chloro-2-fluorophenyl)amino)pyrido[3,2-d]pyrimidin-6-yl)-3,6-diazabicyclo[3.2.1]octan-6-yl)prop-2-en-1-one | 572.20 | $^1H$ NMR (400 MHz, $CDCl_3$) δ 9.15-9.07 (m, 1H), 9.05-8.93 (m, 1H), 8.68-8.62 (m, 1H), 8.57-8.50 (m, 1H), 8.25 (s, 1H), 8.02-7.93 (m, 1H), 7.26-7.11 (m, 1H), 6.96-6.88 (m, 2H), 6.66-6.32 (m, 2H), 5.86-5.61 (m, 1H), 4.55-4.13 (m, 3H), 3.85-3.51 (m, 2H), 3.49-3.11 (m, 2H), 2.98-2.73 (m, 1H), 2.33-1.79 (m, 2H). |
| 305 (Ex 167) | 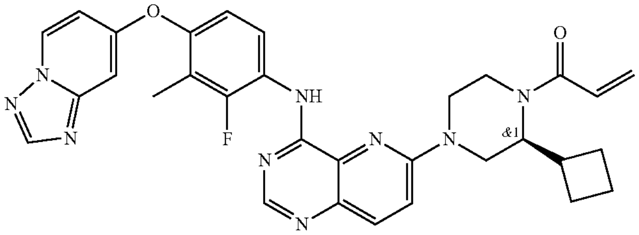 rac-(R)-1-(4-(4-((4-([1,2,4]triazolo[1,5-a]pyridin-7-yloxy)-2-fluoro-3-methylphenyl)amino)pyrido[3,2-d]pyrimidin-6-yl)-2-cyclobutylpiperazin-1-yl)prop-2-en-1-one | 580.25 | $^1H$ NMR (400 MHz, $CDCl_3$) δ 9.05 (d, J = 3.6 Hz, 1H), 8.85 (t, J = 9.0 Hz, 1H), 8.64 (s, 1H), 8.51 (dd, J = 7.4, 0.8 Hz, 1H), 8.23 (s, 1H), 7.99 (d, J = 9.3 Hz, 1H), 7.25-7.20 (m, 1H), 7.00 (dd, J = 9.0, 1.8 Hz, 1H), 6.93-6.84 (m, 2H), 6.83-6.23 (m, 1H), 5.79 (d, J = 10.5 Hz, 1H), 5.12-3.77 (m, 4H), 3.62-2.61 (m, 4H), 2.20 (d, J = 2.2 Hz, 3H), 2.16-1.64 (m, 4H). |
| 306 (Ex 166) | 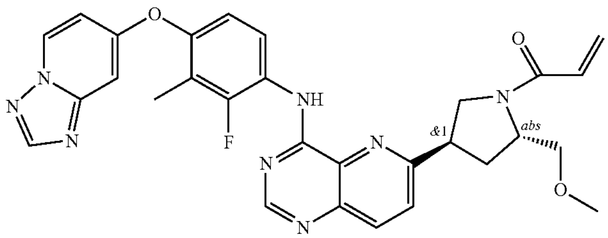 1-((2S,4RS)-4-(4-((4-([1,2,4]triazolo[1,5-a]pyridin-7-yloxy)-2-fluoro-3-methylphenyl)amino)pyrido[3,2-d]pyrimidin-6-yl)-2-(methoxymethyl)pyrrolidin-1-yl)prop-2-en-1-one | 555.20 | $^1H$ NMR (400 MHz, $CDCl_3$) δ 9.52-9.29 (m, 1H), 8.85-8.76 (m, 1H), 8.55-8.48 (m, 1H), 8.24 (s, 1H), 8.21-8.14 (m, 1H), 7.76-7.66 (m, 1H), 7.06-6.98 (m, 1H), 6.94-6.87 (m, 2H), 6.72-6.37 (m, 2H), 5.78-5.69 (m, 1H), 4.73-4.31 (m, 1H), 4.28-3.90 (m, 3H), 3.83-3.47 (m, 2H), 3.46-3.35 (m, 3H), 2.72-2.31 (m, 2H), 2.25-2.19 (m, 3H). 4:1 ratio of diastereomers |

TABLE 3-continued

| Example No. (Method) | Structure; IUPAC name | LCMS $M^{+1}$ | $^{1}H$ NMR (ppm); $^{19}F$ NMR (ppm); optical rotation; Chiral HPLC/SFC conditions |
|---|---|---|---|
| 307 (Ex 162) | 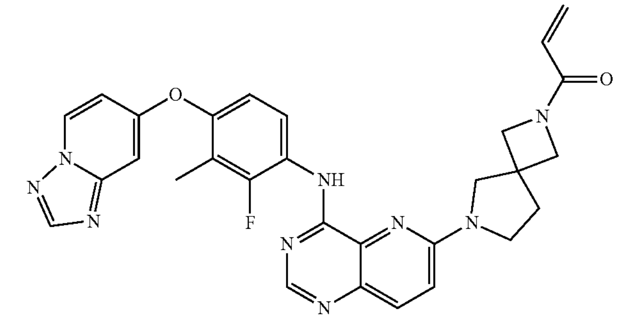 1-(6-(4-((4-([1,2,4]triazolo[1,5-a]pyridin-7-yloxy)-2-fluoro-3-methyphenyl)amino)pyrido[3,2-d]pyrimidin-6-yl)-2,6-diazaspiro[3.4]octan-2-yl)prop-2-en-1-one | 552.20 | $^{1}H$ NMR (400 MHz, $CDCl_3$) δ 9.13 (d, J = 3.4 Hz, 1H), 8.82 (t, J = 9.0 Hz, 1H), 8.64 (d, J = 2.2 Hz, 1H), 8.54-8.47 (m, 1H), 8.23 (s, 1H), 7.96 (dd, J = 9.1, 3.2 Hz, 1H), 6.99 (dd, J = 9.0, 1.6 Hz, 1H), 6.93-6.84 (m, 3H), 6.53-6.38 (m, 2H), 5.80-5.69 (m, 1H), 4.26-4.12 (m, 4H), 3.85 (s, 2H), 3.72 (t, J = 6.9 Hz, 2H), 2.35 (t, J = 6.9 Hz, 1H), 2.24 (t, J = 7.1 Hz, 1H), 2.21-2.16 (m, 3H). |
| 308 (Ex 167) | 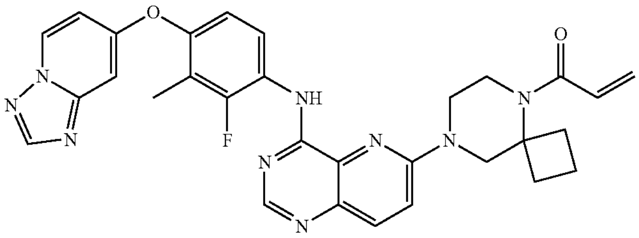 1-(8-(4-((4-([1,2,4]triazolo[1,5-a]pyridin-7-yloxy)-2-fluoro-3-methylphenyl)amino)pyrido[3,2-d]pyrimidin-6-yl)-5,8-diazaspiro[3.5]nonan-5-yl)prop-2-en-1-one | 566.20 | $^{1}H$ NMR (400 MHz, $CDCl_3$) δ 9.10 (d, J = 3.6 Hz, 1H), 8.85 (t, J = 9.0 Hz, 1H), 8.64 (s, 1H), 8.51 (dd, J = 7.3, 0.9 Hz, 1H), 8.23 (s, 1H), 8.00 (d, J = 9.3 Hz, 1H), 7.33-7.24 (m, 1H), 7.01 (dd, J = 9.1, 1.7 Hz, 1H), 6.93-6.85 (m, 2H), 6.53 (dd, J = 16.8, 10.4 Hz, 1H), 6.34 (dd, J = 16.8, 1.9 Hz, 1H), 5.72 (dd, J = 10.4, 1.9 Hz, 1H), 3.99 (s, 2H), 3.75-3.68 (m, 4H), 2.61-2.51 (m, 2H), 2.30-2.18 (m, 5H), 1.94 (dt, J = 18.7, 9.5 Hz, 2H). |
| 309 (Ex 167) | 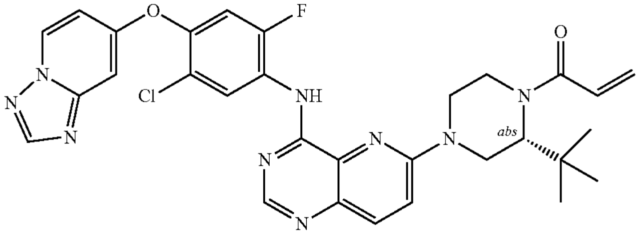 (R)-1-(4-(4-((4-([1,2,4]triazolo[1,5-a]pyridin-7-yloxy)-5-chloro-2-fluorophenyl)amino)pyrido[3,2-d]pyrimidin-6-yl)-2-(tert-butyl)piperazin-1-yl)prop-2-en-1-one | 602.20 | $^{1}H$ NMR (400 MHz, $CDCl_3$) δ 9.37-9.29 (m, 1H), 9.12 (s, 1H), 8.70 (s, 1H), 8.57-8.50 (m, 1H), 8.26 (s, 1H), 8.01 (dd, J = 9.4, 1.3 Hz, 1H), 7.21 (t, J = 9.7 Hz, 1H), 7.11 (dd, J = 11.0, 1.9 Hz, 1H), 6.95-6.87 (m, 2H), 6.68 (ddd, J = 16.9, 10.6, 1.7 Hz, 1H), 6.33 (ddd, J = 28.7, 16.7, 1.8 Hz, 1H), 5.74 (ddd, J = 15.1, 10.5, 1.8 Hz, 1H), 4.98-4.71 (m, 1H), 4.37-3.67 (m, 5H), 3.51-3.23 (m, 1H), 1.10 (d, J = 10.7 Hz, 9H). |

TABLE 3-continued

| Example No. (Method) | Structure; IUPAC name | LCMS $M^{+1}$ | $^1H$ NMR (ppm); $^{19}F$ NMR (ppm); optical rotation; Chiral HPLC/SFC conditions |
|---|---|---|---|
| 310 (Ex 167) | 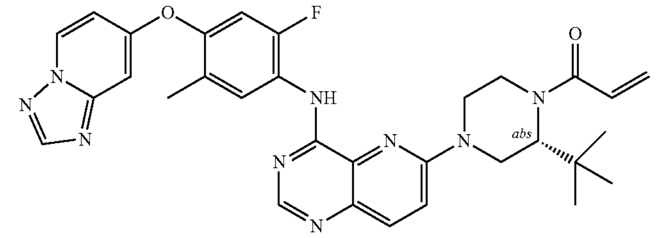 (R)-1-(4-(4-((4-([1,2,4]triazolo[1,5-a]pyridin-7-yloxy)-2-fluoro-5-methylphenyl)amino)pyrido[3,2-d]pyrimidin-6-yl)-2-(tert-butyl)piperazin-1-yl)prop-2-en-1-one | 582.30 | $^1H$ NMR (400 MHz, $CDCl_3$) δ 9.11-9.04 (m, 1H), 8.94 (t, J = 8.6 Hz, 1H), 8.66 (s, 1H), 8.54-8.48 (m, 1H), 8.24 (s, 1H), 7.99 (dd, J = 9.3, 0.8 Hz, 1H), 7.19 (dd, J = 9.4, 7.0 Hz, 1H), 6.95 (dd, J = 11.1, 1.9 Hz, 1H), 6.92-6.84 (m, 2H), 6.68 (ddd, J = 16.8, 10.6, 2.4 Hz, 1H), 6.33 (ddd, J = 27.4, 16.7, 1.9 Hz, 1H), 5.73 (ddd, J = 15.3, 10.5, 1.9 Hz, 1H), 5.01-4.63 (m, 1H), 4.40-3.63 (m, 5H), 3.50-3.22 (m, 1H), 2.27 (s, 3H), 1.10 (d, J = 10.5 Hz, 9H). |
| 311 (Ex 167) | 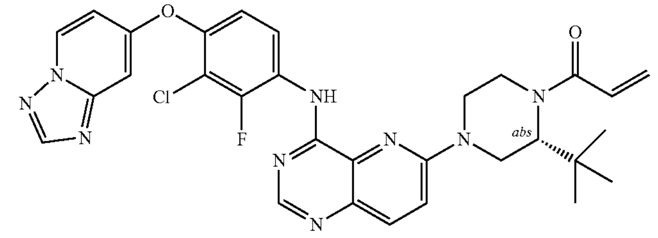 (R)-1-(4-(4-((4-([1,2,4]triazolo[1,5-a]pyridin-7-yloxy)-3-chloro-2-fluorophenyl)amino)pyrido[3,2-d]pyrimidin-6-yl)-2-(tert-butyl)piperazin-1-yl)prop-2-en-1-one | 602.20 | $^1H$ NMR (400 MHz, $CDCl_3$) δ 9.16-9.10 (m, 1H), 9.10-8.99 (m, 1H), 8.66 (s, 1H), 8.56-8.50 (m, 1H), 8.25 (s, 1H), 8.01 (d, J = 9.3 Hz, 1H), 7.27-7.19 (m, 1H), 7.16 (dt, J = 9.2, 2.3 Hz, 1H), 6.96-6.88 (m, 2H), 6.69 (ddd, J = 16.8, 10.6, 2.0 Hz, 1H), 6.34 (ddd, J = 28.4, 16.7, 1.8 Hz, 1H), 5.74 (ddd, J = 14.7, 10.5, 1.8 Hz, 1H), 5.05-4.64 (m, 1H), 4.46-3.65 (m, 5H), 3.51-3.24 (m, 1H), 1.12 (d, J = 12.3 Hz, 9H). |
| 312 (Ex 162) | 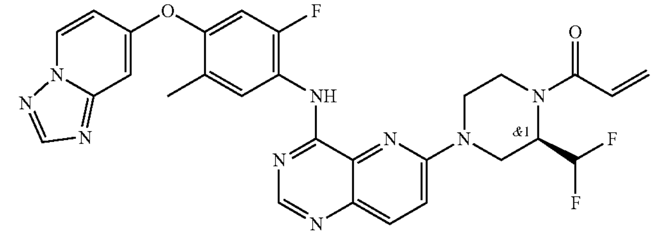 rac-(R)-1-(4-(4-((4-([1,2,4]triazolo[1,5-a]pyridin-7-yloxy)-2-fluoro-5-methylphenyl)amino)pyrido[3,2-d]pyrimidin-6-yl)-2-(difluoromethyl)piperazin-1-yl)prop-2-en-1-one | 576.20 | $^1H$ NMR (400 MHz, $CDCl_3$) δ 9.01 (d, J = 3.3 Hz, 1H), 8.87 (d, J = 9.1 Hz, 1H), 8.69 (s, 1H), 8.54-8.48 (m, 1H), 8.24 (s, 1H), 8.05 (d, J = 9.3 Hz, 1H), 7.35-7.28 (m, 1H), 6.96 (d, J = 11.0 Hz, 1H), 6.92-6.85 (m, 2H), 6.65 (dd, J = 16.7, 10.6 Hz, 1H), 6.42 (dd, J = 16.8, 1.7 Hz, 1H), 6.06 (t, J = 56.4 Hz, 1H), 5.88-5.81 (m, 1H), 5.20-4.26 (m, 3H), 4.22-2.87 (m, 3H), 2.27 (d, J = 1.0 Hz, 3H). |
| 313 (Ex 166) | 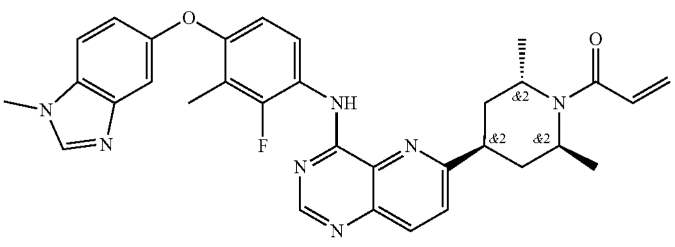 rac-1-(-4-(4-((2-fluoro-3-methyl-4-((1-methyl-1H-benzo[d]imidazol-5-yl)oxy)phenyl)amino)pyrido[3,2-d]pyrimidin-6-yl)-2,6-dimethylpiperidin-1-yl)prop-2-en-1-one | 566.30 | $^1H$ NMR (400 MHz, $CDCl_3$) δ 9.33 (s, 1H), 8.75 (s, 1H), 8.55 (t, J = 9.0 Hz, 1H), 8.13 (d, J = 8.6 Hz, 1H), 7.88 (s, 1H), 7.67 (d, J = 8.6 Hz, 1H), 7.38-7.32 (m, 2H), 7.07 (d, J = 8.7 Hz, 1H), 6.77 (d, J = 8.9 Hz, 1H), 6.67 (dd, J = 16.6, 10.4 Hz, 1H), 6.41 (d, J = 16.5 Hz, 1H), 5.71 (d, J = 10.2 Hz, 1H), 4.51 (s, 1H), 4.40-4.31 (m, 1H), 3.86 (s, 3H), 3.68-3.56 (m, 1H), 2.56-2.33 (m, 6H), 2.30 (s, 3H), 2.21-2.11 (m, 1H), 1.50 (dd, J = 20.4, 6.7 Hz, 6H)-mixture of diastereomers |

TABLE 3-continued

| Example No. (Method) | Structure; IUPAC name | LCMS $M^{+1}$ | $^1H$ NMR (ppm); $^{19}F$ NMR (ppm); optical rotation; Chiral HPLC/SFC conditions |
|---|---|---|---|
| 314 (Ex 166) | 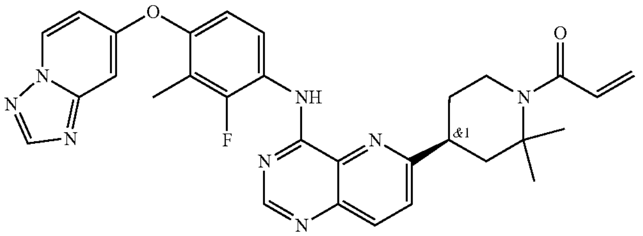 rac-(R)-1-(4-(4-((4-([1,2,4]triazolo[1,5-a]pyridin-7-yloxy)-2-fluoro-3-methylphenyl)amino)pyrido[3,2-d]pyrimidin-6-yl)-2,2-dimethylpiperidin-1-yl)prop-2-en-1-one | 553.20 | $^1H$ NMR (400 MHz, $CDCl_3$) δ 9.49 (d, J = 2.9 Hz, 1H), 8.86-8.74 (m, 2H), 8.56-8.49 (m, 1H), 8.24 (s, 1H), 8.17 (d, J = 8.6 Hz, 1H), 7.68 (d, J = 8.7 Hz, 1H), 7.02 (dd, J = 9.0, 1.4 Hz, 1H), 6.94-6.85 (m, 2H), 6.58 (dd, J = 16.9, 10.5 Hz, 1H), 6.20 (dd, J = 16.9, 1.8 Hz, 1H), 5.62 (dd, J = 10.5, 1.8 Hz, 1H), 3.90 (ddd, J = 14.1, 6.6, 4.4 Hz, 1H), 3.53-3.31 (m, 2H), 2.31-2.02 (m, 6H), 1.91-1.82 (m, 1H), 1.69 (s, 3H), 1.62 (s, 3H). |
| 315 (Ex 176) | 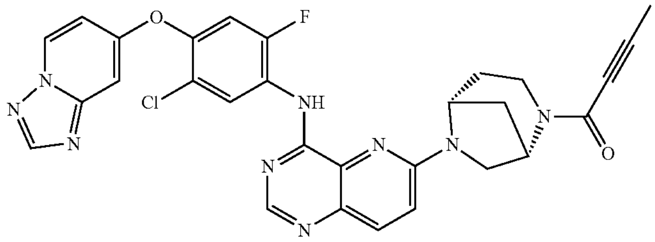 1-((2S,5R)-6-(4-((4-([1,2,4]triazolo[1,5-a]pyridin-7-yloxy)-5-chloro-2-fluorophenyl)amino)pyrido[3,2-d]pyrimidin-6-yl)-2,6-diazabicyclo[3.2.1]octan-2-yl)but-2-yn-1-one | 584.1 | $^1H$ NMR (400 MHz, $CDCl_3$) δ 9.29 (d, J = 8.4 Hz, 1H), 9.15 (t, J = 3.4 Hz, 1H), 8.68 (d, J = 1.2 Hz, 1H), 8.55-8.50 (m, 1H), 8.25 (s, 1H), 8.00 (dd, J = 9.2, 2.6 Hz, 1H), 7.11 (dd, J = 10.9, 3.1 Hz, 1H), 7.05 (d, J = 9.2 Hz, 1H), 6.93-6.89 (m, 2H), 5.40 (d, J = 73.4 Hz, 1H), 4.77 (br s, 1H), 4.38 (ddd, J = 64.7, 14.0, 6.4 Hz, 1H), 3.90 (dd, J = 24.7, 10.4 Hz, 1H), 3.71 (br s, 1H), 3.32-2.78 (m, 2H), 2.30-2.09 (m, 2H), 2.04 (d, J = 28.9 Hz, 3H), 2.00-1.77 (m, 2H). |
| 316 (Ex 176) | 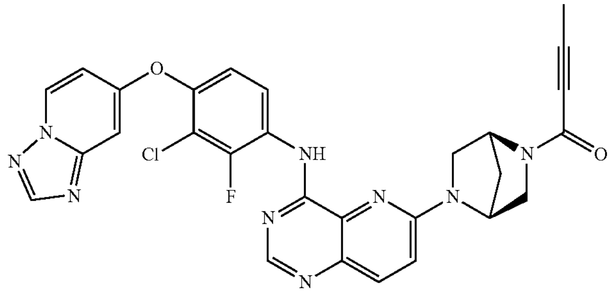 1-((1S,4S)-5-(4-((4-([1,2,4]triazolo[1,5-a]pyridin-7-yloxy)-3-chloro-2-fluorophenyl)amino)pyrido[3,2-d]pyrimidin-6-yl)-2,5-diazabicyclo[2.2.1]heptan-2-yl)but-2-yn-1-one | 570.2 | $^1H$ NMR (400 MHz, $CDCl_3$) δ 9.14 (dd, J = 7.8, 3.4 Hz, 1H), 9.00 (td, J = 8.9, 5.6 Hz, 1H), 8.65 (s, 1H), 8.53 (ddd, J = 7.0, 1.8, 1.0 Hz, 1H), 8.25 (s, 1H), 8.00 (dd, J = 9.2, 2.8 Hz, 1H), 7.16 (dtt, J = 9.2, 2.4 Hz, 1H), 7.00 (t, J = 9.4 Hz, 1H), 6.95-6.89 (m, 2H), 5.22-5.00 (m, 2H), 3.88-3.58 (m, 4H), 2.20-2.08 (m, 2H), 2.01 (d, J = 44.0 Hz, 3H). |

TABLE 3-continued

| Example No. (Method) | Structure; IUPAC name | LCMS $M^{+1}$ | $^1H$ NMR (ppm); $^{19}F$ NMR (ppm); optical rotation; Chiral HPLC/SFC conditions |
|---|---|---|---|
| 317 (Ex 176) | 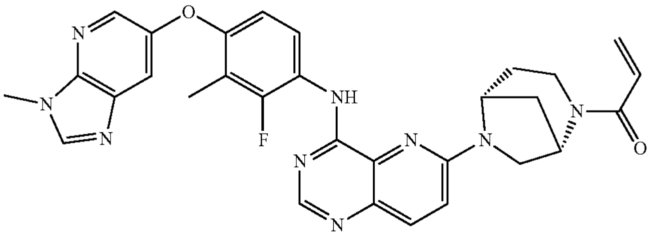 1-((1S,5R)-6-(4-((2-fluoro-3-methyl-4-((3-methyl-3H-imidazo[4,5-b]pyridin-6-yl)oxy)phenyl)amino)pyrido[3,2-d]pyrimidin-6-yl)-2,6-diazabicyclo[3.2.1]octan-2-yl)prop-2-en-1-one | 566.2 | $^1H$ NMR (400 MHz, $CDCl_3$) δ 9.06 (br s, 1H), 8.62 (t, J = 9.1 Hz, 1H), 8.57 (s, 1H), 8.29 (d, J = 2.6 Hz, 1H), 8.03 (s, 1H), 7.95 (d, J = 9.1 Hz, 1H), 7.60 (d, J = 2.5 Hz, 1H), 7.01 (d, J = 9.2 Hz, 1H), 6.75 (dd, J = 9.0, 1.7 Hz, 1H), 6.61 (ddd, J = 53.2, 16.8, 10.5 Hz, 1H), 6.38-6.29 (m, 1H), 5.75 (dd, J = 17.3, 10.7 Hz, 1H), 5.61 (br s, 1H), 4.96-4.43 (m, 2H), 3.93 (s, 3H), 3.92-3.86 (m, 1H), 3.79-3.57 (br m, 1H), 3.33-2.84 (m, 1H), 2.30 (d, J = 2.2 Hz, 3H), 2.27-2.09 (m, 2H), 2.03-1.82 (m, 2H). |
| 318 (Ex 175) | 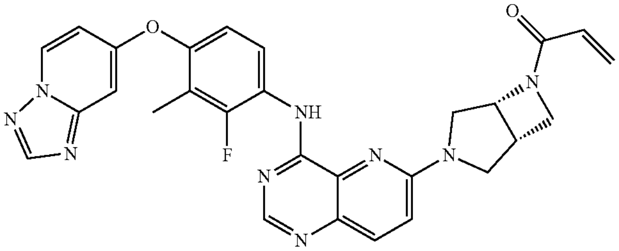 1-((1S,5R)-3-(4-((4-([1,2,4]triazolo[1,5-a]pyridin-7-yloxy)-2-fluoro-3-methylphenyl)amino)pyrido[3,2-d]pyrimidin-6-yl)-3,6-diazabicyclo[3.2.0]heptan-6-yl)prop-2-en-1-one | 538.2 | $^1H$ NMR (400 MHz, $CDCl_3$) δ 9.16-9.13 (m, 1H), 8.86-8.79 (m, 1H), 8.65 (d, J = 4.6 Hz, 1H), 8.55-8.46 (m, 1H), 8.23 (s, 1H), 8.02-7.97 (m, 1H), 7.19-7.15 (m, 1H), 7.00 (dd, J = 9.0, 1.8 Hz, 1H), 6.90-6.86 (m, 2H), 6.48-6.29 (m, 1H), 6.16 (dd, J = 16.9, 10.3 Hz, 1H), 5.80-5.65 (m, 1H), 5.16 (dd, J = 6.8, 4.9 Hz, 1H), 4.50-4.15 (m, 3H), 3.93 (ddd, J = 66.8, 9.5, 4.2 Hz, 1H), 3.58-3.35 (m, 3H), 2.20 (d, J = 2.1 Hz, 3H). |
| 319 (Ex 175) | 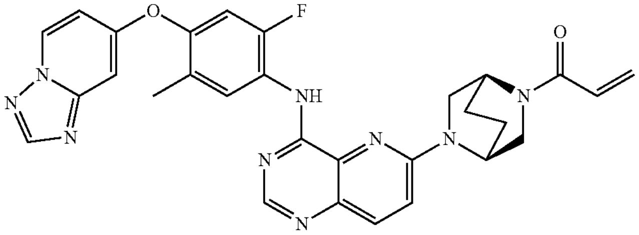 1-((2S,4S)-5-(4-((4-([1,2,4]triazolo[1,5-a]pyridin-7-yloxy)-2-fluoro-5-methylphenyl)amino)pyrido[3,2-d]pyrimidin-6-yl)-2,5-diazabicyclo[2.2.2]octan-2-yl)prop-2-en-1-one | 552.2 | $^1H$ NMR (400 MHz, $CDCl_3$) δ 9.02-8.98 (m, 1H), 8.87 (dd, J = 9.0, 3.6 Hz, 1H), 8.65 (s, 1H), 8.54-8.48 (m, 1H), 8.24 (s, 1H), 8.00 (dd, J = 9.3, 3.6 Hz, 1H), 7.10-7.03 (m, 1H), 6.95 (dd, J = 11.1, 1.6 Hz, 1H), 6.91-6.85 (m, 2H), 6.63-6.35 (m, 2H), 5.81-5.72 (m, 1H), 5.13-4.40 (m, 2H), 4.03-3.66 (m, 4H), 2.27 (s, 3H), 2.24-2.10 (m, 2H), 2.07-1.90 (m, 2H). |

TABLE 3-continued

| Example No. (Method) | Structure; IUPAC name | LCMS $M^{+1}$ | $^1H$ NMR (ppm); $^{19}F$ NMR (ppm); optical rotation; Chiral HPLC/SFC conditions |
|---|---|---|---|
| 320 (Ex 176) | 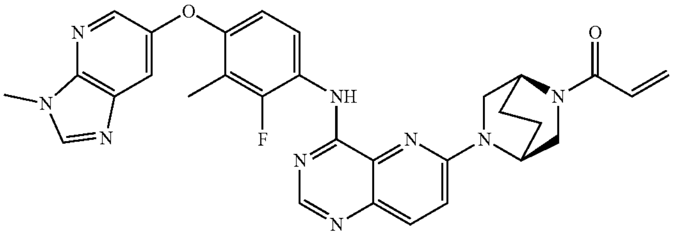 1-((1S,4S)-5-(4-((2-fluoro-3-methyl-4-((3-methyl-3H-imidazo[4,5-b]pyridin-6-yl)oxy)phenyl)amino)pyrido[3,2-d]pyrimidin-6-yl)-2,5-diazabicyclo[2.2.2]octan-2-yl)prop-2-en-1-one | 566.3 | $^1H$ NMR (400 MHz, $CDCl_3$) δ 8.96 (br s, 1H), 8.63-8.55 (m, 2H), 8.30 (d, J = 2.5 Hz, 1H), 8.03 (s, 1H), 7.97 (dd, J = 9.2, 3.5 Hz, 1H), 7.61 (t, J = 2.4 Hz, 1H), 7.09-7.01 (m, 1H), 6.76 (dd, J = 9.1, 1.8 Hz, 1H), 6.64-6.36 (m, 2H), 5.80-5.73 (m, 1H), 5.17-4.40 (m, 2H), 4.00 (dt, J = 10.4, 2.7 Hz, 1H), 3.93 (s, 3H), 3.92-3.69 (m, 3H), 2.30 (d, J = 2.1 Hz, 3H), 2.26-2.11 (m, 2H), 2.08-1.90 (m, 2H). |
| 321 (Ex 175) | 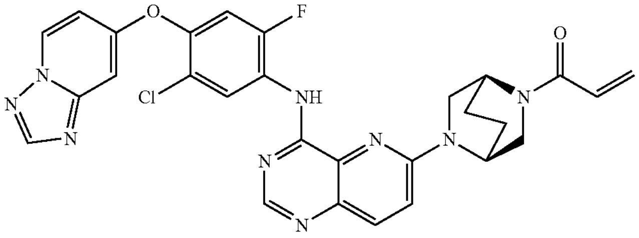 1-((1S,4S)-5-(4-((4-([1,2,4]triazolo[1,5-a]pyridin-7-yloxy)-5-chloro-2-fluorophenyl)amino)pyrido[3,2-d]pyrimidin-6-yl)-2,5-diazabicyclo[2.2.2]octan-2-yl)prop-2-en-1-one | 572.1 | $^1H$ NMR (400 MHz, $CDCl_3$) δ 9.28 (dd, J = 8.4, 1.7 Hz, 1H), 9.09-9.04 (m, 1H), 8.68 (s, 1H), 8.56-8.51 (m, 1H), 8.26 (s, 1H), 8.01 (dd, J = 9.3, 2.9 Hz, 1H), 7.14-7.05 (m, 2H), 6.92-6.89 (m, 2H), 6.64-6.36 (m, 2H), 5.80-5.73 (m, 1H), 5.71-4.41 (m, 2H), 4.04-3.68 (m, 4H), 2.27-2.10 (m, 2H), 2.09-1.89 (m, 2H). |
| 322 (Ex 175) | 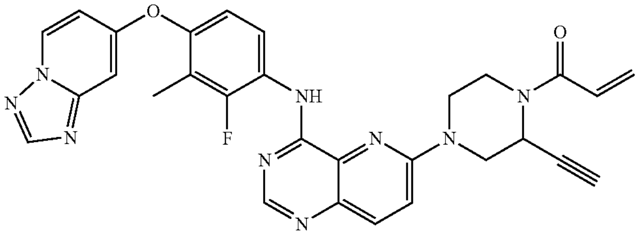 1-(4-(4-((4-([1,2,4]triazolo[1,5-a]pyridin-7-yloxy)-2-fluoro-3-methylphenyl)amino)pyrido[3,2-d]pyrimidin-6-yl)-2-ethynylpiperazin-1-yl)prop-2-en-1-one | 550.2 | $^1H$ NMR (400 MHz, $CDCl_3$) δ 9.08 (d, J = 3.6 Hz, 1H), 8.83 (t, J = 9.0 Hz, 1H), 8.66 (s, 1H), 8.51 (dd, J = 7.3, 0.9 Hz, 1H), 8.24 (s, 1H), 8.01 (d, J = 9.3 Hz, 1H), 7.36 (d, J = 9.3 Hz, 1H), 7.01 (dd, J = 9.1, 1.7 Hz, 1H), 6.93-6.84 (m, 2H), 6.63 (dd, J = 16.8, 10.5 Hz, 1H), 6.42 (dd, J = 16.7, 1.7 Hz, 1H), 5.83 (dd, J = 10.5, 1.8 Hz, 1H), 5.75 (s, 1H), 4.76-4.45 (m, 2H), 3.93 (d, J = 86.0 Hz, 2H), 3.32 (d, J = 93.5 Hz, 2H), 2.29-2.22 (m, 1H), 2.21 (d, J = 2.2 Hz, 3H). |

TABLE 3-continued

| Example No. (Method) | Structure; IUPAC name | LCMS $M^{+1}$ | $^1$H NMR (ppm); $^{19}$F NMR (ppm); optical rotation; Chiral HPLC/SFC conditions |
|---|---|---|---|
| 323 (Ex 175) | 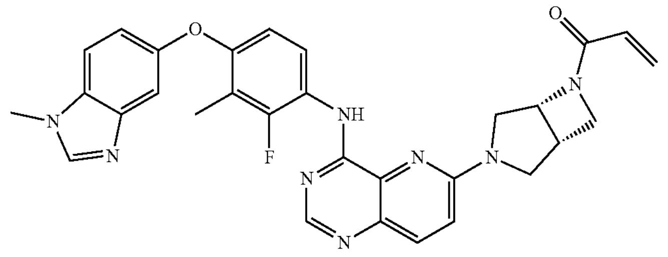 1-((1S,5R)-3-(4-((2-fluoro-3-methyl-4-((1-methyl-1H-benzo[d]imidazol-5-yl)oxy)phenyl)amino)pyrido[3,2-d]pyrimidin-6-yl)-3,6-diazabicyclo[3.2.0]heptan-6-yl)prop-2-en-1-one | 551.2 | $^1$H NMR (400 MHz, $CDCl_3$) δ 9.04-8.99 (m, 1H), 8.60-8.58 (m, 1H), 8.54 (t, J = 9.1 Hz, 1H), 8.00-7.94 (m, 1H), 7.86 (s, 1H), 7.34 (dd, J = 5.5, 3.1 Hz, 2H), 7.15 (dd, J = 9.2, 6.0 Hz, 1H), 7.06 (dd, J = 8.8, 2.2 Hz, 1H), 6.77 (dd, J = 9.0, 1.7 Hz, 1H), 6.49-6.29 (m, 1H), 6.16 (dd, J = 17.0, 10.4 Hz, 1H), 5.74 (ddd, J = 37.3, 10.3, 1.9 Hz, 1H), 5.17-5.12 (m, 1H), 4.49-4.15 (m, 3H), 4.01 (dd, J = 8.6, 4.2 Hz, 1H), 3.85 (s, 3H), 3.45 (ddt, J = 44.2, 11.9, 5.8 Hz, 3H), 2.28 (d, J = 2.1 Hz, 3H). |
| 324 (Ex 176) | 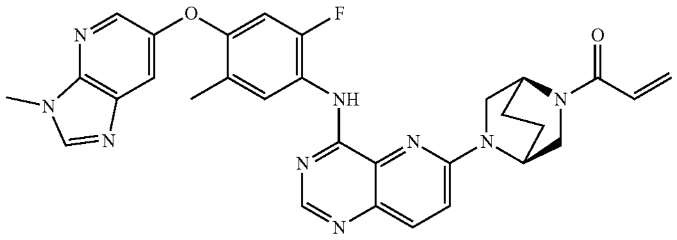 1-((2S,4S)-5-(4-((2-fluoro-5-methyl-4-((3-methyl-3H-imidazo[4,5-b]pyridin-6-yl)oxy)phenyl)amino)pyrido[3,2-d]pyrimidin-6-yl)-2,5-diazabicyclo[2.2.2]octan-2-yl)prop-2-en-1-one | 566.2 | $^1$H NMR (400 MHz, $CDCl_3$) δ 8.86-8.83 (m, 1H), 8.70 (dd, J = 9.2, 5.5 Hz, 1H), 8.62 (s, 1H), 8.29 (dd, J = 2.5, 1.0 Hz, 1H), 8.04 (s, 1H), 7.97 (dd, J = 9.3, 3.8 Hz, 1H), 7.62 (dd, J = 2.5, 1.1 Hz, 1H), 7.07-7.01 (m, 1H), 6.69 (dd, J = 11.7, 1.1 Hz, 1H), 6.62-6.34 (m, 2H), 5.79-5.70 (m, 1H), 5.11-4.39 (m, 2H), 4.00-3.67 (obs m, 4H), 3.94 (s, 3H), 2.37 (s, 3H), 2.23-2.10 (m, 2H), 2.05-1.88 (m, 2H). |
| 325 (Ex 175) | 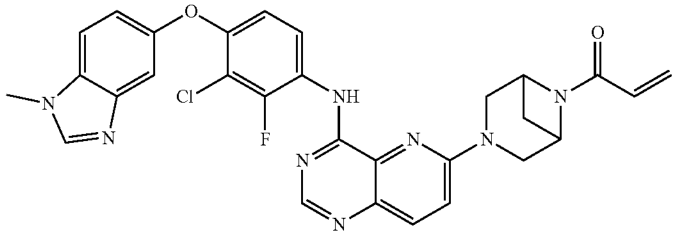 1-(3-(4-((3-chloro-2-fluoro-4-((1-methyl-1H-benzo[d]imidazol-5-yl)oxy)phenyl)amino)pyrido[3,2-d]pyrimidin-6-yl)-3,6-diazabicyclo[3.1.1]heptan-6-yl)prop-2-en-1-one | 571.1 | $^1$H NMR (400 MHz, $CDCl_3$) δ 9.01 (d, J = 3.1 Hz, 1H), 8.70 (t, J = 9.0 Hz, 1H), 8.59 (s, 1H), 8.00 (d, J = 9.3 Hz, 1H), 7.88 (s, 1H), 7.42 (d, J = 2.3 Hz, 1H), 7.37 (d, J = 8.7 Hz, 1H), 7.15 (d, J = 9.3 Hz, 1H), 7.10 (dd, J = 8.8, 2.4 Hz, 1H), 6.84 (dd, J = 9.3, 2.1 Hz, 1H), 6.41-6.25 (m, 2H), 5.73 (dd, J = 9.8, 2.2 Hz, 1H), 4.82-4.70 (m, 2H), 4.35 (d, J = 11.1 Hz, 1H), 4.00 (br s, 2H), 3.87 (s, 3H), 3.82-3.68 (br s, 1H), 2.95-2.86 (m, 1H), 1.77 (d, J = 8.9 Hz, 1H). |

TABLE 3-continued

| Example No. (Method) | Structure; IUPAC name | LCMS $M^{+1}$ | $^{1}H$ NMR (ppm); $^{19}F$ NMR (ppm); optical rotation; Chiral HPLC/SFC conditions |
|---|---|---|---|
| 326 (Ex 175) | 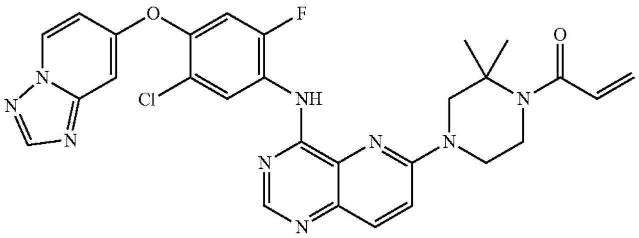 1-(4-(4-((4-([1,2,4]triazolo[1,5-a]pyridin-7-yloxy)-5-chloro-2-fluorophenyl)amino)pyrido[3,2-d]pyrimidin-6-yl)-2,2-dimethylpiperazin-1-yl)prop-2-en-1-one | 574.2 | $^{1}H$ NMR (400 MHz, $CDCl_3$) δ 9.29 (d, J = 8.4 Hz, 1H), 9.13 (d, J = 3.5 Hz, 1H), 8.70 (s, 1H), 8.57-8.50 (m, 1H), 8.26 (s, 1H), 8.03 (d, J = 9.3 Hz, 1H), 7.18 (d, J = 9.4 Hz, 1H), 7.11 (d, J = 10.9 Hz, 1H), 6.95-6.87 (m, 2H), 6.57 (dd, J = 16.8, 10.6 Hz, 1H), 6.26 (dd, J = 16.8, 1.8 Hz, 1H), 5.69 (dd, J = 10.5, 1.8 Hz, 1H), 4.00 (t, J = 5.7 Hz, 2H), 3.92 (s, 2H), 3.84 (t, J = 6.1 Hz, 2H), 1.61 (s, 6H). |
| 327 (Ex 175) | 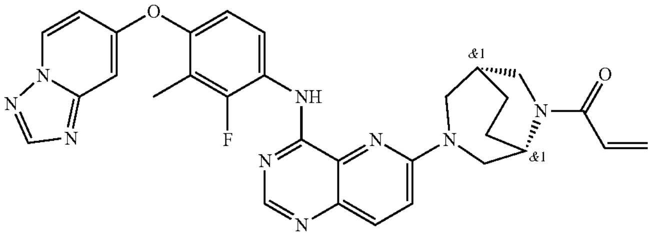 rac-1-((1R,5S)-3-(4-((4-([1,2,4]triazolo[1,5-a]pyridin-7-yloxy)-2-fluoro-3-methylphenyl)amino)pyrido[3,2-d]pyrimidin-6-yl)-3,6-diazabicyclo[3.2.2]nonan-6-yl)prop-2-en-1-one | 566.2 | $^{1}H$ NMR (400 MHz, $CDCl_3$) δ 9.08 (dd, J = 18.7, 3.5 Hz, 1H), 8.81 (td, J = 9.0, 3.3 Hz, 1H), 8.63 (d, J = 4.0 Hz, 1H), 8.53-8.48 (m, 1H), 8.23 (s, 1H), 7.97 (dd, J = 9.4, 7.0 Hz, 1H), 7.33 (dd, J = 9.5, 1.8 Hz, 1H), 7.00 (ddd, J = 9.0, 3.8, 1.7 Hz, 1H), 6.92-6.86 (m, 2H), 6.62 (ddd, J = 42.4, 16.7, 10.4 Hz, 1H), 6.40 (ddd, J = 16.8, 9.7, 2.0 Hz, 1H), 5.75 (dt, J = 10.3, 2.2 Hz, 1H), 5.07-4.54 (m, 2H), 4.50-4.38 (m, 1H), 3.96-3.75 (m, 1H), 3.70-3.43 (m, 3H), 2.63 (s, 1H), 2.21 (dd, J = 4.4, 2.1 Hz, 3H), 2.07-1.71 (m, 4H). |
| 328 (Ex 175) | 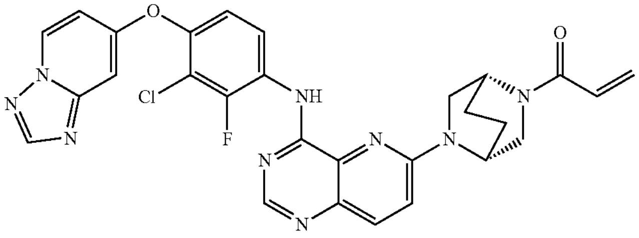 1-((1R,4R)-5-(4-((4-([1,2,4]triazolo[1,5-a]pyridin-7-yloxy)-3-chloro-2-fluorophenyl)amino)pyrido[3,2-d]pyrimidin-6-yl)-2,5-diazabicyclo[2.2.2]octan-2-yl)prop-2-en-1-one | 572.2 | $^{1}H$ NMR (400 MHz, $CDCl_3$) δ 9.11-9.06 (m, 1H), 8.99 (td, J = 8.9, 1.4 Hz, 1H), 8.64 (s, 1H), 8.57-8.50 (m, 1H), 8.25 (s, 1H), 8.01 (dd, J = 9.3, 4.4 Hz, 1H), 7.18-7.05 (m, 2H), 6.96-6.89 (m, 2H), 6.65-6.36 (m, 2H), 5.81-5.73 (m, 1H), 5.23-4.42 (m, 2H), 4.04-3.69 (m, 4H), 2.28-2.12 (m, 2H), 2.10-1.91 (m, 2H). |

TABLE 3-continued

| Example No. (Method) | Structure; IUPAC name | LCMS $M^{+1}$ | $^1$H NMR (ppm); $^{19}$F NMR (ppm); optical rotation; Chiral HPLC/SFC conditions |
|---|---|---|---|
| 329 (Ex 176) | 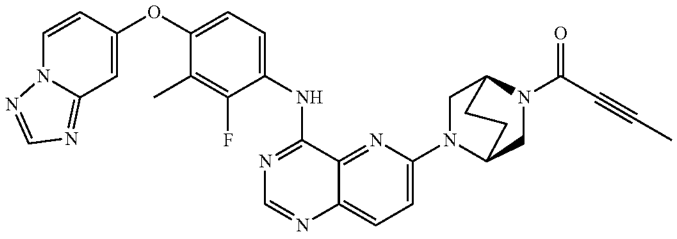 1-((1S,4S)-5-(4-((4-([1,2,4]triazolo[1,5-a]pyridin-7-yloxy)-2-fluoro-3-methylphenyl)amino)pyrido[3,2-d]pyrimidin-6-yl)-2,5-diazabicyclo[2.2.2]octan-2-yl)but-2-yn-1-one | 564.2 | $^1$H NMR (400 MHz, $CDCl_3$) δ 9.07-9.03 (m, 1H), 8.86-8.78 (m, 1H), 8.63 (s, 1H), 8.53-8.48 (m, 1H), 8.23 (s, 1H), 8.00 (dd, J = 9.3, 2.3 Hz, 1H), 7.10-7.03 (m, 1H), 7.00 (dd, J = 9.0, 1.7 Hz, 1H), 6.92-6.85 (m, 2H), 5.15-4.77 (m, 2H), 4.06-3.66 (m, 4H), 2.25-2.13 (m, 5H), 2.07-1.96 (m, 5H). |
| 330 (Ex 175) | 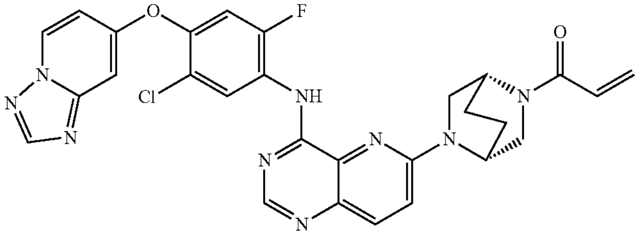 1-((1R,4R)-5-(4-((4-([1,2,4]triazolo[1,5-a]pyridin-7-yloxy)-5-chloro-2-fluorophenyl)amino)pyrido[3,2-d]pyrimidin-6-yl)-2,5-diazabicyclo[2.2.2]octan-2-yl)prop-2-en-1-one | 572.1 | $^1$H NMR (400 MHz, $CDCl_3$) δ 9.28 (dd, J = 8.3, 1.7 Hz, 1H), 9.08-9.04 (m, 1H), 8.68 (s, 1H), 8.56-8.50 (m, 1H), 8.26 (s, 1H), 8.01 (dd, J = 9.3, 2.9 Hz, 1H), 7.14-7.06 (m, 2H), 6.94-6.89 (m, 2H), 6.63-6.36 (m, 2H), 5.80-5.73 (m, 1H), 5.16-4.41 (m, 2H), 4.03-3.67 (m, 4H), 2.24-2.13 (m, 2H), 2.08-1.91 (m, 2H). |
| 331 (Ex 175) | 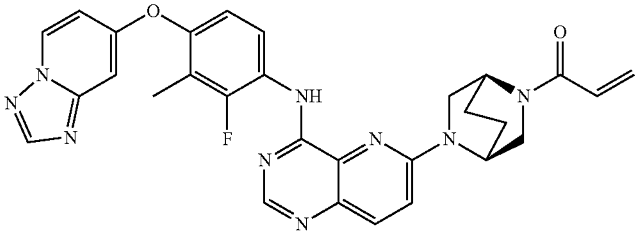 1-((1S,4S)-5-(4-((4-([1,2,4]triazolo[1,5-a]pyridin-7-yloxy)-2-fluoro-3-methylphenyl)amino)pyrido[3,2-d]pyrimidin-6-yl)-2,5-diazabicyclo[2.2.2]octan-2-yl)prop-2-en-1-one | 552.2 | $^1$H NMR (400 MHz, $CDCl_3$) δ 9.07 (s, 1H), 8.86-8.79 (m, 1H), 8.63 (s, 1H), 8.53-8.48 (m, 1H), 8.23 (s, 1H), 7.99 (dd, J = 9.3, 3.2 Hz, 1H), 7.10-7.04 (m, 1H), 7.02-6.98 (m, 1H), 6.92-6.85 (m, 2H), 6.64-6.36 (m, 2H), 5.81-5.73 (m, 1H), 5.16-4.40 (m, 2H), 4.05-3.69 (m, 4H), 2.26-2.13 (m, 5H), 2.09-1.90 (m, 2H). |

TABLE 3-continued

| Example No. (Method) | Structure; IUPAC name | LCMS $M^{+1}$ | $^1H$ NMR (ppm); $^{19}F$ NMR (ppm); optical rotation; Chiral HPLC/SFC conditions |
|---|---|---|---|
| 332 (Ex 175) | 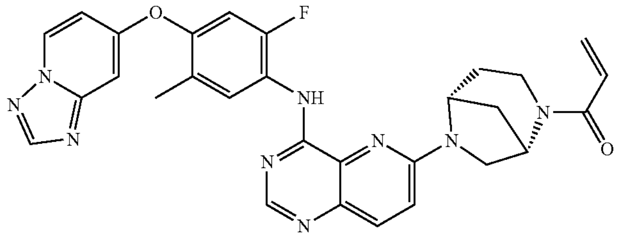 1-((1S,5R)-6-(4-((4-([1,2,4]triazolo[1,5-a]pyridin-7-yloxy)-2-fluoro-5-methylphenyl)amino)pyrido[3,2-d]pyrimidin-6-yl)-2,6-diazabicyclo[3.2.1]octan-2-yl)prop-2-en-1-one | 552.2 | $^1H$ NMR (400 MHz, $CDCl_3$) δ 9.10 (s, 1H), 8.89 (d, J = 9.2 Hz, 1H), 8.64 (s, 1H), 8.54-8.46 (m, 1H), 8.24 (s, 1H), 7.97 (d, J = 9.2 Hz, 1H), 7.04 (d, J = 9.2 Hz, 1H), 6.95 (d, J = 11.0 Hz, 1H), 6.91-6.84 (m, 2H), 6.60 (ddd, J = 52.0, 16.8, 10.5 Hz, 1H), 6.33 (d, J = 16.7 Hz, 1H), 5.79-5.57 (m, 2H), 4.91-4.46 (m, 2H), 3.96-3.56 (m, 3H), 3.37-2.85 (m, 1H), 2.27 (s, 3H), 2.18-2.12 (m, 1H), 2.03-1.80 (m, 2H). |
| 333 (Ex 176) | 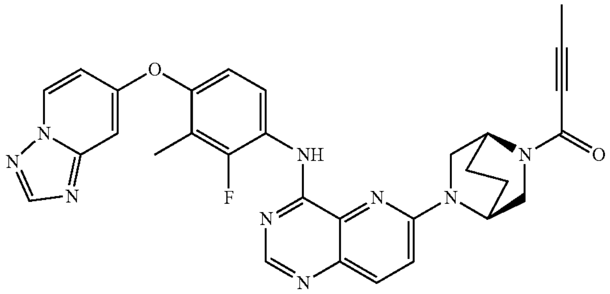 1-((1S,4S)-5-(4-((4-([1,2,4]triazolo[1,5-a]pyridin-7-yloxy)-2-fluoro-3-methylphenyl)amino)pyrido[3,2-d]pyrimidin-6-yl)-2,5-diazabicyclo[2.2.1]heptan-2-yl)but-2-yn-1-one | 550.2 | $^1H$ NMR (400 MHz, $CDCl_3$) δ 9.10 (dd, J = 11.4, 3.5 Hz, 1H), 8.83 (q, J = 8.7 Hz, 1H), 8.63 (s, 1H), 8.53-8.48 (m, 1H), 8.23 (s, 1H), 7.98 (dd, J = 9.2, 2.9 Hz, 1H), 7.03-6.95 (m, 2H), 6.93-6.85 (m, 2H), 5.19-5.00 (m, 2H), 3.89-3.60 (m, 4H), 2.20 (t, J = 2.2 Hz, 3H), 2.18-2.07 (m, 2H), 2.00 (d, J = 42H, 3H). |
| 334 (Ex 164) | 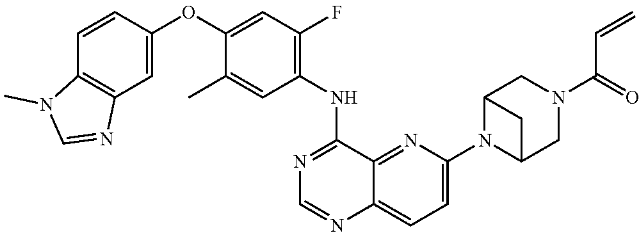 1-(6-(4-((2-fluoro-5-methyl-4-((1-methyl-1H-benzo[d]imidazol-5-yl)oxy)phenyl)amino)pyrido[3,2-d]pyrimidin-6-yl)-3,6-diazabicyclo[3.1.1]heptan-3-yl)prop-2-en-1-one | 551.3 | $^1H$ NMR (400 MHz, $CDCl_3$) δ 8.94 (d, J = 3.1 Hz, 1H), 8.60 (s, 1H), 8.50 (d, J = 9.1 Hz, 1H), 7.96 (d, J = 9.0 Hz, 1H), 7.86 (s, 1H), 7.34 (m, 2H), 7.05 (dd, J = 8.8, 2.2 Hz, 1H), 6.93 (d, J = 9.0 Hz, 1H), 6.76 (dd, J = 9.0, 1.7 Hz, 1H), 6.47 (dd, J = 16.7, 10.3 Hz, 1H), 6.32 (16.7, 2.1 Hz, 1H), 5.67 (dd, J = 10.3, 2.1 Hz, 1H), 4.68 (m, 2H), 4.44 (m, 1H), 4.14 (m, 1H), 3.86 (s, 3H), 3.75 (d, J = 11.4, 1.5 Hz, 1H), 2.94 (m, 1H), 2.29 (d, J = 2.2 Hz, 3H), 1.73 (d, J = 8.8 Hz, 1H) |

TABLE 3-continued

| Example No. (Method) | Structure; IUPAC name | LCMS $M^{+1}$ | $^1H$ NMR (ppm); $^{19}F$ NMR (ppm); optical rotation; Chiral HPLC/SFC conditions |
|---|---|---|---|
| 335 (Ex 164) | 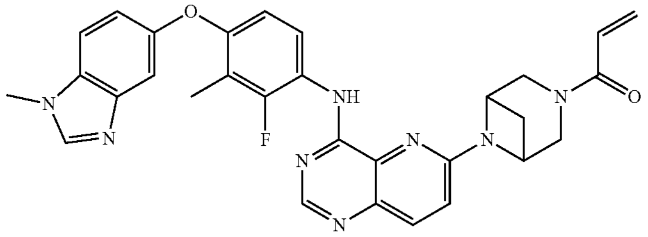 1-(6-(4-((2-fluoro-3-methyl-4-((1-methyl-1H-benzo[d]imidazol-5-yl)oxy)phenyl)amino)pyrido[3,2-d]pyrimidin-6-yl)-3,6-diazabicyclo[3.1.1]heptan-3-yl)prop-2-en-1-one | 551.3 | $^1H$ NMR (400 MHz, $CDCl_3$) δ 8.82 (d, J = 2.8 Hz, 1H), 8.65 (s, 1H), 8.60 (d, J = 9.2 Hz, 1H), 7.96 (d, J = 9.0 Hz, 1H), 7.87 (s, 1H), 7.36 (m, 2H), 7.05 (dd, J = 8.7, 2.3 Hz, 1H), 6.92 (d, J = 9.0 Hz, 1H), 6.69 (d, J = 11.9 Hz, 1H), 6.45 (dd, J = 16.7, 10.3 Hz, 1H), 6.31 (16.7, 2.1 Hz, 1H), 5.66 (dd, J = 10.3, 2.1 Hz, 1H), 4.65 (m, 2H), 4.42 (m, 1H), 4.15 (m, 1H), 3.86 (s, 3H), 3.80 (d, J = 14.0 Hz, 1H), 3.73 (m, 1H), 2.91 (m, 1H), 2.36 (s, 3H), 1.71 (d, J = 8.8 Hz, 1H) |
| 336 (Ex 164) | 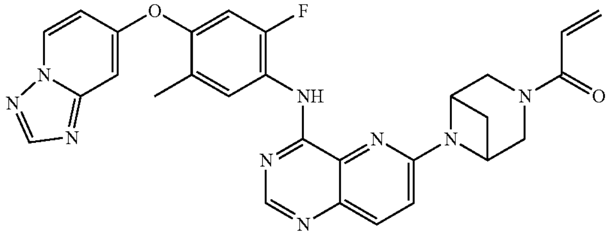 1-(6-(4-((4-([1,2,4]-triazolo[1,5-a]pyridin-7-yloxy)-2-fluoro-5-methylphenyl)amino)pyrido[3,2-d]pyrimidin-6-yl)-3,6-diazabicyclo[3.1.1]heptan-3-yl)prop-2-en-1-one | 538.3 | $^1H$ NMR (400 MHz, $CDCl_3$) δ 9.00 (d, J = 3.2 Hz, 1H), 8.84 (d, J = 9.0 Hz, 1H), 8.68 (s, 1H), 8.24 (s, 1H), 7.99 (d, J = 9.0 Hz, 1H), 6.96 (m, 1H), 6.93 (d, J = 3.3 Hz, 1H), 6.89 (m, 2H), 6.50 (s, 1H), 6.47 (dd, J = 16.7, 10.3 Hz, 1H), 6.32 (dd, J = 16.7, 2.1 Hz, 1H), 5.67 (dd, J = 10.3, 2.1 Hz, 1H), 4.68 (d, J = 6.1 Hz, 2H), 4.42 (m, 1H), 4.15 (m, 1H), 3.80 (m, 2H), 2.94 (q, J = 7.0 Hz, 1H), 2.27 (d, J = 0.9 Hz, 3H) 1.73 (d, 8.9 Hz, 1H) |
| 337 (Ex 164) | 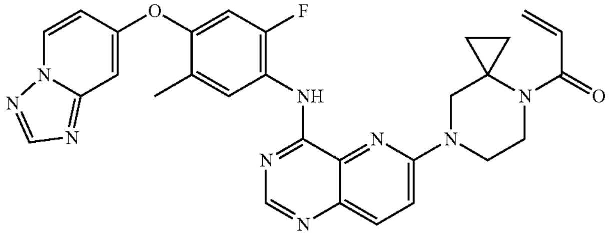 1-(7-(4-((4-([1,2,4]triazolo[1,5-a]pyridin-7-yloxy)-2-fluoro-5-methylphenyl)amino)pyrido[3,2-d]pyrimidin-6-yl)-4,7-diazaspiro[2.5]octan-4-yl)prop-2-en-1-one | 552.2 | $^1H$ NMR (400 MHz, $CDCl_3$) δ 8.98 (d, J = 3.3 Hz, 1H), 8.87 (d, J = 9.1 Hz, 1H), 8.66 (s, 1H), 8.51 (m, 1H), 8.24 (s, 1H), 7.99 (d, J = 9.3 Hz, 1H), 7.24 (m, 1H), 6.95 (d, J = 11.0 Hz, 1H), 6.87 (m, 2H), 6.42 (m, 1H), 5.77 (dd, J = 10.4, 1.9 Hz, 1H), 4.01 (bs, 2H), 3.83 (s, 2H), 3.70 (s, 2H), 2.27 (s, 3H), 1.14 (s, 4H) |
| 338 (Ex 164) | 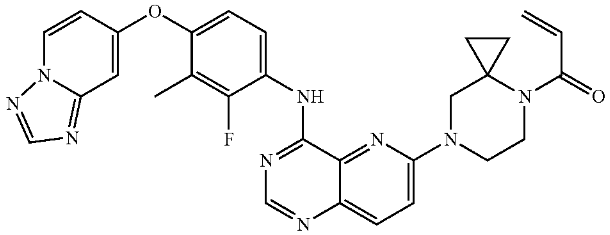 1-(7-(4-((4-([1,2,4]triazolo[1,5-a]pyridin-7-yloxy)-2-fluoro-3-methylphenyl)amino)pyrido[3,2-d]pyrimidin-6-yl)-4,7-diazaspiro[2.5]octan-4-yl)prop-2-en-1-one | 552.2 | $^1H$ NMR (400 MHz, $CDCl_3$) δ 9.03 (d, J = 3.6 Hz, 1H), 8.82 (t, J = 9.0 Hz, 1H), 8.64 (s, 1H), 8.51 (dd, J = 7.3, 0.9 Hz, 1H), 8.23 (s, 1H), 7.99 (d, J = 9.3 Hz, 1H), 7.23 (m, 1H), 7.00 (m, 1H), 6.88 (m, 2H), 6.42 (m, 1H), 5.77 (dd, J = 10.4, 1.9 Hz, 1H), 4.02 (bs, 2H), 3.84 (s, 2H), 3.70 (s, 2H), 2.21 (d, J = 2.1 Hz, 3H), 1.16 (s, 4H) |

TABLE 3-continued

| Example No. (Method) | Structure; IUPAC name | LCMS $M^{+1}$ | $^1H$ NMR (ppm); $^{19}F$ NMR (ppm); optical rotation; Chiral HPLC/SFC conditions |
|---|---|---|---|
| 339 (Ex 164) | 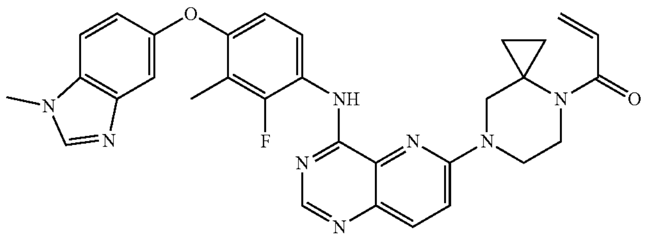 1-(7-(4-((2-fluoro-3-methyl-4-((1-methyl-3a,7a-dihydro-1H-benzo[d]imidazol-5-yl)oxy)phenyl)amino)pyrido[3,2-d]pyrimidin-6-yl)-4,7-diazaspiro[2.5]octan-4-yl)prop-2-en-1-one | 565.3 | $^1H$ NMR (400 MHz, $CDCl_3$) δ 8.91 (d, J = 3.4 Hz, 1H), 8.58 (s, 1H), 8.53 (t, J = 9.1 Hz, 1H), 7.96 (d, J = 9.3 Hz, 1H), 7.86 (s, 1H), 7.33 (m, 2H), 7.22 (d, J = 9.3, Hz, 1H), 7.06 (dd, J = 8.7, 2.4 Hz, 1H), 6.77 (dd, J = 9.0, 1.7 Hz, 1H), 6.42 (dd, J = 16.8, 1.9 Hz, 1H), 5.77 (dd, J = 10.4, 1.9 Hz, 1H), 4.02 (m, 3H), 3.86 (s, 3H), 3.82 (m, 2H), 3.69 (s, 2H), 2.29 (d, J = 2.1 Hz, 3H), 1.12 (s, 4H) |
| 340 (Ex 164) | 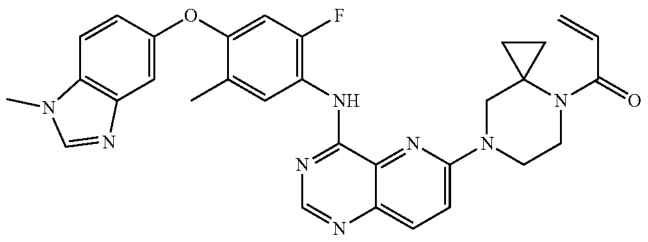 1-(7-(4-((2-fluoro-5-methyl-4-((1-methyl-3a,7a-dihydro-1H-benzo[d]imidazol-5-yl)oxy)phenyl)amino)pyrido[2,3-d]pyrimidin-6-yl)-4,7-diazaspiro[2.5]octan-4-yl)prop-2-en-1-one | 565.3 | $^1H$ NMR (400 MHz, $CDCl_3$) δ 8.80 (d, J = 2.9 Hz, 1H), 8.64 (m, 2H), 7.96 (d, J = 9.4 Hz, 1H), 7.87 (s, 1H), 7.35 (m, 2H), 7.21 (d, J = 9.4 Hz, 1H), 7.05 (dd, J = 8.8, 2.3 Hz, 1H), 6.70 (d, 1H), 6.40 (d, J = 16.8 Hz, 1H), 5.75 (dd, J = 10.4, 1.9 Hz, 1H), 3.99 (m, 3H), 3.86 (s, 3H), 3.80 (m, 2H), 3.66 (s, 2H), 2.36 (s, 3H), 1.12 (s, 4H) |
| 341 (Ex 164) | 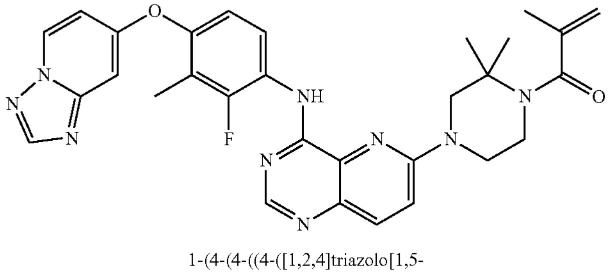 1-(4-(4-((4-([1,2,4]triazolo[1,5-a]pyridin-7-yloxy)-2-fluoro-3-methylphenyl)amino)pyrido[2,3-d]pyrimidin-6-yl)-2,2-dimethylpiperazin-1-yl)-2-methylprop-2-en-1-one | 568.3 | $^1H$ NMR (400 MHz, $CDCl_3$) δ 9.11 (d, J = 3.6 Hz, 1H), 8.86 (t, J = 9.0 Hz, 1H), 8.64 (s, 1H), 8.51 (dd, J = 7.3, 0.9 Hz, 1H), 8.23 (s, 1H), 8.01 (d, J = 9.3 Hz, 1H), 7.16 (d, J = 9.3 Hz, 1H), 7.01 (m, 1H), 6.88 (m, 2H), 5.21 (m, 1H), 5.09 (m, 1H), 3.95 (t, J = 5.7 Hz, 2H), 3.92 (s, 2H), 3.79 (t, J = 5.6 Hz, 2H), 2.21 (d, J = 2.2 Hz, 3H), 1.99 (m, 3H), 1.63 (s, 6H) |

TABLE 3-continued

| Example No. (Method) | Structure; IUPAC name | LCMS $M^{+1}$ | $^1H$ NMR (ppm); $^{19}F$ NMR (ppm); optical rotation; Chiral HPLC/SFC conditions |
|---|---|---|---|
| 342 (Ex 164) | 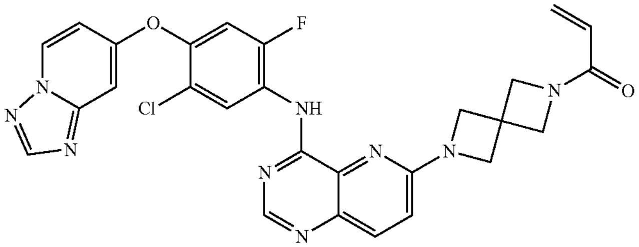 1-(6-(4-((4-([1,2,4]triazolo[1,5-a]pyridin-7-yloxy)-5-chloro-2-fluorophenyl)amino)pyrido[3,2-d]pyrimidin-6-yl)-2,6-diazaspiro[3.3]heptan-2-yl)prop-2-en-1-one | 558.1 | $^1H$ NMR (400 MHz, $CDCl_3$) δ 9.27 (d, J = 8.3 Hz, 1H), 9.15 (d, J = 3.4 Hz, 1H), 8.69 (s, 1H), 8.53 (m, 1H), 8.26 (s, 1H), 7.98 (d, J = 9.1 Hz, 1H), 7.11 (d, J = 10.9 Hz, 1H), 6.90 (m, 3H), 6.38 (dd, J = 16.9, 1.9 Hz, 1H), 6.20 (dd, J = 17.0, 10.3 Hz, 1H), 5.73 (dd, J = 10.3, 1.9 Hz, 1H), 4.40 (m, 8H) |
| 343 (Ex 164) | 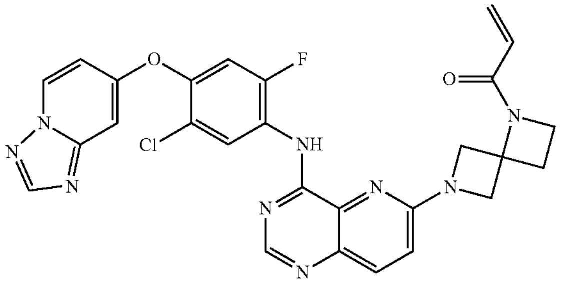 1-(6-(4-((4-([1,2,4]triazolo[1,5-a]pyridin-7-yloxy)-5-chloro-2-fluorophenyl)amino)pyrido[3,2-d]pyrimidin-6-yl)-1,6-diazaspiro[3.3]heptan-1-yl)prop-2-en-1-one | 558.2 | $^1H$ NMR (400 MHz, $CDCl_3$) δ 9.28 (dd, J = 8.4, 5.5 Hz, 1H), 9.15 (m, 1H), 8.67 (m, 1H), 8.53 (m, 1H), 8.26 (s, 1H), 7.94 (d, J = 9.1 Hz, 1H), 7.08 (m, 1H), 6.92 (m, 3H), 6.40 (dd, J = 16.8, 1.8 Hz, 1H), 6.18 (dd, J = 16.9, 10.3 Hz, 1H), 5.74 (m, 1H), 5.08 (d, J = 9.1 Hz, 2H), 4.29 (d, J = 8.8 Hz, 2H), 4.22 (t, J = 7.4 Hz, 2H), 2.70 (t, J = 7.4 Hz, 2H) |
| 344 (Ex 164) | 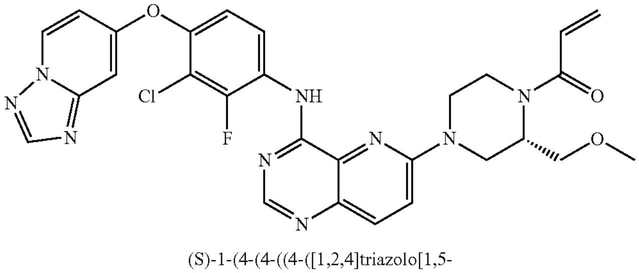 (S)-1-(4-(4-((4-([1,2,4]triazolo[1,5-a]pyridin-7-yloxy)-3-chloro-2-fluorophenyl)amino)pyrido[3,2-d]pyrimidin-6-yl)-2-(methoxymethyl)piperazin-1-yl)prop-2-en-1-one | 590.3 | $^1H$ NMR (400 MHz, $CDCl_3$) δ 9.11 (d, J = 3.4 Hz, 1H), 8.99 (t, J = 8.9, 1H), 8.66 (s, 1H), 8.54 (dd, J = 7.2, 1.0 Hz, 1H), 8.25 (s, 1H), 8.01 (d, J = 9.3 Hz, 1H), 7.34 (d, J = 9.4 Hz, 1H), 7.16 (dd, J = 9.2, 2.1 Hz, 1H), 6.91 (m, 2H), 6.68 (bs, 1H), 6.40 (m, 1H), 5.79 (dd, J = 10.5, 1.8 Hz, 1H), 4.48 (m, 3H), 3.43 (m, 8H) |

TABLE 3-continued

| Example No. (Method) | Structure; IUPAC name | LCMS $M^{+1}$ | $^1H$ NMR (ppm); $^{19}F$ NMR (ppm); optical rotation; Chiral HPLC/SFC conditions |
|---|---|---|---|
| 345 (Ex 164) | 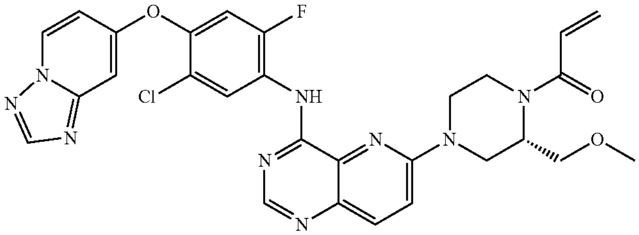 (S)-1-(4-(4-((4-([1,2,4]triazolo[1,5-a]pyridin-7-yloxy)-5-chloro-2-fluorophenyl)amino)pyrido[3,2-d]pyrimidin-6-yl)-2-(methoxymethyl)piperazine-1-yl)prop-2-en-1-one | 590.3 | $^1H$ NMR (400 MHz, $CDCl_3$) δ 9.28 (d, J = 8.3 Hz, 1H), 8.09 (d, J = 3.5 Hz, 1H), 8.70 (s, 1H), 8.54 (m, 1H), 8.26 (s, 1H), 8.02 (d, J = 9.4 Hz, 1H), 7.33 (d, J = 9.4 Hz, 1H), 7.12 (d, J = 10.1 Hz, 1H), 6.92 (m, 2H), 6.65 (m, 1H), 6.39 (m, 1H), 5.78 (dd, J = 10.5, 1.9 Hz, 1H), 4.48 (m, 3H), 3.43 (m, 8H) |
| 346 (Ex 164) | 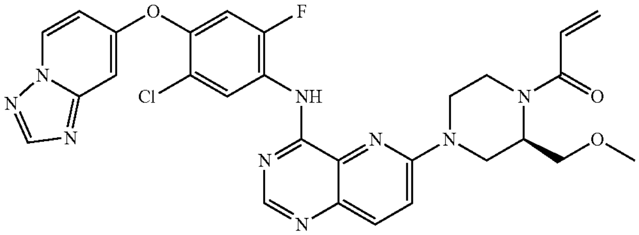 (R)-1-(4-(4-((4-([1,2,4]triazolo[1,5-a]pyridin-7-yloxy)-5-chloro-2-fluorophenyl)amino)pyrido[3,2-d]pyrimidin-6-yl)-2-(methoxymethyl)piperazin-1-yl)prop-2-en-1-one | 590.3 | $^1H$ NMR (400 MHz, $CDCl_3$) δ 9.28 (d, J = 8.3 Hz, 1H), 9.09 (d, J = 3.5 Hz, 1H), 8.70 (s, 1H), 8.54 (m, 1H), 8.26 (s, 1H), 8.02 (d, J = 9.4 Hz, 1H), 7.33 (d, J = 9.4 Hz, 1H), 7.12 (d, J = 10.1 Hz, 1H), 6.92 (m, 2H), 6.65 (m, 1H), 6.39 (m, 1H), 5.78 (dd, J = 10.5, 1.9 Hz, 1H), 4.48 (m, 3H), 3.43 (m, 8H) |
| 347 (Ex 164) | 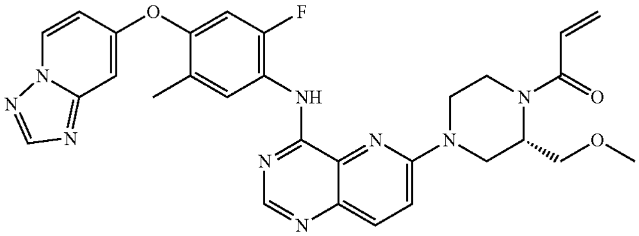 (S)-1-(4-(4-((4-([1,2,4]triazolo[1,5-a]pyridin-7-yloxy)-2-fluoro-5-methylphenyl)amino)pyrido[3,2-d]pyrimidin-6-yl)-2-(methoxymethyl)piperazin-1-yl)prop-2-en-1-one | 570.3 | $^1H$ NMR (400 MHz, $CDCl_3$) δ 9.03 (d, J = 3.2 Hz, 1H), 8.88 (d, J = 9.1 Hz, 1H), 8.67 (s, 1H), 8.51 (m, 1H), 8.24 (s, 1H), 8.00 (d, J = 9.3 Hz, 1H), 7.31 (d, J = 9.4 Hz, 1H), 6.96 (d, J = 11.1 Hz, 1H), 6.89 (d, J = 6.5 Hz, 2H), 6.65 (m, 1H), 6.38 (d, J = 16.7 Hz, 1H), 5.78 (dd, J = 10.5, 1.9 Hz, 1H), 4.48 (m, 3H), 3.43 (m, 8H), 2.27 (s, 3H) |
| 348 (Ex 164) | 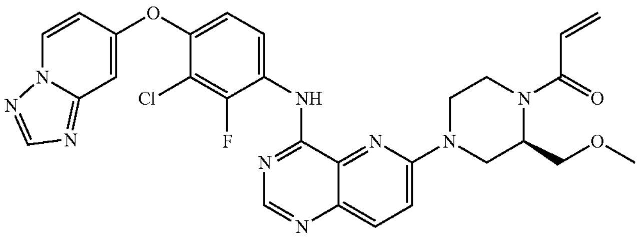 (R)-1-(4-(4-((4-([1,2,4]triazolo[1,5-a]pyridin-7-yloxy)-3-chloro-2-fluorophenyl)amino)pyrido[3,2-d]pyrimidin-6-yl)-2-(methoxymethyl)piperazin-1-yl)prop-2-en-1-one | 590.2 | $^1H$ NMR (400 MHz, $CDCl_3$) δ 9.11 (d, J = 3.4 Hz, 1H), 8.99 (t, J = 8.9 Hz, 1H), 8.66 (s, 1H), 8.54 (dd, J = 7.2, 1.0 Hz, 1H), 8.25 (s, 1H), 8.02 (d, J = 9.4 Hz, 1H), 7.34 (d, J = 9.4 Hz, 1H), 7.16 (dd, J = 9.2, 2.0 Hz, 1H), 6.92 (m, 2H), 6.66 (s, 1H), 6.39 (m, 1H), 5.79 (dd, J = 10.5, 1.8 Hz, 1H), 4.48 (m, 3H), 3.43 (m, 8H) |

TABLE 3-continued

| Example No. (Method) | Structure; IUPAC name | LCMS $M^{+1}$ | $^{1}H$ NMR (ppm); $^{19}F$ NMR (ppm); optical rotation; Chiral HPLC/SFC conditions |
|---|---|---|---|
| 349 (Ex 164) | 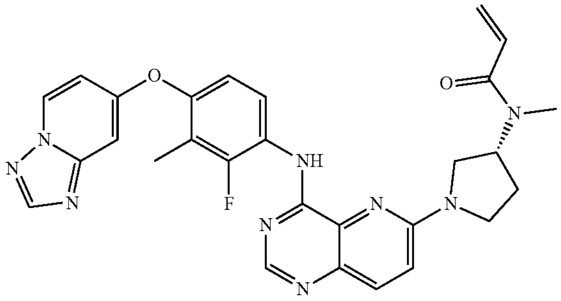 (R)-N-(1-(4-((4-([1,4]triazolo[1,5-a]pyridin-7-yloxy)-2-fluoro-3-methylphenyl)amino)pyrido[3,2-d]pyrimidin-6-yl)pyrrolidin-3-yl)-N-methylacrylamide | 540.3 | $^{1}H$ NMR (400 MHz, $CDCl_3$) δ 9.15 (d, J = 3.5 Hz, 1H), 8.83 (t, J = 9.0 Hz, 1H), 8.63 (s, 1H), 8.50 (m, 1H), 8.23 (s, 1H), 7.97 (s, J = 9.2 Hz, 1H), 7.01 (m, 2H), 6.89 (m, 2H), 6.64 (m, 1H), 6.39 (m, 1H), 5.77 (dd, J = 10.5, 2.0 Hz, 1H), 3.93 (m, 2H), 3.67 (m, 2H), 3.07 (s, 3H), 2.27 (s, 5H) |
| 350 (Ex 164) | 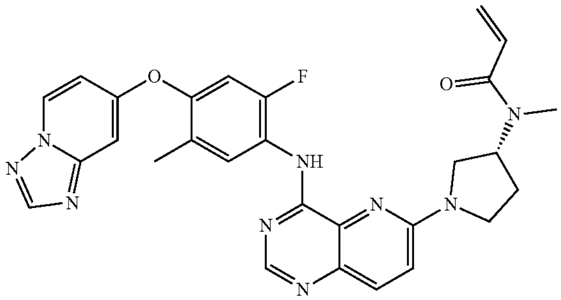 (R)-N-(1-(4-((4-([1,2,4]triazolo[1,5-a]pyridin-7-yloxy)-2-fluoro-5-methylphenyl)amino)pyrido[3,2-d]pyrimidin-6-yl)pyrrolidin-3-yl)-N-methylacrylamide | 540.3 | $^{1}H$ NMR (400 MHz, $CDCl_3$) δ 9.09 (d, J = 3.1 Hz, 1H), 8.88 (d, J = 9.0 Hz, 1H), 8.65 (s, 1H), 8.51 (m, 1H), 8.24 (s, 1H), 7.97 (d, J = 9.2 Hz, 1H), 7.03 (d, J = 9.2 Hz, 1H), 6.94 (d, J = 11.0 Hz, 1H), 6.87 (m, 2H), 6.62 (m, 1H), 6.38 (m, 1H), 5.75 (d, J = 1.9 Hz, 1H), 3.92 (m, 2H), 3.67 (m, 2H), 3.06 (s, 3H), 2.22 (s, 5H) |
| 351 (Ex 164) | 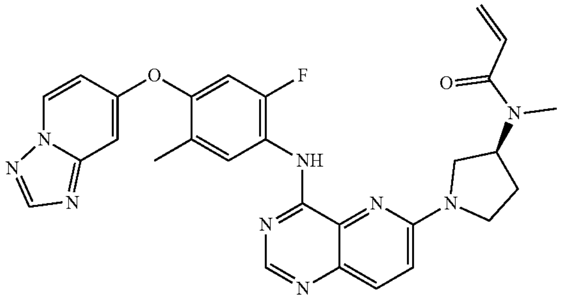 (S)-N-(1-(4-((4-([1,2,4]triazolo[1,5-a]pyridin-7-yloxy)-2-fluoro-5-methylphenyl)amino)pyrido[3,2-d]pyrimidin-6-yl)pyrrolidin-3-yl)-N-methylacrylamide | 540.3 | $^{1}H$ NMR (400 MHz, $CDCl_3$) δ 9.09 (d, J = 3.1 Hz, 1H), 8.88 (d, J = 9.0 Hz, 1H), 8.65 (s, 1H), 8.51 (m, 1H), 8.24 (s, 1H), 7.97 (d, J = 9.2 Hz, 1H), 7.03 (d, J = 9.2 Hz, 1H), 6.94 (d, J = 11.0 Hz, 1H), 6.87 (m, 2H), 6.62 (m, 1H), 6.38 (m, 1H), 5.75 (d, J = 1.9 Hz, 1H), 3.92 (m, 2H), 3.67 (m, 2H), 3.06 (s, 3H), 2.22 (s, 5H) |

TABLE 3-continued

| Example No. (Method) | Structure; IUPAC name | LCMS $M^{+1}$ | $^1H$ NMR (ppm); $^{19}F$ NMR (ppm); optical rotation; Chiral HPLC/SFC conditions |
|---|---|---|---|
| 352 (Ex 164) | 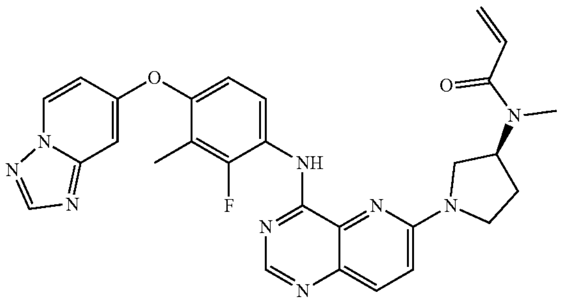 (S)-N-(1-(4-((4-([1,2,4]triazolo[1,5-a]pyridin-7-yloxy)-2-fluoro-3-methylphenyl)amino)pyrido[3,2-d]pyrimidin-6-yl)pyrrolidin-3-yl)-N-methylacrylamide | 540.2 | $^1H$ NMR (400 MHz, $CDCl_3$) δ 9.15 (d, J = 3.5 Hz, 1H), 8.83 (t, J = 9.0 Hz, 1H), 8.63 (s, 1H), 8.50 (m, 1H), 8.23 (s, 1H), 7.97 (s, J = 9.2 Hz, 1H), 7.01 (m, 2H), 6.89 (m, 2H), 6.64 (m, 1H), 6.39 (m, 1H), 5.77 (dd, J = 10.5, 2.0 Hz, 1H), 3.93 (m, 2H), 3.67 (m, 2H), 3.07 (s, 3H), 2.27 (s, 5H) |
| 353 (Ex 164) | 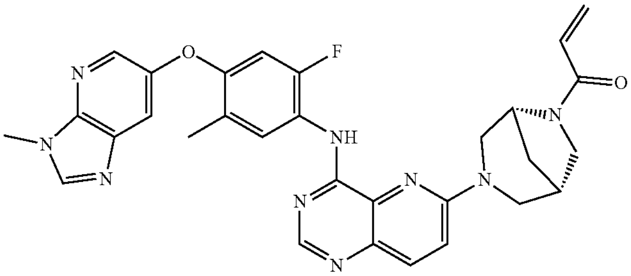 1-((1S,5R)-3-(4-((2-fluoro-5-methyl-4-((3-methyl-3H-imidazo[4,5-b]pyridin-6-yl)oxy)phenyl)amino)pyrido[3,2-d]pyrimidin-6-yl)-3,6-diazabicyclo[3.2.1]octan-6-yl)prop-2-en-1-one | 566.3 | $^1H$ NMR (400 MHz, $CDCl_3$) δ 8.87 (d, J = 3.2 Hz, 1H), 8.70 (dd, J = 18.6, 9.2 Hz, 1H), 8.63 (d, J = 5.1 Hz, 1H), 8.29 (d, J = 2.5 Hz, 1H), 8.04 (s, 1H), 7.94 (m, 1H), 7.62 (m, 1H), 7.19 (dd, J = 15.3, 9.4 Hz, 1H), 6.69 (d, J = 11.7 Hz, 1H), 6.37 (m, 1H), 5.70 (m, 1H), 4.80 (s, 1H), 4.40 (m, 2H), 3.94 (s, 3H), 3.65 (m, 2H), 3.35 (m, 1H), 3.18 (m, 1H), 2.83 (m, 1H), 2.36 (s, 3H) 1.97 (m, 2H) |
| 354 (Ex 164) | 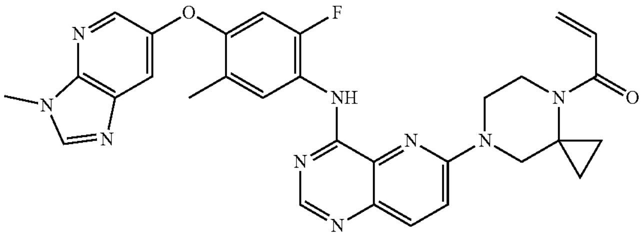 1-(7-(4-((2-fluoro-5-methyl-4-((3-methyl-3H-imidazo[4,5-b]pyridin-6-yl)oxy)phenyl)amino)pyrido[3,2-d]pyrimidin-6-yl)-4,7-diazaspiro[2.5]octan-4-yl)prop-2-en-1-one | 566.2 | $^1H$ NMR (400 MHz, $CDCl_3$) δ 8.83 (d, J = 2.9 Hz, 1H), 8.70 (d, J = 9.1 Hz, 1H), 8.64 (s, 1H), 8.29 (d, J = 2.5 Hz, 1H), 8.04 (s, 1H), 7.97 (d, J = 9.4 Hz, 1H), 7.62 (d, J = 2.5, 1H), 7.22 (m, 1H), 6.70 (d, J = 11.7 Hz, 1H), 6.41 (m, 1H), 5.76 (dd, J = 10.4, 1.9 Hz, 1H), 3.99 (bs, 2H), 3.94 (s, 3H), 3.80 (bs, 2H), 3.67 (s, 2H), 2.37 (s, 3H), 1.13 (bs, 4H) |

TABLE 3-continued

| Example No. (Method) | Structure; IUPAC name | LCMS $M^{+1}$ | $^1$H NMR (ppm); $^{19}$F NMR (ppm); optical rotation; Chiral HPLC/SFC conditions |
|---|---|---|---|
| 355 (Ex 164) | 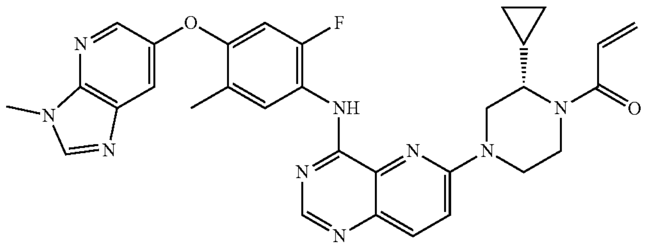 (S)-1-(2-cyclopropyl-4-(4-((2-fluoro-5-methyl-4-((3-methyl-3H-imidazo[4,5-b]pyridin-6-yl)oxy)phenyl)amino)pyrido[3,2-d]pyrimidin-6-yl)piperazin-1-yl)prop-2-en-1-one | 580.3 | $^1$H NMR (400 MHz, $CDCl_3$) δ 8.91 (d, J = 3.1 Hz, 1H), 8.73 (d, J = 9.1 Hz, 1H), 8.65 (s, 1H), 8.30 (d, J = 8.3 Hz, 1H), 8.05 (s, 1H), 7.98 (d, J = 9.3 Hz, 1H), 7.62 (d, J = 2.5 Hz, 1H), 7.32 (d, J = 9.4 Hz, 1H), 6.70 (d, J = 11.7 Hz, 1H), 6.35 (d, J = 16.8, 1.8 Hz, 1H), 5.75 (dd, J = 10.5, 1.9 Hz, 1H), 4.54 (bs, 2H), 3.94 (m, 5H), 3.23 (m, 2H) 3.15 (m, 2H), 2.37 (s, 3H), 0.61 (m, 1H), 0.50 (m, 3H) |
| 356 (Ex 164) | 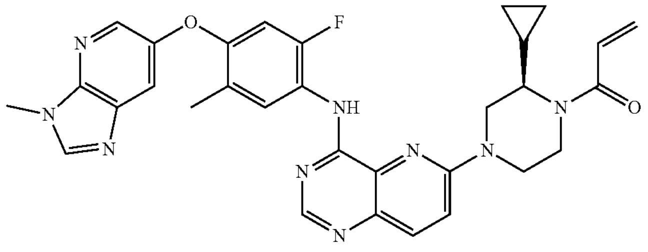 (R)-1-(2-cyclopropyl-4-(4-((2-fluoro-5-methyl-4-((3-methyl-3H-imidazo[4,5-b]pyridin-6-yl)oxy)phenyl)amino)pyrido[3,2-d]pyrimidin-6-yl)piperazin-1-yl)prop-2-en-1-one | 580.4 | $^1$H NMR (400 MHz, $CDCl_3$) δ 8.91 (d, J = 3.1 Hz, 1H), 8.73 (d, J = 9.1 Hz, 1H), 8.65, (s, 1H), 8.30 (d, J = 8.3 Hz, 1H), 8.05 (s, 1H), 7.98 (d, J = 9.3 Hz, 1H), 7.62 (d, J = 2.5 Hz, 1H), 7.32, (d, J = 9.4 Hz, 1H), 6.70 (d, J = 11.7 Hz, 1H), 6.35 (d, J = 16.8, 1.8 Hz, 1H), 5.75 (dd, J = 10.5, 1.9 Hz, 1H), 4.54 (bs, 2H), 3.94 (m, 5H), 3.23 (m, 2H) 3.15 (m, 2H), 2.37 (s, 3H), 0.61 (m, 1H), 0.50 (m, 3H) |
| 357 (Ex 164) | 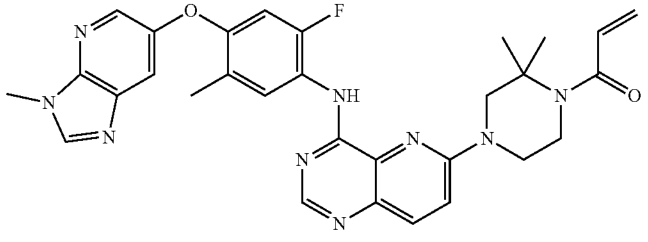 1-(4-(4-((2-fluoro-5-methyl-4-((3-methyl-3H-imidazo[4,5-b]pyridin-6-yl)oxy)phenyl)amino)pyrido[3,2-d]pyrimidin-6-yl)-2,2-dimethylpiperazin-1-yl)prop-2-en-1-one | 568.3 | $^1$H NMR (400 MHz, $CDCl_3$) δ 8.92 (d, J = 3.0 Hz, 1H), 8.72 (d, J = 9.2 Hz, 1H), 8.64 (s, 1H), 8.29 (d, 1H), 8.04 (s, 1H), 7.99 (s, J = 9.3 Hz, 1H), 7.61 (d, J = 2.5 Hz, 1H), 7.14 (d, J = 9.4 Hz, 1H), 6.70 (d, J = 11.7 Hz, 1H), 6.56 (dd, J = 16.8 Hz, 10.6 Hz, 1H), 5.67 (dd, J = 10.6, 1.8 Hz, 1H), 3.98 (t, J = 5.6 Hz, 2H), 3.94 (s, 3H), 3.89 (s, 3H), 3.82 (t, J = 5.7 Hz, 2H), 2.27 (s, 3H) 1.60 (s, 6H) |
| 358 (Ex 164) | 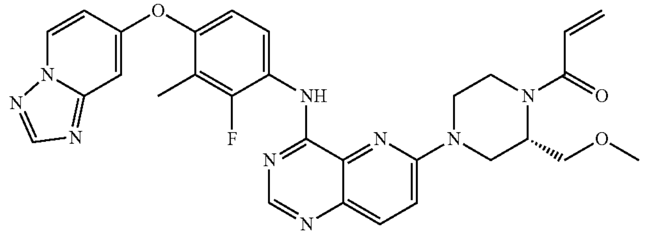 (S)-1-(4-(4-((4-([1,2,4]triazolo[1,5-a]pyridin-7-yloxy)-3-chloro-2-fluorophenyl)amino)pyrido[3,2-d]pyrimidin-6-yl)-2-(methoxymethyl)piperazin-1-yl)prop-2-en-1-one | 570.3 | $^1$H NMR (400 MHz, $CDCl_3$) δ 9.09 (d, J = 3.6 Hz, 1H), 8.83 (t, J = 9.0 Hz, 1H), 8.65 (s, 1H), 8.51 (dd, J = 7.31, 0.83 Hz, 1H), 8.24 (s, 1H), 8.00 (d, J = 9.3 Hz, 1H), 7.32 (d, J = 9.4 Hz, 1H), 7.01 (m, 1H), 6.88 (m, 2H), 6.66 (bs, 1H) 6.39 (m, 1H), 5.78 (dd, J = 10.5, 1.9 Hz, 1H), 4.48 (m, 3H), 3.48 (m, 2H) 3.33 (m, 5H), 3.26 (m, 1H), 2.21 (d, J = 2.2 Hz, 3H) |

TABLE 3-continued

| Example No. (Method) | Structure; IUPAC name | LCMS $M^{+1}$ | $^1$H NMR (ppm); $^{19}$F NMR (ppm); optical rotation; Chiral HPLC/SFC conditions |
|---|---|---|---|
| 359 (Ex 164) | 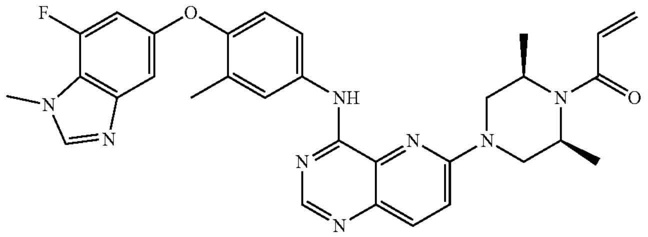 1-(4-(4-((2-fluoro-5-methyl-4-((3-methyl-3H-imidazo[4,5-b]pyridin-6-yl)oxy)phenyl)amino)pyrido[3,2-d]pyrimidin-6-yl)-2,2-dimethylpiperazin-1-yl)prop-2-en-1-one | 567.3 | $^1$H NMR (400 MHz, $CDCl_3$) δ 8.60 (s, 2H), 7.97 (d, J = 9.3 Hz, 1H), 7.75 (s, 2H), 7.68 (m, 1H), 7.29 (d, J = 9.3 Hz, 2H), 7.04 (s, J = 2.0 Hz, 1H), 7.00 (d, J = 8.7 Hz, 1H), 6.75 (dd, J = 12.2, 1.7 Hz, 1H), 6.64 (dd, J = 16.7, 10.5 Hz, 1H), 6.40 (dd, J = 16.7, 1.9 Hz, 1H), 5.76 (dd, J = 10.5, 1.9 Hz, 1H), 4.37 (d, J = 13.2 Hz, 2H), 4.00 (d, J = 1.2 Hz, 3H), 3.34 (dd, J = 13.4, 4.5 Hz, 2H), 2.31 (s, 3H), 1.41 (d, J = 1.4 Hz, 6H) |
| 360 (Ex 164) | 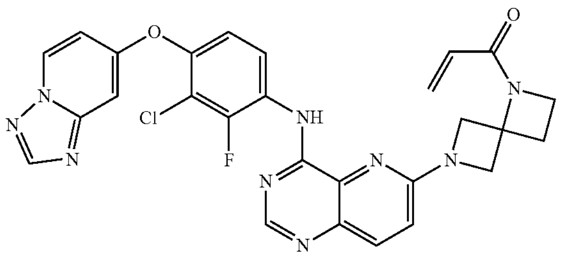 1-(6-(4-((4-([1,2,4]triazolo[1,5-a]pyridin-7-yloxy)-3-chloro-2-fluorophenyl)amino)pyrido[3,2-d]pyrimidin-6-yl)-1,6-diazaspiro[3.3]heptan-1-yl)prop-2-en-1-one | 558.2 | $^1$H NMR (400 MHz, $CDCl_3$) δ 9.17 (m, 1H), 8.98 (m, 1H), 8.63 (m, 1H), 8.53 (m, 1H), 8.25 (s, 1H), 7.98 (m, 1H), 7.14 (m, 1H), 6.92 (m, 2H), 6.38 (dd, J = 16.9, 1.8 Hz, 1H), 6.17 (dd, J = 16.9, 10.3 Hz, 1H), 5.72 (m, 1H), 5.07 (d, J = 9.6 Hz, 2H), 4.56 (m, 1H), 4.28 (d, J = 10.2 Hz, 1H), 4.21 (t, J = 7.41 Hz, 2H), 2.65 (m, 3H) |
| 361 (Ex 164) | 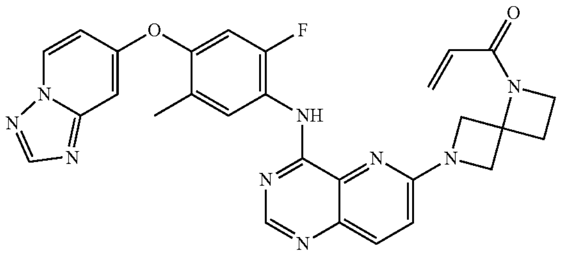 1-(6-(4-((4-([1,2,4]triazolo[1,5-a]pyridin-7-yloxy)-2-fluoro-5-methylphenyl)amino)pyrido[3,2-d]pyrimidin-6-yl)-1,6-diazaspiro[3.3]heptan-1-yl)prop-2-en-1-one | 538.2 | $^1$H NMR (400 MHz, $CDCl_3$) δ 9.07 (m, 1H), 8.88 (m, 1H), 8.66 (m, 1H), 8.50 (m, 1H), 8.24 (s, 1H), 7.96 (m, 1H), 7.14 (m, 1H), 6.89 (m, 2H), 6.38 (dd, J = 17.0, 1.8 Hz, 1H), 6.16 (dd, J = 16.9, 10.3 Hz, 1H), 5.72 (m, 1H), 5.05 (d, J = 10.1 Hz, 1H), 4.51 (m, 1H), 4.27 (d, J = 10.1 Hz, 1H), 4.20 (t, J = 7.38 Hz, 2H), 2.67 (m, 3H), 2.26 (d, J = 2.3 Hz, 3H) |

TABLE 3-continued

| Example No. (Method) | Structure; IUPAC name | LCMS $M^{+1}$ | $^{1}$H NMR (ppm); $^{19}$F NMR (ppm); optical rotation; Chiral HPLC/SFC conditions |
|---|---|---|---|
| 362 (Ex 164) | 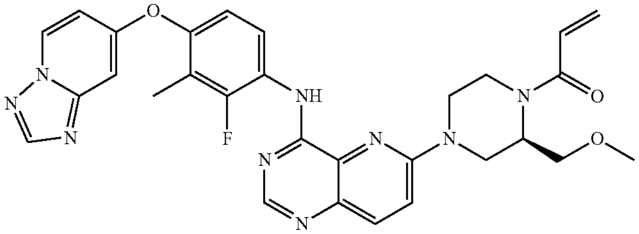 (R)-1-(4-(4-((4-([1,2,4]triazolo[1,5-a]pyridin-7-yloxy)-3-chloro-2-fluorophenyl)amino)pyrido[3,2-d]pyrimidin-6-yl)-2-(methoxymethyl)piperazin-1-yl)prop-2-en-1-one | 570.2 | $^{1}$H NMR (400 MHz, $CDCl_3$) δ 9.09 (d, J = 3.6 Hz, 1H), 8.83 (t, J = 9.0 Hz, 1H), 8.65 (s, 1H), 8.51 (dd, J = 7.31, 0.83 Hz, 1H), 8.24 (s, 1H), 8.00 (d, J = 9.3 Hz, 1H), 7.32 (d, J = 9.4 Hz, 1H), 7.01 (m, 1H), 6.88 (m, 2H), 6.66 (bs, 1H), 6.39 (m, 1H), 5.78 (dd, J = 10.5, 1.9 Hz, 1H), 4.48 (m, 3H), 3.48 (m, 2H), 3.33 (m, 5H), 3.26 (m, 1H), 2.21 (d, J = 2.2 Hz, 3H) |
| 363 (Ex 164) | 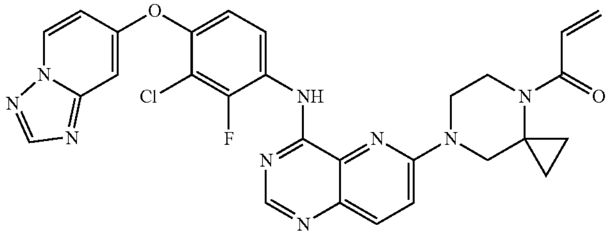 1-(7-(4-((4-([1,2,4]triazolo[1,5-a]pyridin-7-yloxy)-3-chloro-2-fluorophenyl)amino)pyrido[3,2-d]pyrimidin-6-yl)-4,7-diazaspiro[2.5]octan-4-yl)prop-2-en-1-one | 572.2 | $^{1}$H NMR (400 MHz, $CDCl_3$) δ 9.05 (d, J = 3.4 Hz, 1H), 8.99 (t, J = 8.9 Hz, 1H), 8.66 (s, 1H), 8.53 (dd, J = 7.2, 1.0 Hz, 1H), 8.25 (s, 1H), 8.00 (d, J = 9.4 Hz, 1H), 7.28 (s, 1H), 7.15 (dd, J = 9.2, 2.1 Hz, 1H), 6.92 (m, 2H), 6.43 (d, 16.9, 1.8 Hz, 1H), 5.78 (dd, J = 10.4, 1.9 Hz, 1H), 4.02 (bs, 2H), 3.84 (bs, 2H), 3.70 (s, 2H), 1.13 (s, 4H) |
| 364 (Ex 164) | 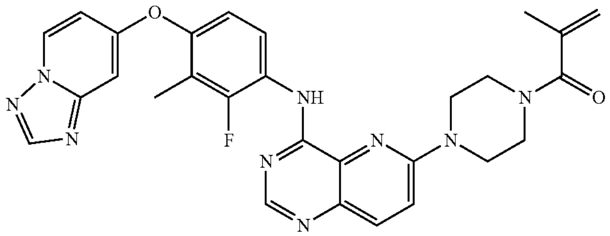 1-(4-(4-((4-([1,2,4]triazolo[1,5-a]pyridin-7-yloxy)-2-fluoro-3-methylphenyl)amino)pyrido[3,2-d]pyrimidin-6-yl)piperazin-1-yl)-2-methylprop-2-en-1-one | 540.2 | $^{1}$H NMR (400 MHz, $CDCl_3$) δ 9.07 (d, J = 3.6 Hz, 1H), 8.82 (t, J = 9.0 Hz, 1H), 8.66 (s, 1H), 8.51 (dd, J = 7.4, 0.8 Hz, 1H), 8.24 (s, 1H), 8.02 (d, J = 9.3 Hz, 1H), 7.01 (dd, J = 9.0, 1.8 Hz, 1H), 6.89 (m, 2H), 5.30 (m, 1H), 5.14 (m, 1H), 3.80 (m, 8H), 2.21 (d, J = 2.1 Hz, 3H) 2.03 (m, 3H) |
| 365 (Ex 164) | 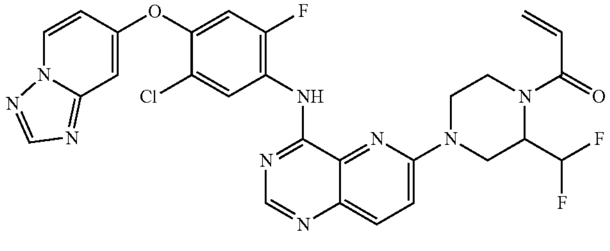 1-(4-(4-((4-([1,2,4]triazolo[1,5-a]pyridin-7-yloxy)-5-chloro-2-fluorophenyl)amino)pyrido[3,2-d]pyrimidin-6-yl)-2-(difluoromethyl)piperazin-1-yl)prop-2-en-1-one | 596.1 | $^{1}$H NMR (400 MHz, $CDCl_3$) δ 9.28 (d, J = 8.3 Hz, 1H), 9.07 (d, J = 3.5 Hz, 1H), 8.73 (s, 1H), 8.53 (m, 1H), 8.26 (s, 1H), 8.06 (d, J = 9.3 Hz, 1H), 7.32 (m, 1H), 7.12 (d, J = 10.8 Hz, 1H), 6.91 (m, 2H) 6.65 (dd, J = 16.8, 10.8 Hz, 1H), 6.42 (dd, J = 16.8, 1.7 Hz, 1H), 6.05 (t, J = 55.6 Hz, 1H), 5.84 (m, 1H), 4.86 (m, 2H), 4.28 (m, 2H), 3.68 (m, 1H), 3.25 (m, 2H) |

TABLE 3-continued

| Example No. (Method) | Structure; IUPAC name | LCMS $M^{+1}$ | $^1H$ NMR (ppm); $^{19}F$ NMR (ppm); optical rotation; Chiral HPLC/SFC conditions |
|---|---|---|---|
| 366 (Ex 164) | 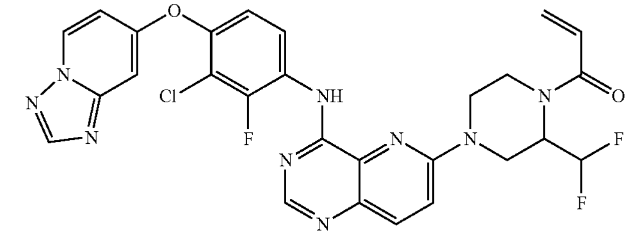 1-(4-(4-((4-([1,2,4]triazolo[1,5-a]pyridin-7-yloxy)-3-chloro-2-fluorophenyl)amino)pyrido[3,2-d]pyrimidin-6-yl)-2-(difluoromethyl)piperazin-1-yl)prop-2-en-1-one | 596.2 | $^1H$ NMR (400 MHz, $CDCl_3$) δ 9.09 (s, 1H), 8.99 (t, J = 8.9 Hz, 1H), 8.69 (s, 1H), 8.53 (m, 1H), 8.25 (s, 1H), 8.06 (d, J = 9.3 Hz, 1H), 7.33 (d, J = 9.2 Hz, 1H), 7.16 (d, J = 9.2, 2.1 Hz, 1H), 6.92 (m, 2H), 6.66 (dd, J = 16.8, 10.8 Hz, 1H), 6.43 (dd, J = 16.8, 1.7 Hz, 1H), 6.06 (t, J = 55.1 Hz, 1H), 5.85 (d, J = 10.6 Hz, 1H), 4.85 (m, 2H), 4.26 (m, 2H), 3.69 (m, 1H), 3.26 (m, 2H) |
| 367 (Ex 164) | 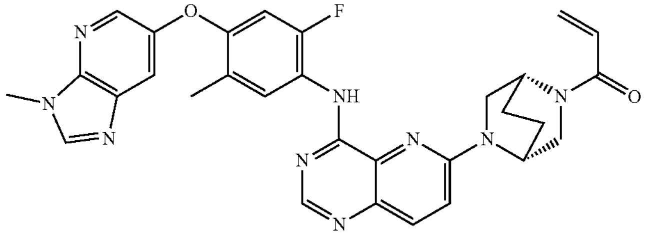 1-((1R,4R)-5-(4-((2-fluoro-5-methyl-4-((3-methyl-3H-imidazo[4,5-b]pyridin-6-yl)oxy)phenyl)amino)pyrido[3,2-d]pyrimidin-6-yl)-2,5-diazabicyclo[2.2.2]octan-2-yl)prop-2-en-1-one | 566.2 | $^1H$ NMR (400 MHz, $CDCl_3$) δ 8.85 (s, 1H), 8.70 (m, 1H), 8.63 (s, 1H), 8.29 (d, J = 2.6 Hz, 1H), 8.04 (s, 1H), 7.98 (dd, J = 9.3, 3.8 Hz, 1H), 7.62 (d, J = 2.5, 1.1 Hz, 1H), 7.04 (m, 1H), 6.70 (d, J = 11.7 Hz, 1H), 6.46 (m, 1H), 5.75 (m, 1H), 3.91 (m, 6H), 2.37 (s, 3H), 2.18 (m, 2H), 1.99 (m, 2H), 1.31 (m, 4H) |
| 368 (Ex 189) | 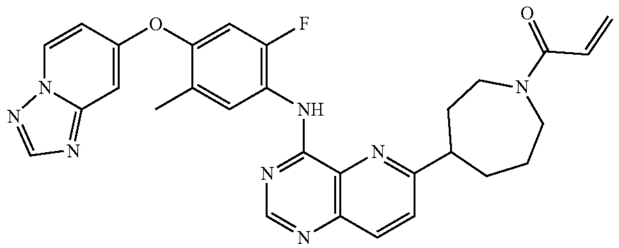 1-(4-(4-((4-([1,2,4]triazolo[1,5-a]pyridin-7-yloxy)-2-fluoro-5-methylphenyl)amino)pyrido[3,2-d]pyrimidin-6-yl)azepan-1-yl)prop-2-en-1-one | 539.2 | $^1H$ NMR (400 MHz, $CDCl_3$) δ 9.41-9.35 (m, 1H), 8.86-8.77 (m, 2H), 8.55-8.48 (m, 1H), 8.24 (s, 1H), 8.17-8.09 (m, 1H), 7.65-7.59 (m, 1H), 7.01-6.93 (m, 1H), 6.92-6.85 (m, 2H), 6.71-6.59 (m, 1H), 6.45-6.35 (m, 1H), 5.77-5.69 (m, 1H), 4.00-3.52 (m, 4H), 3.22-3.06 (m, 1H), 2.40-2.23 (m, 4H), 2.22-2.06 (m, 3H), 2.02-1.81 (m, 2H). |

TABLE 3-continued

| Example No. (Method) | Structure; IUPAC name | LCMS $M^{+1}$ | $^1H$ NMR (ppm); $^{19}F$ NMR (ppm); optical rotation; Chiral HPLC/SFC conditions |
|---|---|---|---|
| 369 (Ex 195) | 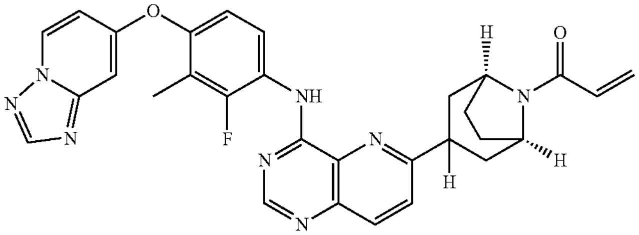 1-((1R,5S)-3-(4-((4-([1,2,4]triazolo[1,5-a]pyridin-7-yloxy)-2-fluoro-3-methylphenyl)amino)pyrido[3,2-d]pyrimidin-6-yl)-8-azabicyclo[3.2.1]octan-8-yl)prop-2-en-1-one | 551.2 | $^1H$ NMR (400 MHz, $CDCl_3$) δ 9.55-9.34 (m, 1H), 8.89-8.71 (m, 2H), 8.55-8.48 (m, 1H), 8.24 (s, 1H), 8.19-8.10 (m, 1H), 7.87-7.57 (m, 1H), 7.07-6.97 (m, 1H), 6.94-6.85 (m, 2H), 6.66-6.54 (m, 1H), 6.50-6.41 (m, 1H), 5.79-5.71 (m, 1H), 5.09-4.80 (m, 1H), 4.58-4.42 (m, 1H), 3.68-3.26 (m, 1H), 2.74-2.37 (m, 1H), 2.26-2.18 (m, 4H), 2.19-1.77 (m, 5H). |
| 370 (Ex 189) | 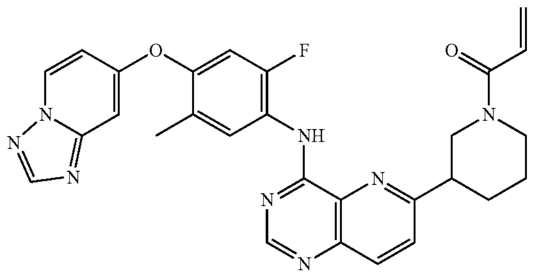 1-(3-(4-((4-([1,2,4]triazolo[1,5-a]pyridin-7-yloxy)-2-fluoro-5-methylphenyl)amino)pyrido[3,2-d]pyrimidin-6-yl)piperidin-1-yl)prop-2-en-1-one | 525.2 | $^1H$ NMR (400 MHz, $CDCl_3$) δ 9.51-9.36 (m, 1H), 8.89-8.67 (m, 2H), 8.55-8.49 (m, 1H), 8.24 (s, 1H), 8.22-8.13 (m, 1H), 7.74-7.65 (m, 1H), 7.01-6.94 (m, 1H), 6.92-6.86 (m, 2H), 6.71-6.59 (m, 1H), 6.35-6.26 (m, 1H), 5.74-5.67 (m, 1H), 4.89-4.64 (m, 1H), 4.41-3.95 (m, 1H), 3.64-2.71 (m, 3H), 2.33-2.20 (m, 4H), 2.14-1.87 (m, 2H), 1.70 (s, 1H). |
| 371 (Ex 189) | 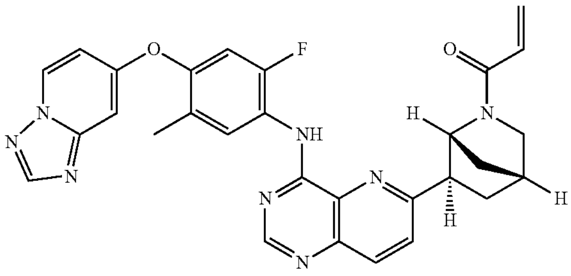 rac-1-((1R,4R,6R)-6-(4-((4-([1,2,4]triazolo[1,5-a]pyridin-7-yloxy)-2-fluoro-5-methylphenyl)amino)pyrido[3,2-d]pyrimidin-6-yl)-2-azabicyclo[2.2.1]heptan-2-yl)prop-2-en-1-one | 537.2 | $^1H$ NMR (400 MHz, $CDCl_3$) δ 9.43-9.36 (m, 1H), 8.91-8.82 (m, 2H), 8.55-8.48 (m, 1H), 8.24 (s, 1H), 8.20-8.12 (m, 1H), 7.73-7.63 (m, 1H), 7.02-6.94 (m, 1H), 6.93-6.84 (m, 2H), 6.62-6.31 (m, 2H), 5.76-5.68 (m, 1H), 4.98-4.49 (m, 1H), 3.70-3.55 (m, 1H), 3.55-3.42 (m, 1H), 3.39-3.29 (m, 1H), 3.09-2.89 (m, 1H), 2.54-2.19 (m, 5H), 2.19-2.05 (m, 1H), 1.85-1.69 (m, 1H). |

TABLE 3-continued

| Example No. (Method) | Structure; IUPAC name | LCMS $M^{+1}$ | $^{1}H$ NMR (ppm); $^{19}F$ NMR (ppm); optical rotation; Chiral HPLC/SFC conditions |
|---|---|---|---|
| 372 (Ex 189) | 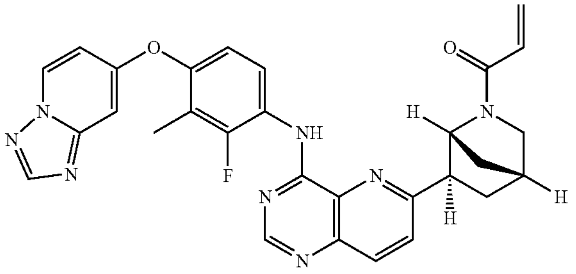 rac-1-((1R,4R,6R)-6-(4-((4-([1,2,4]triazolo[1,5-a]pyridin-7-yloxy)-2-fluoro-3-methylphenyl)amino)pyrido[3,2-d]pyrimidin-6-yl)-2-azabicyclo[2.2.1]heptan-2-yl)prop-2-en-1-one | 537.2 | $^{1}H$ NMR (400 MHz, $CDCl_3$) δ 9.49-9.43 (m, 1H), 8.88-8.77 (m, 2H), 8.55-8.48 (m, 1H), 8.24 (s, 1H), 8.20-8.13 (m, 1H), 7.73-7.64 (m, 1H), 7.07-6.99 (m, 1H), 6.94-6.84 (m, 2H), 6.65-6.31 (m, 2H), 5.77-5.69 (m, 1H), 5.00-4.51 (m, 1H), 3.74-3.56 (m, 1H), 3.56-3.42 (m, 1H), 3.40-3.30 (m, 1H), 3.13-2.90 (m, 1H), 2.52-2.24 (m, 2H), 2.23 (d, J = 2.1 Hz, 3H), 2.20-2.06 (m, 1H), 1.87-1.70 (m, 1H). |
| 373 (Ex 189) | 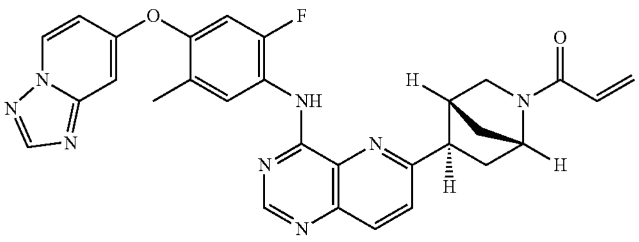 rac-1-((1R,4S,5R)-5-(4-((4-([1,2,4]triazolo[1,5-a]pyridin-7-yloxy)-2-fluoro-5-methylphenyl)amino)pyrido[3,2-d]pyrimidin-6-yl)-2-azabicyclo[2.2.1]heptan-2-yl)prop-2-en-1-one | 537.2 | $^{1}H$ NMR (400 MHz, $CDCl_3$) δ 9.40 (s, 1H), 8.92-8.81 (m, 2H), 8.56-8.48 (m, 1H), 8.24 (s, 1H), 8.22-8.12 (m, 1H), 7.90-7.61 (m, 1H), 7.03-6.93 (m, 1H), 6.93-6.84 (m, 2H), 6.71-6.31 (m, 2H), 5.78-5.70 (m, 1H), 4.94-4.61 (m, 1H), 3.68-3.46 (m, 2H), 3.43-3.32 (m, 1H), 2.93-2.84 (m, 1H), 2.69-2.32 (m, 1H), 2.31-2.26 (m, 3H), 2.17-1.92 (m, 2H), 1.85-1.61 (m, 1H). |
| 374 (Ex 189) | 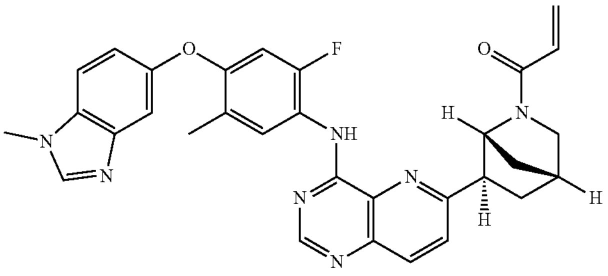 rac-1-((1R,4R,6R)-6-(4-((2-fluoro-5-methyl-4-((1-methyl-1H-benzo[d]imidazol-5-yl)oxy)phenyl)amino)pyrido[3,2-d]pyrimidin-6-yl)-2-azabicyclo[2.2.1]heptan-2-yl)prop-2-en-1-one | 550.2 | $^{1}H$ NMR (500 MHz, $CDCl_3$) δ 9.23-9.18 (m, 1H), 8.82-8.78 (m, 1H), 8.65-8.58 (m, 1H), 8.15-8.09 (m, 1H), 7.88 (s, 1H), 7.69-7.60 (m, 1H), 7.39-7.34 (m, 2H), 7.10-7.40 (m, 1H), 6.74-6.67 (m, 1H), 6.60-6.30 (m, 2H), 5.74-5.67 (m, 1H), 4.95-4.44 (m, 1H), 3.87 (s, 3H), 3.67-3.53 (m, 1H), 3.52-3.42 (m, 1H), 3.36-3.27 (m, 1H), 3.08-2.87 (m, 1H), 2.49-2.26 (m, 5H), 2.21 (td, J = 9.6, 8.7, 5.0 Hz, 1H), 2.09 (dd, J = 34.6, 10.2 Hz, 1H), 1.74 (dd, J = 40.4, 10.3 Hz, 1H). |

TABLE 3-continued

| Example No. (Method) | Structure; IUPAC name | LCMS $M^{+1}$ | $^1$H NMR (ppm); $^{19}$F NMR (ppm); optical rotation; Chiral HPLC/SFC conditions |
|---|---|---|---|
| 375 (Ex 189) | 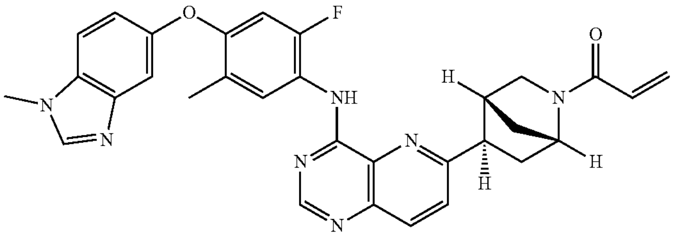 rac-1-((1R,4S,5R)-5-(4-((2-fluoro-5-methyl-4-((1-methyl-1H-benzo[d]imidazol-5-yl)oxy)phenyl)amino)pyrido[3,2-d]pyrimidin-6-yl)-2-azabicyclo[2.2.1]heptan-2-yl)prop-2-en-1-one | 550.2 | $^1$H NMR (500 MHz, $CDCl_3$) δ 9.21-(s, 1H), 8.83-8.78 (m, 1H), 8.67-8.58 (m, 1H), 8.17-8.09 (m, 1H), 7.88 (s, 1H), 7.81-7.56 (m, 1H), 7.40-7.34 (m, 2H), 7.10-7.03 (m, 1H), 6.74-6.68 (m, 1H), 6.65-6.33 (m, 2H), 5.76-5.70 (m, 1H), 4.90-4.62 (m, 1H), 3.87 (s, 3H), 3.63-3.44 (m, 2H), 3.41-3.31 (m, 1H), 2.90-2.79 (m, 1H), 2.68-2.26 (m, 4H), 2.16-2.03 (m, 1H), 2.01-1.89 (m, 1H), 1.82-1.57 (m, 1H). |
| 376 (Ex 189) | 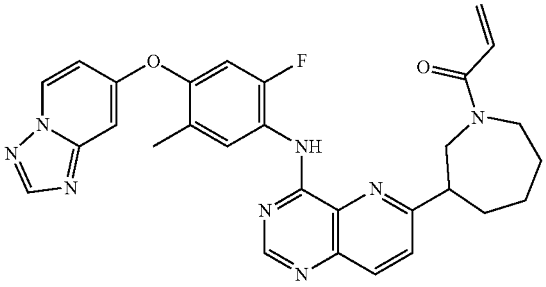 1-(3-(4-((4-([1,2,4]triazolo[1,5-a]pyridin-7-yloxy)-2-fluoro-5-methylphenyl)amino)pyrido[3,2-d]pyrimidin-6-yl)azepan-1-yl)prop-2-en-1-one | 539.2 | $^1$H NMR (400 MHz, $CDCl_3$) δ 9.53-9.34 (m, 1H), 8.93-8.79 (m, 2H), 8.55-8.49 (m, 1H), 8.24 (s, 1H), 8.22-8.13 (m, 1H), 7.85-7.62 (m, 1H), 7.03-6.93 (m, 1H), 6.93-6.85 (m, 2H), 6.74-6.60 (m, 1H), 6.47-6.36 (m, 1H), 5.78-5.69 (m, 1H), 4.56-3.67 (m, 2H), 3.65-3.25 (m, 3H), 2.31-2.26 (m, 3H), 2.19-1.75 (m, 5H), 1.70-1.60 (m, 1H). |
| 377 (Ex 189) | 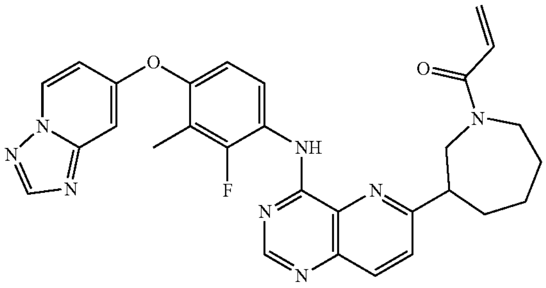 1-(3-(4-((4-([1,2,4]triazolo[1,5-a]pyridin-7-yloxy)-2-fluoro-3-methylphenyl)amino)pyrido[3,2-d]pyrimidin-6-yl)azepan-1-yl)prop-2-en-1-one | 539.2 | $^1$H NMR (400 MHz, $CDCl_3$) δ 9.61-9.39 (m, 1H), 8.86-8.75 (m, 2H), 8.55-8.48 (m, 1H), 8.25-8.23 (m, 1H), 8.22-8.12 (m, 1H), 7.84-7.64 (m, 1H), 7.05-6.98 (m, 1H), 6.94-6.86 (m, 2H), 6.75-6.60 (m, 1H), 6.48-6.37 (m, 1H), 5.79-5.70 (m, 1H), 4.57-3.69 (m, 2H), 3.62-3.23 (m, 3H), 2.22 (d, J = 2.3 Hz, 3H), 2.20-1.78 (m, 5H), 1.63 (t, J = 11.5 Hz, 1H). |

TABLE 3-continued

| Example No. (Method) | Structure; IUPAC name | LCMS $M^{+1}$ | $^1H$ NMR (ppm); $^{19}F$ NMR (ppm); optical rotation; Chiral HPLC/SFC conditions |
|---|---|---|---|
| 378 (Ex 189) | 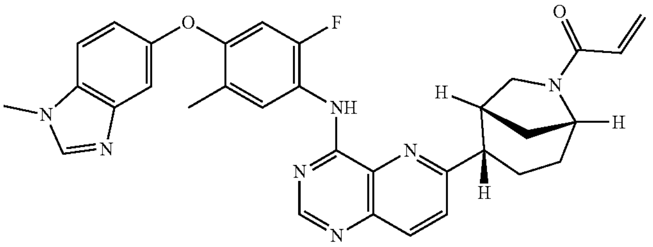 rac-1-((1R,2S,5R)-2-(4-((2-fluoro-5-methyl-4-((1-methyl-1H-benzo[d]imidazol-5-yl)oxy)phenyl)amino)pyrido[3,2-d]pyrimidin-6-yl)-6-azabicyclo[3.2.1]octan-6-yl)prop-2-en-1-one | 564.2 | $^1H$ NMR (400 MHz, $CDCl_3$) δ 9.44-9.22 (m, 1H), 8.86-8.77 (m, 1H), 8.74-8.84 (m, 1H), 8.22-8.14 (m, 1H), 8.12-7.98 (m, 1H), 7.74-7.61 (m, 1H), 7.44-7.31 (m, 2H), 7.11 (dd, J = 14.2, 8.2 Hz, 1H), 6.78-6.67 (m, 1H), 6.54-6.34 (m, 2H), 5.79-5.56 (m, 1H), 4.70-4.23 (m, 1H), 4.05-3.76 (m, 5H), 3.61 (ddd, J = 39.3, 11.7, 5.6 Hz, 1H), 3.42-3.23 (m, 1H), 3.07-2.80 (m, 1H), 2.39-2.35 (m, 3H), 2.24-1.88 (m, 3H), 1.86-1.60 (m, 2H). |
| 379 (Ex 189) | 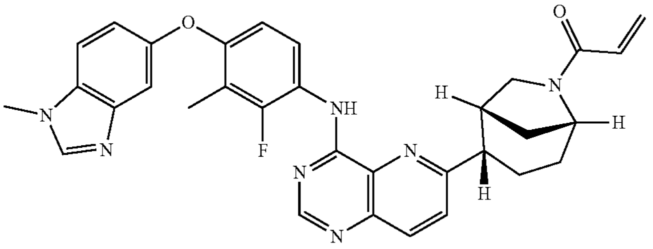 rac-1-((1R,2S,5R)-2-(4-((2-fluoro-3-methyl-4-((1-methyl-1H-benzo[d]imidazol-5-yl)oxy)phenyl)amino)pyrido[3,2-d]pyrimidin-6-yl)-6-azabicyclo[3.2.1]octan-6-yl)prop-2-en-1-one | 564.2 | $^1H$ NMR (400 MHz, $CDCl_3$) δ 9.53-9.32 (m, 1H), 8.80-8.72 (m, 1H), 8.67-8.41 (m, 1H), 8.19-8.12 (m, 1H), 8.00 (s, 1H), 7.74-7.61 (m, 1H), 7.41-7.30 (m, 2H), 7.14-7.04 (m, 1H), 6.83-6.73 (m, 1H), 6.61-6.39 (m, 2H), 5.79-5.65 (m, 1H), 4.74-4.26 (m, 1H), 4.14-3.79 (m, 4H), 3.79-3.54 (m, 1H), 3.46-3.26 (m, 1H), 3.12-2.80 (m, 1H), 2.46-2.20 (m, 4H), 2.18-1.90 (m, 3H), 1.92-1.60 (m, 2H). |
| 380 (Ex 189) | 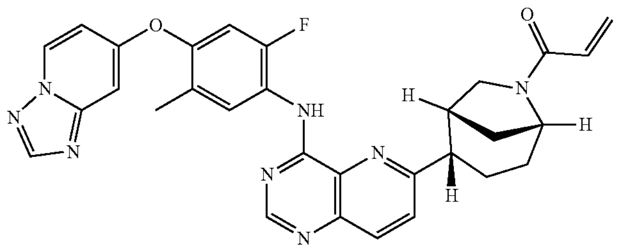 rac-1-((1R,2S,5R)-2-(4-((4-([1,2,4]triazolo[1,5-a]pyridin-7-yloxy)-2-fluoro-5-methylphenyl)amino)pyrido[3,2-d]pyrimidin-6-yl)-6-azabicyclo[3.2.1]octan-6-yl)prop-2-en-1-one | 551.2 | $^1H$ NMR (400 MHz, $CDCl_3$) δ 9.56-9.37 (m, 1H), 8.98-8.77 (m, 2H), 8.56-8.48 (m, 1H), 8.24 (s, 1H), 8.22-8.12 (m, 1H), 7.81-7.62 (m, 1H), 7.03-6.94 (m, 1H), 6.92-6.84 (m, 2H), 6.58-6.36 (m, 2H), 5.78-5.64 (m, 1H), 4.71-4.28 (m, 1H), 4.11-3.75 (m, 1H), 3.77-3.55 (m, 1H), 3.44-3.20 (m, 1H), 3.15-2.78 (m, 1H), 2.49-2.19 (m, 4H), 2.19-1.90 (m, 3H), 1.88-1.65 (m, 2H). |

TABLE 3-continued

| Example No. (Method) | Structure; IUPAC name | LCMS $M^{+1}$ | $^1H$ NMR (ppm); $^{19}F$ NMR (ppm); optical rotation; Chiral HPLC/SFC conditions |
|---|---|---|---|
| 381 (Ex 189) | 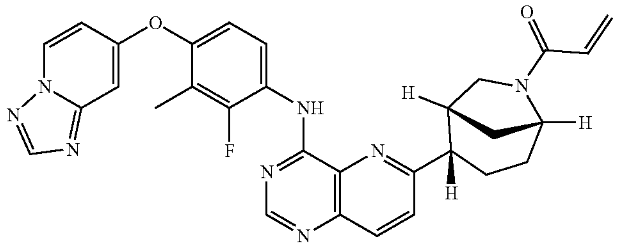 rac-1-((1R,2S,5R)-2-(4-((4-([1,2,4]triazolo[1,5-a]pyridin-7-yloxy)-2-fluoro-3-methylphenyl)amino)pyrido[3,2-d]pyrimidin-6-yl)-6-azabicyclo[3.2.1]octan-6-yl)prop-2-en-1-one | 551.2 | $^1H$ NMR (400 MHz, $CDCl_3$) δ 9.62-9.35 (m, 1H), 8.93-8.72 (m, 2H), 8.56-8.48 (m, 1H), 8.24 (s, 1H), 8.22-8.15 (m, 1H), 7.77-7.64 (m, 1H), 7.07-6.98 (m, 1H), 6.95-6.86 (m, 2H), 6.61-6.38 (m, 2H), 5.81-5.61 (m, 1H), 4.75-4.26 (m, 1H), 4.09-3.58 (m, 2H), 3.46-3.25 (m, 1H), 3.12-2.79 (m, 1H), 2.45-2.25 (m, 1H), 2.24-2.19 (m, 3H), 2.18-1.99 (m, 3H), 2.00-1.61 (m, 2H). |
| 382 (Ex 189) | 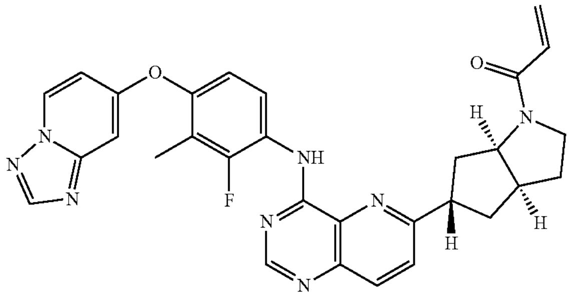 rac-1-((3aR,5S,6aR)-5-(4-((4-([1,2,4]triazolo[1,5-a]pyridin-7-yloxy)-2-fluoro-3-methylphenyl)amino)pyrido[3,2-d]pyrimidin-6-yl)hexahydrocyclopenta[b]pyrrol-1(2H)-yl)prop-2-en-1-one | 551.2 | $^1H$ NMR (400 MHz, $CDCl_3$) δ 9.52 (s, 1H), 8.84-8.72 (m, 2H), 8.55-8.49 (m, 1H), 8.24 (s, 1H), 8.22-8.17 (m, 1H), 7.70-7.61 (m, 1H), 7.06-6.99 (m, 1H), 6.94-6.85 (m, 2H), 6.68-6.31 (m, 2H), 5.81-5.61 (m, 1H), 4.77-4.59 (m, 1H), 4.13-3.78 (m, 1H), 3.76-3.43 (m, 2H), 3.24-2.92 (m, 0H), 2.67-2.26 (m, 2H), 2.27-2.19 (m, 3H), 2.16-1.75 (m, 4H). |
| 383 (Ex 189) | 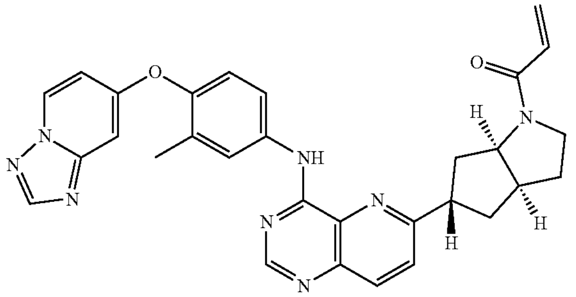 rac-1-((3aR,5S,6aR)-5-(4-((4-([1,2,4]triazolo[1,5-a]pyridin-7-yloxy)-3-methylphenyl)amino)pyrido[3,2-d]pyrimidin-6-yl)hexahydrocyclopenta[b]pyrrol-1(2H)-yl)prop-2-en-1-one | 533.2 | $^1H$ NMR (400 MHz, $CDCl_3$) δ 9.31-9.09 (m, 1H), 8.80-8.75 (m, 1H), 8.53-8.47 (m, 1H), 8.23 (s, 1H), 8.18-8.11 (m, 1H), 7.94-7.89 (m, 2H), 7.68-7.61 (m, 1H), 7.18-7.12 (m, 1H), 6.93-6.84 (m, 3H), 6.59-6.37 (m, 2H), 5.75-5.61 (m, 1H), 4.78-4.51 (m, 1H), 3.94-3.43 (m, 3H), 3.32-2.93 (m, 1H), 2.62-2.33 (m, 2H), 2.28 (s, 3H), 2.26-1.73 (m, 4H). |

TABLE 3-continued

| Example No. (Method) | Structure; IUPAC name | LCMS $M^{+1}$ | $^{1}H$ NMR (ppm); $^{19}F$ NMR (ppm); optical rotation; Chiral HPLC/SFC conditions |
|---|---|---|---|
| 384 (Ex 189) | 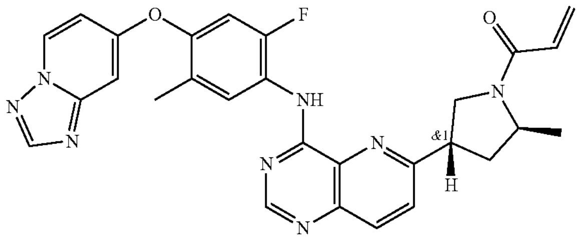 1-((2S,4SR)-4-(4-((4-([1,2,4]triazolo[1,5-a]pyridin-7-yloxy)-2-fluoro-5-methylphenyl)amino)pyrido[3,2-d]pyrimidin-6-yl)-2-methylpyrrolidin-1-yl)prop-2-en-1-one | 525.2 | $^{1}H$ NMR (400 MHz, $CDCl_3$) δ 9.45-9.24 (m, 1H), 8.87-8.80 (m, 1H), 8.78-8.70 (m, 1H), 8.55-8.49 (m, 1H), 8.27-8.22 (m, 1H), 8.22-8.14 (m, 1H), 7.73-7.66 (m, 1H), 7.02-6.93 (m, 1H), 6.93-6.85 (m, 2H), 6.60-6.35 (m, 2H), 5.78-5.66 (m, 1H), 4.65-4.27 (m, 1H), 4.23-3.53 (m, 3H), 2.92-2.38 (m, 1H), 2.32-2.27 (m, 3H), 2.26-1.97 (m, 1H), 1.49-1.39 (m, 3H). |
| 385 (Ex 1) | 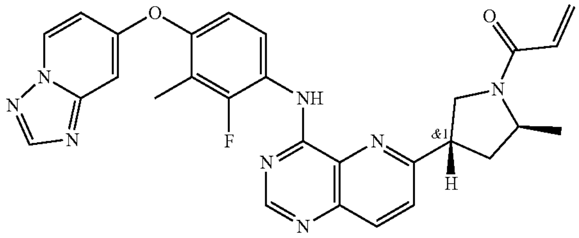 1-((2S,4SR)-4-(4-((4-([1,2,4]triazolo[1,5-a]pyridin-7-yloxy)-2-fluoro-3-methylphenyl)amino)pyrido[3,2-d]pyrimidin-6-yl)-2-methylpyrrolidin-1-yl)prop-2-en-1-one | 525.2 | $^{1}H$ NMR (400 MHz, $CDCl_3$) δ 9.48-9.29 (m, 1H), 8.85-8.78 (m, 1H), 8.75-8.66 (m, 1H), 8.55-8.48 (m, 1H), 8.24 (s, 1H), 8.22-8.14 (m, 1H), 7.73-7.66 (m, 1H), 7.05-6.98 (m, 1H), 6.94-6.86 (m, 2H), 6.61-6.36 (m, 2H), 5.79-5.67 (m, 1H), 4.73-4.33 (m, 1H), 4.22-3.62 (m, 3H), 2.97-2.35 (m, 1H), 2.33-1.98 (m, 4H), 1.50-1.40 (m, 3H). |
| 386 (Ex 189) | 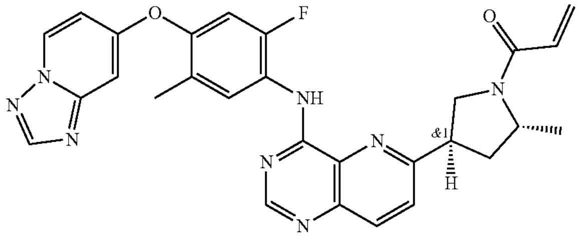 1-((2R,4RS)-4-(4-((4-([1,2,4]triazolo[1,5-a]pyridin-7-yloxy)-2-fluoro-5-methylphenyl)amino)pyrido[3,2-d]pyrimidin-6-yl)-2-methylpyrrolidin-1-yl)prop-2-en-1-one | 525.2 | $^{1}H$ NMR (400 MHz, $CDCl_3$) δ 9.45-9.24 (m, 1H), 8.87-8.80 (m, 1H), 8.78-8.70 (m, 1H), 8.55-8.49 (m, 1H), 8.27-8.22 (m, 1H), 8.22-8.14 (m, 1H), 7.73-7.66 (m, 1H), 7.02-6.93 (m, 1H), 6.93-6.85 (m, 2H), 6.60-6.35 (m, 2H), 5.78-5.66 (m, 1H), 4.65-4.27 (m, 1H), 4.23-3.53 (m, 3H), 2.92-2.38 (m, 1H), 2.32-2.27 (m, 3H), 2.26-1.97 (m, 1H), 1.49-1.39 (m, 3H). |
| 387 (Ex 189) | 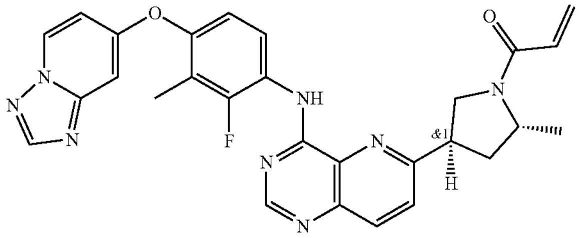 1-((2R,4RS)-4-(4-((4-([1,2,4]triazolo[1,5-a]pyridin-7-yloxy)-2-fluoro-3-methylphenyl)amino)pyrido[3,2-d]pyrimidin-6-yl)-2-methylpyrrolidin-1-yl)prop-2-en-1-one | 525.2 | $^{1}H$ NMR (400 MHz, $CDCl_3$) δ 9.48-9.29 (m, 1H), 8.85-8.78 (m, 1H), 8.75-8.66 (m, 1H), 8.55-8.48 (m, 1H), 8.24 (s, 1H), 8.22-8.14 (m, 1H), 7.73-7.66 (m, 1H), 7.05-6.98 (m, 1H), 6.94-6.86 (m, 2H), 6.61-6.36 (m, 2H), 5.79-5.67 (m, 1H), 4.73-4.33 (m, 1H), 4.22-3.62 (m, 3H), 2.97-2.35 (m, 1H), 2.33-1.98 (m, 4H), 1.50-1.40 (m, 3H). |

TABLE 3-continued

| Example No. (Method) | Structure; IUPAC name | LCMS $M^{+1}$ | $^1$H NMR (ppm); $^{19}$F NMR (ppm); optical rotation; Chiral HPLC/SFC conditions |
|---|---|---|---|
| 388 (Ex 189) | 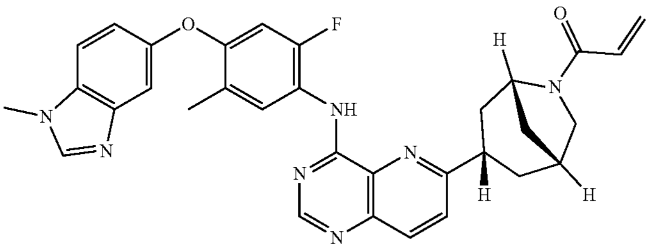 rac-1-((1R,3S,5R)-3-(4-((2-fluoro-5-methyl-4-((1-methyl-1H-benzo[d]imidazol-5-yl)oxy)phenyl)amino)pyrido[3,2-d]pyrimidin-6-yl)-6-azabicyclo[3.2.1]octan-6-yl)prop-2-en-1-one | 564.2 | $^1$H NMR (400 MHz, $CDCl_3$) δ 9.23-9.18 (m, 1H), 8.80-8.75 (m, 1H), 8.61-8.52 (m, 1H), 8.13-8.05 (m, 1H), 7.90 (s, 1H), 7.65-7.55 (m, 1H), 7.40-7.33 (m, 2H), 7.11-7.03 (m, 1H), 6.75-6.67 (m, 1H), 6.61-6.41 (m, 2H), 5.79-5.66 (m, 1H), 4.80-4.37 (m, 1H), 3.87 (s, 3H), 3.78-3.59 (m, 2H), 3.38-3.16 (m, 1H), 2.81-2.65 (m, 1H), 2.63-2.19 (m, 4H), 2.16-1.93 (m, 4H), 1.90-1.73 (m, 1H). |
| 389 (Ex 189) | 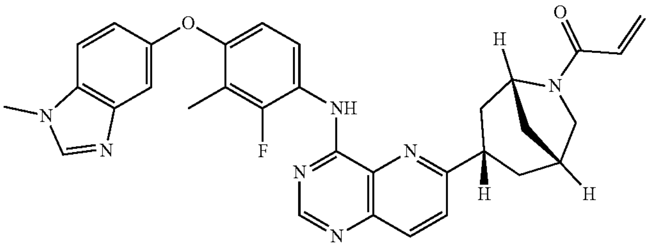 rac-1-((1R,3S,5R)-3-(4-((2-fluoro-3-methyl-4-((1-methyl-1H-benzo[d]imidazol-5-yl)oxy)phenyl)amino)pyrido[3,2-d]pyrimidin-6-yl)-6-azabicyclo[3.2.1]octan-6-yl)prop-2-en-1-one | 564.2 | $^1$H NMR (400 MHz, $CDCl_3$) δ 9.36-9.31 (m, 1H), 8.75-8.70 (m, 1H), 8.53-8.43 (m, 1H), 8.12-8.04 (m, 1H), 7.88 (s, 1H), 7.65-7.55 (m, 1H), 7.39-7.30 (m, 2H), 7.11-7.03 (m, 1H), 6.80-6.72 (m, 1H), 6.62-6.43 (m, 2H), 5.80-5.68 (m, 1H), 4.77-4.38 (m, 1H), 3.86 (s, 3H), 3.80-3.61 (m, 2H), 3.39-3.17 (m, 1H), 2.85-2.67 (m, 1H), 2.62-2.22 (m, 4H), 2.16-1.95 (m, 4H), 1.93-1.73 (m, 1H). |
| 390 (Ex 189) | 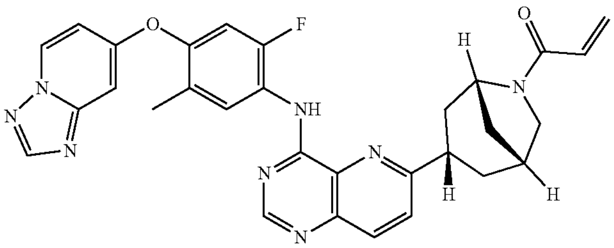 rac-1-((1R,3S,5R)-3-(4-((4-([1,2,4]triazolo[1,5-a]pyridin-7-yloxy)-2-fluoro-5-methylphenyl)amino)pyrido[3,2-d]pyrimidin-6-yl)-6-azabicyclo[3.2.1]octan-6-yl)prop-2-en-1-one | 551.2 | $^1$H NMR (400 MHz, $CDCl_3$) δ 9.40 (s, 1H), 8.88-8.79 (m, 2H), 8.56-8.49 (m, 1H), 8.24 (s, 1H), 8.16-8.08 (m, 1H), 7.68-7.58 (m, 1H), 7.02-6.94 (m, 1H), 6.93-6.85 (m, 2H), 6.62-6.42 (m, 2H), 5.80-5.68 (m, 1H), 4.76-4.36 (m, 1H), 3.81-3.59 (m, 2H), 3.40-3.19 (m, 1H), 2.83-2.67 (m, 1H), 2.62-2.20 (m, 4H), 2.17-1.92 (m, 4H), 1.92-1.75 (m, 1H). |

TABLE 3-continued

| Example No. (Method) | Structure; IUPAC name | LCMS $M^{+1}$ | $^1H$ NMR (ppm); $^{19}F$ NMR (ppm); optical rotation; Chiral HPLC/SFC conditions |
|---|---|---|---|
| 391 (Ex 189) | 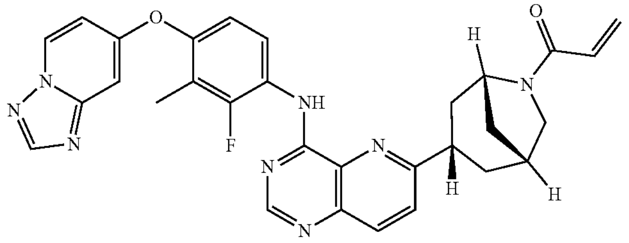 rac-1-((1R,3S,5R)-3-(4-((4-([1,2,4]triazolo[1,5-a]pyridin-7-yloxy)-2-fluoro-3-methylphenyl)amino)pyrido[3,2-d]pyrimidin-6-yl)-2-azabicyclo[3.2.1]octan-6-yl)prop-2-en-1-one | 551.2 | $^1H$ NMR (400 MHz, $CDCl_3$) δ 9.33 (d, J = 2.9 Hz, 1H), 8.84-8.76 (m, 2H), 8.55-8.48 (m, 1H), 8.24 (s, 1H), 8.14 (d, J = 8.7 Hz, 1H), 7.64 (d, J = 8.7 Hz, 1H), 6.97 (d, J = 10.9 Hz, 1H), 6.92-6.83 (m, 2H), 6.59 (dd, J = 16.8, 10.2 Hz, 1H), 6.44 (dd, J = 16.8, 2.1 Hz, 1H), 5.74 (dd, J = 10.2, 2.1 Hz, 1H), 4.99-4.92 (m, 1H), 4.56-4.50 (m, 1H), 3.65-3.52 (m, 1H), 2.27 (s, 3H), 2.26-2.06 (m, 5H), 2.06-1.90 (m, 3H). |
| 392 (Ex 189) | 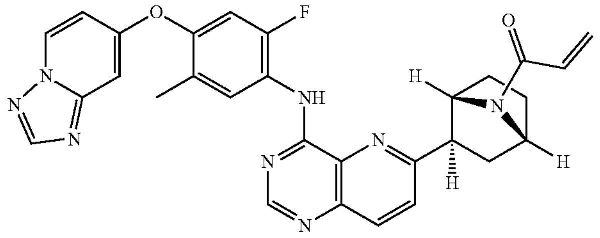 rac-1-((1S,2R,4R)-2-(4-((4-([1,2,4]triazolo[1,5-a]pyridin-7-yloxy)-2-fluoro-5-methylphenyl)amino)pyrido[3,2-d]pyrimidin-6-yl)-7-azabicyclo[2.2.1]heptan-7-yl)prop-2-en-1-one | 537.2 | $^1H$ NMR (400 MHz, $CDCl_3$) δ 9.77-9.18 (m, 1H), 8.78-8.72 (m, 1H), 8.55-8.49 (m, 1H), 8.49-8.30 (m, 1H), 8.25 (s, 1H), 8.14-8.06 (m, 1H), 7.66-7.58 (m, 1H), 6.99-6.92 (m, 2H), 6.92-6.85 (m, 1H), 6.66-6.24 (m, 1H), 6.21-6.03 (m, 1H), 5.75-5.35 (m, 1H), 5.26-4.88 (m, 1H), 4.63-4.41 (m, 1H), 3.48-3.38 (m, 1H), 2.66-2.17 (m, 5H), 2.16-1.87 (m, 2H), 1.89-1.60 (m, 2H). |
| 393 (Ex 189) | 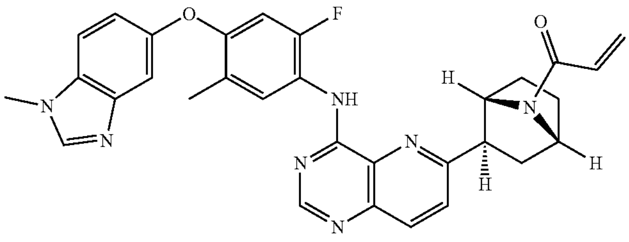 rac-1-((1S,2R,4R)-2-(4-((2-fluoro-5-methyl-4-((1-methyl-1H-benzo[d]imidazol-5-yl)oxy)phenyl)amino)pyrido[3,2-d]pyrimidin-6-yl)-7-azabicyclo[2.2.1]heptan-7-yl)prop-2-en-1-one | 550.2 | $^1H$ NMR (400 MHz, $CDCl_3$) δ 9.58-9.03 (m, 1H), 8.73-8.68 (m, 1H), 8.20-8.03 (m, 2H), 7.88 (s, 1H), 7.62-7.53 (m, 1H), 7.45-7.34 (m, 2H), 7.11-7.04 (m, 1H), 6.71-6.62 (m, 1H), 6.56-6.18 (m, 1H), 6.19-6.03 (m, 1H), 5.74-5.35 (m, 1H), 5.25-4.93 (m, 1H), 4.57-4.48 (m, 1H), 3.87 (s, 3H), 3.45-3.35 (m, 1H), 2.59-2.15 (m, 5H), 2.14-1.87 (m, 2H), 1.87-1.58 (m, 2H). |

TABLE 3-continued

| Example No. (Method) | Structure; IUPAC name | LCMS $M^{+1}$ | $^1$H NMR (ppm); $^{19}$F NMR (ppm); optical rotation; Chiral HPLC/SFC conditions |
|---|---|---|---|
| 394 (Ex 189) | 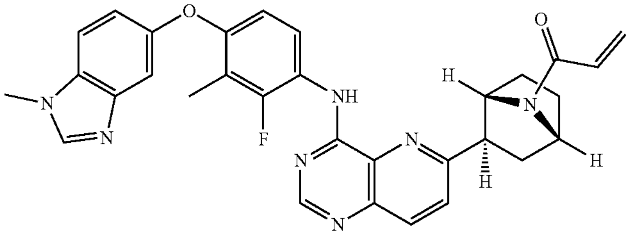 rac-1-((1S,2R,4R)-2-(4-((2-fluoro-3-methyl-4-((1-methyl-1H-benzo[d]imidazol-5-yl)oxy)phenyl)amino)pyrido[3,2-d]pyrimidin-6-yl)-7-azabicyclo[2.2.1]heptan-7-yl)prop-2-en-1-one | 550.2 | $^1$H NMR (400 MHz, $CDCl_3$) δ 9.60-9.10 (m, 1H), 8.68 (s, 1H), 8.21-7.98 (m, 2H), 7.87 (s, 1H), 7.64-7.54 (m, 1H), 7.43-7.31 (m, 2H), 7.11-7.03 (m, 1H), 6.75-6.68 (m, 1H), 6.58-6.24 (m, 1H), 6.23-6.07 (m, 1H), 5.73-5.36 (m, 1H), 5.24-4.95 (m, 1H), 4.59-4.50 (m, 1H), 3.86 (s, 4H), 3.47-3.39 (m, 1H), 2.55-2.27 (m, 4H), 2.25-1.88 (m, 3H), 1.87-1.60 (m, 2H). |
| 395 (Ex 189) | 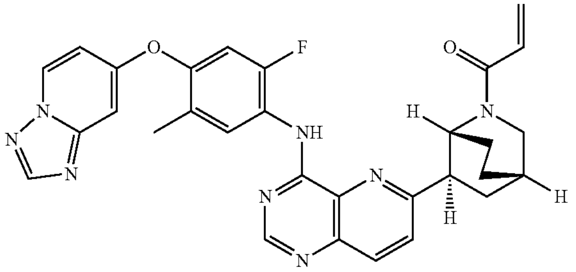 rac-1-((1R,4S,6R)-6-(4-((4-([1,2,4]triazolo[1,5-a]pyridin-7-yloxy)-2-fluoro-5-methylphenyl)amino)pyrido[3,2-d]pyrimidin-6-yl)-2-azabicyclo[2.2.2]octan-2-yl)prop-2-en-1-one | 551.2 | $^1$H NMR (400 MHz, $CDCl_3$) δ 9.55-9.47 (m, 1H), 8.96-8.88 (m, 1H), 8.88-8.83 (m, 1H), 8.55-8.48 (m, 1H), 8.24 (s, 1H), 8.23-8.13 (m, 1H), 7.84-7.63 (m, 1H), 7.03-6.94 (m, 1H), 6.93-6.84 (m, 2H), 6.70-6.53 (m, 1H), 6.53-6.31 (m, 1H), 5.82-5.69 (m, 1H), 4.94-4.29 (m, 1H), 3.77-3.61 (m, 2H), 2.79-2.40 (m, 1H), 2.29 (s, 4H), 2.28-2.05 (m, 1H), 2.06-1.62 (m, 4H). |
| 396 (Ex 189) | 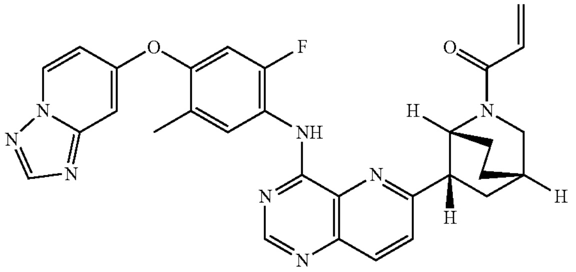 rac-1-((1R,4S,6S)-6-(4-((4-([1,2,4]triazolo[1,5-a]pyridin-7-yloxy)-2-fluoro-5-methylphenyl)amino)pyrido[3,2-d]pyrimidin-6-yl)-2-azabicyclo[2.2.2]octan-2-yl)prop-2-en-1-one | 551.2 | $^1$H NMR (400 MHz, $CDCl_3$) δ 9.75-9.27 (m, 1H), 8.80-8.74 (m, 1H), 8.70-8.41 (m, 2H), 8.25 (s, 1H), 8.14-8.07 (m, 1H), 7.70-7.57 (m, 1H), 7.01-6.84 (m, 3H), 6.54-6.04 (m, 1H), 5.89-5.48 (m, 1H), 5.20-5.09 (m, 1H), 4.15-3.88 (m, 1H), 3.82-3.61 (m, 1H), 3.57-3.41 (m, 2H), 2.39-2.23 (m, 6H), 2.23-1.92 (m, 2H), 1.92-1.76 (m, 2H). |

TABLE 3-continued

| Example No. (Method) | Structure; IUPAC name | LCMS $M^{+1}$ | $^{1}H$ NMR (ppm); $^{19}F$ NMR (ppm); optical rotation; Chiral HPLC/SFC conditions |
|---|---|---|---|
| 397 (Ex 189) | 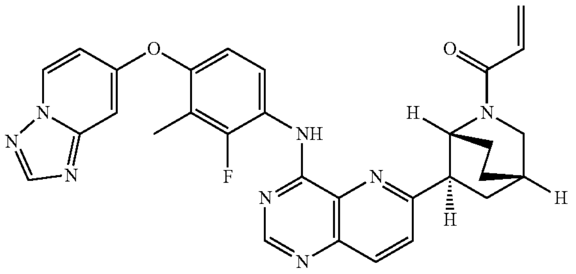 rac-1-((1R,4S,6R)-6-(4-((4-([1,2,4]triazolo[1,5-a]pyridin-7-yloxy)-2-fluoro-3-methylphenyl)amino)pyrido[3,2-d]pyrimidin-6-yl)-2-azabicyclo[2.2.2]octan-2-yl)prop-2-en-1-one | 551.2 | $^{1}H$ NMR (400 MHz, $CDCl_3$) δ 9.60-9.52 (m, 1H), 8.92-8.81 (m, 2H), 8.55-8.48 (m, 1H), 8.24 (s, 1H), 8.22-8.13 (m, 1H), 7.85-7.66 (m, 1H), 7.09-6.84 (m, 3H), 6.71-6.55 (m, 1H), 6.55-6.34 (m, 1H), 5.83-5.70 (m, 1H), 5.01-4.27 (m, 1H), 3.79-3.62 (m, 3H), 2.87-2.41 (m, 1H), 2.38-2.20 (m, 4H), 2.17-1.87 (m, 2H), 1.86-1.69 (m, 3H). |
| 398 (Ex 189) | 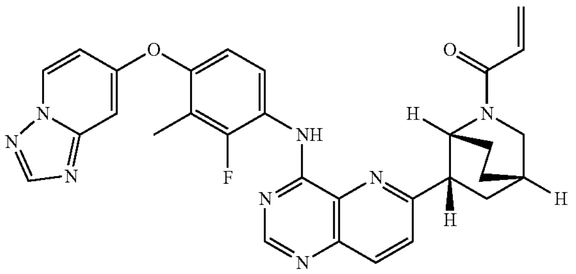 rac-1-((1R,4S,6S)-6-(4-((4-([1,2,4]triazolo[1,5-a]pyridin-7-yloxy)-2-fluoro-3-methylphenyl)amino)pyrido[3,2-d]pyrimidin-6-yl)-2-azabicyclo[2.2.2]octan-2-yl)prop-2-en-1-one | 551.2 | $^{1}H$ NMR (400 MHz, $CDCl_3$) δ 9.75-9.35 (m, 1H), 8.79-8.72 (m, 1H), 8.70-8.36 (m, 2H), 8.24 (s, 1H), 8.14-8.07 (m, 1H), 7.73-7.59 (m, 1H), 7.08-6.83 (m, 3H), 6.53-6.02 (m, 1H), 5.86-5.50 (m, 1H), 5.19-5.09 (m, 1H), 4.16-3.91 (m, 1H), 3.86-3.63 (m, 1H), 3.58-3.47 (m, 2H), 2.46-2.19 (m, 5H), 2.17-1.91 (m, 3H), 1.88-1.79 (m, 2H). |
| 399 (Ex 189) | 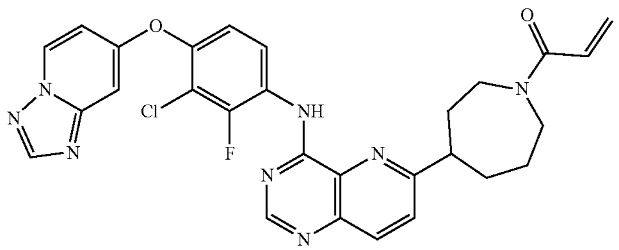 1-(4-(4-((4-([1,2,4]triazolo[1,5-a]pyridin-7-yloxy)-3-chloro-2-fluorophenyl)amino)pyrido[3,2-d]pyrimidin-6-yl)azepan-1-yl)prop-2-en-1-one | 551.2 | $^{1}H$ NMR (400 MHz, $CDCl_3$) δ 9.51-9.44 (m, 1H), 8.99-8.88 (m, 1H), 8.85-8.79 (m, 1H), 8.57-8.51 (m, 1H), 8.26 (s, 1H), 8.20-8.12 (m, 1H), 7.68-7.61 (m, 1H), 7.22-7.13 (m, 1H), 6.97-6.89 (m, 2H), 6.73-6.60 (m, 1H), 6.47-6.36 (m, 1H), 5.79-5.70 (m, 1H), 4.02-3.51 (m, 4H), 3.20-3.11 (m, 1H), 2.36-2.23 (m, 1H), 2.18-2.10 (m, 3H), 2.05-1.78 (m, 2H). |

TABLE 3-continued

| Example No. (Method) | Structure; IUPAC name | LCMS $M^{+1}$ | $^1H$ NMR (ppm); $^{19}F$ NMR (ppm); optical rotation; Chiral HPLC/SFC conditions |
|---|---|---|---|
| 400 (Ex 189) | 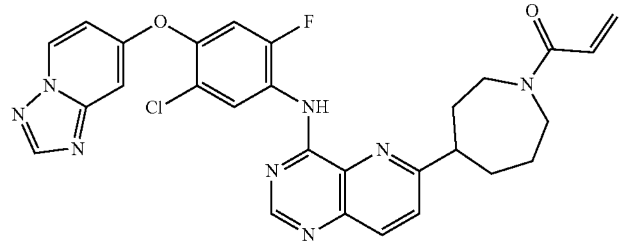 1-(4-(4-((4-([1,2,4]triazolo[1,5-a]pyridin-7-yloxy)-5-chloro-2-fluorophenyl)amino)pyrido[3,2-d]pyrimidin-6-yl)azepan-1-yl)prop-2-en-1-one | 559.2 | $^1H$ NMR (400 MHz, $CDCl_3$) δ 9.49-9.42 (m, 1H), 9.29-9.20 (m, 1H), 8.89-8.84 (m, 1H), 8.58-8.51 (m, 1H), 8.26 (s, 1H), 8.21-8.12 (m, 1H), 7.68-7.61 (m, 1H), 7.17-7.10 (m, 1H), 6.96-6.88 (m, 2H), 6.71-6.59 (m, 1H), 6.46-6.35 (m, 1H), 5.77-5.70 (m, 1H), 4.01-3.53 (m, 4H), 3.20-3.11 (m, 1H), 2.34-2.22 (m, 1H), 2.21-2.05 (m, 3H), 2.02-1.81 (m, 2H). |
| 401 (Ex 189) | 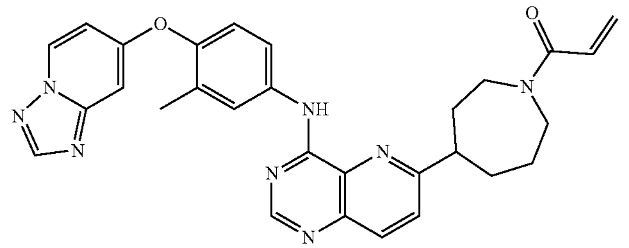 1-(4-(4-((4-([1,2,4]triazolo[1,5-a]pyridin-7-yloxy)-3-methylphenyl)amino)pyrido[3,2-d]pyrimidin-6-yl)azepan-1-yl)prop-2-en-1-one | 521.2 | $^1H$ NMR (400 MHz, $CDCl_3$) δ 9.26-9.03 (m, 1H), 8.80-8.74 (m, 1H), 8.53-8.46 (m, 1H), 8.22 (s, 1H), 8.16-8.07 (m, 1H), 7.99-7.88 (m, 2H), 7.64-7.57 (m, 1H), 7.18-7.10 (m, 1H), 6.93-6.83 (m, 2H), 6.72-6.55 (m, 1H), 6.48-6.33 (m, 1H), 5.78-5.67 (m, 1H), 4.16-3.82 (m, 1H), 3.82-3.53 (m, 3H), 3.29-3.06 (m, 1H), 2.28 (s, 4H), 2.21-1.80 (m, 5H). |
| 402 (Ex 189) | 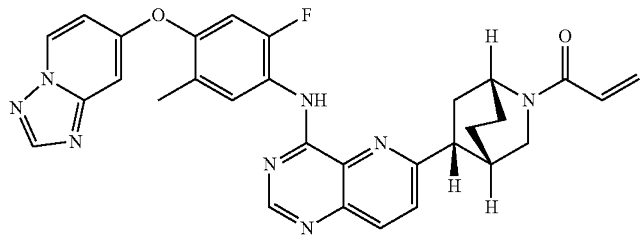 rac-1-((1R,4S,5R)-5-(4-((4-([1,2,4]triazolo[1,5-a]pyridin-7-yloxy)-2-fluoro-5-methylphenyl)amino)pyrido[3,2-d]pyrimidin-6-yl)-2-azabicyclo[2.2.2]octan-2-yl)prop-2-en-1-one | 551.2 | $^1H$ NMR (400 MHz, $CDCl_3$) δ 9.29 (s, 1H), 8.85-8.78 (m, 1H), 8.75-8.63 (m, 1H), 8.55-8.48 (m, 1H), 8.27-8.22 (m, 1H), 8.19-8.11 (m, 1H), 7.71-7.63 (m, 1H), 7.01-6.84 (m, 3H), 6.73-6.22 (m, 2H), 5.69-5.58 (m, 1H), 4.92-4.18 (m, 1H), 3.83-3.62 (m, 1H), 3.51-3.38 (m, 2H), 2.79-2.65 (m, 1H), 2.49-2.16 (m, 5H), 2.15-1.78 (m, 4H). |
| 403 (Ex 189) | 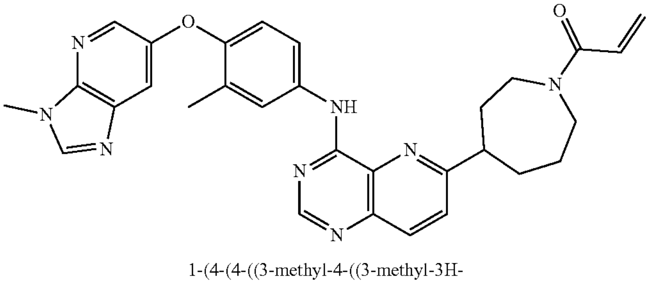 1-(4-(4-((3-methyl-4-((3-methyl-3H-imidazo[4,5-b]pyridin-6-yl)oxy)phenyl)amino)pyrido[3,2-d]pyrimidin-6-yl)azepan-1-yl)prop-2-en-1-one | 535.3 | $^1H$ NMR (400 MHz, $CDCl_3$) δ 9.17-8.97 (m, 1H), 8.76-8.71 (m, 1H), 8.33-8.28 (m, 1H), 8.13-8.05 (m, 1H), 8.02 (s, 1H), 7.89-7.71 (m, 2H), 7.62-7.54 (m, 2H), 6.96-6.90 (m, 1H), 6.71-6.56 (m, 1H), 6.47-6.34 (m, 1H), 5.77-5.67 (m, 1H), 4.11-3.82 (m, 4H), 3.81-3.69 (m, 1H), 3.69-3.55 (m, 2H), 3.36-2.99 (m, 1H), 2.37 (s, 3H), 2.32-2.10 (m, 3H), 2.10-1.77 (m, 3H). |

TABLE 3-continued

| Example No. (Method) | Structure; IUPAC name | LCMS $M^{+1}$ | $^1$H NMR (ppm); $^{19}$F NMR (ppm); optical rotation; Chiral HPLC/SFC conditions |
|---|---|---|---|
| 404 (Ex 189) | 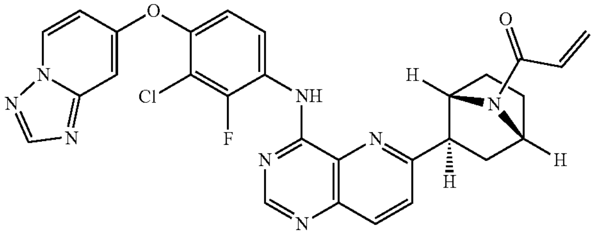 rac-1-((1S,2R,4R)-2-(4-((4-([1,2,4]triazolo[1,5-a]pyridin-7-yloxy)-3-chloro-2-fluorophenyl)amino)pyrido[3,2-d]pyrimidin-6-yl)-7-azabicyclo[2.2.1]heptan-7-yl)prop-2-en-1-one | 557.2 | $^1$H NMR (400 MHz, $CDCl_3$) δ 9.91-9.25 (m, 1H), 8.78-8.73 (m, 1H), 8.63-8.42 (m, 2H), 8.27 (s, 1H), 8.16-8.09 (m, 1H), 7.67-7.61 (m, 1H), 7.17-7.10 (m, 1H), 7.01-6.89 (m, 2H), 6.62-5.96 (m, 2H), 5.74-5.35 (m, 1H), 5.24-4.89 (m, 1H), 4.64-4.42 (m, 1H), 3.48-3.39 (m, 1H), 2.63-2.18 (m, 2H), 2.17-1.89 (m, 2H), 1.90-1.59 (m, 2H). |
| 405 (Ex 189) | 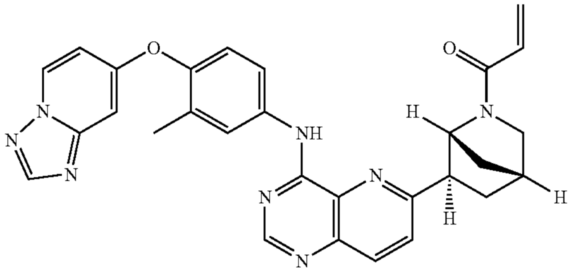 rac-1-((1R,4R,6R)-6-(4-((4-([1,2,4]triazolo[1,5-a]pyridin-7-yloxy)-3-methylphenyl)amino)pyrido[3,2-d]pyrimidin-6-yl)-2-azabicyclo[2.2.1]heptan-2-yl)prop-2-en-1-one | 519.2 | $^1$H NMR (400 MHz, $CDCl_3$) δ 9.07-9.00 (m, 1H), 8.82-8.77 (m, 1H), 8.54-8.47 (m, 1H), 8.23 (s, 1H), 8.18-8.11 (m, 1H), 7.91-7.81 (m, 2H), 7.72-7.63 (m, 1H), 7.19-7.12 (m, 1H), 6.94-6.88 (m, 1H), 6.88-6.82 (m, 1H), 6.65-6.33 (m, 2H), 5.77-5.69 (m, 1H), 5.03-4.47 (m, 1H), 3.72-3.57 (m, 1H), 3.56-3.43 (m, 1H), 3.41-3.31 (m, 1H), 3.07-2.99 (m, 1H), 2.51-2.42 (m, 1H), 2.42-2.20 (m, 4H), 2.11-1.96 (m, 1H), 1.88-1.68 (m, 1H). |
| 406 (Ex 189) | 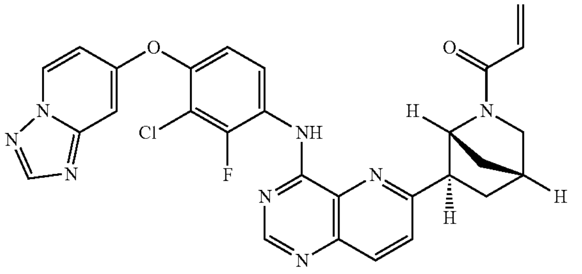 rac-1-((1R,4R,6R)-6-(4-((4-([1,2,4]triazolo[1,5-a]pyridin-7-yloxy)-3-chloro-2-fluorophenyl)amino)pyrido[3,2-d]pyrimidin-6-yl)-2-azabicyclo[2.2.1]heptan-2-yl)prop-2-en-1-one | 557.2 | $^1$H NMR (400 MHz, $CDCl_3$) δ 9.47 (s, 1H), 9.04-8.93 (m, 1H), 8.87-8.82 (m, 1H), 8.58-8.50 (m, 1H), 8.26 (s, 1H), 8.22-8.15 (m, 1H), 7.76-7.65 (m, 1H), 7.22-7.14 (m, 1H), 6.97-6.88 (m, 2H), 6.64-6.32 (m, 2H), 5.77-5.69 (m, 1H), 4.97-4.55 (m, 1H), 3.72-3.56 (m, 1H), 3.55-3.43 (m, 1H), 3.41-3.31 (m, 1H), 3.12-2.92 (m, 1H), 2.52-2.37 (m, 1H), 2.33-2.20 (m, 1H), 2.18-2.05 (m, 1H), 1.88-1.74 (m, 1H). |

TABLE 3-continued

| Example No. (Method) | Structure; IUPAC name | LCMS $M^{+1}$ | $^{1}H$ NMR (ppm); $^{19}F$ NMR (ppm); optical rotation; Chiral HPLC/SFC conditions |
|---|---|---|---|
| 407 (Ex 189) | 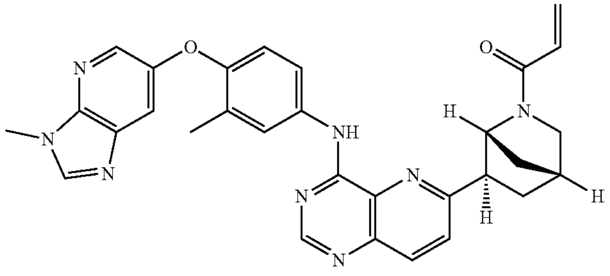 rac-1-((1R,4R,6S)-6-(4-((3-methyl-4-((3-methyl-3H-imidazo[4,5-b]pyridin-6-yl)oxy)phenyl)amino)pyrido[3,2-d]pyrimidin-6-yl)-2-azabicyclo[2.2.1]heptan-2-yl)prop-2-en-1-one | 533.2 | $^{1}H$ NMR (400 MHz, $CDCl_3$) δ 8.98-8.91 (m, 1H), 8.78-8.73 (m, 1H), 8.33-8.28 (m, 1H), 8.16-8.08 (m, 1H), 8.03 (s, 1H), 7.81-7.76 (m, 1H), 7.73-7.62 (m, 2H), 7.62-7.57 (m, 1H), 6.97-6.90 (m, 1H), 6.66-6.32 (m, 2H), 5.77-5.68 (m, 1H), 5.03-4.49 (m, 1H), 3.93 (s, 3H), 3.71-3.56 (m, 1H), 3.55-3.43 (m, 1H), 3.40-3.29 (m, 1H), 3.08-2.91 (m, 1H), 2.51-2.41 (m, 1H), 2.38 (s, 3H), 2.30-2.20 (m, 1H), 2.09-1.97 (m, 1H), 1.87-1.69 (m, 1H). |
| 408 (Ex 189) | 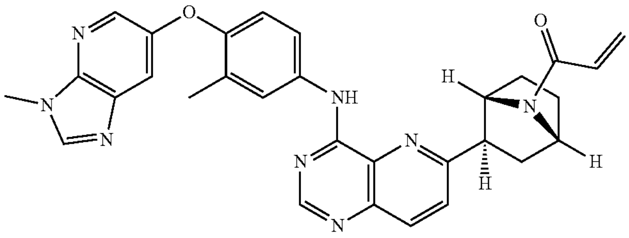 rac-1-((1R,2S,4S)-2-(4-((3-methyl-4-((3-methyl-3H-imidazo[4,5-b]pyridin-6-yl)oxy)phenyl)amino)pyrido[3,2-d]pyrimidin-6-yl)-7-azabicyclo[2.2.1]heptan-7-yl)prop-2-en-1-one | 533.2 | $^{1}H$ NMR (400 MHz, $CDCl_3$) δ 10.21-9.25 (m, 1H), 8.70 (s, 1H), 8.33-8.28 (m, 1H), 8.26-8.11 (m, 1H), 8.09-7.96 (m, 2H), 7.61-7.56 (m, 1H), 7.56-7.40 (m, 1H), 7.00-6.91 (m, 1H), 6.51-5.87 (m, 2H), 5.71-4.99 (m, 2H), 4.39 (dd, J = 111.8, 4.7 Hz, 1H), 3.93 (s, 3H), 3.43-3.31 (m, 1H), 2.72-2.24 (m, 4H), 2.15-1.88 (m, 2H), 1.88-1.56 (m, 4H). |
| 409 (Ex 189) | 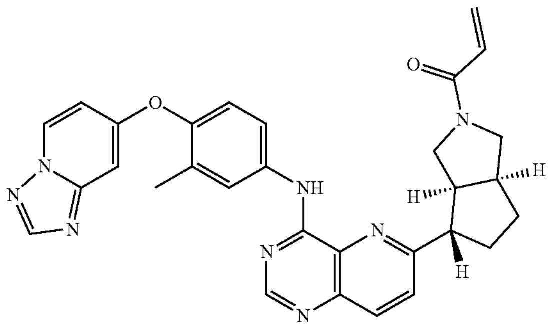 rac-1-((3aS,4S,6aS)-4-(4-((4-([1,2,4]triazolo[1,5-a]pyridin-7-yloxy)-3-methylphenyl)amino)pyrido[3,2-d]pyrimidin-6-yl)hexahydrocyclopenta[c]pyrrol-2(1H)-yl)prop-2-en-1-one | 533.2 | $^{1}H$ NMR (400 MHz, $CDCl_3$) δ 9.15-9.09 (m, 1H), 8.82-8.76 (m, 1H), 8.53-8.46 (m, 1H), 8.23 (s, 1H), 8.18-8.10 (m, 1H), 7.94-7.85 (m, 2H), 7.68-7.62 (m, 1H), 7.18-7.11 (m, 1H), 6.94-6.83 (m, 2H), 6.63-6.33 (m, 2H), 5.76-5.65 (m, 1H), 3.99-3.61 (m, 3H), 3.61-3.48 (m, 1H), 3.35-3.24 (m, 1H), 3.21-2.90 (m, 2H), 2.48-2.24 (m, 5H), 2.18-2.01 (m, 1H), 1.80-1.66 (m, 1H). |

TABLE 3-continued

| Example No. (Method) | Structure; IUPAC name | LCMS $M^{+1}$ | $^{1}H$ NMR (ppm); $^{19}F$ NMR (ppm); optical rotation; Chiral HPLC/SFC conditions |
|---|---|---|---|
| 410 (Ex 189) | 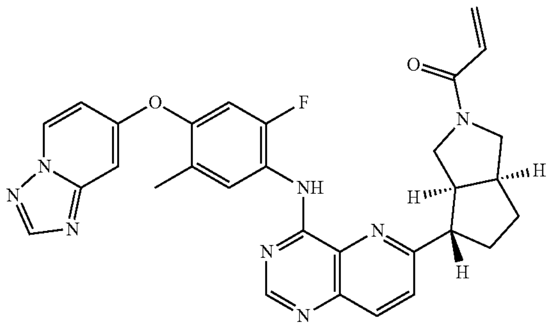 rac-1-((3aS,4S,6aS)-4-(4-((4-([1,2,4]triazolo[1,5-a]pyridin-7-yloxy)-2-fluoro-5-methylphenyl)amino)pyrido[3,2-d]pyrimidin-6-yl)hexahydrocyclopenta[c]pyrrol-2(1H)-yl)prop-2-en-1-one | 551.2 | $^{1}H$ NMR (400 MHz, $CDCl_3$) δ 9.44 (s, 1H), 8.92-8.83 (m, 2H), 8.55-8.48 (m, 1H), 8.24 (s, 1H), 8.20-8.11 (m, 1H), 7.70-7.62 (m, 1H), 7.02-6.94 (m, 1H), 6.93-6.85 (m, 2H), 6.55-6.43 (m, 1H), 6.43-6.34 (m, 1H), 5.74-5.64 (m, 1H), 3.92-3.67 (m, 3H), 3.61-3.48 (m, 1H), 3.37-3.26 (m, 1H), 3.24-2.93 (m, 2H), 2.49-2.22 (m, 5H), 2.17-1.97 (m, 1H), 1.80-1.62 (m, 1H). |
| 411 (Ex 189) | 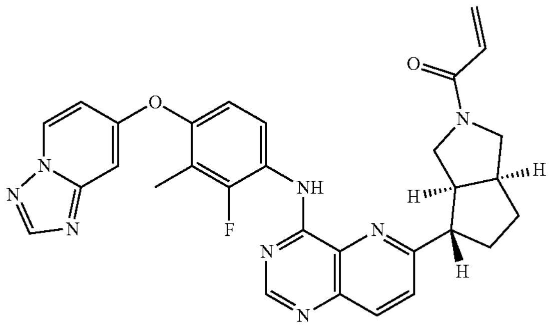 rac-1-((3aS,4S,6aS)-4-(4-((4-([1,2,4]triazolo[1,5-a]pyridin-7-yloxy)-2-fluoro-3-methylphenyl)amino)pyrido[3,2-d]pyrimidin-6-yl)hexahydrocyclopenta[c]pyrrol-2(1H)-yl)prop-2-en-1-one | 551.2 | $^{1}H$ NMR (400 MHz, $CDCl_3$) δ 9.53-9.47 (m, 1H), 8.88-8.76 (m, 2H), 8.55-8.47 (m, 1H), 8.24 (s, 1H), 8.20-8.11 (m, 1H), 7.70-7.62 (m, 1H), 7.06-6.99 (m, 1H), 6.94-6.85 (m, 2H), 6.56-6.45 (m, 1H), 6.45-6.35 (m, 1H), 5.75-5.65 (m, 1H), 3.94-3.68 (m, 3H), 3.62-3.49 (m, 1H), 3.32 (p, J = 8.1, 7.4 Hz, 1H), 3.27-2.94 (m, 2H), 2.53-2.27 (m, 2H), 2.25-2.18 (m, 3H), 2.18-1.98 (m, 1H), 1.81-1.67 (m, 1H). |
| 412 (Ex 189) | 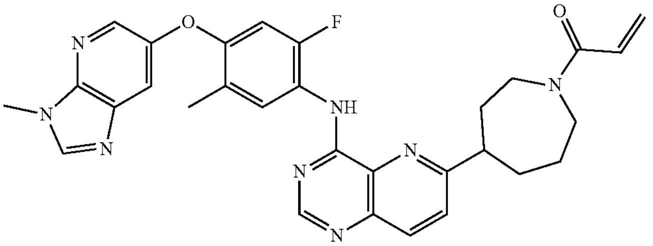 1-(4-(4-((2-fluoro-5-methyl-4-((3-methyl-3H-imidazo[4,5-b]pyridin-6-yl)oxy)phenyl)amino)pyrido[3,2-d]pyrimidin-6-yl)azepan-1-yl)prop-2-en-1-one | 553.2 | $^{1}H$ NMR (400 MHz, $CDCl_3$) δ 9.21 (s, 1H), 8.81-8.76 (m, 1H), 8.67-8.57 (m, 1H), 8.32-8.27 (m, 1H), 8.15-8.07 (m, 1H), 8.05 (s, 1H), 7.67-7.62 (m, 1H), 7.62-7.56 (m, 1H), 6.73-6.58 (m, 2H), 6.44-6.34 (m, 1H), 5.76-5.68 (m, 1H), 3.93 (s, 3H), 3.92-3.50 (m, 4H), 3.20-3.04 (m, 1H), 2.41-2.36 (m, 3H), 2.35-2.20 (m, 1H), 2.18-2.04 (m, 3H), 2.00-1.79 (m, 2H). |

TABLE 3-continued

| Example No. (Method) | Structure; IUPAC name | LCMS $M^{+1}$ | $^1$H NMR (ppm); $^{19}$F NMR (ppm); optical rotation; Chiral HPLC/SFC conditions |
| --- | --- | --- | --- |
| 413 (Ex 189) | 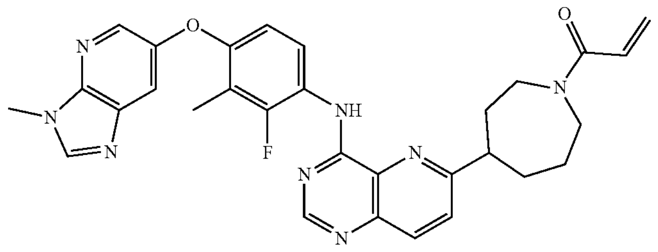 1-(4-(4-((2-fluoro-3-methyl-4-((3-methyl-3H-imidazo[4,5-b]pyridin-6-yl)oxy)phenyl)amino)pyrido[3,2-d]pyrimidin-6-yl)azepan-1-yl)prop-2-en-1-one | 553.2 | $^1$H NMR (400 MHz, $CDCl_3$) δ 9.33 (s, 1H), 8.76-8.71 (m, 1H), 8.58-8.46 (m, 1H), 8.33-8.27 (m, 1H), 8.14-8.06 (m, 1H), 8.04 (s, 1H), 7.66-7.56 (m, 2H), 6.78-6.60 (m, 2H), 6.47-6.36 (m, 1H), 5.78-5.70 (m, 1H), 3.96-3.92 (m, 4H), 3.19-3.52 (m, 3H), 3.20-3.06 (m, 1H), 2.37-2.22 (m, 4H), 2.22-2.06 (m, 3H), 2.03-1.79 (m, 2H). |
| 414 (Ex 189) | 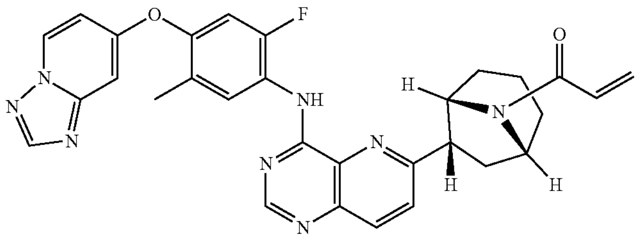 rac-1-(6-(4-((4-([1,2,4]triazolo[1,5-a]pyridin-7-yloxy)-2-fluoro-5-methylphenyl)amino)pyrido[3,2-d]pyrimidin-6-yl)-8-azabicyclo[3.2.1]octan-8-yl)prop-2-en-1-one | 551.2 | $^1$H NMR (400 MHz, $CDCl_3$) δ 9.56-9.10 (m, 1H), 8.81-8.74 (m, 1H), 8.68-8.42 (m, 2H), 8.25 (s, 1H), 8.16-8.07 (m, 1H), 7.63-7.55 (m, 1H), 7.01-6.85 (m, 3H), 6.67-6.41 (m, 1H), 6.40-6.30 (m, 1H), 5.76-5.53 (m, 1H), 5.24-5.00 (m, 1H), 4.66-4.57 (m, 1H), 3.79-3.65 (m, 1H), 2.53-2.30 (m, 2H), 2.31-2.20 (m, 3H), 2.17-1.63 (m, 6H). |
| 415 (Ex 189) | 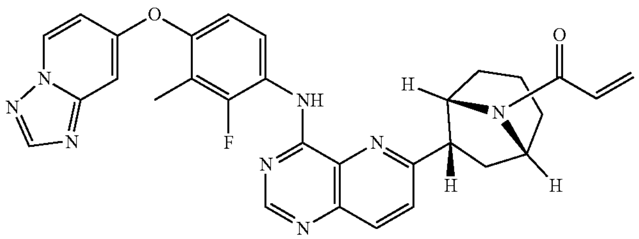 rac-1-(6-(4-((4-([1,2,4]triazolo[1,5-a]pyridin-7-yloxy)-2-fluoro-3-methylphenyl)amino)pyrido[3,2-d]pyrimidin-6-yl)-8-azabicyclo[3.2.1]octan-8-yl)prop-2-en-1-one | 551.2 | $^1$H NMR (400 MHz, $CDCl_3$) δ 9.61-9.21 (m, 1H), 8.79-8.72 (m, 1H), 8.63-8.41 (m, 2H), 8.24 (s, 1H), 8.16-8.07 (m, 1H), 7.63-7.55 (m, 1H), 7.03-6.95 (m, 1H), 6.95-6.86 (m, 2H), 6.66-6.44 (m, 1H), 6.42-6.31 (m, 1H), 5.75-5.57 (m, 1H), 5.22-5.01 (m, 1H), 4.67-4.58 (m, 1H), 3.80-3.66 (m, 1H), 2.54-2.29 (m, 2H), 2.25-2.18 (m, 3H), 2.11-1.92 (m, 2H), 1.92-1.65 (m, 4H). |

TABLE 3-continued

| Example No. (Method) | Structure; IUPAC name | LCMS $M^{+1}$ | $^1H$ NMR (ppm); $^{19}F$ NMR (ppm); optical rotation; Chiral HPLC/SFC conditions |
|---|---|---|---|
| 416 (Ex 189) | 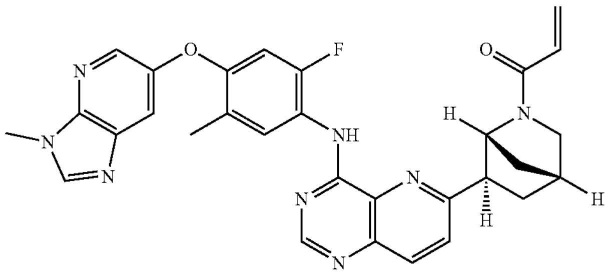 rac-1-((1R,4R,6R)-6-(4-((2-fluoro-5-methyl-4-((3-methyl-3H-imidazo[4,5-b]pyridin-6-yl)oxy)phenyl)amino)pyrido[3,2-d]pyrimidin-6-yl)-2-azabicyclo[2.2.1]heptan-2-yl)prop-2-en-1-one | 551.2 | $^1H$ NMR (400 MHz, $CDCl_3$) δ 9.27-9.20 (m, 1H), 8.84-8.79 (m, 1H), 8.73-8.65 (m, 1H), 8.32-8.27 (m, 1H), 8.16-8.08 (m, 1H), 8.05 (s, 1H), 7.70-7.60 (m, 2H), 6.74-6.66 (m, 1H), 6.62-6.48 (m, 1H), 6.49-6.32 (m, 1H), 5.75-5.67 (m, 1H), 4.95-4.47 (m, 1H), 3.94 (s, 3H), 3.70-3.54 (m, 1H), 3.53-3.41 (m, 1H), 3.37-3.27 (m, 1H), 3.10-2.84 (m, 1H), 2.49-2.17 (m, 5H), 2.17-2.00 (m, 1H), 1.85-1.65 (m, 1H). |
| 417 (Ex 189) | 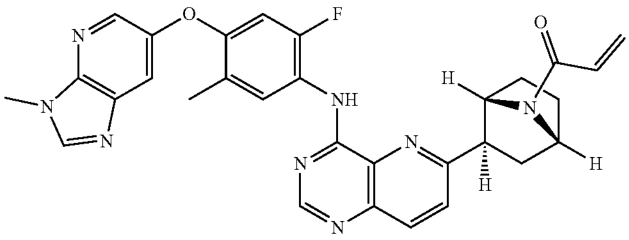 rac-1-((1S,2R,4R)-2-(4-((2-fluoro-5-methyl-4-((3-methyl-3H-imidazo[4,5-b]pyridin-6-yl)oxy)phenyl)amino)pyrido[3,2-d]pyrimidin-6-yl)-7-azabicyclo[2.2.1]heptan-7-yl)prop-2-en-1-one | 551.2 | $^1H$ NMR (400 MHz, $CDCl_3$) δ 9.62-8.99 (m, 1H), 8.74-8.68 (m, 1H), 8.33-8.28 (m, 1H), 8.25-8.14 (m, 1H), 8.10-8.04 (m, 2H), 7.71-7.66 (m, 1H), 7.62-7.54 (m, 1H), 6.70-6.61 (m, 1H), 6.54-6.24 (m, 1H), 6.21-6.04 (m, 1H), 5.67-5.34 (m, 1H), 5.25-4.88 (m, 1H), 4.61-4.45 (m, 1H), 3.94 (s, 3H), 3.45-3.35 (m, 1H), 2.51-2.44 (m, 1H), 2.40-2.34 (m, 3H), 2.26-2.17 (m, 1H), 2.12-1.78 (m, 3H), 1.78-1.59 (m, 1H). |
| 418 (Ex 189) | 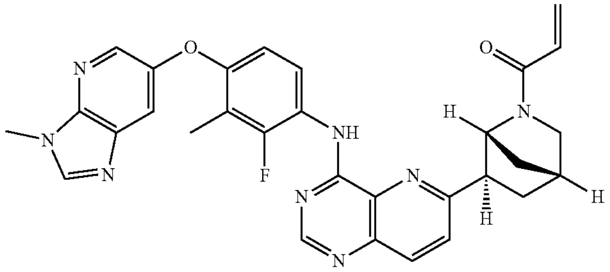 rac-1-((1R,2R,4R)-2-(4-((2-fluoro-3-methyl-4-((3-methyl-3H-imidazo[4,5-b]pyridin-6-yl)oxy)phenyl)amino)pyrido[3,2-d]pyrimidin-6-yl)-7-azabicyclo[2.2.1]heptan-7-yl)prop-2-en-1-one | 551.2 | $^1H$ NMR (400 MHz, $CDCl_3$) δ 9.38-9.31 (m, 1H), 8.78-8.73 (m, 1H), 8.64-8.53 (m, 1H), 8.33-8.27 (m, 1H), 8.16-8.09 (m, 1H), 8.04 (s, 1H), 7.79-7.56 (m, 2H), 6.79-6.71 (m, 1H), 6.63-6.51 (m, 1H), 6.50-6.34 (m, 1H), 5.77-5.68 (m, 1H), 5.01-4.51 (m, 1H), 3.94 (s, 3H), 3.72-3.55 (m, 1H), 3.55-3.43 (m, 1H), 3.38-3.28 (m, 1H), 3.07-2.93 (m, 1H), 2.52-2.36 (m, 1H), 2.36-2.20 (m, 4H), 2.19-2.07 (m, 1H), 1.89-1.71 (m, 1H). |

TABLE 3-continued

| Example No. (Method) | Structure; IUPAC name | LCMS $M^{+1}$ | $^1$H NMR (ppm); $^{19}$F NMR (ppm); optical rotation; Chiral HPLC/SFC conditions |
|---|---|---|---|
| 419 (Ex 189) | 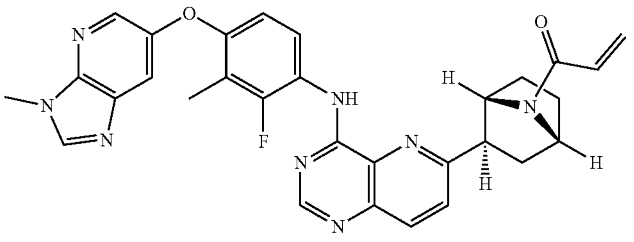 rac-1-((1S,2R,4R)-2-(4-fluoro-3-methyl-4-((3-methyl-3H-imidazo[4,5-b]pyridin-6-yl)oxy)phenyl)amino)pyrido[3,2-d]pyrimidin-6-yl)-7-azabicyclo[2.2.1]heptan-7-yl)prop-2-en-1-one | 551.2 | $^1$H NMR (400 MHz, $CDCl_3$) δ 9.69-9.09 (m, 1H), 8.71-8.66 (m, 1H), 8.33-8.28 (m, 1H), 8.23-8.01 (m, 3H), 7.69-7.64 (m, 1H), 7.64-7.55 (m, 1H), 6.73-6.66 (m, 1H), 6.56-6.21 (m, 1H), 6.18-6.06 (m, 1H), 5.67-5.35 (m, 1H), 5.26-4.91 (m, 1H), 4.64-4.43 (m, 1H), 3.94 (s, 3H), 3.47-3.36 (m, 1H), 2.56-2.18 (m, 4H), 2.14-1.87 (m, 2H), 1.87-1.60 (m, 2H). |
| 420 (Ex 189) | 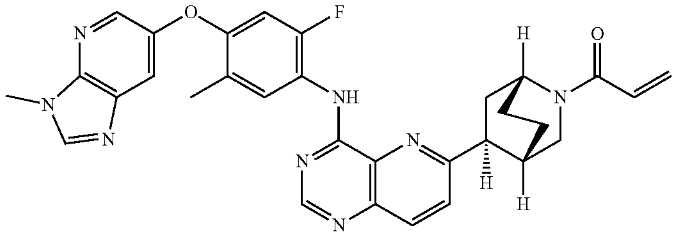 rac-1-((1R,4S,5S)-5-(4-((2-fluoro-5-methyl-4-((3-methyl-3H-imidazo[4,5-b]pyridin-6-yl)oxy)phenyl)amino)propyl[3,2-d]pyrimidin-6-yl)-2-azabicyclo[2.2.2]octan-2-yl)prop-2-en-1-one | 565.2 | $^1$H NMR (400 MHz, $CDCl_3$) δ 9.35 (s, 1H), 8.87-8.80 (m, 1H), 8.80-8.68 (m, 1H), 8.32-8.27 (m, 1H), 8.18-8.08 (m, 1H), 8.05 (s, 1H), 7.71-7.59 (m, 2H), 6.75-6.67 (m, 1H), 6.65-6.51 (m, 1H), 6.50-6.22 (m, 1H), 5.79-5.65 (m, 1H), 4.88-4.14 (m, 1H), 3.94 (s, 3H), 3.91-3.80 (m, 1H), 3.79-3.62 (m, 1H), 3.52-3.44 (m, 1H), 2.78-2.51 (m, 1H), 2.39 (s, 3H), 2.38-2.24 (m, 3H), 2.03-1.87 (m, 2H), 1.85-1.64 (m, 1H). |
| 421 (Ex 189) | 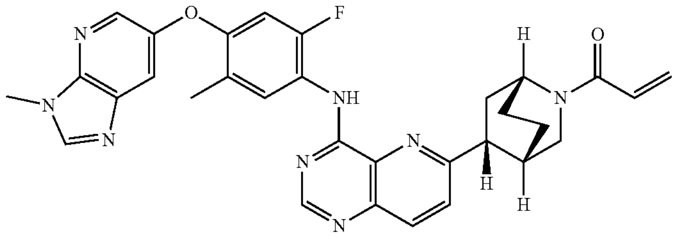 rac-1-((1R,4S,5R)-5-(4-((2-fluoro-5-methyl-4-((3-methyl-3H-imidazo[4,5-b]pyridin-6-yl)oxy)phenyl)amino)pyrido[3,2-d]pyrimidin-6-yl)-2-azabicyclo[2.2.2]octan-2-yl)prop-2-en-1-one | 565.2 | $^1$H NMR (400 MHz, $CDCl_3$) δ 9.16-9.09 (m, 1H), 8.83-8.74 (m, 1H), 8.54-8.41 (m, 1H), 8.32-8.27 (m, 1H), 8.16-8.08 (m, 1H), 8.05 (s, 1H), 7.69-7.59 (m, 2H), 6.71-6.55 (m, 1H), 6.43-6.21 (m, 2H), 5.66-5.55 (m, 1H), 4.88-4.19 (m, 1H), 3.97-3.92 (m, 3H), 3.80-3.63 (m, 1H), 3.53-3.34 (m, 2H), 2.77-2.61 (m, 1H), 2.42-2.35 (m, 4H), 2.30-2.15 (m, 1H), 2.08-1.77 (m, 4H). |

TABLE 3-continued

| Example No. (Method) | Structure; IUPAC name | LCMS $M^{+1}$ | $^1$H NMR (ppm); $^{19}$F NMR (ppm); optical rotation; Chiral HPLC/SFC conditions |
|---|---|---|---|
| 422 (Ex 189) | 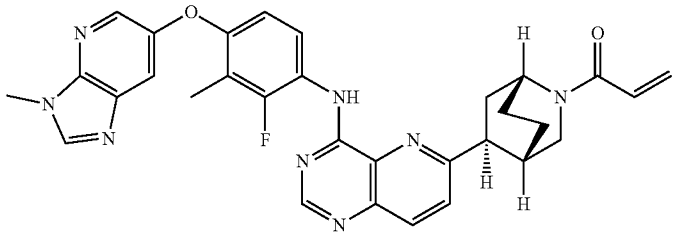 rac-1-((1R,4S,5S)-5-(4-((2-fluoro-3-methyl-4-((3-methyl-3H-imidazo[4,5-b]pyridin-6-yl)oxy)phenyl)amino)pyrido[3,2-d]pyrimidin-6-yl)-2-azabicyclo[2.2.2]octan-2-yl)prop-2-en-1-one | 565.2 | $^1$H NMR (400 MHz, $CDCl_3$) δ 9.45 (s, 1H), 8.80-8.71 (m, 1H), 8.70-8.58 (m, 1H), 8.33-8.27 (m, 1H), 8.18-8.11 (m, 1H), 8.07-8.02 (m, 1H), 7.79-7.58 (m, 2H), 6.80-6.70 (m, 1H), 6.69-6.53 (m, 1H), 6.51-6.32 (m, 1H), 5.81-5.67 (m, 1H), 4.93-4.19 (m, 1H), 3.96-3.92 (m, 3H), 3.91-3.83 (m, 1H), 3.80-3.63 (m, 1H), 3.56-3.42 (m, 1H), 2.80-2.55 (m, 1H), 2.48-2.26 (m, 5H), 2.05-1.94 (m, 2H), 1.86-1.58 (m, 2H). |
| 423 (Ex 189) | 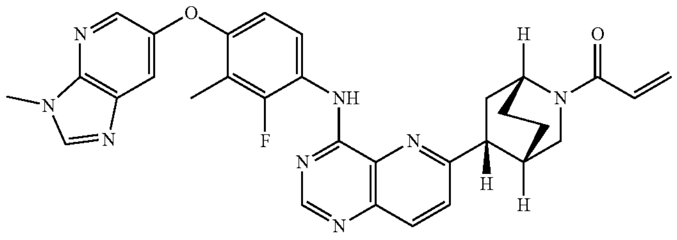 rac-1-((1R,4S,5R)-5-(4-((2-fluoro-3-methyl-4-((3-methyl-3H-imidazo[4,5-b]pyridin-6-yl)oxy)phenyl)amino)pyrido[3,2-d]pyrimidin-6-yl)-2-azabicyclo[2.2.2]octan-2-yl)prop-2-en-1-one | 565.2 | $^1$H NMR (400 MHz, $CDCl_3$) δ 9.27-9.21 (m, 1H), 8.80-8.71 (m, 1H), 8.47-8.33 (m, 1H), 8.32-8.27 (m, 1H), 8.18-8.08 (m, 1H), 8.04 (s, 1H), 7.72-7.59 (m, 2H), 6.76-6.59 (m, 1H), 6.47-6.25 (m, 2H), 5.68-5.58 (m, 1H), 4.89-4.20 (m, 1H), 3.94 (s, 3H), 3.86-3.60 (m, 1H), 3.53-3.38 (m, 2H), 2.80-2.64 (m, 1H), 2.45-2.37 (m, 1H), 2.35-2.30 (m, 3H), 2.29-2.15 (m, 1H), 2.15-1.77 (m, 4H). |
| 424 (Ex 189) | 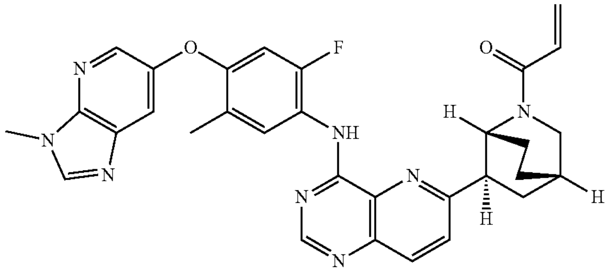 rac-1-((1R,4S,6R)-6-(4-((2-fluoro-5-methyl-4-((3-methyl-3H-imidazo[4,5-b]pyridin-6-yl)oxy)phenyl)amino)pyrido[3,2-d]pyrimidin-6-yl)-2-azabicyclo[2.2.2]octan-2-yl)prop-2-en-1-one | 565.2 | $^1$H NMR (400 MHz, $CDCl_3$) δ 9.40-9.33 (m, 1H), 8.86-8.80 (m, 1H), 8.80-8.70 (m, 1H), 8.32-8.27 (m, 1H), 8.21-8.09 (m, 1H), 8.07-8.02 (m, 1H), 7.81-7.64 (m, 1H), 7.65-7.60 (m, 1H), 6.78-6.54 (m, 2H), 6.51-6.32 (m, 1H), 5.82-5.64 (m, 1H), 4.92-4.31 (m, 1H), 3.96-3.92 (m, 3H), 3.76-3.59 (m, 2H), 2.78-2.41 (m, 1H), 2.41-2.36 (m, 3H), 2.32-2.00 (m, 1H), 1.95-1.66 (m, 4H). |

TABLE 3-continued

| Example No. (Method) | Structure; IUPAC name | LCMS $M^{+1}$ | $^{1}H$ NMR (ppm); $^{19}F$ NMR (ppm); optical rotation; Chiral HPLC/SFC conditions |
| --- | --- | --- | --- |
| 425 (Ex 189) | 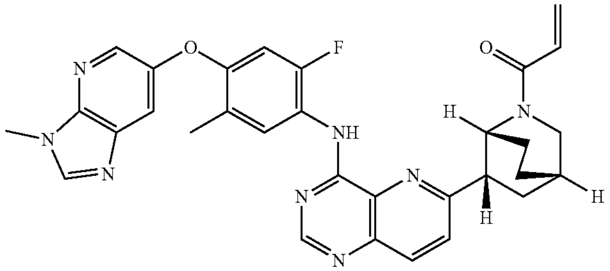 rac-1-((1R,4S,6S)-6-(4-((2-fluoro-5-methyl-4-((3-methyl-3H-imidazo[4,5-b]pyridin-6-yl)oxy)phenyl)amino)pyrido[3,2-d]pyrimidin-6-yl)-2-azabicyclo[2.2.2]octan-2-yl)prop-2-en-1-one | 565.2 | $^{1}H$ NMR (400 MHz, $CDCl_3$) δ 9.65-9.13 (m, 1H), 8.77-8.70 (m, 1H), 8.61-8.24 (m, 2H), 8.11-8.03 (m, 2H), 7.70-7.54 (m, 2H), 6.71-6.64 (m, 1H), 6.51-6.02 (m, 1H), 5.93-5.47 (m, 1H), 5.22-5.09 (m, 1H), 4.17-3.86 (m, 3H), 3.77-3.59 (m, 1H), 3.54-3.44 (m, 2H), 2.40-2.34 (m, 3H), 2.34-2.15 (m, 3H), 2.15-1.90 (m, 2H), 1.90-1.74 (m, 2H). |
| 426 (Ex 189) | 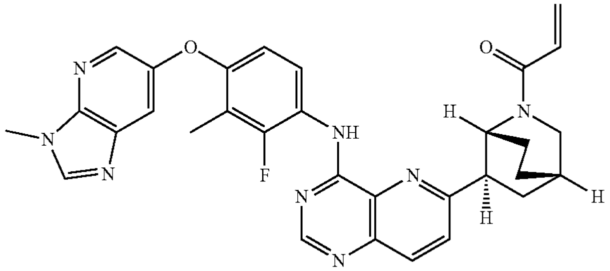 rac-1-((1R,4S,6R)-6-(4-((2-fluoro-3-methyl-4-((3-methyl-3H-imidazo[4,5-b]pyridin-6-yl)oxy)phenyl)amino)pyrido[3,2-d]pyrimidin-6-yl)-2-azabicyclo[2.2.2]octan-2-yl)prop-2-en-1-one | 565.3 | $^{1}H$ NMR (400 MHz, $CDCl_3$) δ 9.50-9.42 (m, 1H), 8.80-8.75 (m, 1H), 6.89-8.59 (m, 1H), 8.33-8.27 (m, 1H), 8.20-8.10 (m, 1H), 8.04 (s, 1H), 7.80-7.66 (m, 1H), 7.64-7.60 (m, 1H), 6.80-6.72 (m, 1H), 6.71-6.54 (m, 1H), 6.52-6.36 (m, 1H), 5.83-5.67 (m, 1H), 4.96-4.32 (m, 1H), 3.94 (s, 3H), 3.78-3.61 (m, 3H), 2.81-2.43 (m, 1H), 2.36-2.30 (m, 4H), 2.29-2.05 (m, 1H), 2.03-1.69 (m, 4H). |
| 427 (Ex 189) | 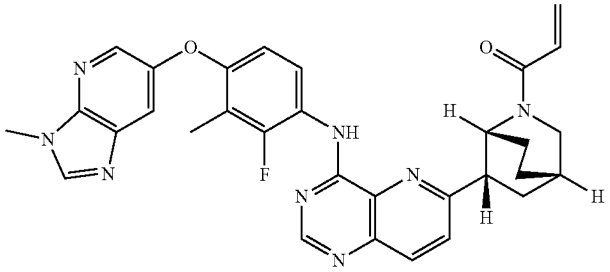 rac-1-((1R,4S,6S)-6-(4-((2-fluoro-3-methyl-4-((3-methyl-3H-imidazo[4,5-b]pyridin-6-yl)oxy)phenyl)amino)pyrido[3,2-d]pyrimidin-6-yl)-2-azabicyclo[2.2.2]octan-2-yl)prop-2-en-1-one | 565.4 | $^{1}H$ NMR (400 MHz, $CDCl_3$) δ 9.71-9.23 (m, 1H), 8.73-8.67 (m, 1H), 8.46-8.17 (m, 2H), 8.11-8.02 (m, 2H), 7.68-7.55 (m, 2H), 6.75-6.68 (m, 1H), 6.55-6.01 (m, 1H), 5.91-5.48 (m, 1H), 5.21-5.09 (m, 1H), 3.94 (s, 4H), 3.84-3.63 (m, 1H), 3.59-3.45 (m, 1H), 2.41-2.32 (m, 3H), 2.31-1.90 (m, 6H), 1.89-1.77 (m, 2H). |

TABLE 3-continued

| Example No. (Method) | Structure; IUPAC name | LCMS $M^{+1}$ | $^1H$ NMR (ppm); $^{19}F$ NMR (ppm); optical rotation; Chiral HPLC/SFC conditions |
|---|---|---|---|
| 428 (Ex 189) | 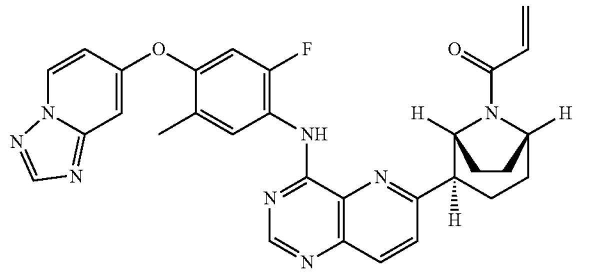 rac-1-((1R,2R,5R)-2-(4-((4-([1,2,4]triazolo[1,5-a]pyridin-7-yloxy)-2-fluoro-5-methylphenyl)amino)pyridio[3,2-d]pyrimidin-6-yl)-8-azabicyclo[3.2.1]octan-8-yl)prop-2-en-1-one | 551.2 | $^1H$ NMR (400 MHz, $CDCl_3$) δ 9.48 (s, 1H), 8.96-8.84 (m, 2H), 8.56-8.48 (m, 1H), 8.24 (s, 1H), 8.22-8.12 (m, 1H), 7.89-7.64 (m, 1H), 7.03-6.94 (m, 1H), 6.93-6.84 (m, 2H), 6.80-6.52 (m, 1H), 6.52-6.42 (m, 1H), 5.82-5.72 (m, 1H), 5.17-4.37 (m, 2H), 3.62-3.27 (m, 1H), 2.52-2.36 (m, 1H), 2.35-2.25 (m, 3H), 2.22-2.02 (m, 4H), 1.98-1.71 (m, 3H). |
| 429 (Ex 189) | 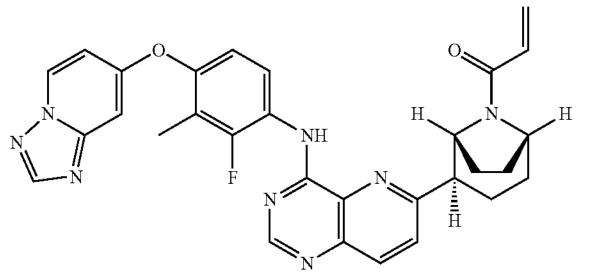 rac-1-((1R,2R,5R)-2-(4-((4-([1,2,4]triazolo[1,5-a]pyridin-7-yloxy)-2-fluoro-3-methylphenyl)amino)pyrido[3,2-d]pyrimidin-6-yl)-8-azabicyclo[3.2.1]octan-8-yl)prop-2-en-1-one | 551.2 | $^1H$ NMR (400 MHz, $CDCl_3$) δ 9.56-9.50 (m, 1H), 8.92-8.83 (m, 1H), 8.55-8.48 (m, 1H), 8.24 (s, 1H), 8.22-8.12 (m, 1H), 7.87-7.62 (m, 1H), 7.07-6.99 (m, 1H), 6.94-6.84 (m, 2H), 6.81-6.56 (m, 1H), 6.53-6.42 (m, 1H), 5.78 (ddd, J = 12.3, 10.3, 2.1 Hz, 1H), 5.18-4.39 (m, 2H), 3.68-3.25 (m, 1H), 2.55-2.25 (m, 1H), 2.25-2.21 (m, 3H), 2.21-2.01 (m, 4H), 1.99-1.73 (m, 3H). |
| 430 (Ex 238) | 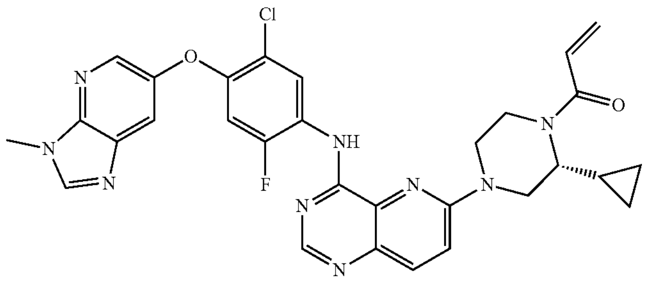 (R)-1-(4-(4-((5-chloro-2-fluoro-4-((3-methyl-3H-imidazo[4,5-b]pyridin-6-yl)oxy)phenyl)amino)pyrido[3,2-d]pyrimidin-6-yl)-2-cyclopropylpiperazin-1-yl)prop-2-en-1-one | 600.3 | $^1H$ NMR (400 MHz, $CDCl_3$) δ 9.17 (d, J = 8.4 Hz, 1H), 8.96 (d, J = 3.3 Hz, 1H), 8.68 (s, 1H), 8.33 (d, J = 2.5 Hz, 1H), 8.07 (s, 1H), 8.00 (d, J = 9.3 Hz, 1H), 7.69 (d, J = 2.5 Hz, 1H), 7.33 (d, J = 9.4 Hz, 1H), 6.83 (d, J = 11.6 Hz, 1H), 6.62-6.56 (m, 1H), 6.35 (dd, J = 16.8, 1.8 Hz, 1H), 5.75 (dd, J = 10.5, 1.9 Hz, 1H), 4.77-3.52 (m, 5H), 3.95 (s, 3H), 3.32 (dd, J = 13.1, 3.7 Hz, 1H), 3.16 (td, J = 12.5, 3.6 Hz, 1H), 1.32-1.27 (m, 1H), 0.61-0.47 (m, 4H) |

TABLE 3-continued

| Example No. (Method) | Structure; IUPAC name | LCMS $M^{+1}$ | $^1H$ NMR (ppm); $^{19}F$ NMR (ppm); optical rotation; Chiral HPLC/SFC conditions |
|---|---|---|---|
| 431 (Ex 238) | 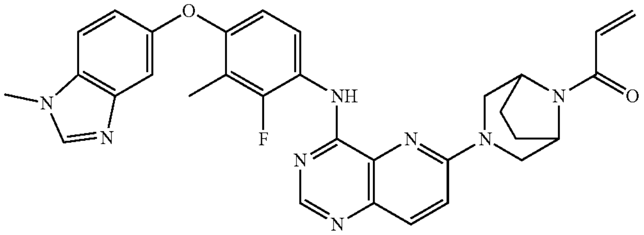 1-(3-(4-((2-fluoro-3-methyl-4-((1-methyl-1H-benzo[d]imidazol-5-yl)oxy)phenyl)amino)pyrido[3,2-d]pyrimidin-6-yl)-3,8-diazabicyclo[3.2.1]octan-8-yl)prop-2-en-1-one | 565.3 | $^1H$ NMR (400 MHz, $CDCl_3$) δ 8.95 (d, J = 3.2 Hz, 1H), 8.59 (s, 1H), 8.54 (t, J = 9.1 Hz, 1H), 7.97 (d, J = 9.3 Hz, 1H), 7.87 (s, 1H), 7.40-7.30 (m, 2H), 7.25-7.17 (m, 1H), 7.06 (dd, J = 8.7, 2.4 Hz, 1H), 6.77 (dd, J = 9.0, 1.7 Hz, 1H), 6.60 (dd, J = 16.8, 10.2 Hz, 1H), 6.45 (dd, 16.8, 2.0 Hz, 1H), 5.79 (dd, J = 10.2, 2.0 Hz, 1H), 5.02 (m, 1H), 4.57 (d, J = 6.3 Hz, 1H), 4.33 (d, J = 12.4 Hz, 1H), 4.08 (d, J = 12.1 Hz, 1H), 3.86 (s, 3H), 3.42 (d, J = 12.0 Hz, 1H), 3.25 (d, J = 12.3 Hz, 1H), 2.29 (d, J = 2.1 Hz, 3H), 2.17-1.84 (m, 4H) |
| 432 (Ex 238) | 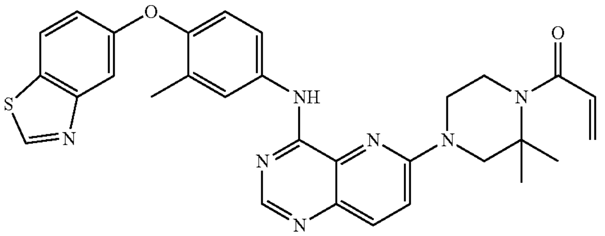 1-(4-(4-((4-(benzo[d]thiazol-5-yloxy)-3-methylphenyl)amino)pyrido[3,2-d]pyrimidin-6-yl)-2,2-dimethylpiperazin-1-yl)prop-2-en-1-one | 552.2 | $^1H$ NMR (400 MHz, $CDCl_3$) δ 8.98 (s, 1H), 8.64 (s, 1H), 8.59 (s, 1H), 7.97 (d, J = 9.3 Hz, 1H), 7.86 (d, J = 8.8 Hz, 1H), 7.79 (d, J = 3.4 Hz, 1H), 7.72 (dd, J = 8.7, 2.8 Hz, 1H), 7.57 (d, J = 2.3 Hz, 1H), 7.19 (dd, J = 8.8, 2.5 Hz, 1H), 7.13 (d, J = 9.3 Hz, 1H), 7.06 (d, J = 8.7 Hz, 1H), 6.57 (dd, J = 16.8, 10.6 Hz, 1H), 6.25 (dd, J = 16.8, 1.8 Hz, 1H), 5.68 (dd, J = 10.6, 1.8 Hz, 1H), 3.99 (t, J = 5.4 Hz, 2H), 3.88 (s, 2H), 3.83 (t, J = 5.4 Hz, 2H), 2.31 (s, 3H), 1.62 (s, 6H) |
| 433 (Ex 238) | 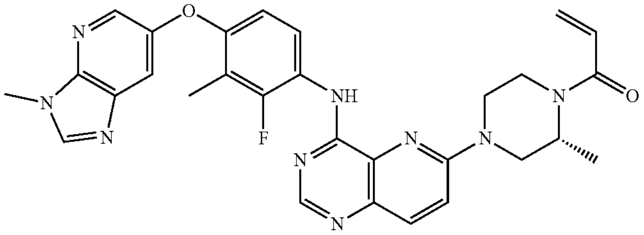 (R)-1-(4-(4-((2-fluoro-3-methyl-4-((3-methyl-3H-imidazo[4,5-b]pyridin-6-yl)oxy)phenyl)amino)pyrido[3,2-d]pyrimidin-6-yl)-2-methylpiperazin-1-yl)prop-2-en-1-one | 554.2 | $^1H$ NMR (400 MHz, $CDCl_3$) δ 8.98 (d, J = 3.3 Hz, 1H), 8.65-8.56 (m, 2H), 8.30 (d, J = 2.5 Hz, 1H), 8.04 (s, 1H), 7.98 (d, J = 9.3 Hz, 1H), 7.61 (d, J = 2.5 Hz, 1H), 7.25 (d, J = 9.8 Hz, 1H), 6.76 (dd, J = 9.0, 1.7 Hz, 1H), 6.64 (dd, J = 16.8, 10.5 Hz, 1H), 6.43-6.34 (m, 1H), 5.77 (dd, J = 10.5, 1.9 Hz, 1H), 4.73-4.13 (m, 4H), 3.93 (s, 3H), 3.70-3.43 (m, 2H), 3.29 (t, J = 11.2, 1H), 2.31 (d, J = 2.1 Hz, 3H), 1.35 (d, J = 6.7 Hz, 3H) |
| 434 (Ex 238) | 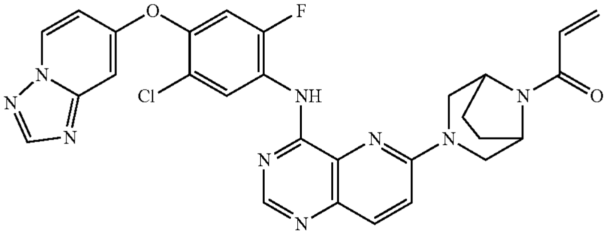 1-(3-(4-((4-([1,2,4]triazolo[1,5-a]pyridin-7-yloxy)-5-chloro-2-fluorophenyl)amino)pyrido[3,2-d]pyrimidin-6-yl)-3,8-diazabicyclo[3.2.1]octan-8-yl)prop-2-en-1-one | 572.2 | $^1H$ NMR (400 MHz, $CDCl_3$) δ 9.28 (d, J = 8.3 Hz, 1H), 9.06 (d, J = 3.5 Hz, 1H), 8.70 (s, 1H), 8.57-8.49 (m, 1H), 8.26 (s, 1H), 8.02 (d, J = 9.4 Hz, 1H), 7.26 (d, J = 9.5 Hz, 1H), 7.12 (d, J = 10.8 Hz, 1H), 6.91 (m, 2H), 6.59 (dd, J = 16.8. 10.2 Hz, 1H), 6.45 (dd, J = 16.8, 2.0 Hz, 1H), 5.79 (dd, J = 10.2, 2.0 Hz, 1H), 5.02 (s, 1H), 4.57 (s, 1H), 4.30 (d, J = 12.3 Hz, 1H), 4.10 (d, J = 12.1 Hz, 1H), 3.43 (d, J = 12.0 Hz, 1H), 3.27 (d, J = 12.3 Hz, 1H), 2.36-1.77 (m, 4H) |

TABLE 3-continued

| Example No. (Method) | Structure; IUPAC name | LCMS $M^{+1}$ | $^{1}H$ NMR (ppm); $^{19}F$ NMR (ppm); optical rotation; Chiral HPLC/SFC conditions |
|---|---|---|---|
| 435 (Ex 238) | 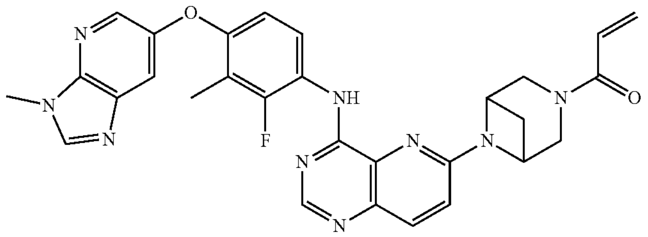 1-(6-(4-((2-fluoro-3-methyl-4-((3-methyl-3H-imidazo[4,5-b]pyridin-6-yl)oxy)phenyl)amino)pyrido[3,2-d]pyrimidin-6-yl)-3,6-diazabicyclo[3.1.1]heptan-3-yl)prop-2-en-1-one | 552.3 | $^{1}H$ NMR (400 MHz, $CDCl_3$) δ 8.96 (d, J = 3.3 Hz, 1H), 8.61 (s, 1H), 8.56 (t, J = 9.1 Hz, 1H), 8.29 (d, J = 2.5 Hz, 1H), 8.04 (s, 1H), 7.96 (d, J = 9.0 Hz, 1H), 7.61 (d, J = 2.5 Hz, 1H), 6.93 (d, J = 9.0 Hz, 1H), 6.74 (dd, J = 9.1, 1.7 Hz, 1H), 6.47 (dd, J = 16.7, 10.3 Hz, 1H), 6.32 (dd, J = 16.7, 2.1 Hz, 1H), 5.67 (dd, J = 10.3, 2.1 Hz, 1H), 4.71-4.65 (m, 2H), 4.43 (d, J = 11.2 Hz, 1H), 4.15 (d, J = 13.9 Hz, 1H), 3.93 (s, 3H), 3.87-3.49 (m, 2H), 2.99-2.89 (m, 1H), 2.30 (d, J = 2.2 Hz, 3H), 1.73 (d, J = 8.8 Hz, 1H) |
| 436 (Ex 238) | 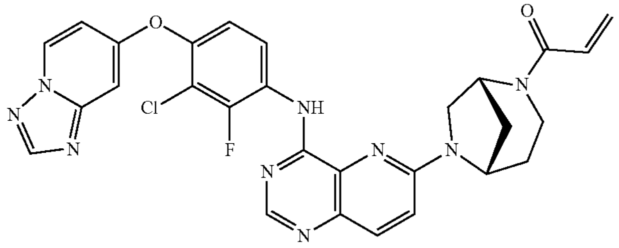 1-((1R,5S)-6-(4-((4-([1,2,4]triazolo[1,5-a]pyridin-7-yloxy)-3-chloro-2-fluorophenyl)amino)pyrido[3,2-d]pyrimidin-6-yl)-2,6-diazabicyclo[3.2.1]octan-2-yl)prop-2-en-1-one | 572.2 | $^{1}H$ NMR (400 MHz, $CDCl_3$) δ 9.18 (s, 1H), 9.00 (t, J = 8.9 Hz, 1H), 8.63 (s, 1H), 8.53 (dd, J = 7.1, 1.0 Hz, 1H), 8.25 (s, 1H), 7.99 (d, J = 9.2 Hz, 1H), 7.15 (dd, J = 9.2, 2.0 Hz, 1H), 7.05 (d, J = 9.2 Hz, 1H), 6.96-6.88 (m, 2H), 6.71-6.52 (m, 1H), 6.32 (d, J = 2.1 Hz, 1H), 5.81-5.69 (m, 1H), 5.08-4.40 (m, 2H), 3.96-3.82 (m, 2H), 3.71-3.49 (m, 1H), 3.30-2.93 (m, 1H), 2.22-2.09 (m, 2H), 2.07-1.81 (m, 2H). |
| 437 (Ex 238) | 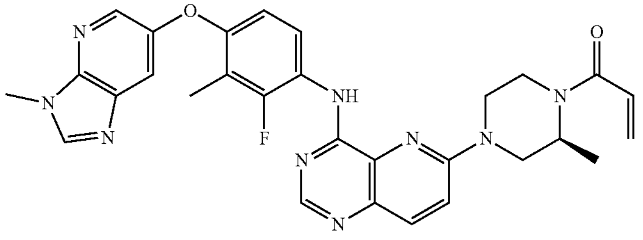 (S)-1-(4-(4-((2-fluoro-3-methyl-4-((3-methyl-3H-imidazo[4,5-b]pyridin-6-yl)oxy)phenyl)amino)pyrido[3,2-d]pyrimidin-6-yl)-2-methylpiperazin-1-yl)prop-2-en-1-one | 554.2 | $^{1}H$ NMR (400 MHz, $CDCl_3$) δ 8.98 (d, J = 3.3 Hz, 1H), 8.65-8.56 (m, 2H), 8.30 (d, J = 2.5 Hz, 1H), 8.04 (s, 1H), 7.98 (d, J = 9.3 Hz, 1H), 7.61 (d, J = 2.5 Hz, 1H), 7.25 (d, J = 9.8 Hz, 1H), 6.76 (dd, J = 9.0, 1.7 Hz, 1H), 6.64 (dd, J = 16.8, 10.5 Hz, 1H), 6.43-6.34 (m, 1H), 5.77 (dd, J = 10.5, 1.9 Hz, 1H), 4.73-4.13 (m, 4H), 3.93 (s, 3H), 3.70-3.43 (m, 2H), 3.29 (t, J = 11.2, 1H), 2.31 (d, J = 2.1 Hz, 3H), 1.35 (d, J = 6.7 Hz, 3H) |

TABLE 3-continued

| Example No. (Method) | Structure; IUPAC name | LCMS $M^{+1}$ | $^1H$ NMR (ppm); $^{19}F$ NMR (ppm); optical rotation; Chiral HPLC/SFC conditions |
|---|---|---|---|
| 438 (Ex 238) | 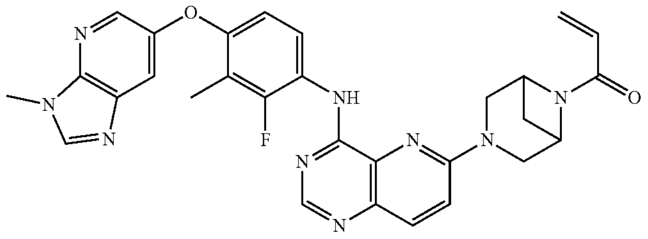 1-(3-(4-((2-fluoro-3-methyl-4-((3-methyl-3H-imidazo[4,5-b]pyridin-6-yl)oxy)phenyl)amino)pyrido[3,2-d]pyrimidin-6-yl)-3,6-diazabicyclo[3.1.1]heptan-6-yl)prop-2-en-1-one | 552.2 | $^1H$ NMR (400 MHz, $CDCl_3$) δ 9.04 (d, J = 3.2 Hz, 1H), 8.66-8.57 (m, 2H), 8.30 (d, J = 2.5 Hz, 1H), 8.09-7.95 (m, 2H), 7.61 (d, J = 2.5 Hz, 1H), 7.14 (d, J = 9.3 Hz, 1H), 6.75 (dd, J = 9.0, 1.7 Hz, 1H), 6.42-6.23 (m, 2H), 5.72 (dd, J = 9.9, 2.1 Hz, 1H), 4.80-4.72 (m, 2H), 4.36 (d, J = 11.2 Hz, 1H), 3.99 (br s, 2H), 3.93 (s, 3H), 3.84-3.66 (m, 1H), 2.98-2.86 (m, 1H), 2.31 (d, J = 2.2 Hz, 3H), 1.77 (d, J = 8.8 Hz, 1H). |
| 439 (Ex 238) | 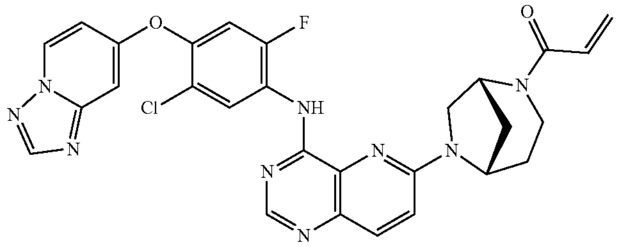 1-((1R,5S)-6-(4-((3-([1,2,4]triazolo[1,5-a]pyridin-6-yloxy)-5-chloro-2-fluorophenyl)amino)pyrido[3,2-d]pyrimidin-6-yl)-2,6-diazabicyclo[3.2.1]octan-2-yl)prop-2-en-1-one | 572.1 | $^1H$ NMR (400 MHz, $CDCl_3$) δ 9.28 (d, J = 8.3 Hz, 1H), 9.15 (d, J = 3.8 Hz, 1H), 8.67 (s, 1H), 8.53 (d, J = 8.3 Hz, 1H), 8.25 (s, 1H), 7.98 (d, J = 9.2 Hz, 1H), 7.08 (dd, J = 21.5, 10.0 Hz, 2H), 6.95-6.87 (m, 2H), 6.74-6.46 (m, 1H), 6.38-6.29 (m, 1H), 5.81-5.69 (m, 1H), 5.11-4.46 (m, 2H), 3.95-3.81 (m, 2H), 3.69-3.63 (m, 1H), 3.34-2.88 (m, 1H), 2.39-2.11 (m, 2H), 2.05-1.83 (m, 2H). |
| 440 (Ex 238) | 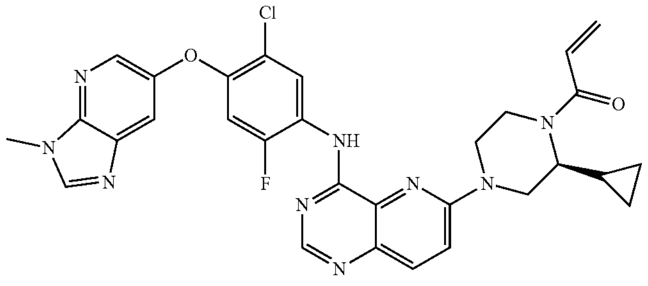 (S)-1-(4-(4-((5-chloro-2-fluoro-4-((3-methyl-3H-imidazo[4,5-b]pyridin-6-yl)oxy)phenyl)amino)pyrido[3,2-d]pyrimidin-6-yl)-2-cyclopropylpiperazin-1-yl)prop-2-en-1-one | 600.2 | $^1H$ NMR (400 MHz, $CDCl_3$) δ 9.17 (d, J = 8.4 Hz, 1H), 8.96 (d, J = 3.3 Hz, 1H), 8.68 (s, 1H), 8.33 (d, J = 2.5 Hz, 1H), 8.07 (s, 1H), 8.00 (d, J = 9.3 Hz, 1H), 7.69 (d, J = 2.5 Hz, 1H), 7.33 (d, J = 9.4 Hz, 1H), 6.83 (d, J = 11.6 Hz, 1H), 6.62-6.56 (m, 1H), 6.35 (dd, J = 16.8, 1.8 Hz, 1H), 5.75 (dd, J = 10.5, 1.9 Hz, 1H), 4.77-3.52 (m, 5H), 3.95 (s, 3H), 3.32 (dd, J = 13.1, 3.7 Hz, 1H), 3.16 (td, J = 12.5, 3.6 Hz, 1H), 1.32-1.27 (m, 1H), 0.61-0.47 (m, 4H) |

TABLE 3-continued

| Example No. (Method) | Structure; IUPAC name | LCMS $M^{+1}$ | $^1H$ NMR (ppm); $^{19}F$ NMR (ppm); optical rotation; Chiral HPLC/SFC conditions |
|---|---|---|---|
| 441 (Ex 238) | 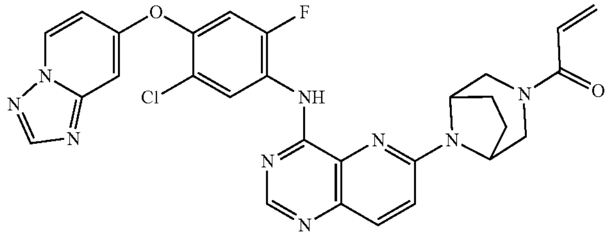 1-(8-(4-((4-([1,2,4]triazolo[1,5-a]pyridin-7-yloxy)-5-chloro-2-fluorophenyl)amino)pyrido[3,2-d]pyrimidin-6-yl)-3,8-diazabicyclo[3.2.1]octan-3-yl)prop-2-en-1-one | 572.1 | $^1H$ NMR (400 MHz, $CDCl_3$) δ 9.27 (d, J = 8.4 Hz, 1H), 9.09 (d, J = 3.5 Hz, 1H), 8.70 (s, 1H), 8.57-8.49 (m, 1H), 8.26 (s, 1H), 8.02 (d, J = 9.2 Hz, 1H), 7.25 (d, J = 9.3 Hz, 1H), 7.12 (d, J = 10.9 Hz, 1H), 6.95-6.88 (m, 2H), 6.55 (dd, J = 16.8, 10.5 Hz, 1H), 6.33 (dd, J = 16.8, 1.9 Hz, 1H), 5.74 (dd, J = 10.5, 1.8 Hz, 1H), 4.83 (s, 1H), 4.72 (s, 1H), 4.54 (d, J = 13.3 Hz, 1H), 3.81 (d, J = 12.4 Hz, 1H), 3.66 (d, J = 12.2 Hz, 1H), 3.13 (d, J = 13.3 Hz, 1H), 2.18-2.12 (m, 2H), 2.06-1.84 (m, 2H) |
| 442 (Ex 238) | 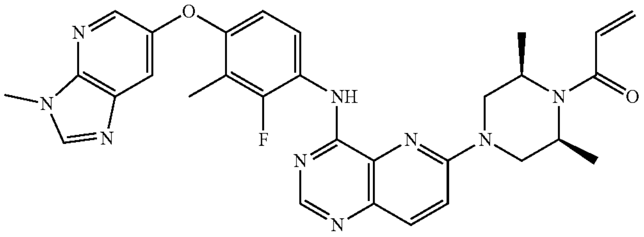 1-((2S,6R)-4-(4-((2-fluoro-3-methyl-4-((3-methyl-3H-imidazo[4,5-b]pyridin-6-yl)oxy)phenyl)amino)pyrido[3,2-d]pyrimidin-6-yl)-2,6-dimethylpiperazin-1-yl)prop-2-en-1-one | 568.2 | $^1H$ NMR (400 MHz, $CDCl_3$) δ 9.01 (d, J = 3.4 Hz, 1H), 8.68-8.57 (m, 2H), 8.30 (d, J = 2.5 Hz, 1H), 8.03 (s, 1H), 7.98 (d, J = 9.3 Hz, 1H), 7.60 (d, J = 2.5 Hz, 1H), 7.29 (d, 9.4 Hz, 1H), 6.80-6.72 (m, 1H), 6.65 (dd, J = 16.7, 10.5 Hz, 1H), 6.40 (dd, J = 16.7, 2.0 Hz, 1H), 5.76 (dd, J = 10.5, 1.9 Hz, 1H), 4.85-4.27 (m, 4H), 3.93 (s, 3H), 3.35 (dd, J = 13.5, 4.5 Hz, 2H), 2.31 (d, J = 2.2 Hz, 3H), 1.41 (d, J = 6.9 Hz, 6H) |
| 443 (Ex 238) | 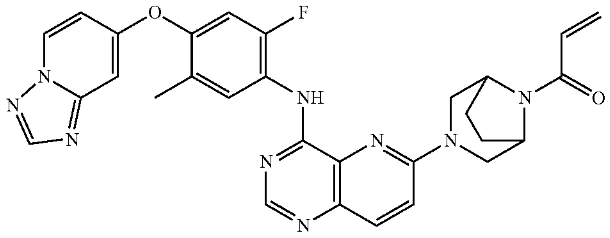 1-(3-(4-((4-([1,2,4]triazolo[1,5-a]pyridin-7-yloxy)-2-fluoro-5-methylphenyl)amino)pyrido[3,2-d]pyrimidin-6-yl)-3,8-diazaspiro[3.2.1]octan-8-yl)prop-2-en-1-one | 552.2 | $^1H$ NMR (400 MHz, $CDCl_3$) δ 9.00 (d, J = 3.2 Hz, 1H), 8.88 (dd, J = 9.1, 0.8 Hz, 1H), 8.67 (s, 1H), 8.55-8.48 (m, 1H), 8.24 (s, 1H), 8.00 (d, J = 9.3 Hz, 1H), 7.24 (d, J = 9.4 Hz, 1H), 6.96 (d, J = 11.0 Hz, 1H), 6.92-6.85 (m, 2H), 6.59 (dd, J = 16.8, 10.2 Hz, 1H), 6.45 (dd, J = 16.8, 1.9 Hz, 1H), 5.79 (dd, J = 10.2, 2.0 Hz, 1H), 5.02 (s, 1H), 4.57 (s, 1H), 4.31 (d, J = 12.3 Hz, 1H), 4.08 (d, J = 12.1 Hz, 1H), 3.43 (d, J = 11.8 Hz, 1H), 3.26 (d, J = 12.3 Hz, 1H), 2.27 (s, 3H), 2.17-1.85 (m, 4H) |

TABLE 3-continued

| Example No. (Method) | Structure; IUPAC name | LCMS $M^{+1}$ | $^1H$ NMR (ppm); $^{19}F$ NMR (ppm); optical rotation; Chiral HPLC/SFC conditions |
|---|---|---|---|
| 444 (Ex 238) | 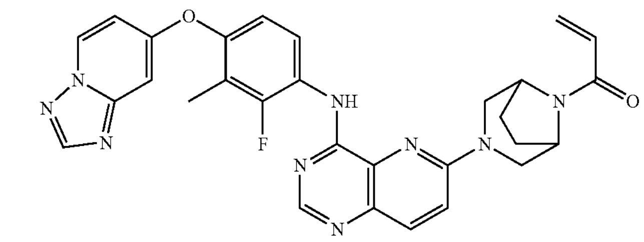 1-(3-(4-((4-([1,2,4]triazolo[1,5-a]pyridin-7-yloxy)-2-fluoro-3-methylphenyl)amino)pyrido[3,2-d]pyrimidin-6-yl)-3,8-diazabicyclo[3.2.1]octan-8-yl)prop-2-en-1-one | | $^1H$ NMR (400 MHz, $CDCl_3$) δ 9.07 (d, J = 3.6 Hz, 1H), 8.83 (t, J = 9.0 Hz, 1H), 8.65 (s, 1H), 8.52 (d, J = 0.9 Hz, 1H), 8.24 (s, 1H), 8.00 (d, J = 9.3 Hz, 1H), 7.24 (d, J = 9.4 Hz, 1H), 7.00 (dd, J = 9.0, 1.8 Hz, 1H), 6.93-6.85 (m, 2H), 6.60 (dd, J = 16.8, 10.2 Hz, 1H), 6.46 (dd, J = 16.8, 2.0 Hz, 1H), 5.79 (dd, J = 10.2, 2.0 Hz, 1H), 5.03 (s, 1H), 4.58 (s, 1H), 4.32 (d, J = 12.3 Hz, 1H), 4.11 (d, J = 12.1 Hz, 1H), 3.44 (d, J = 12.0 Hz, 1H), 3.27 (d, J = 12.2 Hz, 1H), 2.21 (d, J = 2.1 Hz, 3H), 2.17-1.81 (m, 4H) |
| 445 (Ex 238) | 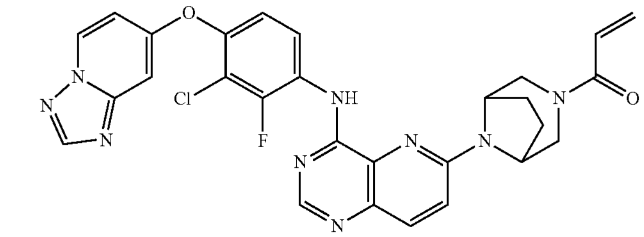 1-(8-(4-((4-([1,2,4]triazolo[1,5-a]pyridin-7-yloxy)-3-chloro-2-fluorophenyl)amino)pyrido[3,2-d]pyrimidin-6-yl)-3,8-diazabicyclo[3.2.1]octan-3-yl)prop-2-en-1-one | 572.2 | $^1H$ NMR (400 MHz, $CDCl_3$) δ 9.13 (d, J = 3.4 Hz, 1H), 8.99 (t, J = 8.9 Hz, 1H), 8.66 (s, 1H), 8.54 (dd, J = 7.1, 1.1 Hz, 1H), 8.25 (s, 1H), 8.02 (d, J = 9.2 Hz, 1H), 7.24 (d, J = 12 Hz, 1H), 7.16 (dd, J = 9.1, 2.0 Hz, 1H), 6.96-6.88 (m, 2H), 6.56 (dd, J = 16.8, 10.5 Hz, 1H), 6.34 (dd, J = 16.8, 1.9 Hz, 1H), 5.74 (dd, J = 10.5, 1.8 Hz, 1H), 4.87 (s, 1H), 4.71 (s, 1H), 4.55 (d, J = 13.3 Hz, 1H), 3.83 (d, J = 12.5 Hz, 1H), 3.68 (d, J = 12.5 Hz, 1H), 3.12 (d, J = 13.3 Hz, 1H), 2.19-2.13 (m, 2H), 2.07-1.84 (m, 2H) |
| 446 (Ex 238) | 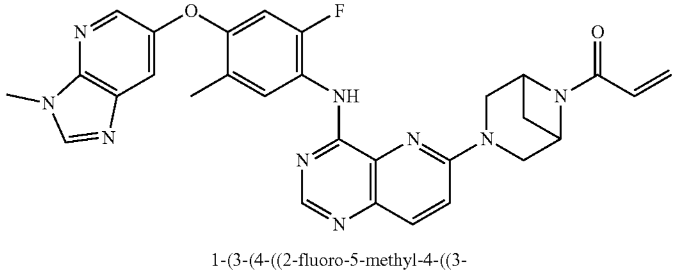 1-(3-(4-((2-fluoro-5-methyl-4-((3-methyl-3H-imidazo[4,5-b]pyridin-6-yl)oxy)phenyl)amino)pyrido[3,2-d]pyrimidin-6-yl)-3,6-diazabicyclo[3.1.1]heptan-6-yl)prop-2-en-1-one | 552.3 | $^1H$ NMR (400 MHz, $CDCl_3$) δ 8.92 (d, J = 2.9 Hz, 1H), 8.73 (d, J = 8.9 Hz, 1H), 8.64 (s, 1H), 8.29 (d, J = 2.5 Hz, 1H), 8.04 (s, 1H), 8.00 (d, J = 9.3 Hz, 1H), 7.62 (d, J = 2.5 Hz, 1H), 7.13 (d, J = 9.3 Hz, 1H), 6.69 (d, J = 11.8 Hz, 1H), 6.36 (dd, J = 16.9, 2.1 Hz, 1H), 6.26 (dd, J = 16.9, 9.9 Hz, 1H), 5.71 (dd, J = 10.0, 2.0 Hz, 1H), 4.74 (t, J = 7.0 Hz, 2H), 4.34 (d, J = 11.2 Hz, 1H), 3.97 (s, 2H), 3.94 (s, 3H), 3.85-3.74 (m, 1H), 2.93-2.84 (m, 1H), 2.37 (d, J = 1.0 Hz, 3H), 1.75 (d, J = 8.8 Hz, 1H). |

TABLE 3-continued

| Example No. (Method) | Structure; IUPAC name | LCMS $M^{+1}$ | $^1H$ NMR (ppm); $^{19}F$ NMR (ppm); optical rotation; Chiral HPLC/SFC conditions |
|---|---|---|---|
| 447 (Ex 238) | 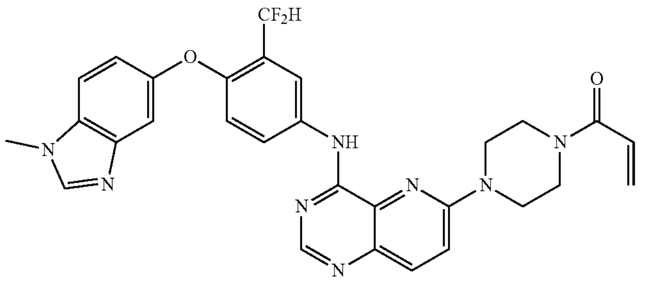 1-(4-(4-((3-(difluoromethyl)-4-((1-methyl-1H-benzo[d]imidazol-5-yl)oxy)phenyl)amino)pyrido[3,2-d]pyrimidin-6-yl)piperazin-1-yl)prop-2-en-1-one | 557.2 | $^1H$ NMR (400 MHz, $CDCl_3$) δ 8.65 (s, 1H), 8.58 (s, 1H), 8.06 (dd, J = 9.0, 2.7 Hz, 1H), 8.03-7.93 (m, 2H), 7.89 (s, 1H), 7.46 (d, J = 2.3 Hz, 1H), 7.37 (d, J = 8.8 Hz, 1H), 7.29-7.25 (m, 1H), 7.14-7.03 (m, 2H), 6.91 (dd, J = 8.9, 1.3 Hz, 1H), 6.65 (dd, J = 16.8, 10.5 Hz, 1H), 6.38 (dd, J = 16.8, 1.8 Hz, 1H), 5.79 (dd, J = 10.5, 1.9 Hz, 1H), 3.90-3.83 (m, 11H) |
| 448 (Ex 242) | 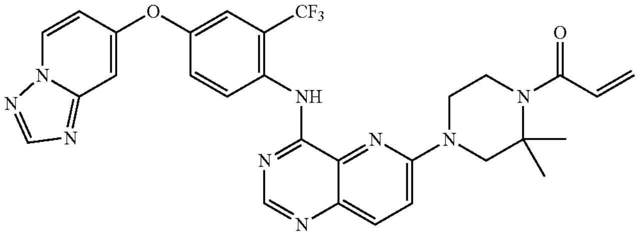 1-(4-(4-((4-([1,2,4]triazolo[1,5-a]pyridin-7-yloxy)-2-(trifluoromethyl)phenyl)amino)pyrido [3,2-d]pyrimidin-6-yl)-2,2-dimethylpiperazin-1-yl)prop-2-en-1-one | 590.2 | 1H NMR (400 MHz, CDCl3 ) δ 9.61-9.56 (m, 1H), 9.19 (d, J = 8.9 Hz, 1H), 8.64 (s, 1H), 8.54 (dd, J = 7.4, 0.7 Hz, 1H), 8.26 (s, 1H), 8.02 (d, J = 9.3 Hz, 1H), 7.50-7.41 (m, 2H), 7.16 (d, J = 9.3 Hz, 1H), 7.03 (dd, J = 2.6, 0.7 Hz, 1H), 6.90 (dd, J = 7.5, 2.6 Hz, 1H), 6.58 (dd, J = 16.8, 10.6 Hz, 1H), 6.26 (dd, J = 16.8, 1.8 Hz, 1H), 5.70 (dd, J = 10.5, 1.8 Hz, 1H), 4.05-3.96 (m, 4H), 3.81 (t, J = 5.4 Hz, 2H), 1.61 (s, 6H). |
| 449 (Ex 242) | 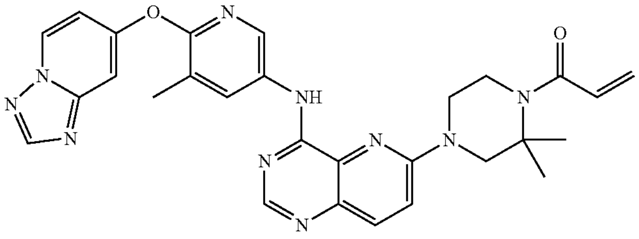 1-(4-(4-((6-([1,2,4]triazolo[1,5-a]pyridin-7-yloxy)-5-methylpyridin-3-yl)amino)pyrido[3,2-d]pyrimidin-6-yl)-2,2-dimethylpiperazin-1-yl)prop-2-en-1-one | 537.3 | 1H NMR (400 MHz, CDCL3) δ 8.69 (s, 1H), 8.62 (s, 1H), 8.56 (dd, J = 7.4, 0.7 Hz, 1H), 8.44 (dd, J = 2.7, 0.9 Hz, 1H), 8.38 (dd, J = 2.7, 0.7 Hz, 1H), 8.29 (s, 1H), 8.11 (d, J = 9.4 Hz, 1H), 7.40 (dd, J = 2.5, 0.7 Hz, 1H), 7.19 (d, J = 9.4 Hz, 1H), 6.95 (dd, J = 7.5, 2.5 Hz, 1H), 6.56 (dd, J = 16.8, 10.6 Hz, 1H), 6.25 (dd, J = 16.8, 1.8 Hz, 1H), 5.69 (dd, J = 10.5, 1.8 Hz, 1H), 4.00 (dd, J = 6.5, 4.8 Hz, 2H), 3.90-3.81 (m, 4H), 2.44 (d, J = 0.8 Hz, 3H), 1.61 (s, 6H). |
| 450 (Ex 244) | 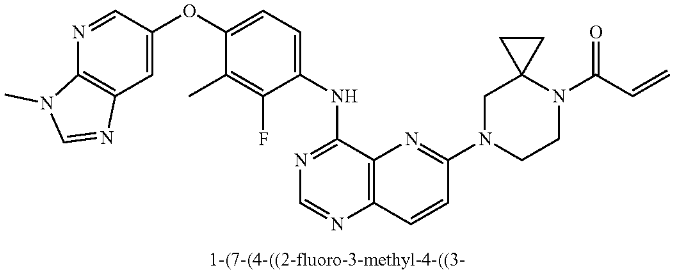 1-(7-(4-((2-fluoro-3-methyl-4-((3-methyl-3H-imidazo[4,5-b]pyridin-6-yl)oxy)phenyl)amino)pyrido[3,2-d]pyrimidin-6-yl)-4,7-diazaspiro[2.5]octan-4-yl)prop-2-en-1-one | 566.2 | 1H NMR (400 MHz, MeOD) δ 8.60 (d, J = 10.6 Hz, 2H), 8.37 (d, J = 2.4 Hz, 1H), 7.98 (d, J = 9.5 Hz, 1H), 7.76-7.64 (m, 4H), 6.79 (dd, J = 8.9, 1.6 Hz, 1H), 6.30 (dd, J = 16.9, 1.9 Hz, 1H), 5.81 (dd, J = 10.5, 1.9 Hz, 1H), 4.02-3.97 (m, 5H), 3.89 (s, 2H), 3.33-3.27 (m, 2H), 2.33 (d, J = 2.1 Hz, 3H), 1.31-1.11 (m, 4H). |

TABLE 3-continued

| Example No. (Method) | Structure; IUPAC name | LCMS $M^{+1}$ | $^1$H NMR (ppm); $^{19}$F NMR (ppm); optical rotation; Chiral HPLC/SFC conditions |
|---|---|---|---|
| 451 (Ex 242) | 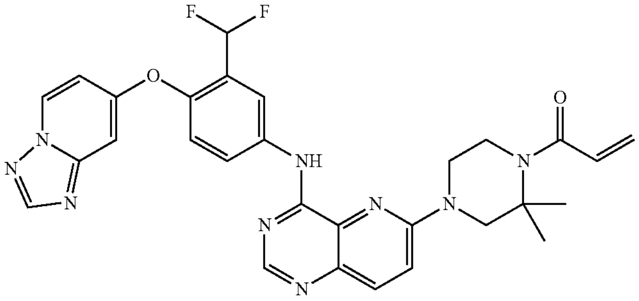 1-(4-(4-((4-([1,2,4]triazolo[1,5-a]pyridin-7-yloxy)-3-(difluoromethyl)phenyl)amino)pyrido[3,2-d]pyrimidin-6-yl)-2,2-dimethylpiperazin-1-yl)prop-2-en-1-one | 572.2 | 1H NMR (400 MHz, CDCl3) δ 8.81 (s, 1H), 8.63 (s, 1H), 8.54 (d, J = 7.4 Hz, 1H), 8.29 (dd, J = 8.9, 2.7 Hz, 1H), 8.26 (s, 1H), 8.13 (d, J = 2.7 Hz, 1H), 8.01 (d, J = 9.3 Hz, 1H), 7.19 (dd, J = 9.1, 7.8 Hz, 2H), 7.03 (d, J = 2.8 Hz, 1H), 6.94-6.88 (m, 1H), 6.89 (s, 1H), 6.59 (dd, J = 16.8, 10.6 Hz, 1H), 6.26 (dd, J = 16.8, 1.8 Hz, 1H), 5.70 (dd, J = 10.5, 1.8 Hz, 1H), 4.05-3.98 (m, 2H), 3.91-3.84 (m, 2H), 3.49 (s, 1H), 1.63 (s, 6H). |
| 452 (Ex 241) | 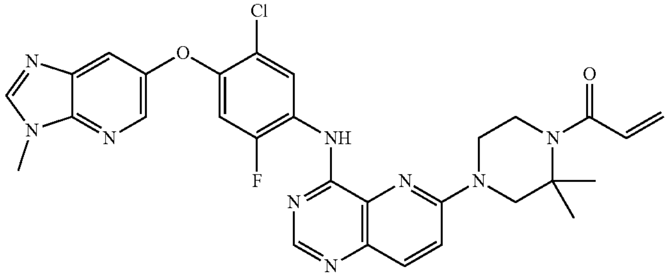 1-(4-(4-((5-chloro-2-fluoro-4-((3-methyl-3H-imidazo[4,5-b]pyridin-6-yl)oxy)phenyl)amino)pyrido[3,2-d]pyrimidin-6-yl)-2,2-dimethylpiperazin-1-yl)prop-2-en-1-one | 588.3 | 1H NMR (400 MHz, CDCl3) δ 9.16 (d, J = 8.4 Hz, 1H), 8.97 (d, J = 3.3 Hz, 1H), 8.66 (s, 1H), 8.33 (d, J = 2.5 Hz, 1H), 8.06 (s, 1H), 8.00 (d, J = 9.3 Hz, 1H), 7.68 (d, J = 2.5 Hz, 1H), 7.15 (d, J = 9.3 Hz, 1H), 6.82 (d, J = 11.5 Hz, 1H), 6.56 (dd, J = 16.8, 10.6 Hz, 1H), 6.24 (dd, J = 16.8, 1.8 Hz, 1H), 5.68 (dd, J = 10.6, 1.8 Hz, 1H), 3.98 (t, J = 5.7 Hz, 2H), 3.94 (s, 3H), 3.89 (s, 2H), 3.81 (t, J = 5.7 Hz, 2H), 1.59 (s, 6H). |
| 453 (Ex 242) | 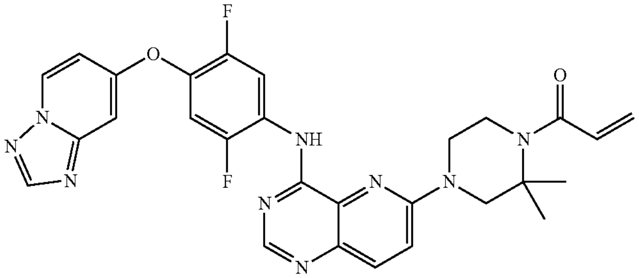 1-(4-(4-((4-([1,2,4]triazolo[1,5-a]pyridin-7-yloxy)-2,5-difluorophenyl)amino)pyrido[3,2-d]pyrimidin-6-yl)-2,2-dimethylpiperazin-1-yl)prop-2-en-1-one | 558.3 | 1H NMR (400 MHz, CDCl3) δ 9.16 (d, J = 3.6 Hz, 1H), 9.09 (dd, J = 12.5, 7.7 Hz, 1H), 8.68 (s, 1H), 8.53 (dd, J = 7.5, 0.7 Hz, 1H), 8.26 (s, 1H), 8.03 (d, J = 9.3 Hz, 1H), 7.18 (d, J = 9.3 Hz, 1H), 7.11 (dd, J = 10.8, 6.9 Hz, 1H), 7.02-6.97 (m, 1H), 6.92 (dd, J = 7.5, 2.6 Hz, 1H), 6.57 (dd, J = 16.8, 10.5 Hz, 1H), 6.26 (dd, J = 16.8, 1.8 Hz, 1H), 5.69 (dd, J = 10.5, 1.8 Hz, 1H), 5.30 (s, 12H), 4.00 (t, J = 5.7 Hz, 2H), 3.92 (s, 2H), 3.84 (t, J = 5.7 Hz, 2H), 1.62 (s, 6H). |

TABLE 3-continued

| Example No. (Method) | Structure; IUPAC name | LCMS $M^{+1}$ | $^1$H NMR (ppm); $^{19}$F NMR (ppm); optical rotation; Chiral HPLC/SFC conditions |
|---|---|---|---|
| 454 (Ex 242) | 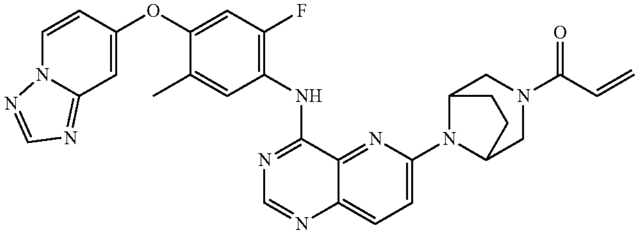 1-(8-(4-((4-([1,2,4]triazolo[1,5-a]pyridin-7-yloxy)-2-fluoro-5-methylphenyl)amino)pyrido[3,2-d]pyrimidin-6-yl)-3,8 diazabicyclo[3.2.1]octan-3-yl)prop-2-en-1-one | 552.2 | 1H NMR (400 MHz, CDCl3) δ 9.04 (d, J = 3.3 Hz, 1H), 8.87 (d, J = 9.0 Hz, 1H), 8.67 (s, 1H), 8.55-8.48 (m, 1H), 8.24 (s, 1H), 8.00 (d, J = 9.2 Hz, 1H), 7.23 (d, J = 9.3 Hz, 1H), 6.96 (d, J = 11.1 Hz, 1H), 6.92-6.85 (m, 2H), 6.55 (dd, J = 16.8, 10.5 Hz, 1H), 6.33 (dd, J = 16.8, 1.9 Hz, 1H), 5.73 (dd, J = 10.5, 1.9 Hz, 1H), 4.84 (s, 1H), 4.71 (s, 1H), 4.53 (d, J = 13.4 Hz, 1H), 3.80 (d, J = 12.5 Hz, 1H), 3.67 (d, J = 12.6 Hz, 1H), 3.13 (d, J = 13.3 Hz, 1H), 2.27 (s, 3H), 2.21-2.07 (m, 2H), 2.03-1.92 (m, 1H), 1.92-1.85 (m, 1H). |
| 455 (Ex 242) | 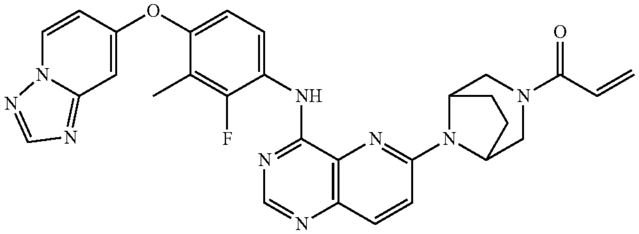 1-(8-(4-((4-([1,2,4]triazolo[1,5-a]pyridin-7-yloxy)-2-fluoro-3-methylphenyl)amino)pyrido[3,2-d]pyrimidin-6-yl)-3,8-diazabicyclo[3.2.1]octan-3-yl)prop-2-en-1-one | 552.2 | 1H NMR (400 MHz, CDCl3) δ 9.10 (d, J = 3.6 Hz, 1H), 8.82 (t, J = 9.0 Hz, 1H), 8.65 (s, 1H), 8.51 (dd, J = 7.3, 0.9 Hz, 1H), 8.24 (s, 1H), 8.00 (d, J = 9.2 Hz, 1H), 7.23 (d, J = 9.2 Hz, 1H), 7.01 (dd, J = 9.0, 1.8 Hz, 1H), 6.93-6.85 (m, 2H), 6.56 (dd, J = 16.8, 10.5 Hz, 1H), 6.33 (dd, J = 16.8, 1.8 Hz, 1H), 5.74 (dd, J = 10.5, 1.9 Hz, 1H), 4.85 (s, 1H), 4.73 (s, 1H), 4.55 (d, J = 13.3 Hz, 1H), 3.86-3.78 (m, 1H), 3.68 (d, J = 12.5 Hz, 1H), 3.15 (d, J = 13.2 Hz, 1H), 2.23-2.13 (m, 5H), 2.07-1.94 (m, 1H), 1.93-1.84 (m, 1H). |
| 456 (Ex 241) | 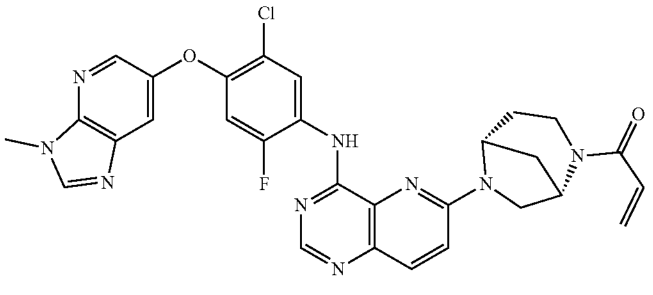 1-((1S,5R)-6-(4-((5-chloro-2-fluoro-4-((3-methyl-3H-imidazo[4,5-b]pyridin-6-yl)oxy)phenyl)amino)pyrido[3,2-d]pyrimidin-6-yl)-2,6-diazabicyclo[3.2.1]octan-2-yl)prop-2-en-1-one | 586.2 | 1H NMR (400 MHz, CDCl3) δ 9.16 (d, J = 8.4 Hz, 1H), 9.01 (d, J = 3.7 Hz, 1H), 8.65 (s, 1H), 8.32 (d, J = 2.5 Hz, 1H), 8.06 (s, 1H), 7.96 (d, J = 9.2 Hz, 1H), 7.68 (d, J = 2.6 Hz, 1H), 7.02 (d, J = 9.3 Hz, 1H), 6.81 (d, J = 11.5 Hz, 1H), 6.53 (dd, J = 16.8, 10.5 Hz, 1H), 6.32 (dd, J = 16.9, 2.3 Hz, 1H), 5.79-5.68 (m, 1H), 4.77-4.73 (m, 1H), 3.94 (s, 3H), 3.93-3.84 (m, 2H), 3.72-3.63 (m, 1H), 3.34-3.22 (m, 1H), 2.32-2.10 (m, 1H), 2.02-1.90 (m, 1H), 1.90-1.79 (m, 1H). |

Biochemical Assays

Construction of His8x-Tb-ErbB2(676-775)YVMA$_{insert}$ (776-1255) Expressing Vector and Protein Expression A DNA fragment optimized for insect cell expression that encodes a recombinant protein having the amino sequence shown in SEQ ID NO: 1 was synthesized with a 5'-flanking NcoI restriction enzyme site and two stop codons followed by a NotI restriction enzyme site at the 3'-end. In the sequence shown below, the ErbB2(676-775)YVMA$_{insert}$ (776-1255) amino sequence is underlined. The YVMA (SEQ ID NO: 2) insertion is marked with double underline.

SEQ ID NO: 1: Amino Sequence of Recombinant His8x-Tb-ErbB2(676-775)YVMA$_{insert}$(776-1255) Protein

```
                                          (SEQ ID NO: 1)
1    MAHHHHHHHH GGGGGLVPRG KRRQQKIRKY TMRRLLQETE LVEPLTPSGA MPNQAQMRIL

61   KETELRKVKV LGSGAFGTVY KGIWIPDGEN VKIPVAIKVL RENTSPKANK EILDEAYVMA

121  YVMAGVGSPY VSRLLGICLT STVQLVTQLM PYGCLLDHVR ENRGRLGSQD LLNWCMQIAK

181  GMSYLEDVRL VHRDLAARNV LVKSPNHVKI TDFGLARLLD IDETEYHADG GKVPIKWMAL

241  ESILRRRFTH QSDVWSYGVT VWELMTFGAK PYDGIPAREI PDLLEKGERL PQPPICTIDV

301  YMIMVKCWMI DSECRPRFRE LVSEFSRMAR DPQRFVVIQN EDLGPASPLD STFYRSLLED

361  DDMGDLVDAE EYLVPQQGFF CPDPAPGAGG MVHHRHRSSS TRSGGGDLTL GLEPSEEEAP

421  RSPLAPSEGA GSDVFDGDLG MGAAKGLQSL PTHDPSPLQR YSEDPTVPLP SETDGYVAPL

481  TCSPQPEYVN QPDVRPQPPS PREGPLPAAR PAGATLERAK TLSPGKNGVV KDVFAFGGAV

541  ENPEYLTPQG GAAPQPHPPP AFSPAFDNLY YWDQDPPERG APPSTFKGTP TAENPEYLGL

601  DVPV
```

This synthesized DNA fragment was subsequently cloned into the baculovirus transfer vector, pAcSG2, between the NcoI and NotI sites. The resulting plasmid was used along with BestBac™ linearized Baculovirus DNA from Expression Systems (Davis, CA, USA) to transfect Sf9 cells for generating recombinant Baculovirus that expresses the His8x-Tb-ErbB2(676-775)YVMA$_{insert}$(776-1255) (referred to as HER2-YVMA (SEQ ID NO: 2)) protein. High-titer Baculovirus stock was obtained by amplifying the virus twice from the initial transfection. For HER2-YVMA (SEQ ID NO: 2) protein expression, 10 L of Sf9 cell culture grown in a Wave cellbag (Cytiva, Marlborough, MA, USA), were infected with the recombinant virus stock at multiplicity of infection ("MOI") equal to 2.5 for 68 hours. At the end of the infection period, cells were harvested by centrifugation.

HER2-YVMA (SEQ ID NO: 2) Protein Purification

Insect cells expressing HER2-YVMA (SEQ ID NO: 2) were disrupted with a fluidizer in cold lysis buffer consisting of 50 mM Tris-HCl, pH8.0, 500 mM NaCl, 5 mM Imidazole, 10% glycerol, 1 mM TCEP [Tris-2-carboxyethyl)phosphine], 0.25% CHAPS {3-[(3-Cholamidopropyl)dimethylammonio]-1-propanesulfonate}, and protease inhibitor cocktail (Complete EDTA-free, Roche Applied Science). Cellular debris were removed from the homogenate by centrifugation at 4° C. HER2-YVMA (SEQ ID NO: 2) protein was enriched from the lysate using Talon metal affinity resin (TaKaRa Bio USA, Mountain View, CA, USA) and eluted from the metal resin in a buffer similar with the lysis buffer except an increased imidazole concentration to 200 mM and the omission of protease inhibitors. HER2-YVMA (SEQ ID NO: 2) pool collected from Talon affinity resin was passed through a Superdex-200 size-exclusion column (Cytiva Life Sciences, Marlborough, MA, USA) in 25 mM Tris-CI, pH8.5 buffer with 500 mM NaCl, 10% glycerol, 1 mM TCEP, and 0.25% CHAPS. Monomeric HER2-YVMA (SEQ ID NO: 2) protein eluted from the size-exclusion column was further fractionated by a Resource Q anionic exchange column (Cytiva Life Sciences, Marlborough, MA, USA) with a linear salt gradient from 50 to 250 mM NaCl in a buffer containing 25 mM Tris-HCl, pH8.5, 10% glycerol, 1 mM TCEP, and 0.25% CHAPS. HER2-YVMA (SEQ ID NO: 2) fractions with the highest kinase activity were combined and designated as the source for HER2-YVMA (SEQ ID NO: 2) in vitro assays and studies.

ErbB Enzyme Assay

Compound potencies were determined using CisBio's HTRF Kinease-TK assay technology. The kinases were incubated with 250 nM TK-substrate biotin (CisBio, part of cat #62TKOPEC) at 1 mM ATP along with test compounds in a buffer consisting of 25 mM HEPES, pH 7.4, 10 mM MgCl2, 0.01% Triton X-100, and 2% DMSO in a volume of 8 μL. Compounds were prepared as a three-fold serial dilution in DMSO and added to the assay to give the appropriate final concentration. After 30-minute incubation at 22° C., the reaction was quenched by adding 8 μL of quench solution containing 62.5 nM Sa-XL665 and 0.25× TK-Ab-Cryptate in HTRF detection buffer (all from CisBio, part of cat #62TKOPEC). After a 1-hour incubation at 22° C., the extent of reaction was determined using a PerkinElmer EnVision multimode plate reader via HTRF dual wavelength detection, and the percent of control (POC) was calculated using a ratiometric emission factor. One hundred POC was determined using DMSO only samples (no compound present), and 0 POC was determined using prequenched control reactions. A 4-parameter logistic curve was fit to the POC values as a function of the concentration of compound, and the $IC_{50}$ value was the point where the best-fit curve crossed 50 POC.

Enzyme lots and concentration used are in Table 4.

TABLE 4

| Assay # | Enzyme Form | Vendor | Lot Number | Enzyme Concentration in assay (nM) |
|---|---|---|---|---|
| Assay 1 | ErbB2 insYVMA (SEQ ID NO: 2) | Pfizer | 190510B-P2 | 0.075 |
| Assay 2 | ErbB2 WT | ProQinase | 015 | 2.5 |
| Assay 3 | EGFR | ProQinase | 018 | 0.25 |

Cellular Phosphorylation Assay

Inhibition of constitutive ErbB2 and EGF-stimulated EGFR phosphorylation was determined by the following in vitro cellular mechanistic assay using the compounds that exhibited a level activity in an enzyme assay.

NIH 3T3 cells were engineered to express ErbB2 with Exon 20 YVMA insertion (HER2-YVMA (SEQ ID NO: 2); Assay 4) or EGFR wild type (EGFR WT; Assay 5) with constructs obtained from GenScript and grown in DMEM supplemented with 10% fetal bovine serum and 15 μg/ml blasticidin. Cells were plated in 96-well plates at 40,000 or 45,000 cells/well for HER2-YVMA (SEQ ID NO: 2) and EGFR WT assays, respectively, and allowed to attach overnight at 37° C./5% $CO_2$. Serially diluted compounds were added to the plates for 1 hour at 37° C./5% $CO_2$. EGFR WT cells were stimulated with 100 ng/ml rEGF for an additional 10 minutes at 37° C./5% $CO_2$.

After compound incubation, medium was removed from the cells, which were then fixed in 3.7% formaldehyde in PBS at room temperature for 20 minutes. Following a wash with PBS, cells were permeabilized with 100% methanol at room temperature for 10 minutes. Cells were then washed with PBS/0.05% Tween-20 and blocked with Odyssey blocking buffer (LI-COR Biosciences) for at least 1 hour at room temperature. Antibodies to phosphorylated ErbB2 (Y1196, Cell Signaling #6942) or phosphorylated EGFR (Y1068, Cell Signaling #3777) and GAPDH (Millipore #MAB374) were added to the cells in blocking buffer containing 0.05% azide and incubated overnight at 4° C. After washing with PBS/0.05% Tween-20, the cells were incubated with fluorescently labeled secondary anti-rabbit antibody (LiCOR, IRDye 800CW #926-32211) and anti-mouse antibody (Molecular Probes, Alexa Fluor 680 #A21058) for 1 hour at room temperature in the dark. Cells were then washed and analyzed for fluorescence at both wavelengths using the Odyssey Infrared Imaging System (LI-COR Biosciences). Phosphorylated ErbB2 and EGFR signal was normalized to GAPDH signal to generate curves and calculate $IC_{50}$ values.

MDR1 LLC-PK1 (Assay 6) and BCRP MDCKII (Assay 7) Cell Culture and Experimental Conditions Both LLC-PK1 and MDR1 transfected LLC-PK1 cells were cultured and plated according to manufacturer's recommendations with the exception that the passage media contained only 2% fetal bovine serum so as to extend passage time out to seven days.

BCRP transfected MDCKII cells were cultured and plated according to manufacturer's recommendations. Assay conditions included with and without the BCRP-specific inhibitor, KO143, at a concentration of 0.3 μM to ascertain the contribution of BCRP to the efflux value of the test compound.

Both positive and negative controls were used to assess functionality of P-gp or BCRP efflux in the assays. Stock solutions for assay controls and the test article were prepared in DMSO for final test concentrations of 10 μM and 1 μM, respectively. Final organic concentration in the assay was 1%. All dosing solutions contained 10 μM lucifer yellow to monitor LLC PK1 or MDCKII cell monolayer integrity.

For the apical to basolateral determination (A to B), 75 μL of the test article in transport buffer were added to the apical side of the individual transwells and 250 μL of basolateral media, without compound or lucifer yellow, were added to each well. For the basolateral to apical determination (B to A), 250 μL of test article in transport buffer were added to each well and 75 μL transport buffer, without compound or lucifer yellow, were added to each transwell. All tests were performed in triplicate, and each compound was tested for both apical to basolateral and basolateral to apical transport. The plates were incubated for 2 hours on a Lab-Line Instruments Titer Orbital Shaker (VWR, West Chester, PA) at 50 rpm and 37° C. with 5% $CO_2$. All culture plates were removed from the incubator, 50 μL of media were removed from the apical and basolateral portion of each well, and added to 150 μL of 1 μM labetalol in 2:1 acetonitrile (ACN):$H_2O$, v/v.

The plates were read using a Molecular Devices (Sunnyvale, CA) Gemini Fluorometer to evaluate the lucifer yellow concentrations at excitation/emission wavelengths of 425/535 nm. These values were accepted when found to be below 2% for apical to basolateral and 5% basolateral to apical flux across the MDR1-transfected LLC-PK1 or BCRP-transfected MDCKII cell monolayers. The plates were sealed, and the contents of each well analyzed by LC MS/MS. The compound concentrations were determined from the ratio of the peak areas of the compound to the internal standard (labetalol) in comparison to the dosing solution.

The LC-MS/MS system was comprised of an HTS-PAL autosampler (Leap Technologies, Carrboro, NC), an HP1200 HPLC (Agilent, Palo Alto, CA), and a MDS Sciex 4000 Q Trap system (Applied Biosystems, Foster City, CA). Chromatographic separation of the analyte and internal standard was achieved at room temperature using a C18 column (Kinetics®, 50×300 mm, 2.6 μm particle size, Phenomenex, Torrance, CA) in conjunction with gradient conditions using mobile phases A (water containing 1% isopropyl alcohol and 0.1% formic acid) and B (0.1% formic acid in ACN). The total run time, including re-equilibration, for a single injection was 1.2 minutes. Mass spectrometric detection of the analytes was accomplished using the ion spray positive mode. Analyte responses were measured by multiple reaction monitoring (MRM) of transitions unique to each compound (the protonated precursor ion and selected product ions for each test article and m/z 329 to m/z 162 for labetalol, the internal standard).

The permeability coefficient ($P_{app}$) is calculated from the following equation:

$$P_{app}=[((C_d*V*(1\times10^6))/(t*0.12\ \mathrm{cm}^2*C_0)]$$

where $C_d$, V, t and $C_0$ are the detected concentration (μM), the volume on the dosing side (mL), the incubation time(s) and the initial dosing concentration (μM), respectively. The calculations for $P_{app}$ were made for each replicate and then averaged.

An efflux ratio is calculated from the mean apical to basolateral (A-B) Papp data and basolateral to apical (B-A) Papp data:

$$\text{Efflux ratio}=P_{app}(B-A)/P_{app}(A-B)$$

Biological activity data for representative compounds of the invention are provided in Table 5 below.

TABLE 5

| Example No. | Assay 1 $IC_{50}$ (nM) | Assay 2 $IC_{50}$ (nM) | Assay 3 $IC_{50}$ (nM) | Assay 4 $IC_{50}$ (nM) | Assay 5 $IC_{50}$ (nM) | Assay 6 Pe Ratio | Assay 7 Pe Ratio |
|---|---|---|---|---|---|---|---|
| 1 | 24 | 33.6 | 4427.3 | 12.5 | 1007.4 | 11.4 | 7.3 |
| 2 | 243 | 1293.1 | 10000 | 1136.6 | 5000 | | |
| 3 | 67.8 | 259.7 | 10000 | 60.6 | 5000 | 2 | 1.5 |
| 4 | 226 | 876.1 | 10000 | 392.3 | 5000 | | |
| 5 | 257 | 2335.2 | 10000 | 406.6 | 5000 | | |
| 6 | 176.2 | 3297.7 | 10000 | 54.2 | 2918.3 | 1.3 | 2.5 |
| 7 | 760.5 | 2088.4 | 10000 | | | | |
| 8 | 56.3 | 76.5 | 1348.5 | 47.3 | 799 | 3.1 | |
| 9 | 93 | 977.1 | 10000 | 66 | 840.2 | 1.7 | 2.4 |
| 10 | 931.8 | 2397.9 | 10000 | | | | |
| 11 | 257 | 2335.2 | 10000 | 406.6 | 5000 | | |
| 12 | 234.9 | 1031.5 | 10000 | 193.5 | 5000 | | |
| 13 | 10.5 | 8.4 | 219.9 | 4 | 104.4 | 1.2 | 1.4 |

TABLE 5-continued

| Example No. | Assay 1 $IC_{50}$ (nM) | Assay 2 $IC_{50}$ (nM) | Assay 3 $IC_{50}$ (nM) | Assay 4 $IC_{50}$ (nM) | Assay 5 $IC_{50}$ (nM) | Assay 6 Pe Ratio | Assay 7 Pe Ratio |
|---|---|---|---|---|---|---|---|
| 14 | 94 | 431.6 | 10000 | 48.4 | 5000 | 5.8 | |
| 15 | 34.6 | 45.5 | 1683.3 | 12.8 | 555 | 10.2 | |
| 16 | 1845.9 | 10000 | 10000 | | | | |
| 17 | 28.9 | 48.3 | 2109.7 | 14 | 1216.2 | 2.7 | |
| 18 | 30.3 | 42.3 | 369.4 | 443.2 | | | |
| 19 | 21.2 | 17.8 | 205 | 87.8 | | | |
| 20 | 54 | 47.9 | 340.4 | 1738.8 | | | |
| 21 | 52.3 | 83.2 | 466 | 250.3 | | | |
| 22 | 43.1 | 167 | 10000 | 80.6 | | | |
| 23 | 41.5 | 72.7 | 708.9 | 63.9 | | | |
| 24 | 137 | 193.8 | 10000 | 70.6 | 5000 | | |
| 25 | 15.2 | 50.1 | 558.2 | 12.1 | 323.9 | 2.2 | 6.8 |
| 26 | 120.9 | 121 | 10000 | 20.4 | 5000 | | 8.3 |
| 27 | 179.6 | 486.5 | 10000 | 380.9 | 5000 | | |
| 28 | 36 | 275.4 | 10000 | 26.4 | 5000 | 2 | 5.2 |
| 29 | 12.1 | 36.5 | 311.3 | 5.8 | 118.2 | | |
| 30 | 5.8 | 6 | 199.8 | 2.3 | 87.6 | 1.5 | 5 |
| 31 | 26.6 | 14.3 | 6536.9 | 22.7 | 928.5 | 1.3 | 1.8 |
| 32 | 70.5 | 45.8 | 5534.2 | 130.6 | 5000 | 1.9 | |
| 33 | 20.2 | 15.8 | 1153.4 | 3.8 | 869.1 | | 42.7 |
| 34 | 27.8 | 28.7 | 6865.6 | 9.5 | 5000 | | 6.7 |
| 35 | 11.5 | 6.2 | 1397.1 | 10.4 | 2728.4 | | 2.7 |
| 36 | 24.5 | 104.7 | 10000 | 18.9 | 1701.5 | 0.8 | 4.2 |
| 37 | 30.7 | 119.2 | 10000 | 20.3 | 5000 | 1.5 | 1.8 |
| 38 | 12.2 | 8.5 | 152.9 | 22.6 | 381.7 | | |
| 39 | 5.4 | 5.5 | 49.3 | 5.3 | 46.8 | 2.3 | 2.6 |
| 40 | 16.2 | 11.3 | 300 | 7.8 | 111.1 | | |
| 41 | 181.6 | 130 | 5073 | 31 | 5000 | | 16.7 |
| 42 | 22.4 | 14.7 | 777.9 | 17 | 5000 | 2.5 | 2.9 |
| 43 | 187.7 | 120.1 | 10000 | 21.3 | 5000 | 3 | 4.1 |
| 44 | 190.9 | 81.5 | 10000 | 55.7 | 5000 | | |
| 45 | 158.8 | 222 | 8300.2 | 17.1 | 2762.1 | 2.5 | 5.6 |
| 46 | 62.4 | 118.8 | 1267.2 | 18.2 | 2098.8 | 2.5 | 2.5 |
| 47 | 45.9 | 60.9 | 3718.6 | 13.7 | 2128.9 | | 9.6 |
| 48 | 50.8 | 264 | 10000 | 16.6 | 5000 | | 10.2 |
| 49 | 16 | 18.6 | 1174.3 | 10.5 | 2807 | 1.5 | 3 |
| 50 | 37.2 | 34.5 | 10000 | 16.7 | 3216.5 | 1.3 | 4.5 |
| 51 | 176.2 | 3297.7 | 10000 | 54.2 | 2918.3 | 1.3 | 2.5 |
| 52 | 127.1 | 395.4 | 10000 | 34.7 | 5000 | 34.5 | |
| 53 | 47.6 | 99.1 | 1448.4 | 41.1 | 1244.7 | | |
| 54 | 68.5 | 423.4 | 1380.7 | 40 | 1468.3 | | |
| 55 | 368.6 | 2043.4 | 10000 | 50.8 | 929.8 | | |
| 56 | 80.2 | 233.4 | 1444.1 | 19.7 | 374.3 | 25.9 | |
| 57 | 28.9 | 48.3 | 2109.7 | 14 | 1216.2 | | |
| 58 | 87.9 | 475.9 | 10000 | 76.1 | 2232.2 | 2.6 | |
| 59 | 4.5 | 25.4 | 533.9 | 19 | 5000 | | 10.8 |
| 60 | 30.1 | 54.3 | 10000 | 49.4 | 1214.3 | | |
| 61 | 16.1 | 16.3 | 283 | 34.4 | 976.2 | | |
| 62 | 29 | 15.3 | 333.4 | 28.1 | 638.9 | | |
| 63 | 15.1 | 31.4 | 507.6 | 19.5 | 426.2 | | 3.8 |
| 64 | 57.2 | 37.4 | 10000 | 32.9 | 5000 | 2.4 | 4.2 |
| 65 | 9.6 | 17.4 | 170.4 | 4.2 | 145.8 | 1.4 | 4 |
| 66 | 21.7 | 6.8 | 84.5 | 6.1 | 152.9 | | |
| 67 | 46 | 421.9 | 10000 | 35.8 | 5000 | | |
| 68 | 33.9 | 664.1 | 10000 | 73.8 | 5000 | | |
| 69 | 31.5 | 141 | 10000 | 19.9 | 5000 | 3 | 2.4 |
| 70 | 16.2 | 10 | 2954.9 | 21.6 | 5000 | | 41.8 |
| 71 | 53.7 | 86.5 | 10000 | 80.5 | 5000 | | |
| 72 | 5.6 | 8.7 | 880.1 | 4.7 | 511.2 | | 15.4 |
| 73 | 27.1 | 36.4 | 5078.9 | 28.9 | 2419.5 | 1.1 | 4.3 |
| 74 | 6.9 | 9.2 | 1714.5 | 5.7 | 297.7 | | 6.4 |
| 75 | 19.6 | 65.2 | 10000 | 13.7 | 5000 | | 3.8 |
| 76 | 47.3 | 33.4 | 10000 | 17.1 | 5000 | | |
| 77 | 19.3 | 9 | 2553.8 | 9.3 | 873.9 | | 11.6 |
| 78 | 210.7 | 447.7 | 10000 | 145.2 | 5000 | | |
| 79 | 108.6 | 103.8 | 10000 | 42.6 | 5000 | | |
| 80 | 12.9 | 17 | 218.3 | 4.1 | 245.5 | | 12.4 |
| 81 | 22.5 | 33.2 | 9431.2 | 9.5 | 5000 | | 17.4 |
| 82 | 17.1 | 58.2 | 7324.1 | 12.6 | 4395.2 | 2 | 3.9 |
| 83 | 31.9 | 81.5 | 5582.3 | 9.6 | 5000 | | 6.3 |
| 84 | 30.5 | 41 | 221.3 | 7.7 | 253.8 | 1.9 | 3.8 |
| 85 | 19.4 | 3.1 | 204.8 | 25 | 445.7 | | |
| 86 | 7.3 | 2.3 | 30 | 5.7 | 45.4 | | |
| 87 | 13.5 | 7.5 | 462.7 | 8.8 | 178.4 | | |
| 88 | 21.3 | 81.3 | 2948 | 17.8 | 1854.7 | 1.6 | 5.2 |
| 89 | 34.8 | 76.5 | 3633.5 | 10.9 | 449.4 | 1.4 | 5.9 |
| 90 | 5.4 | 13.4 | 519.1 | 5.9 | 575.3 | 1.5 | 9.8 |
| 91 | 5.7 | 9.8 | 358 | 2.8 | 56.8 | | |
| 92 | 28.8 | 126 | 2429.5 | 15.4 | 1881.5 | 2.1 | 5.5 |
| 93 | 8.4 | 12.6 | 137 | 3.7 | 53.5 | | |
| 94 | 24.8 | 169.6 | 10000 | 30.6 | 5000 | | 6.8 |
| 95 | 12.9 | 38 | 377.5 | 5 | 49.5 | | |
| 96 | 14 | 16.7 | 835.1 | 6.8 | 538.5 | 1.8 | 6.1 |
| 97 | 3.1 | 3.2 | 343.7 | 3.2 | 413.2 | | 47 |
| 98 | 74.3 | 51.1 | 3363.7 | 18.9 | 2682.5 | | 11 |
| 99 | 31.2 | 19 | 5842 | 35.2 | 5000 | | |
| 100 | 26.5 | 132.2 | 9571.9 | 66.1 | 5000 | | |
| 101 | 25.5 | 39.2 | 1381.4 | 32 | 5000 | 1.9 | 2.5 |
| 102 | 39.8 | 460.6 | 10000 | 15.4 | 5000 | 2.8 | 5.7 |
| 103 | 8.7 | 2.9 | 10000 | 4.6 | 1320.9 | | 10.9 |
| 104 | 51.6 | 88.3 | 10000 | 12.1 | 5000 | | 24.7 |
| 105 | 8.7 | 11.9 | 680 | 5 | 1351.1 | | 31.6 |
| 106 | 23.3 | 18.5 | 7791.1 | 6 | 5000 | | 10.1 |
| 107 | 18.5 | 237.4 | 10000 | 17.8 | 5000 | 1.6 | 2.7 |
| 108 | 14.8 | 29.4 | 10000 | 7.4 | 5000 | | 30.1 |
| 109 | 45.8 | 281.7 | 10000 | 13.4 | 5000 | 2 | 2 |
| 110 | 27.9 | 58 | 6164.1 | 5 | 2532.5 | | 84.4 |
| 111 | 18.4 | 38 | 10000 | 13.1 | 5000 | | 35.4 |
| 112 | 29 | 57.5 | 3333.3 | 19.8 | 5000 | 1.4 | 5.2 |
| 113 | 10.7 | 184.1 | 10000 | 30.2 | 5000 | | 37.5 |
| 114 | 32.7 | 254.9 | 10000 | 29.9 | 5000 | | 23.5 |
| 115 | 30.6 | 55.4 | 10000 | 82.8 | 5000 | | |
| 116 | 33.7 | 52.3 | 2578.2 | 10.2 | 1582.6 | | 22.4 |
| 117 | 11.7 | 36.2 | 10000 | 9.3 | 5000 | | 29 |
| 118 | 20.7 | 54.1 | 6087.8 | 10.1 | 5000 | 2.2 | 4.1 |
| 119 | 31 | 60.4 | 10000 | 9.4 | 5000 | | 6.8 |
| 120 | 29.2 | 42 | 7267.9 | 8.4 | 5000 | | 15.8 |
| 121 | 34 | 30.8 | 5565.2 | 9.1 | 4582.3 | 1.9 | 4 |
| 122 | 5.5 | 9.3 | 3879 | 13 | 5000 | 2.7 | 6.4 |
| 123 | 14.7 | 60.4 | 10000 | 7.6 | 5000 | | 7.3 |
| 124 | 25 | 29.9 | 3903.4 | 11.4 | 1940.5 | 1.6 | 5.2 |
| 125 | 22.4 | 48.2 | 7484.6 | 40 | 5000 | | |
| 126 | 24.2 | 12.3 | 1264.3 | 12.2 | 1769.1 | 1.4 | 3.8 |
| 127 | 58.7 | 271.2 | 10000 | 32.7 | 5000 | 1.2 | 1.6 |
| 128 | 40.5 | 44.4 | 10000 | 27.7 | 2621.5 | 0.6 | 2.7 |
| 129 | 25.1 | 65.9 | 7931.7 | 16.6 | 5000 | 1.4 | 1.4 |
| 130 | 29.1 | 134.9 | 7336.7 | 19.9 | 5000 | 1.9 | 2 |
| 131 | 18.3 | 55.9 | 2162.6 | 9.6 | 4763.7 | | 6.4 |
| 132 | 17.6 | 75.9 | 10000 | 18.8 | 5000 | | 7.9 |
| 133 | 24.4 | 41.5 | 3171.9 | 34 | 3775.9 | 3.2 | 1.8 |
| 134 | 62.1 | 86.3 | 10000 | 221.7 | 5000 | | |
| 135 | 32.1 | 121.4 | 10000 | 44.5 | 5000 | | |
| 136 | 20.8 | 39.9 | 10000 | 28.6 | 5000 | 1.7 | 1.7 |
| 137 | 22.8 | 27.9 | 2633.4 | 16.8 | 4370.3 | | 1.9 |
| 138 | 18.3 | 22.1 | 4166.9 | 25.1 | 5000 | 6.8 | 1.8 |
| 139 | 54.8 | 10000 | 10000 | 32.5 | 5000 | | |
| 140 | 42.2 | 225.1 | 10000 | 31.1 | 5000 | 1.2 | 1.9 |
| 141 | 30.1 | 179.6 | 10000 | 17.6 | 5000 | | 2.4 |
| 142 | 36.3 | 49.9 | 10000 | 79.5 | 5000 | | |
| 143 | 22.2 | 32.7 | 1847.7 | 20.9 | 2944.1 | 1.7 | 3 |
| 144 | 29.9 | 25 | 649.8 | 11.7 | 1065.1 | 1.2 | 0.6 |
| 145 | 9.5 | 5.9 | 409.5 | 15.3 | 581.8 | 6.4 | 1.4 |
| 146 | 35.3 | 15.8 | 2583.2 | 36.7 | 5000 | | 4.3 |
| 147 | 22.3 | 18.6 | 782 | 23 | 2593.6 | 2.9 | 2.3 |
| 148 | 0.9 | 0.6 | 16.1 | 4.4 | 69 | | |
| 149 | 147.2 | 323.2 | 6695.1 | 192.2 | 5000 | | |
| 150 | 43.4 | 16.6 | 1546.1 | 47 | 5000 | | |
| 151 | 14.9 | 41.6 | 125.5 | 28.1 | 548.2 | | |
| 152 | 36.8 | 37.3 | 1042.6 | 20.9 | 612.9 | | 17.5 |
| 153 | 4.1 | 4 | 264.8 | 38.3 | 1794.5 | | |
| 154 | 14.2 | 18 | 447.3 | 67.8 | 3070.9 | | |
| 155 | 9749 | 9720.4 | 10000 | 3954.4 | 5000 | | |
| 156 | 26.2 | 20.3 | 110.2 | 19.6 | 215.1 | | |
| 157 | 32.2 | 209.4 | 2271.4 | 21.3 | 1735.6 | | 6.8 |
| 158 | 9.7 | 39.1 | 320.6 | 16.5 | 366.1 | | |
| 159 | 13.9 | 20.4 | 452.2 | 12 | 493.3 | | 15 |
| 160 | 323.8 | 514.6 | 10000 | 165.4 | 5000 | | |
| 161 | 21.4 | 19.9 | 569.8 | | 368.3 | | |
| 162 | 89.6 | 341.6 | 10000 | 25.7 | 5000 | 0.8 | 2.3 |
| 163 | 31.8 | 42.3 | 8789.1 | 18.8 | 1513.9 | 0.9 | 2.1 |

TABLE 5-continued

| Example No. | Assay 1 $IC_{50}$ (nM) | Assay 2 $IC_{50}$ (nM) | Assay 3 $IC_{50}$ (nM) | Assay 4 $IC_{50}$ (nM) | Assay 5 $IC_{50}$ (nM) | Assay 6 Pe Ratio | Assay 7 Pe Ratio |
|---|---|---|---|---|---|---|---|
| 164 | 51.6 | 45.8 | 10000 | 14.7 | 664.9 | 1.1 | 2.5 |
| 165 | 21.7 | 177.3 | 10000 | 15.8 | 5000 | 0.9 | 1.6 |
| 166 | 56 | 64.2 | 10000 | 64.6 | 5000 | | |
| 167 | 77.5 | 519.3 | 10000 | 25.1 | 5000 | 0.9 | 1.7 |
| 168 | 36.5 | 74.3 | 1794.8 | 16.5 | 355.8 | | |
| 169 | 50.8 | 111.4 | 1811.3 | 23.6 | 5000 | 1 | 2.1 |
| 170 | 33.1 | 261.3 | 10000 | 44.9 | 5000 | | |
| 171 | 9.7 | 13.4 | 10000 | 26.3 | 5000 | 2.1 | 5.3 |
| 172 | 6.6 | 5.2 | 719.8 | 13.9 | 1958 | | 4.7 |
| 173 | 42.5 | 104.7 | 10000 | 21 | 2307.4 | 0.7 | 3 |
| 174 | 22.3 | 23.8 | 736 | 7.9 | 270.2 | | |
| 175 | 91.6 | 171.6 | 5348.7 | 22.2 | 2406.2 | 3.3 | 4.8 |
| 176 | 39.2 | 48.5 | 6691.6 | 24.4 | 3617.2 | 1 | 2.4 |
| 177 | 8.3 | 9.7 | 128.9 | 5.7 | 156.4 | 1.9 | 3.6 |
| 178 | 7.8 | 8 | 442.8 | 27.7 | 437.3 | | |
| 179 | 36.8 | 74 | 7631.5 | 103.1 | 5000 | | |
| 180 | 183.2 | 313.7 | 10000 | 73.4 | 5000 | | |
| 181 | 7 | 11.7 | 552.7 | 35.3 | 879.1 | | |
| 182 | 12.6 | 27.3 | 6139.8 | 76.1 | 2725.7 | | |
| 183 | 7 | 6.2 | 73.3 | 4.4 | 79.3 | | |
| 184 | 39.5 | 88.1 | 10000 | 242.9 | 5000 | | |
| 185 | 77.4 | 128 | 10000 | 315 | 5000 | | |
| 186 | 48.2 | 69.1 | | 407.8 | 5000 | | |
| 187 | 56.9 | 100.4 | 10000 | 272.7 | 5000 | | |
| 188 | 1222.2 | 1449.6 | 10000 | 2015.2 | 5000 | | |
| 189 | 14.6 | 11.1 | 1278.4 | 41.2 | 1791.1 | 1.1 | 1.1 |
| 190 | 26.2 | 41.1 | 3796.5 | 16 | 5000 | 3.9 | |
| 191 | 18.9 | 26.7 | 1815.1 | 15 | 2904.5 | 0.9 | 2.5 |
| 192 | 31.2 | 131.9 | 10000 | 22.1 | 5000 | | 2.1 |
| 193 | 25.6 | 61.8 | 10000 | 16 | 5000 | 0.7 | 3.4 |
| 194 | 18.5 | 170.8 | 5800.5 | 33.9 | 2776 | 1.2 | 4.9 |
| 195 | 36.6 | 59.7 | 2546.6 | 17.9 | 1060 | | 1.7 |
| 196 | 28.8 | 42.9 | 1159.5 | 33.8 | 2012.8 | | 2.5 |
| 197 | 4.6 | 21.1 | 650.2 | 35.2 | 853 | 1.2 | 2.5 |
| 198 | 23.3 | 24.2 | 342.5 | 17 | 808.8 | 1.7 | 2.7 |
| 199 | 18.8 | 17.4 | 483.4 | 22.3 | 941.7 | 0.6 | 3.2 |
| 200 | 13.7 | 16.2 | 2784.3 | 83.5 | 5000 | | |
| 201 | 57 | 68.1 | 9453.6 | 213.2 | 5000 | | |
| 202 | 18.1 | 15.5 | 549.7 | 20.6 | 4218.7 | 1.2 | 2.8 |
| 203 | 10.2 | 13.3 | 401.3 | 16.7 | 1451.7 | 1.1 | 0.6 |
| 204 | 12.6 | 13.2 | 899.9 | 20.8 | 2935.5 | 1.5 | 2 |
| 205 | 27.2 | 58.7 | 2420.2 | 24 | 2564.7 | 1.2 | 4.5 |
| 206 | 81.1 | 151.2 | 4770.6 | 114.6 | 5000 | | |
| 207 | 108.6 | 149.9 | 10000 | 685.3 | 5000 | | |
| 208 | 102.7 | 171.9 | 10000 | 327.9 | 5000 | | |
| 209 | 19.6 | 16.4 | 871.8 | 20.1 | 503.2 | | |
| 210 | 16.2 | 10.7 | 1613.9 | 67.7 | 5000 | | |
| 211 | 54.7 | 65.4 | 5399.5 | 316.5 | 5000 | | |
| 212 | 62.3 | 66.2 | 3379.1 | 386.2 | 5000 | | |
| 213 | 9 | 7.3 | 263.7 | 23.9 | 5000 | 1.5 | 3.4 |
| 214 | 8.8 | 21.6 | 278.7 | 25 | 5000 | 1.4 | 3.8 |
| 215 | 12.2 | 29.5 | 3313.9 | 29.5 | 5000 | 1.4 | 5.5 |
| 216 | 38.3 | 43.3 | 5000.2 | 23.3 | 5000 | 1.3 | 2.4 |
| 217 | 19.7 | 18.8 | 1462.8 | 11.1 | 1851 | 0.8 | 1.9 |
| 218 | 23.9 | 24.4 | 1419.8 | 32.7 | 5000 | 1.4 | 2.6 |
| 219 | 41.6 | 111.2 | 3662.2 | 20.1 | 5000 | | 9.3 |
| 220 | 39 | 17.9 | 411.9 | 18.5 | 5000 | 1.3 | 2.2 |
| 221 | 20.1 | 28.5 | 2692.2 | 78 | 5000 | 1.2 | 2.1 |
| 222 | 59.6 | 133.3 | 5828.6 | 308.9 | 5000 | 1.3 | 1.4 |
| 223 | 38.1 | 48.9 | 1959.2 | 145.2 | 5000 | 1.3 | 1.2 |
| 224 | 71.4 | 58 | 2286.9 | 91.3 | 5000 | | |
| 225 | 42.1 | 26.5 | 421.9 | 8.4 | 768 | 1.2 | 2 |
| 226 | 63.7 | 310.3 | 10000 | 37.5 | 5000 | | |
| 227 | 25.4 | 138.5 | 3790.6 | 26.8 | 5000 | 1.2 | 5.5 |
| 228 | 52 | 130.1 | 4554.1 | 33.6 | 5000 | 0.8 | 3.3 |
| 229 | 23.1 | 16.7 | 380.4 | 29.9 | 5000 | 0.7 | 3 |
| 230 | 18.8 | 13.6 | 311.7 | 21.4 | 996.3 | 0.8 | 2.7 |
| 231 | 11.9 | 10 | 70.5 | 8.7 | 147.6 | | |
| 232 | 19.2 | 10.5 | 203.4 | 31.9 | 5000 | 0.8 | 2.6 |
| 233 | 67 | 121.5 | 4877 | 83.8 | 5000 | | |
| 234 | 40.1 | 37.3 | 959.6 | 33 | 875.1 | | |
| 235 | 50.6 | 31 | 1024 | 92.1 | 5000 | | |
| 236 | 65.7 | 1170.1 | 10000 | 24.6 | 5000 | | 6.8 |
| 237 | 108.8 | 1332.1 | 10000 | 256.4 | 5000 | | |
| 238 | 16.9 | 11.7 | 114.4 | 5.5 | 90.3 | | |
| 239 | 15.3 | 36.7 | 954.7 | 24.3 | 2250.6 | 1.8 | 5.2 |
| 240 | 62.7 | 142.6 | 4895.4 | 92.4 | 2020.3 | | |
| 241 | 57.5 | 354.2 | 10000 | 22.2 | 5000 | 1.5 | |
| 242 | 190.9 | 184 | 4428.6 | 95.6 | 3457.5 | | |
| 243 | 136 | 338.1 | 1205.1 | 50.2 | 665.5 | | |
| 244 | 43.7 | 46.4 | 177.7 | 16.7 | 317.5 | | |
| 245 | 36.4 | 83.1 | 10000 | 177 | 5000 | 1.2 | 4.2 |
| 246 | 32.9 | 34.8 | 1801.4 | 16.2 | 1302 | 0.5 | 1.3 |
| 247 | 23.8 | 71.5 | 10000 | 8.9 | 5000 | 0.8 | 1.9 |
| 248 | 18.6 | 108.4 | 10000 | 14.4 | 5000 | | 15.2 |
| 249 | 11.9 | 11.8 | 1333.1 | 8.7 | 2046.4 | 1.4 | 5.9 |
| 250 | 19.3 | 27.9 | 4121.2 | 9 | 3197 | 1.6 | 11.1 |
| 251 | 166.1 | 493.9 | 10000 | 27.3 | 5000 | 1.5 | 4.8 |
| 252 | 109.8 | 170.5 | 4583 | 21.1 | 5000 | 1 | 2.9 |
| 253 | 69.7 | 162 | 10000 | 31 | 5000 | | |
| 254 | 57.2 | 92.6 | 5339.3 | 23.2 | 5000 | 1.3 | 2.4 |
| 255 | 74.7 | 795.3 | 10000 | 171.7 | 5000 | | |
| 256 | 45.6 | 57.2 | 10000 | 66.9 | 5000 | | |
| 257 | 36.1 | 54.2 | 10000 | 115 | 5000 | | |
| 258 | 10000 | 10000 | 10000 | 99.9 | 5000 | | |
| 259 | 37.9 | 20.4 | 10000 | 78.5 | 3430.1 | | |
| 260 | 47.9 | 41.5 | 4505.8 | 113.6 | 5000 | | |
| 261 | 19.6 | 13.4 | 10000 | 27.9 | 716.5 | 1.3 | 3.6 |
| 262 | 13.3 | 18.9 | 10000 | 32.4 | 5000 | 1.7 | 4.6 |
| 263 | 65.4 | 148 | 10000 | 204.3 | 5000 | | |
| 264 | 41.7 | 87.8 | 6674 | 40.5 | 4551.4 | | |
| 265 | 15.8 | 17.2 | 7761.2 | 33.9 | 4041.3 | 1.2 | 3.4 |
| 266 | 84.5 | 178.3 | 10000 | 91.2 | 5000 | | |
| 267 | 27.5 | 45.8 | 8968.5 | 29.8 | 1069.8 | | 1.7 |
| 268 | 40.7 | 155.8 | 4775.9 | 33.8 | 5000 | | 11.8 |
| 269 | 64.8 | 93.6 | 8201 | 86.8 | 5000 | | |
| 270 | 16.8 | 21 | 942.1 | 20.1 | 493.6 | 1.6 | 1.1 |
| 271 | 20.5 | 51.9 | 3449.1 | 31.6 | 5000 | | 37 |
| 272 | 40.2 | 124.1 | 10000 | 76.9 | 5000 | | |
| 273 | 25.2 | 76.3 | 5635.3 | 25.7 | 5000 | | 15.3 |
| 274 | 45.2 | 34.7 | 2345.3 | 16.1 | 680.7 | 1.1 | 4.1 |
| 275 | 103.7 | 86.9 | 895.3 | 15.8 | 526.1 | 3.8 | 1.6 |
| 276 | 24.1 | 10 | 350.4 | 6.7 | 302 | | 25.2 |
| 277 | 45.9 | 23.7 | 992.4 | 12.5 | 975 | | 7.3 |
| 278 | 116.4 | 54.6 | 6633.1 | 18.1 | 1822.3 | | |
| 279 | 334.8 | 144.9 | 10000 | 62.1 | 5000 | | |
| 280 | 77.9 | 50.4 | 2087.4 | 21.1 | 1893.9 | | 8.7 |
| 281 | 26.7 | 10.4 | 102 | 10.9 | 129.1 | | |
| 282 | 10.3 | 12.9 | 2351.2 | 14.4 | 1233.7 | | 7.6 |
| 283 | 15 | 28.2 | 4552.1 | 33.6 | 1380.6 | | |
| 284 | 35.2 | 24.9 | 10000 | 67.9 | 5000 | | |
| 285 | 73.1 | 65.8 | 10000 | 34.1 | 5000 | 1 | 1.6 |
| 286 | 23.1 | 14.8 | 10000 | 16.5 | 5000 | 1 | 2 |
| 287 | 19.2 | 12.4 | 1103.3 | 9.8 | 1959.7 | 1 | 1.7 |
| 288 | 13.1 | 11 | 1337.4 | 10.5 | 778.1 | | 4.4 |
| 289 | 15.2 | 22.4 | 2868.2 | 53.7 | 5000 | | 26 |
| 290 | 60.4 | 53.6 | 8705.4 | 38.5 | 5000 | 1.5 | 4.8 |
| 291 | 16.6 | 14.9 | 462.5 | 9.5 | 276.4 | 1.5 | 3.5 |
| 292 | 104.6 | 75.5 | 10000 | 71 | 5000 | | 15.6 |
| 293 | 42.3 | 50.5 | 2326.1 | 21.2 | 5000 | | |
| 294 | 50.6 | 1167.2 | 10000 | 22.2 | 5000 | | 7.2 |
| 295 | 151.3 | 153.2 | 1033.3 | 79.3 | 5000 | | |
| 296 | 45.9 | 58.5 | 880.5 | 36.1 | 1439.3 | | |
| 297 | 25.1 | 11.4 | 167.8 | 12.8 | 238.8 | | |
| 298 | 28.5 | 36.5 | 254.9 | 29.9 | 901.8 | | |
| 299 | 3.7 | 1.2 | 29.4 | 4.1 | 66.2 | | |
| 300 | 8.3 | 11.3 | 277 | 9.5 | 652.7 | | 5.8 |
| 301 | 46.4 | 94.8 | 2248.1 | 51.1 | 2551 | | |
| 302 | 7.9 | 8.2 | 712.4 | 17.4 | 1449.9 | 1.3 | 3.5 |
| 303 | 19.7 | 20 | 5071.8 | 18.3 | 2584.3 | 1.3 | 1.1 |
| 304 | 13 | 16.9 | 756.8 | 11.6 | 1667 | | 13.8 |
| 305 | 90.9 | 126.8 | 7970.8 | 66.1 | 5000 | | |
| 306 | 25.8 | 59.2 | 1934.3 | 20.2 | 3089.2 | | 6.8 |
| 307 | 69.2 | 104.5 | 10000 | 36.6 | 5000 | | |
| 308 | 20.6 | 15.5 | 432.3 | 8.4 | 110.3 | | |
| 309 | 3325.2 | 10000 | 10000 | 16.1 | 5000 | | |
| 310 | 5742 | 10000 | 10000 | 33.4 | 5000 | | |
| 311 | 135.3 | 80.3 | 10000 | 16.2 | 562 | | |
| 312 | 27.7 | 23.8 | 891.7 | 13.4 | 311.9 | | |
| 313 | 91.3 | 79.7 | 10000 | 51.9 | 5000 | | |

TABLE 5-continued

| Example No. | Assay 1 $IC_{50}$ (nM) | Assay 2 $IC_{50}$ (nM) | Assay 3 $IC_{50}$ (nM) | Assay 4 $IC_{50}$ (nM) | Assay 5 $IC_{50}$ (nM) | Assay 6 Pe Ratio | Assay 7 Pe Ratio |
|---|---|---|---|---|---|---|---|
| 314 | 55 | 59.4 | 5548.1 | 123.9 | 5000 | | |
| 315 | 136.7 | 118.7 | 10000 | 68.8 | 5000 | | |
| 316 | 16.7 | 23.1 | 1967 | 61.6 | 1453.5 | | |
| 317 | 49.6 | 44 | 267.5 | 6.4 | 116.6 | | |
| 318 | 16.7 | 47.3 | 1380.6 | 29.8 | 2054.6 | | 12.8 |
| 319 | 11.3 | 8.1 | 192 | 5.7 | 264.1 | 4.8 | 3.6 |
| 320 | 29 | 45.6 | 436.1 | 9.4 | 78.3 | | |
| 321 | 9.1 | 4.6 | 86.4 | 3.8 | 123.9 | | |
| 322 | 9.8 | 8.1 | 488.6 | 15.3 | 431.2 | | 11.3 |
| 323 | 15.6 | 36.4 | 10000 | 23.8 | 5000 | | 6.7 |
| 324 | 21.9 | 50.8 | 419 | 10.2 | 275.9 | | |
| 325 | 31.4 | 21.3 | 254.7 | 11.6 | 555.9 | | 10.3 |
| 326 | 23.7 | 18.7 | 2858.2 | 19.7 | 961.3 | 1.5 | 2.1 |
| 327 | 12.7 | 12.8 | 1164 | 9.3 | 3502.7 | | 5.4 |
| 328 | 26.2 | 50 | 691.7 | 15.7 | 1504.6 | | 7.7 |
| 329 | 71.5 | 102.8 | 1087.2 | 73.7 | 1422.3 | | |
| 330 | 106.3 | 238.7 | 10000 | 241.4 | 5000 | | |
| 331 | 7.4 | 4.7 | 48.8 | 3.2 | 79 | | |
| 332 | 18.2 | 10.9 | 196 | 5.9 | 341.1 | 1.2 | 3.2 |
| 333 | 74.9 | 154.8 | 5767 | 31 | 2126.1 | | 6.8 |
| 334 | 28.9 | 55.6 | 430.1 | 21.8 | 1075.7 | 3.7 | 1.9 |
| 335 | 58 | 164.2 | 10000 | 15.4 | 5000 | | 3 |
| 336 | 513.6 | 203.2 | 5704.4 | 50.5 | 4875.7 | | |
| 337 | 7.4 | 13 | 362.3 | 8.2 | 416.9 | 1.4 | 3.6 |
| 338 | 6.9 | 7 | 108.3 | 4.9 | 68.9 | | |
| 339 | 16.7 | 14.1 | 10000 | 16.4 | 360.6 | | |
| 340 | 20.5 | 19.5 | 881.4 | 19.6 | 2017 | | 8.9 |
| 341 | 73.2 | 112.6 | 10000 | 528.6 | 5000 | | |
| 342 | 99.4 | 132.4 | 10000 | 86.4 | 5000 | | |
| 343 | 31.1 | 44.6 | 841 | 9.4 | 371.8 | | |
| 344 | 13.3 | 7.7 | 88.4 | 3.4 | 46.8 | | |
| 345 | 9.5 | 9.4 | 173.7 | 5.1 | 114.8 | | |
| 346 | 21.1 | 14.3 | 1368.2 | 15.4 | 1444.5 | | 14.2 |
| 347 | 25.6 | 38 | 772.1 | 8.2 | 380.3 | | |
| 348 | 11 | 12.1 | 414.1 | 8.2 | 347.8 | | |
| 349 | 22.9 | 29.3 | 2676.1 | 35.8 | 5000 | | |
| 350 | 61.8 | 69.4 | 10000 | 96 | 5000 | | |
| 351 | 75.9 | 66.4 | 2858.5 | 31 | 5000 | | 6.4 |
| 352 | 31.8 | 25.4 | 2913.5 | 11.5 | 5000 | 1.9 | 5.1 |
| 353 | 35.9 | 474.3 | 10000 | 49.5 | 5000 | | 17.2 |
| 354 | 13.6 | 31.6 | 10000 | 8.8 | 5000 | | 13.4 |
| 355 | 45.6 | 158.5 | 10000 | 28.5 | 5000 | 1.5 | 7.2 |
| 356 | 38.6 | 234.4 | 10000 | 27.1 | 5000 | 0.9 | 4.8 |
| 357 | 22.8 | 121.6 | 5049.2 | 17.1 | 5000 | 1.6 | 6.2 |
| 358 | 12.4 | 10 | 237 | 2.9 | 83.2 | | 8.5 |
| 359 | 29.3 | 47.2 | 3372.3 | 21 | 5000 | | 14.4 |
| 360 | 11 | 8.8 | 121.5 | 4.1 | 178.5 | 1.4 | 1.3 |
| 361 | 30 | 33.6 | 907.9 | 8 | 760.3 | 2.9 | 2.3 |
| 362 | 13.8 | 9.7 | 1075.6 | 5.5 | 818.4 | | 7.4 |
| 363 | 4.2 | 1.8 | 22.3 | 3.2 | 35.8 | | |
| 364 | 63.7 | 126.9 | 10000 | 555.8 | 5000 | | |
| 365 | 16.4 | 17.6 | 464.6 | 16.5 | 238.5 | | |
| 366 | 6 | 7.3 | 68.3 | 5.3 | 35.6 | | |
| 367 | 75.5 | 2327.5 | 10000 | 70.4 | 5000 | | |
| 368 | 46.4 | 76.1 | 9630.3 | 34.7 | 5000 | 1.4 | 2.7 |
| 369 | 33.1 | 67.1 | 2475 | 22.4 | 1361.7 | 1.1 | 4.3 |
| 370 | 32.4 | 56 | 1988.9 | 47.3 | 3174.3 | | |
| 371 | 35.9 | 55 | 3438.6 | 82.4 | 5000 | | |
| 372 | 10.5 | 19 | 1131.4 | 52.7 | 4084.4 | | |
| 373 | 40.3 | 55.5 | 1579.6 | 44 | 3356.3 | | |
| 374 | 21.5 | 16.5 | 2661.9 | 20.5 | 5000 | | 3.4 |
| 375 | 26.5 | 43.6 | 1034.7 | 19 | 2017 | | 4 |
| 376 | 39.6 | 33.5 | 2112.3 | 36 | 4494.6 | | |
| 377 | 16.1 | 13 | 187.2 | 16.3 | 425.7 | | |
| 378 | 16.1 | 54 | 4561.1 | 66.3 | 5000 | | |
| 379 | 16.1 | 29.2 | 4213 | 36.5 | 5000 | 2.8 | 1.1 |
| 380 | 36 | 68.1 | 5679.6 | 124.7 | 5000 | | |
| 381 | 19.7 | 28.9 | 1720.3 | 67.3 | 2639.5 | | |
| 382 | 10.8 | 15 | 584.2 | 21 | 338.8 | | |
| 383 | 7.8 | 12.5 | 979.1 | 17.5 | 487.9 | | 9.5 |
| 384 | 64.5 | 100.8 | 2997.6 | 58.3 | 5000 | | |
| 385 | 14.8 | 28.3 | 847.6 | 29.4 | 1952 | 1.3 | 5 |
| 386 | 103.4 | 219.9 | 10000 | 235.5 | 5000 | | |
| 387 | 29.5 | 52.1 | 2199 | 60.8 | 4282.7 | | |
| 388 | 18.6 | 40.7 | 1804.6 | 28.1 | 1697.2 | 3.2 | 1.8 |
| 389 | 14.8 | 20.4 | 276.6 | 31.1 | 685.5 | | |
| 390 | 35.1 | 68.1 | 2212.5 | 30.2 | 1251.3 | 1.3 | 1.8 |
| 391 | 21 | 23.9 | 368.1 | 19.8 | 238.4 | | |
| 392 | 22.5 | 9.8 | 1477.1 | 82 | 5000 | | |
| 393 | 8.6 | 13.4 | 714.5 | 15.4 | 5000 | 1.8 | 2.2 |
| 394 | 14.1 | 11.4 | 251.9 | 10.7 | 5000 | 2.6 | 1.8 |
| 395 | 57.5 | 87.5 | 10000 | 138.9 | 5000 | | |
| 396 | 33 | 59.3 | 4061.9 | 158.2 | 5000 | | |
| 397 | 8.9 | 9.7 | 1122.2 | 49.2 | 5000 | | |
| 398 | 23 | 15.4 | 736.4 | 74 | 5000 | | |
| 399 | 1.7 | 1.9 | 177 | 19 | 461.4 | | |
| 400 | 5.1 | 16 | 3244.7 | 45.6 | 5000 | | |
| 401 | 5.5 | 9.2 | 2717.3 | 30 | 5000 | 1.5 | 5.5 |
| 402 | 17.7 | 38.9 | 4941.4 | 85.4 | 5000 | 1.4 | 3.1 |
| 403 | 25.5 | 61.3 | 1289.3 | 13.4 | 5000 | 2 | 4 |
| 404 | 20.9 | 7.2 | 104.2 | 11.5 | 5000 | 1.2 | 5.2 |
| 405 | 20.4 | 19.5 | 1635.4 | 17.2 | 4550.2 | | 13.7 |
| 406 | 11.7 | 8.7 | 335.8 | 9.3 | 737.4 | 0.9 | 4.3 |
| 407 | 24.4 | 38 | 1508.5 | 20.4 | 5000 | | 16 |
| 408 | 30.5 | 32 | 498.2 | 23.7 | 5000 | 1.1 | 2.2 |
| 409 | 48 | 43.1 | 1969.2 | 34.6 | 5000 | 1.3 | 4.9 |
| 410 | 128.7 | 120.1 | 3665.4 | 82.7 | 5000 | | |
| 411 | 51 | 44.9 | 597.5 | 35.2 | 1442.2 | | |
| 412 | 59.5 | 206 | 10000 | 29.2 | 5000 | 1.6 | 3 |
| 413 | 28 | 78.6 | 2223.1 | 24.6 | 5000 | 1 | 2 |
| 414 | 54.2 | 30.1 | 866.1 | 57.6 | 5000 | | |
| 415 | 19.5 | 9.8 | 246.6 | 32 | 5000 | 1 | 1.8 |
| 416 | 40.1 | 79.5 | 2713.4 | 36.6 | 5000 | 0.9 | 2 |
| 417 | 50.8 | 214.7 | 10000 | 51.6 | 5000 | | |
| 418 | 33.8 | 119.2 | 5596.3 | 33.6 | 5000 | 1.3 | 3.6 |
| 419 | 26.8 | 42.3 | 1043.9 | 21.5 | 5000 | 0.8 | 2.2 |
| 420 | 49.9 | 288.7 | 10000 | 33.8 | 5000 | | 2.5 |
| 421 | 45.9 | 217.3 | 10000 | 94.3 | 5000 | | |
| 422 | 38.2 | 157.1 | 4006.6 | 51.7 | 5000 | | |
| 423 | 27.9 | 125.3 | 2547.4 | 70.8 | 5000 | | |
| 424 | 76.4 | 404.9 | 10000 | 44.8 | 5000 | | |
| 425 | 152.7 | 211.6 | 10000 | 50.5 | 5000 | | |
| 426 | 48.6 | 183.4 | 10000 | 33.2 | 5000 | 0.7 | 2 |
| 427 | 83.4 | 104.3 | 2993 | 56.4 | 5000 | | |
| 428 | 61.9 | 62.4 | 1477.1 | 24.7 | 954.5 | | |
| 429 | 32 | 28.4 | 520.2 | 13.8 | 447.2 | | |
| 430 | 36.1 | 307.5 | 10000 | 38.2 | 5000 | 1.7 | 3.1 |
| 431 | 46.7 | 44.9 | 712.4 | 13.1 | 393.4 | | |
| 432 | 25.9 | 37 | 210.1 | 15.2 | 281.4 | | |
| 433 | 40.4 | 101.4 | 4830.2 | 9.4 | 2893.3 | 1.1 | 3.8 |
| 434 | 11.6 | 20.8 | 1233.4 | 9.8 | 3488.2 | | 13.6 |
| 435 | 78.2 | 314.5 | 587.1 | 16 | 1139.7 | 1.5 | 2 |
| 436 | 65.8 | 36.3 | 1921.2 | 458.9 | 5000 | | |
| 437 | 51.3 | 148.3 | 9730.9 | 18.6 | 4912.9 | | 9.3 |
| 438 | 33.4 | 351.7 | 10000 | 9.8 | 5000 | 1 | 4.1 |
| 439 | 240.5 | 147.5 | 10000 | 933.1 | 5000 | | |
| 440 | 61.5 | 189.4 | 10000 | 42.8 | 5000 | | |
| 441 | 62 | 31.1 | 681.6 | 17.8 | 770 | | 7.3 |
| 442 | 52.3 | 463.7 | 10000 | 29.7 | 5000 | 1 | 1.9 |
| 443 | 67.5 | 90.6 | 4153 | 25.5 | 2822.3 | | 10 |
| 444 | 10.1 | 12 | 378.9 | 5.9 | 352.3 | | 9 |
| 445 | 8.9 | 4.7 | 33.6 | 5.7 | 60.1 | | |
| 446 | 75.7 | 2557.3 | 10000 | 28 | 5000 | | 19.4 |
| 447 | 12.6 | 29.2 | 10000 | 17.5 | 5000 | | 20.3 |
| 448 | 238.5 | 369.8 | 10000 | 87.6 | 3445 | | |
| 449 | 32.1 | 91.9 | 7512.5 | 56.2 | 5000 | | |
| 450 | 52 | 67.3 | 479.6 | 9.8 | 1160.8 | 2.5 | 3.2 |
| 451 | 81.5 | 106.5 | 6262.1 | 49.3 | 3337.1 | | |
| 452 | 28.8 | 452.3 | 1055.2 | 12.8 | 5000 | | 6.2 |
| 453 | 159.2 | 146.8 | 10000 | 56.3 | 5000 | | |
| 454 | 33.9 | 35.6 | 1183.6 | 14.1 | 679.8 | 0.8 | 0.6 |
| 455 | 11.6 | 4.1 | 87.3 | 4.8 | 193 | | 9.6 |
| 456 | 174 | 710.9 | 10000 | 252.7 | 5000 | | |

All publications and patent applications cited in the specification are herein incorporated by reference in their entirety. It will be apparent to those of ordinary skill in the art that certain changes and modifications may be made thereto without departing from the spirit or scope of the appended claims.

The invention claimed is:

1. A compound of Formula (I):

(I)

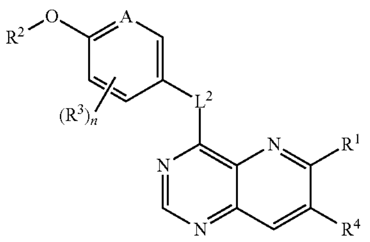

or a pharmaceutically acceptable salt thereof, wherein:

A is selected from carbon and nitrogen, wherein $R^3$ may be bound to A when it is carbon;

$R^1$ is selected from the group consisting of $-L^1-R^5$, $—NR^6R^7$, N-methyl-3-acrylamide, and prop-1-en-2-yl;

$R^2$ is

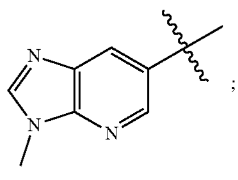 [SMILES: *c1cnc2c(c1)ncn2C ; ";"]

;

each $R^3$ is independently selected from halogen, methyl, difluoromethyl and trifluoromethyl;

$R^4$ is hydrogen, Cl or methoxy;

$L^1$ is selected from the group consisting of a bond, $CHR^8$, O, $NR^8$ and S;

$L^2$ is selected from NH and 0;

$R^5$ is a 4 to 10 membered heterocycle containing 1 to 3 heteroatoms selected from the group consisting of N, O and S, wherein the heterocycle is substituted by $R^6$, and wherein the heterocycle may be optionally substituted with 1 or 2 groups independently selected from methyl, ethyl, isopropyl, tert-butyl, difluoromethyl, trifluoromethyl methoxymethyl, ethynyl, cyclopropyl, and cyclobutyl;

$R^6$ is selected from the group consisting of cyano, 1-prop-2-en-1-one, 1-(2-fluoroprop-2-en-1-one), 1-(2-methylprop-2-en-1-one), N—(N-methylacrylamide), 1-but-2-yn-1-one, vinylsulfonyl, and (bicyclo[1.1.0]butan-1-yl)methanone;

$R^7$ and $R^8$ are independently hydrogen or methyl; and n is 0, 1 or 2.

2. The compound or salt of claim 1, wherein $R^4$ is hydrogen.

3. The compound or salt of claim 2, wherein each $R^3$ is independently selected from the group consisting of fluoro, chloro, and methyl, and n is 1 or 2.

4. The compound or salt of claim 1, wherein $R^1$ is selected from the group consisting of 1-acryloylpiperidin-4-olate, 6-acryloyl-3,6-diazabicyclo[3.1.1]heptan-3-yl, 1-acryloylhexahydropyrrolo[3,4-b]pyrrol-5(1H)-yl, 1-(bicyclo[1.1.0]butane-1-carbonyl)hexahydropyrrolo[3,4-b]pyrrol-5(1H)-yl, (1-acryloylpiperidin-4-yl)thio, 2-acryloyl-2,6-diazabicyclo[3.2.1]octan-6-yl, 4-acryloylpiperazin-1-yl, 4-acryloyl-3,3-dimethylpiperazin-1-yl, (1-acryloylpiperidin-4-yl)(methyl)amino, 1-acryloylpiperidin-3-yl, 1-acryloyl-6,6-dimethylpiperidin-3-yl, 1-acryloyloctahydrocyclopenta[b]pyrrol-5-yl, 1-acryloylpiperidin-4-yl, 3-acryloyl-3,6-diazabicyclo[3.1.1]heptan-6-yl, (1-acryloylazetidin-3-yl)thio, 4-acryloyl-5,5-dimethyl-1,4-diazepan-1-yl, 4-acryloyl-3,3-dimethyl-1,4-diazepan-1-yl, 5-acryloyl-2,5-diazabicyclo[2.2.1]heptan-2-yl, 4-acryloyl-3-(trifluoromethyl)piperazin-1-yl, 4-acryloyl-3-methylpiperazin-1-yl, 4-acryloyl-1,4-diazepan-1-yl, 6-acryloyl-2,6-diazaspiro[3.3]heptan-2-yl, 6-acryloyl-3,6-diazabicyclo[3.2.1]octan-3-yl, 4-acryloyl-3,5-dimethylpiperazin-1-yl, 6-acryloyl-3,6-diazabicyclo[3.2.0]heptan-3-yl, 1-acryloylpyrrolidin-3-yl, 1-acryloylazepan-4-yl, 1-acryloyl-2-methylpiperidin-4-yl, 1-acryloyl-5-methylpyrrolidin-3-yl, 1-acryloyl-3-methylpiperidin-4-yl, 1-acryloylazepan-3-yl, 1-acryloyl-2,2-dimethylpiperidin-4-yl, 4-acryloyl-4-azaspiro[2.5]octan-7-yl, 8-acryloyl-8-azabicyclo[3.2.1]octan-3-yl, 1-acryloyloctahydrocyclopenta[b]pyrrol-4-yl, 2-acryloyloctahydrocyclopenta[c]pyrrol-5-yl, 1-acryloyl-6,6-dimethylazepan-4-yl, N-acrylamide, N-but-2-ynamide, N-ethenesulfonamide, N-methyl-N-ethenesulfonamide, N-methyl-3-acrylamide, N-methyl-N-acrylamide, prop-2-en-1-one, 9-acryloyl-3-oxa-9-azabicyclo[3.3.1]nonan-7-yl, 4-acryloyl-3-cyclopropylpiperazin-1-yl, 4-acryloyl-3-ethylpiperazin-1-yl, 1-acryloyl-2,6-dimethylpiperidin-4-yl, 4-(but-2-ynoyl)-3-(difluoromethyl)piperazin-1-yl, 1-acryloyl-6-methylpiperidin-3-yl, 5-acryloyl-2,5-diazabicyclo[2.2.2]octan-2-yl, 2-(but-2-ynoyl)-2,6-diazabicyclo[3.2.1]octan-6-yl, 4-(but-2-ynoyl)-3-methylpiperazin-1-yl, 4-(but-2-ynoyl)-3,3-dimethylpiperazin-1-yl, 4-(but-2-ynoyl)-3-(methoxymethyl)piperazin-1-yl, 4-(but-2-ynoyl)-4,7-diazaspiro[2.5]octan-7-yl, 4-(but-2-ynoyl)-3-(trifluoromethyl)piperazin-1-yl, 4-(2-fluoroacryloyl)piperazin-1-yl, 4-(bicyclo[1.1.0]butane-1-carbonyl)-3,3-dimethylpiperazin-1-yl, 4-(2-fluoroacryloyl)-3,3-dimethylpiperazin-1-yl, 1-(but-2-ynoyl)-1,6-diazaspiro[3.3]heptan-6-yl, 4-acryloyl-4-azaspiro[2.5]octan-6-yl, 2-acryloyl-2-azabicyclo[2.2.1]heptan-5-yl, 2-acryloyl-2-azabicyclo[2.2.1]heptan-6-yl, 8-(2-fluoroacryloyl)-8-azabicyclo[3.2.1]octan-3-yl, 8-(but-2-ynoyl)-8-azabicyclo[3.2.1]octan-3-yl, 1-(but-2-ynoyl)azepan-4-yl, 7-acryloyl-7-azabicyclo[2.2.1]heptan-2-yl, 2-acryloyl-2-azabicyclo[2.2.2]octan-5-yl, 3-acryloyl-3-azabicyclo[3.2.1]octan-8-yl, 8-acryloyl-3,8-diazabicyclo[3.2.1]octan-3-yl, 8-(but-2-ynoyl)-3,8-diazabicyclo[3.2.1]octan-3-yl, 3-acryloyl-3,8-diazabicyclo[3.2.1]octan-8-yl, 4-cyano-3,3-dimethylpiperazin-1-yl, 3-(but-2-ynoyl)-3,8-diazabicyclo[3.2.1]octan-8-yl, 4-acryloyl-3-isopropylpiperazin-1-yl, 1-acryloyl-1,6-diazaspiro[3.3]heptan-6-yl, 1-acryloylazetidin-3-yl, 4-acryloyl-4,7-diazaspiro[2.5]octan-7-yl, 6-acryloyl-1,6-diazaspiro[3.3]heptan-1-yl, 4-acryloyl-3-(tert-butyl)piperazin-1-yl, 1-acryloyl-5,5-dimethylpyrrolidin-3-yl, 4-acryloyl-3-(difluoromethyl)piperazin-1-yl, (1-acryloylazetidin-3-yl)methyl, 1-(1-acryloylazetidin-3-yl)ethyl, 1-acryloyl-5-cyclopropylpyrrolidin-3-yl, 4-acryloyl-3-cyclobutylpiperazin-1-yl, 1-acryloyl-5-(methoxymethyl)pyrrolidin-3-yl, 2-acryloyl-2,6-diazaspiro[3.4]octan-6-yl, 5-acryloyl-5,8-diazaspiro[3.5]nonan-8-yl, 5-(but-2-ynoyl)-2,5-diazabicyclo[2.2.1]heptan-2-yl, 4-acryloyl-3-ethynylpiperazin-1-yl, 6-acryloyl-3,6-diazabicyclo[3.2.2]nonan-3-yl, 4-methacryloyl-3,3-dimethylpiperazin-1-yl, 4-acryloyl-3-(methoxymethyl)piperazin-1-yl, N-(1-pyrrolidin-3-yl)-N-methylacrylamide, 4-methacryloylpiperazin-1-yl, 6-acryloyl-6-azabicyclo[3.2.1]octan-2-yl, 6-acryloyl-6-azabicyclo[3.2.1]octan-3-yl, 2-acryloyl-2-azabicyclo[2.2.2]octan-6-yl, 2-acryloyloctahydrocyclopenta[c]pyrrol-4-yl, 8-acryloyl-8-azabicyclo[3.2.1]octan-6-yl, and 8-acryloyl-8-azabicyclo[3.2.1]octan-2-yl.

5. The compound of claim 1, wherein the compound is selected from the group consisting of:
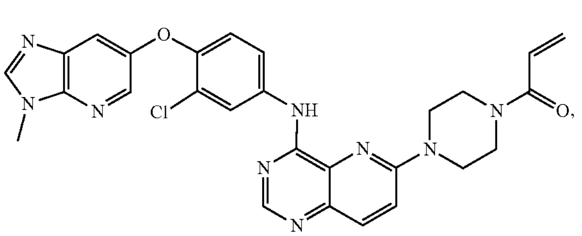
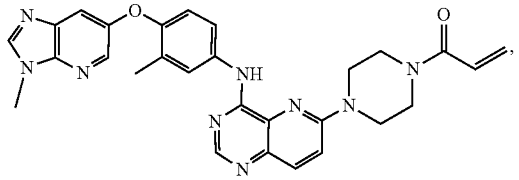
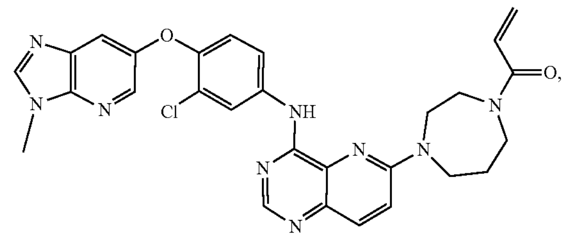
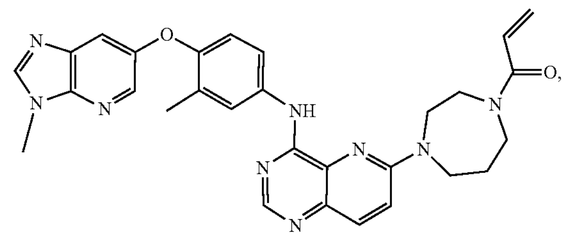
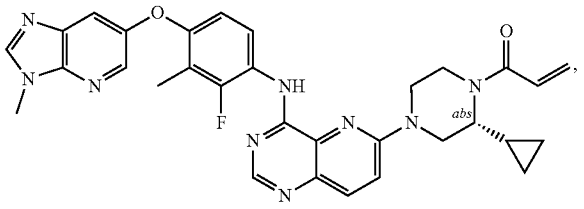
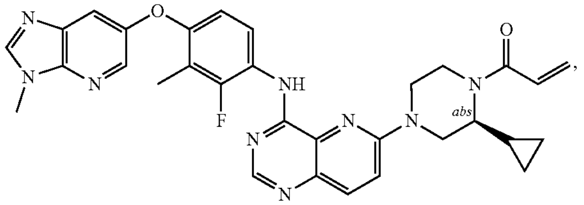
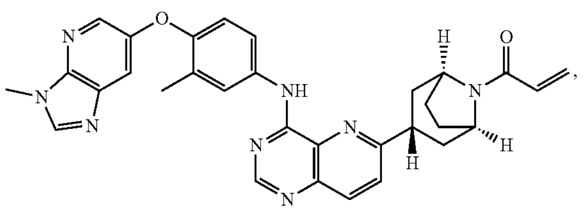
-continued
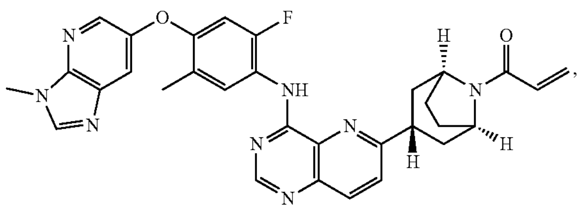
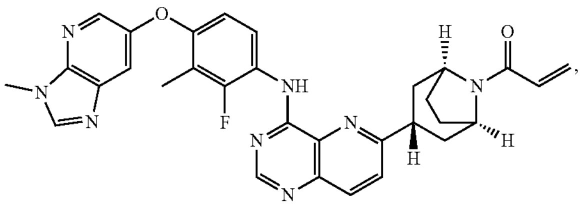
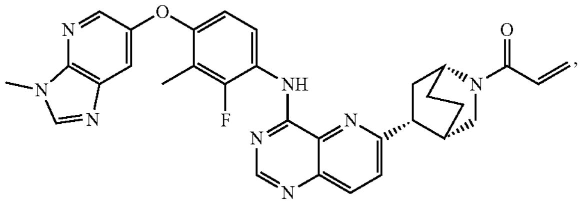
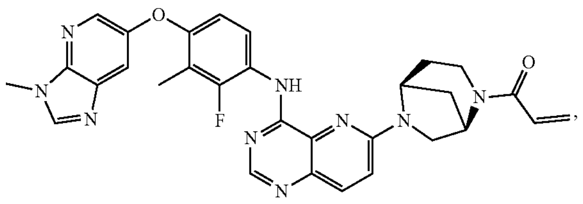
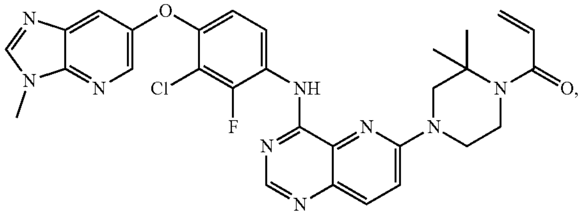
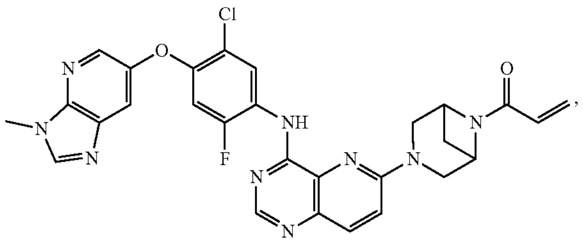
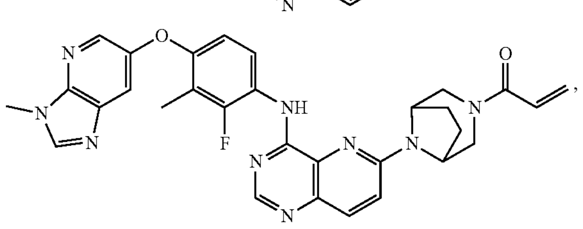
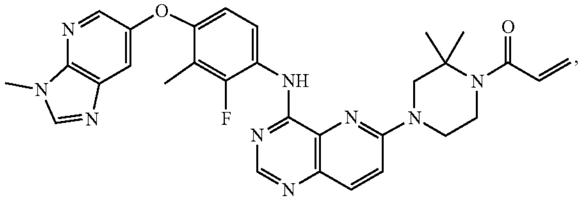

-continued
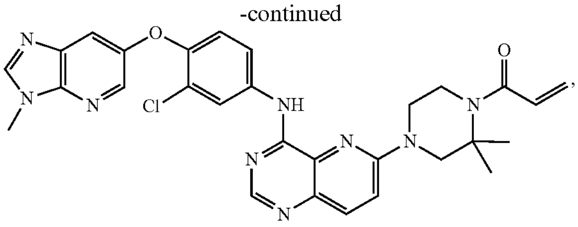,
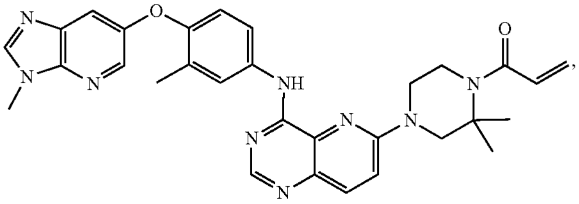,
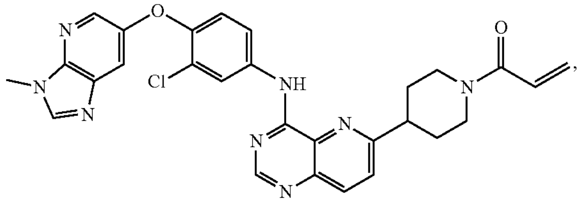,
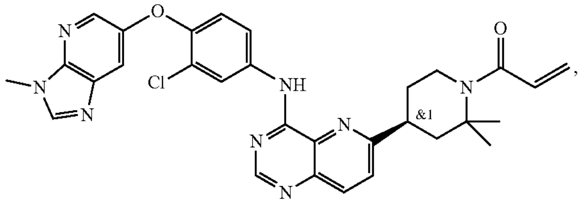,
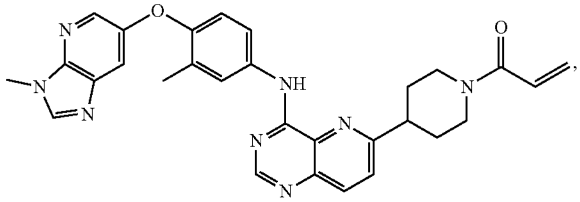,
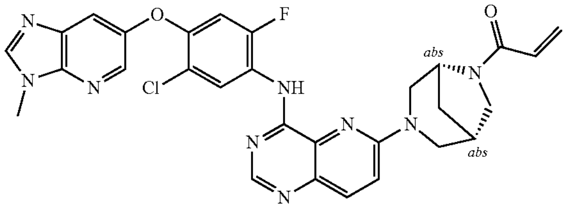,
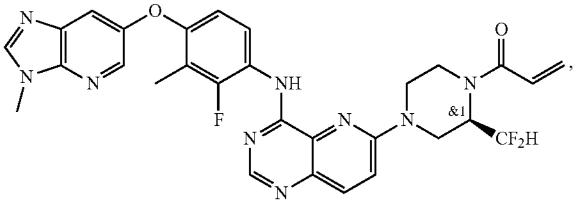,
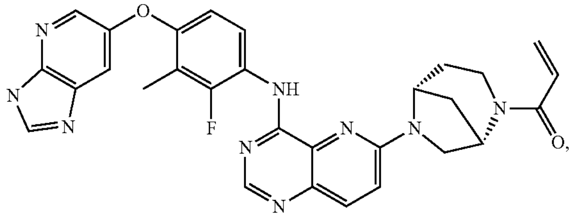,
-continued
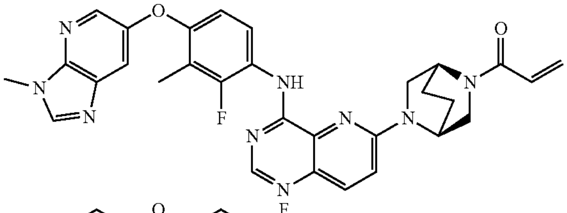,
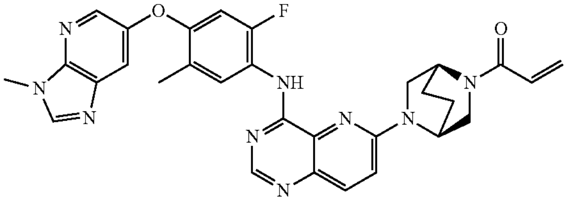,
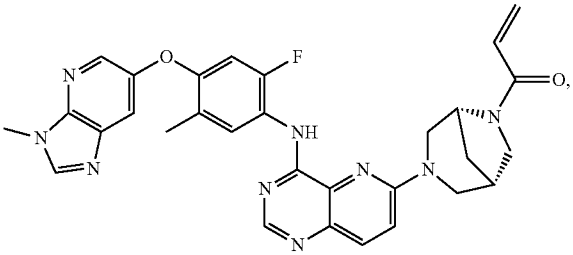,
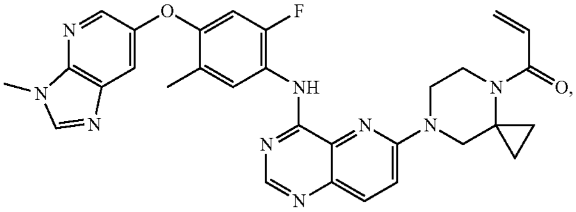,
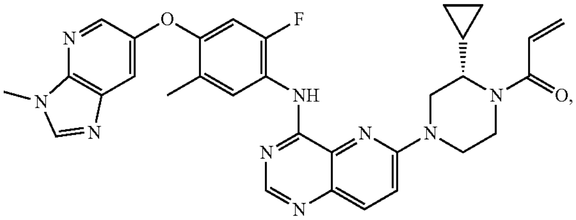,
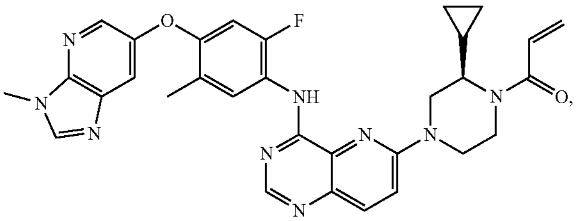,
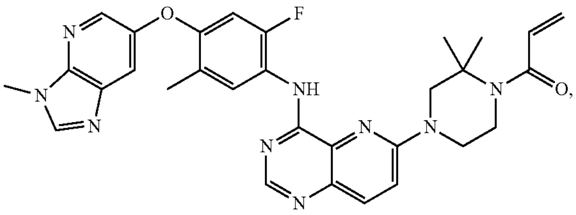,
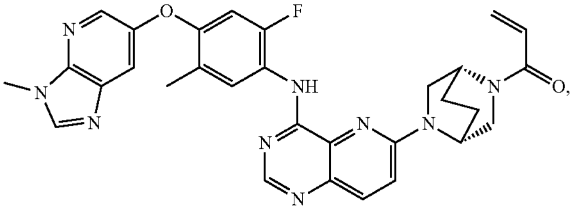,

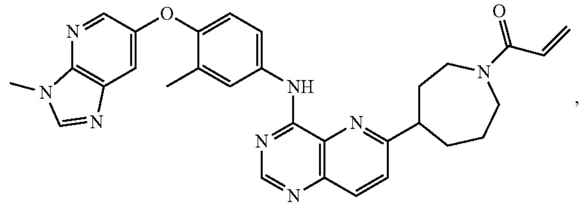
,
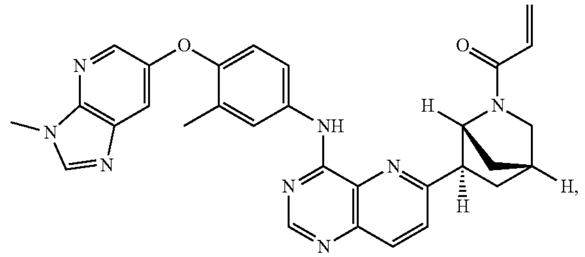
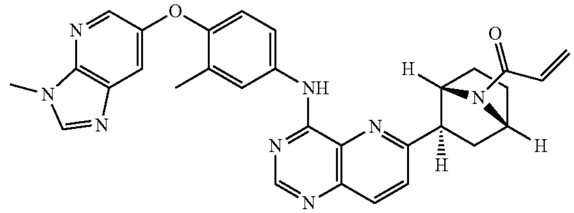
,
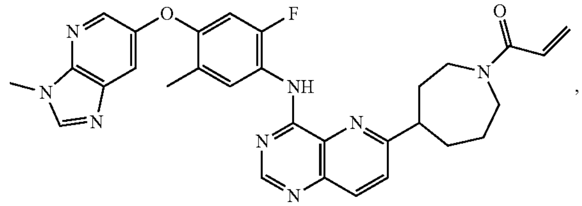
,
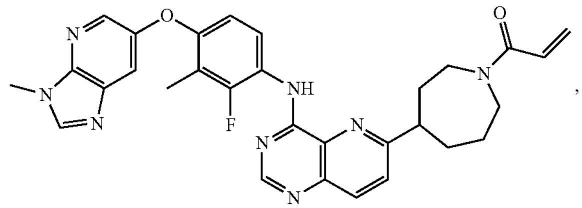
,
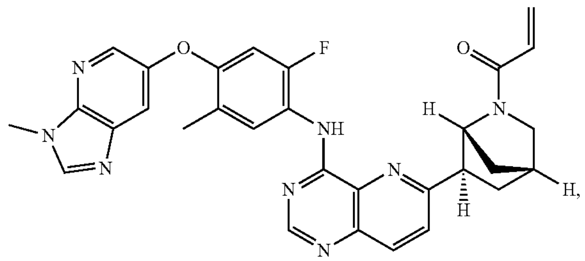
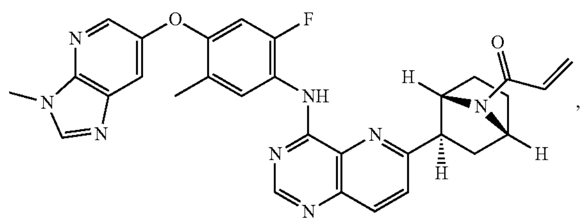
,
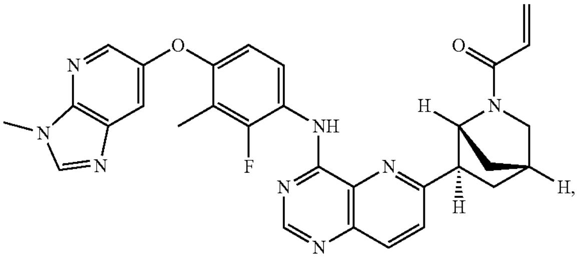
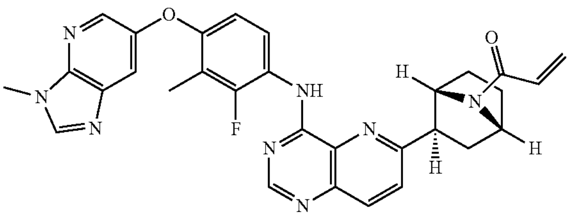
,
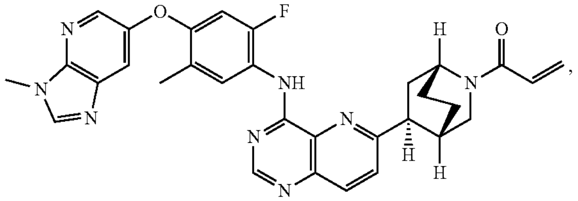
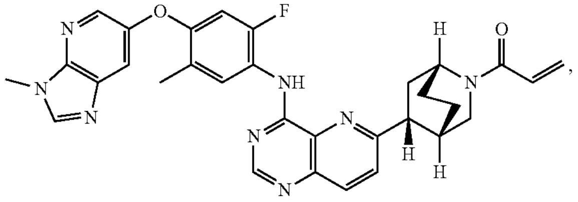
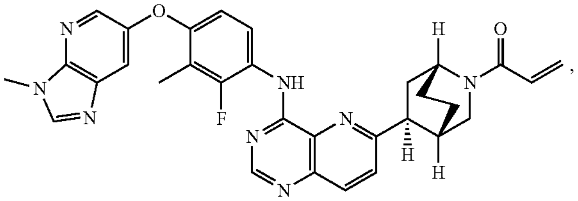
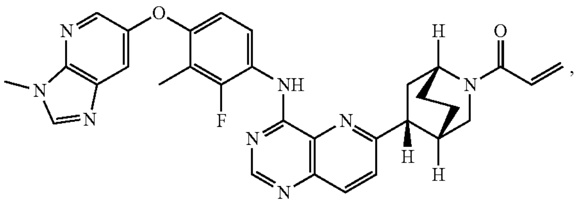
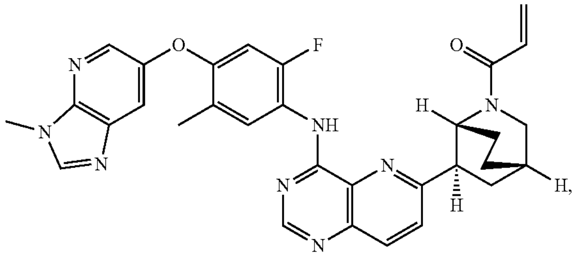

-continued
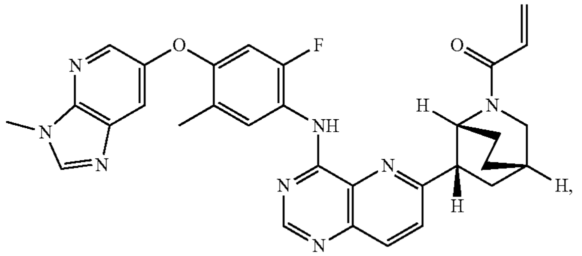
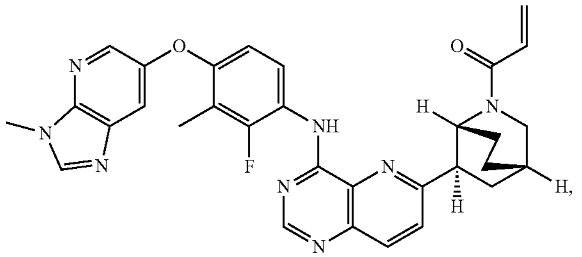
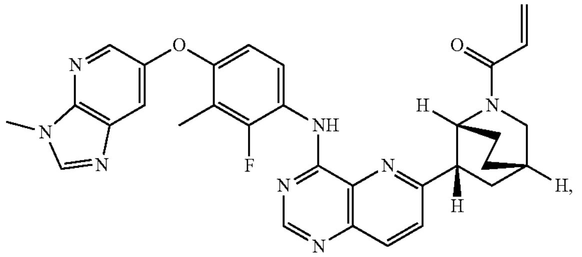
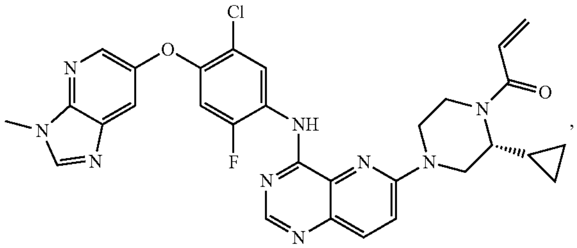
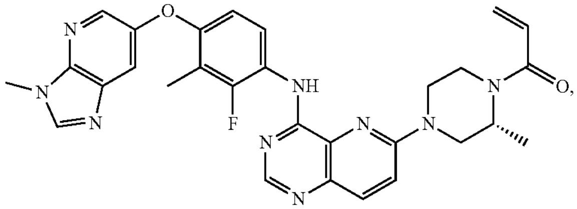
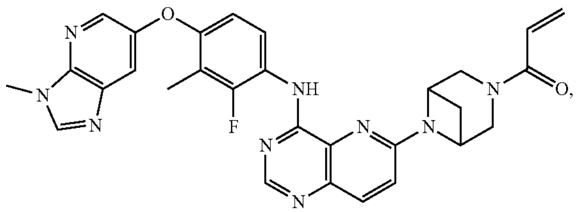
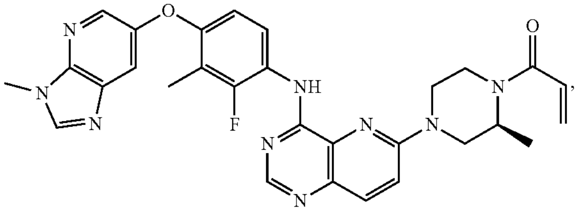
-continued
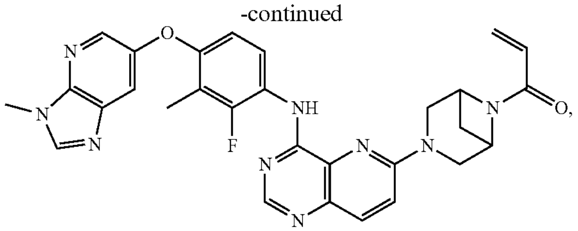
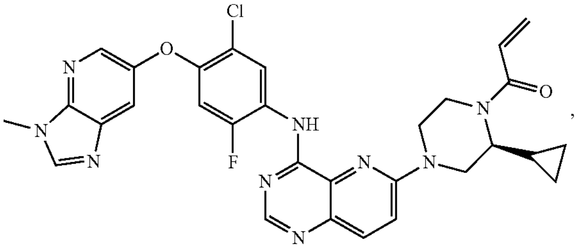
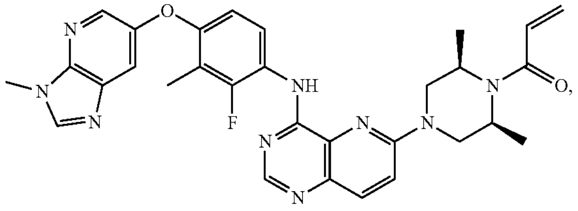
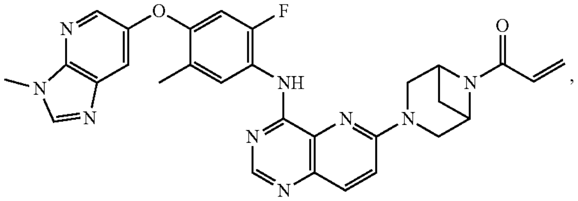
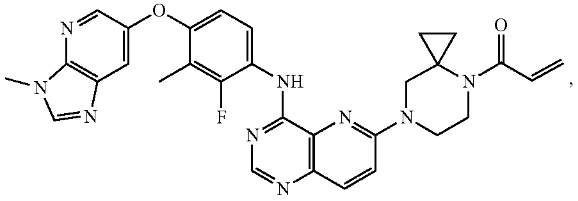
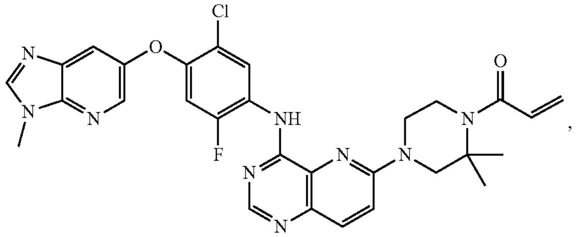
and
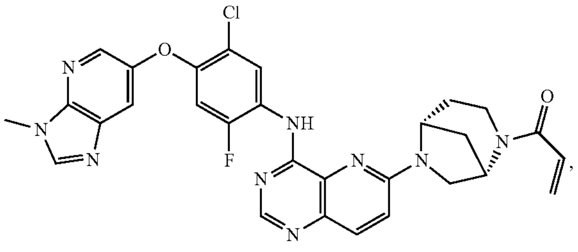
or a pharmaceutically acceptable salt thereof.
6. A pharmaceutical composition comprising a compound of claim 1, or a pharmaceutically acceptable salt thereof, and at least one pharmaceutically acceptable excipient.

7. A method for treating cancer in a subject in need thereof, comprising administering to the subject a therapeutically effective amount of a compound of claim 1, or a pharmaceutically acceptable salt thereof.

8. The method of claim 7, further comprising administering at least one additional anti-cancer therapeutic agent.

9. The method of claim 8, wherein the additional anti-cancer therapeutic agent is selected from the group consisting of trastuzumab, pertuzumab, margetuximab, t-dm1, sacituzumab govitecan-hziy, neratinib, lapatinib, tucatinib, palbociclib, ribociclib, abemaciclib, everolimus, alpelisib, olaparib, talazoparib, cyclophosphamide, methotrexate, 5-fluorouracil, vinorelbine, doxorubicin, paclitaxel, docetaxel, bleomycin, vinblastine, dacarbazine, mustine, vincristine, procarbazine, prednisolone, etoposide, cisplatin, carboplatin, epirubicin, capecitabine, folinic acid and oxaliplatin, cemiplimab, nivolumab, pembrolizumab, avelumab, durvalumab, atezolizumab, aminoglutethimide, testolactone, anastrozole, letrozole, exemestane, vorozole, formetsane, fadrozole, ATD, 6-OXO, fulvestrant, sunitinib, sorafenib, bevacizumab, and pharmaceutically acceptable salts thereof, and combinations thereof.

10. A compound of Formula (III):

(III)

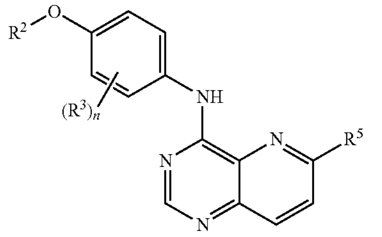

or a pharmaceutically acceptable salt thereof, wherein:

$R^2$ is

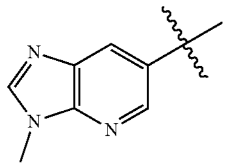 [SMILES: *c1cnc2c(c1)ncn2C]

each $R^3$ is independently selected from halogen and methyl;

$R^5$ is a 4 to 9 membered heterocycle containing 1 to 3 heteroatoms selected from the group consisting of N, O and S, wherein the heterocycle is substituted by $R^6$, and wherein the heterocycle may be optionally substituted with 1 or 2 groups independently selected from methyl, ethyl, isopropyl, tert-butyl, difluoromethyl, trifluoromethyl, methoxymethyl, ethynyl, cyclopropyl, and cyclobutyl;

$R^6$ is selected from the group consisting of 1-prop-2-en-1-one, 1-(2-fluoroprop-2-en-1-one), 1-(2-methylprop-2-en-1-one), and 1-but-2-yn-1-one;

n is 1 or 2.

11. The compound of claim 8, wherein $R^5$ is a 6 membered monocyclic heterocycle containing 1 or 2 nitrogen heteroatoms, wherein the heterocycle is attached via a ring nitrogen atom, wherein the heterocycle is substituted by $R^6$, and wherein the heterocycle may be optionally substituted with 1 or 2 methyl groups.

12. The compound of claim 11, wherein $R^6$ is 1-prop-2-en-1-one.

13. The compound:

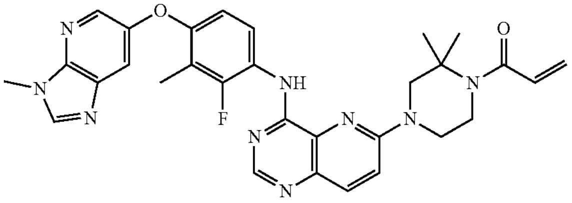 [SMILES: C=CC(=O)N1CCN(c2ccc3ncnc(Nc4ccc(Oc5cnc6c(c5)ncn6C)c(C)c4F)c3n2)CC1(C)C]

or a pharmaceutically acceptable salt thereof.

14. The compound of claim 13:

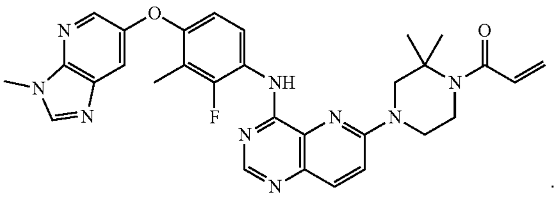 [SMILES: C=CC(=O)N1CCN(c2ccc3ncnc(Nc4ccc(Oc5cnc6c(c5)ncn6C)c(C)c4F)c3n2)CC1(C)C]

15. A pharmaceutical composition comprising a compound of claim 13, or a pharmaceutically acceptable salt thereof, and at least one pharmaceutically acceptable excipient.

16. A method for treating cancer, wherein the cancer is HER2 positive cancer, wherein the HER2 positive cancer is selected from breast cancer, ovarian cancer, bladder cancer, uterine cancer, prostate cancer, small cell lung cancer, non-small cell lung cancer, esophageal cancer, liver cancer, pancreatic cancer, or stomach cancer.

17. The method of claim 16, further comprising administering at least one additional anti-cancer therapeutic agent.

18. The method of claim 17, wherein the additional anti-cancer therapeutic agent is selected from the group consisting of trastuzumab, pertuzumab, margetuximab, t-dm1, sacituzumab govitecan-hziy, neratinib, lapatinib, tucatinib, palbociclib, ribociclib, abemaciclib, everolimus, alpelisib, olaparib, talazoparib, cyclophosphamide, methotrexate, 5-fluorouracil, vinorelbine, doxorubicin, paclitaxel, docetaxel, bleomycin, vinblastine, dacarbazine, mustine, vincristine, procarbazine, prednisolone, etoposide, cisplatin, carboplatin, epirubicin, capecitabine, folinic acid and oxaliplatin, cemiplimab, nivolumab, pembrolizumab, avelumab, durvalumab, atezolizumab, aminoglutethimide, testolactone, anastrozole, letrozole, exemestane, vorozole, formetsane, fadrozole, ATD, 6-OXO, fulvestrant, sunitinib, sorafenib, bevacizumab, and pharmaceutically acceptable salts thereof, and combinations thereof.

* * * * *

SEQUENCE LISTING

<160> NUMBER OF SEQ ID NOS: 2

<210> SEQ ID NO 1
<211> LENGTH: 604
<212> TYPE: PRT
<213> ORGANISM: Artificial Sequence
<220> FEATURE:
<223> OTHER INFORMATION: Synthetic Construct

<400> SEQUENCE: 1

Met Ala His His His His His His His His Gly Gly Gly Gly Gly Leu
1 5 10 15

Val Pro Arg Gly Lys Arg Arg Gln Gln Lys Ile Arg Lys Tyr Thr Met
20 25 30

Arg Arg Leu Leu Gln Glu Thr Glu Leu Val Glu Pro Leu Thr Pro Ser
35 40 45

Gly Ala Met Pro Asn Gln Ala Gln Met Arg Ile Leu Lys Glu Thr Glu
50 55 60

Leu Arg Lys Val Lys Val Leu Gly Ser Gly Ala Phe Gly Thr Val Tyr
65 70 75 80

Lys Gly Ile Trp Ile Pro Asp Gly Glu Asn Val Lys Ile Pro Val Ala
85 90 95

Ile Lys Val Leu Arg Glu Asn Thr Ser Pro Lys Ala Asn Lys Glu Ile
100 105 110

Leu Asp Glu Ala Tyr Val Met Ala Tyr Val Met Ala Gly Val Gly Ser
115 120 125

Pro Tyr Val Ser Arg Leu Leu Gly Ile Cys Leu Thr Ser Thr Val Gln
130 135 140

Leu Val Thr Gln Leu Met Pro Tyr Gly Cys Leu Leu Asp His Val Arg
145 150 155 160

Glu Asn Arg Gly Arg Leu Gly Ser Gln Asp Leu Leu Asn Trp Cys Met
165 170 175

Gln Ile Ala Lys Gly Met Ser Tyr Leu Glu Asp Val Arg Leu Val His
180 185 190

Arg Asp Leu Ala Ala Arg Asn Val Leu Val Lys Ser Pro Asn His Val
195 200 205

Lys Ile Thr Asp Phe Gly Leu Ala Arg Leu Leu Asp Ile Asp Glu Thr
210 215 220

Glu Tyr His Ala Asp Gly Gly Lys Val Pro Ile Lys Trp Met Ala Leu
225 230 235 240

Glu Ser Ile Leu Arg Arg Arg Phe Thr His Gln Ser Asp Val Trp Ser
245 250 255

Tyr Gly Val Thr Val Trp Glu Leu Met Thr Phe Gly Ala Lys Pro Tyr
260 265 270

Asp Gly Ile Pro Ala Arg Glu Ile Pro Asp Leu Leu Glu Lys Gly Glu
275 280 285

Arg Leu Pro Gln Pro Pro Ile Cys Thr Ile Asp Val Tyr Met Ile Met
290 295 300

Val Lys Cys Trp Met Ile Asp Ser Glu Cys Arg Pro Arg Phe Arg Glu
305 310 315 320

Leu Val Ser Glu Phe Ser Arg Met Ala Arg Asp Pro Gln Arg Phe Val
325 330 335

```
Val Ile Gln Asn Glu Asp Leu Gly Pro Ala Ser Pro Leu Asp Ser Thr
            340                 345                 350

Phe Tyr Arg Ser Leu Leu Glu Asp Asp Asp Met Gly Asp Leu Val Asp
        355                 360                 365

Ala Glu Glu Tyr Leu Val Pro Gln Gln Gly Phe Phe Cys Pro Asp Pro
    370                 375                 380

Ala Pro Gly Ala Gly Gly Met Val His His Arg His Arg Ser Ser Ser
385                 390                 395                 400

Thr Arg Ser Gly Gly Gly Asp Leu Thr Leu Gly Leu Glu Pro Ser Glu
                405                 410                 415

Glu Glu Ala Pro Arg Ser Pro Leu Ala Pro Ser Glu Gly Ala Gly Ser
            420                 425                 430

Asp Val Phe Asp Gly Asp Leu Gly Met Gly Ala Ala Lys Gly Leu Gln
        435                 440                 445

Ser Leu Pro Thr His Asp Pro Ser Pro Leu Gln Arg Tyr Ser Glu Asp
    450                 455                 460

Pro Thr Val Pro Leu Pro Ser Glu Thr Asp Gly Tyr Val Ala Pro Leu
465                 470                 475                 480

Thr Cys Ser Pro Gln Pro Glu Tyr Val Asn Gln Pro Asp Val Arg Pro
                485                 490                 495

Gln Pro Pro Ser Pro Arg Glu Gly Pro Leu Pro Ala Ala Arg Pro Ala
            500                 505                 510

Gly Ala Thr Leu Glu Arg Ala Lys Thr Leu Ser Pro Gly Lys Asn Gly
        515                 520                 525

Val Val Lys Asp Val Phe Ala Phe Gly Gly Ala Val Glu Asn Pro Glu
    530                 535                 540

Tyr Leu Thr Pro Gln Gly Gly Ala Ala Pro Gln Pro His Pro Pro Pro
545                 550                 555                 560

Ala Phe Ser Pro Ala Phe Asp Asn Leu Tyr Tyr Trp Asp Gln Asp Pro
                565                 570                 575

Pro Glu Arg Gly Ala Pro Pro Ser Thr Phe Lys Gly Thr Pro Thr Ala
            580                 585                 590

Glu Asn Pro Glu Tyr Leu Gly Leu Asp Val Pro Val
        595                 600


<210> SEQ ID NO 2
<211> LENGTH: 4
<212> TYPE: PRT
<213> ORGANISM: Artificial Sequence
<220> FEATURE:
<223> OTHER INFORMATION: Synthetic Construct

<400> SEQUENCE: 2

Tyr Val Met Ala
1
```